(12) United States Patent
Nomura et al.

(10) Patent No.: US 12,110,274 B2
(45) Date of Patent: Oct. 8, 2024

(54) CARBAZOLE DERIVATIVE, AND LIGHT-EMITTING ELEMENT, LIGHT-EMITTING DEVICE, AND ELECTRONIC DEVICE USING CARBAZOLE DERIVATIVE

(71) Applicant: SEMICONDUCTOR ENERGY LABORATORY CO., LTD., Atsugi (JP)

(72) Inventors: Hiroko Nomura, Kanagawa (JP); Harue Osaka, Kanagawa (JP); Takahiro Ushikubo, Kanagawa (JP); Sachiko Kawakami, Kanagawa (JP); Satoshi Seo, Kanagawa (JP); Satoko Shitagaki, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 0 days.

(21) Appl. No.: 17/861,363

(22) Filed: Jul. 11, 2022

(65) Prior Publication Data

US 2022/0388958 A1 Dec. 8, 2022

Related U.S. Application Data

(63) Continuation of application No. 16/741,830, filed on Jan. 14, 2020, now abandoned, which is a
(Continued)

(30) Foreign Application Priority Data

Dec. 3, 2007 (JP) .................. 2007-312509
May 16, 2008 (JP) .................. 2008-129917

(51) Int. Cl.
*C07D 209/86* (2006.01)
*H01L 51/00* (2006.01)
*H10K 85/60* (2023.01)

(52) U.S. Cl.
CPC ......... *C07D 209/86* (2013.01); *H10K 85/633* (2023.02); *H10K 85/636* (2023.02); *H10K 85/6572* (2023.02)

(58) Field of Classification Search
None
See application file for complete search history.

(56) References Cited

U.S. PATENT DOCUMENTS

| | | | |
|---|---|---|---|
| 5,061,569 A | 10/1991 | VanSlyke et al. |
| 6,423,429 B2 | 7/2002 | Kido et al. |

(Continued)

FOREIGN PATENT DOCUMENTS

| | | | |
|---|---|---|---|
| EP | 0948063 A | 10/1999 |
| EP | 1017118 A | 7/2000 |

(Continued)

OTHER PUBLICATIONS

Ho.M et al., "P-131: Novel Deep Blue Dopants for Organic Light Emitting Devices", SID Digest '05 : SID International Symposium Digest of Technical Papers, May 24, 2005, vol. 36, pp. 802-805.
(Continued)

*Primary Examiner* — Jay Yang
(74) *Attorney, Agent, or Firm* — Fish & Richardson P.C.

(57) ABSTRACT

To provide a light-emitting element having high luminous efficiency and to provide a light-emitting device and an electronic device which consumes low power and is driven at low voltage, a carbazole derivative represented by the general formula (1) is provided. In the formula, $\alpha^1$, $\alpha^2$, $\alpha^3$, and $\alpha^4$ each represent an arylene group having less than or equal to 13 carbon atoms; $Ar^1$ and $Ar^2$ each represent an aryl group having less than or equal to 13 carbon atoms; $R^1$ represents any of a hydrogen atom, an alkyl group having 1 to 6 carbon atoms, a substituted or unsubstituted phenyl group, and a substituted or unsubstituted biphenyl group;
(Continued)

and $R^2$ represents any of an alkyl group having 1 to 6 carbon atoms, a substituted or unsubstituted phenyl group, and a substituted or unsubstituted biphenyl group. In addition, l, n, and n are each independently 0 or 1.

7 Claims, 54 Drawing Sheets

Related U.S. Application Data continuation of application No. 16/139,412, filed on Sep. 24, 2018, now Pat. No. 10,556,864, which is a continuation of application No. 15/713,129, filed on Sep. 22, 2017, now abandoned, which is a continuation of application No. 12/326,311, filed on Dec. 2, 2008, now abandoned.

(56) References Cited

U.S. PATENT DOCUMENTS

| | | |
|---|---|---|
| 6,541,129 B1 | 4/2003 | Kawamura et al. |
| 6,566,807 B1 | 5/2003 | Fujita et al. |
| 6,597,012 B2 | 7/2003 | Kido et al. |
| 6,747,287 B1 | 6/2004 | Toguchi et al. |
| 7,399,537 B2 | 7/2008 | Kawamura et al. |
| 7,431,997 B2 | 10/2008 | Hwang et al. |
| 7,696,348 B2 | 4/2010 | Egawa et al. |
| 7,737,627 B2 | 6/2010 | Hwang et al. |
| 7,816,668 B2 | 10/2010 | Kawakami et al. |
| 7,838,128 B2 | 11/2010 | Kawakami et al. |
| 7,897,964 B2 | 3/2011 | Kawakami et al. |
| 7,919,773 B2 | 4/2011 | Kawakami et al. |
| 7,951,874 B2 | 5/2011 | Kanitz et al. |
| 7,968,904 B2 | 6/2011 | Itai |
| 7,972,387 B2 | 7/2011 | Audousset et al. |
| 8,008,489 B2 | 8/2011 | Egawa et al. |
| 8,021,764 B2 | 9/2011 | Hwang et al. |
| 8,021,765 B2 | 9/2011 | Hwang et al. |
| 8,053,092 B2 | 11/2011 | Miki et al. |
| 8,101,857 B2 | 1/2012 | Kido et al. |
| 8,106,391 B2 | 1/2012 | Endo et al. |
| 8,188,315 B2 | 5/2012 | Hwang et al. |
| 8,198,801 B2 | 6/2012 | Kim et al. |
| 8,394,510 B2 | 3/2013 | Mizuki et al. |
| 8,395,143 B2 | 3/2013 | Lee et al. |
| 8,471,017 B2 | 6/2013 | Egawa et al. |
| 8,723,025 B2 | 5/2014 | Kido et al. |
| 8,759,819 B2 | 6/2014 | Nishimura et al. |
| 8,852,756 B2 | 10/2014 | Vestweber et al. |
| 8,895,159 B2 | 11/2014 | Mizuki et al. |
| 8,968,884 B2 | 3/2015 | Hong et al. |
| 8,974,922 B2 | 3/2015 | Hwang et al. |
| 9,054,319 B2 | 6/2015 | Nishimura et al. |
| 9,461,249 B2 | 10/2016 | Vestweber et al. |
| 9,466,799 B2 | 10/2016 | Kido et al. |
| 9,478,754 B2 | 10/2016 | Hwang et al. |
| 9,653,688 B2 | 5/2017 | Kido et al. |
| 9,917,258 B2 | 3/2018 | Hwang et al. |
| 10,211,406 B2 | 2/2019 | Hwang et al. |
| 10,556,864 B2 | 2/2020 | Nomura et al. |
| 10,573,821 B2 | 2/2020 | Hwang et al. |
| 11,482,678 B2 | 10/2022 | Hwang et al. |
| 2003/0143430 A1 | 7/2003 | Kawamura et al. |
| 2003/0230980 A1 | 12/2003 | Forrest et al. |
| 2004/0151943 A1 | 8/2004 | Lee et al. |
| 2005/0073247 A1 | 4/2005 | Yamazaki et al. |
| 2005/0084712 A1 | 4/2005 | Kido et al. |
| 2005/0095740 A1* | 5/2005 | Hirakata ............... H01L 51/56 438/149 |
| 2005/0142384 A1 | 6/2005 | Itai |
| 2005/0173700 A1 | 8/2005 | Liao et al. |
| 2005/0221124 A1 | 10/2005 | Hwang et al. |
| 2005/0225235 A1 | 10/2005 | Kim et al. |
| 2006/0145604 A1 | 7/2006 | Liao et al. |
| 2007/0145888 A1 | 6/2007 | Yabunouchi et al. |
| 2007/0215867 A1 | 9/2007 | Kawakami et al. |
| 2007/0215889 A1 | 9/2007 | Kawakami et al. |
| 2007/0231503 A1 | 10/2007 | Hwang et al. |
| 2007/0231596 A1 | 10/2007 | Spindler et al. |
| 2007/0287029 A1 | 12/2007 | Kawamura et al. |
| 2008/0014464 A1 | 1/2008 | Kawamura et al. |
| 2008/0124572 A1 | 5/2008 | Mizuki et al. |
| 2008/0241591 A1 | 10/2008 | Kawamura et al. |
| 2008/0242871 A1 | 10/2008 | Kawakami et al. |
| 2008/0268282 A1 | 10/2008 | Spindler et al. |
| 2009/0058261 A1 | 3/2009 | Kawakami et al. |
| 2009/0091244 A1 | 4/2009 | Negishi et al. |
| 2009/0160323 A1 | 6/2009 | Nomura et al. |
| 2009/0284140 A1 | 11/2009 | Osaka et al. |
| 2010/0133519 A1 | 6/2010 | Chen et al. |
| 2010/0244008 A1 | 9/2010 | Lee et al. |
| 2011/0042654 A1 | 2/2011 | Jung et al. |
| 2011/0127495 A1 | 6/2011 | Hong et al. |
| 2011/0147728 A1 | 6/2011 | Kawakami et al. |
| 2014/0131680 A1 | 5/2014 | Nishimura et al. |
| 2018/0009751 A1 | 1/2018 | Nomura et al. |
| 2023/0120805 A1 | 4/2023 | Hwang et al. |

FOREIGN PATENT DOCUMENTS

| | | |
|---|---|---|
| EP | 1029909 A | 8/2000 |
| EP | 1617493 A | 1/2006 |
| EP | 1661888 A | 5/2006 |
| EP | 1806334 A | 7/2007 |
| EP | 1862524 A | 12/2007 |
| EP | 1880990 A | 1/2008 |
| EP | 1950194 A | 7/2008 |
| EP | 1961741 A | 8/2008 |
| EP | 1972619 A | 9/2008 |
| EP | 2085382 A | 8/2009 |
| EP | 2202818 A | 6/2010 |
| EP | 2221896 A | 8/2010 |
| EP | 2505582 A | 10/2012 |
| EP | 2518045 A | 10/2012 |
| EP | 2713416 A | 4/2014 |
| EP | 2757094 A | 7/2014 |
| JP | 63-014156 A | 1/1988 |
| JP | 09-310066 A | 12/1997 |
| JP | 10-095972 A | 4/1998 |
| JP | 11-162649 A | 6/1999 |
| JP | 11-251067 A | 9/1999 |
| JP | 2000-196140 A | 7/2000 |
| JP | 2000-309566 A | 11/2000 |
| JP | 2000-327639 A | 11/2000 |
| JP | 2002-241352 A | 8/2002 |
| JP | 2003-031365 A | 1/2003 |
| JP | 2003-055320 A | 2/2003 |
| JP | 2003-075955 A | 3/2003 |
| JP | 2003-089682 A | 3/2003 |
| JP | 2003-124472 A | 4/2003 |
| JP | 2003-238501 A | 8/2003 |
| JP | 2005-290000 A | 10/2005 |
| JP | 2006-525395 | 11/2006 |
| JP | 2007-015933 A | 1/2007 |
| JP | 2007-045816 A | 2/2007 |
| JP | 2007-045826 A | 2/2007 |
| JP | 2007-110093 A | 4/2007 |
| JP | 2007-119457 A | 5/2007 |
| JP | 2007-520470 | 7/2007 |
| JP | 2007-191465 | 8/2007 |
| JP | 2007-208217 A | 8/2007 |
| JP | 2007-258526 A | 10/2007 |
| JP | 2007-284434 A | 11/2007 |
| JP | 2007-318101 A | 12/2007 |
| JP | 2008-266309 A | 11/2008 |
| JP | 2009-120582 A | 6/2009 |
| JP | 2009-130142 A | 6/2009 |
| JP | 2009-298767 A | 12/2009 |
| JP | 2008/062636 | 3/2010 |
| JP | 2011-503055 | 1/2011 |
| JP | 2011-503055 A | 1/2011 |
| JP | 2011-503056 | 1/2011 |
| JP | 2012-097091 A | 5/2012 |

(56) References Cited

FOREIGN PATENT DOCUMENTS

| | | |
|---|---|---|
| JP | 5268187 | 8/2013 |
| JP | 5268202 | 8/2013 |
| JP | 5268208 | 8/2013 |
| JP | 2015-153864 A | 8/2015 |
| JP | 5785290 | 9/2015 |
| JP | 2018-206889 A | 12/2018 |
| JP | 6783409 | 11/2020 |
| KR | 2005-0097670 A | 10/2005 |
| KR | 2005-0118098 A | 12/2005 |
| KR | 2006-0049942 A | 5/2006 |
| KR | 2007-0095246 A | 9/2007 |
| KR | 2009-0041999 A | 4/2009 |
| KR | 2009-0051140 A | 5/2009 |
| KR | 2009-0051141 A | 5/2009 |
| KR | 2009-0112137 A | 10/2009 |
| KR | 2010-0070350 A | 6/2010 |
| WO | WO-2005/090512 | 9/2005 |
| WO | WO-2006/046441 | 5/2006 |
| WO | WO-2006/120859 | 11/2006 |
| WO | WO-2006/122630 | 11/2006 |
| WO | WO-2007/007885 | 1/2007 |
| WO | WO-2007/043354 | 4/2007 |
| WO | WO-2007/069607 | 6/2007 |
| WO | WO-2007/072838 | 6/2007 |
| WO | WO-2007/108403 | 9/2007 |
| WO | WO-2007/148660 | 12/2007 |
| WO | WO-2008/062636 | 5/2008 |
| WO | WO-2008/069756 | 6/2008 |
| WO | WO-2009/035296 | 3/2009 |
| WO | WO-2009/041635 | 4/2009 |
| WO | WO-2009/061145 | 5/2009 |
| WO | WO-2009/061156 | 5/2009 |
| WO | WO-2009/072587 | 6/2009 |
| WO | WO-2014/163228 | 10/2014 |
| WO | WO-2018/101492 | 6/2018 |

OTHER PUBLICATIONS

Promarak.V et al., "Synthesis and Properties of Stable Amorphous Hole-Transporting Molecules for Electroluminescent Devices", Tetrahedron Letters, 2006, vol. 47, No. 50, pp. 8949-8952.
International Search Report (Application No. PCT/JP2008/072104) Dated Jan. 13, 2009.
Written Opinion (Application No. PCT/JP2008/072104) Dated Jan. 13, 2009.
Goldsmith.C et al., "C—H Bond Activation By a Ferric Methoxide Complex: Modeling the Rate-Determining Step in the Mechanism of Lipoxygenase", J. Am. Chem. Soc. (Journal of the American Chemical Society), 2002, vol. 124, No. 1, pp. 83-96.
Onishi.T et al., "A Method of Measuring an Energy Level", High Molecular El Materials—Development of Light-Emitting High Molecular Compounds, Dec. 25, 2004, pp. 64-67, Kyoritsu Shuppan.
International Search Report (Application No. PCT/JP2009/058787) Dated Aug. 11, 2009.
Written Opinion (Application No. PCT/JP2009/058787) Dated Aug. 11, 2009.
Changqi.M et al., "Progress in Hole-Transport Materials for Use in Organic Light-Emitting Diodes", Progress in Chemistry, Nov. 1, 2003, vol. 15, No. 6, pp. 495-504.
Notice of Division of Application (Application No. 200880126449.5) Dated May 3, 2012.
Shen.J et al., "Ambipolar Conductive 2,7-Carbazole Derivatives for Electroluminescent Devices", Adv. Funct. Mater. (Advanced Functional Materials), 2007, vol. 17, No. 6, pp. 983-995.
European Search Report (Application No. 08858330.7) Dated Sep. 28, 2012.
Korean Office Action (Application No. 2013-7012544) Dated Oct. 21, 2013.
Korean Office Action (Application No. 2010-7014761) Dated Apr. 27, 2015.
European Official Communication (Application No. 14001338.4) Dated Jan. 30, 2017.
Wellmann.P et al., "High-efficiency p-i-n organic light-emitting diodes with long lifetime", J. Soc. Inf. Display (Journal of the Society for Information Display), May 1, 2005, vol. 13, No. 5, pp. 393-397.
Korean Office Action (Application No. 2017-7003975) Dated Feb. 9, 2018.
Notification (Application No. 2018-213648) Dated Apr. 9, 2019.
Information Offer Form (Application No. 2018-213648) Dated Apr. 1, 2019.
Patent Court Decision 2011Heo11491 rendered on May 10, 2012 [Invalidation of Registration (Patent)].
Petition for Cancellation of Patent (Patent No. Korean Patent No. 10-2022839-00-00) Dated Apr. 22, 2020.
Gao.C et al., "Comparative studies on the inorganic and organic p-type dopants in organic light-emitting diodes with enhanced hole injection", Appl. Phys. Lett. (Applied Physics Letters), Apr. 15, 2013, vol. 102, No. 15, pp. 153301-1-153301-5.
Wong.K et al., "Synthesis, Structures, and Photoinduced Electron Transfer Reaction in the 9,9'-Spirobifluorene-Bridged Bipolar Systems", J. Org. Chem. (Journal of Organic Chemistry), Dec. 21, 2005, vol. 71, No. 2, pp. 456-465, American Chemical Society.

\* cited by examiner

CARBAZOLE DERIVATIVE, AND LIGHT-EMITTING ELEMENT, LIGHT-EMITTING DEVICE, AND ELECTRONIC DEVICE USING CARBAZOLE DERIVATIVE

CROSS-REFERENCE TO RELATED APPLICATIONS

This application is a continuation of U.S. application Ser. No. 16/741,830, filed Jan. 14, 2020, now pending, which is a continuation of U.S. application Ser. No. 16/139,412, filed Sep. 24, 2018, now U.S. Pat. No. 10,556,864, which is a continuation of U.S. application Ser. No. 15/713,129, filed Sep. 22, 2017, now abandoned, which is a continuation of U.S. application Ser. No. 12/326,311, filed Dec. 2, 2008, now abandoned, which claims the benefit of foreign priority applications filed in Japan as Serial No. 2007-312509 on Dec. 3, 2007, and Serial No. 2008-129917 on May 16, 2008, all of which are incorporated by reference.

TECHNICAL FIELD

The present invention relates to a carbazole derivative, a light-emitting element, a light-emitting device, and an electronic device using a carbazole derivative.

BACKGROUND ART

In recent years, light-emitting elements using electroluminescence have been actively researched and developed. As a basic structure of these light-emitting elements, a layer containing a light-emitting substance is interposed between a pair of electrodes. By applying voltage to this element, light emission can be obtained from the light-emitting substance.

Since such a light-emitting element is a self-luminous type, it has advantages over a liquid crystal display element, such as high visibility of the pixels and no need of backlight and is considered suitable for a flat panel display element. In addition, such a light-emitting element can be manufactured to be thin and light-weight, which is also a great advantage. Further, extremely high response speed is also a feature thereof.

Furthermore, since such a light-emitting element can be formed into a film form, planar light emission can be easily obtained by forming a large-area element. It is difficult to obtain this characteristic by using a point light source typified by an incandescent lamp or an LED or by using a line light source typified by a fluorescent lamp. Therefore, the light-emitting element described above also has a high utility value as a planar light source which is applicable to lighting or the like.

Such light-emitting elements using electroluminescence are broadly classified according to whether a light-emitting substance is an organic compound or an inorganic compound. When an organic compound is used for a light-emitting substance, electrons and holes are injected into a layer containing a light-emitting organic compound from a pair of electrodes by applying voltage to a light-emitting element, and then a current flows therethrough. Then, by recombination of these carriers (electrons and holes), the light-emitting organic compound forms an excited state, and emits light when the excited state returns to a ground state.

With such a mechanism, such a light-emitting element is referred to as a current-excitation light-emitting element. Note that an excited state of an organic compound can be a singlet excited state or a triplet excited state. Light emission from the singlet excited state is referred to as fluorescence, and light emission from the triplet excited state is referred to as phosphorescence.

In improving element characteristics of such a light-emitting element, there are a lot of problems which depend on a substance, and in order to solve the problems, improvement of an element structure, development of a substance, and the like have been carried out (e.g., Non-Patent Document 1: Meng-Huan Ho, Yao-Shan Wu and Chin H. Chen, 2005 *SID International Symposium Digest of Technical Papers*, Vol. XXXVI. pp. 802-805).

In the light-emitting element described in Non-Patent Document 1, 4,4'-bis[N-(1-naphthyl)-N-phenylamino]biphenyl (abbreviation: NPB) is used as a layer in contact with a light-emitting layer. However, NPB has low singlet excitation energy, and there is a possibility that the energy might be transferred from the light-emitting material in the excited state. Since the energy level of an excited state is particularly high in the case of a light-emitting material which emits blue light having a short wavelength, there is a higher possibility that the energy is transferred to NPB. There has been a problem that luminous efficiency of the light-emitting element is lowered due to transfer of the energy to NPB.

DISCLOSURE OF THE INVENTION

Thus, it is an object of the present invention to provide a light-emitting element having high luminous efficiency by providing a novel carbazole derivative. Further, it is another object of the present invention to provide a light-emitting device and an electronic device which consumes low power and is driven at low voltage.

One feature of the present invention is a carbazole derivative represented by the following general formula (1).

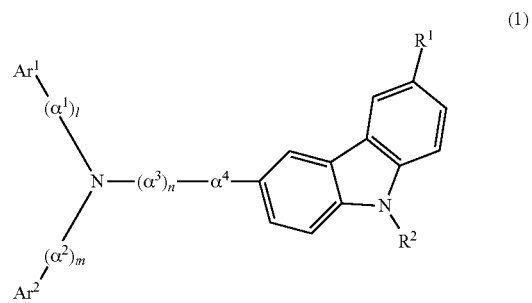

In the formula, $\alpha^1$, $\alpha^2$, $\alpha^3$, and $\alpha^4$ each represent an arylene group having less than or equal to 13 carbon atoms, which forms a ring; $Ar^1$ and $Ar^2$ each represent an aryl group having less than or equal to 13 carbon atoms, which forms a ring; $R^1$ represents any of a hydrogen atom, an alkyl group having 1 to 6 carbon atoms, a substituted or unsubstituted phenyl group, and a substituted or unsubstituted biphenyl group; and $R^2$ represents any of an alkyl group having 1 to 6 carbon atoms, a substituted or unsubstituted phenyl group, and a substituted or unsubstituted biphenyl group. In addition, l, m, and n are each independent, which is 0 or 1.

In addition, in the above structure, $\alpha^1$ to $\alpha^4$ in the general formula (1) are represented by any of the following general formulas (2-1) to (2-12).

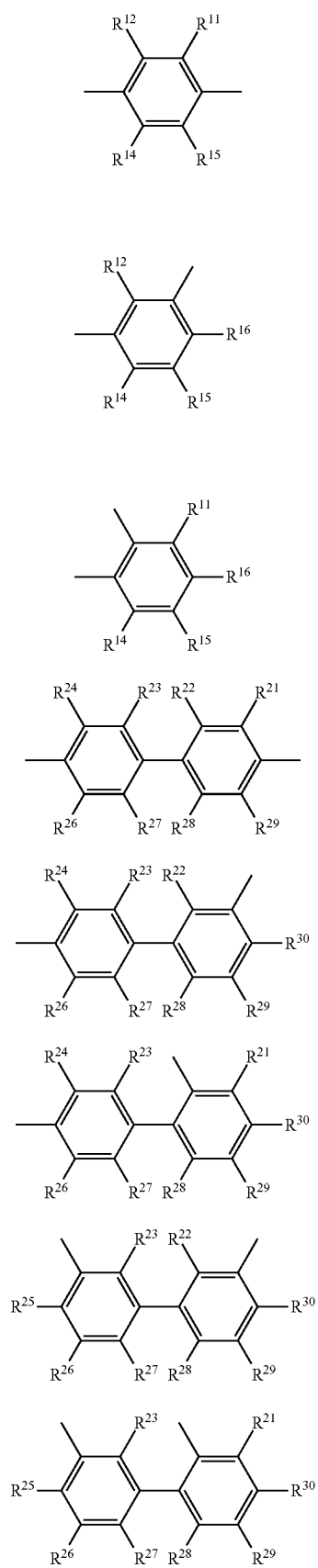

(2-1)
(2-2)
(2-3)
(2-4)
(2-5)
(2-6)
(2-7)
(2-8)

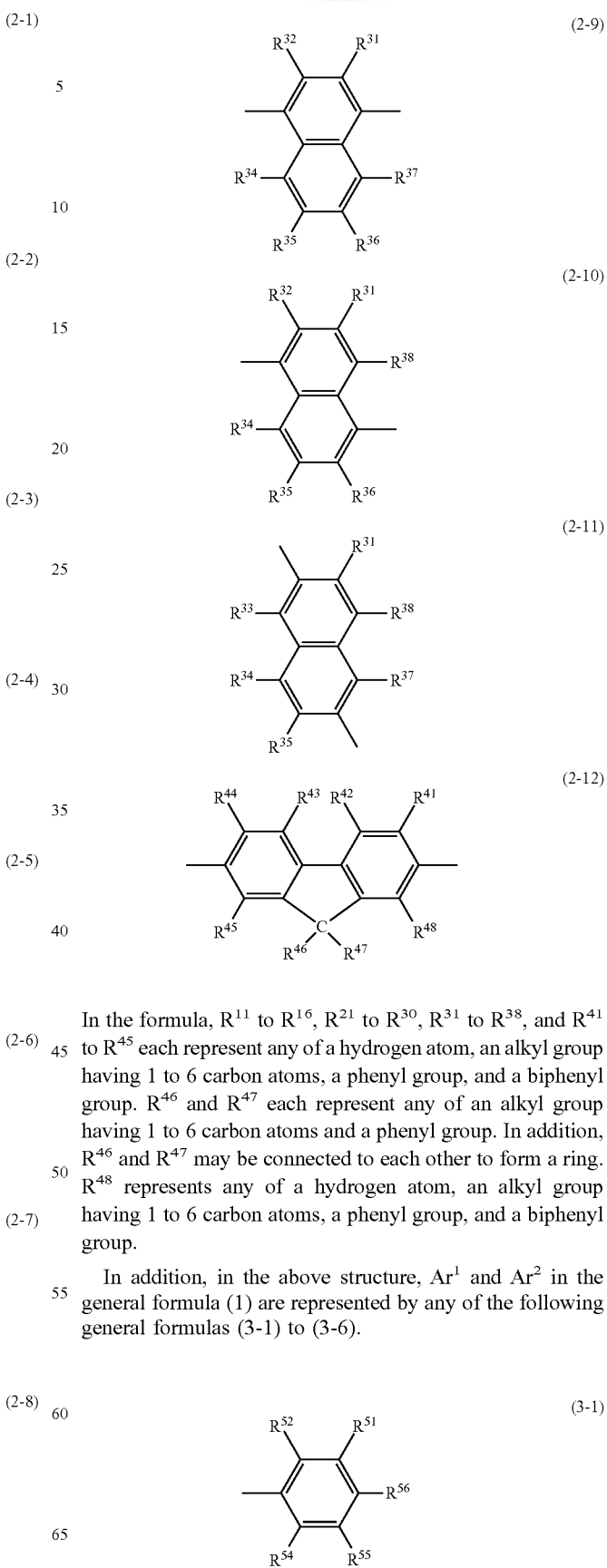

(2-9)
(2-10)
(2-11)
(2-12)

In the formula, $R^{11}$ to $R^{16}$, $R^{21}$ to $R^{30}$, $R^{31}$ to $R^{38}$, and $R^{41}$ to $R^{45}$ each represent any of a hydrogen atom, an alkyl group having 1 to 6 carbon atoms, a phenyl group, and a biphenyl group. $R^{46}$ and $R^{47}$ each represent any of an alkyl group having 1 to 6 carbon atoms and a phenyl group. In addition, $R^{46}$ and $R^{47}$ may be connected to each other to form a ring. $R^{48}$ represents any of a hydrogen atom, an alkyl group having 1 to 6 carbon atoms, a phenyl group, and a biphenyl group.

In addition, in the above structure, $Ar^1$ and $Ar^2$ in the general formula (1) are represented by any of the following general formulas (3-1) to (3-6).

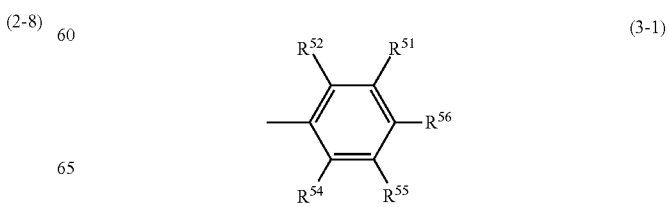

(3-1)

-continued

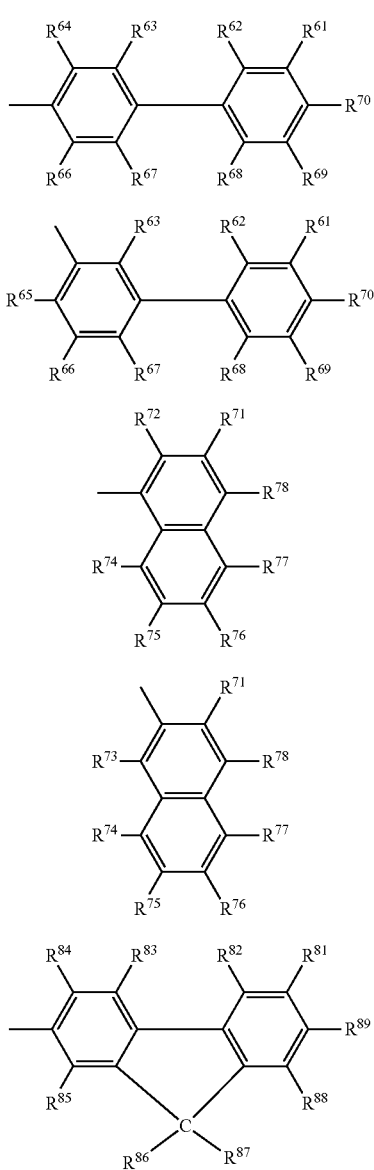

(3-2)

(3-3)

(3-4)

(3-5)

(3-6)

In the formula, $R^{51}$ to $R^{56}$, $R^{61}$ to $R^{70}$, $R^{71}$ to $R^{78}$, and $R^{81}$ to $R^{85}$ each represent any of a hydrogen atom, an alkyl group having 1 to 6 carbon atoms, a phenyl group, and a biphenyl group. $R^{86}$ and $R^{87}$ each represent any of an alkyl group having 1 to 6 carbon atoms and a phenyl group. In addition, $R^{86}$ and $R^{87}$ may be connected to each other to form a ring. $R^{88}$ and $R^{89}$ each represent any of a hydrogen atom, an alkyl group having 1 to 6 carbon atoms, a phenyl group, and a biphenyl group.

Further, in the above structure, $R^1$ in the general formula (1) is represented by any of the following general formulas (4-1) to (4-9), and $R^2$ in the general formula (1) is represented by any of the following general formulas (4-2) to (4-9).

H— (4-1)

CH₃— (4-2)

-continued

C₂H₅— (4-3)

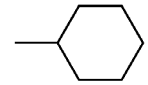 (4-4)

—C₆H₁₃ (4-5)

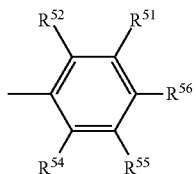 (4-6)

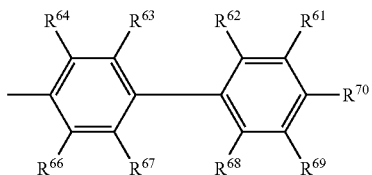 (4-7)

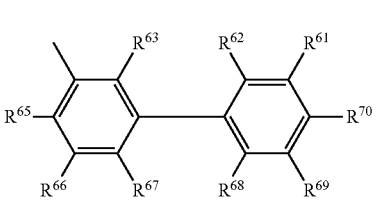 (4-8)

(4-9)

In the formula, $R^{51}$ to $R^{70}$ each represent any of a hydrogen atom, an alkyl group having 1 to 6 carbon atoms, a phenyl group, and a biphenyl group.

In addition, one feature of the present invention is represented by any of the following structural formulas (5) to (8).

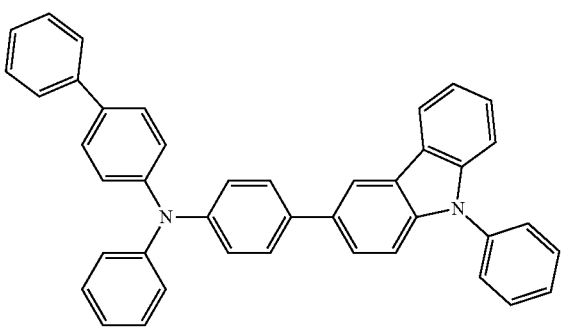 (5)

-continued (6)

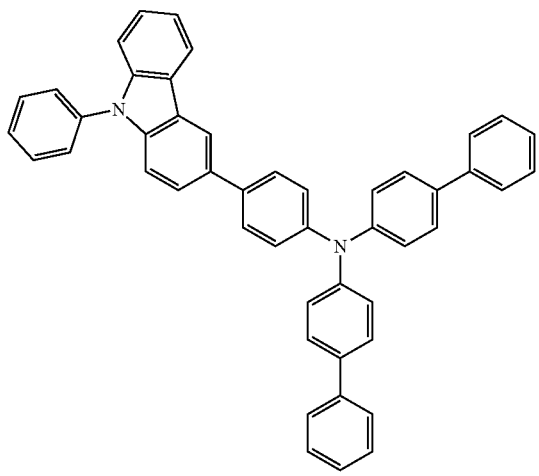

(7)

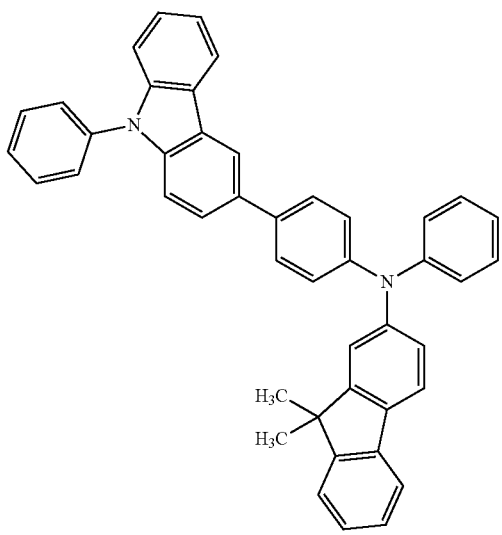

(8)

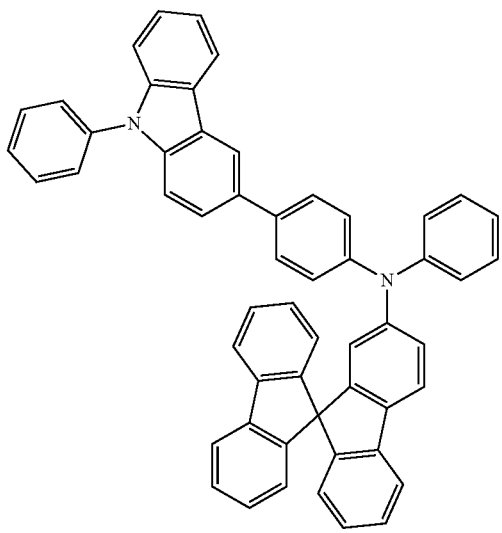

In addition, as another feature of the present invention, a light-emitting element includes an EL layer between a pair of electrodes, the EL layer includes at least a light-emitting layer and a hole-transporting layer, and at least one of the light-emitting layer and the hole-transporting layer contains any of the carbazole derivatives described above.

Further, as another feature of the present invention, a light-emitting element includes an EL layer between an anode and a cathode, the EL layer includes at least a light-emitting layer, a hole-transporting layer, and a hole-injecting layer, the hole-injecting layer is formed in contact with the anode, and at least one of the light-emitting layer, the hole-transporting layer, and the hole-injecting layer contains any of the carbazole derivatives described above.

In addition, in the above structure, a structure may be employed in which the hole-injecting layer contains any of the carbazole derivatives described above and an inorganic compound which exhibits an electron-accepting property with respect to the carbazole derivative. Note that as the inorganic compound, an oxide of a transition metal can be used. Further, as the inorganic compound, one or more kinds of titanium oxide, vanadium oxide, molybdenum oxide, tungsten oxide, rhenium oxide, ruthenium oxide, chromium oxide, zirconium oxide, hafnium oxide, tantalum oxide, and silver oxide can be used.

Further, as another feature of the present invention, a light-emitting device is formed using any of the light-emitting elements described above, and an electronic device is formed using the light-emitting device.

Further, the present invention also includes a light-emitting device having the light-emitting element described above and an electronic devuce having the light-emitting device. A light-emitting device in this specification refers to an image display device, a light-emitting device, or a light source (including a lighting device). In addition, light-emitting devices include all of the following modules: modules in which a connector, for example, a flexible printed circuit (FPC), a tape automated bonding (TAB) tape, or a tape carrier package (TCP) is attached to a light-emitting device; modules provided with a printed wiring board at the end of a TAB tape or a TCP; and modules where an integrated circuit (IC) is directly mounted on a light-emitting element by a chip-on-glass (COG) method.

Since the carbazole derivative of the present invention exhibits a high hole-transporting property, it can be mainly used for a hole-transporting layer which is included in an EL layer of a light-emitting element. In addition, the carbazole derivative of the present invention is used for the hole-transporting layer to form a light-emitting element, whereby a light-emitting element having high luminous efficiency can be formed.

Further, a light-emitting device and an electronic device which consumes low power and is driven at low voltage can be obtained by using this light-emitting element.

BEST MODE FOR CARRYING OUT THE INVENTION

Figure 1A:
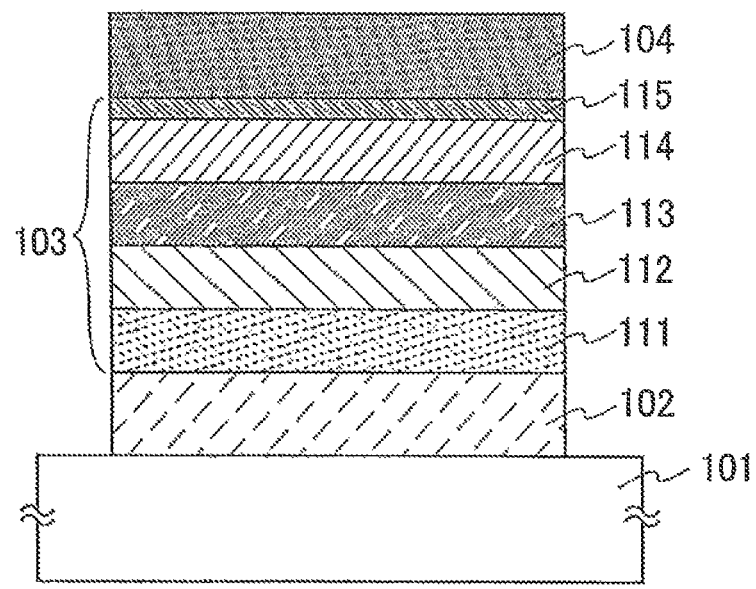
FIGS. 1A and 1B are cross-sectional views each showing a stacked-layer structure of a light-emitting element in Embodiment Mode 2.

The embodiment modes and embodiments according to the present invention will hereinafter be described in detail with reference to the drawings. However, the present invention is not limited to description to be given below, and it is to be easily understood that modes and details thereof can be variously modified without departing from the purpose and the scope of the present invention. Thus, the present invention is not interpreted while limiting to the following description of the embodiment modes and embodiments.

Embodiment Mode 1

In Embodiment Mode 1, a carbazole derivative of the present invention will be described.

The carbazole derivative of the present invention is represented by a general formula (1).

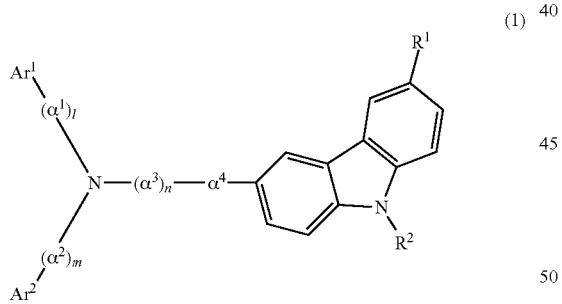
(1)

In the formula, $α^1$, $α^2$, $α^3$, and $α^4$ each represent an arylene group having less than or equal to 13 carbon atoms, which forms a ring; $Ar^1$ and $Ar^2$ each represent an aryl group having less than or equal to 13 carbon atoms, which forms a ring; $R^1$ represents any of a hydrogen atom, an alkyl group having 1 to 6 carbon atoms, a substituted or unsubstituted phenyl group, and a substituted or unsubstituted biphenyl group; and $R^2$ represents any of alkyl group having 1 to 6 carbon atoms, a substituted or unsubstituted phenyl group, and a substituted or unsubstituted biphenyl group. In addition, 1, m, and n are each independent, which is 0 or 1.

In the general formula (1), $α^1$ to $α^4$ each represent an arylene group having less than or equal to 13 carbon atoms, which forms a ring. Specifically, substituents represented by structural formulas (2-1) to (2-12) can be given.

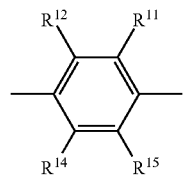
(2-1)

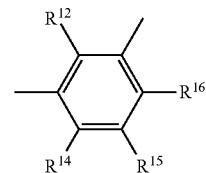
(2-2)

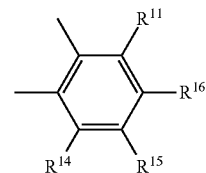
(2-3)

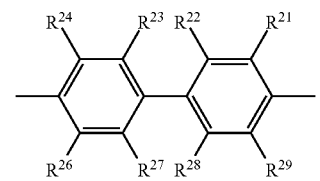
(2-4)

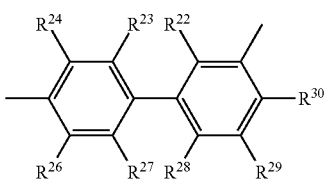
(2-5)

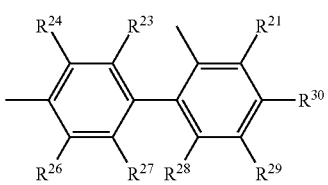
(2-6)

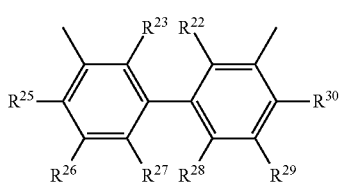
(2-7)

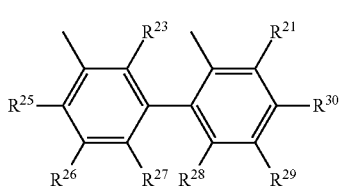
(2-8)

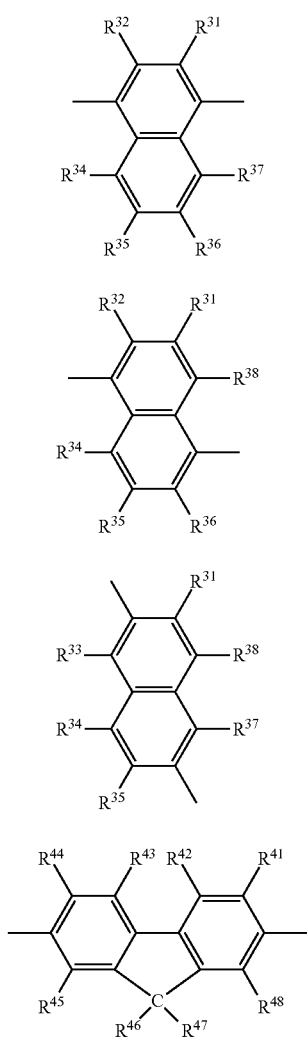

(2-9)

(2-10)

(2-11)

(2-12)

In the formula, $R^{11}$ to $R^{16}$, $R^{21}$ to $R^{30}$, $R^{31}$ to $R^{38}$, and $R^{41}$ to $R^{45}$ each represent any of a hydrogen atom, an alkyl group having 1 to 6 carbon atoms, a phenyl group, and a biphenyl group. $R^{46}$ and $R^{47}$ each represent any of an alkyl group having 1 to 6 carbon atoms and a phenyl group. In addition, $R^{46}$ and $R^{47}$ may be connected to each other to form a ring. $R^{48}$ represents any of a hydrogen atom, an alkyl group having 1 to 6 carbon atoms, a phenyl group, and a biphenyl group.

In the general formula (1), $Ar^1$ and $Ar^2$ each represent an aryl group having less than or equal to 13 carbon atoms, which forms a ring. Specifically, substituents represented by structural formulas (3-1) to (3-6) can be given.

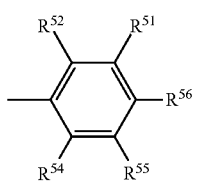

(3-1)

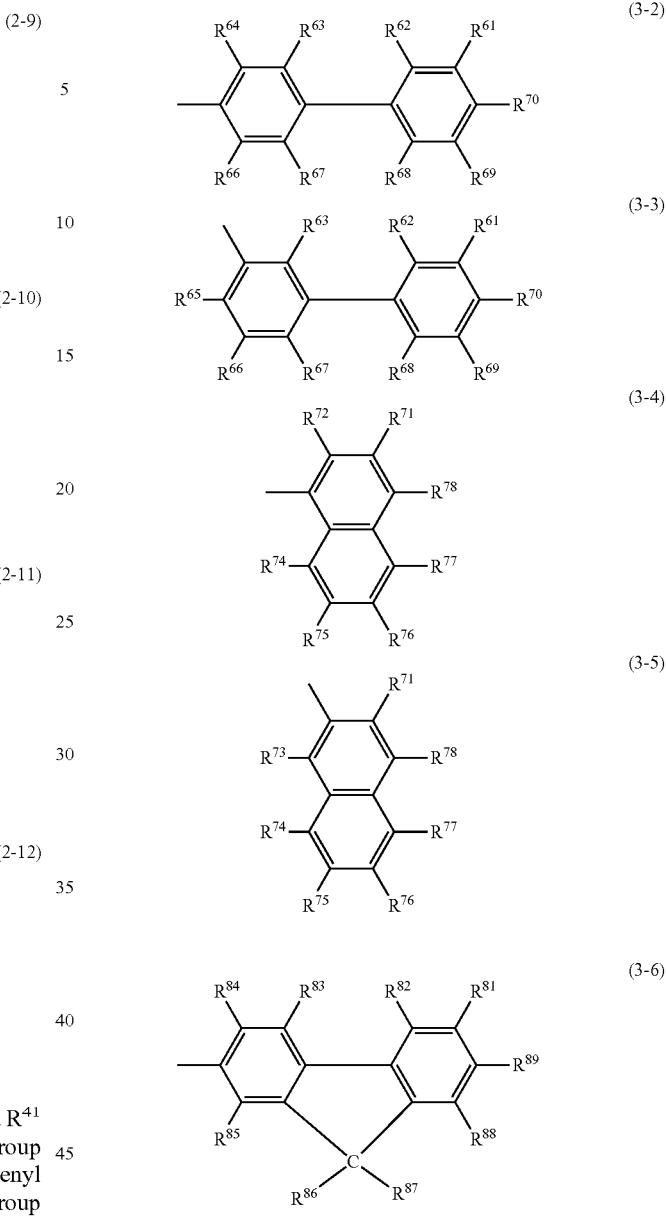

(3-2)

(3-3)

(3-4)

(3-5)

(3-6)

In the formula, $R^{51}$ to $R^{56}$, $R^{61}$ to $R^{70}$, $R^{71}$ to $R^{78}$, and $R^{81}$ to $R^{85}$ each represent any of a hydrogen atom, an alkyl group having 1 to 6 carbon atoms, a phenyl group, and a biphenyl group. $R^{86}$ and $R^{87}$ each represent any of an alkyl group having 1 to 6 carbon atoms and a phenyl group. In addition, $R^{86}$ and $R^{87}$ may be connected to each other to form a ring. $R^{88}$ and $R^{89}$ each represent any of a hydrogen atom, an alkyl group having 1 to 6 carbon atoms, a phenyl group, and a biphenyl group.

In the general formula (1), $R^1$ represents any of a hydrogen atom, an alkyl group having 1 to 6 carbon atoms, a substituted or unsubstituted phenyl group, and a substituted or unsubstituted biphenyl group; and $R^2$ represents any of an alkyl group having 1 to 6 carbon atoms, a substituted or unsubstituted phenyl group, and a substituted or unsubstituted biphenyl group. Specifically, substituents represented by structural formulas (4-1) to (4-9) can be given for $R^1$, and the substituents represented by the structural formulas (4-2) to (4-9) can be given for $R^2$.

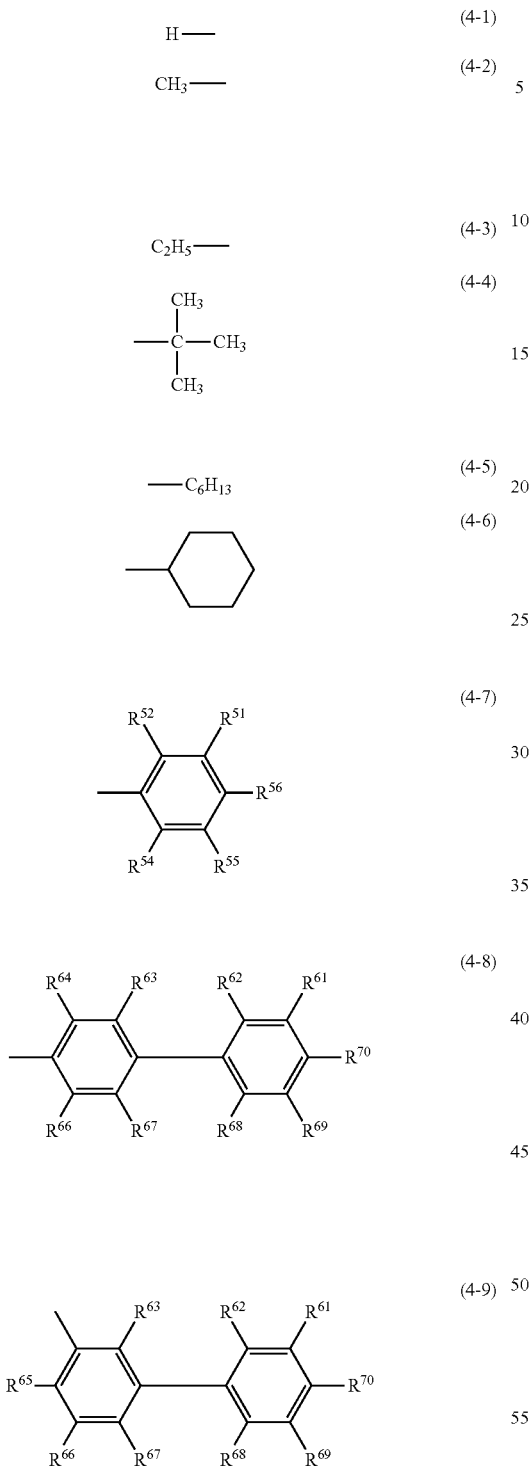
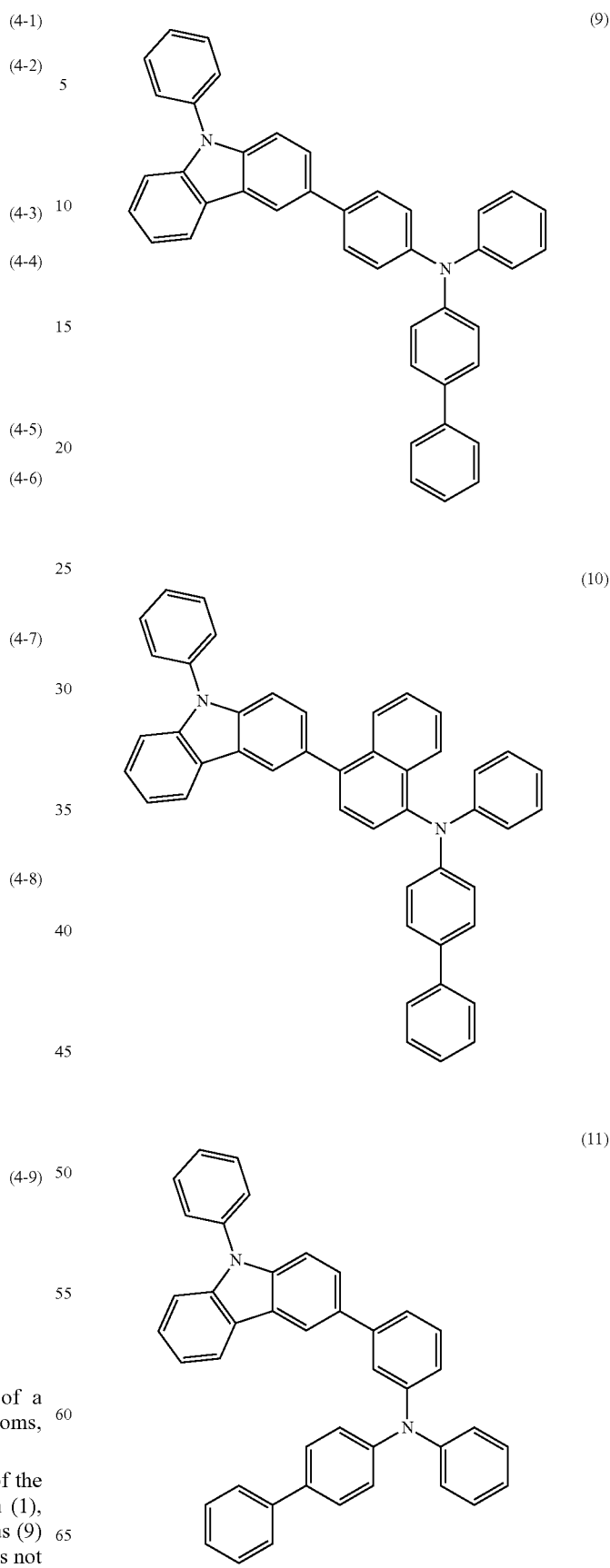

In the formula, $R^{51}$ to $R^{70}$ each represent any of a hydrogen atom, an alkyl group having 1 to 6 carbon atoms, a phenyl group, and a biphenyl group.

As a specific example of the carbazole derivatives of the present invention represented by the general formula (1), carbazole derivatives represented by structural formulas (9) to (425) can be given. However, the present invention is not limited thereto.

(12)
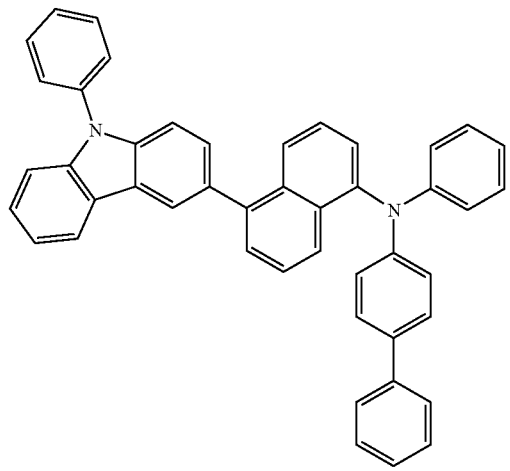
(13)
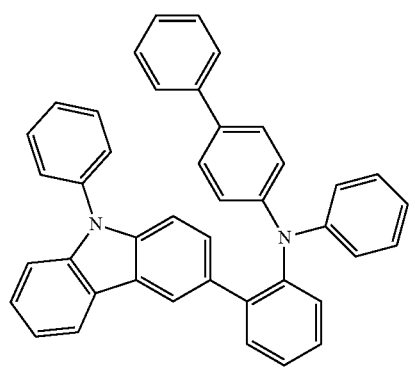
(14)
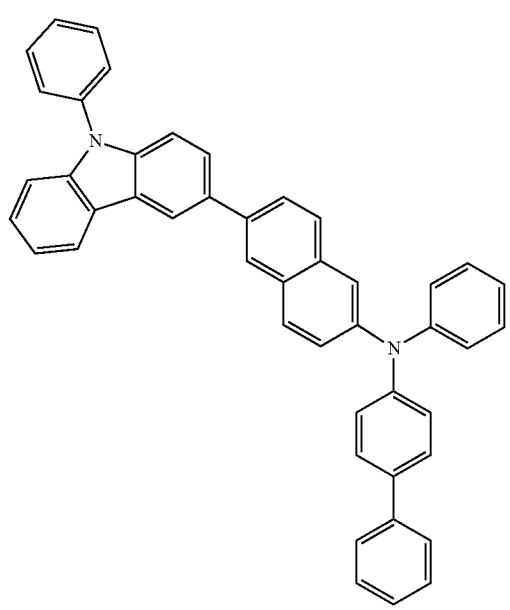
(15)
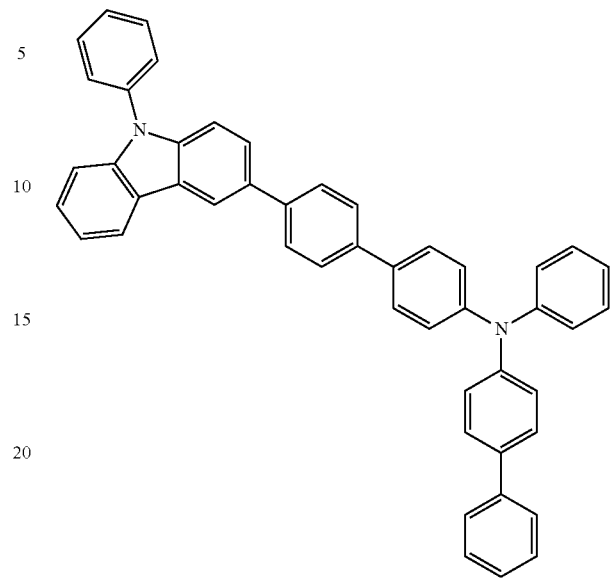
(16)
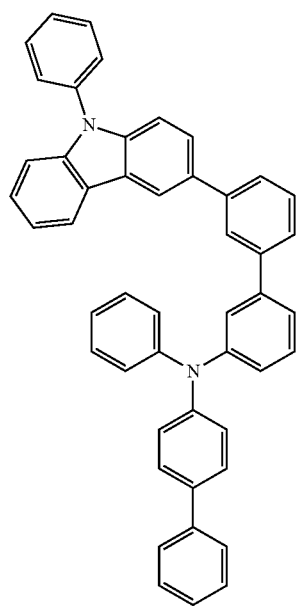

(17)
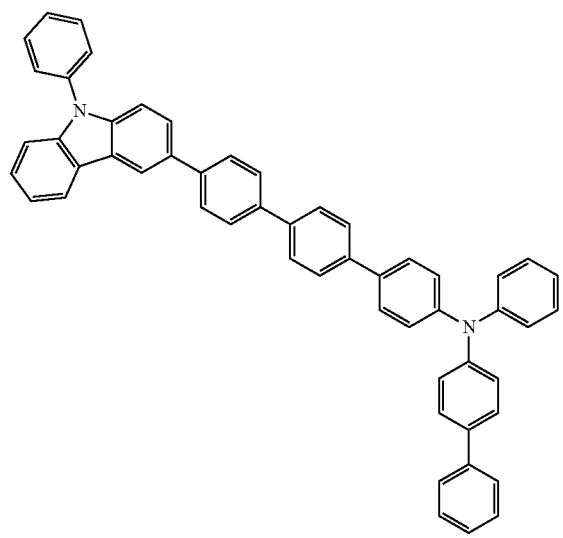
(18)
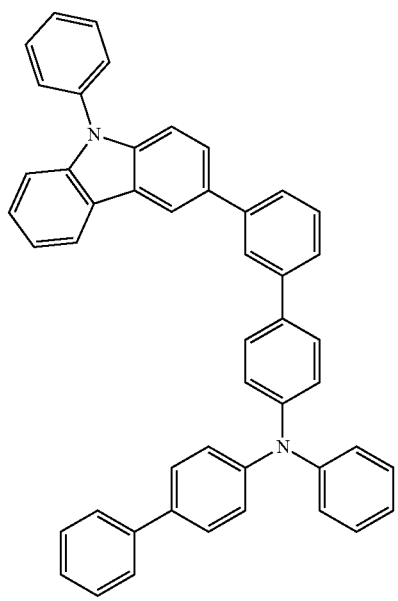
(19)
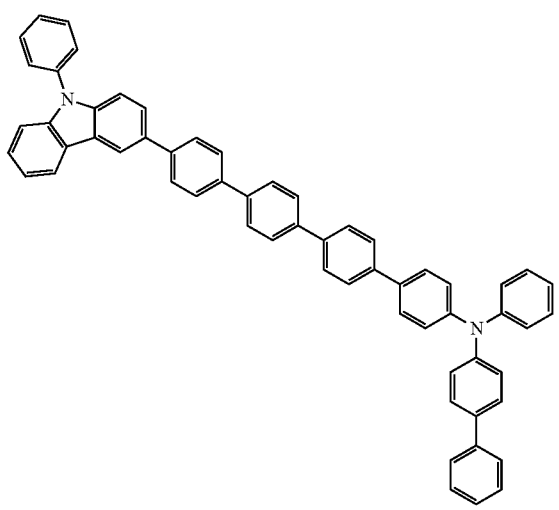
(20)
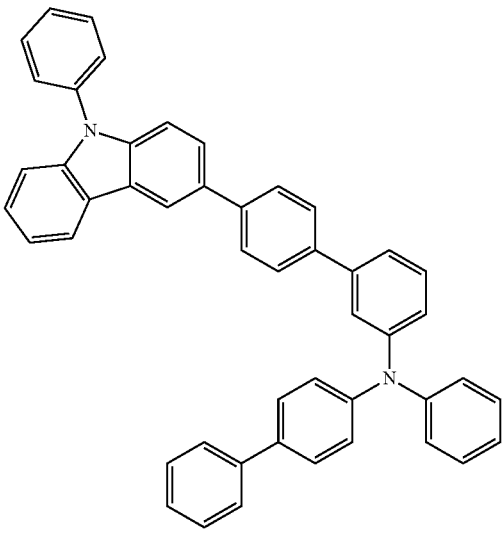
(21)
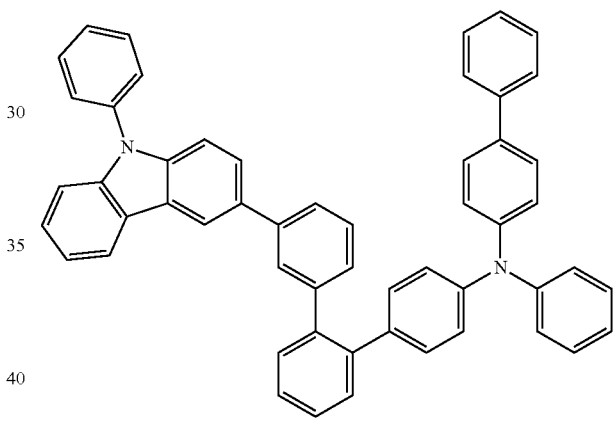
(22)
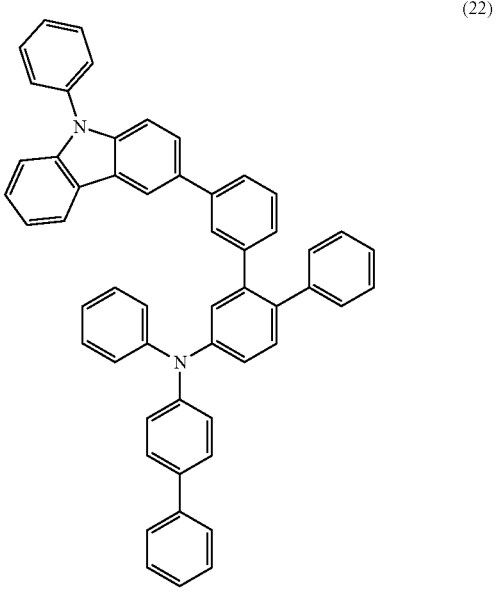

(23)
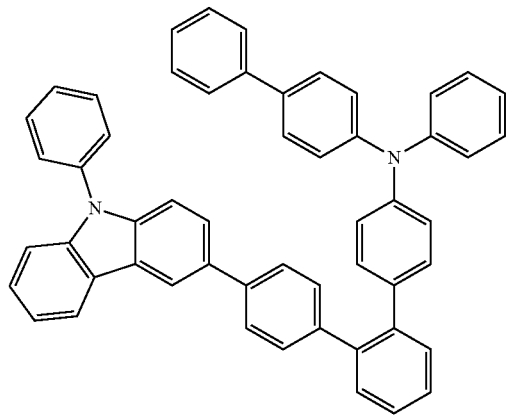
(24)
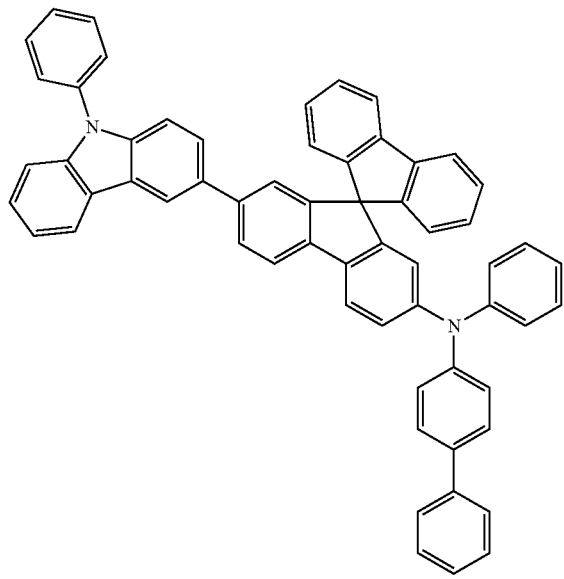
(25)
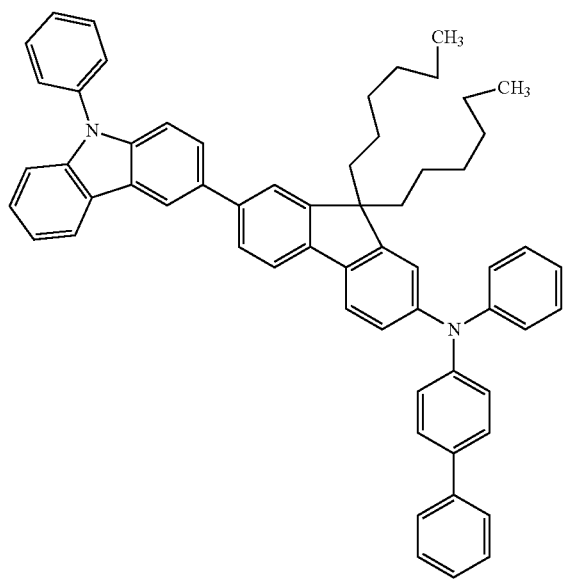
(26)
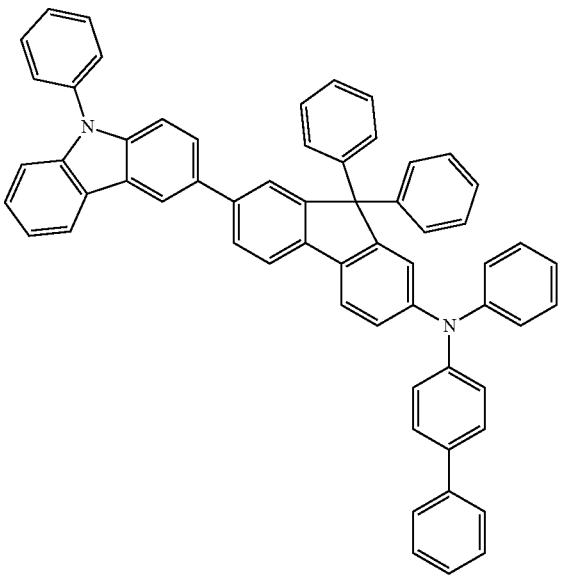
(27)
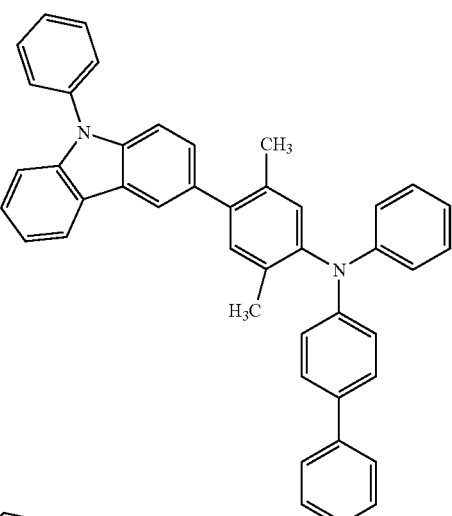
(28)
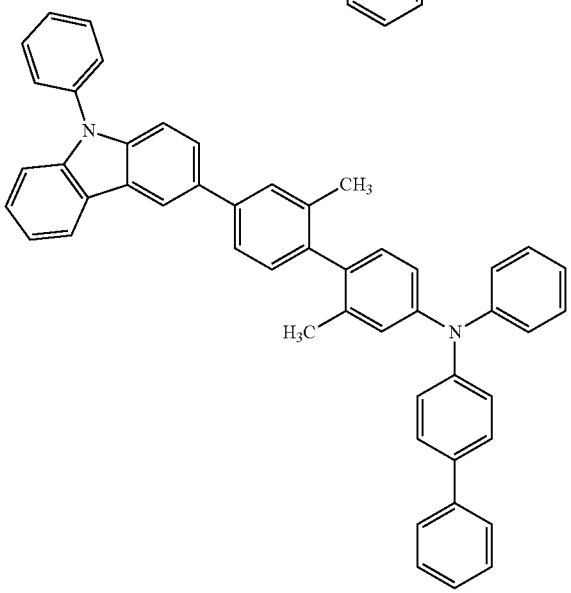

(29)
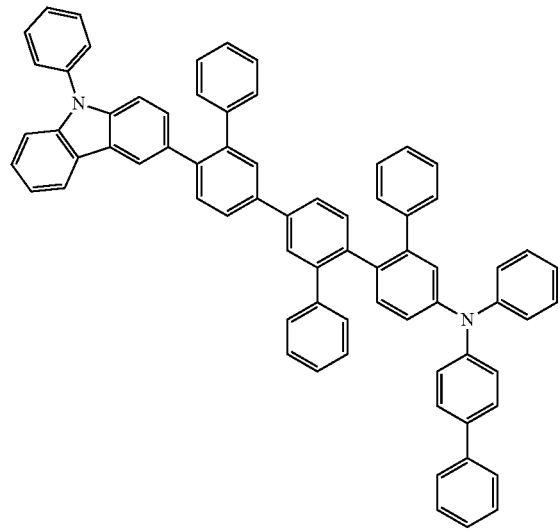
(30)
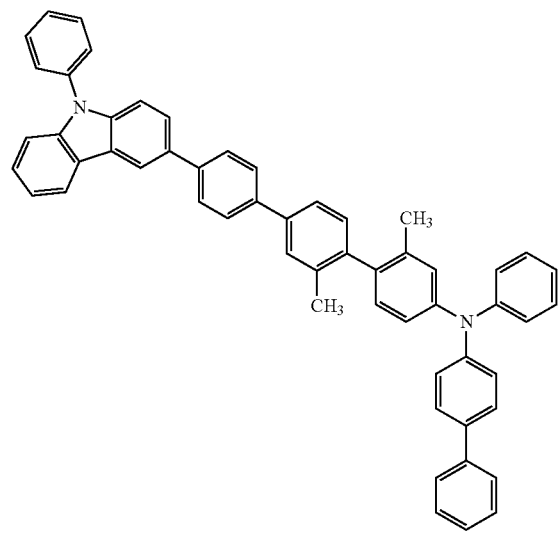
(31)
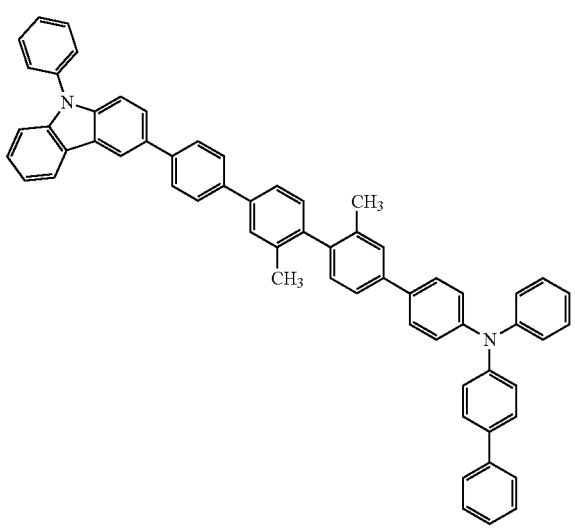
(32)
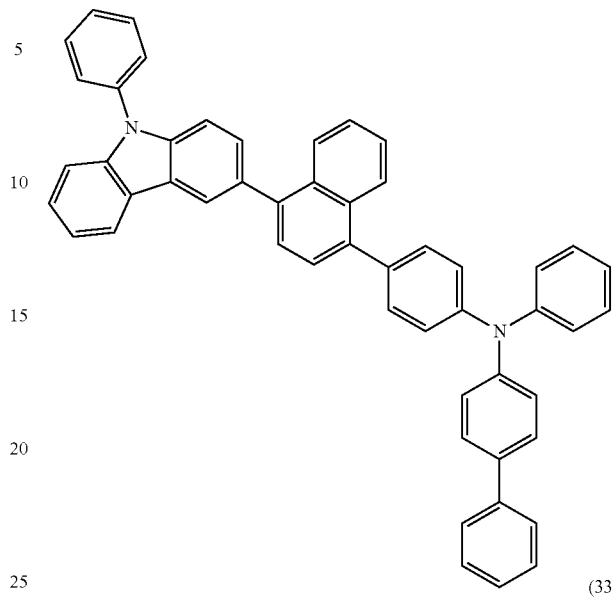
(33)
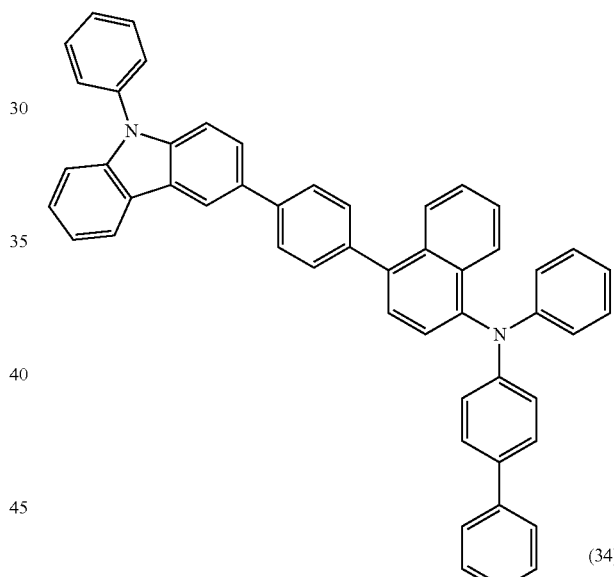
(34)
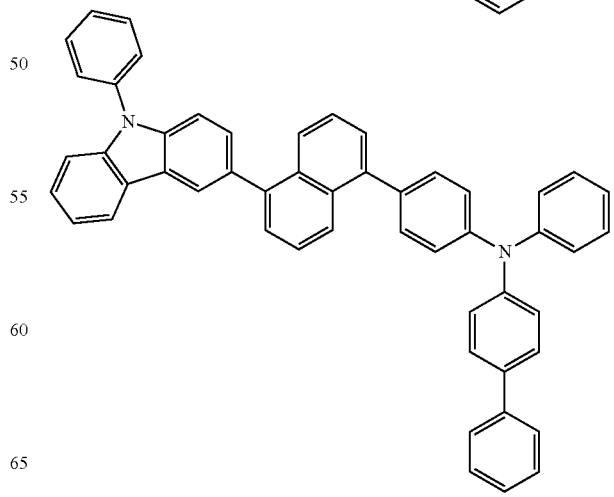

(35)
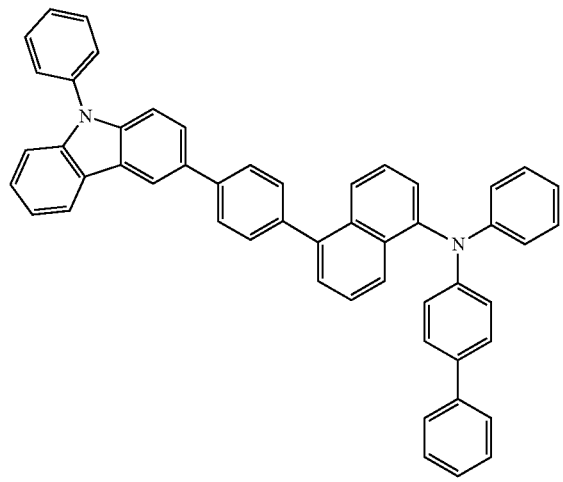
(36)
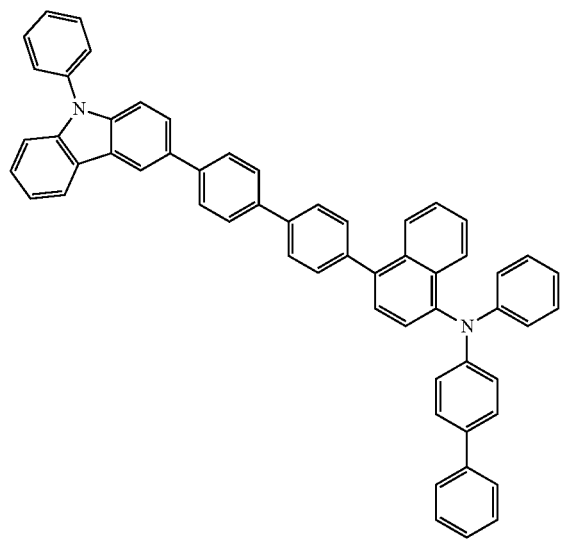
(37)
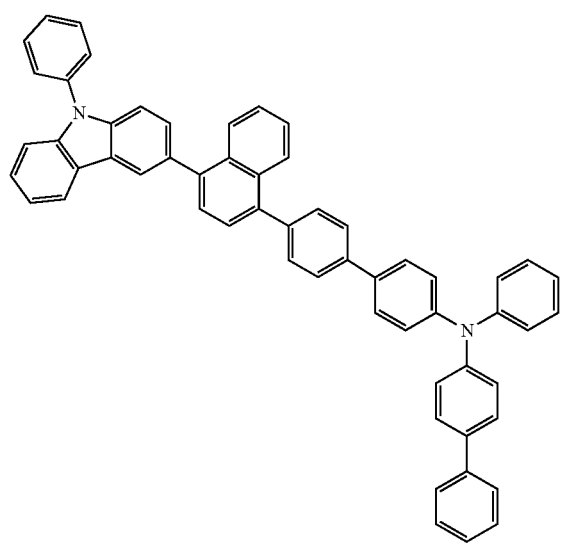
(38)
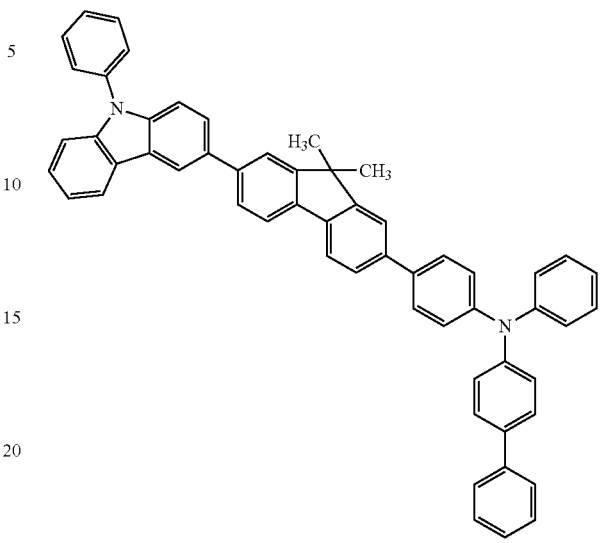
(39)
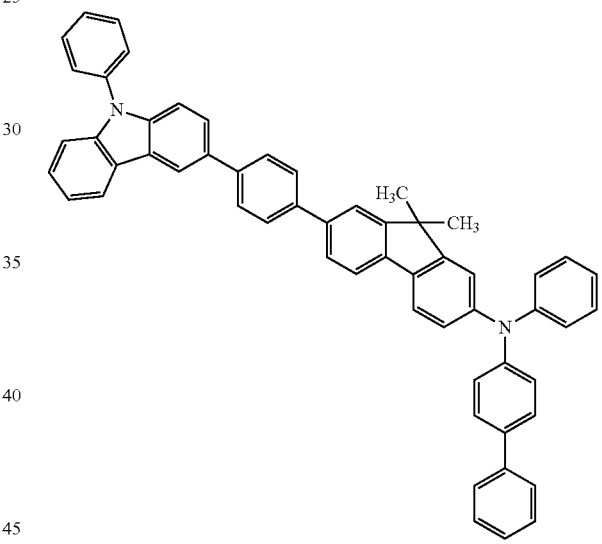
(40)
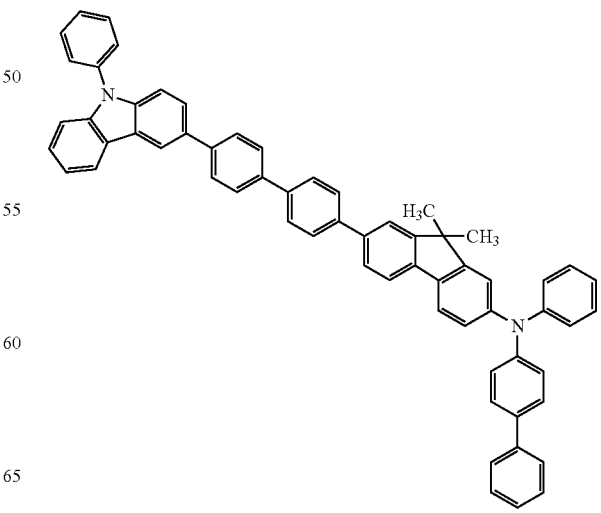

(41)
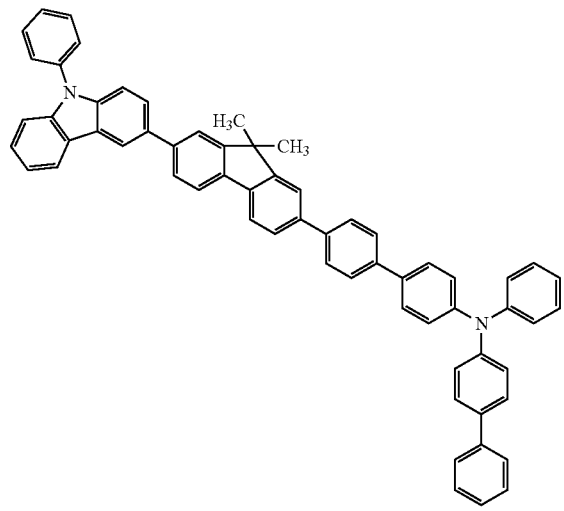
(42)
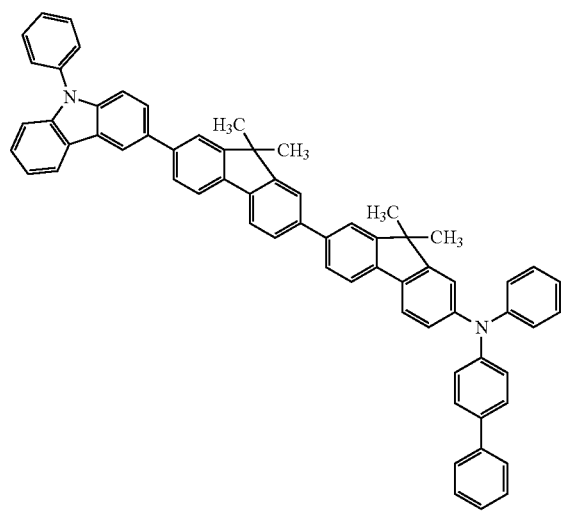
(43)
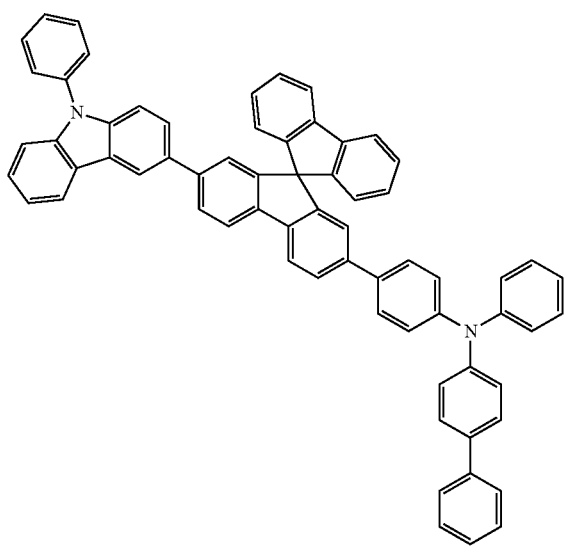
(44)
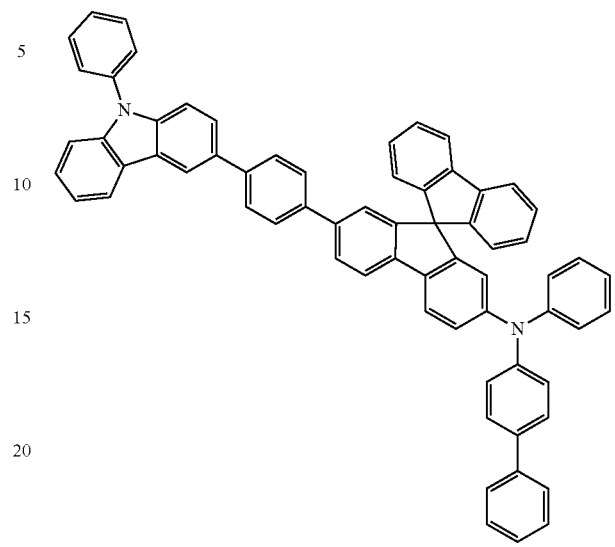
(45)
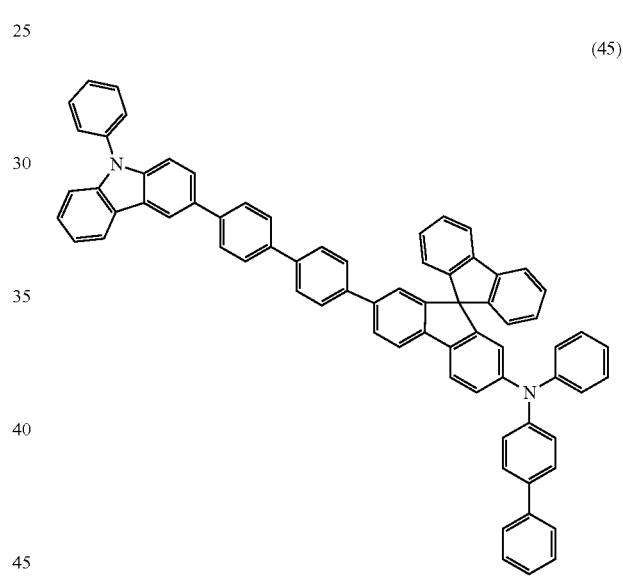
(46)

(47)
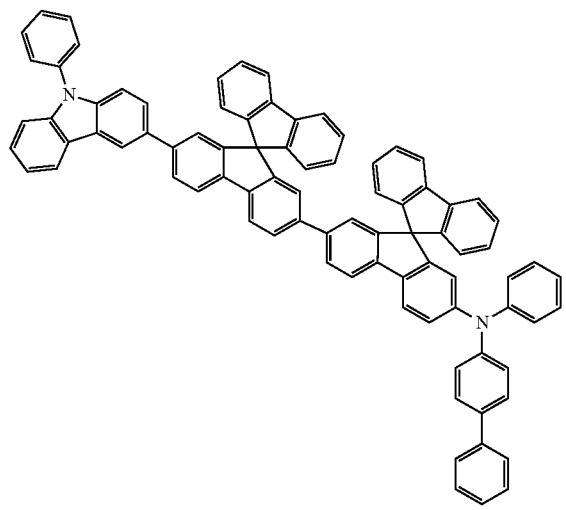
(48)
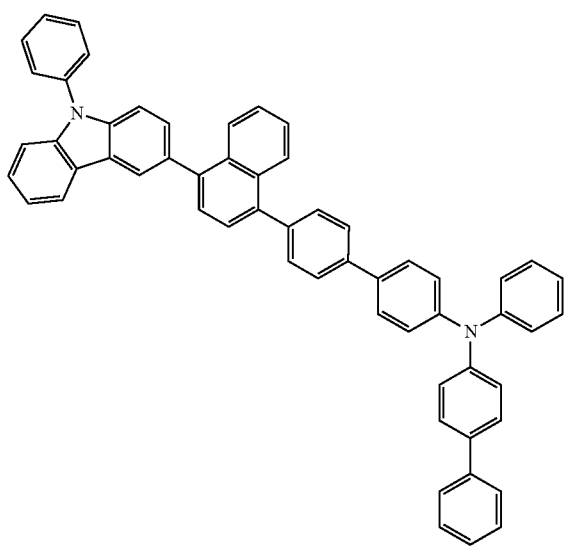
(49)
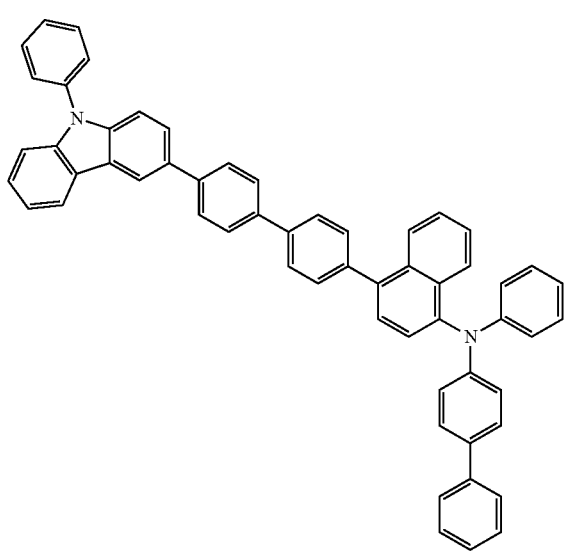
(50)
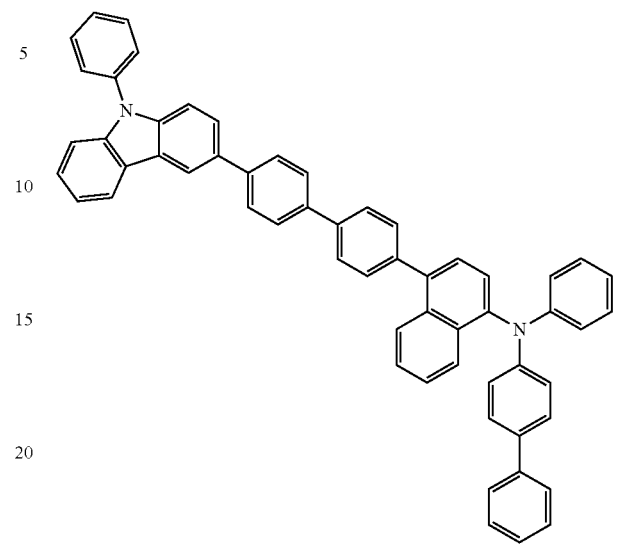
(51)
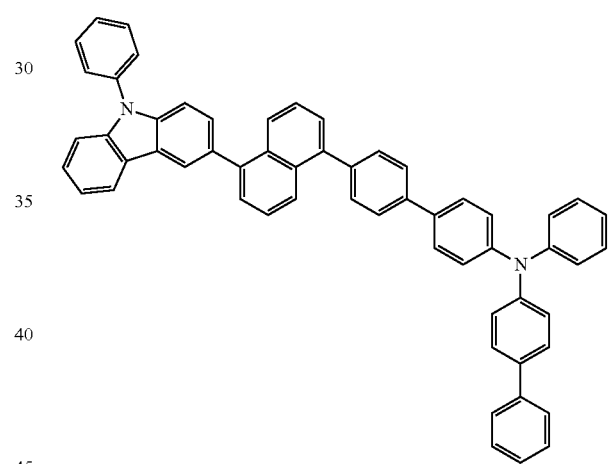
(52)
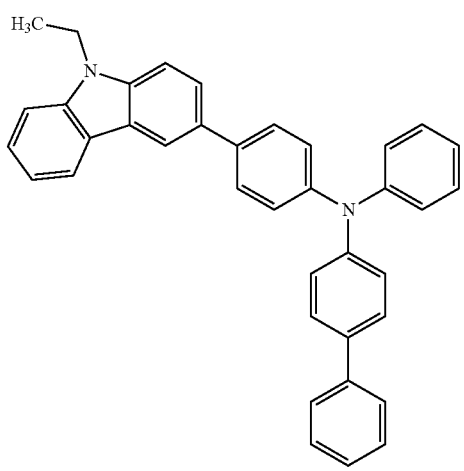

-continued
(53)
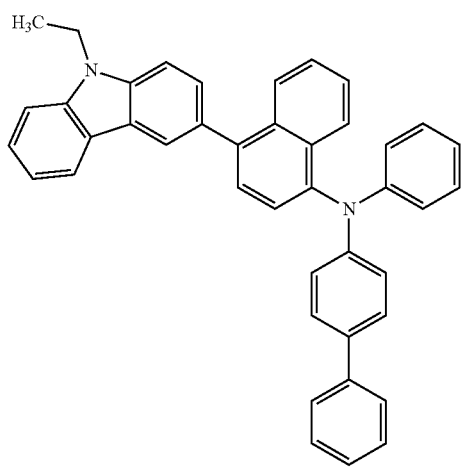
(54)
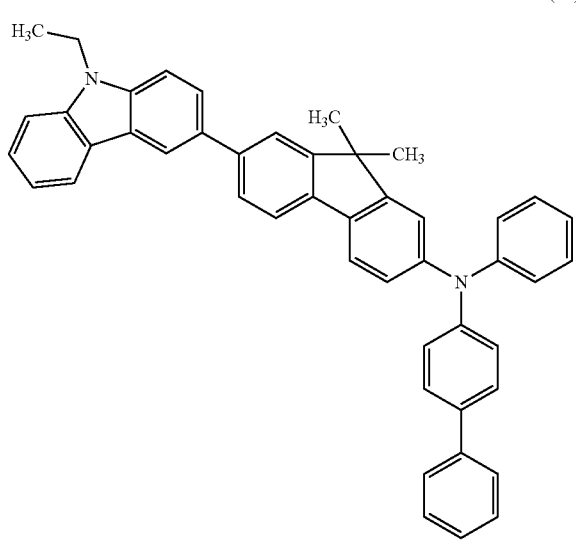
(55)
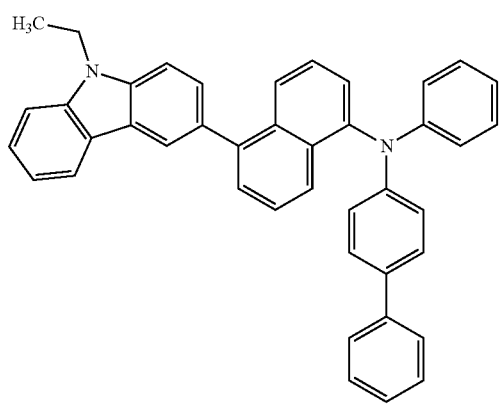
-continued
(56)
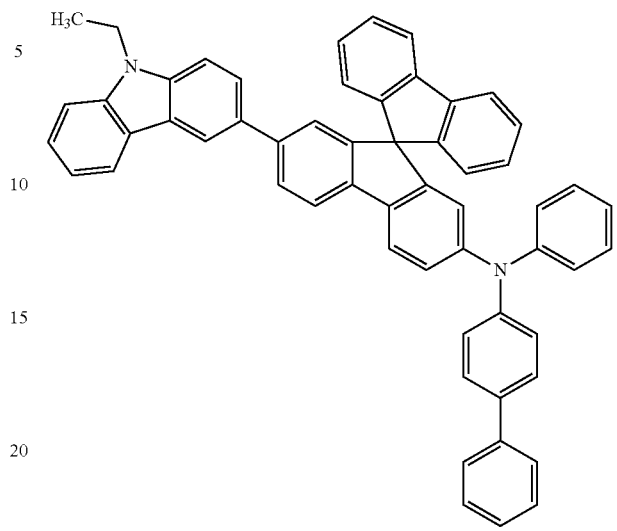
(57)
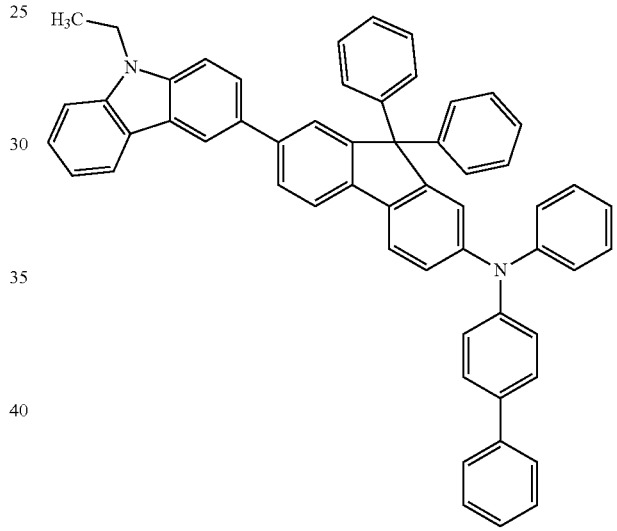
(58)
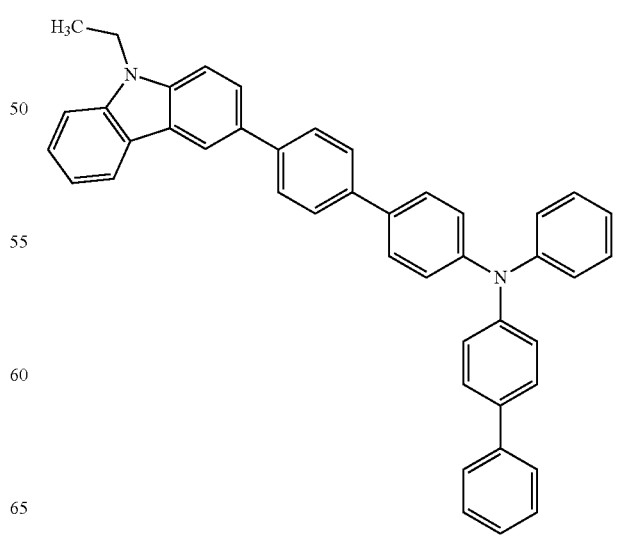

(59)
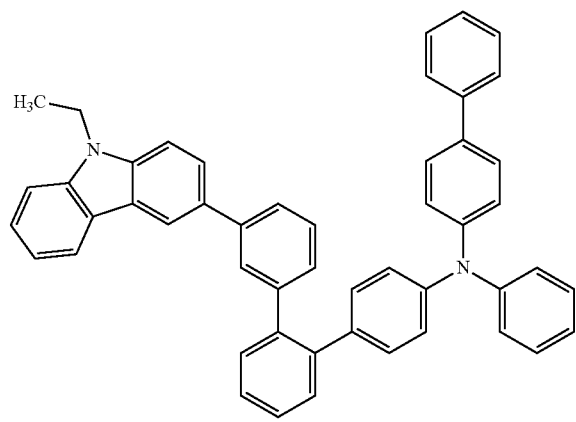
(60)
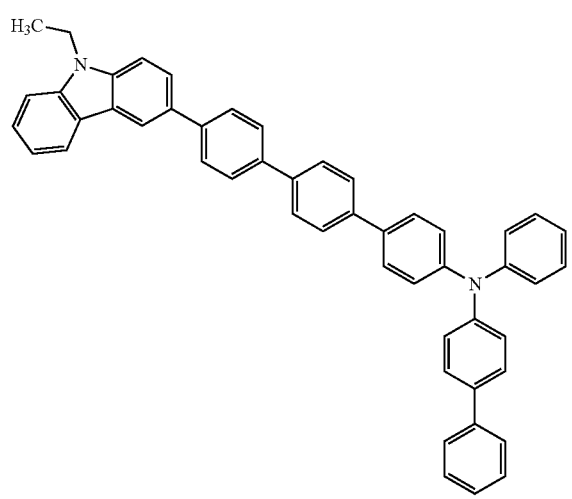
(61)
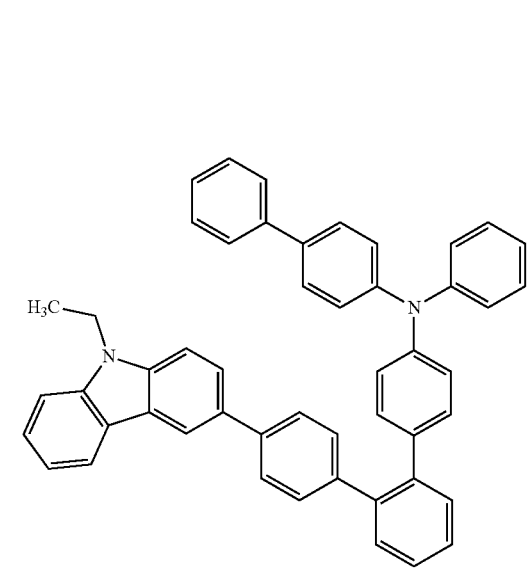
(62)
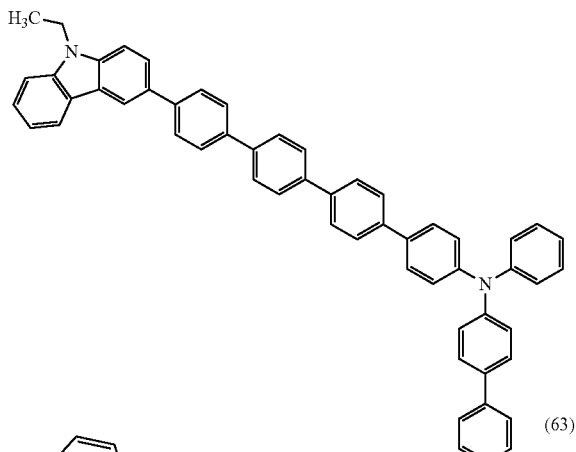
(63)
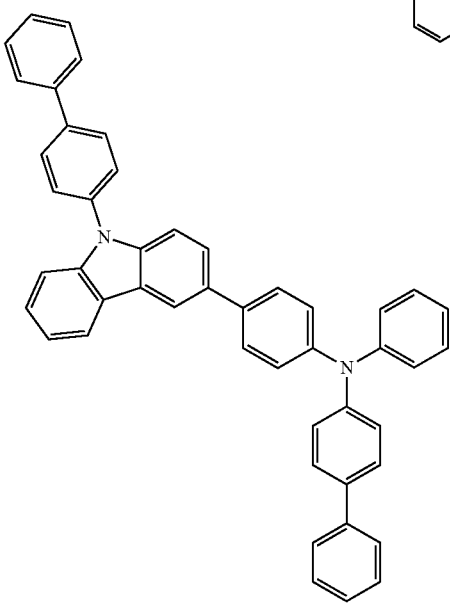
(64)
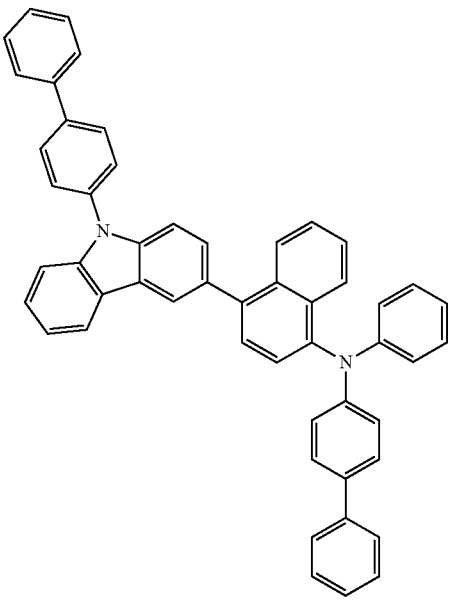

(65)
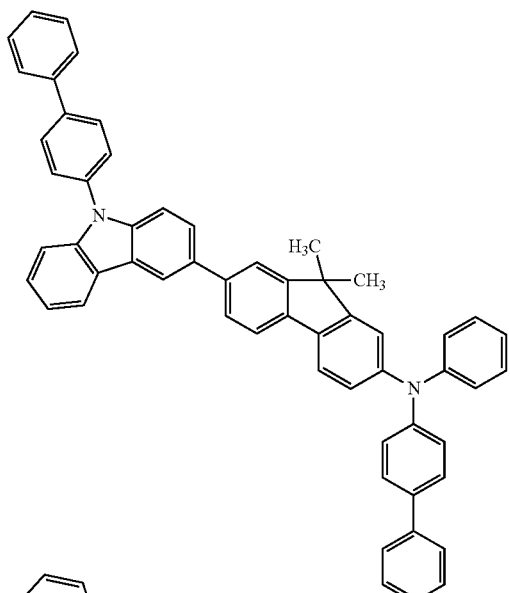
(66)
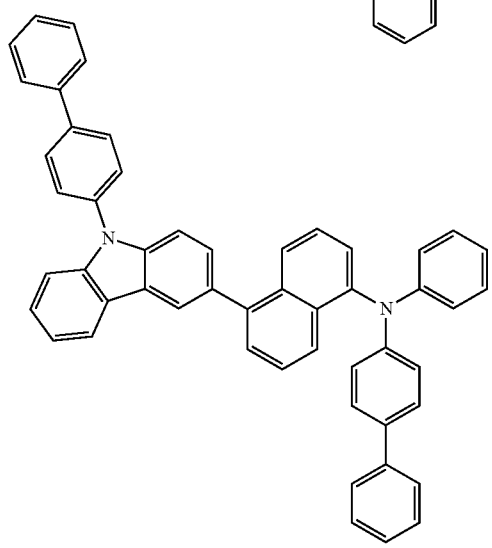
(67)
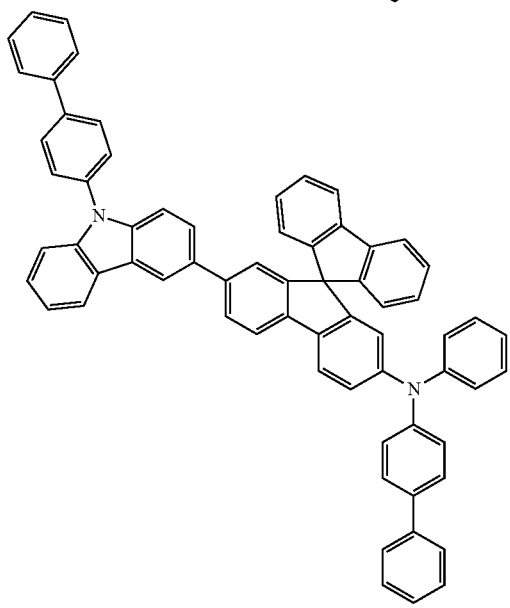
(68)
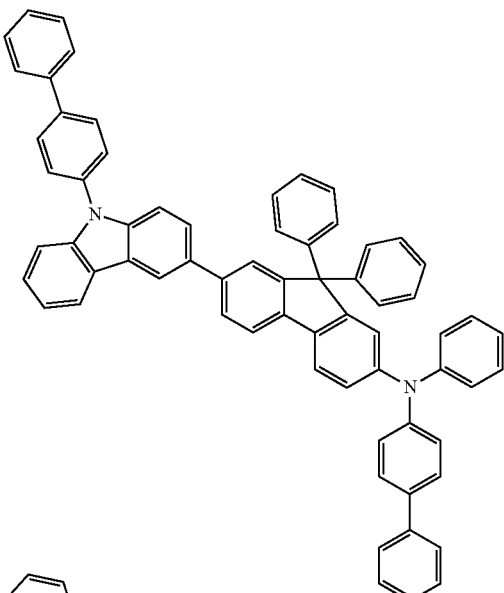
(69)
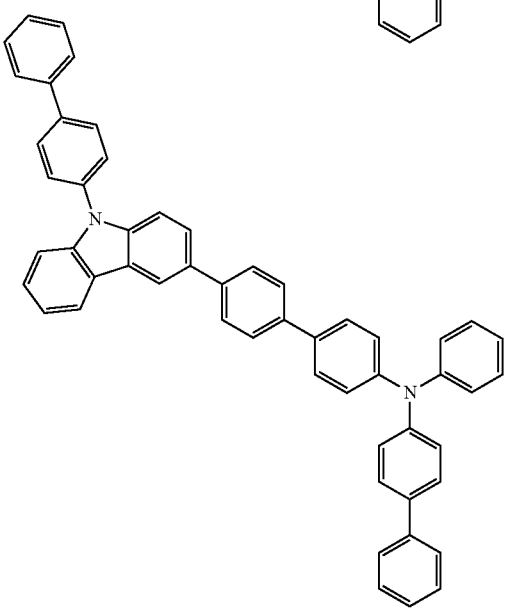
(70)
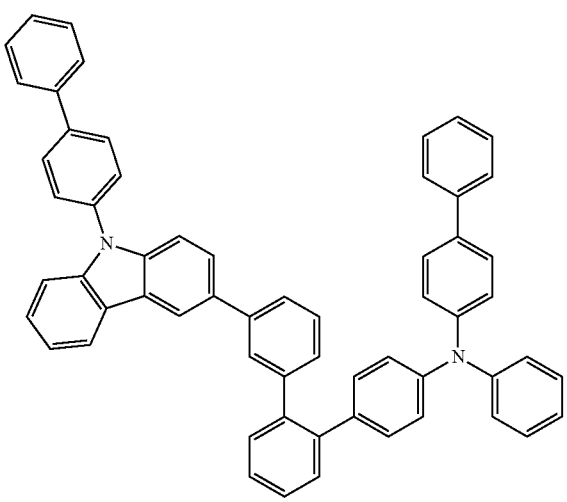

(71) 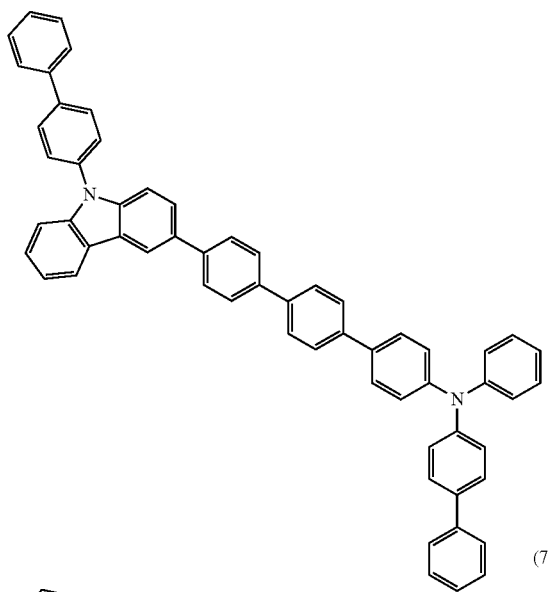
(72) 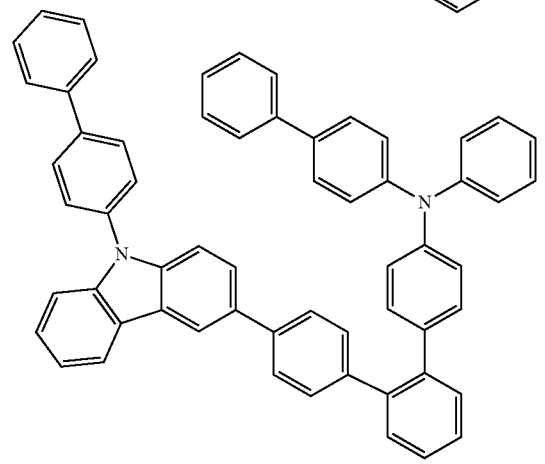
(73) 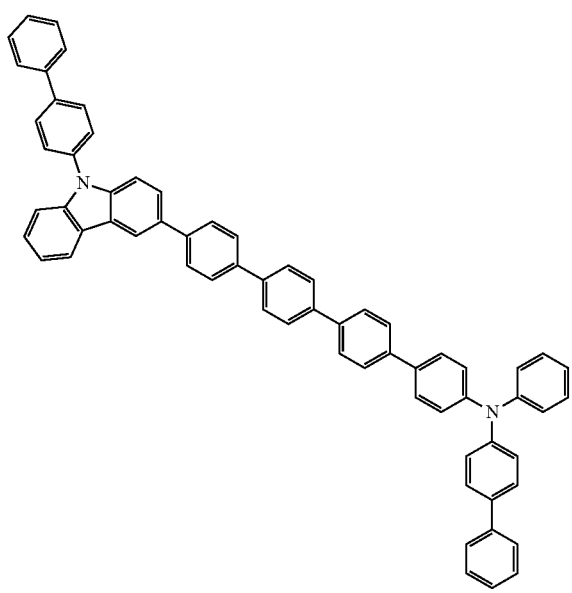
(74) 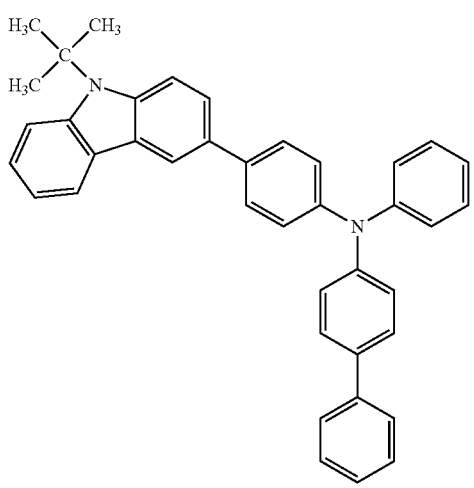
(75) 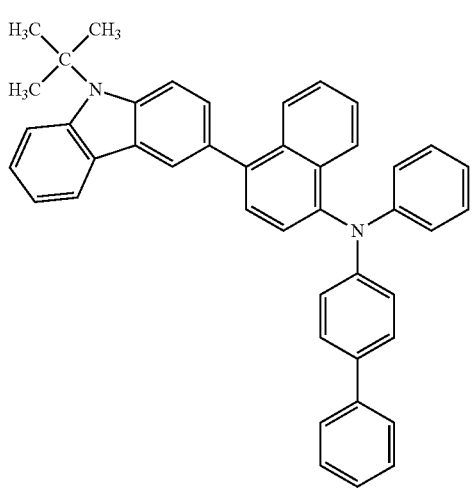
(76) 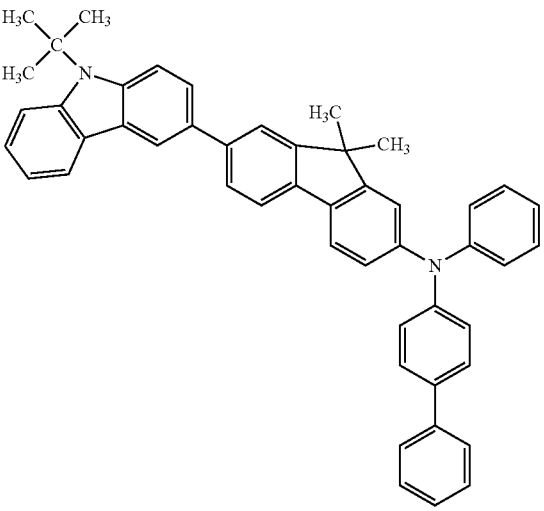

(77)
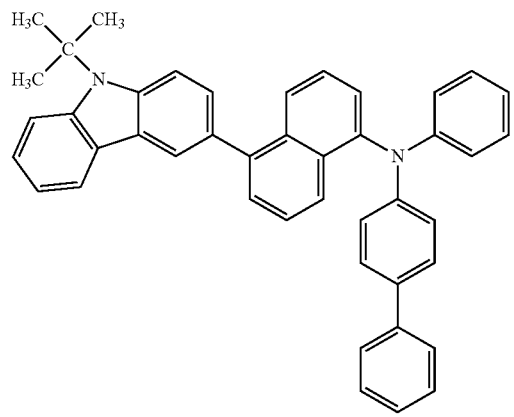
(78)
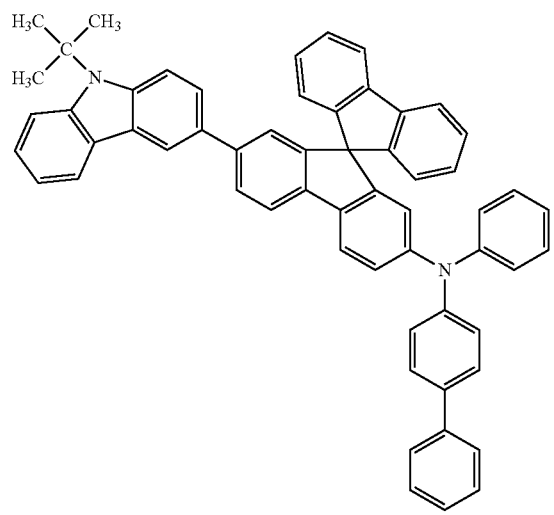
(79)
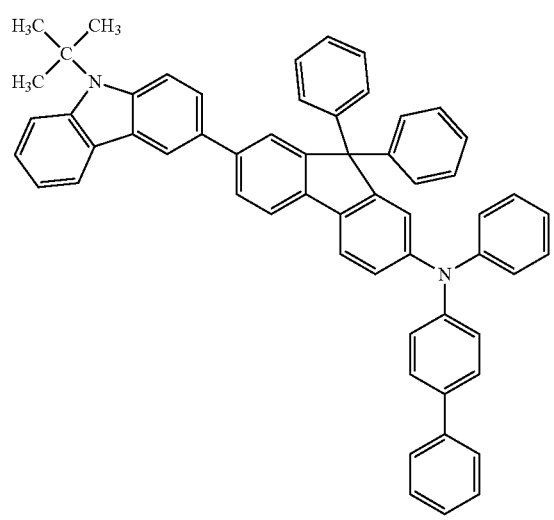
(80)
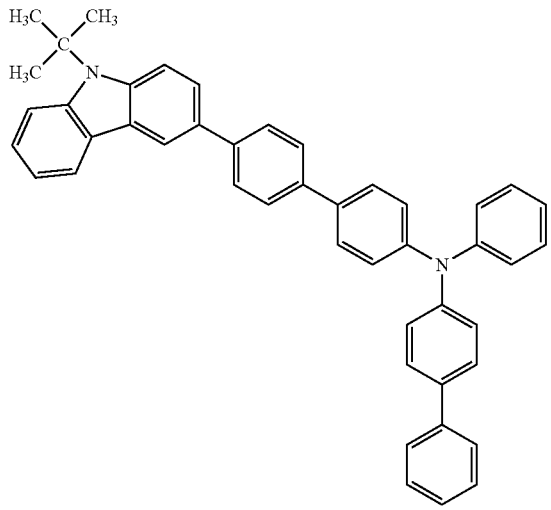
(81)
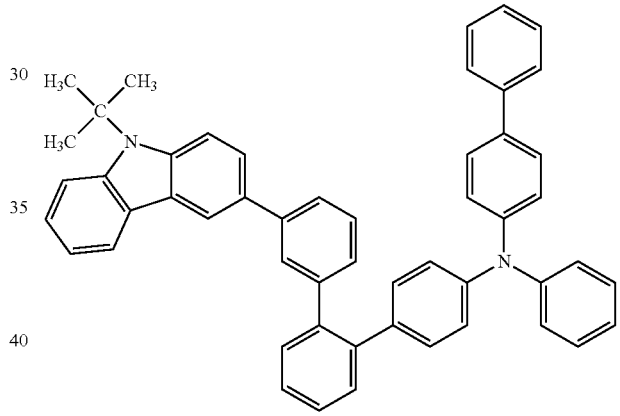
(82)
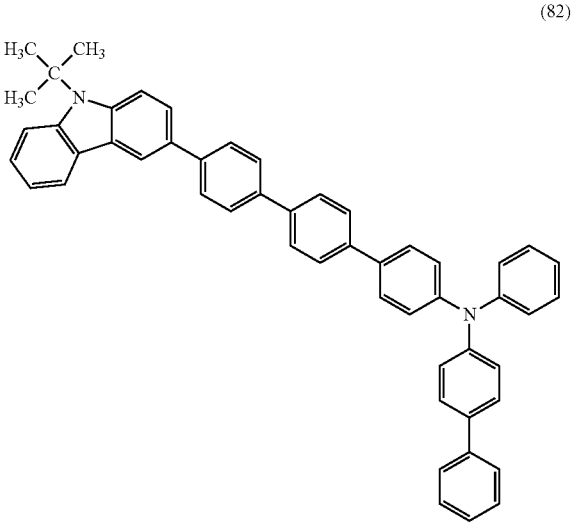

-continued
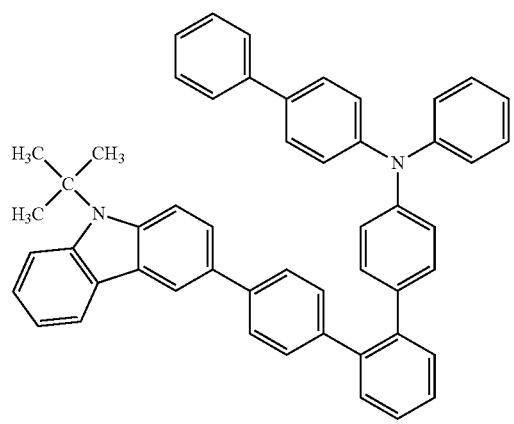
(83)
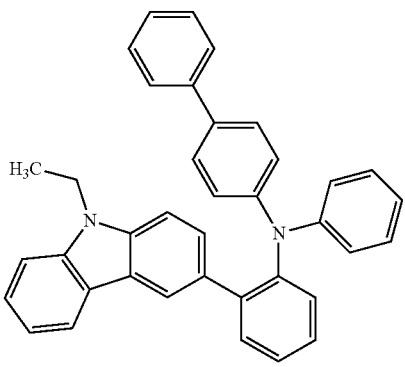
(86)
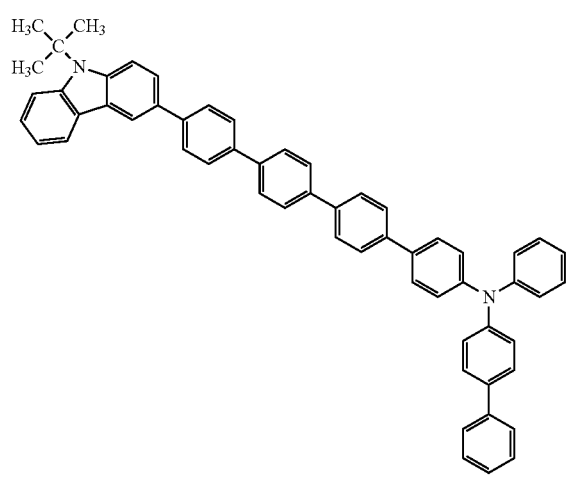
(84)
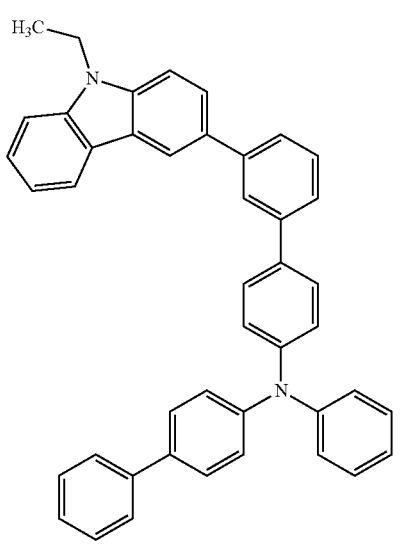
(87)
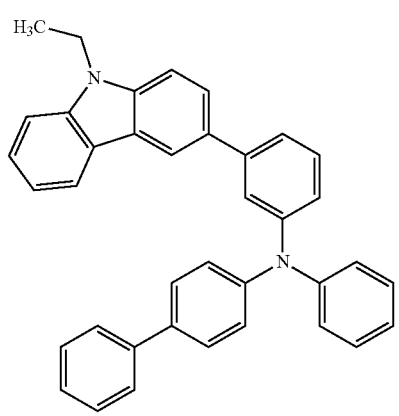
(85)
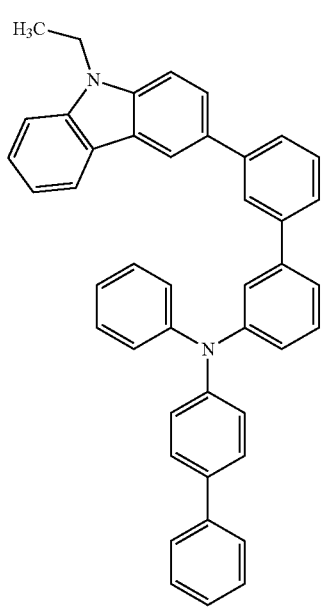
(88)

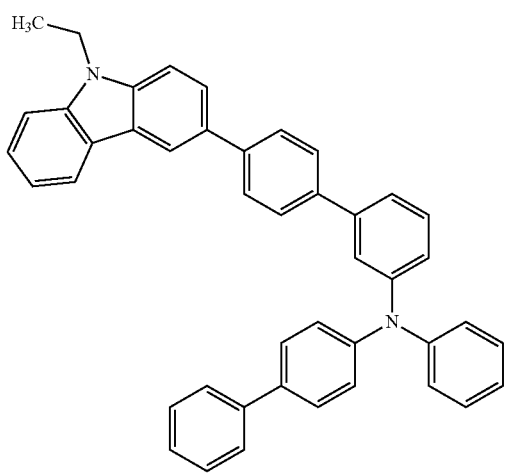
(89)
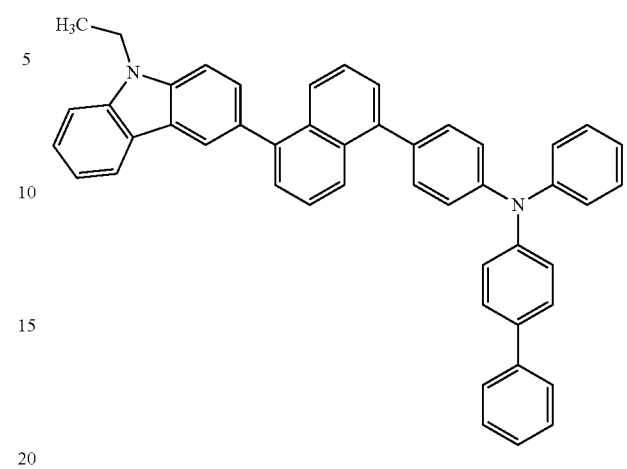
(92)
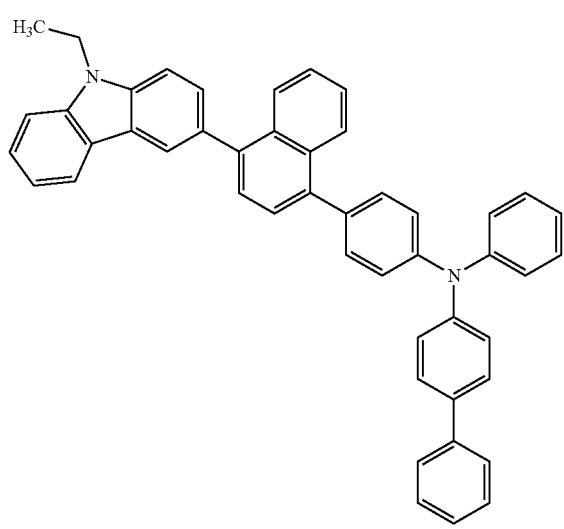
(90)
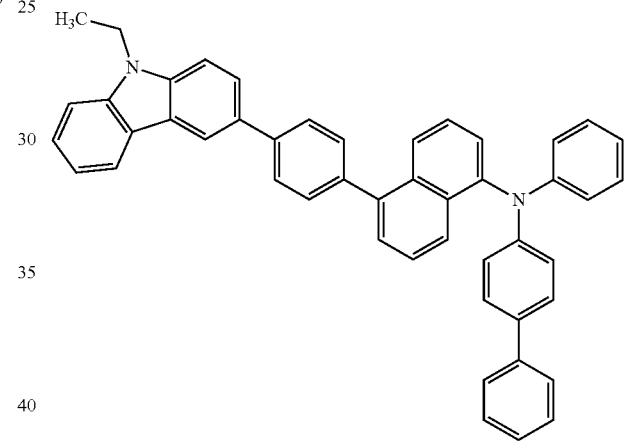
(93)
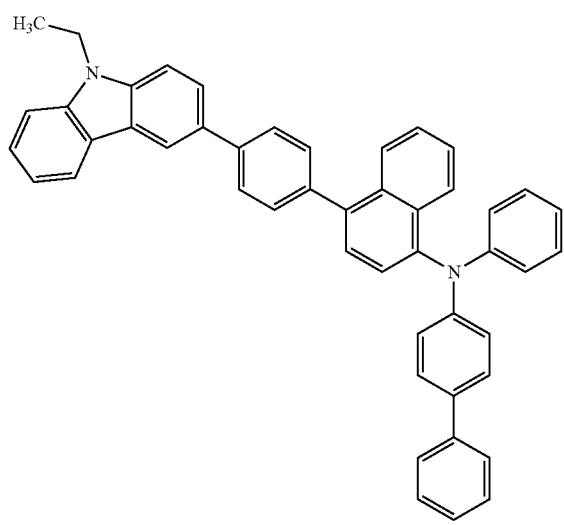
(91)
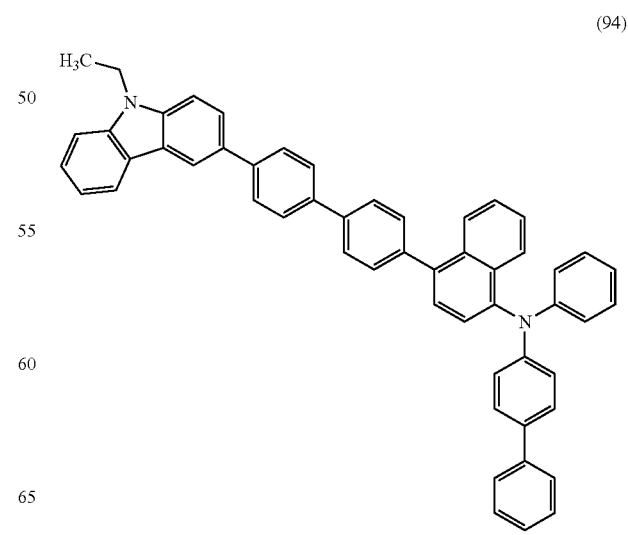
(94)

(95)
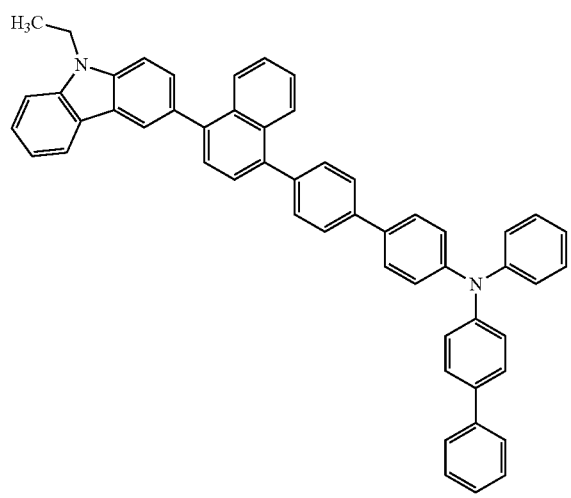
(96)
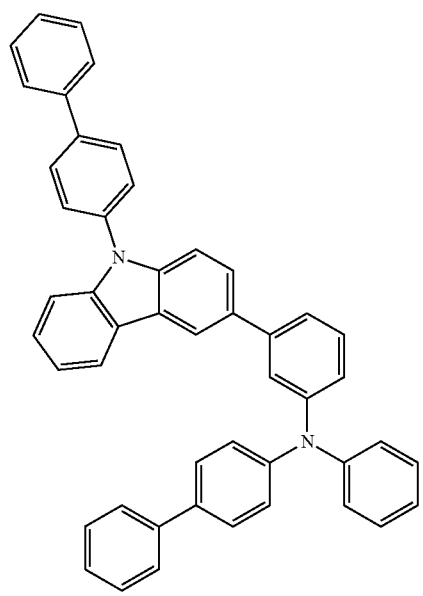
(97)
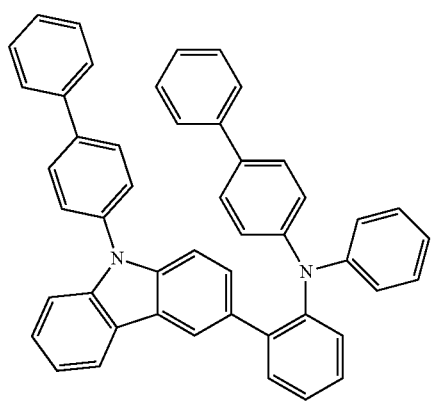
(98)
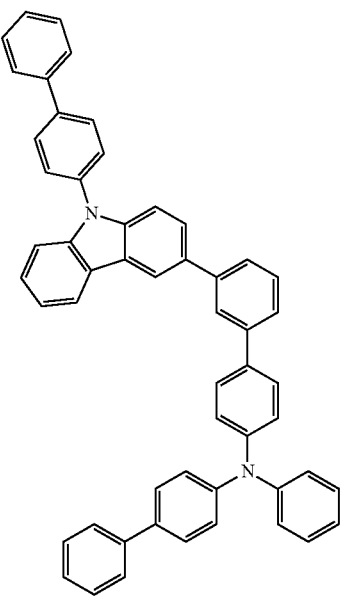
(99)
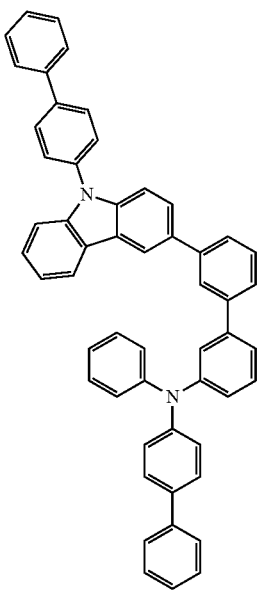

(100)
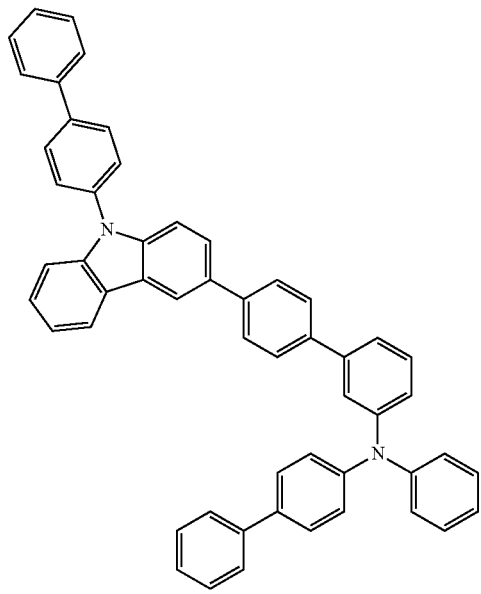
(101)
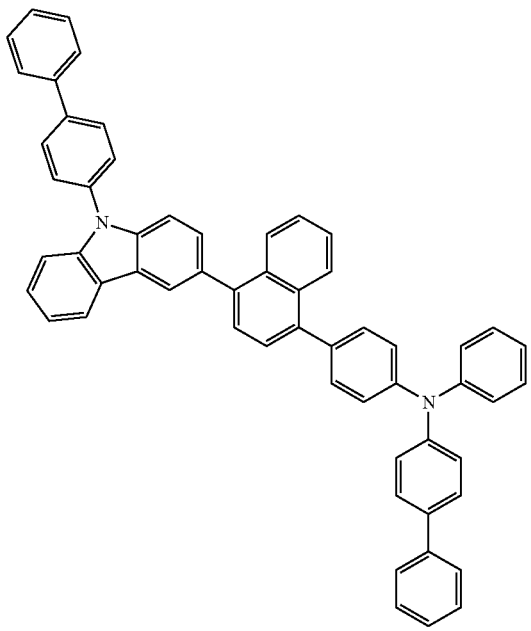
(102)
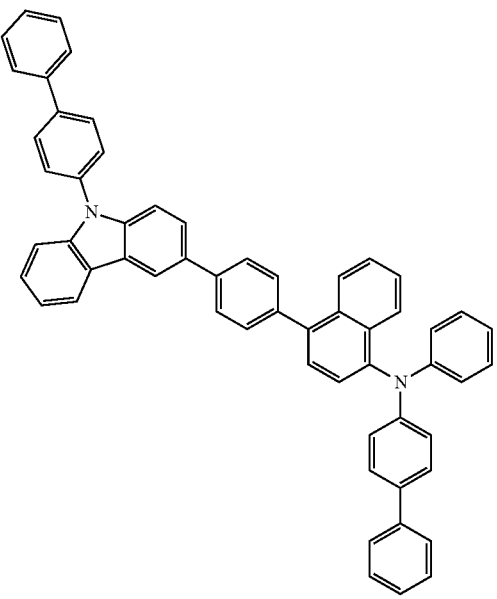
(103)
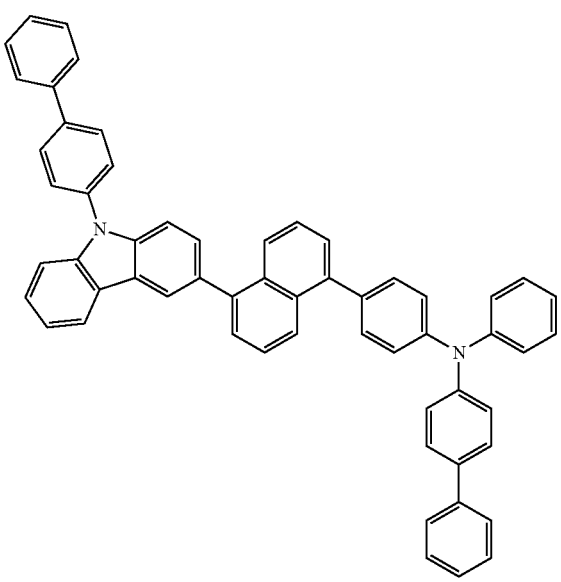

(104)
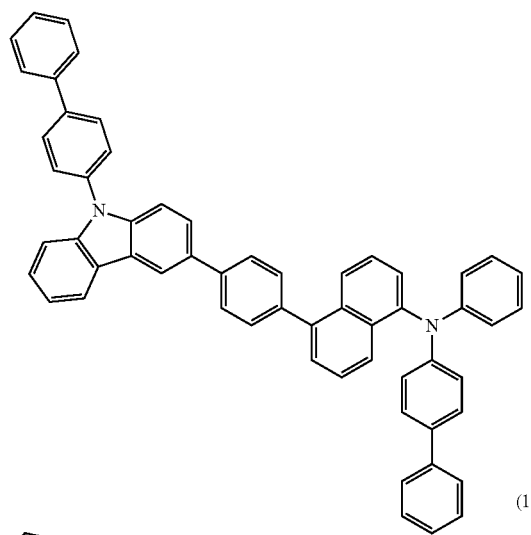
(105)
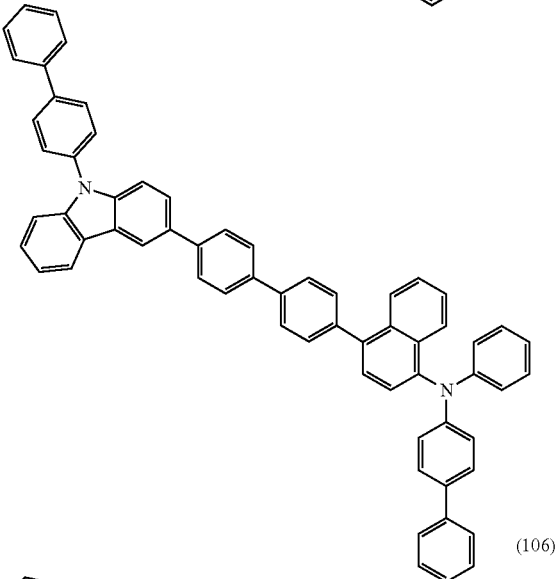
(106)
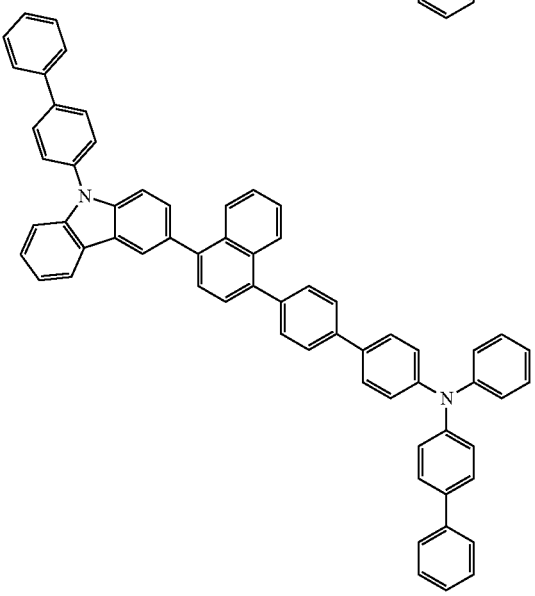
(107)
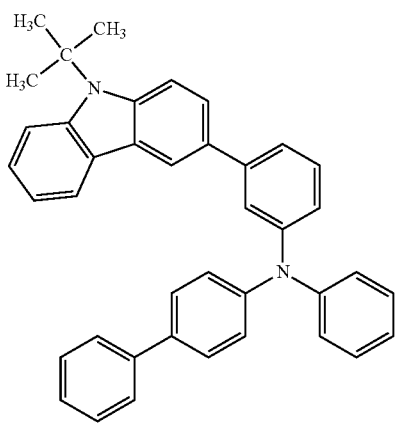
(108)
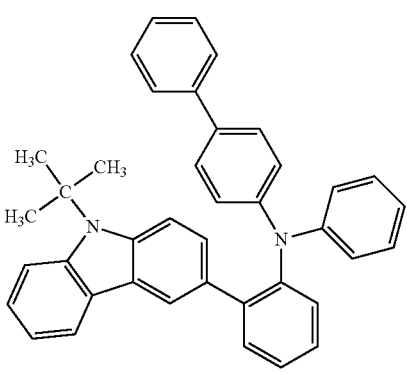
(109)
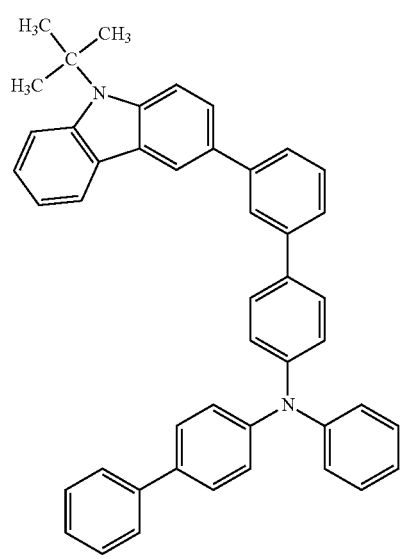

-continued
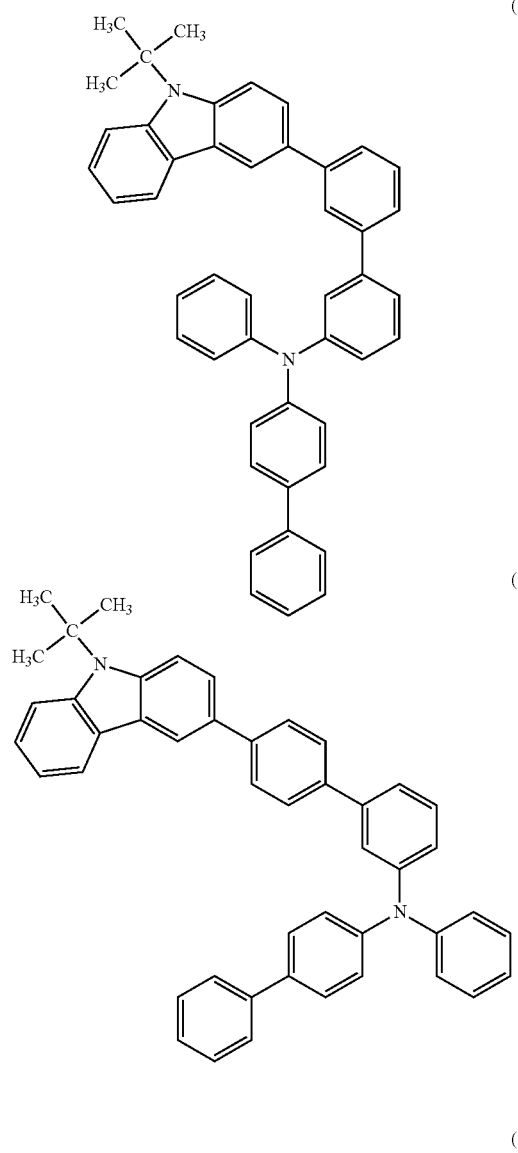
(110)
(111)
(112)
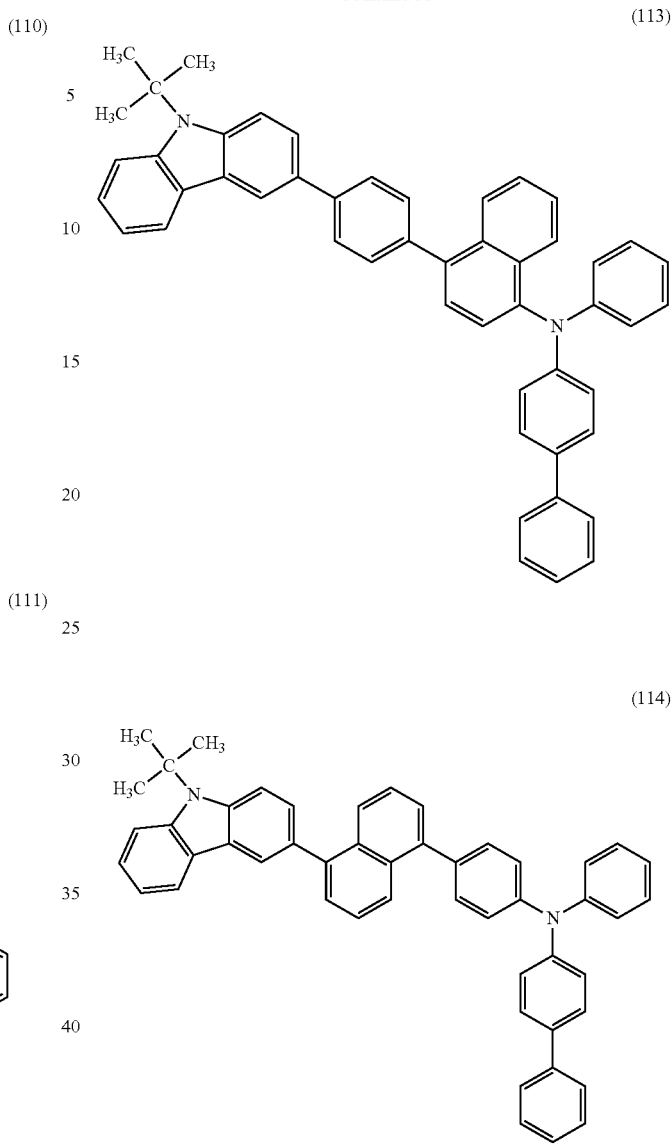
(113)
(114)
(115)

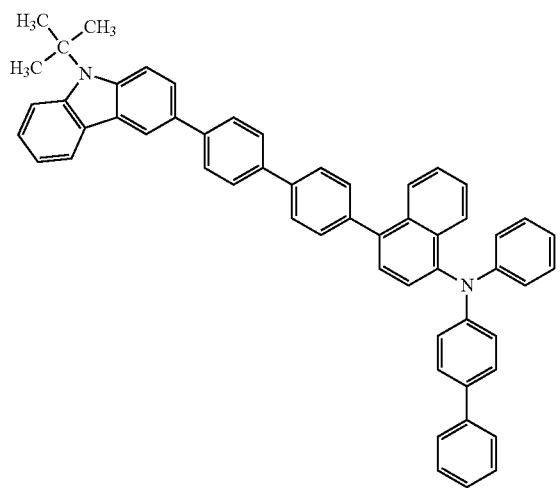
(116)
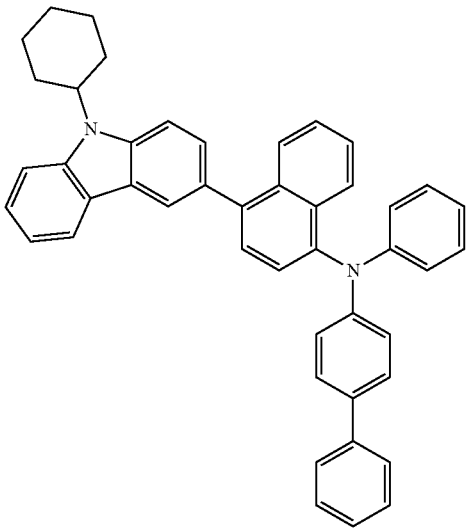
(119)
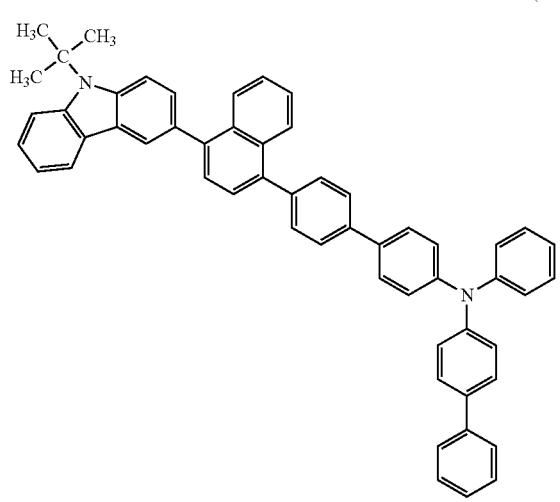
(117)
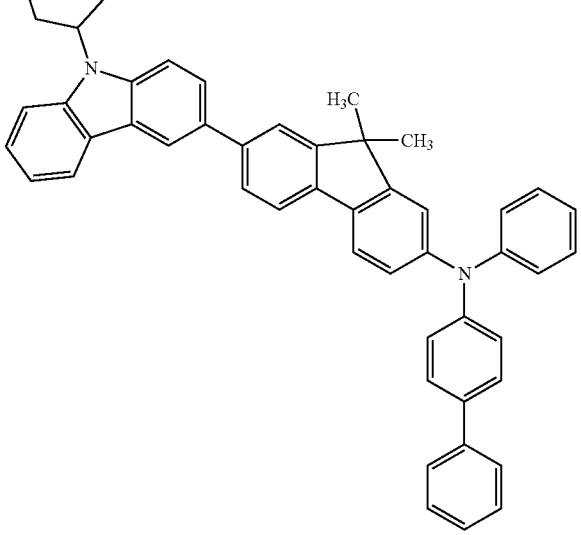
(120)
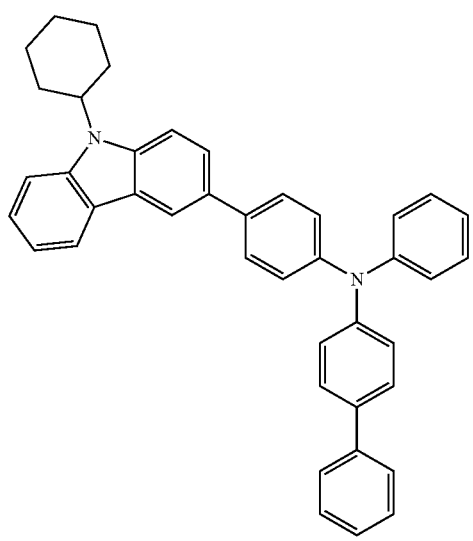
(118)
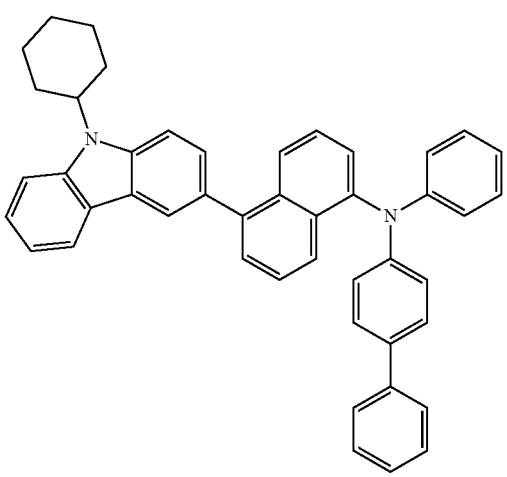
(121)

(122)
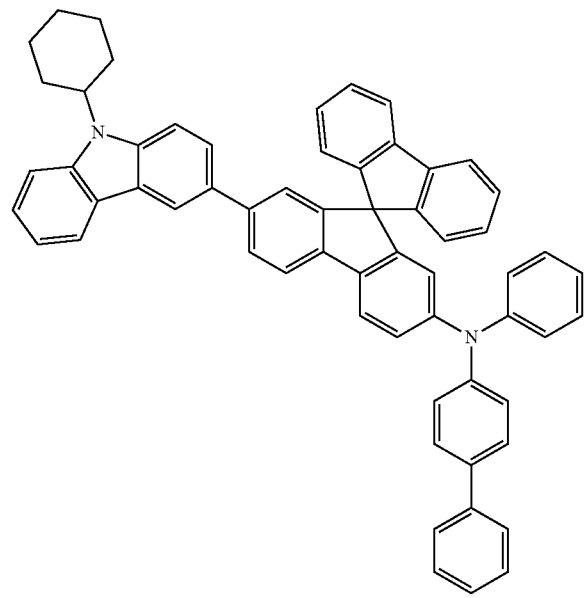
(123)
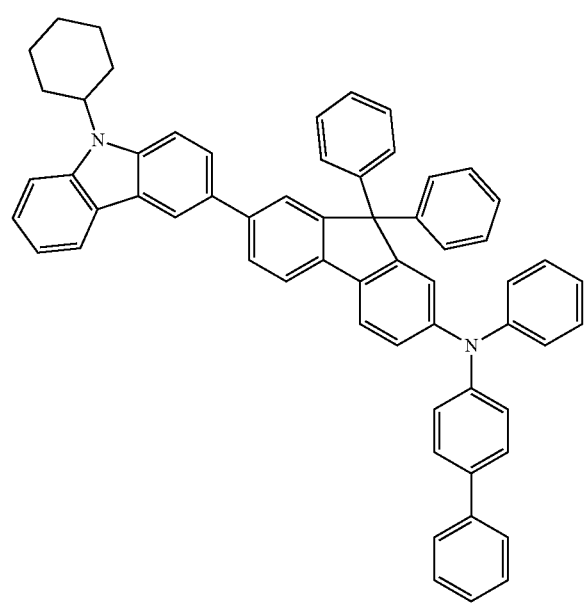
(124)
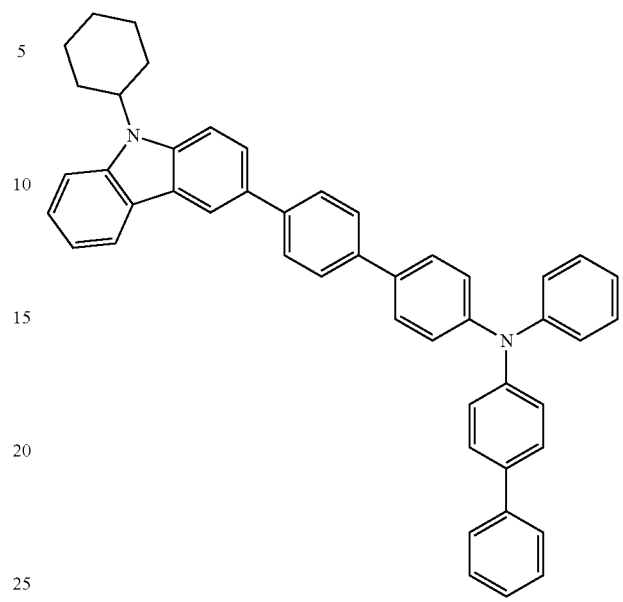
(125)
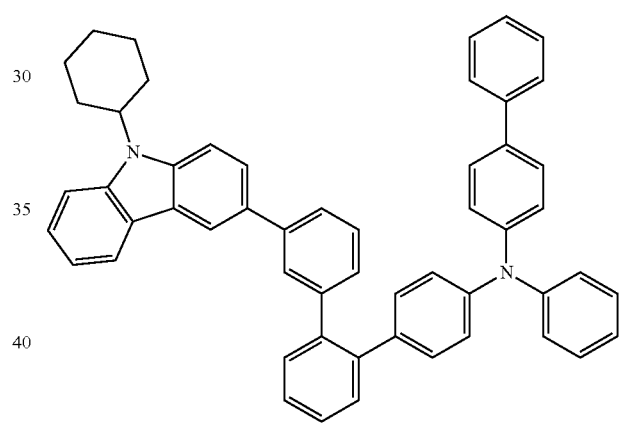
(126)
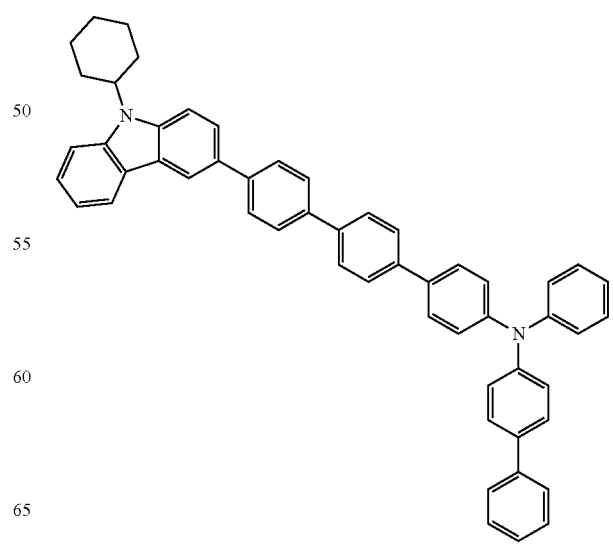

(127)
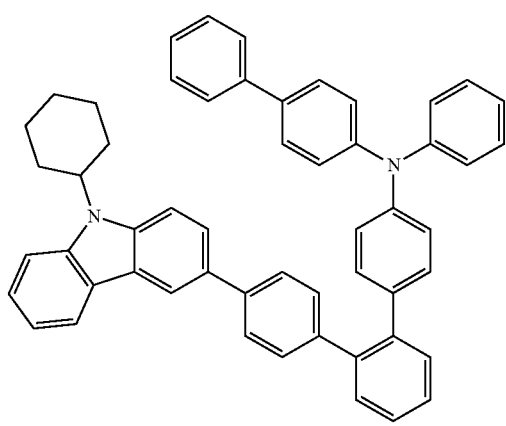
(128)
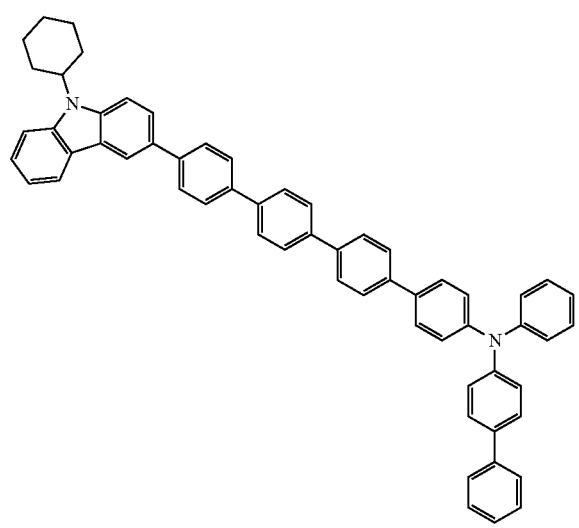
(129)
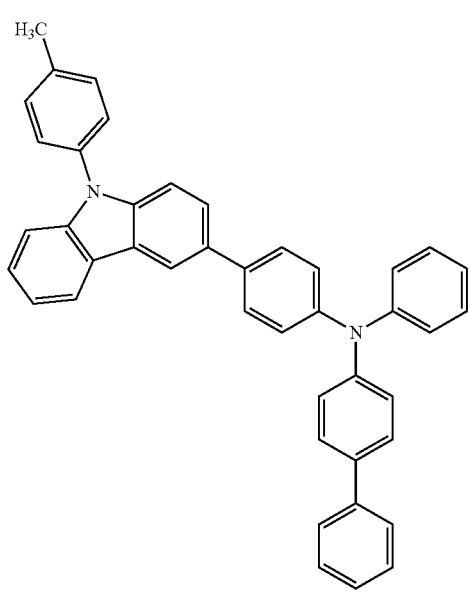
(130)
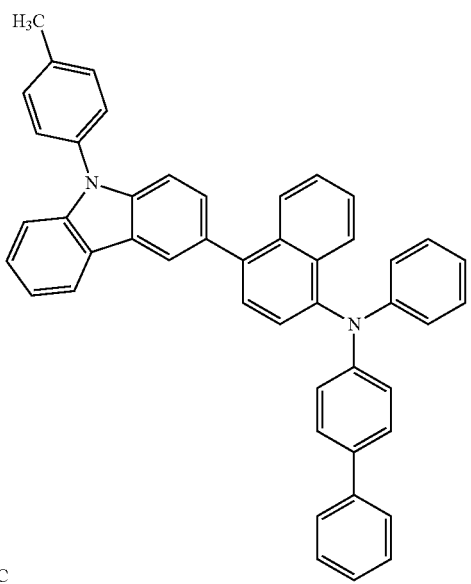
(131)
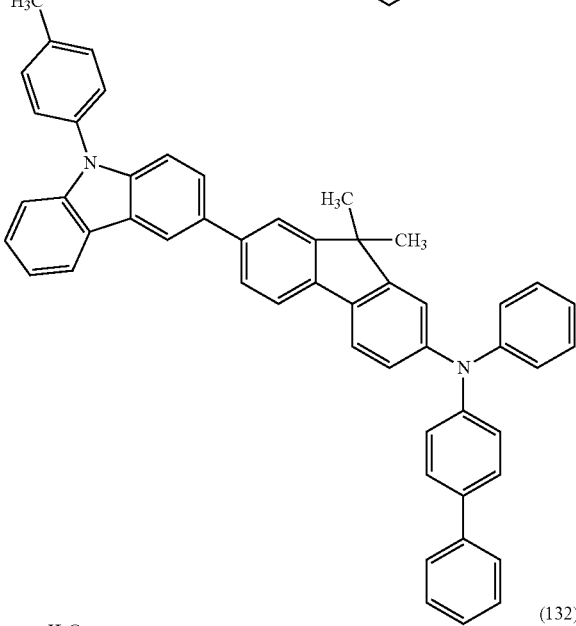
(132)
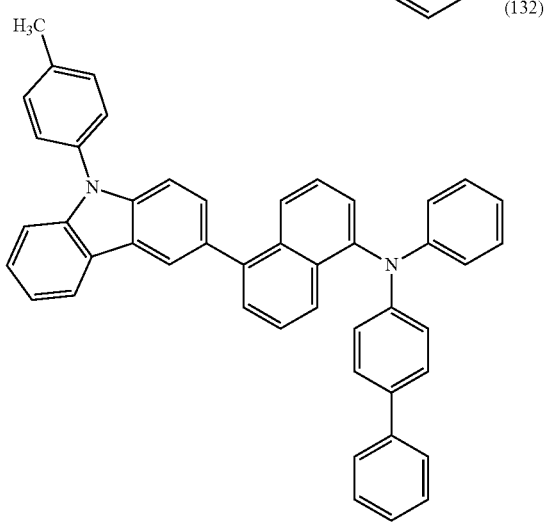

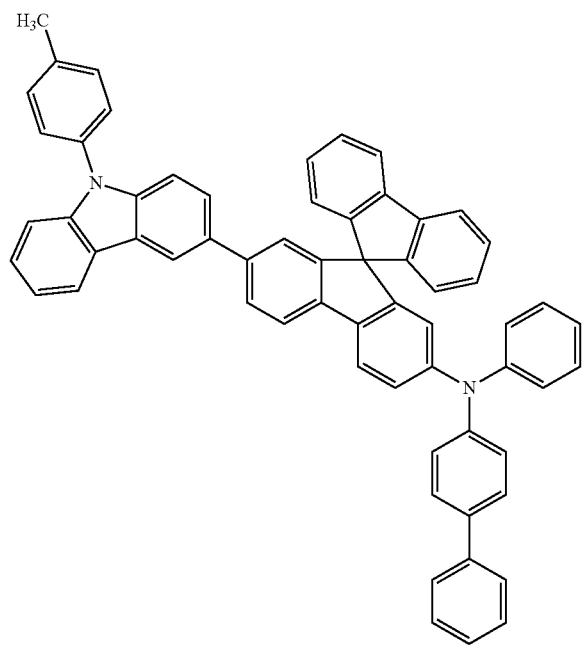
(133)
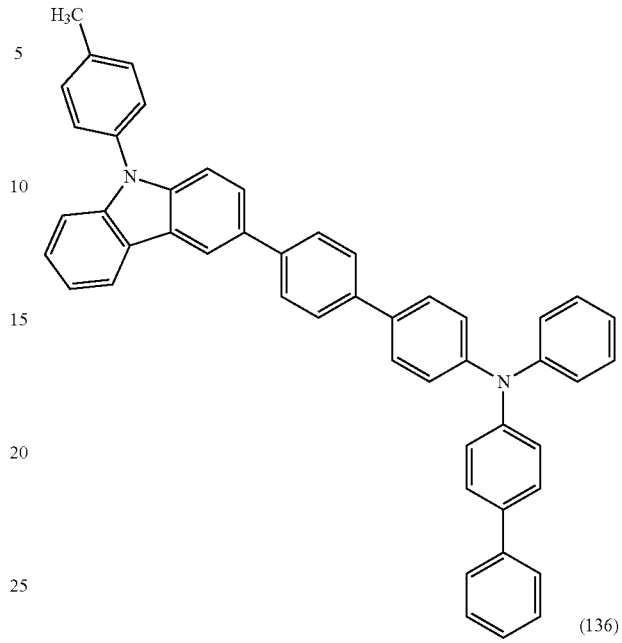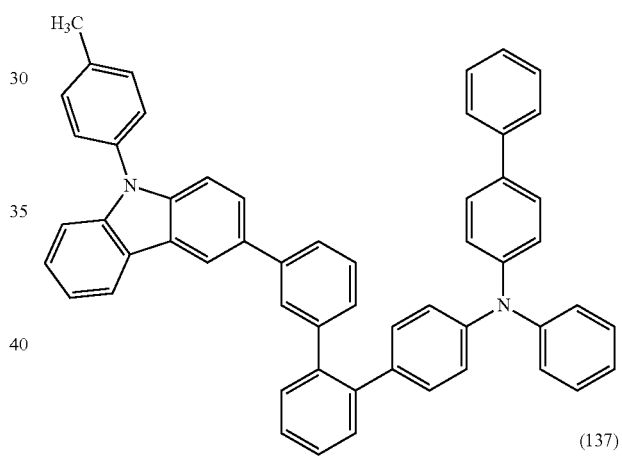
(135)
(136)
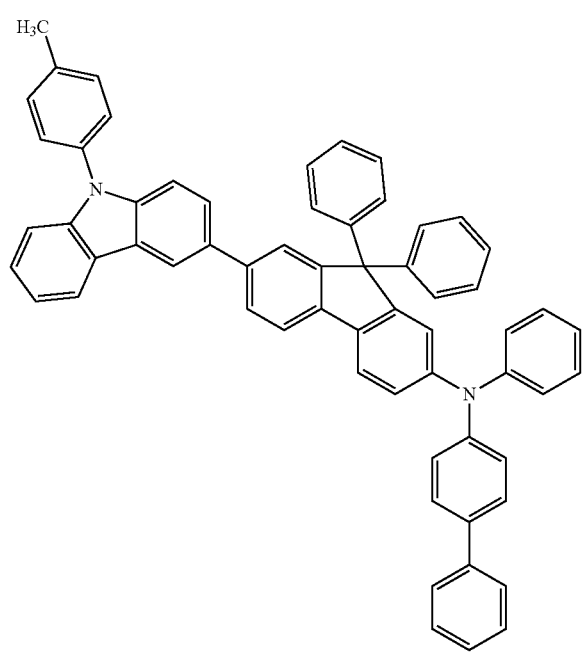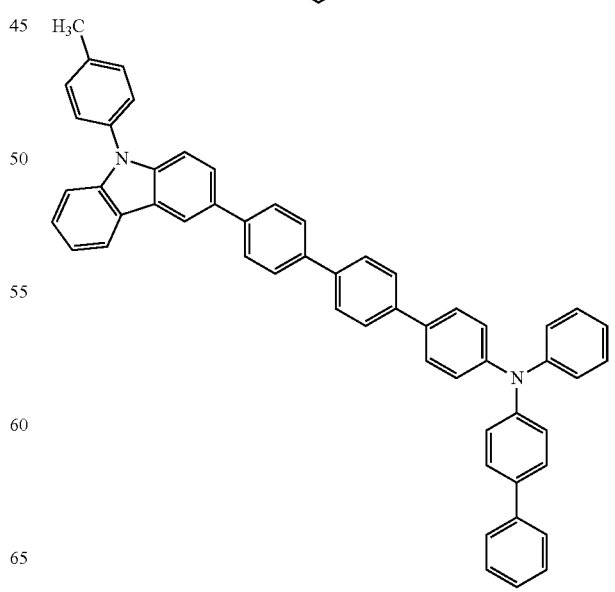
(134)
(137)

(138)
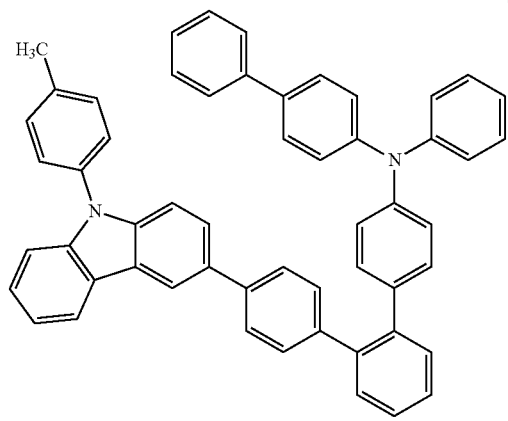
(139)
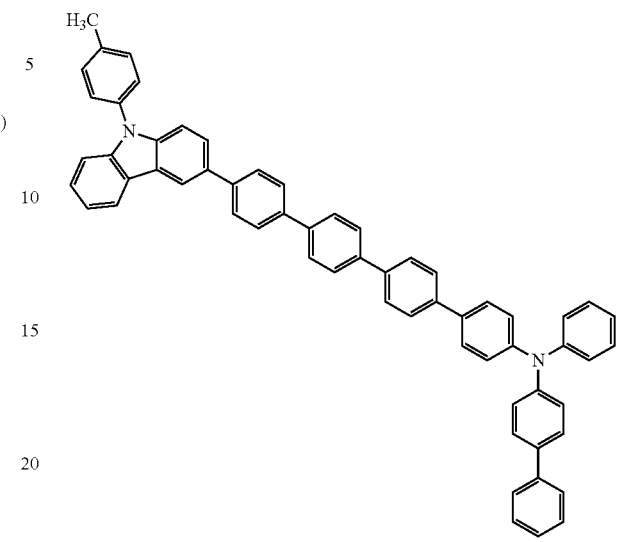
(140)
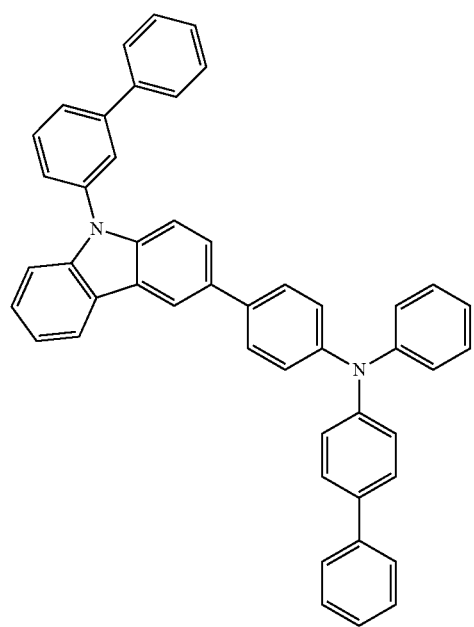
(141)
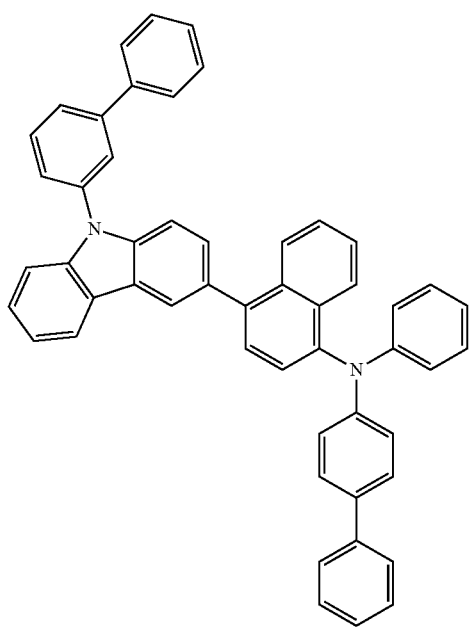

(142)
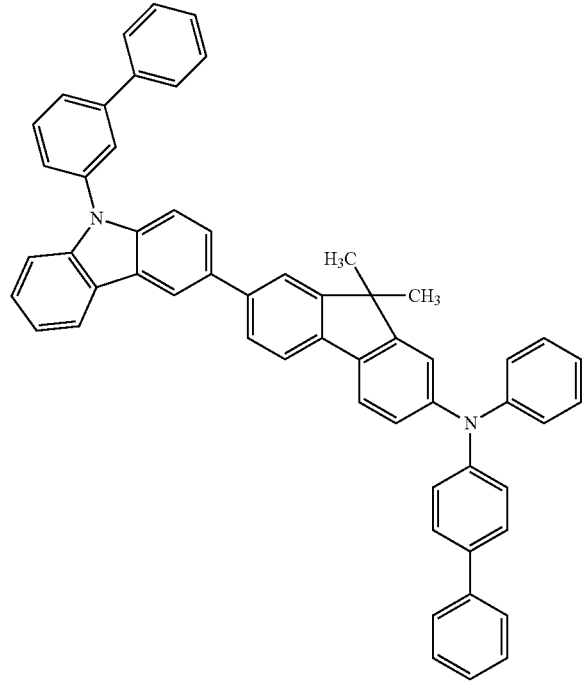
(143)
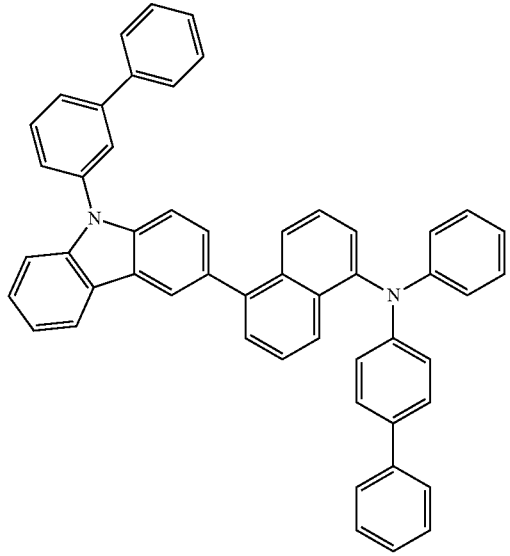
(144)
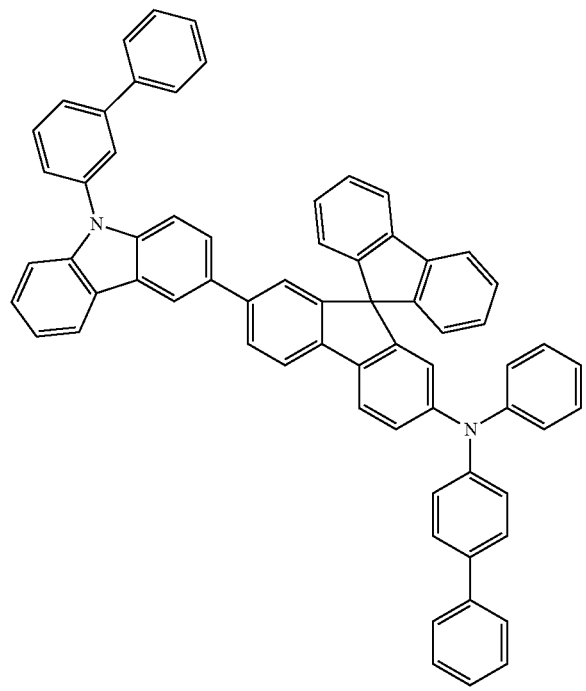
(145)
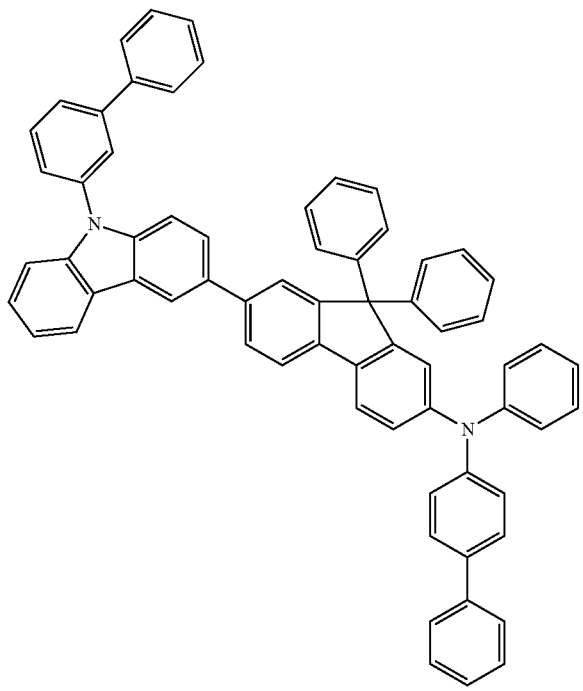

-continued
(146)
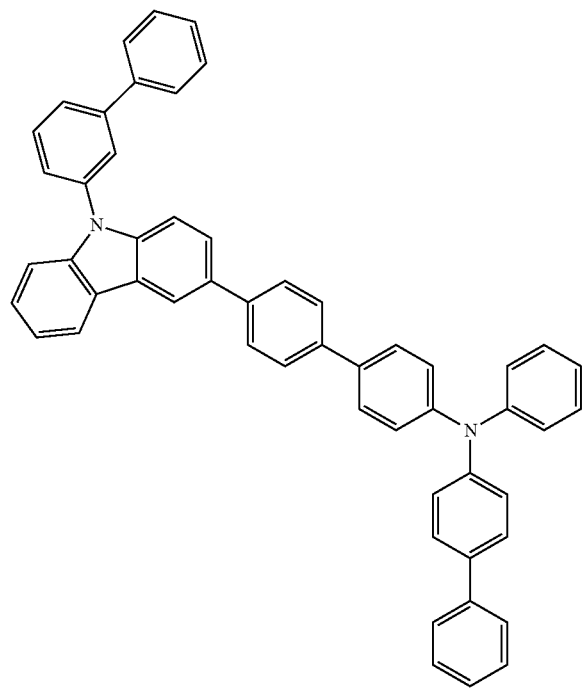
(147)
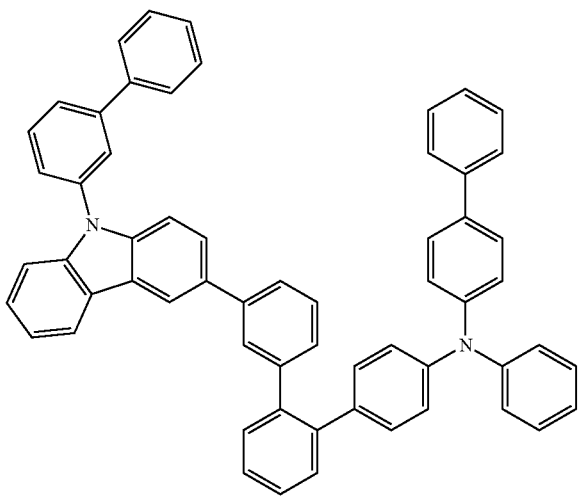
(148)
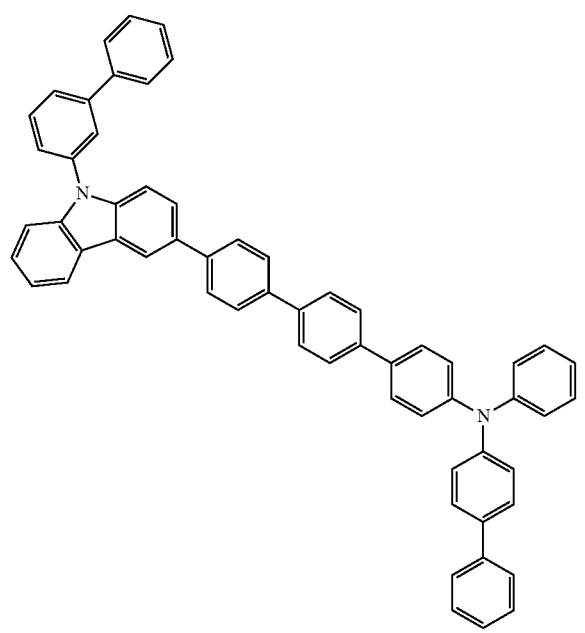
(149)
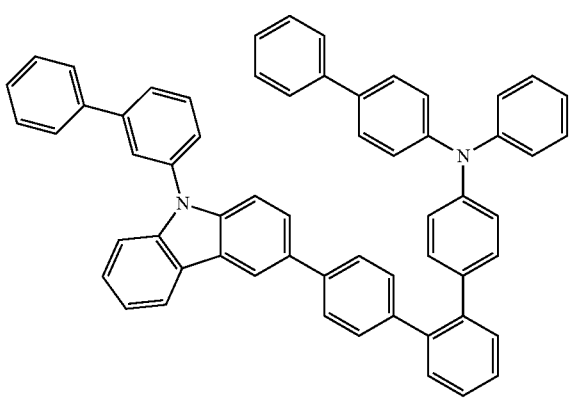

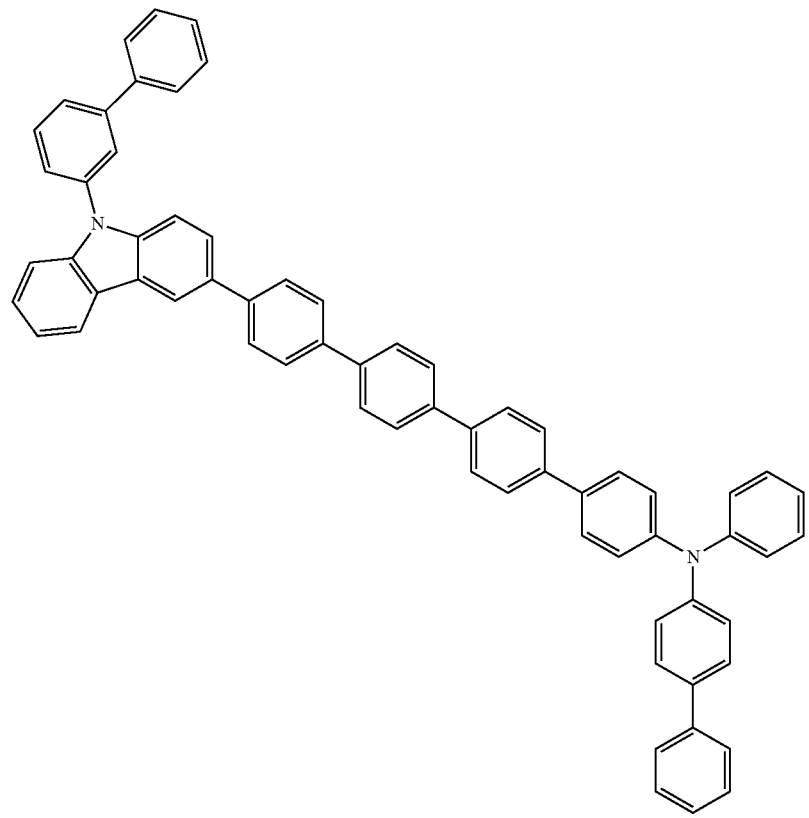
(150)
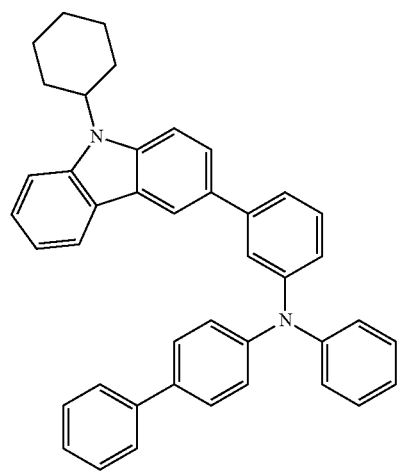
(151)
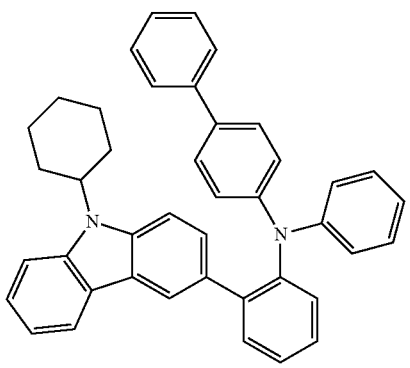
(152)

-continued
(153)
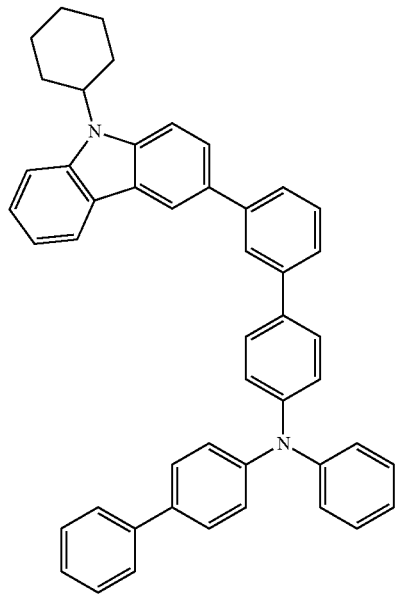
(154)
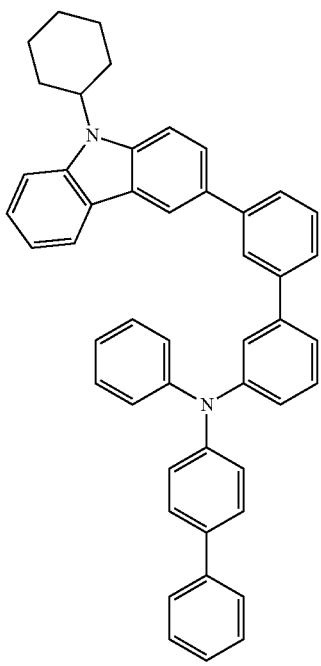
(155)
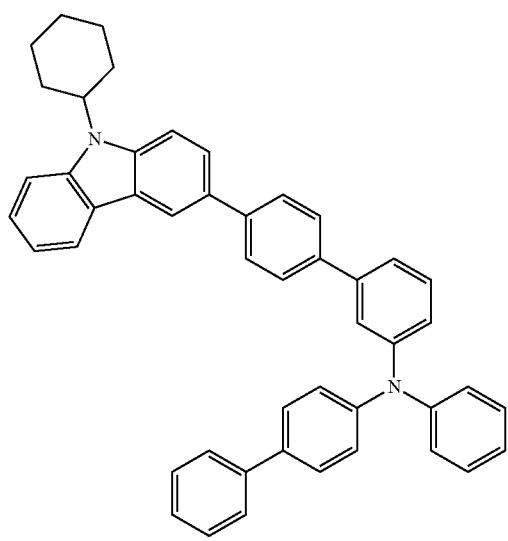
(156)
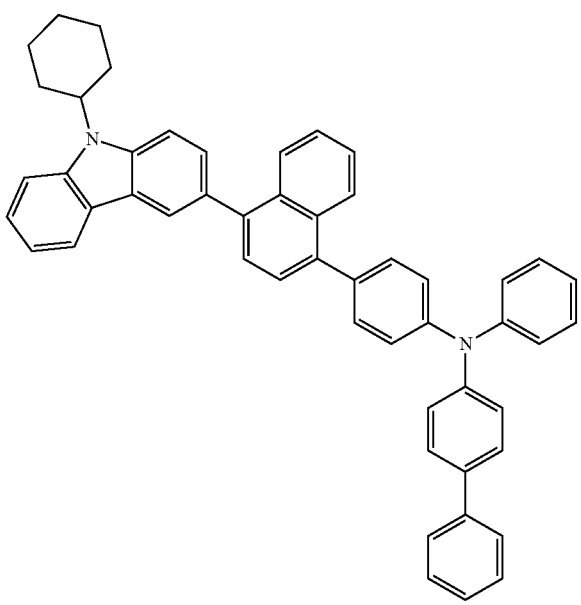

(157)
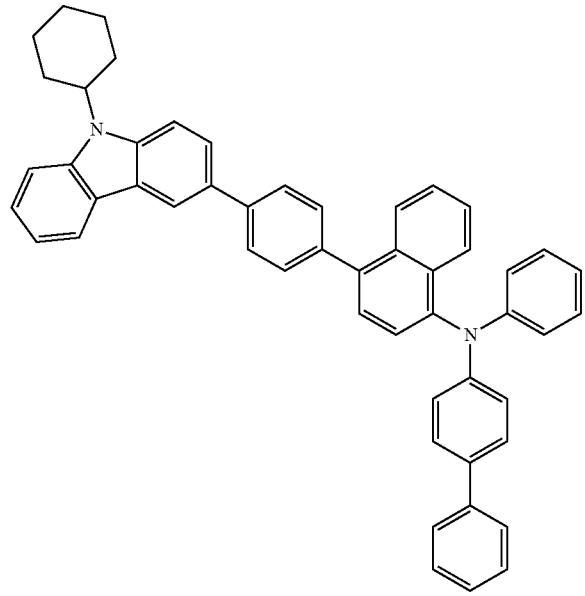
(158)
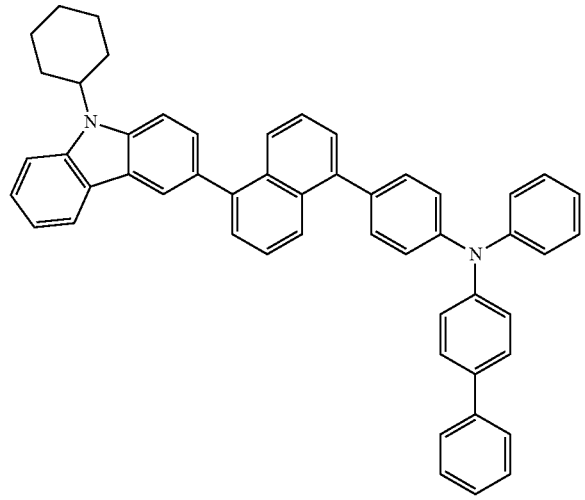
(159)
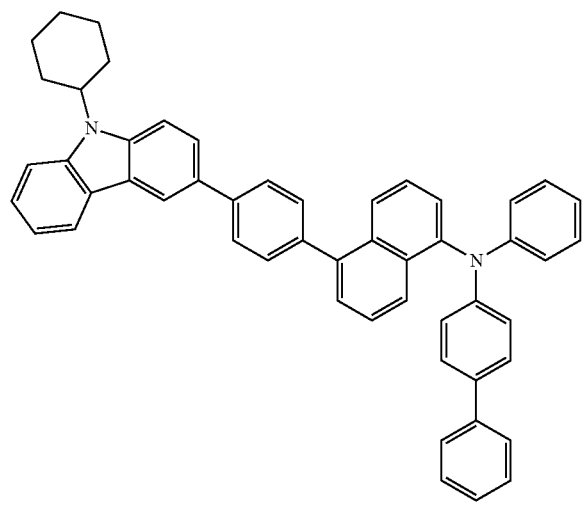
(160)
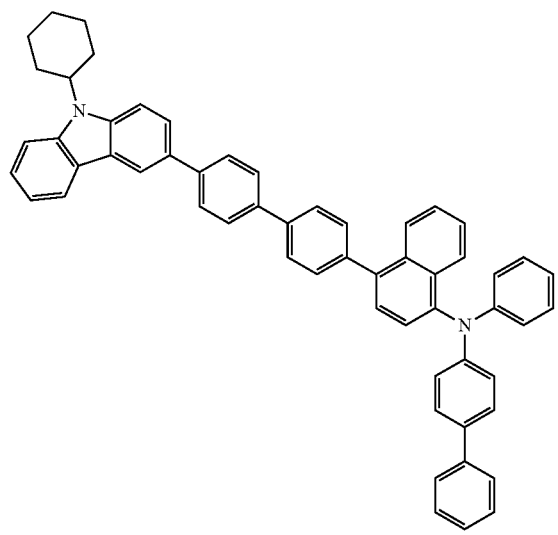

(161)
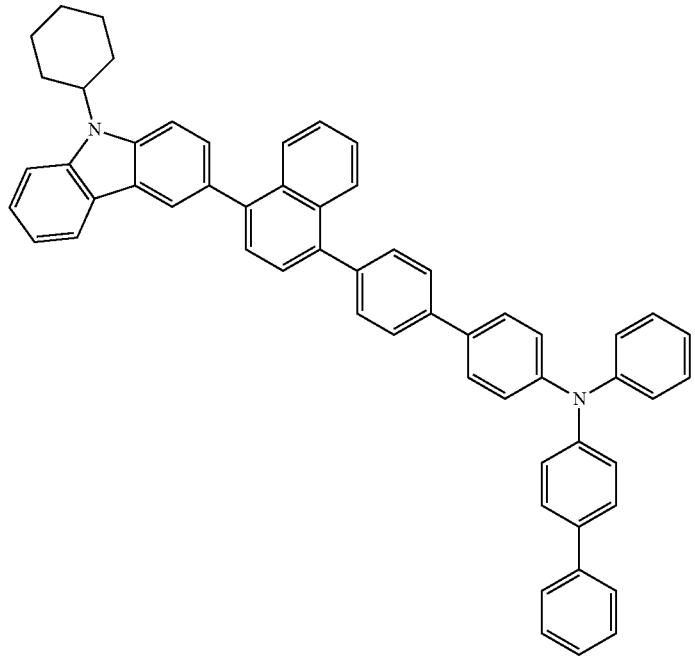
(162)
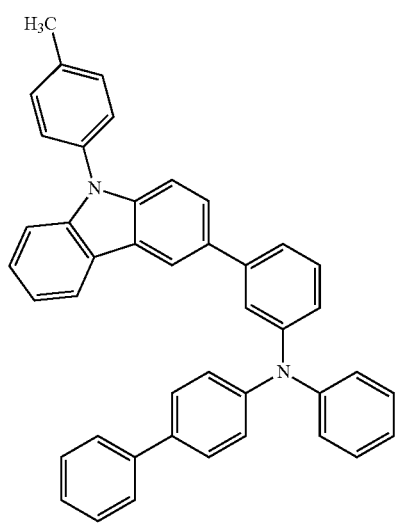
(163)
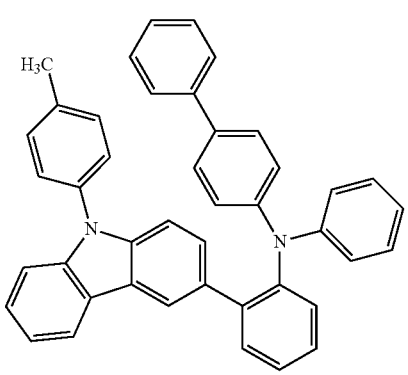
(164)
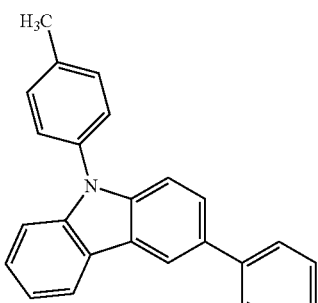

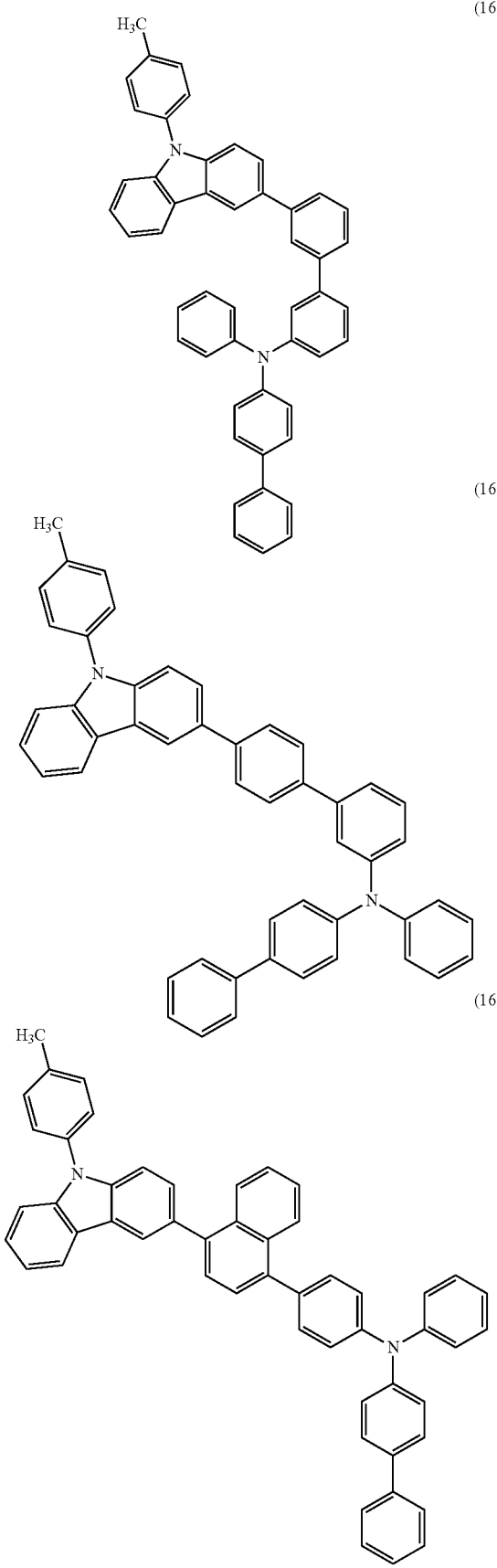
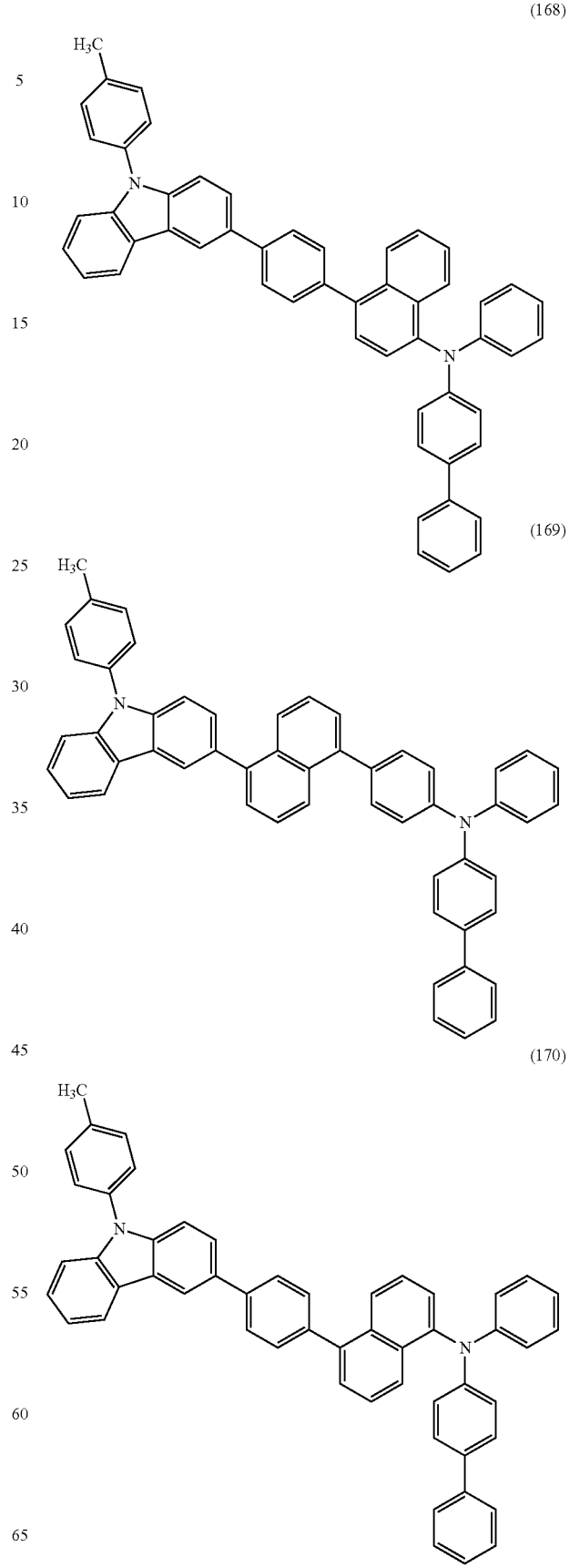

(171)
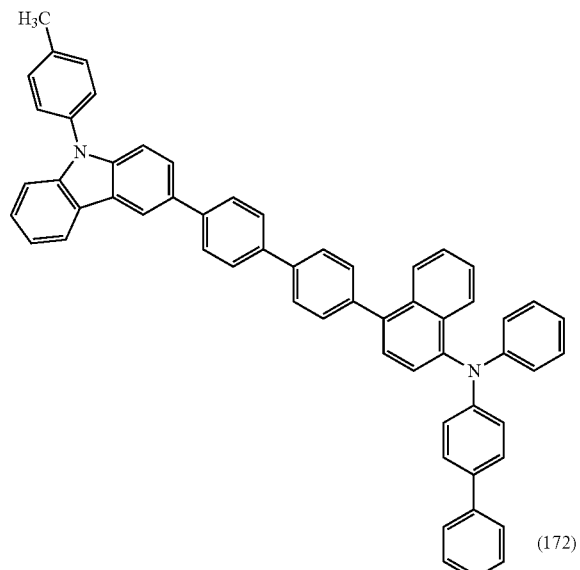
(172)
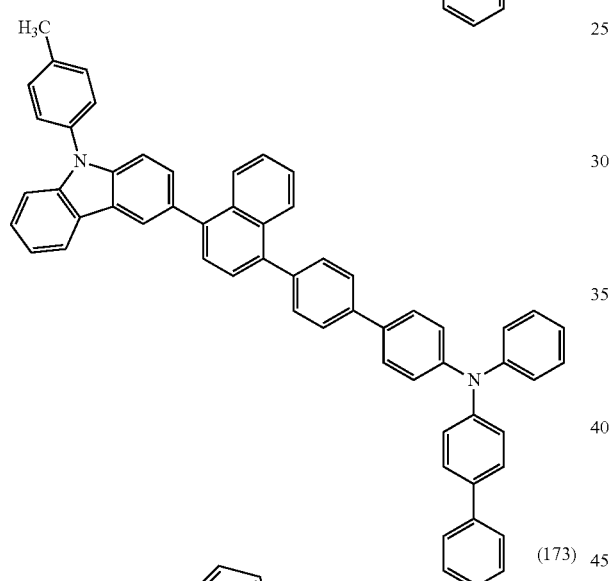
(173)
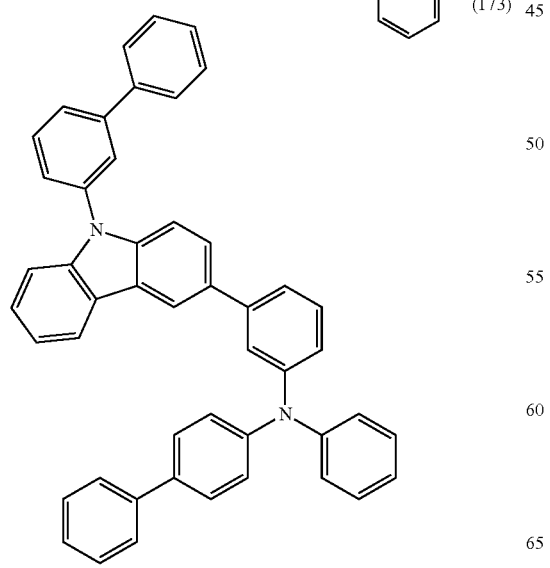
(174)
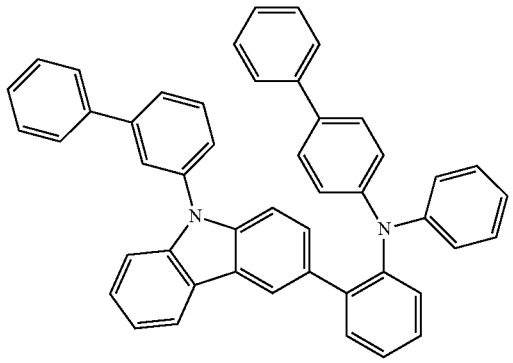
(175)
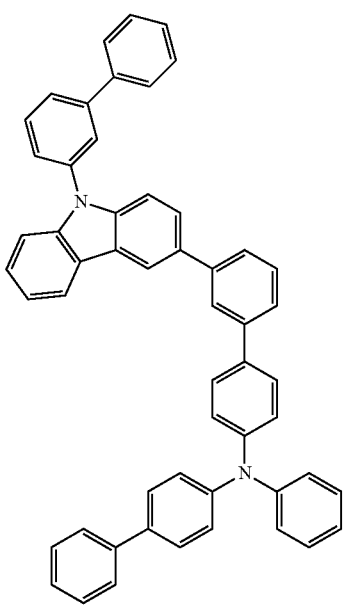
(176)
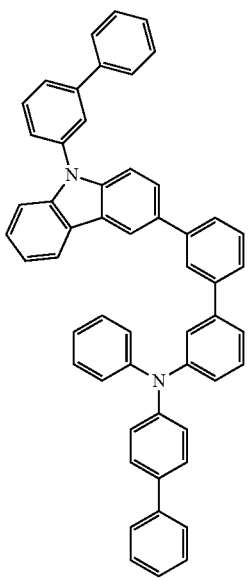

-continued
(177)
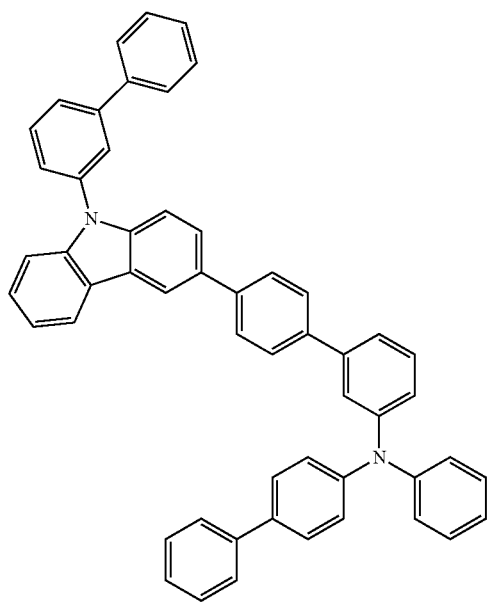
(178)
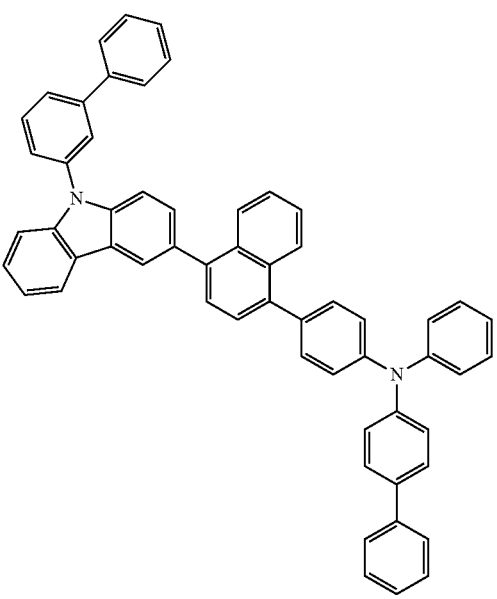
(179)
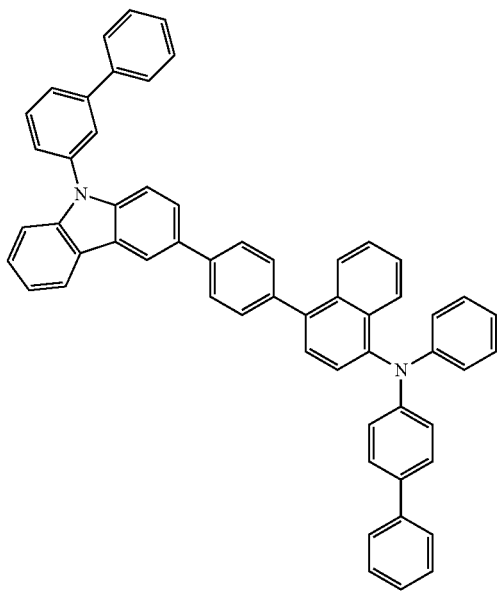
(180)
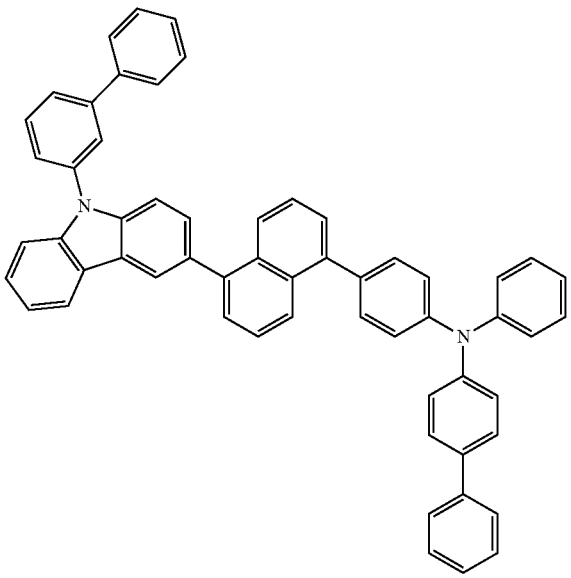

(181)
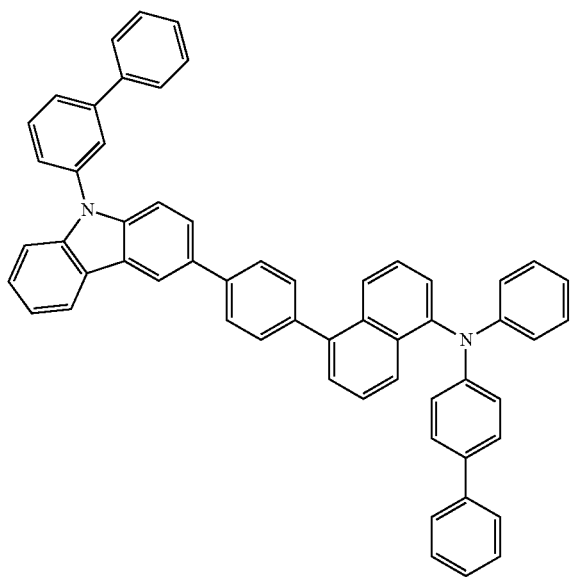
(182)
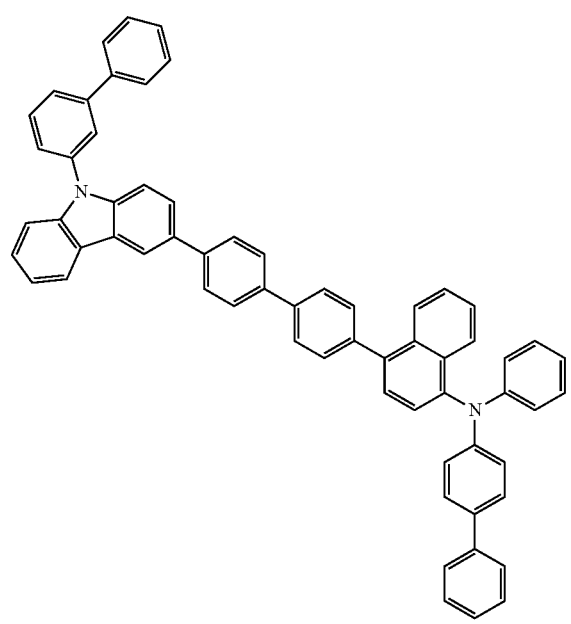
(183)
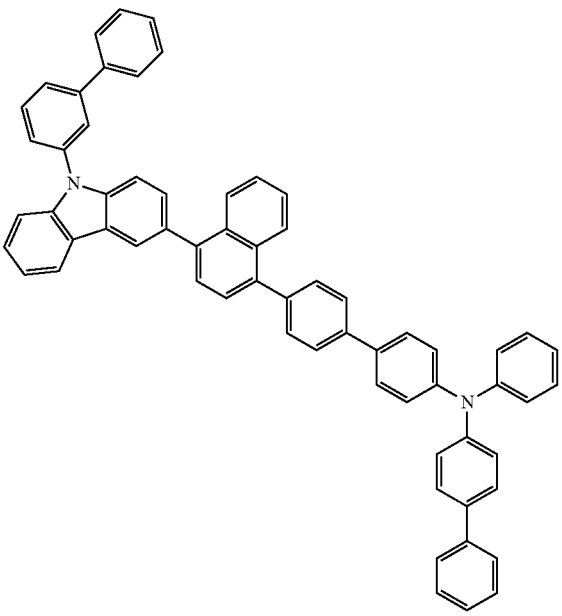
(184)
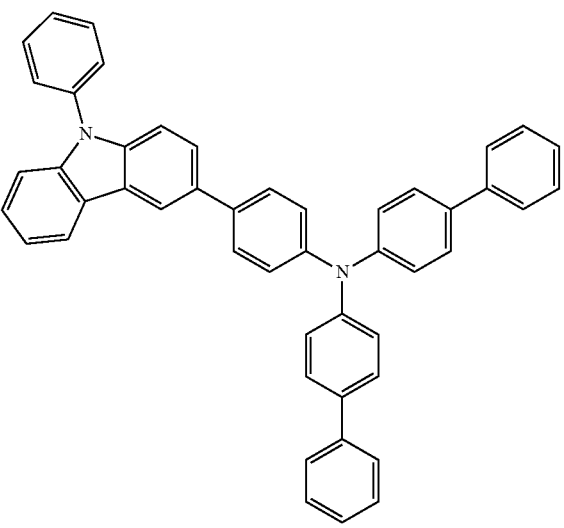

(185)
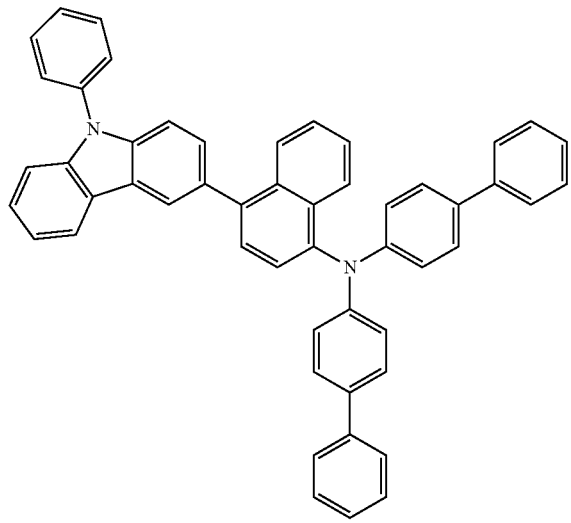
(186)
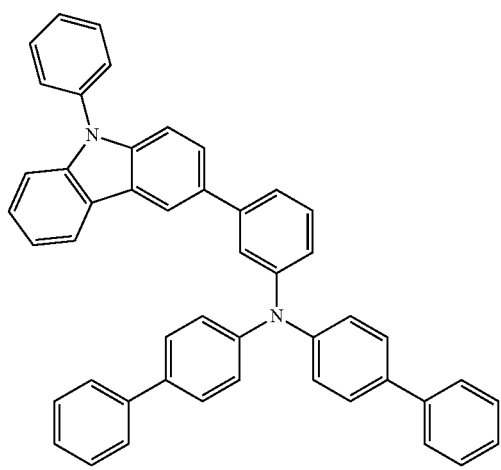
(187)
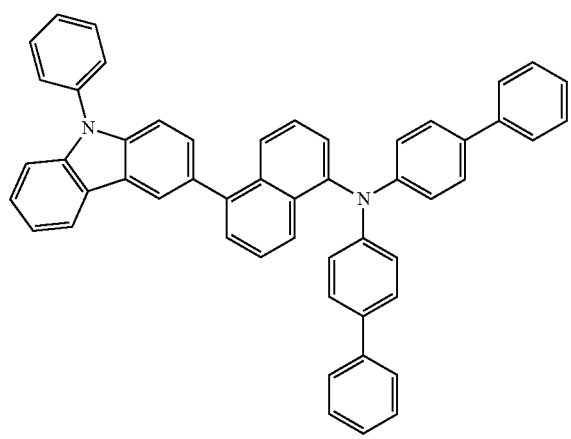
(188)
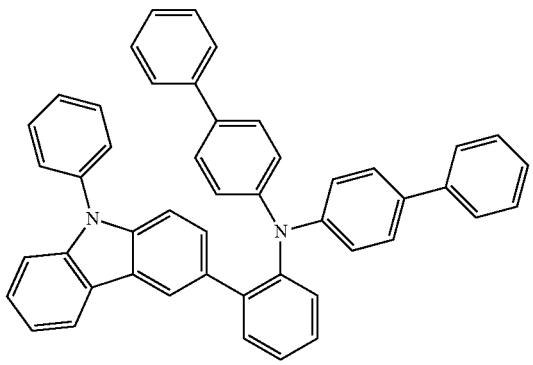
(189)
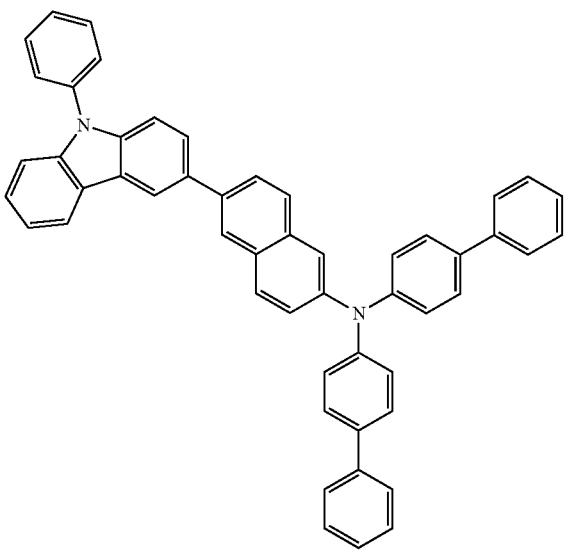
(190)
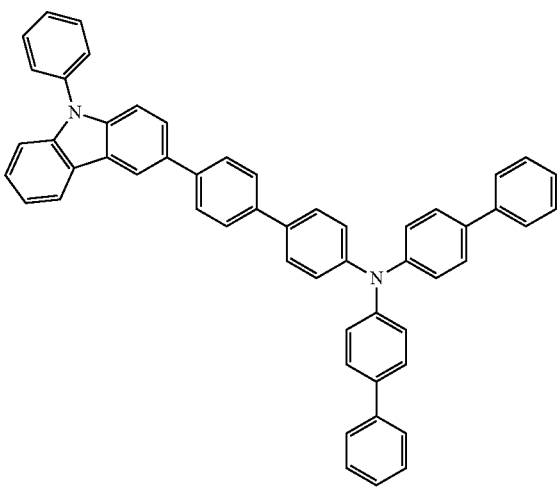

-continued
(191)
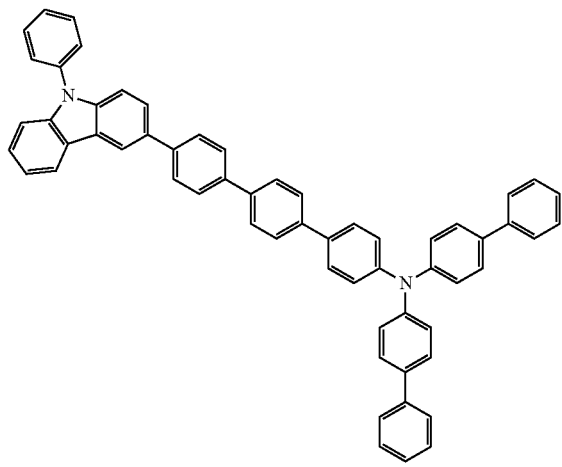
(192)
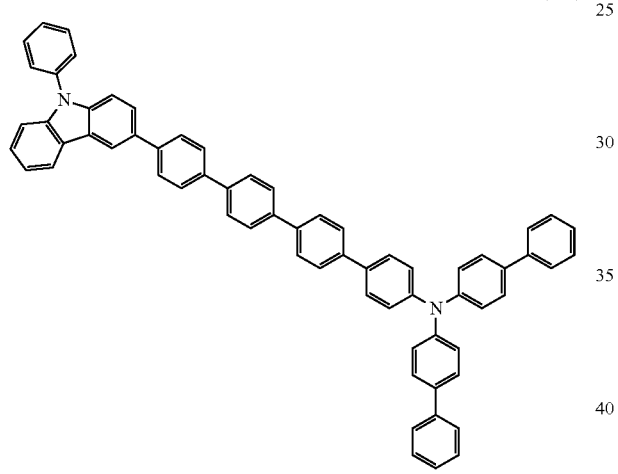
(193)
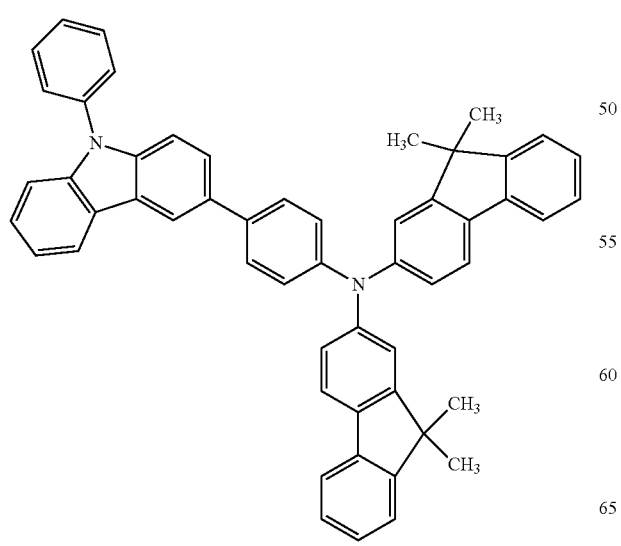
-continued
(194)
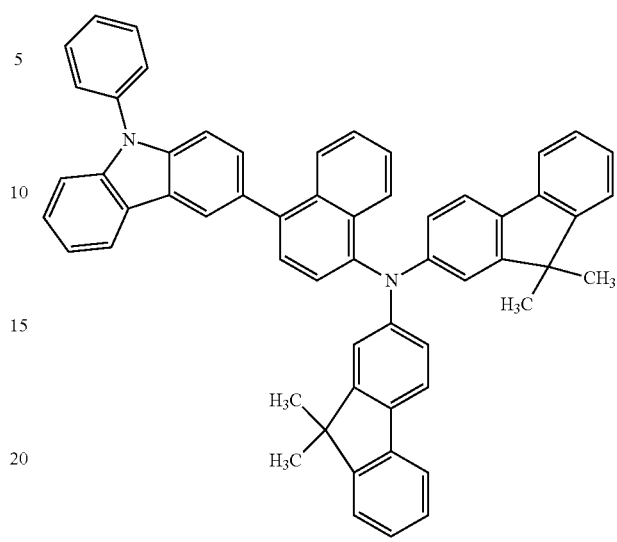
(195)
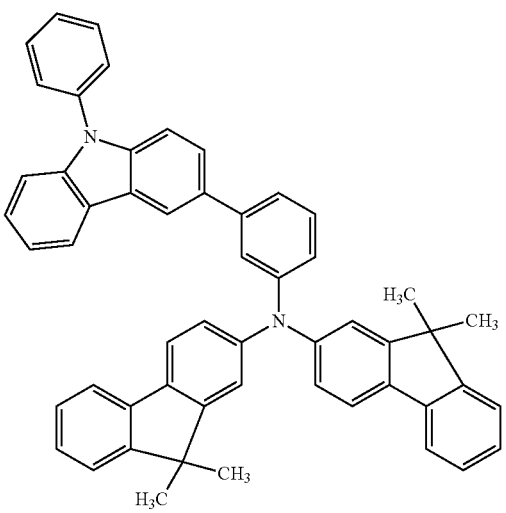
(196)
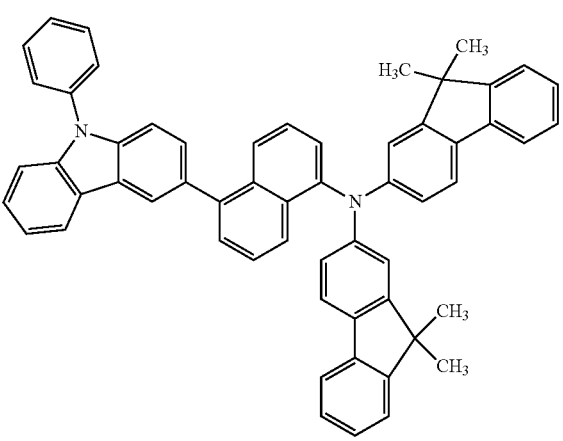

(197)
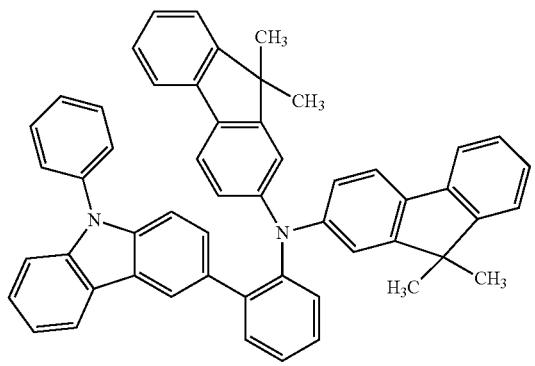
(198)
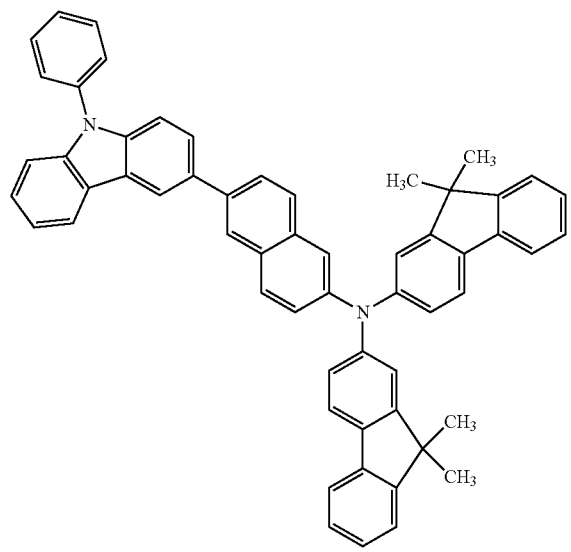
(199)
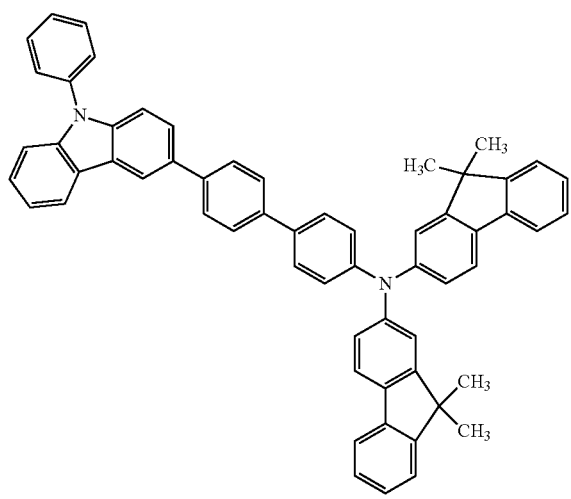
(200)
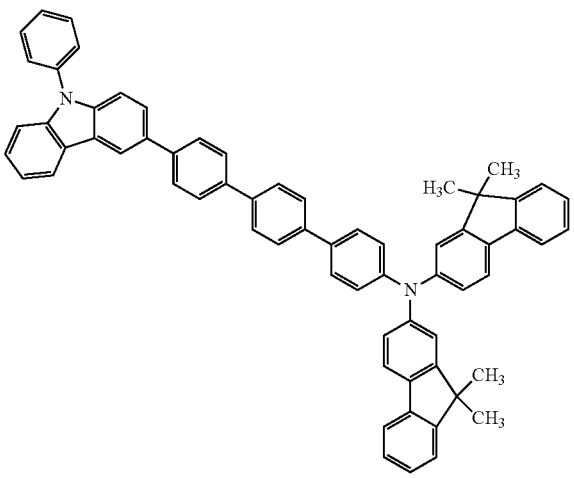
(201)
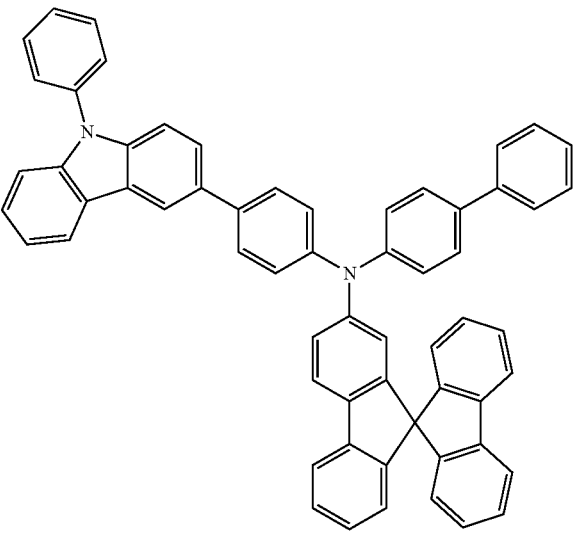
(202)

-continued
(203)
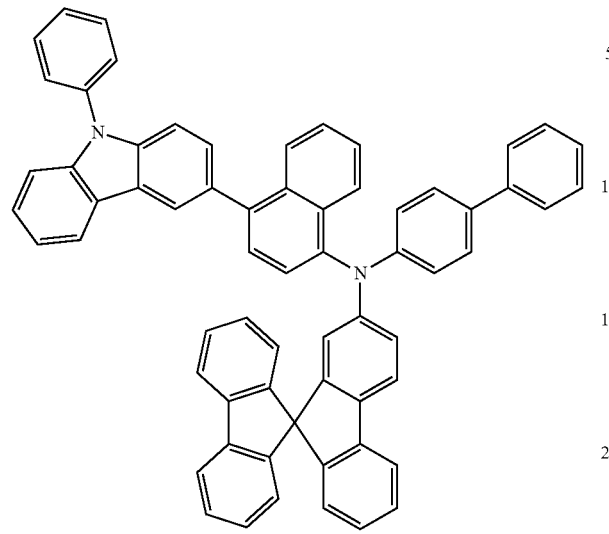
(204)
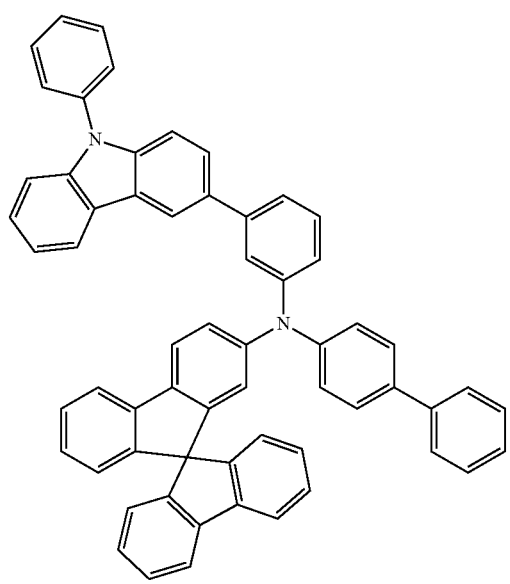
(205)
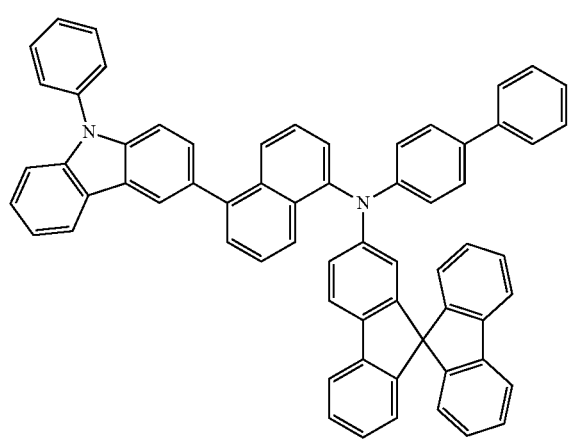
(206)
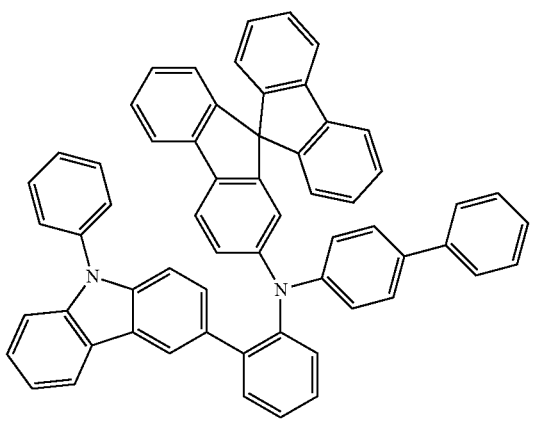
(207)
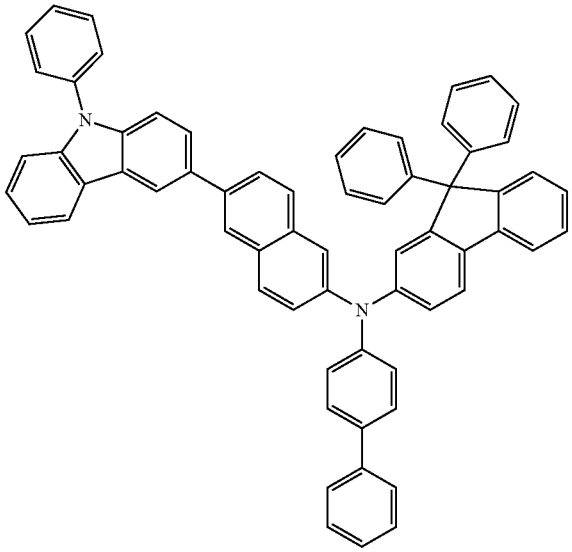
(208)
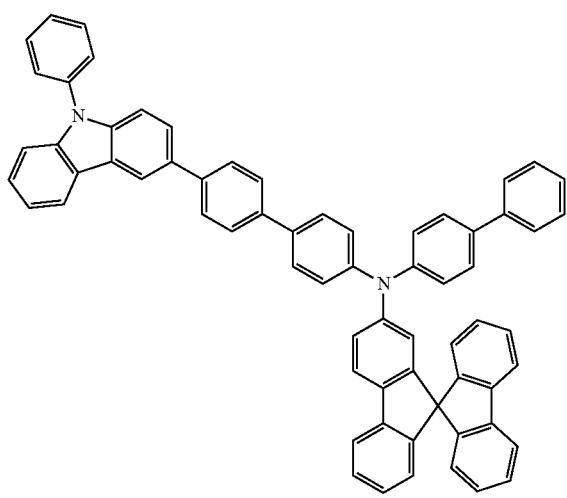

(209)
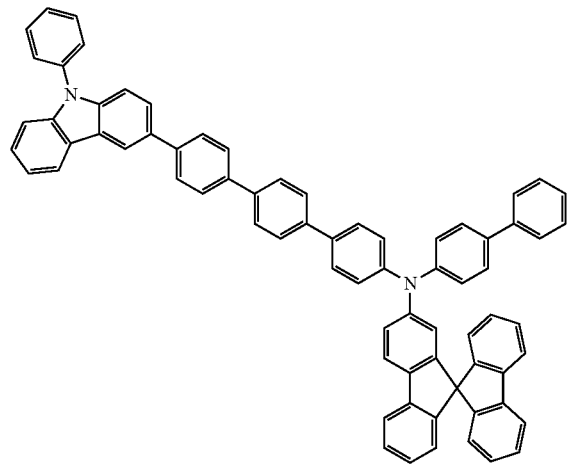
(210)
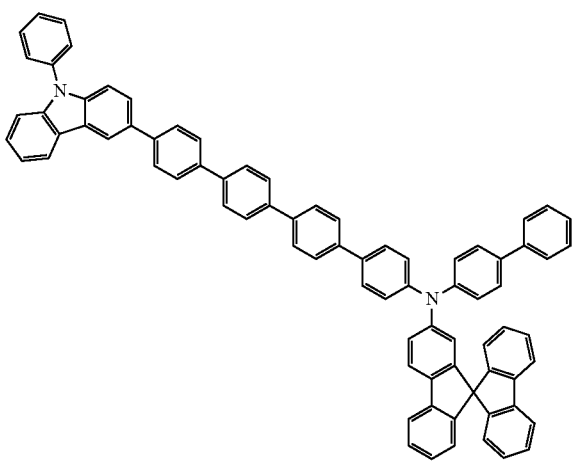
(211)
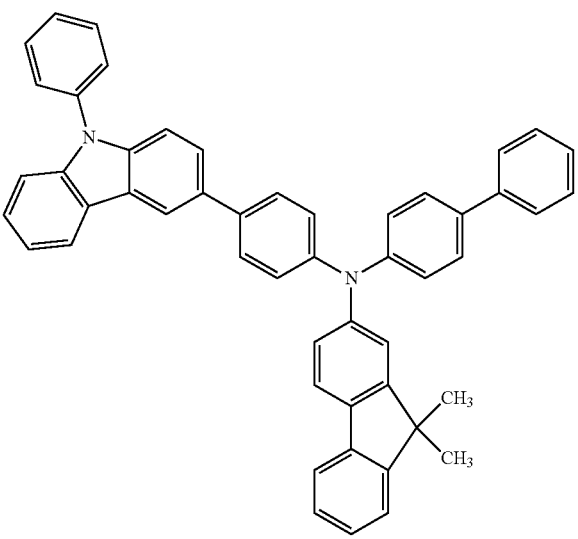
(212)
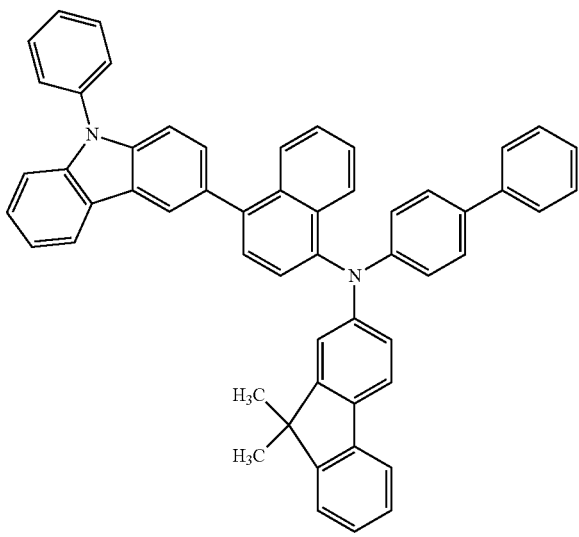
(213)
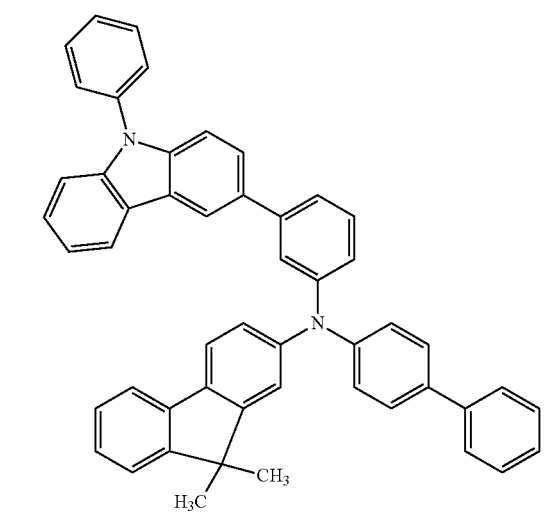
(214)
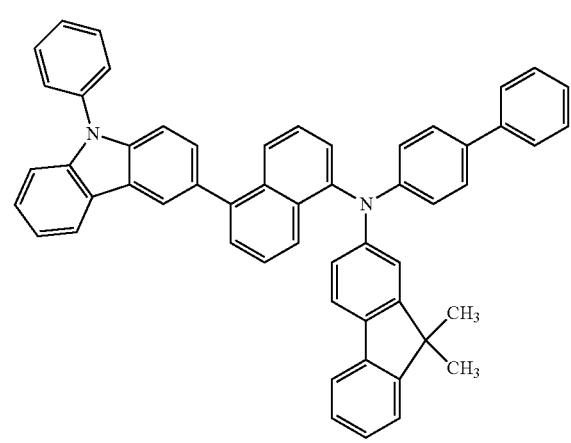

-continued
(215)
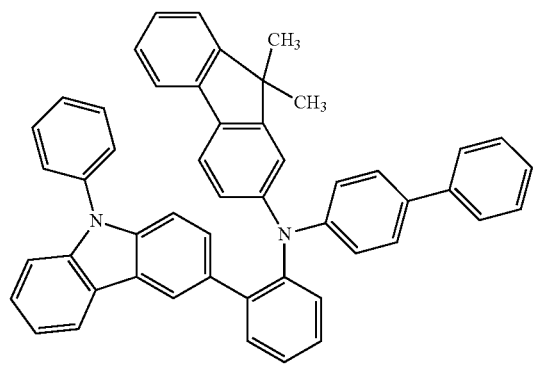
(216)
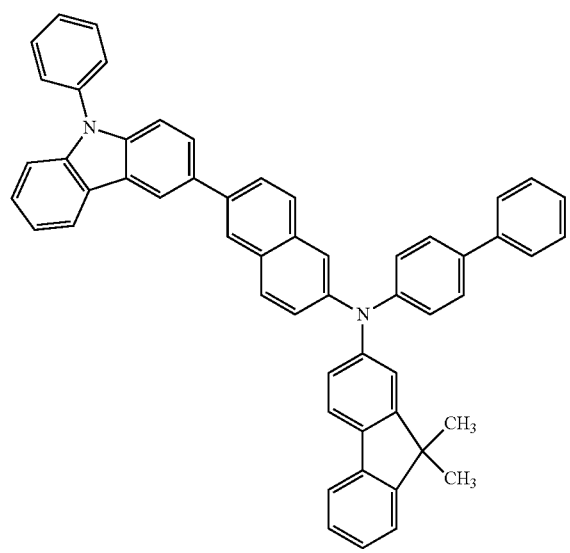
(217)
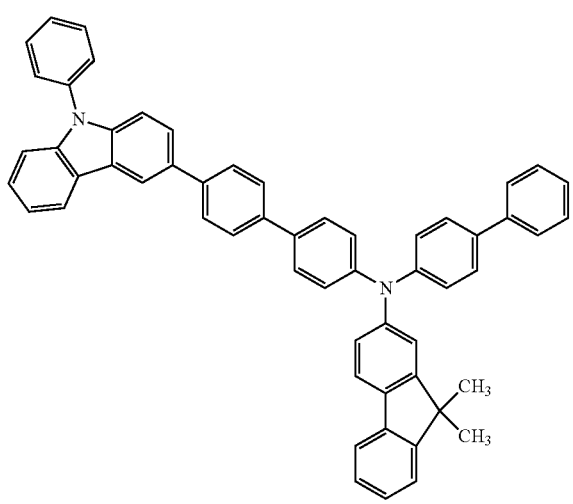
(218)
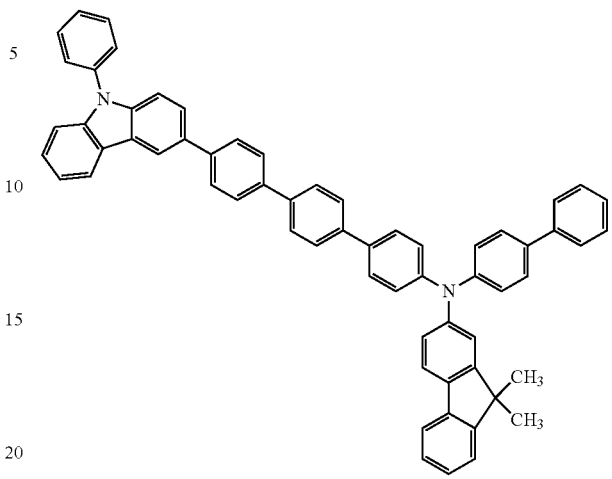
(219)
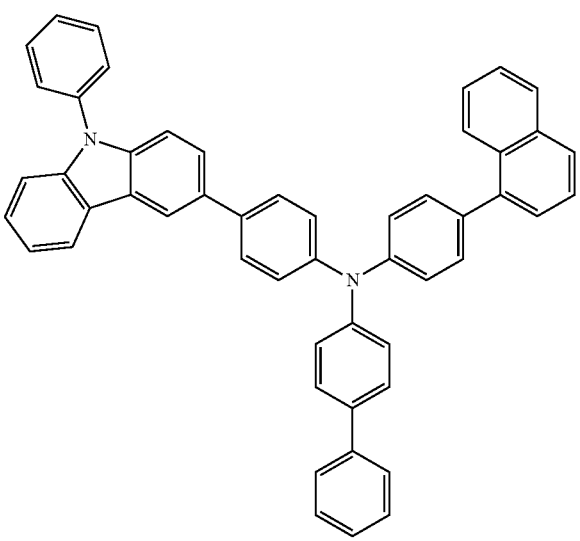
(220)

(221)
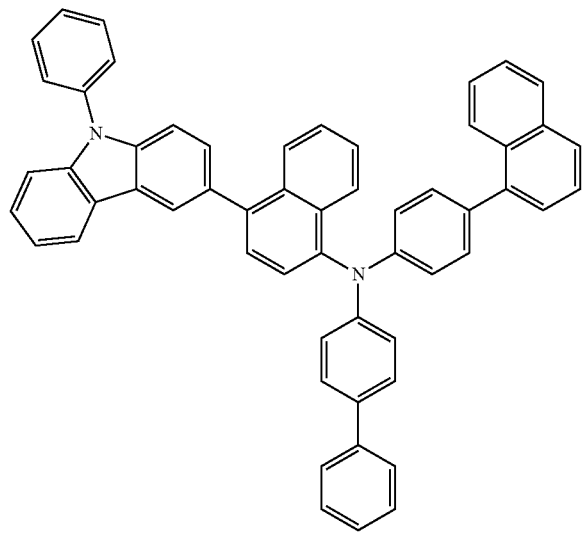
(222)
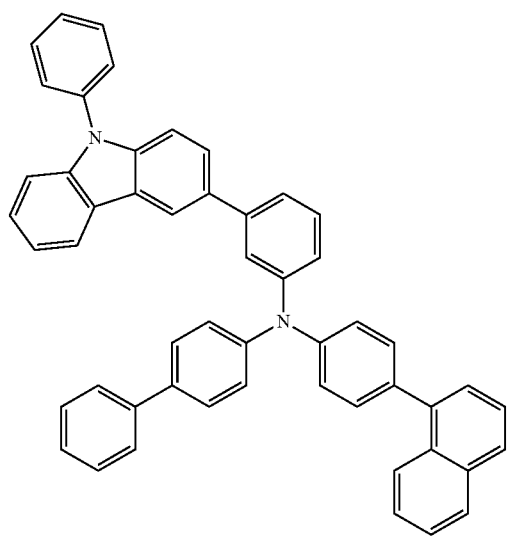
(223)
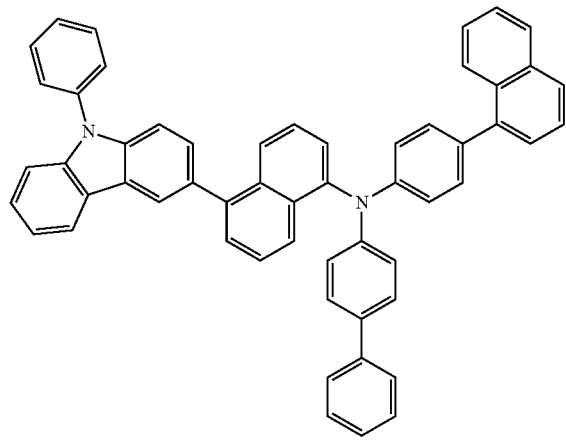
(224)
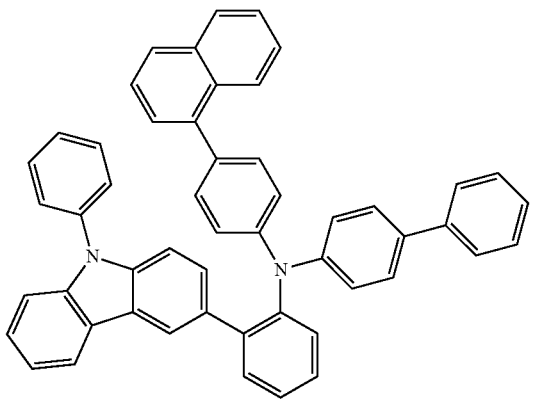
(225)
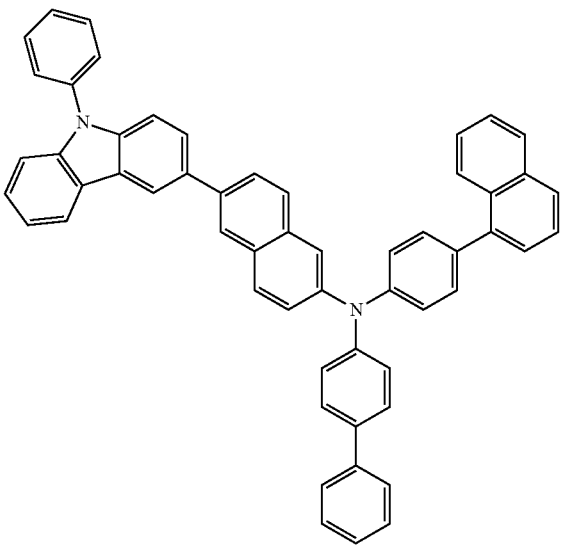
(226)
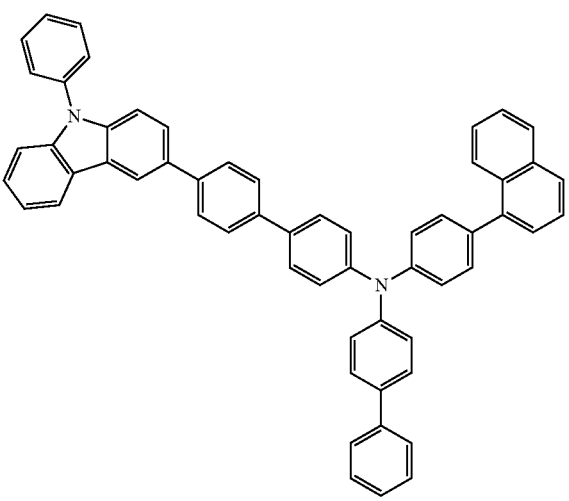

(227)
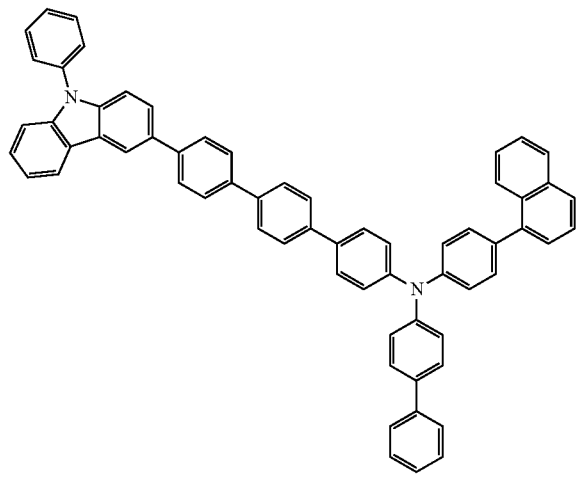
(228)
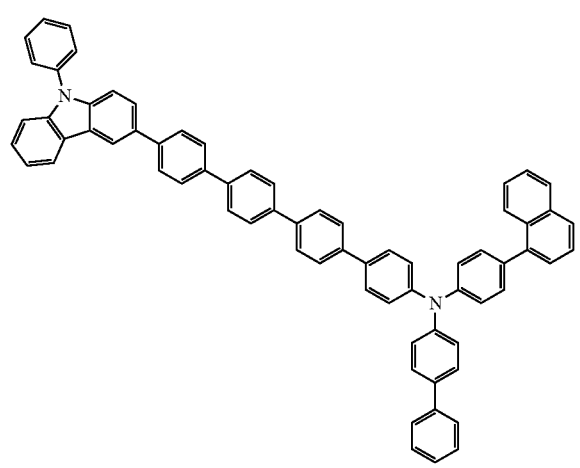
(229)
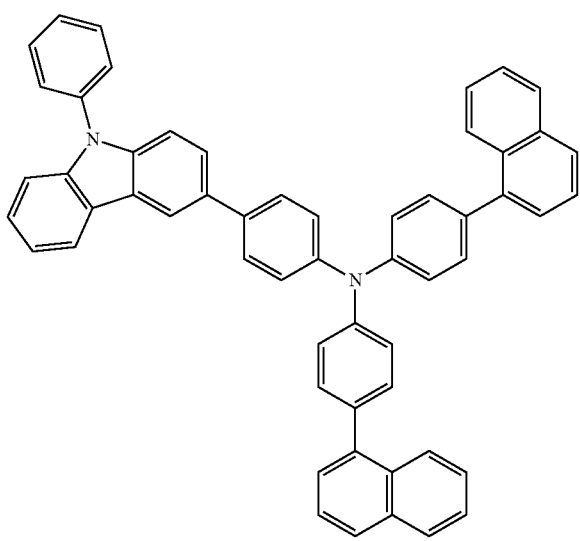
(230)
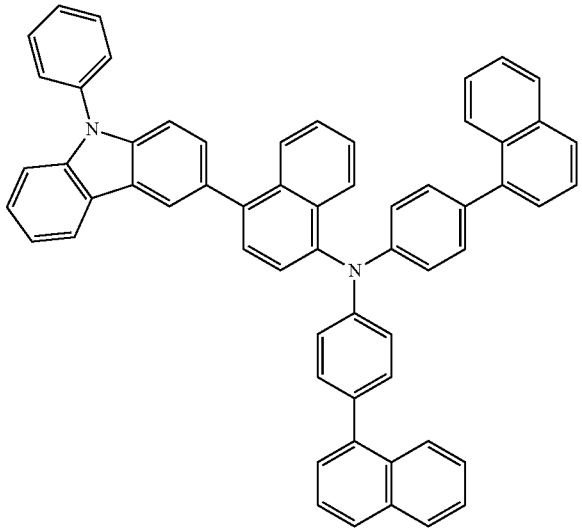
(231)
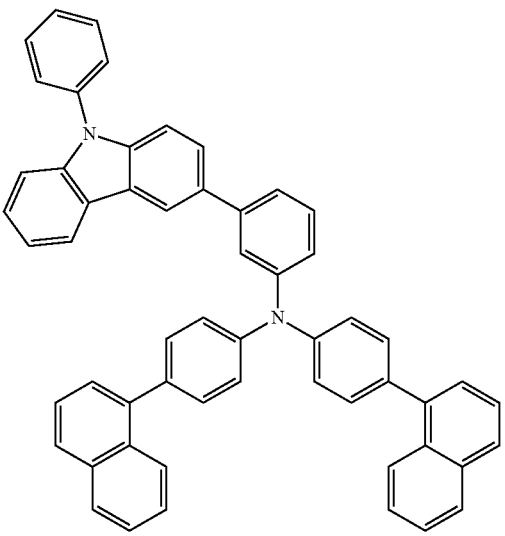
(232)
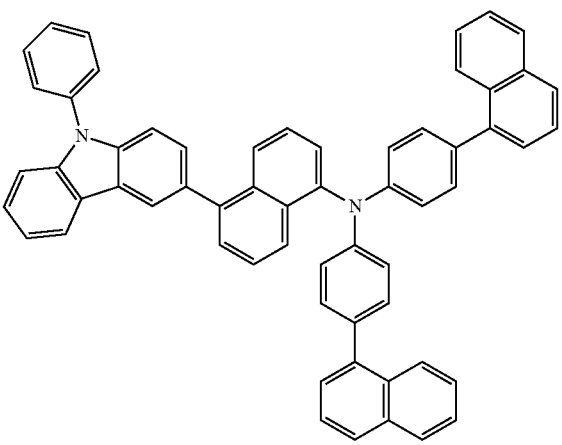

(233)
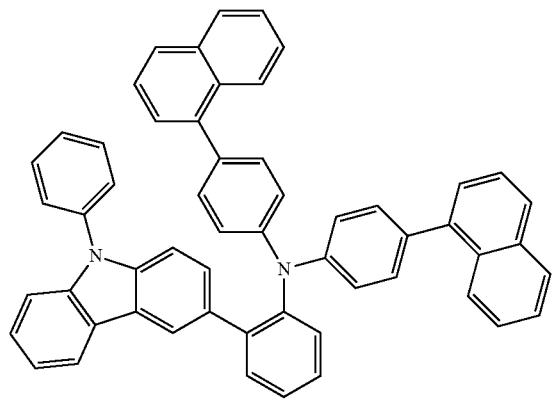
(234)
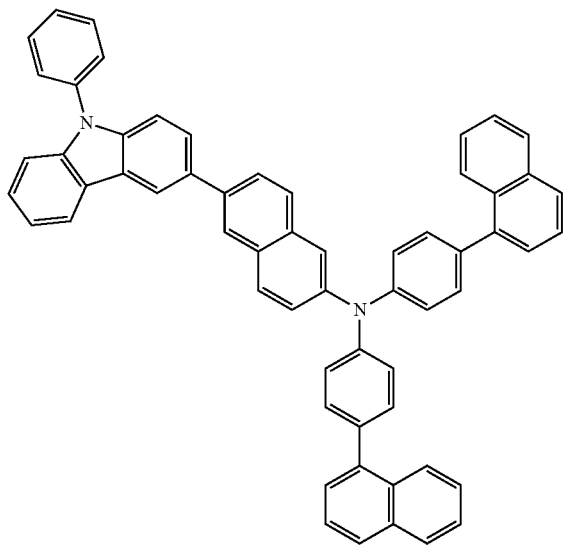
(235)
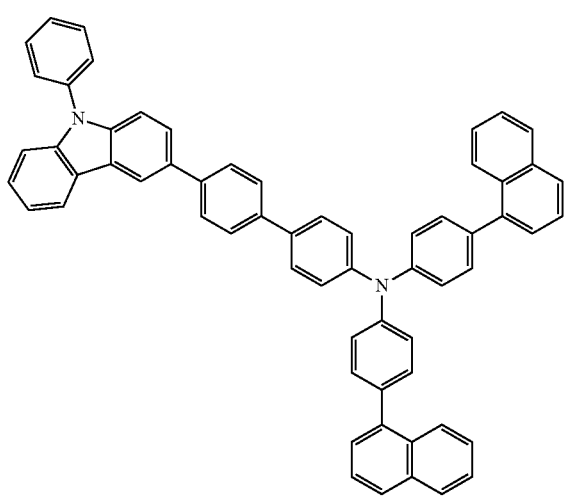
(236)
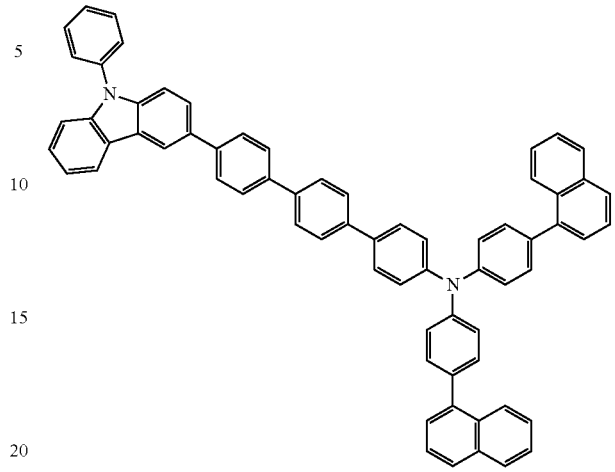
(237)
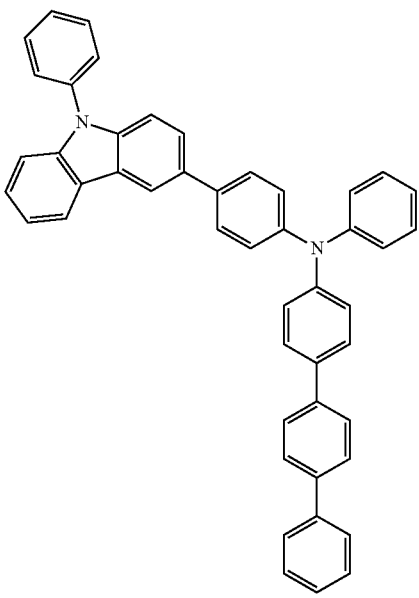
(238)

-continued
(239)
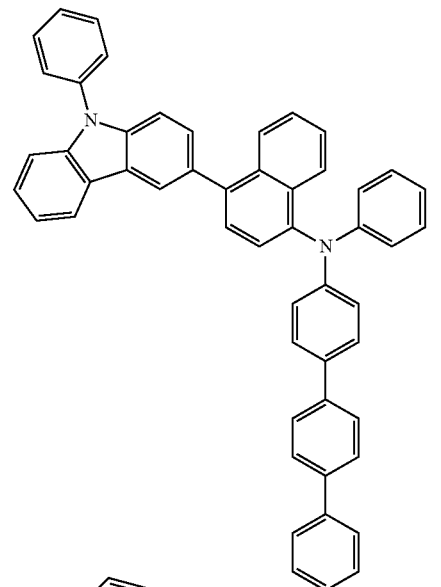
(240)
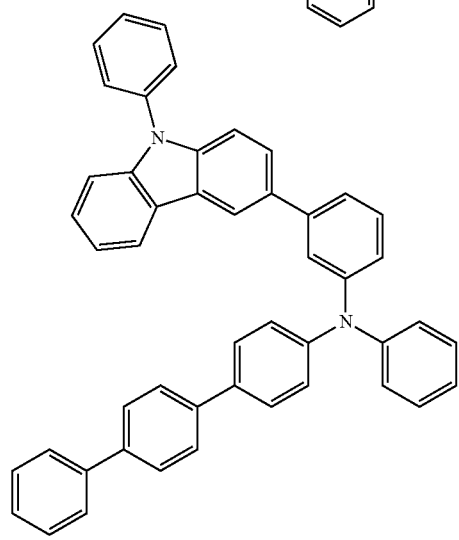
(241)
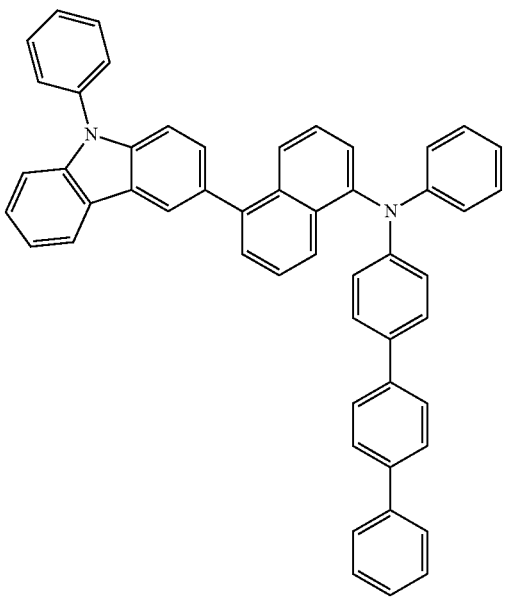
-continued
(242)
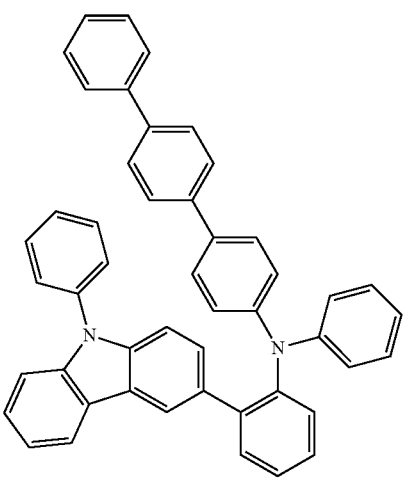
(243)
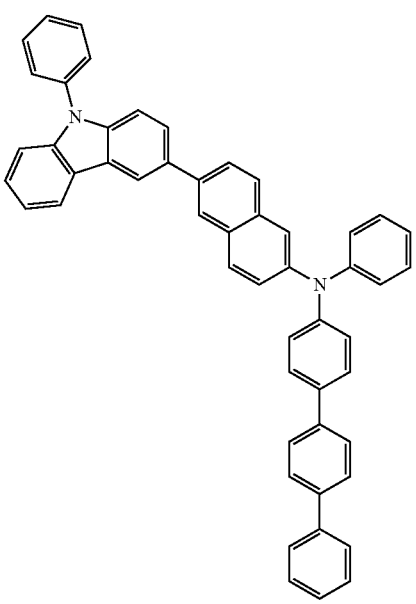
(244)
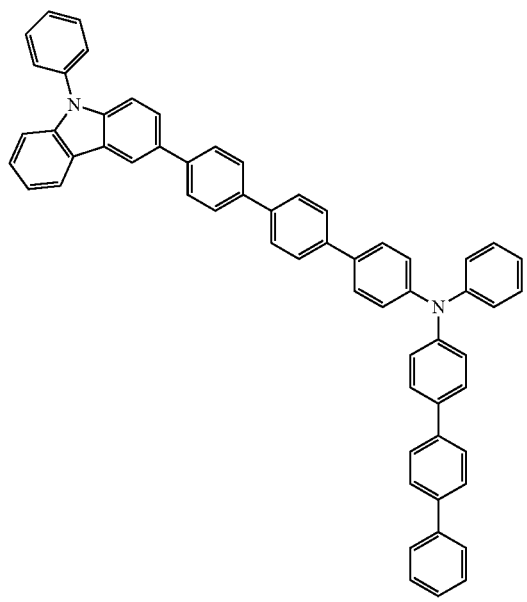

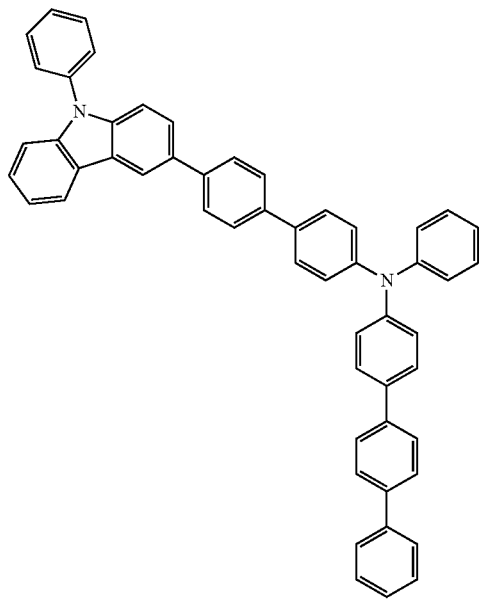
(245)
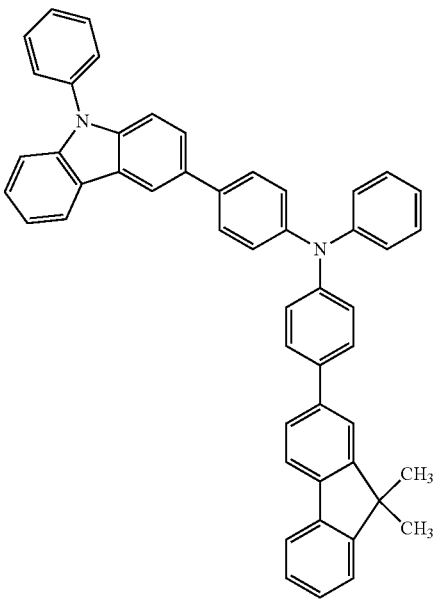
(247)
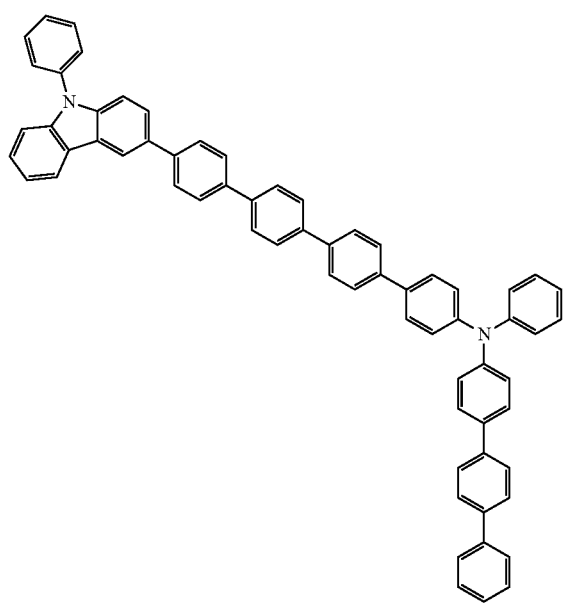
(246)
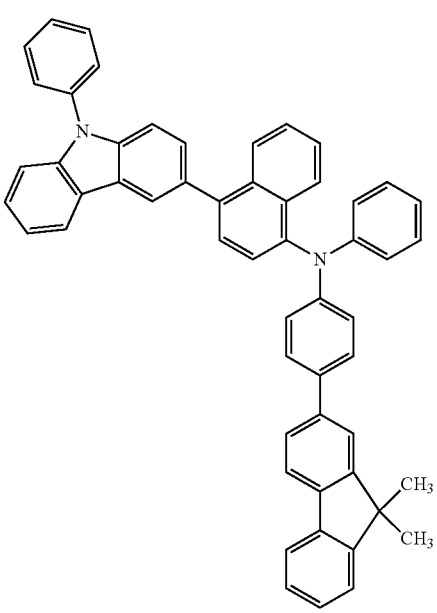
(248)

(249)
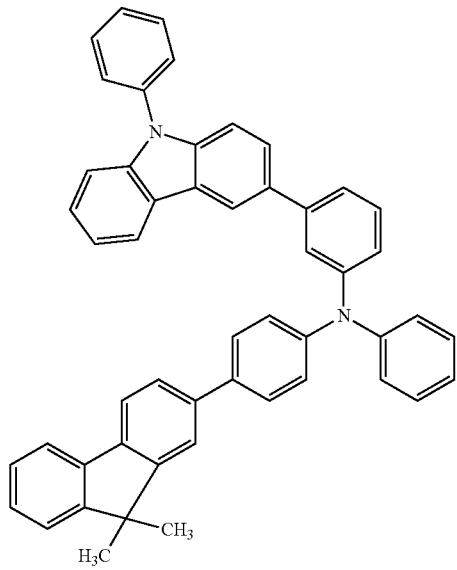
(250)
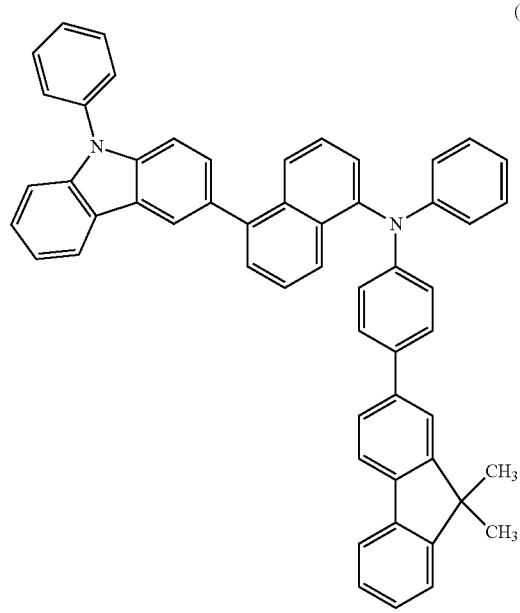
(251)
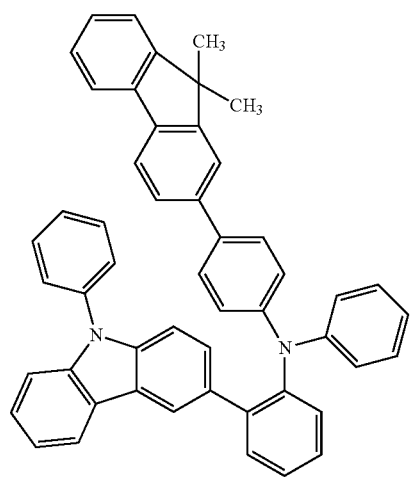
(252)
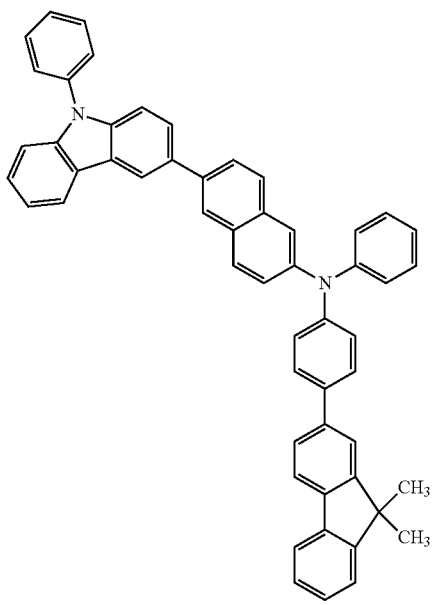
(253)
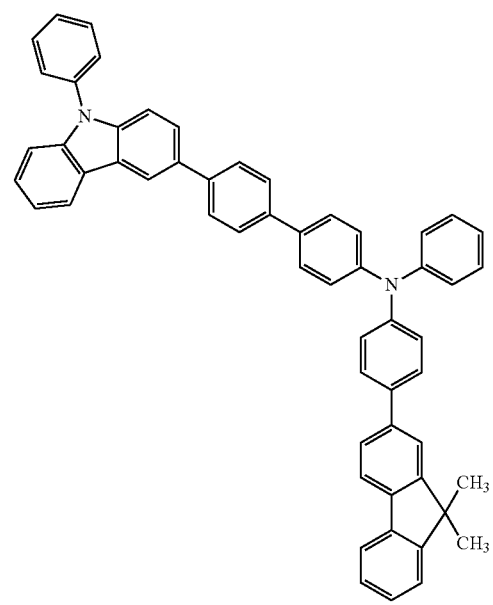

(254)
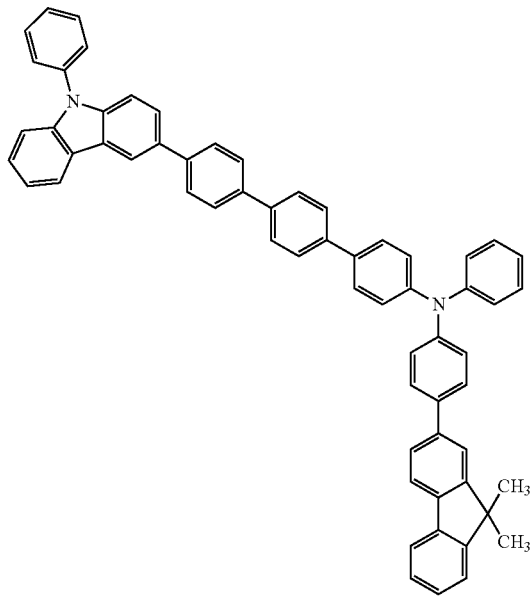
(255)
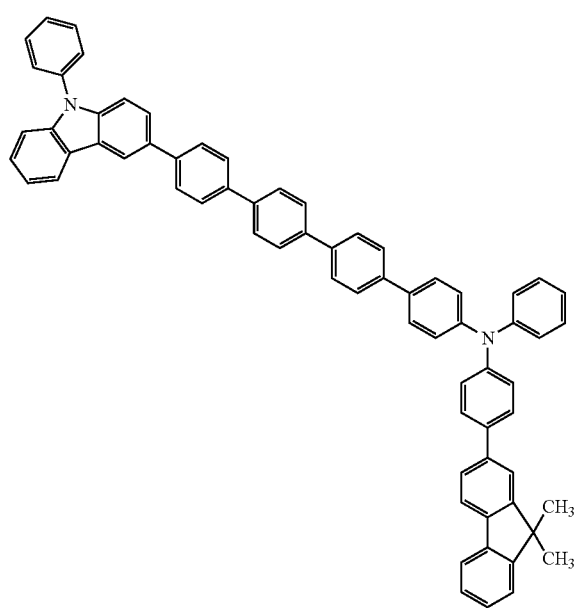
(256)
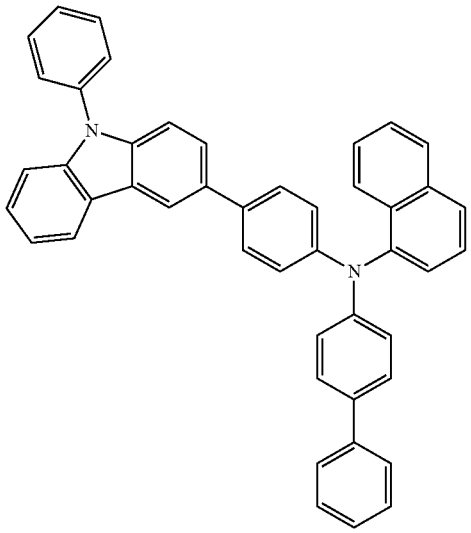
(257)
(258)
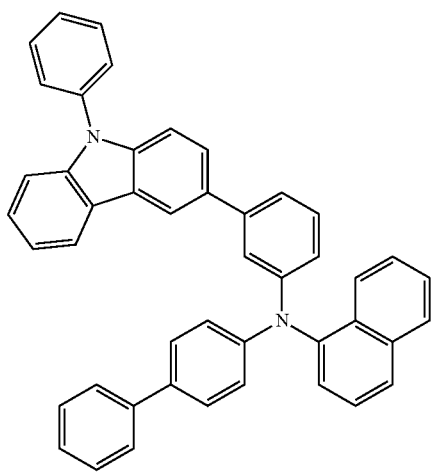

(259)
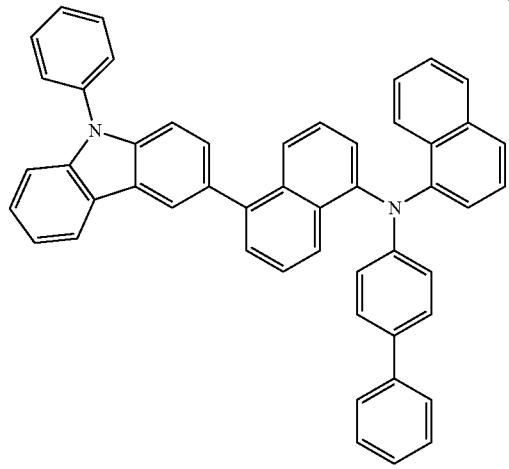
(260)
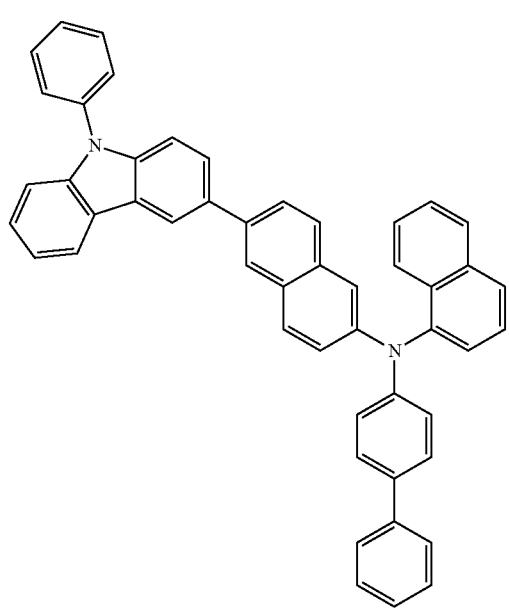
(261)
(262)
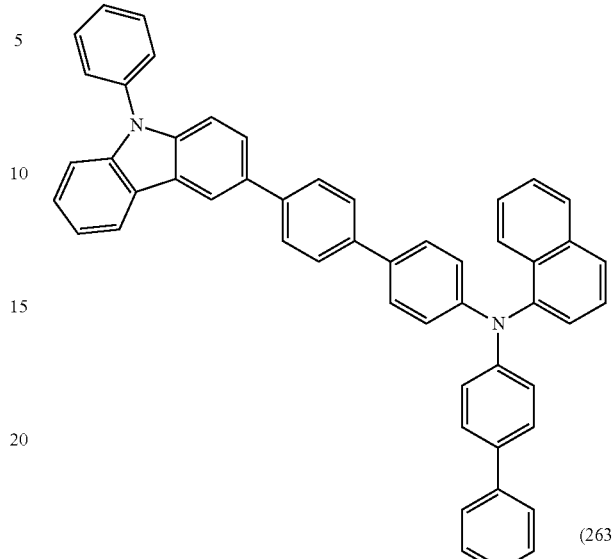
(263)
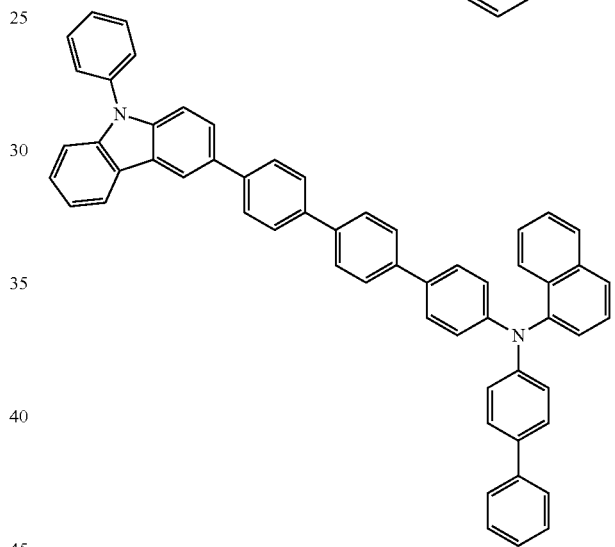
(264)
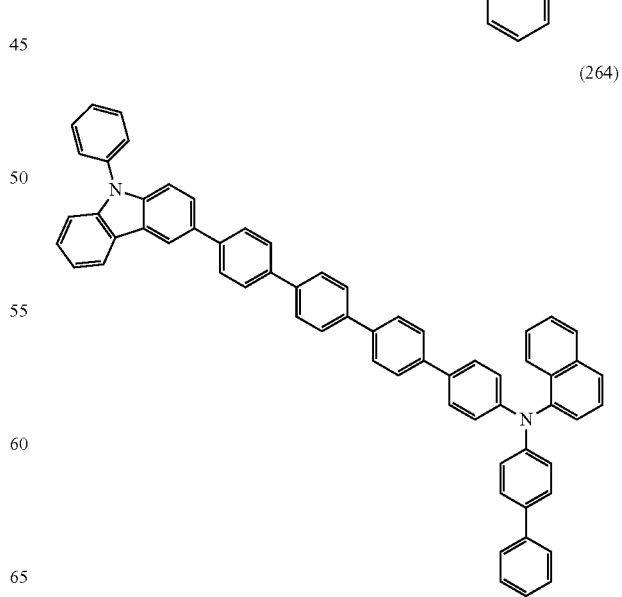

(265)
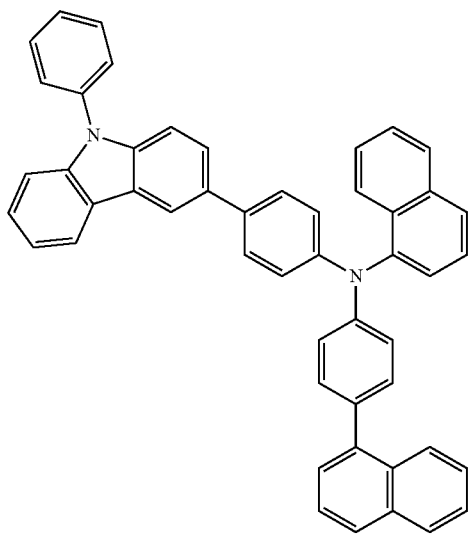
(266)
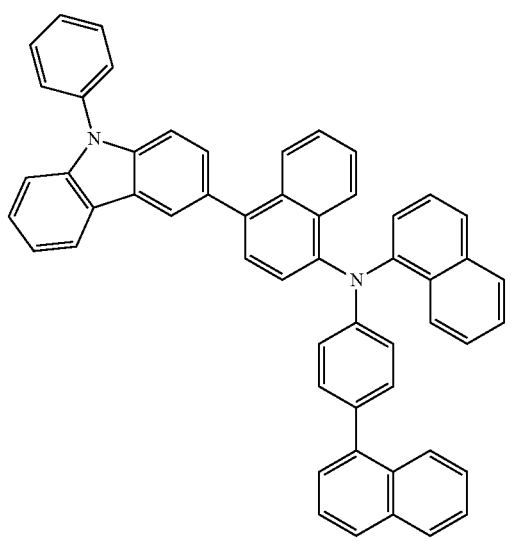
(267)
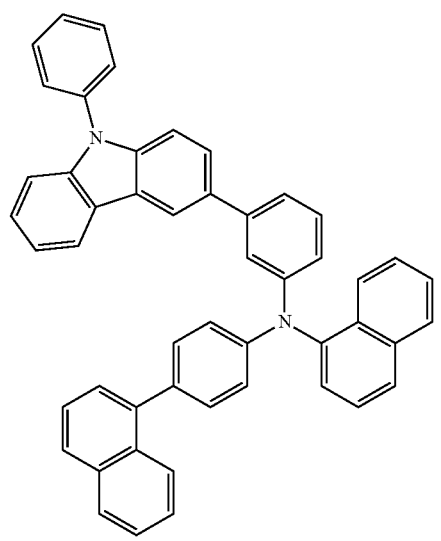
(268)
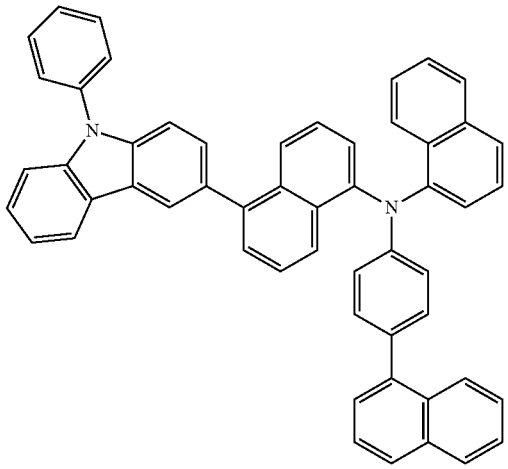
(269)
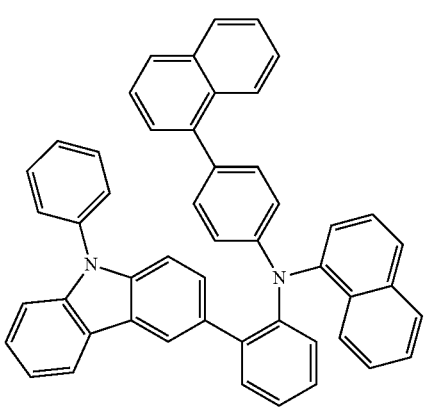
(270)
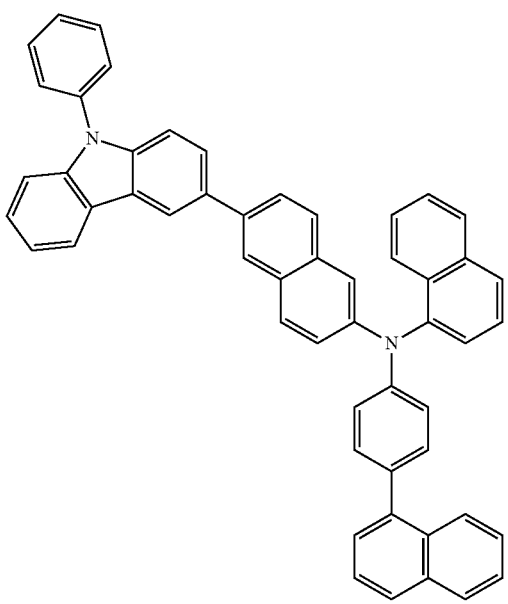

(271)
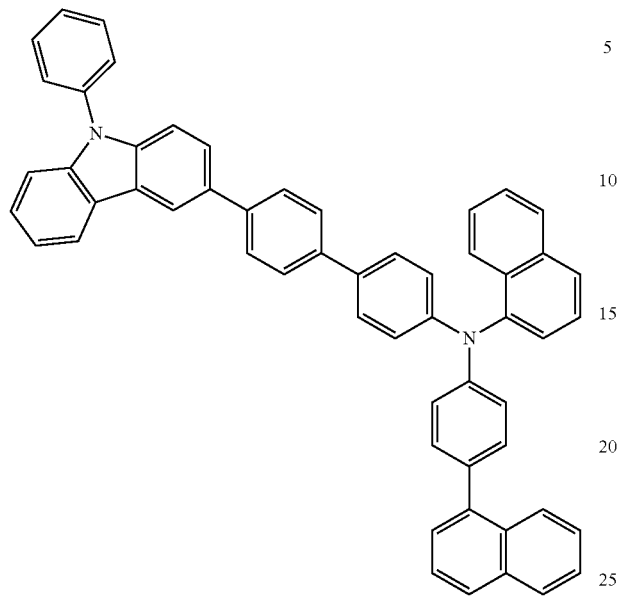
(272)
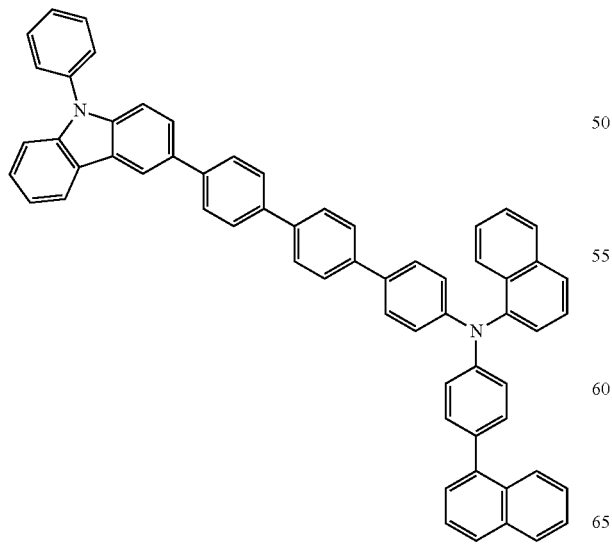
(273)
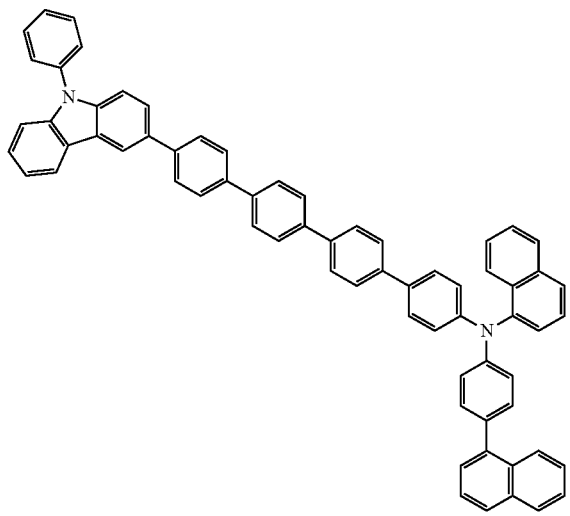
(274)
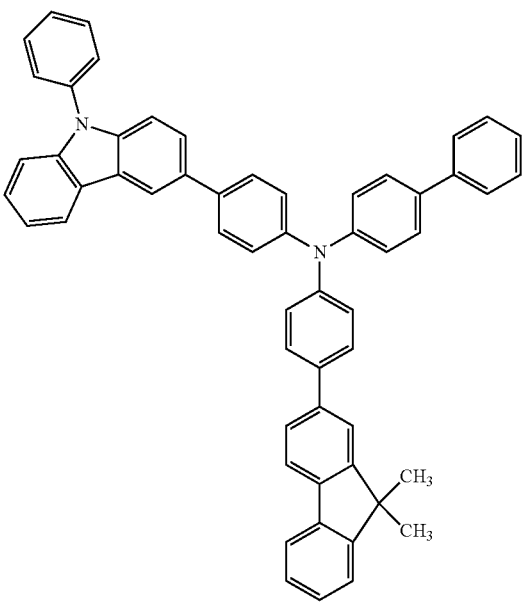

(275)
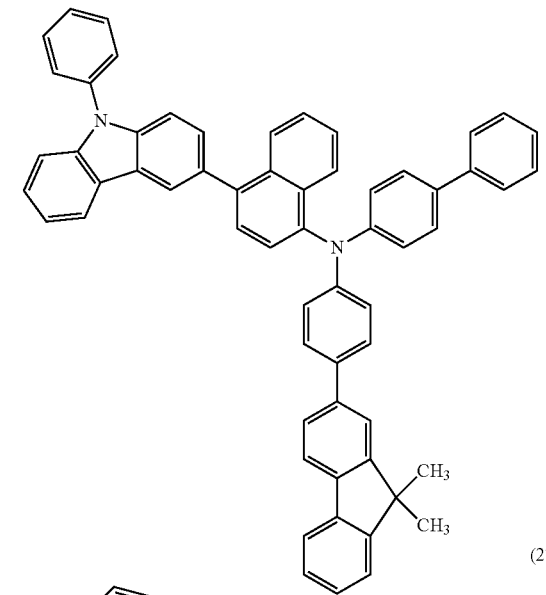
(276)
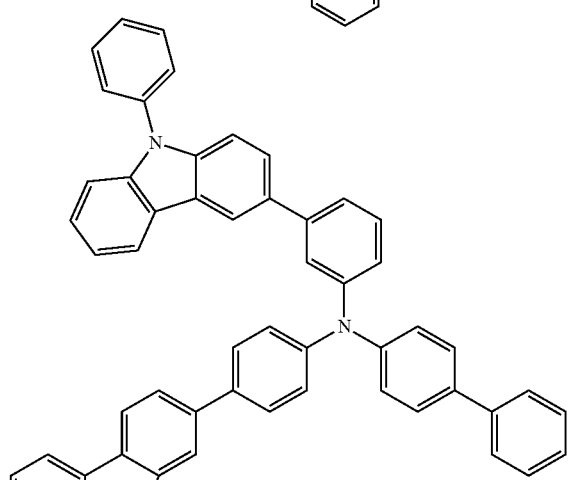
(277)
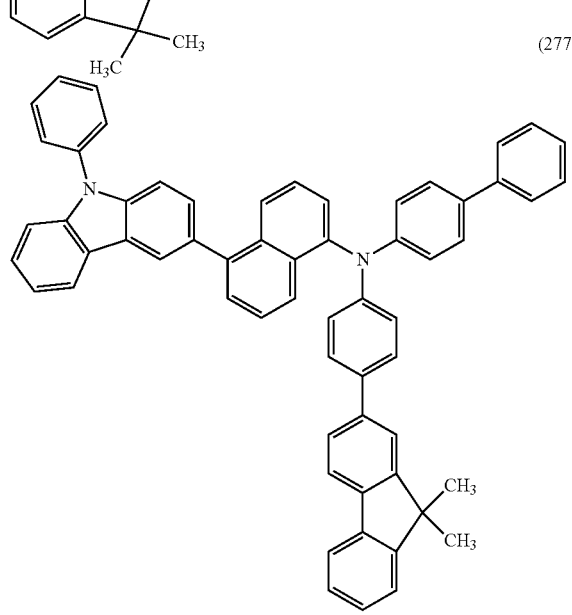
(278)
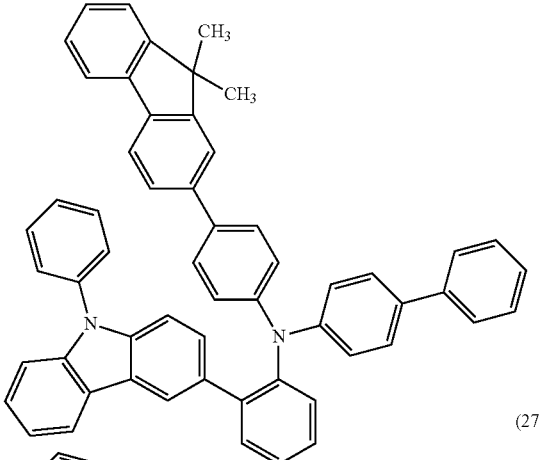
(279)
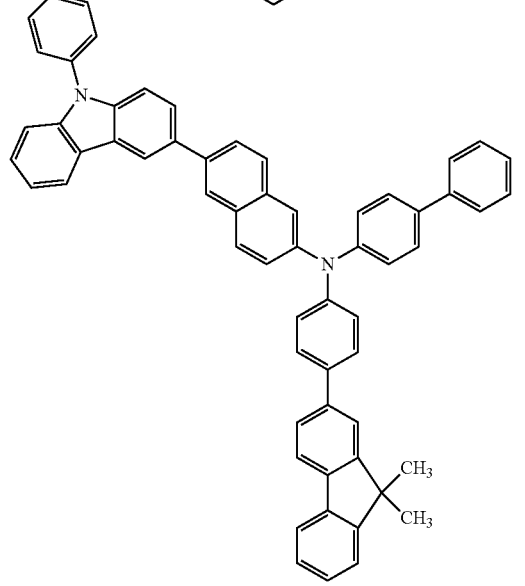
(280)
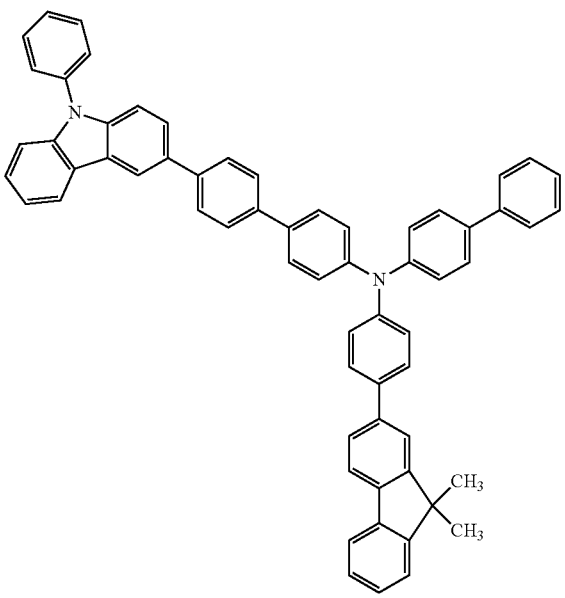

(281)
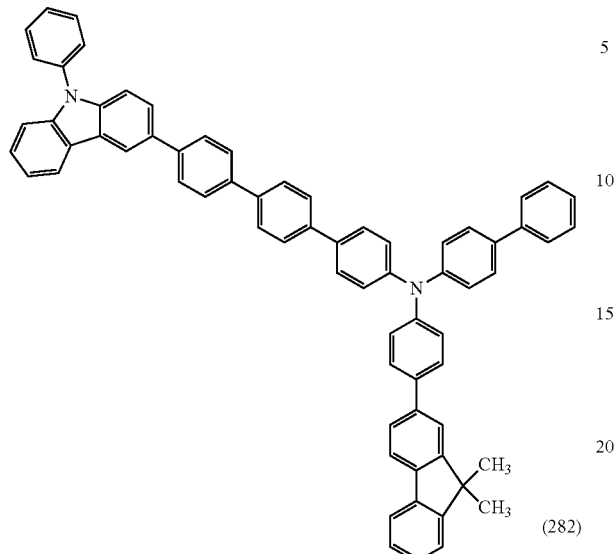
(282)
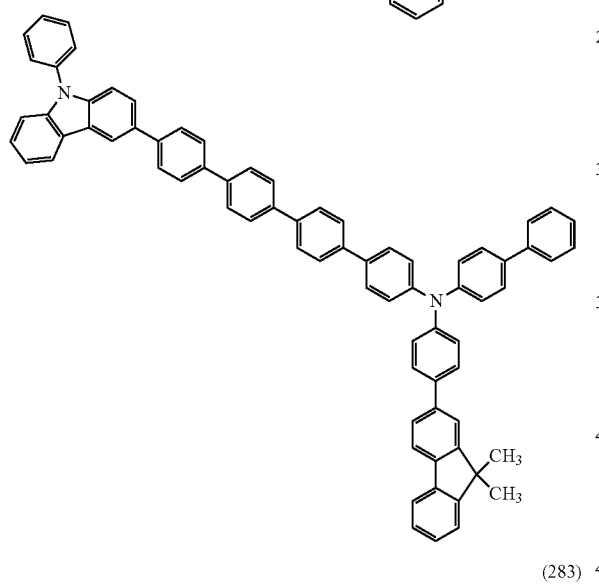
(283)
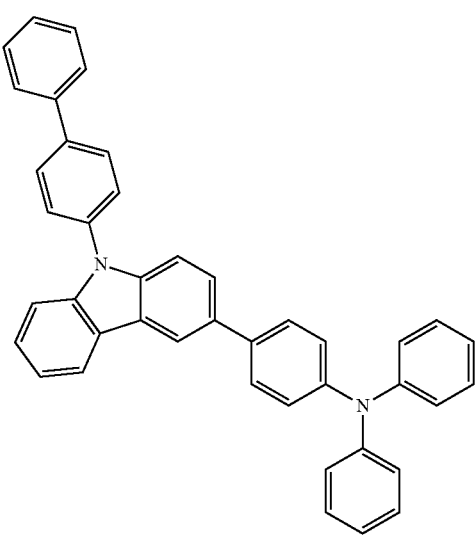
(284)
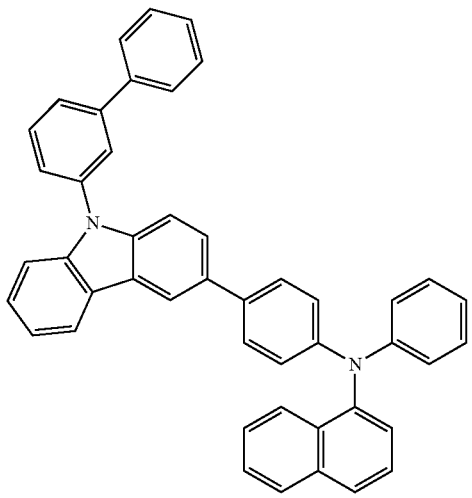
(285)
(286)
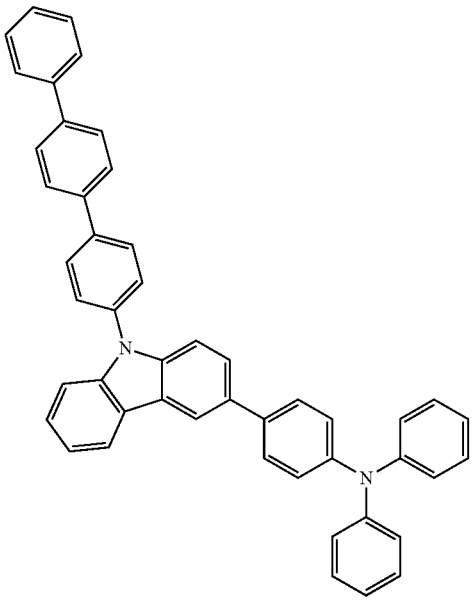

(287)
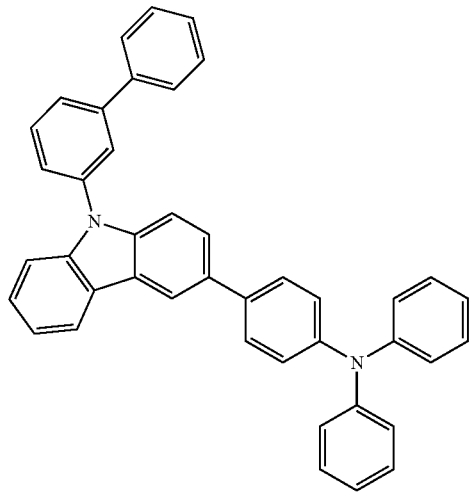
(288)
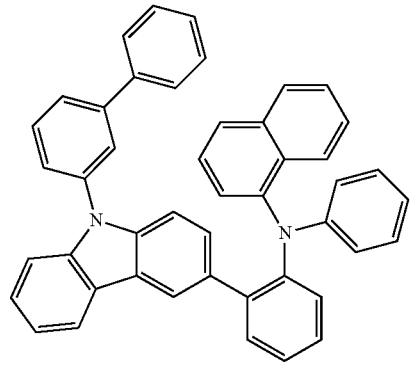
(289)
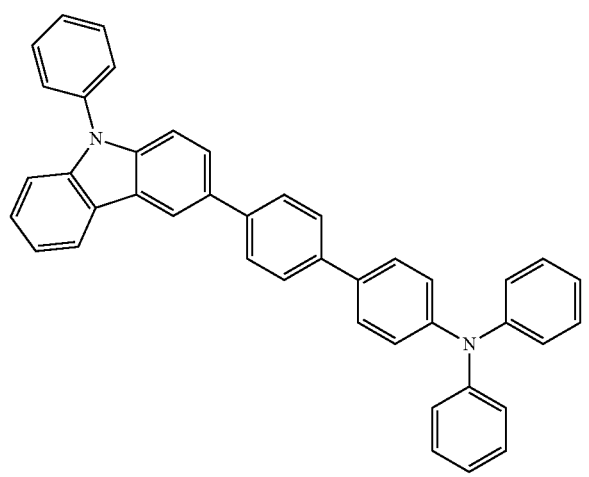
(290)
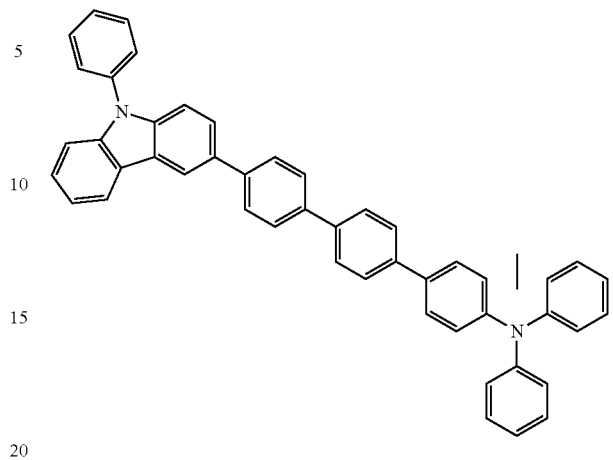
(291)
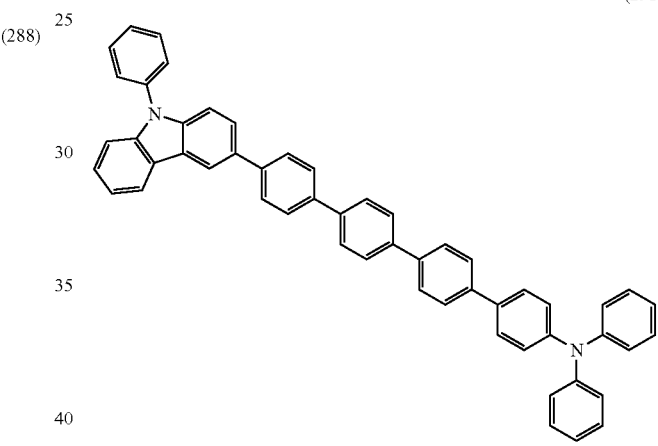
(292)
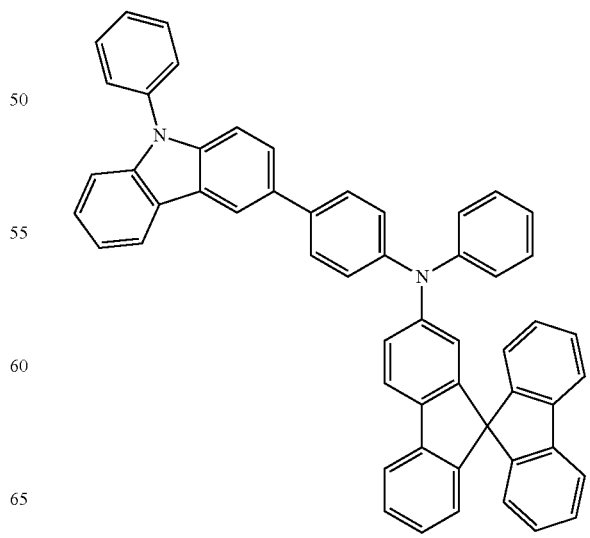

(293)
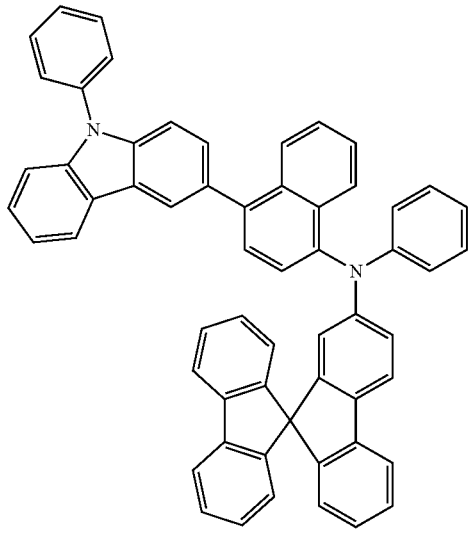
(294)
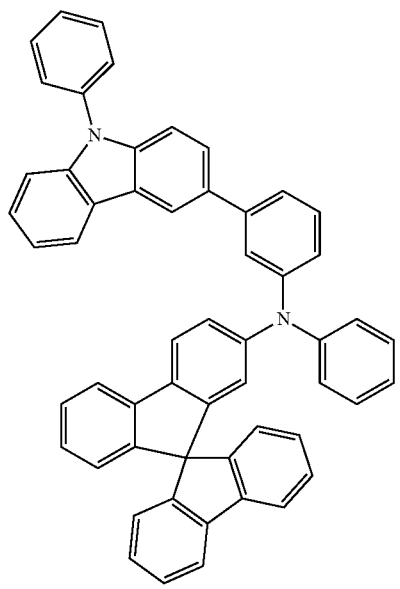
(295)
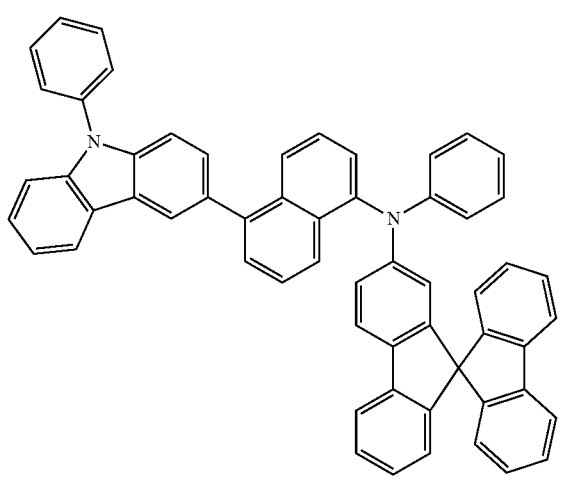
(296)
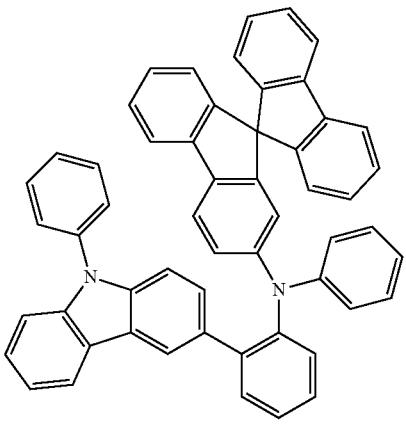
(297)
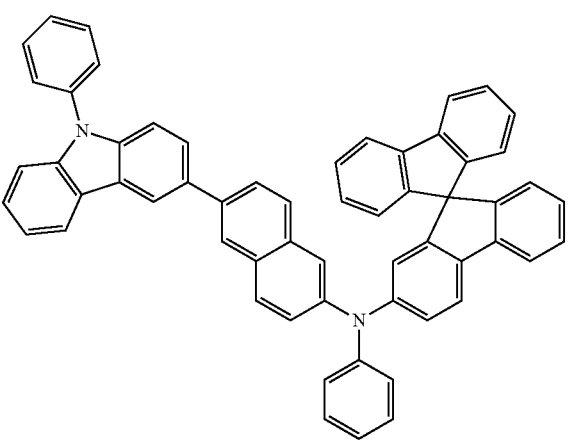
(298)
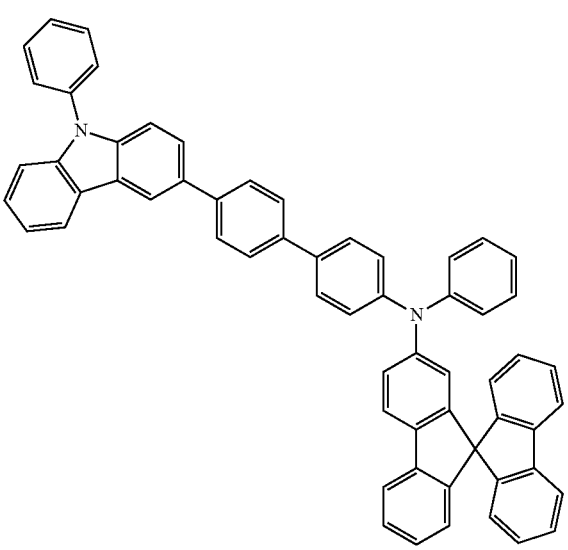

-continued
(299)
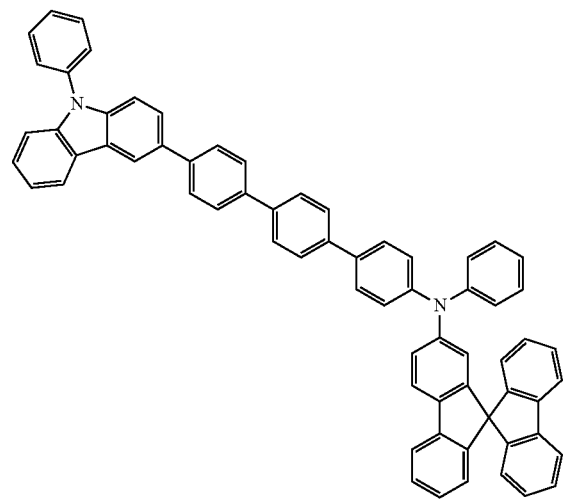
(300)
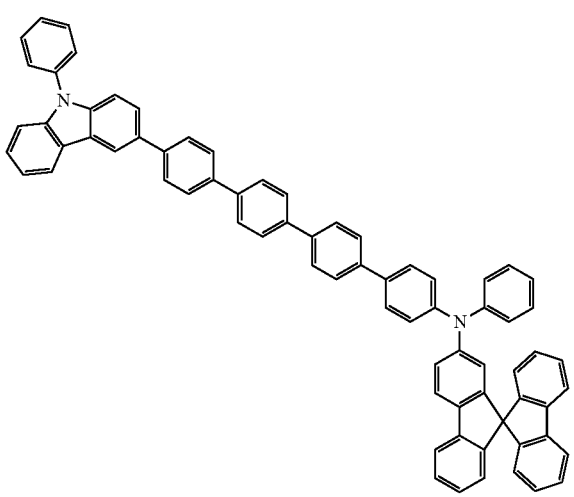
(301)
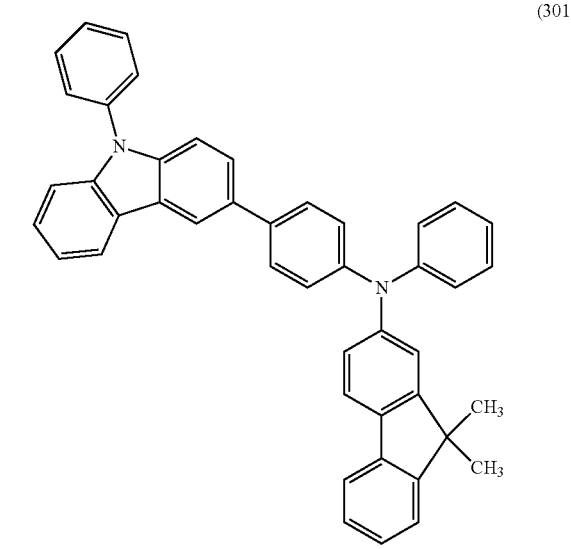
-continued
(302)
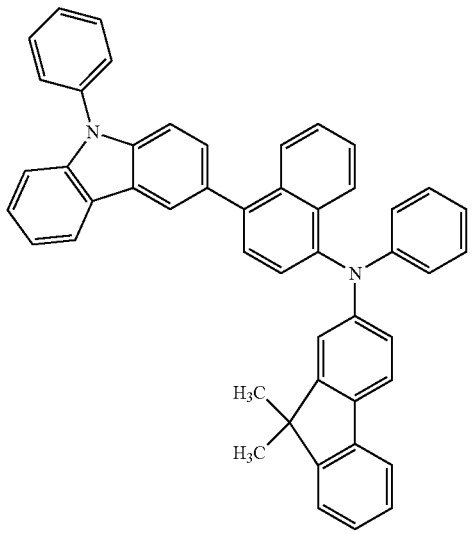
(303)
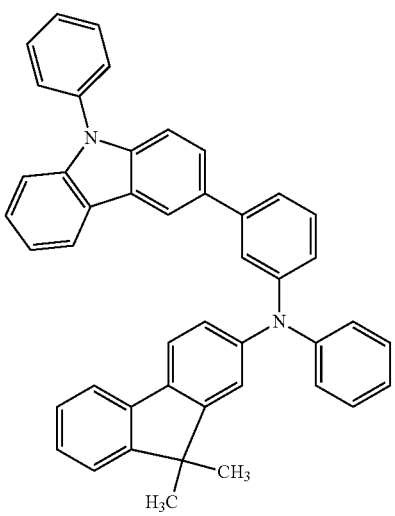
(304)
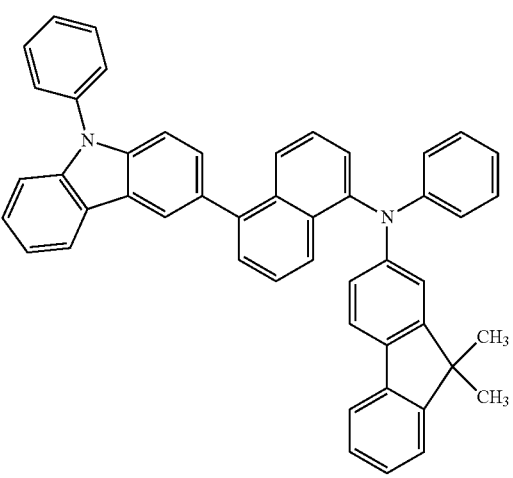

(305)
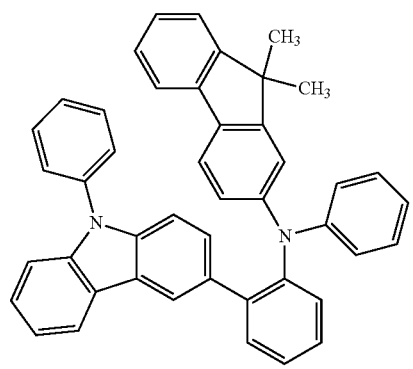
(306)
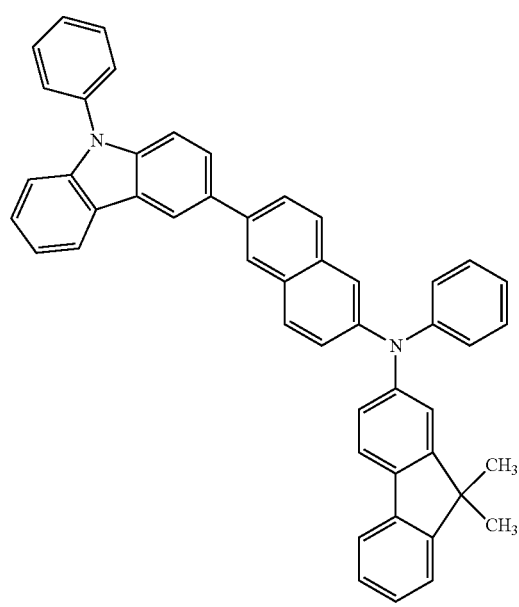
(307)
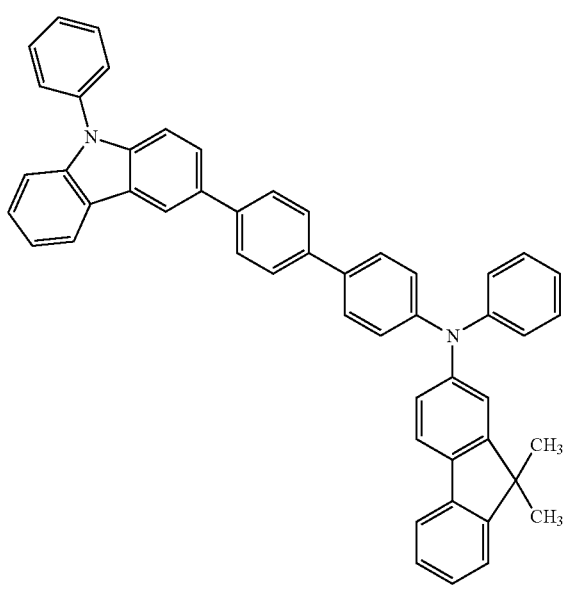
(308)
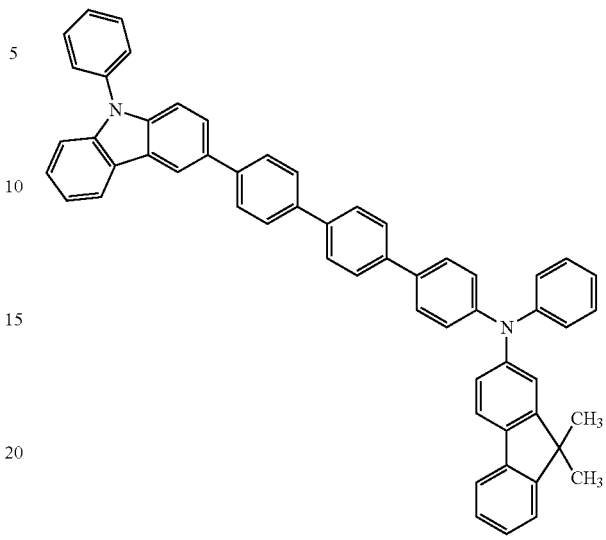
(309)
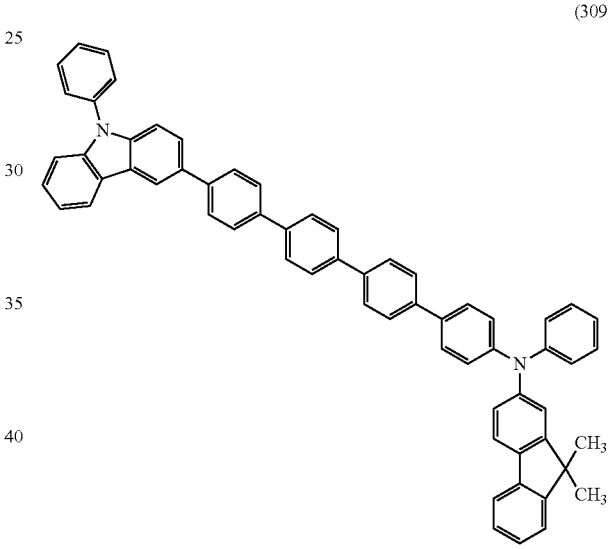
(310)
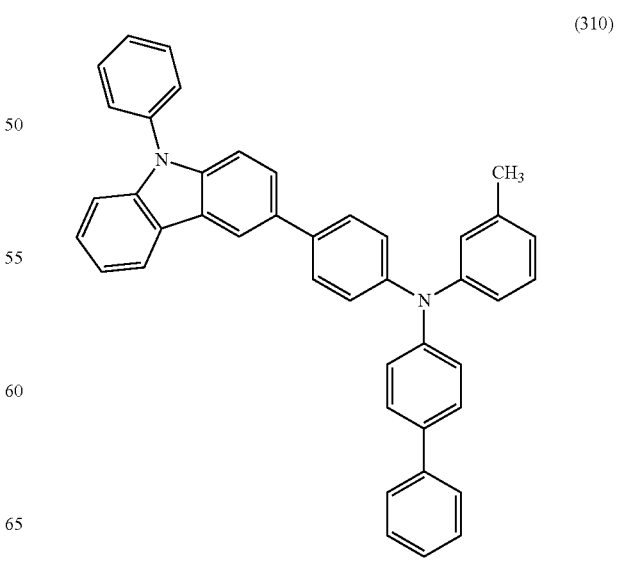

-continued
(311)
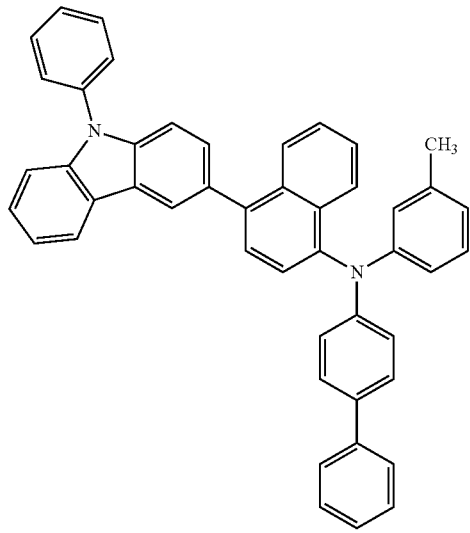
(312)
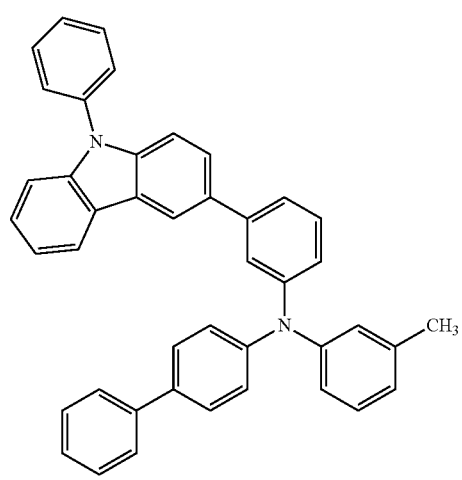
(313)
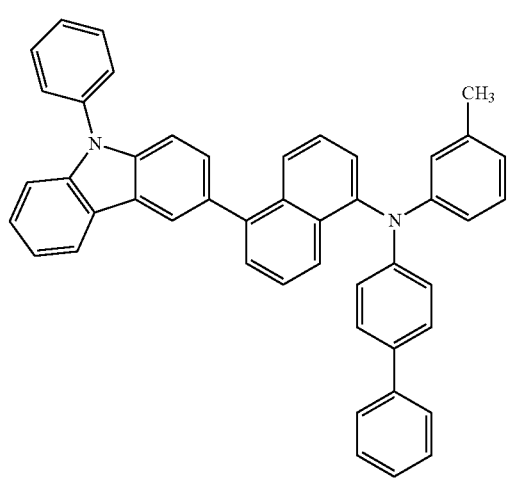
-continued
(314)
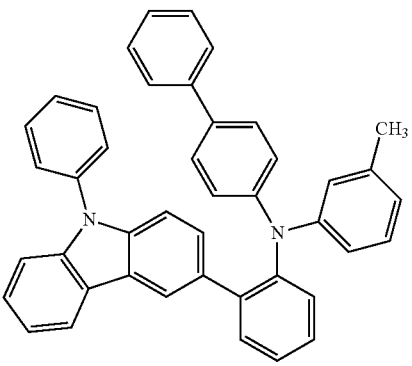
(315)
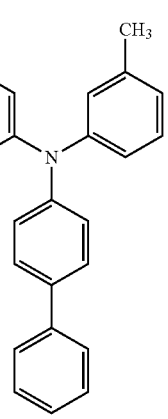
(316)
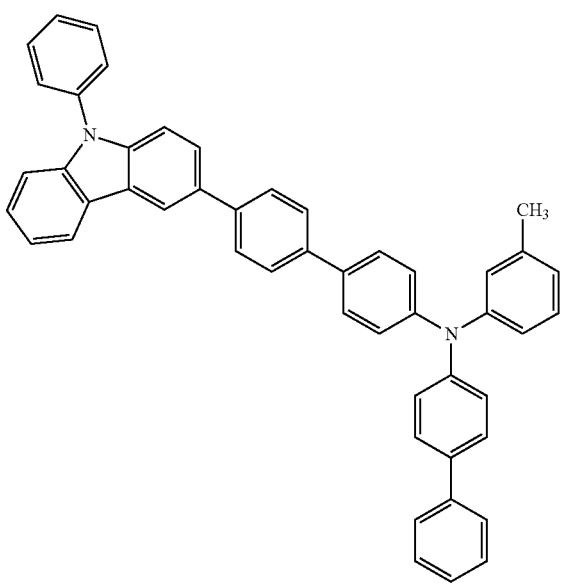

(317)
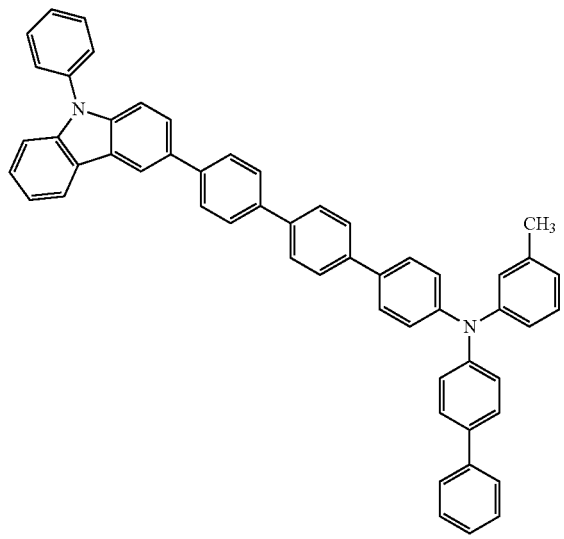
(318)
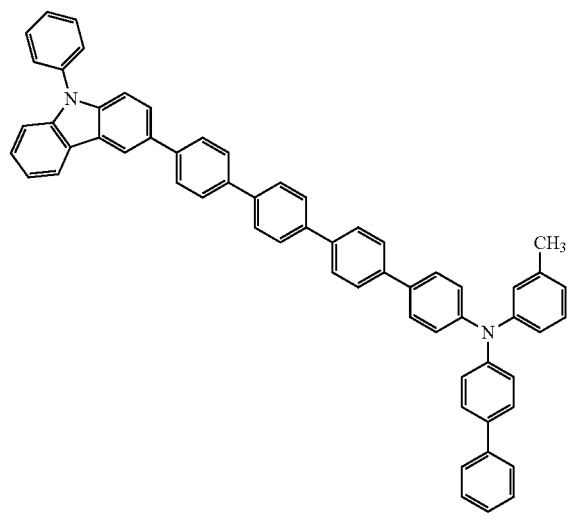
(319)
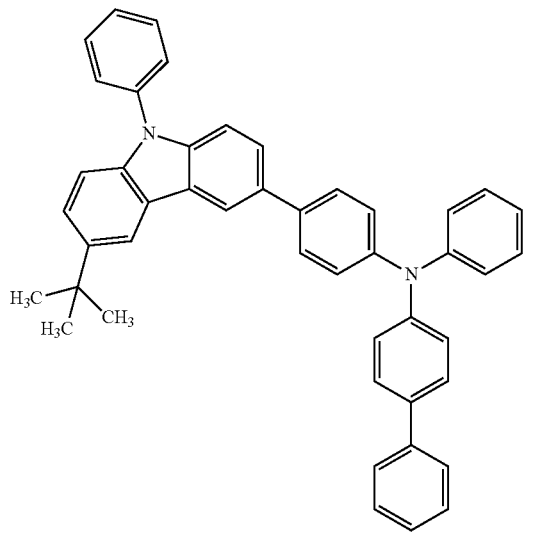
(320)
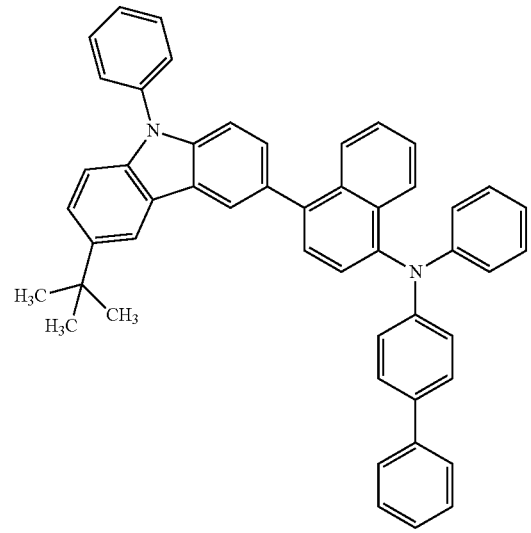
(321)
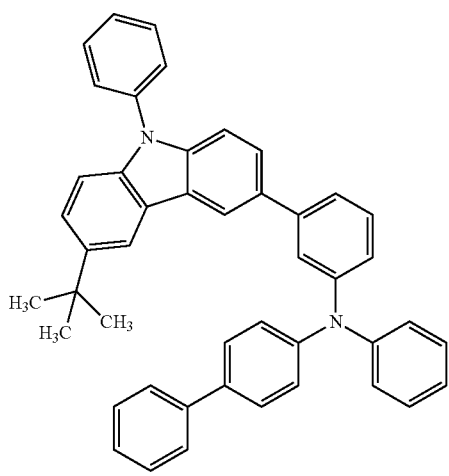
(322)
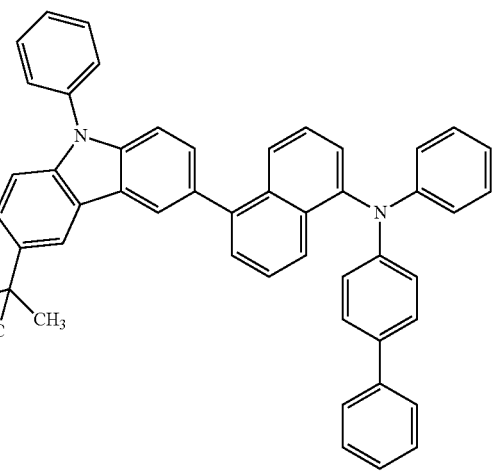

(323)
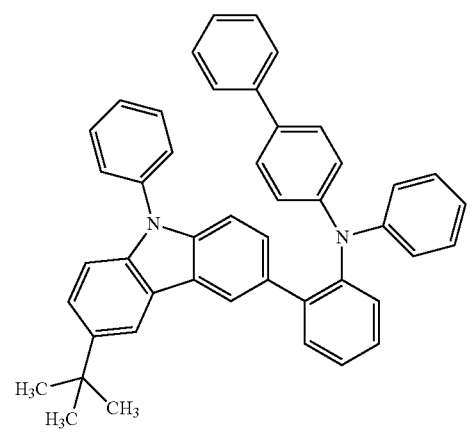
(324)
(325)
(326)
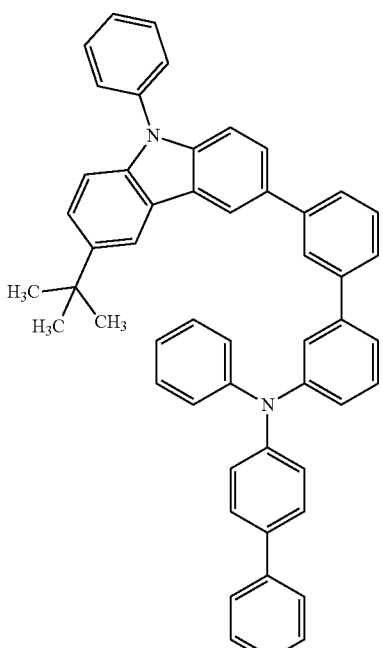
(327)
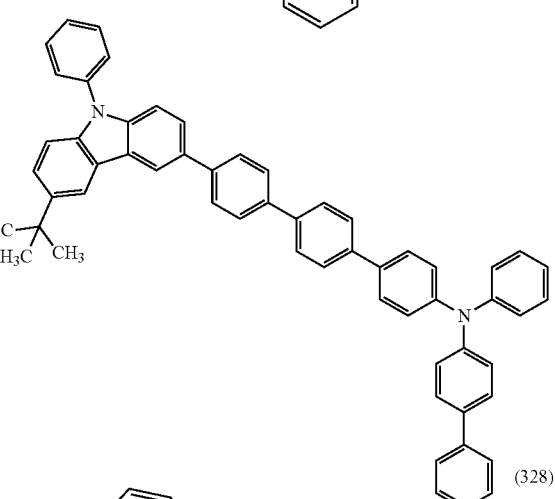
(328)
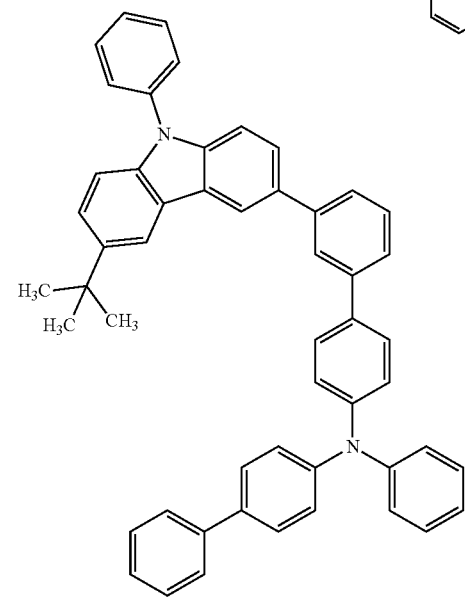

(329)
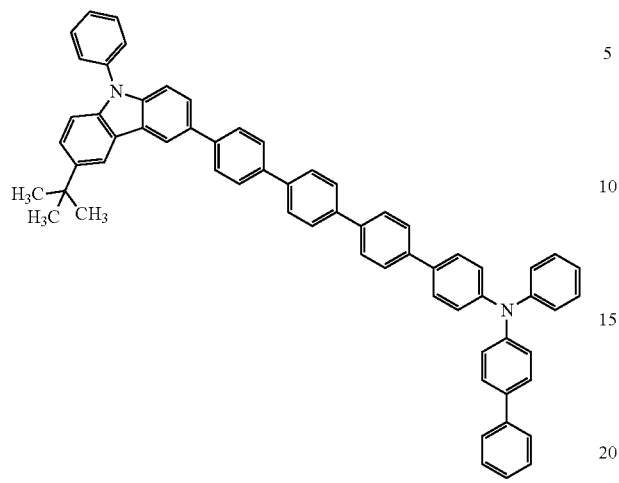
(332)
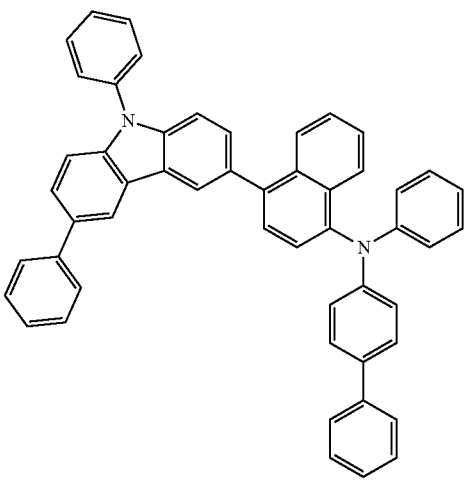
(330)
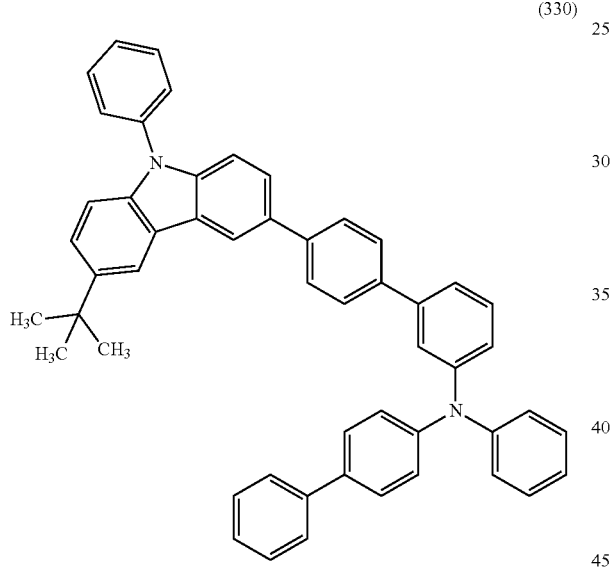
(333)
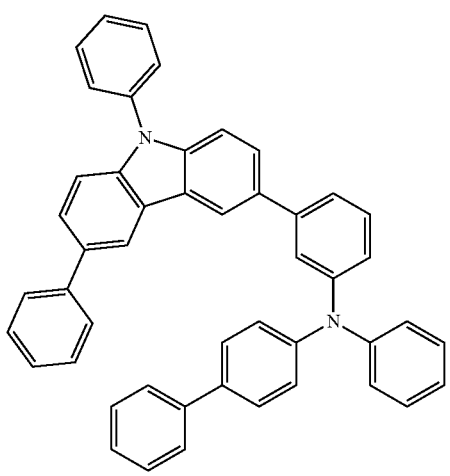
(331)
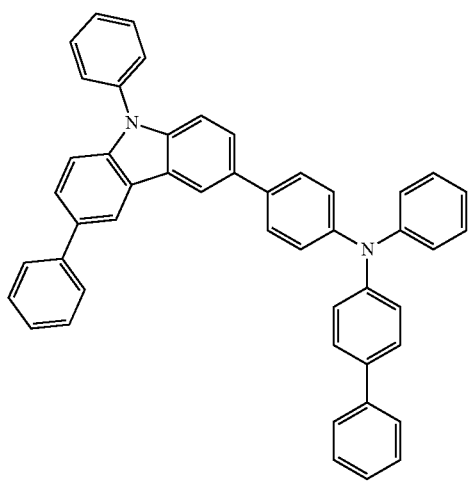
(334)
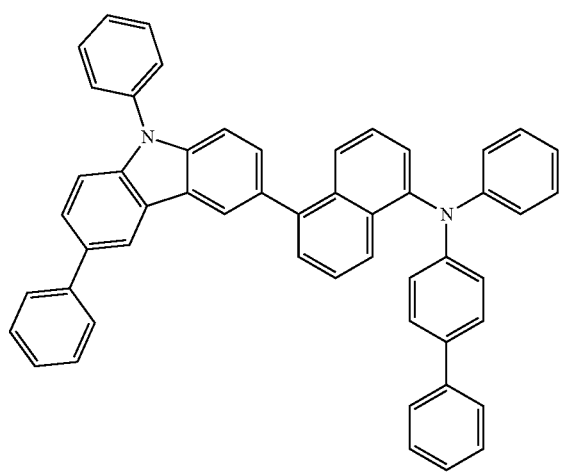

-continued
(335)
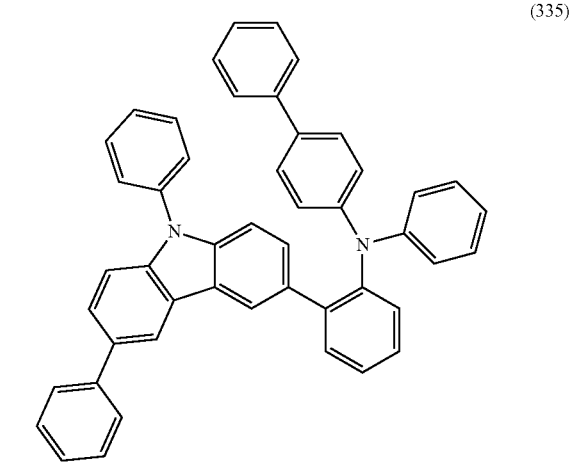
(336)
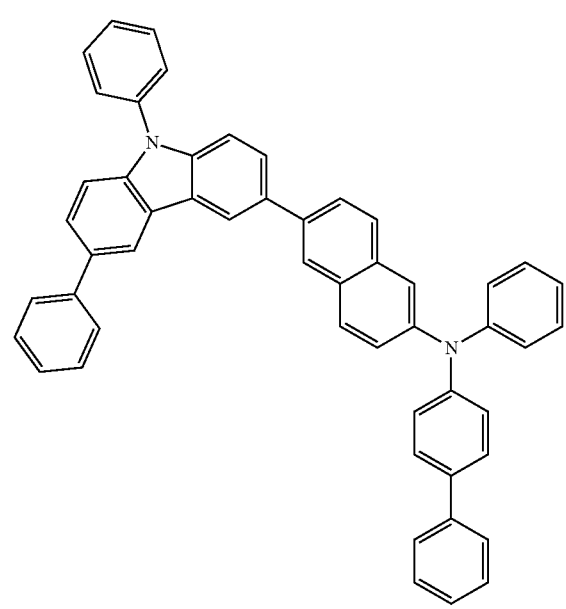
(337)
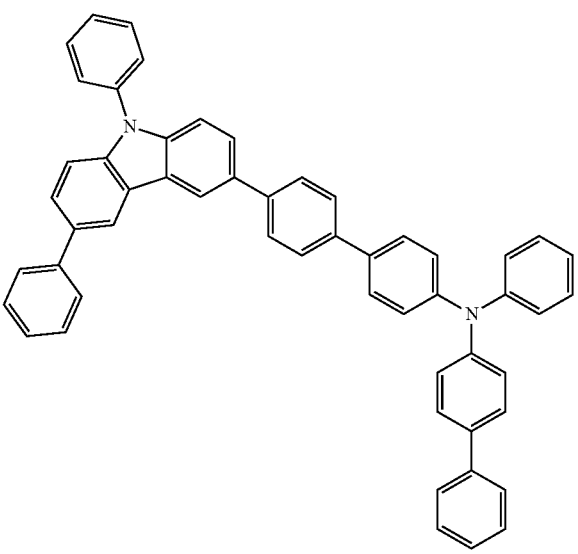
-continued
(338)
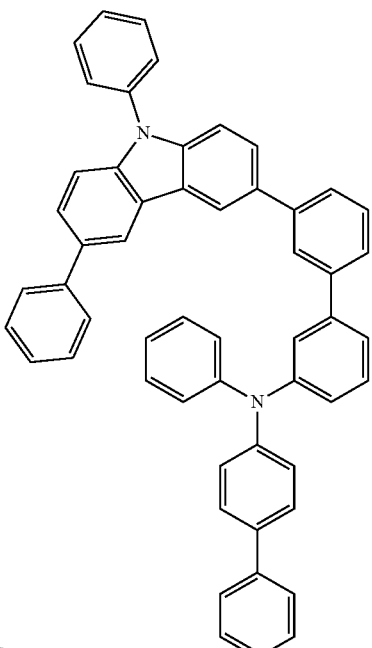
(339)
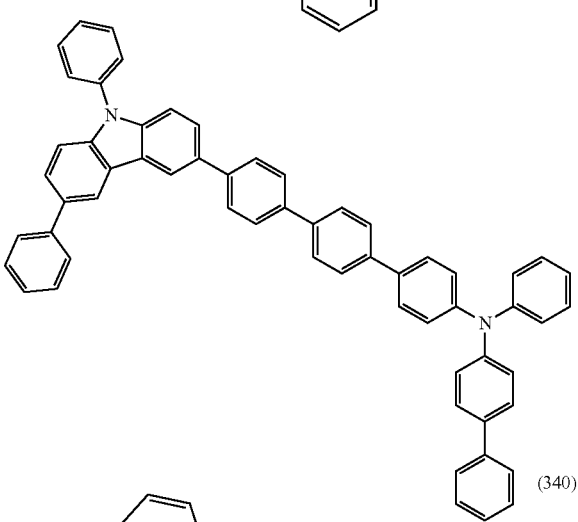
(340)
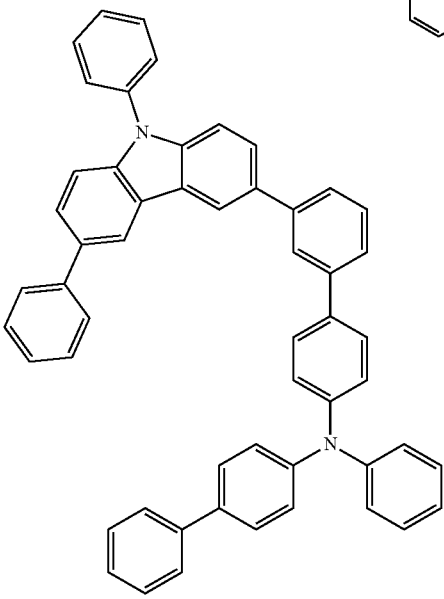

(341)
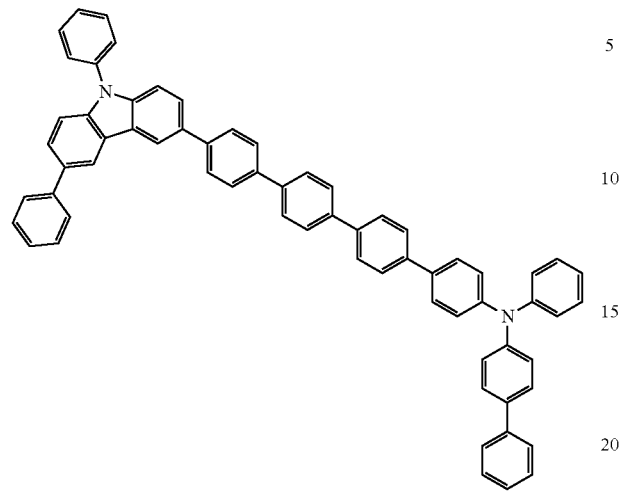
(342)
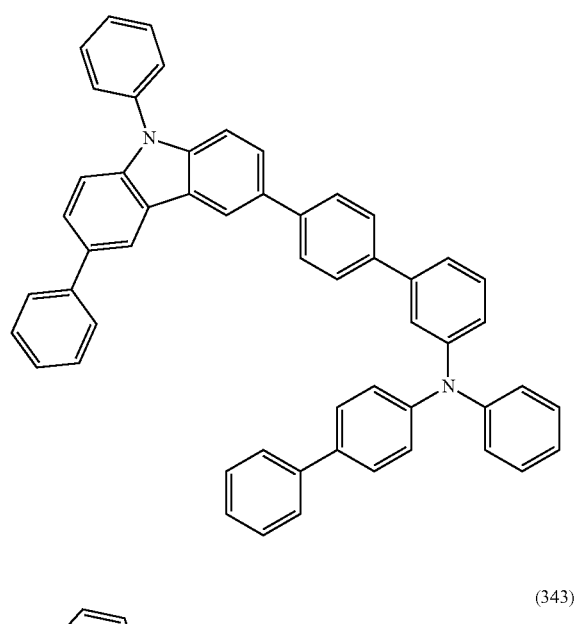
(343)
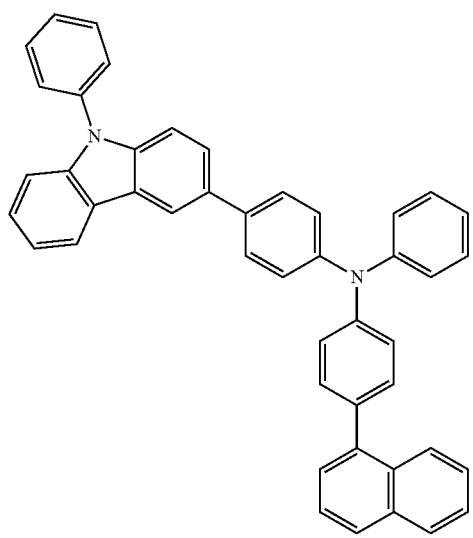
(344)
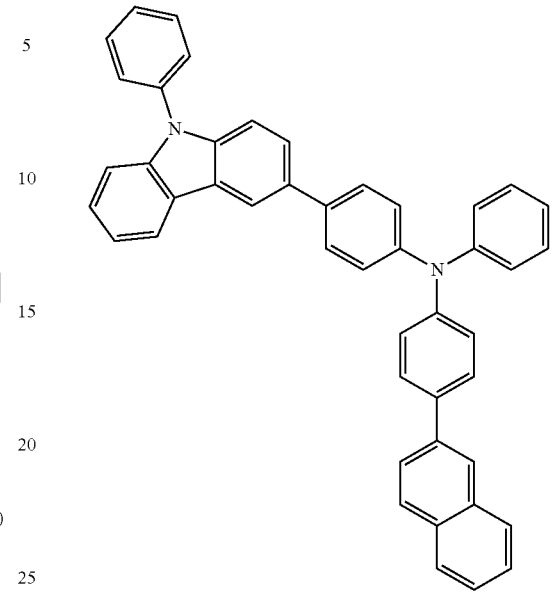
(345)
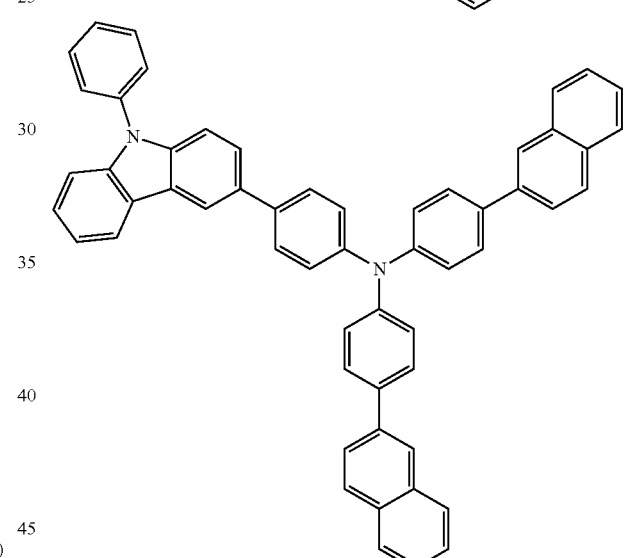
(346)
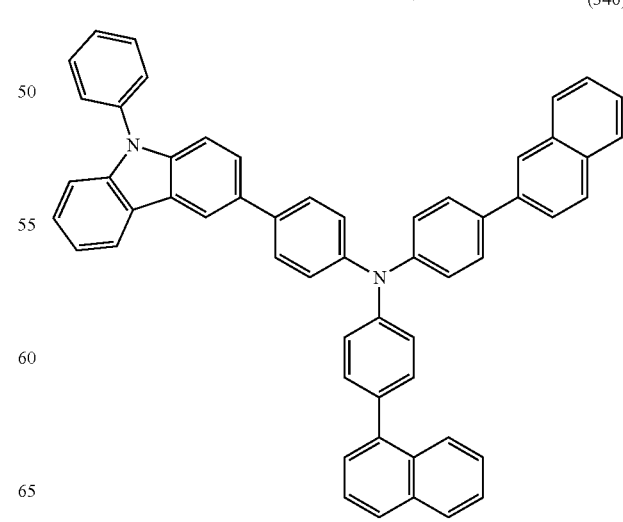

(347)
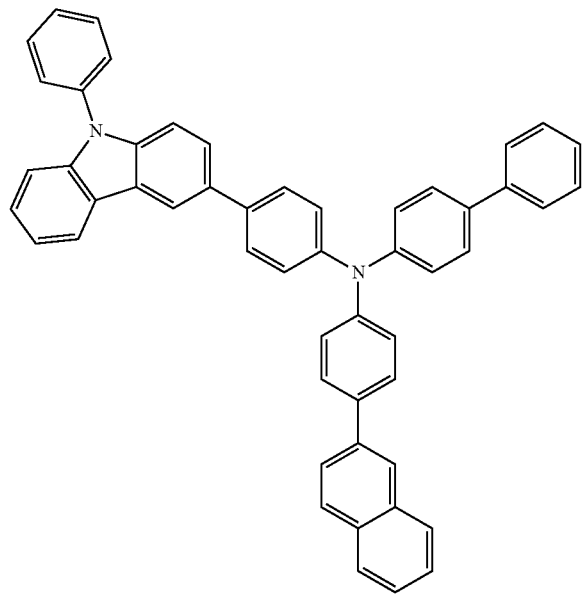
(348)
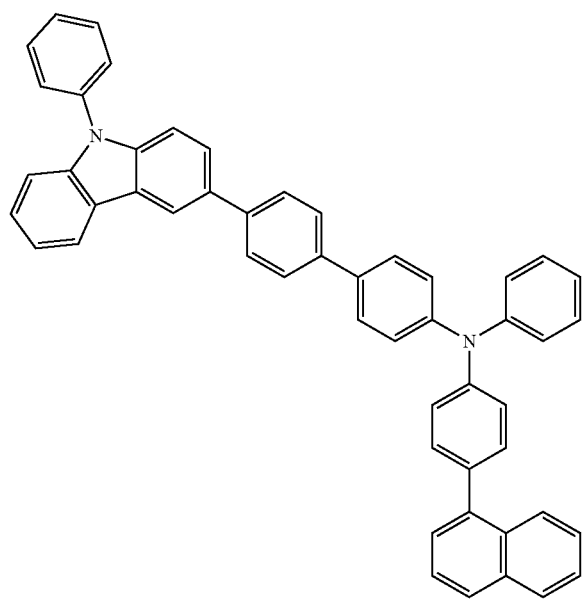
(349)
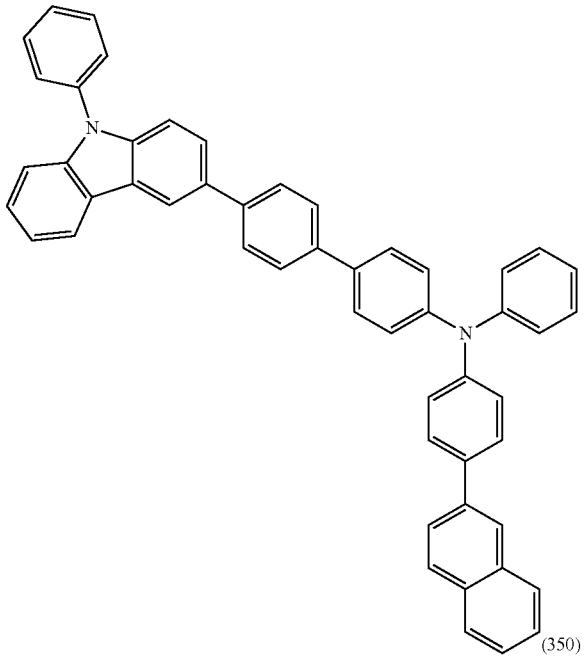
(350)
(351)
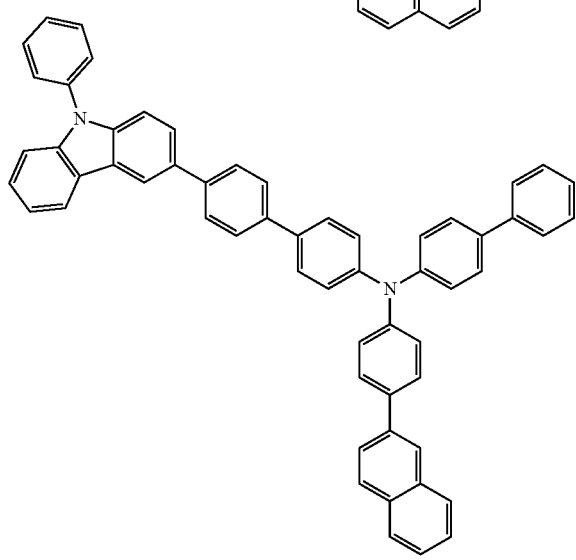

(352)
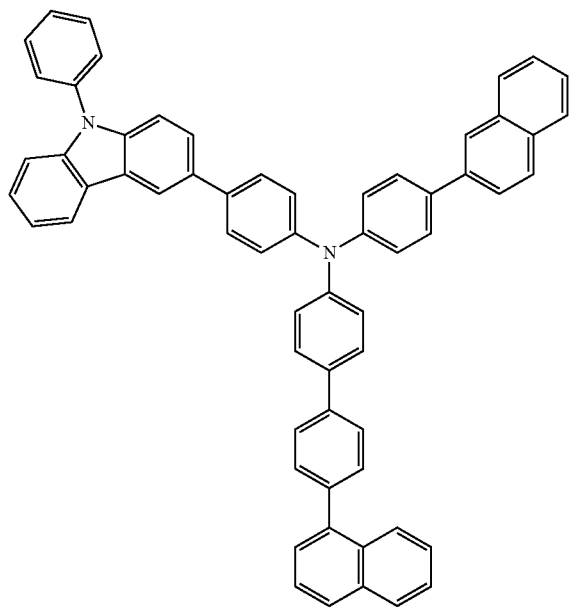
(355)
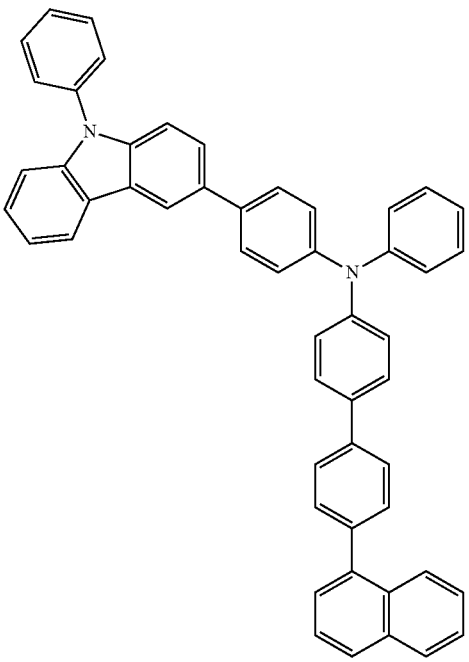
(353)
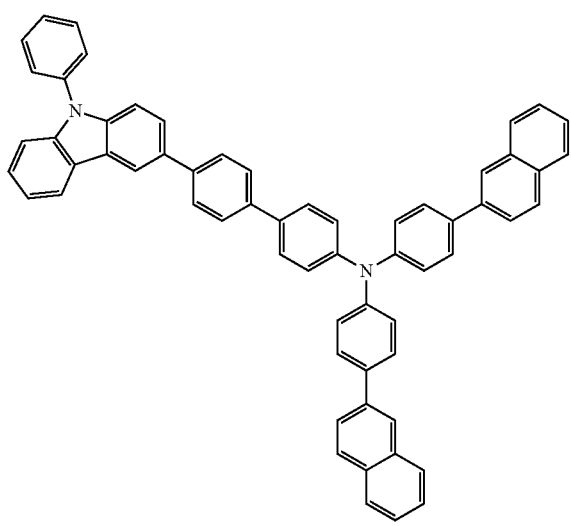
(356)
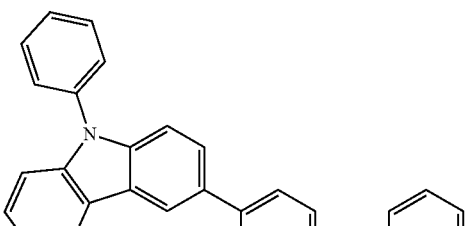
(354)
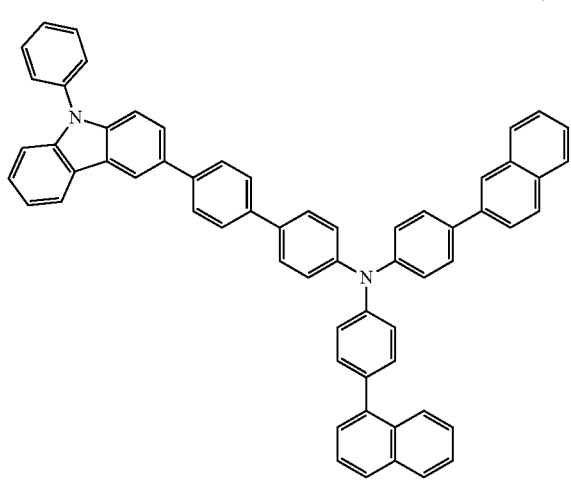
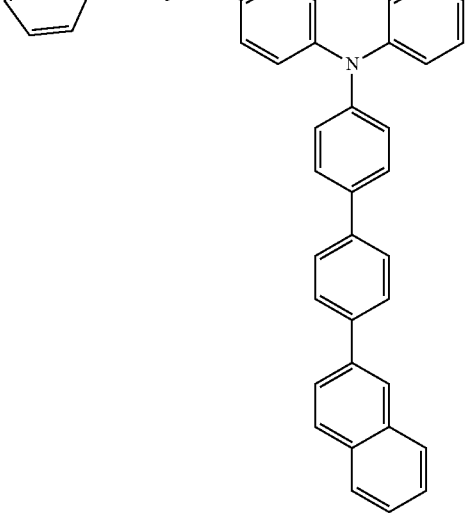

(357)
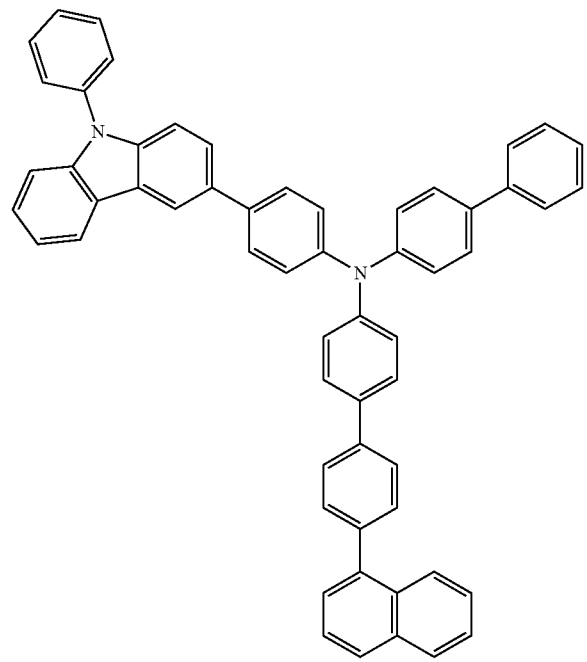
(359)
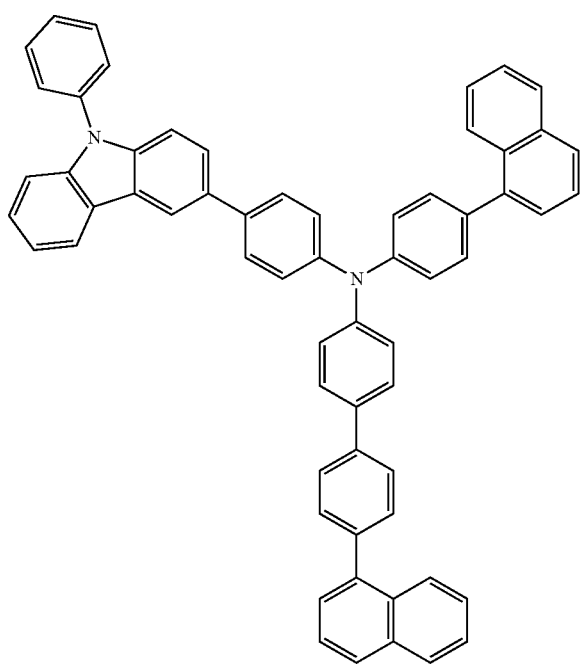
(358)
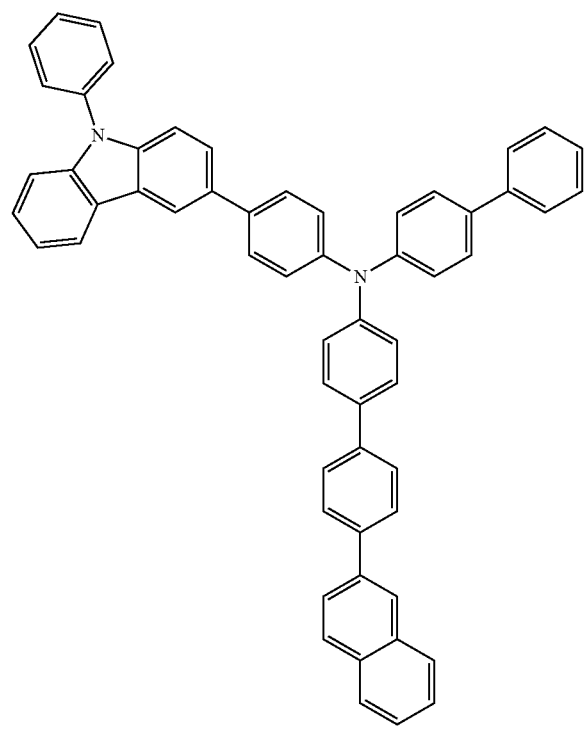
(360)
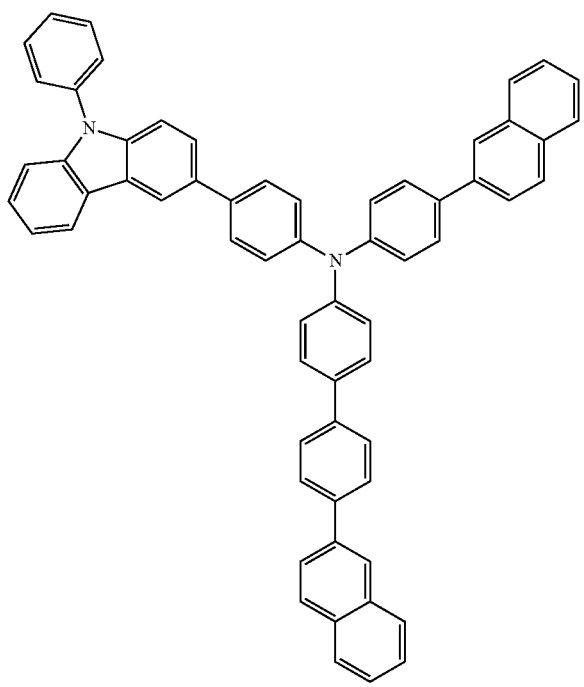

(361)
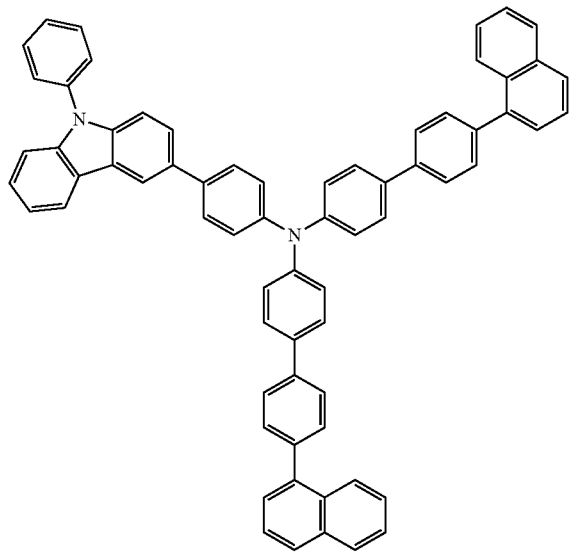
(362)
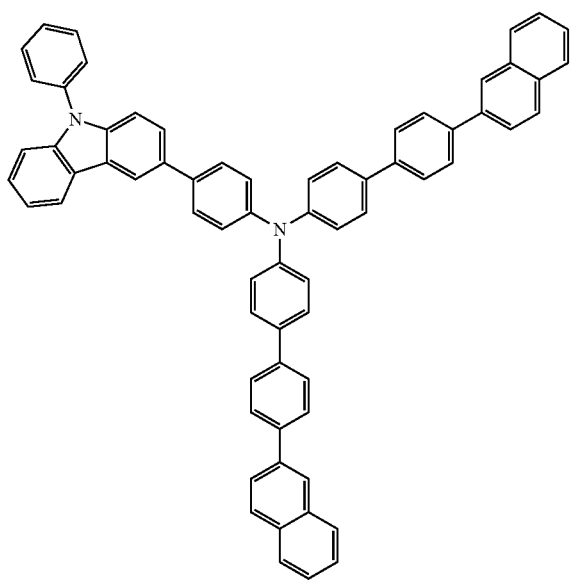
(363)
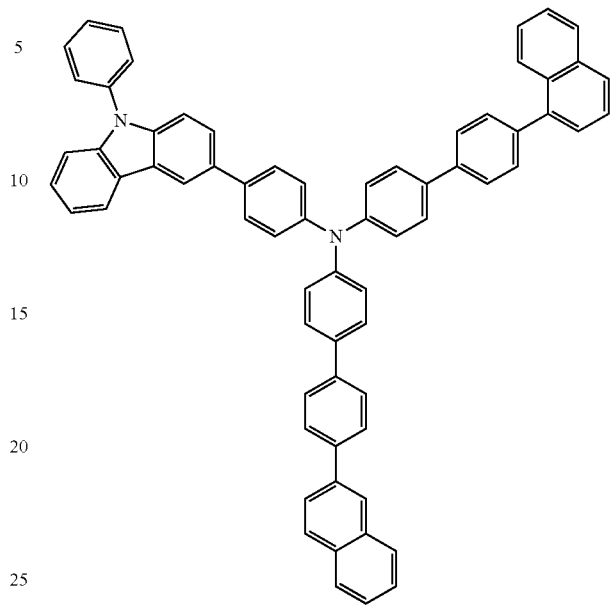
(364)
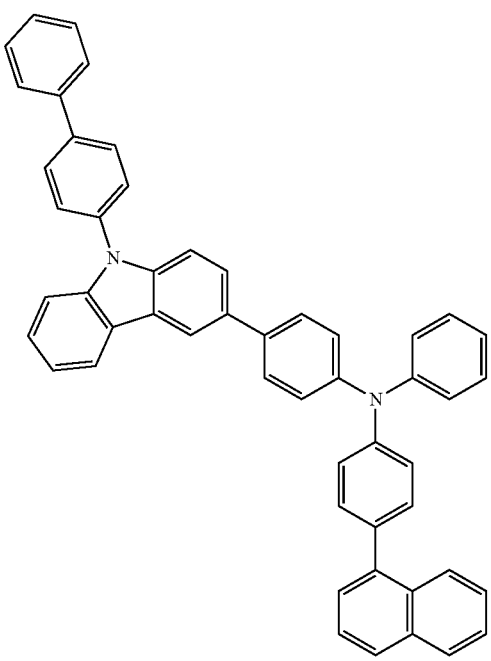

(365)
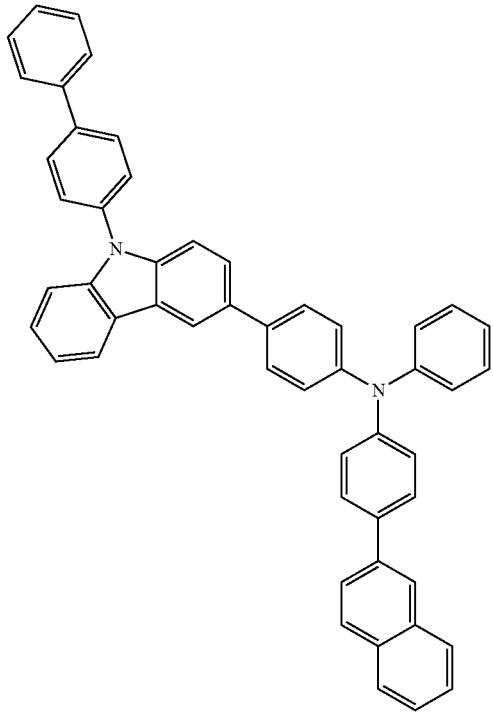
(366)
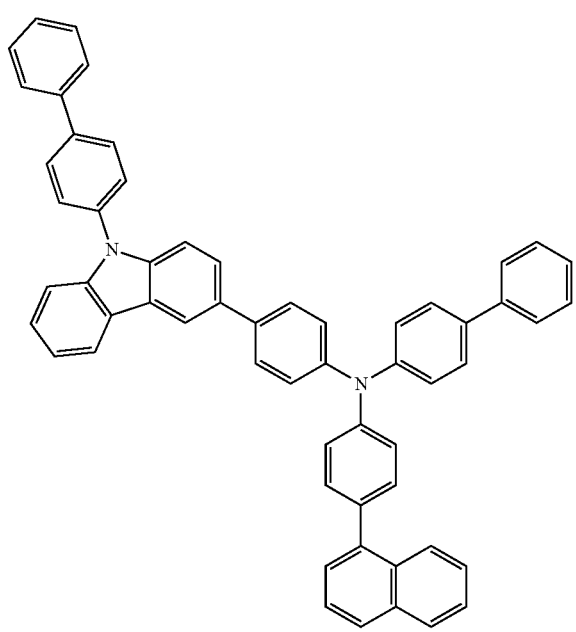
(367)
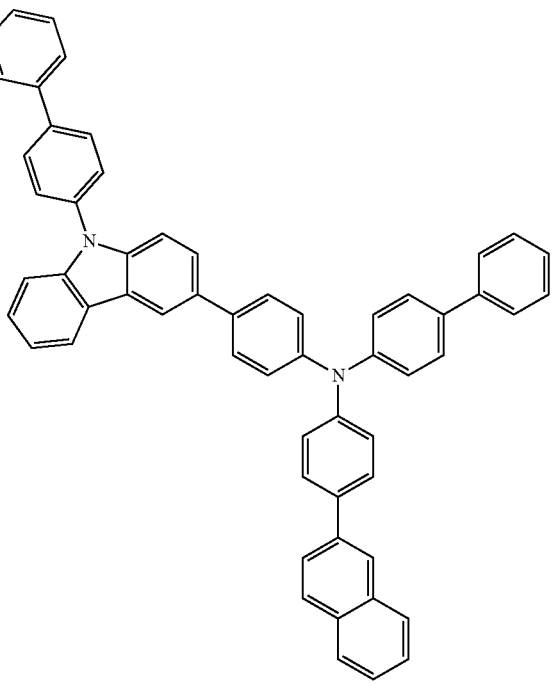
(368)
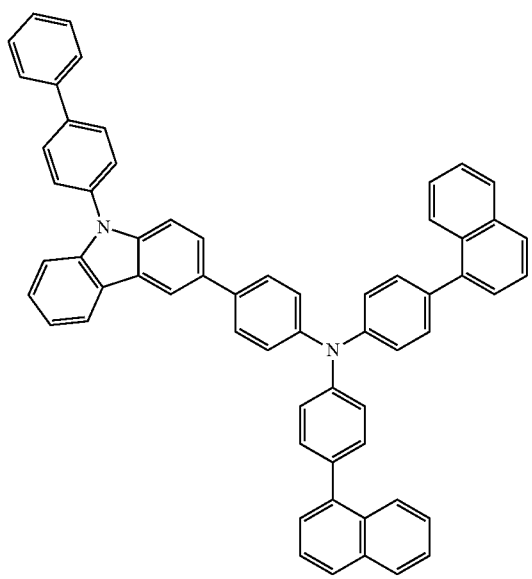

(369)
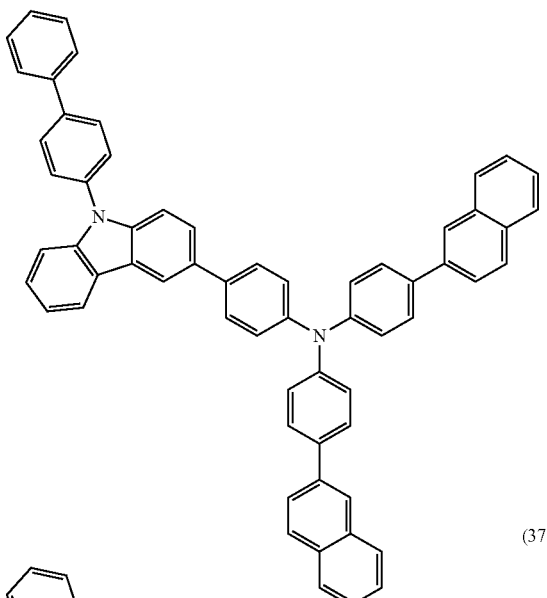
(370)
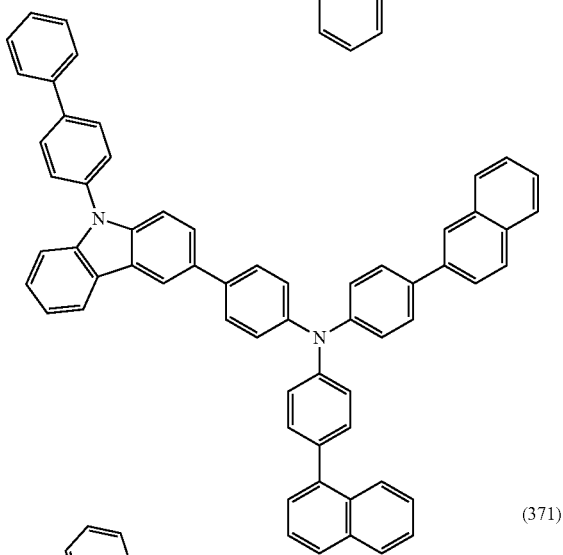
(371)
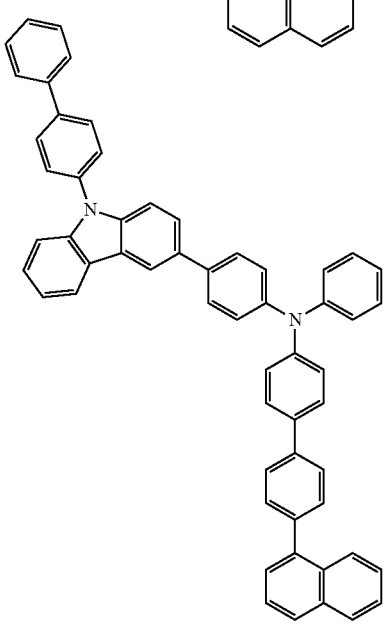
(372)
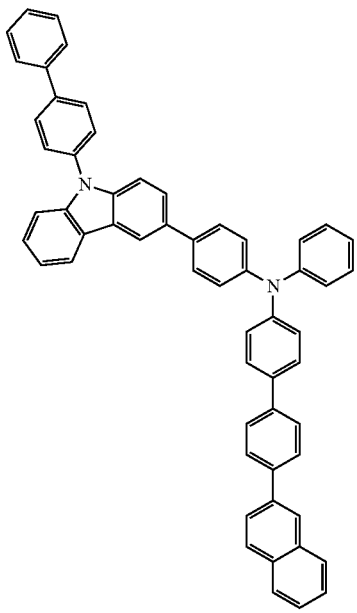
(373)
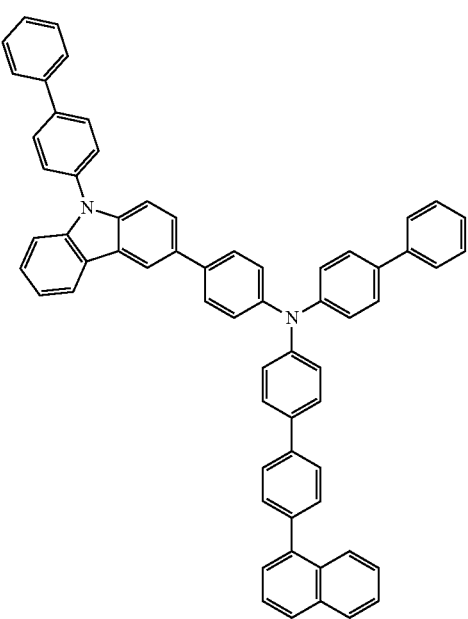

(374)
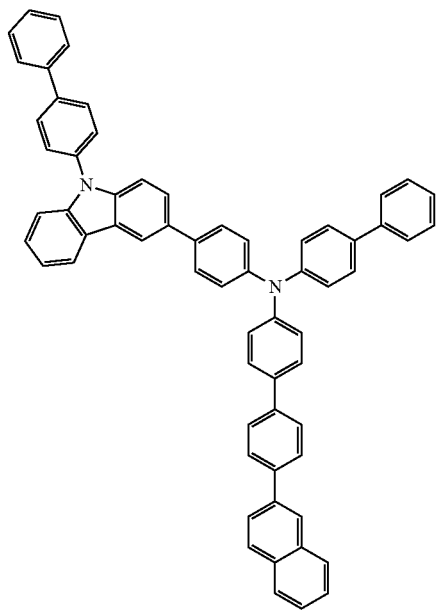
(375)
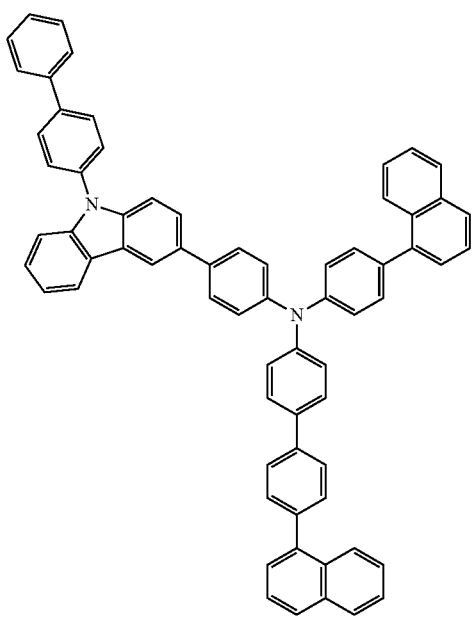
(376)
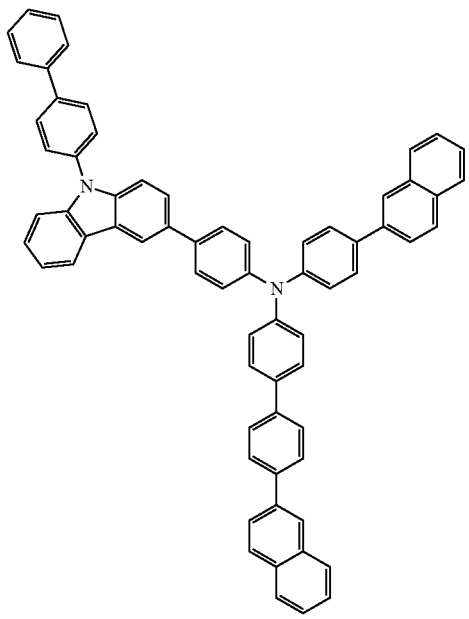
(377)
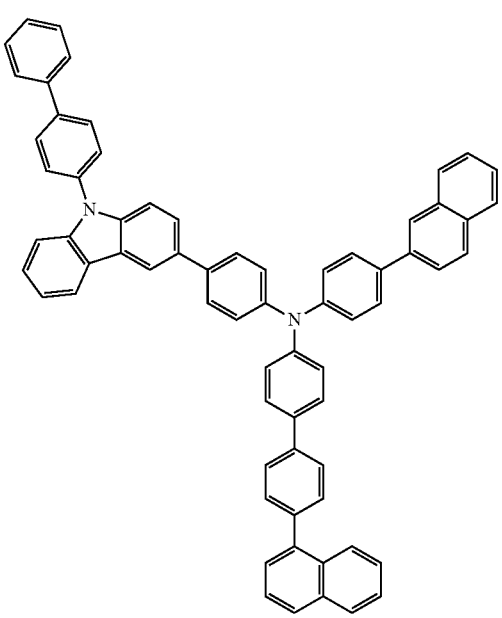

(378)
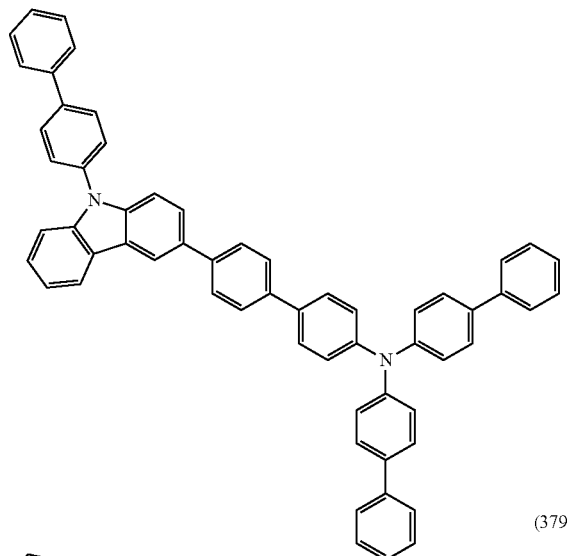
(379)
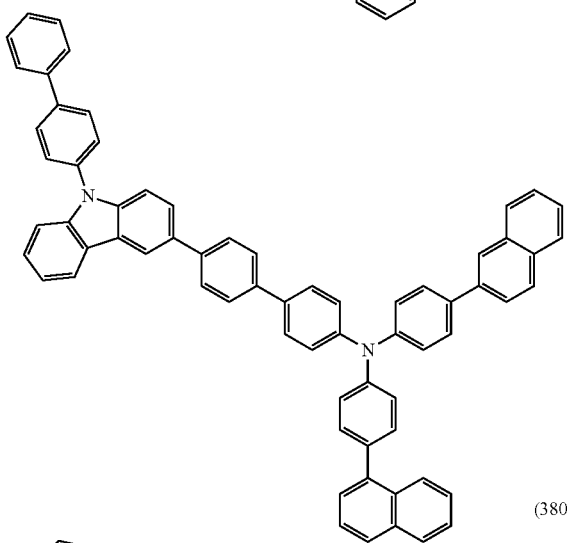
(380)
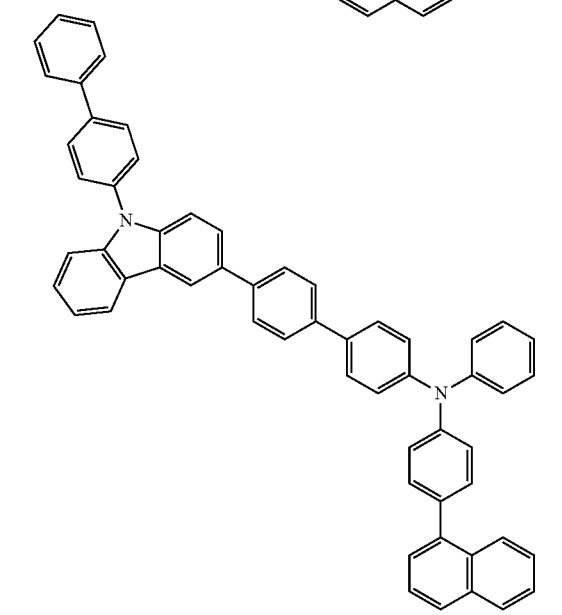
(381)
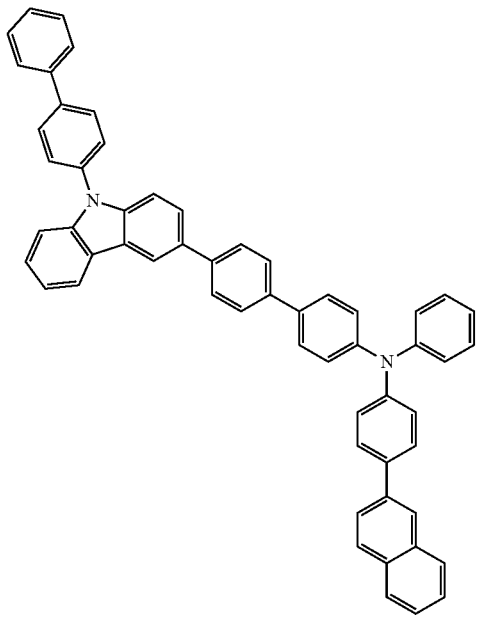
(382)
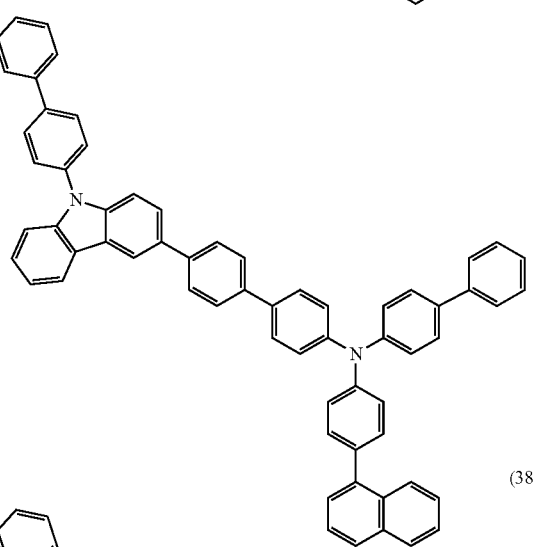
(383)
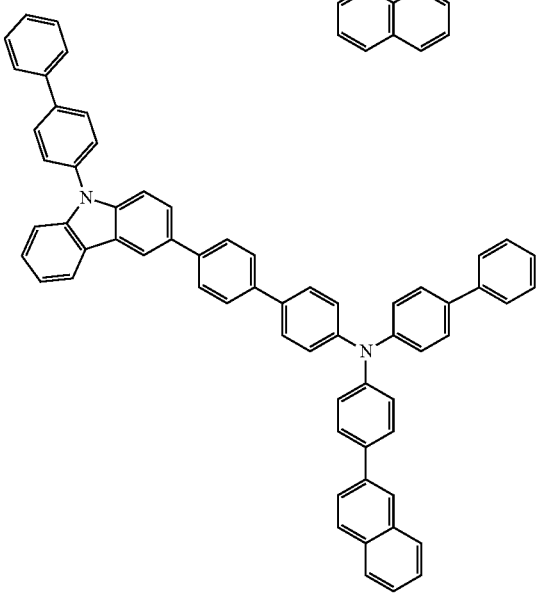

(384)
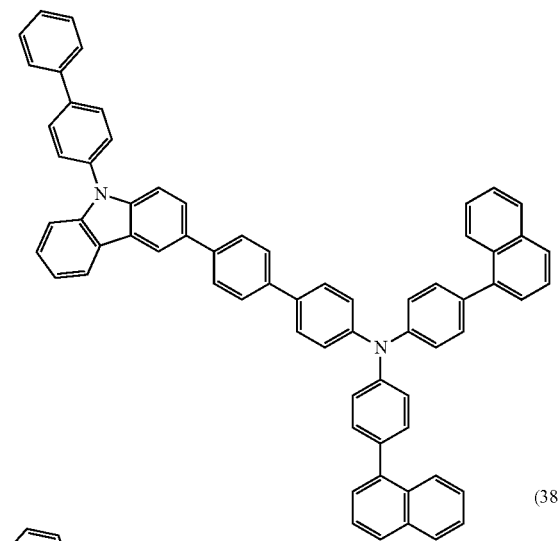
(385)
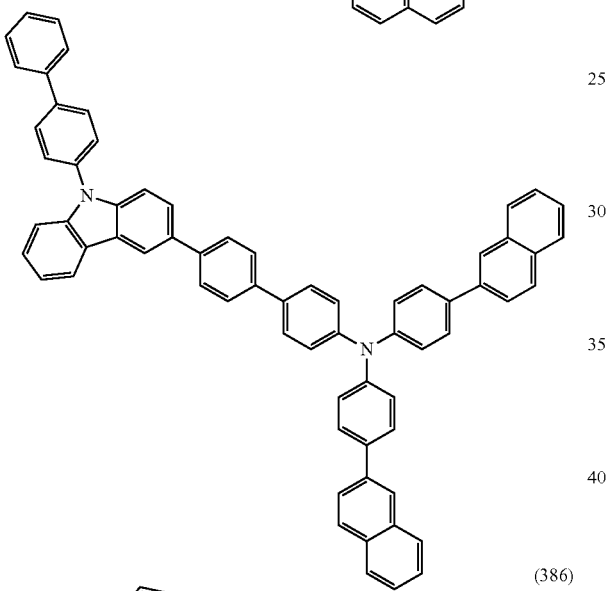
(386)
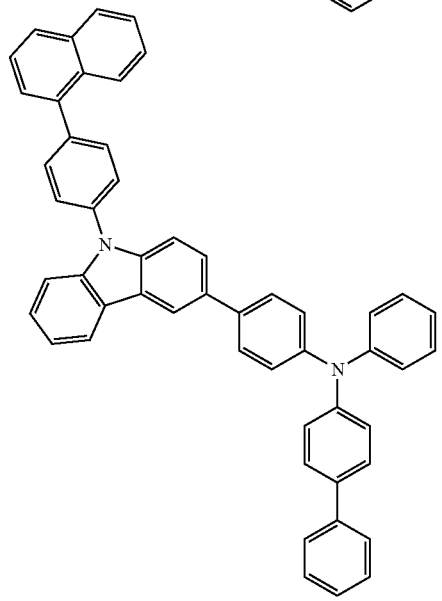
(387)
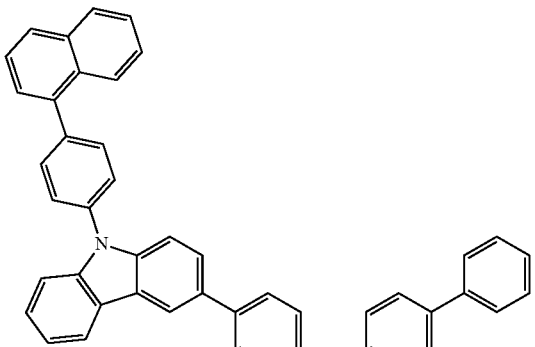
(388)
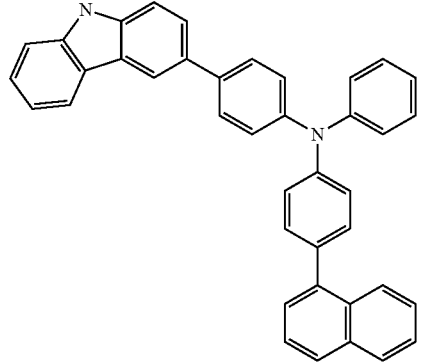
(389)
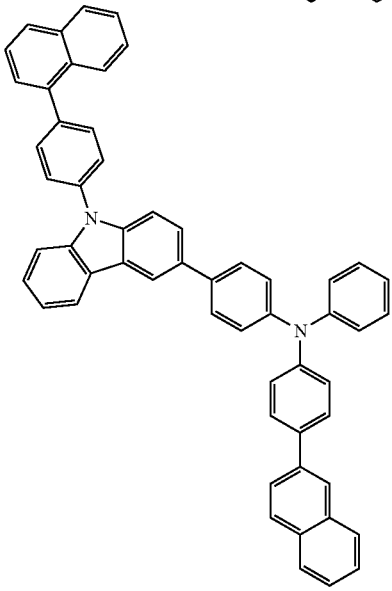

(390)
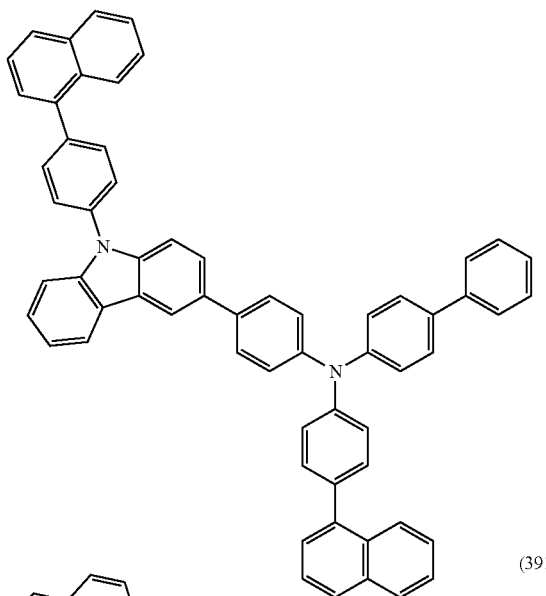
(391)
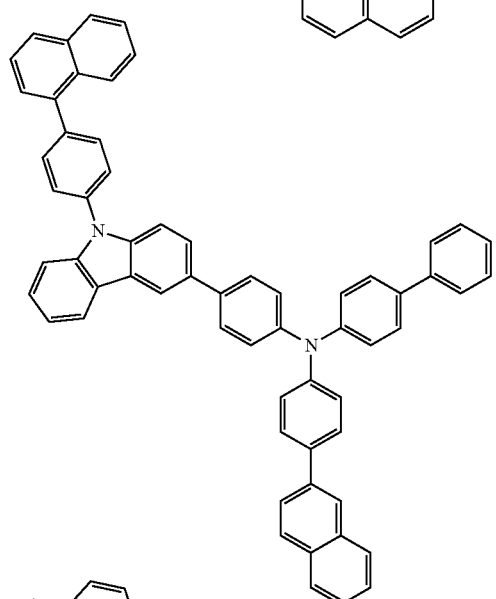
(392)
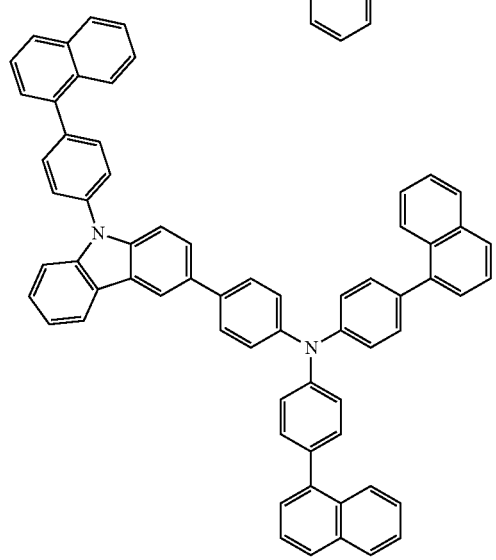
(393)
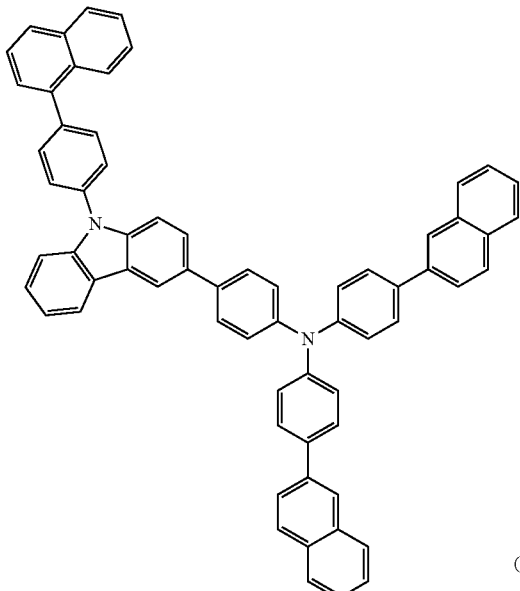
(394)
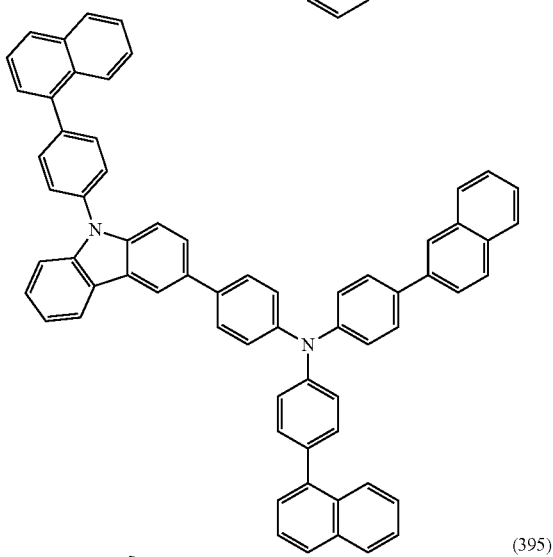
(395)
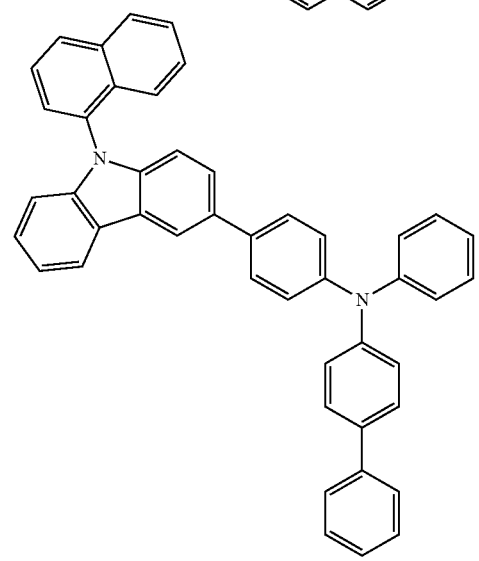

(396)
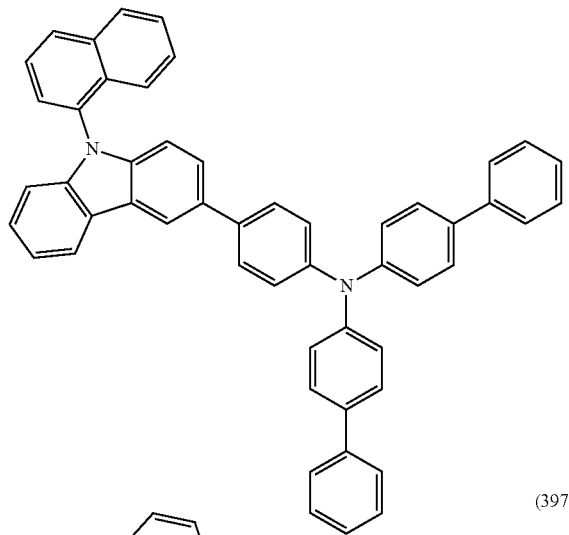
(397)
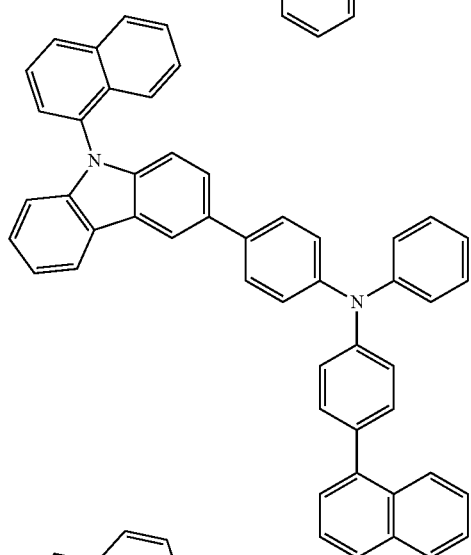
(398)
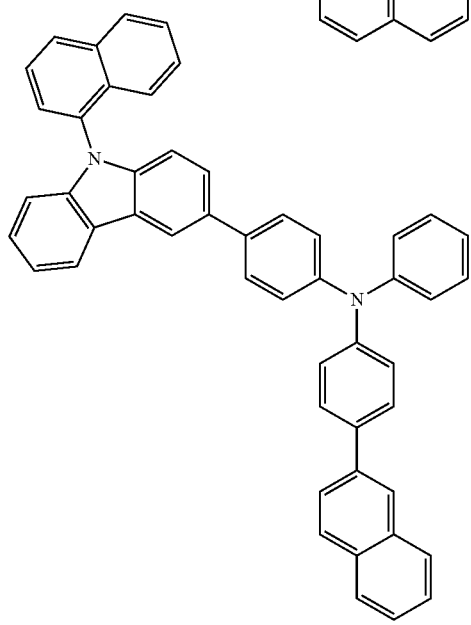
(399)
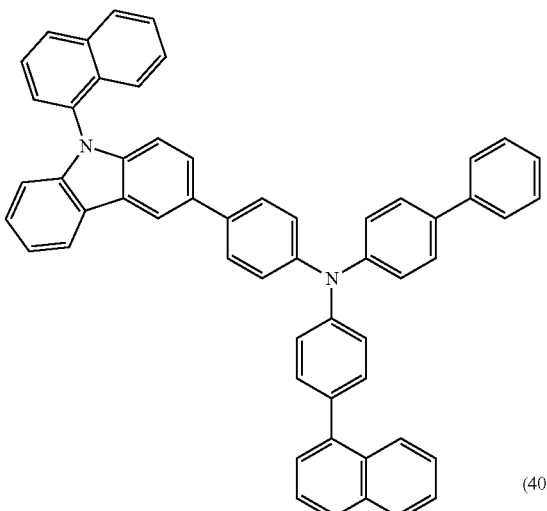
(400)
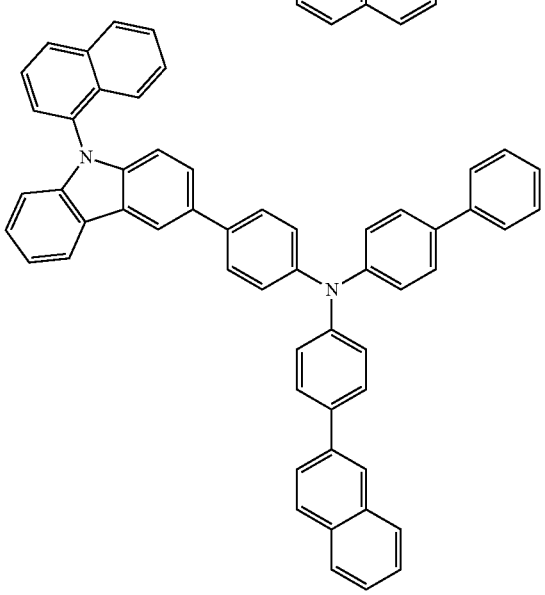
(401)
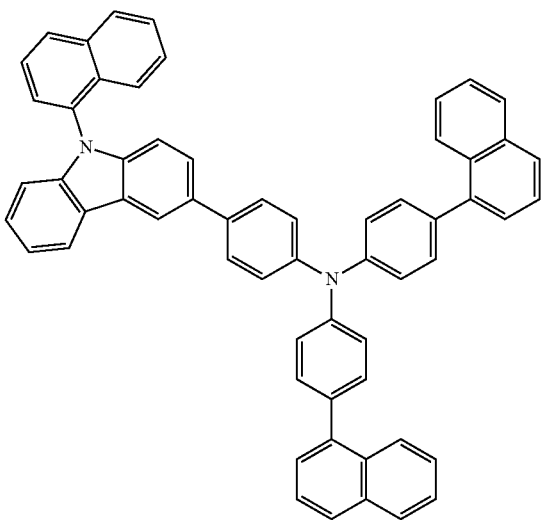

(402)
(403)
(404)
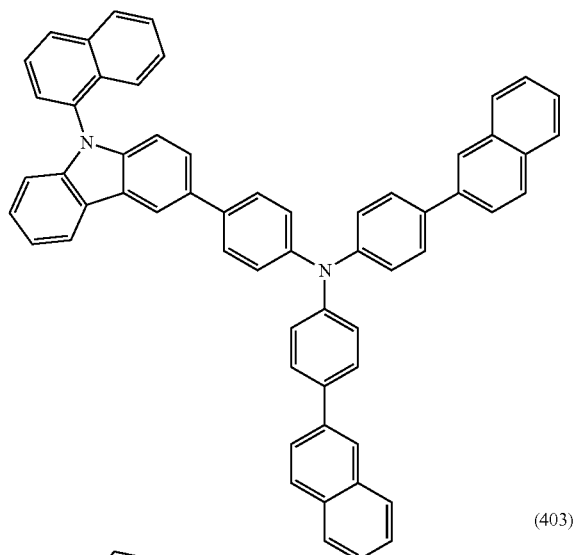
(405)
(406)
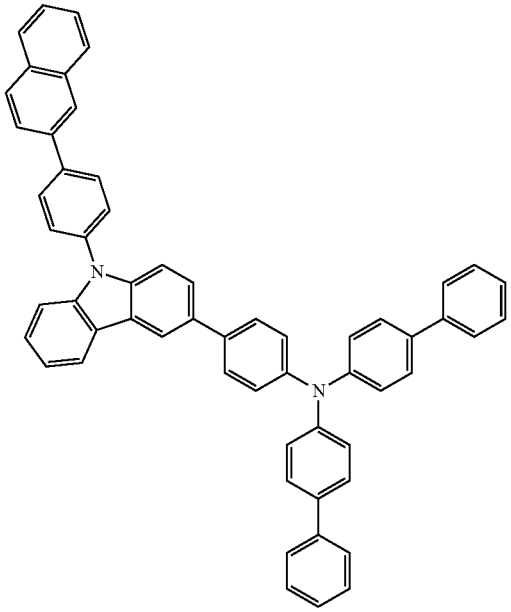
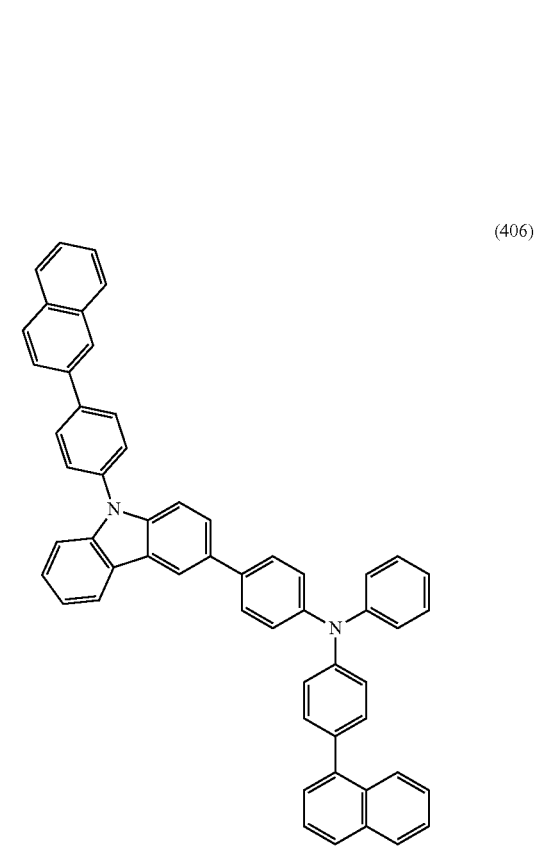

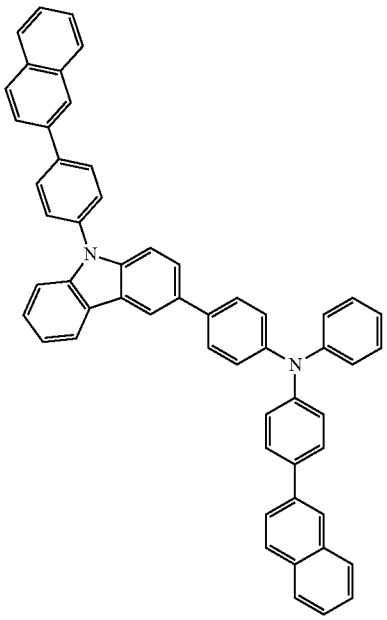
(407)
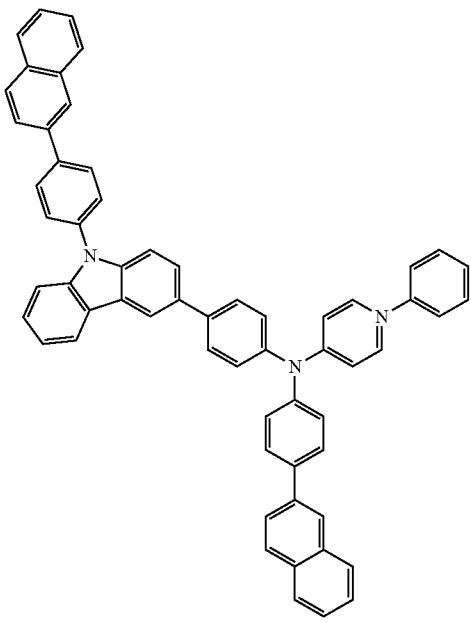
(409)
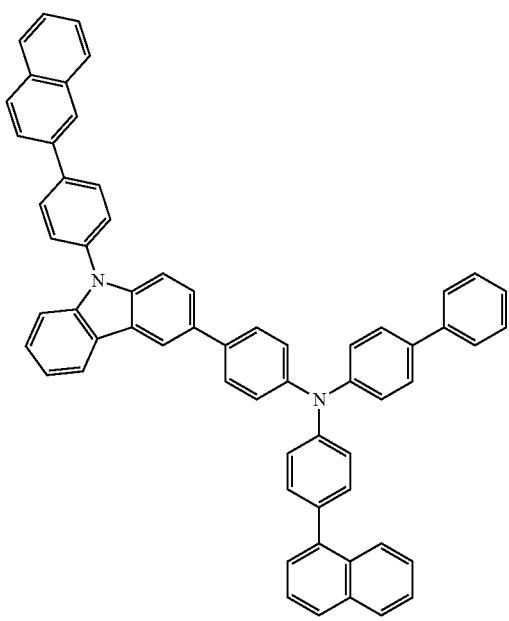
(408)
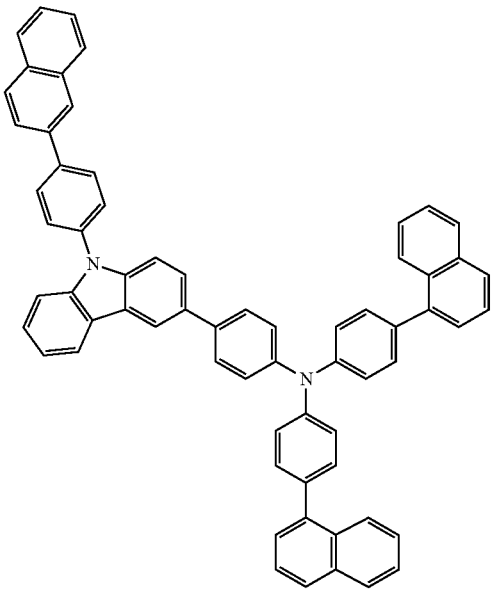
(410)

(411)
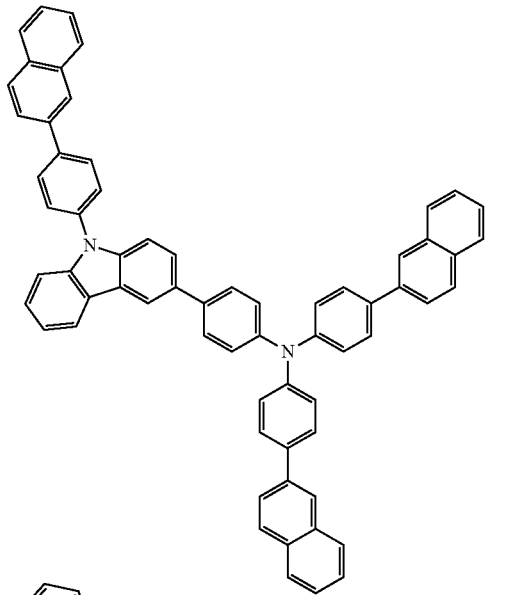
(412)
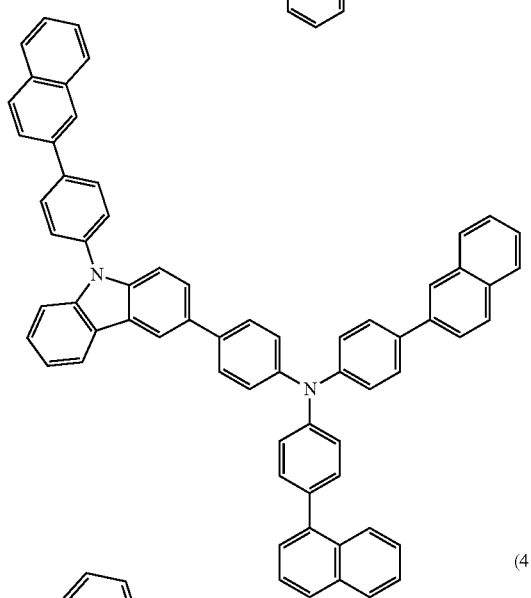
(413)
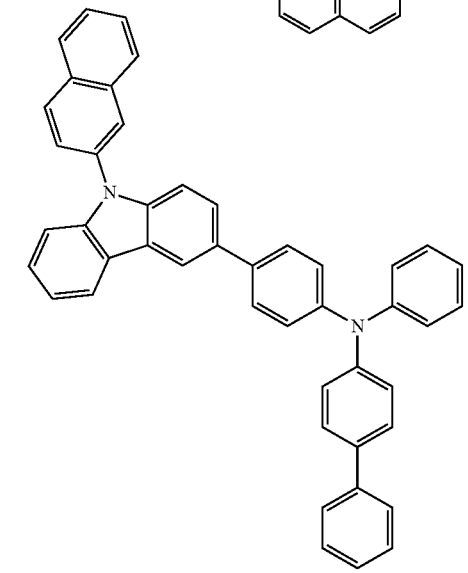
(414)
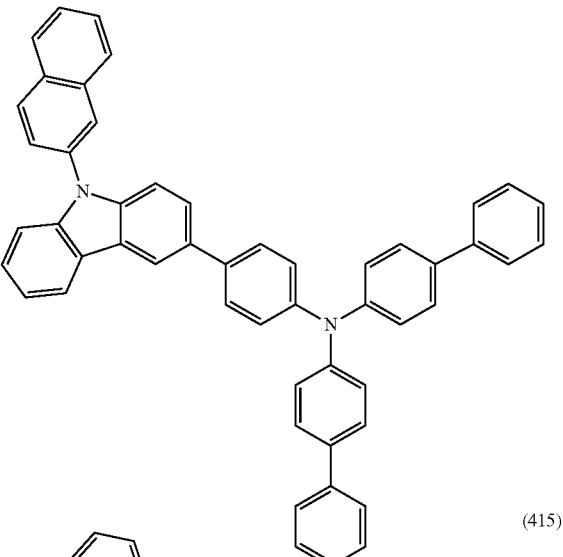
(415)
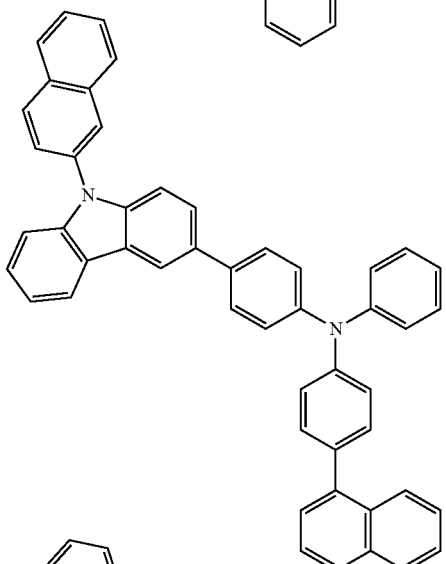
(416)
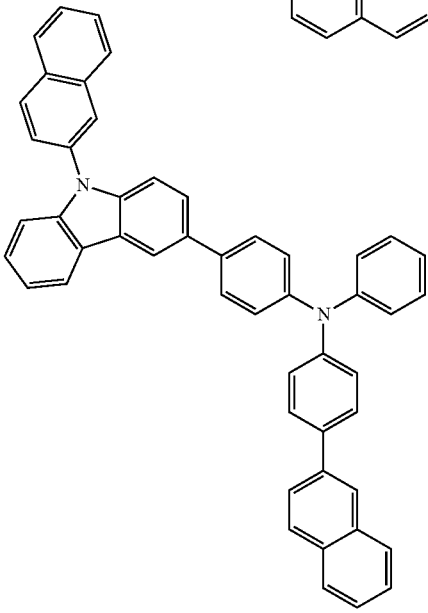

(417)
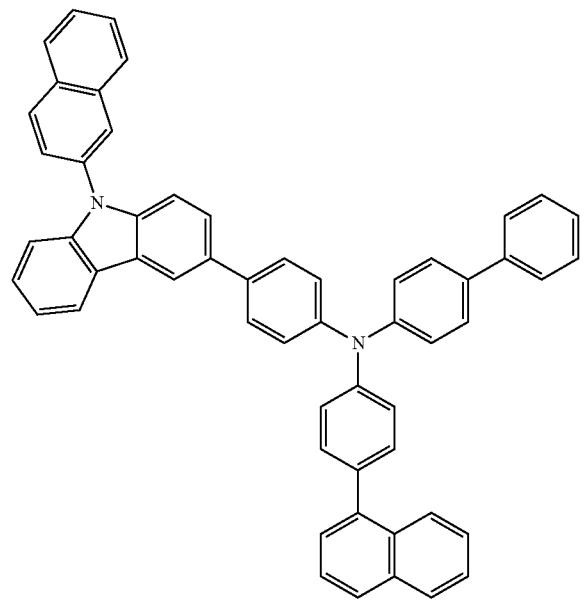
(418)
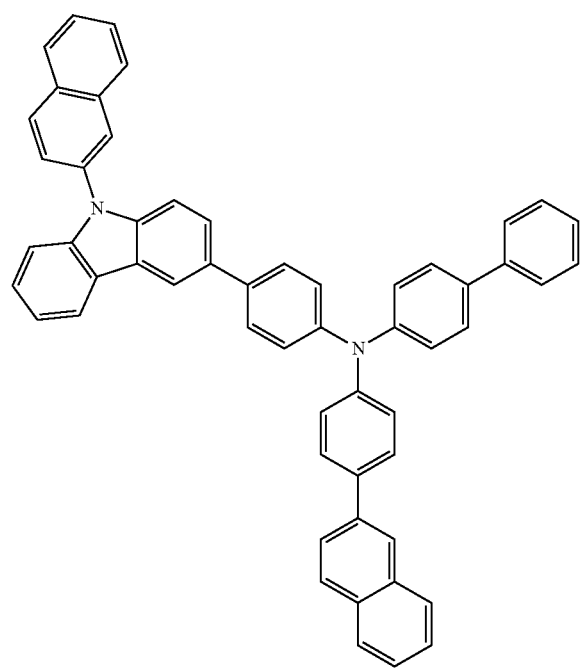
(419)
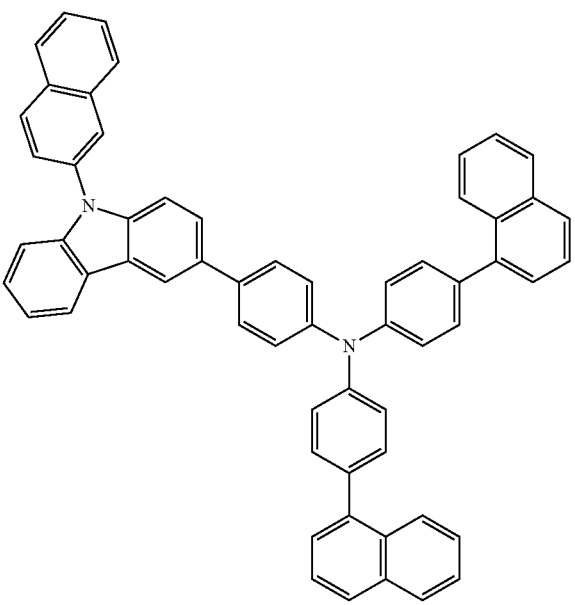
(420)
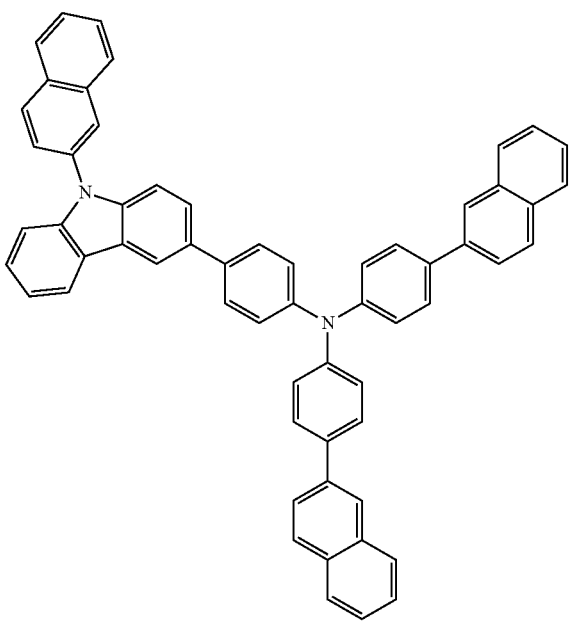

(421)

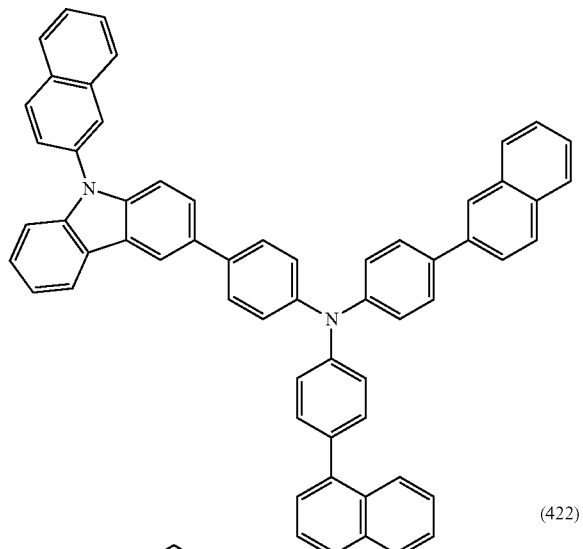

(422)

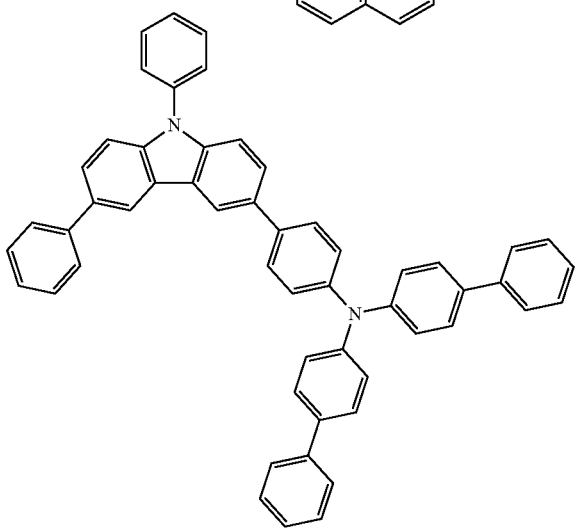

(423)

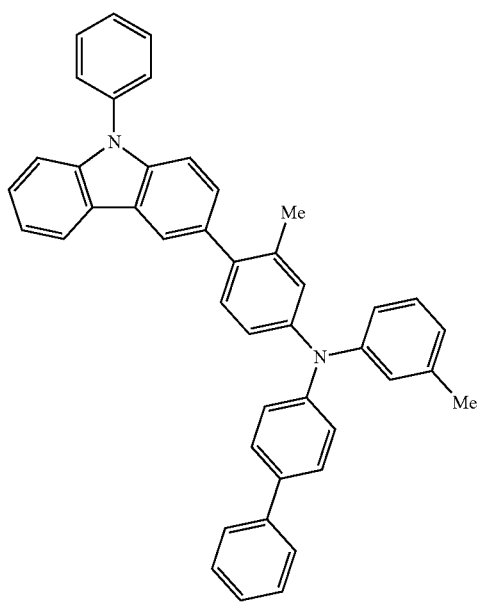

(424)

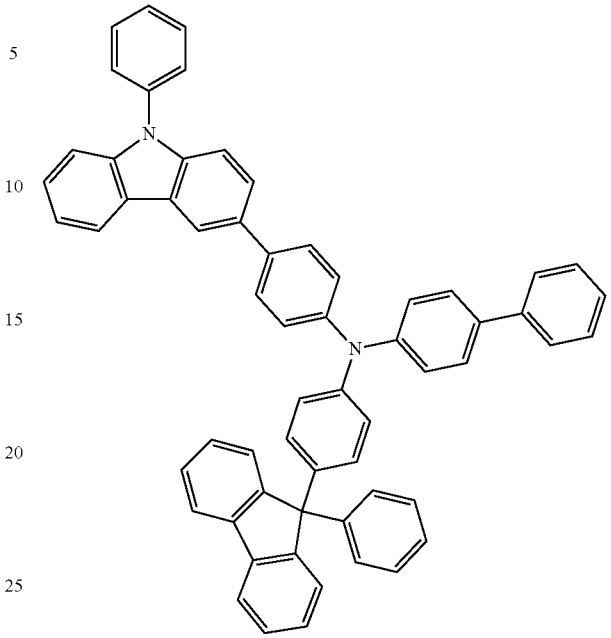

(425)

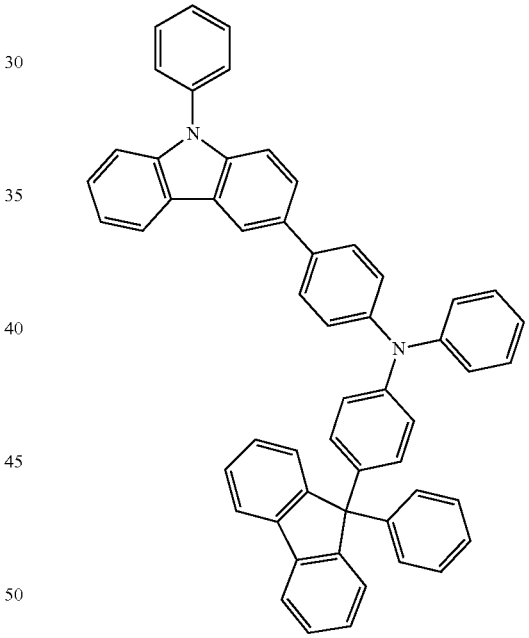

In addition, the carbazole derivative of the present invention represented by the general formula (1) can be synthesized by a synthetic method represented by the following synthetic schemes (A-1) to (A-7), a synthetic scheme (B-1), and synthetic schemes (C-1) to (C-2).

[Synthetic Method of Halogenated Secondary Arylamine (Compound A)]

Halogenated secondary arylamine represented by a general formula (compound A) can be synthesized in a manner like the following synthetic scheme (A-1). In other words, first, secondary arylamine (compound $A_1$) is halogenated by using a halogenating agent, whereby the halogenated secondary arylamine (compound A) can be obtained. Note that as the halogenating agent, N-bromosuccinimide (NBS), N-iodosuccinimide (NIS), bromine, iodine, potassium iodide, or the like can be used. In addition, each $X^1$ represents a halogen group, which is preferably a bromo group or an iodine group.

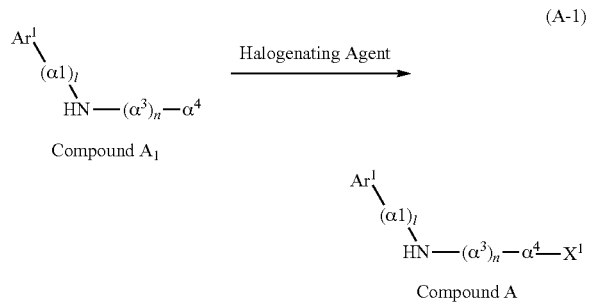

Compound $A_1$

Compound A

[Synthetic Method of a Halogenated Carbazole Derivative (Compound $B_2$)]

A halogenated carbazole derivative represented by a general formula (compound $B_2$) can be synthesized in a manner like the following synthetic scheme (A-2). In other words, first, a carbazole derivative (compound $B_1$) is halogenated by using a halogenating agent, whereby the halogenated carbazole derivative (compound $B_2$) can be obtained. Note that as the halogenating agent, N-bromosuccinimide (NBS), N-iodosuccinimide (NIS), bromine, iodine, potassium iodide, or the like can be used. In addition, each $X^1$ represents a halogen group, which is preferably a bromo group or an iodine group.

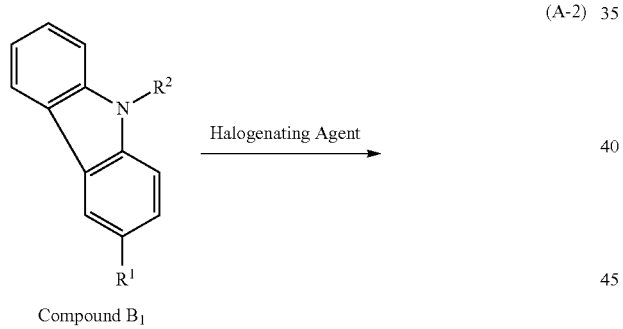

Compound $B_1$

Compound $B_2$

[Synthetic Method of a Compound (Compound B) in which 9H-Carbazol-3-Boronic Acid or the Third Position of 9H-Carbazol is Substituted by Organoboron]

A compound in which the third position of 9H-carbazole is substituted by boronic acid or organoboron, which is represented by a general formula (compound B), can be synthesized in a manner like the following synthetic scheme (A-3). In other words, boron oxidation or organoboronation is performed on the halogenated carbazole derivative (compound $B_2$) using an alkyllithium reagent and a boron reagent, whereby the compound in which the third position of 9H-carbazole is substituted by boronic acid or organoboron (compound B) can be obtained.

Note that $R^{99}$ in the scheme (A-3) represents an alkyl group having 1 to 6 carbon atoms. $R^{98}$ presents an alkyl group having 1 to 6 carbon atoms. In addition, $R^{100}$ and $R^{101}$ each represent a hydrogen atom or an alkyl group having 1 to 6 carbon atoms. $R^{102}$ and $R^{103}$ may be connected to each other to form a ring. In addition, n-butyllithium, methyllithium, or the like can be used as the alkyllithium reagent. Trimethyl borate, isopropyl borate, or the like can be used as the boron reagent.

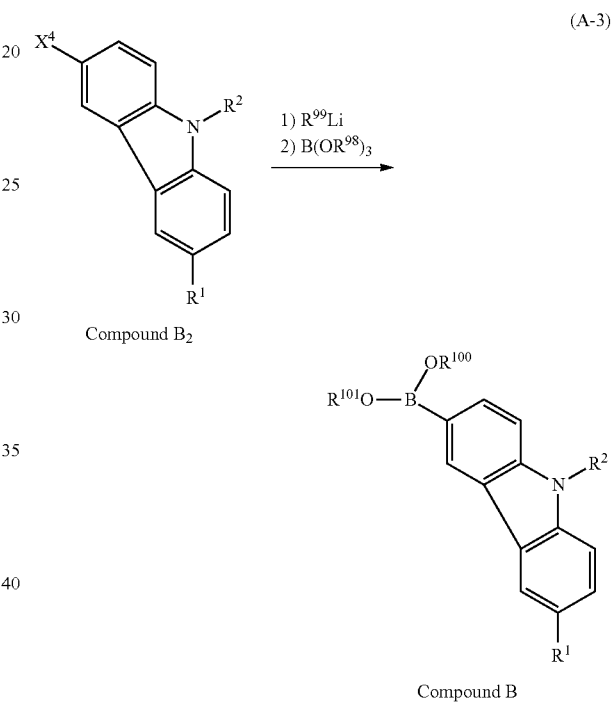

Compound $B_2$

Compound B

[Synthetic Method of Secondary Arylamine (Compound $C_3$)]

Secondary arylamine represented by a general formula (compound $C_3$) can be synthesized in a manner like the following synthetic scheme (A-4). In other words, halogenated aryl (compound $C_1$) and primary arylamine (compound $C_2$) are coupled in the presence of a base using a metal catalyst, whereby the secondary arylamine (compound $C_3$) can be obtained.

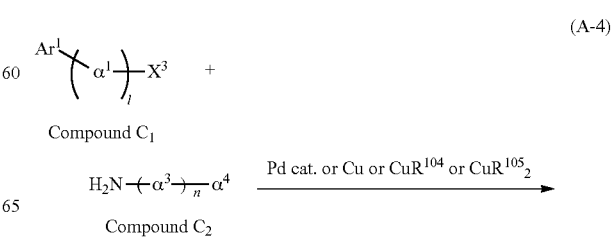

Compound $C_1$

Compound $C_2$

-continued

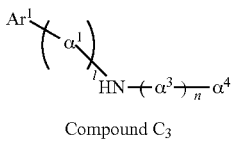

Compound C₃

In the case where a Buchwald-Hartwig reaction is performed, as the palladium catalyst which can be used in the synthetic scheme (A-4), although bis(dibenzylideneacetone)palladium(0), palladium(II) acetate, and the like can be given, the palladium catalyst which can be used is not limited thereto. As a ligand in the palladium catalyst which can be used in the synthetic scheme (A-4), although tri(tert-butyl)phosphine, tri(n-hexyl)phosphine, tricyclohexylphosphine, and the like can be given, the ligand which can be used is not limited thereto.

As a base which can be used in the synthetic scheme (A-4), although an organic base such as sodium tert-butoxide, an inorganic base such as potassium carbonate, and the like can be given, the base which can be used is not limited thereto. In addition, as a solvent that can be used in the synthetic scheme (A-4), although toluene, xylene, benzene, tetrahydrofuran, and the like can be given, the solvent which can be used is not limited thereto.

The case in which an Ullmann reaction is performed in the synthetic scheme (A-4) is described. In the synthetic scheme (A-4), $R^{104}$ and $R^{105}$ each represent a halogen group, an acetyl group, or the like, and chlorine, bromine, and iodine can be given as the halogen group. It is preferable that $R^{104}$ be iodine to form copper(I) iodide or that $R^{105}$ be an acetyl group to form a copper(II) acetate. The copper compound used for the reaction is not limited thereto, and copper can be used as an alternative to the copper compound. As a base which can be used in the synthetic scheme (A-4), although an inorganic base such as potassium carbonate can be given, the base which can be used is not limited thereto.

As a solvent which can be used in the synthetic scheme (A-4), although 1,3-dimethyl-3,4,5,6-tetrahydro-2(1H)pyrimidinone (abbreviation: DMPU), toluene, xylene, benzene, and the like can be given, the solvent which can be used is not limited thereto. DMPU or xylene which has a high boiling point is preferably used because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used.

[Synthetic Method of Tertiary Arylamine (Compound C₅)]

Tertiary arylamine represented by a general formula (compound C₅) can be synthesized in a manner like the following synthetic scheme (A-5). In other words, the secondary arylamine (compound C₃) and halogenated aryl (compound C₄) are coupled in the presence of a base using a metal catalyst, whereby the tertiary arylamine (compound C₅) can be obtained.

(A-5)

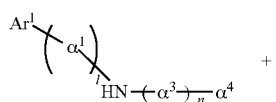

Compound C₃

+

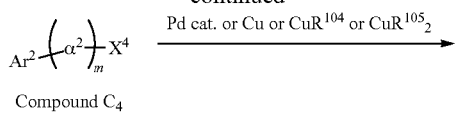

Compound C₄

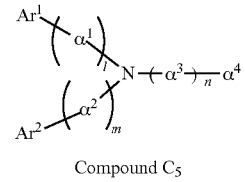

Compound C₅

In the case where a Buchwald-Hartwig reaction is performed, as the palladium catalyst which can be used in the synthetic scheme (A-5), although bis(dibenzylideneacetone)palladium(0), palladium(II) acetate, and the like can be given, the palladium catalyst which can be used is not limited thereto. As a ligand in the palladium catalyst which can be used in the synthetic scheme (A-5), although tri(tert-butyl)phosphine, tri(n-hexyl)phosphine, tricyclohexylphosphine, and the like can be given, the ligand which can be used is not limited thereto.

As a base which can be used in the synthetic scheme (A-5), although an organic base such as sodium tert-butoxide, an inorganic base such as potassium carbonate, and the like can be given, the base which can be used is not limited thereto. In addition, as a solvent that can be used in the synthetic scheme (A-5), although toluene, xylene, benzene, tetrahydrofuran, and the like can be given, the solvent which can be used is not limited thereto.

The case in which an Ullmann reaction is performed in the synthetic scheme (A-5) is described. In the synthetic scheme (A-5), $R^{104}$ and $R^{105}$ each represent a halogen group, an acetyl group, or the like, and chlorine, bromine, and iodine can be given as the halogen group. It is preferable that $R^{104}$ be iodine to form copper(I) iodide or that $R^{105}$ be an acetyl group to form a copper(II) acetate. The copper compound used for the reaction is not limited thereto, and copper can be used as an alternative to the copper compound. As a base which can be used in the synthetic scheme (A-5), although an inorganic base such as potassium carbonate can be given, the base which can be used is not limited thereto.

As a solvent which can be used in the synthetic scheme (A-5), although 1,3-dimethyl-3,4,5,6-tetrahydro-2(1H)pyrimidinone (abbreviation: DMPU), toluene, xylene, benzene, and the like can be given, the solvent which can be used is not limited thereto. DMPU or xylene which has a high boiling point is preferably used because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used.

[Synthetic Method of Tertiary Arylamine (Compound C₅)]

Tertiary arylamine represented by a general formula (compound C₅) can be synthesized in a manner like the following synthetic scheme (A-6). In other words, the primary arylamine (compound C₂) and the halogenated aryl (compounds C₁ and C₄) are coupled in the presence of a base using a metal catalyst, whereby the tertiary arylamine (compound C₅) can be obtained. However, when $Ar^1$ and $Ar^2$ are the same, $\beta^1$ and $\beta^2$ are the same, and l and m are the same, the compound C₅ can be obtained with high yield.

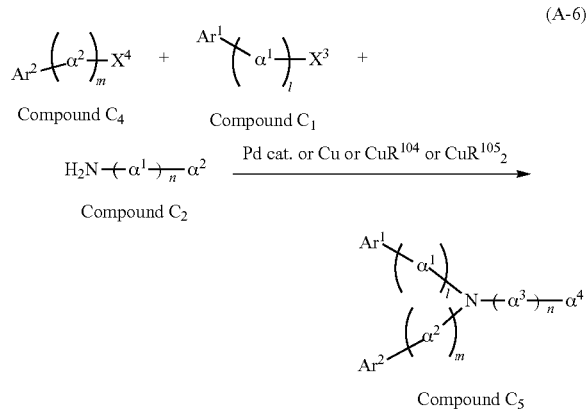

Compound C₄   Compound C₁

$H_2N$―$(α^1)_n$―$α^2$  →  Pd cat. or Cu or CuR¹⁰⁴ or CuR¹⁰⁵₂

Compound C₂

(A-6)

Compound C₅

In the case where a Buchwald-Hartwig reaction is performed, as the palladium catalyst which can be used in the synthetic scheme (A-6), although bis(dibenzylideneacetone)palladium(0), palladium(II) acetate, and the like can be given, the palladium catalyst which can be used is not limited thereto. As a ligand in the palladium catalyst which can be used in the synthetic scheme (A-6), although tri(tert-butyl)phosphine, tri(n-hexyl)phosphine, tricyclohexylphosphine, and the like can be given, the ligand which can be used is not limited thereto.

As a base which can be used in the synthetic scheme (A-6), although an organic base such as sodium tert-butoxide, an inorganic base such as potassium carbonate, and the like can be given, the base which can be used is not limited thereto. In addition, as a solvent that can be used in the synthetic scheme (A-6), although toluene, xylene, benzene, tetrahydrofuran, and the like can be given, the solvent which can be used is not limited thereto.

The case in which an Ullmann reaction is performed in the synthetic scheme (A-6) is described. In the synthetic scheme (A-6), $R^{104}$ and $R^{105}$ each represent a halogen group, an acetyl group, or the like, and chlorine, bromine, and iodine can be given as the halogen group. It is preferable that $R^{104}$ be iodine to form copper(I) iodide or that $R^{105}$ be an acetyl group to form a copper(II) acetate. The copper compound used for the reaction is not limited thereto, and copper can be used as an alternative to the copper compound. As a base which can be used in the synthetic scheme (A-6), although an inorganic base such as potassium carbonate can be given, the base which can be used is not limited thereto.

As a solvent which can be used in the synthetic scheme (A-6), although 1,3-dimethyl-3,4,5,6-tetrahydro-2(1H)pyrimidinone (abbreviation: DMPU), toluene, xylene, benzene, and the like can be given, the solvent which can be used is not limited thereto. DMPU or xylene which has a high boiling point is preferably used because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used.

[Synthetic Method of Halogenated Tertiary Arylamine Derivative (Compound C)]

Halogenated tertiary arylamine represented by a general formula (compound C) can be synthesized in a manner like the following synthetic scheme (A-7). In other words, first, tertiary arylamine (compound C₅) is halogenated by using a halogenating agent, whereby the halogenated tertiary arylamine (compound C) can be obtained. Note that as the halogenating agent, N-bromosuccinimide (NBS), N-iodosuccinimide (NIS), bromine, iodine, potassium iodide, or the like can be used. In addition, each $X^1$ represents a halogen group, which is preferably a bromo group or an iodine group.

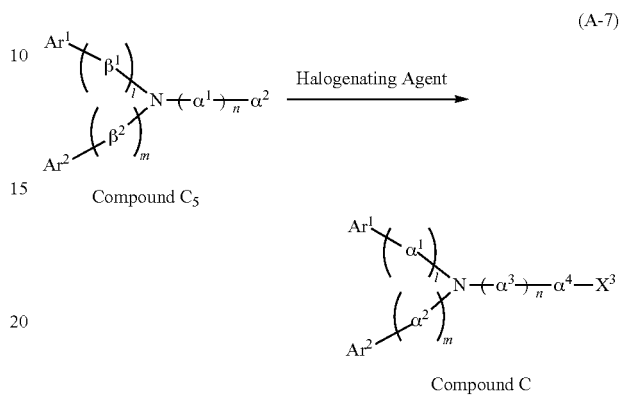

[Synthetic Method of Secondary Arylamine (Compound D)]

Secondary arylamine having carbazole, which is represented by a general formula (compound D), can be synthesized in a manner like the following synthetic scheme (B-1). In other words, the halogenated secondary arylamine (compound A) and the compound in which the third position of 9H-carbazole is substituted by boronic acid or organoboron (compound B) can be coupled in the presence of a base using a metal catalyst. Accordingly, the secondary arylamine having carbazole (compound D) can be obtained.

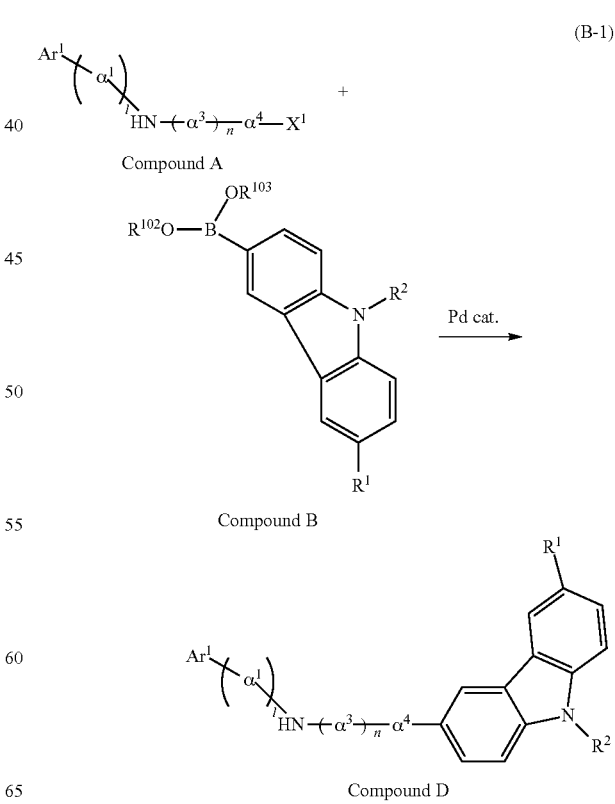

In any of the above schemes, the case of using a Suzuki-Miyaura reaction is described. As a palladium catalyst which can be used as a metal catalyst, palladium(II) acetate, tetrakis(triphenylphosphine)palladium(0), bis(triphenylphosphine)palladium(II)dichloride, and the like can be given. As a ligand in the above palladium catalyst, tri(ortho-tolyl)phosphine, triphenylphosphine, tricyclohexylphosphine, and the like can be given. In addition, as the above base, an organic base such as sodium tert-butoxide, an inorganic base such as potassium carbonate, and the like can be given. As the solvent which can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of ethers such as ethyleneglycoldimethylether and water; and the like can be given.

However, the catalyst, ligand, base, and solvent which can be used are not limited thereto.

In addition, in any of the above schemes, cross coupling using organoaluminum, organozirconium, organozinc, or organotin compound, or the like, in addition to arylboronic acid, may be employed as a base material. However, the present invention is not limited thereto.

[Synthetic Method of Tertiary Arylamine Having Carbazole (Compound E)]

Tertiary arylamine having carbazole represented by a general formula (compound E) can be synthesized in a manner like the following synthetic scheme (C-1). In other words, the secondary arylamine having carbazole (compound D) and the halogenated aryl (compound $C_4$) are coupled in the presence of a base using a metal catalyst, whereby the tertiary arylamine having carbazole (compound E), which is a final product, can be obtained.

In any of the above schemes, the case of using a Suzuki-Miyaura reaction is described. As a palladium catalyst which can be used as a metal catalyst, palladium(II) acetate, tetrakis(triphenylphosphine)palladium(0), bis(triphenylphosphine)palladium(II)dichloride, and the like can be given. As a ligand in the above palladium catalyst, tri(ortho-tolyl)phosphine, triphenylphosphine, tricyclohexylphosphine, and the like can be given. In addition, as the above base, an organic base such as sodium tert-butoxide, an inorganic base such as potassium carbonate, and the like can be given. As the solvent which can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of ethers such as ethyleneglycoldimethylether and water; and the like can be given.

However, the catalyst, ligand, base, and solvent which can be used are not limited thereto.

In addition, in any of the above schemes, cross coupling using organoaluminum, organic zirconium, organozinc, organozirconium, organotin, or the like, in addition to arylboronic acid, may be employed as a base material. However, the present invention is not limited thereto.

[Another Synthetic Method of the Tertiary Arylamine Having Carbazole (Compound E)]

The tertiary arylamine having carbazole represented by the general formula (compound E) can be synthesized in a manner like the following synthetic scheme (C-2). In other words, first, the halogenated tertiary arylamine (compound C) and the compound in which the third position of 9H-carbazole is substituted by boronic acid or organoboron (compound B) are coupled in the presence of a base using a metal catalyst, whereby the tertiary arylamine having carbazole (compound E), which is a final product, can be obtained.

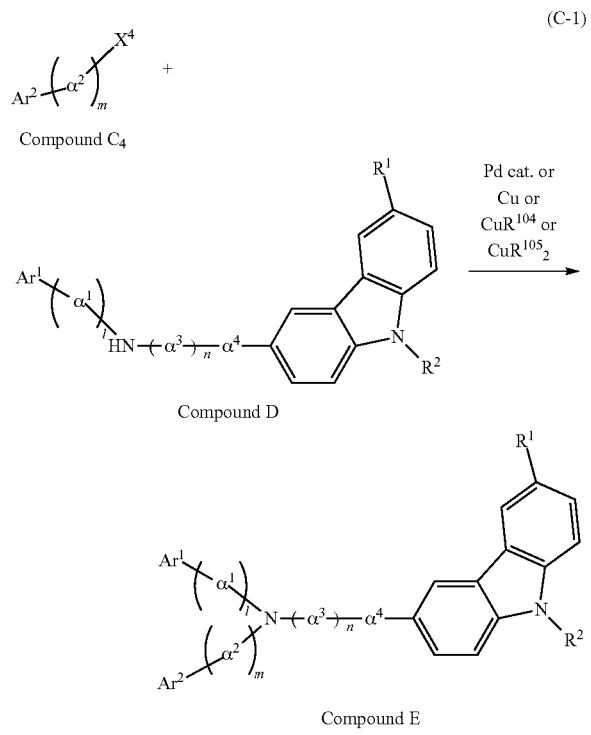

Compound $C_4$

Compound D

Compound E (C-1)

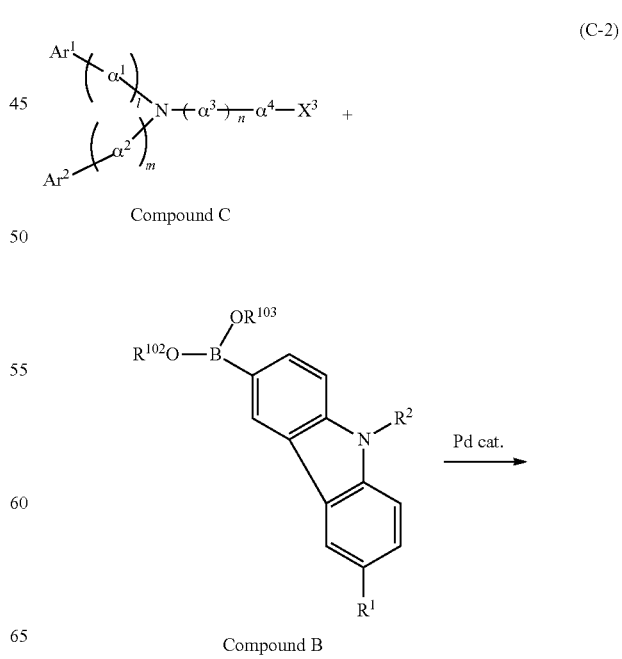

Compound C

Compound B (C-2)

-continued

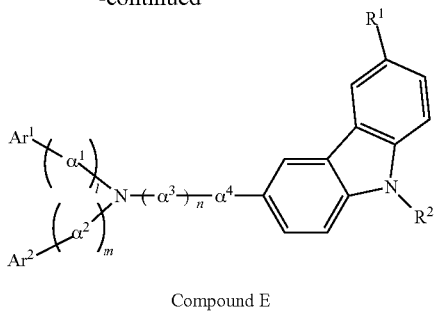

Compound E

Embodiment Mode 2

In Embodiment Mode 2, a light-emitting element which is formed using, for a hole-transporting layer, the carbazole derivative of the present invention described in Embodiment Mode 1 will be described.

The light-emitting element in Embodiment Mode 2 includes a first electrode which functions as an anode, a second electrode which functions as a cathode, and an EL layer interposed between the first electrode and the second electrode. Note that the light-emitting element in Embodiment Mode 2 can obtain light emission when voltage is applied to each electrode so that the potential of the first electrode is higher than that of the second electrode.

In addition, the EL layer of the light-emitting element in Embodiment Mode 2 includes in its structure a first layer (a hole-injecting layer), a second layer (a hole-transporting layer), a third layer (a light-emitting layer), a fourth layer (an electron-transporting layer), and a fifth layer (an electron-injecting layer), from the first electrode side.

A structure of the light-emitting element in Embodiment Mode 2 is described with reference to FIGS. 1A and 1B. A substrate 101 is used as a support of the light-emitting element. For the substrate 101, glass, quartz, plastics, or the like can be used, for example.

Note that although the above substrate 101 may remain in a light-emitting device or an electronic device which is a product utilizing the light-emitting element of the present invention, the substrate 101 may only have a function as the support of the light-emitting element in the manufacturing process of the light-emitting element, without remaining in an end product.

For a first electrode 102 formed over the substrate 101, a metal, an alloy, an electrically conductive compound, a mixture thereof, or the like having a high work function (specifically, a work function of 4.0 eV or more) is preferably used. Specifically, the following examples can be given: indium tin oxide (ITO), indium tin oxide containing silicon or silicon oxide, indium zinc oxide (IZO), and indium oxide containing tungsten oxide and zinc oxide. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of the metal materials (e.g., titanium nitride), and the like can be given. However, in the present invention, a first layer 111 in an EL layer 103 which is formed in contact with the first electrode 102 is formed using a composite material with which holes are easily injected regardless of the work function of the first electrode 102. Therefore, a variety of known methods can be used as long as it is a material that can serve as an electrode material (e.g., a metal, an alloy, an electrically conductive compound, a mixture thereof, or the like, or an element belonging to Group 1 or 2 of the periodic table is also included).

A film of any of those materials is generally formed by a sputtering method. For example, indium zinc oxide (IZO) can be formed by a sputtering method using a target in which 1 wt % to 20 wt % zinc oxide is added to indium oxide; and indium oxide containing tungsten oxide and zinc oxide can be formed by a sputtering method using a target in which 0.5 wt % to 5 wt % tungsten oxide and 0.1 wt % to 1 wt % zinc oxide are added to indium oxide. Alternatively, the first layer 111 may be formed by a vacuum evaporation method, an ink-jet method, a spin-coating method, or the like.

Further, when a layer containing a composite material which will be described later is used as a material used for the first layer 111 formed in contact with the first electrode 102 in the EL layer 103 formed over the first electrode 102, any of a variety of materials such as metals, alloys, and electrically conductive compounds; a mixture thereof; or the like can be used as a substance used for the first electrode 102 regardless of their work functions. For example, aluminum (Al), silver (Ag), an alloy containing aluminum (AlSi), or the like can also be used.

Furthermore, an element belonging to Group 1 or 2 of the periodic table, which is a low work function material, that is, an alkali metal such as lithium (Li) or cesium (Cs), an alkaline earth metal such as magnesium (Mg), calcium (Ca), or strontium (Sr), an alloy containing any of these metals (such as an MgAg alloy or an AlLi alloy), a rare-earth metal such as europium (Eu) or ytterbium (Yb), an alloy containing such rare-earth metals, or the like can also be used.

Note that in the case where the first electrode 102 is formed using an alkali metal, an alkaline-earth metal, or an alloy thereof, a vacuum evaporation method or a sputtering method can be employed. Note that in the case of using a silver paste or the like, a coating method, an ink-jet method, or the like can be used.

For the EL layer 103 formed over the first electrode 102, a known substance can be used, and any of a low molecular compound and a macromolecular compound can be used. Note that the substance used to form the EL layer 103 has not only a structure formed of only an organic compound but also a structure partially containing an inorganic compound.

For forming the EL layer 103, a hole-injecting layer containing a substance having a high hole-injecting property, a hole-transporting layer containing a substance having a high hole-transporting property, a light-emitting layer containing a light-emitting substance, an electron-transporting layer containing a substance having a high electron-transporting property, an electron-injecting layer containing a substance having a high electron-injecting property, and the like are combined with each other and stacked, as appropriate.

Note that in the EL layer 103 shown in FIG. 1A, the first layer (a hole-injecting layer) 111, a second layer (a hole-transporting layer) 112, a third layer (a light-emitting layer) 113, a fourth layer (an electron-transporting layer) 114, and a fifth layer (an electron-injecting layer) 115 are sequentially stacked from the first electrode 102 side.

The first layer 111 which is a hole-injecting layer is a hole-injecting layer containing a substance having a high hole-injecting property. As the substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used. Alternatively, as a low-molecular organic compound, a phthalocyanine-based compound such as phthalocyanine (abbreviation: H₂Pc), copper(II) phthalocyanine (abbreviation: CuPc), or vanadyl phthalocyanine (abbreviation: VOPc) can be given.

In addition, the following aromatic amine compounds which are low-molecular organic compounds can also be given: 4,4',4''-tris(N,N-diphenylamino)triphenylamine (abbreviation: TDATA); 4,4',4''-tris[N-(3-methylphenyl)-N-phenylamino]triphenylamine (abbreviation: MTDATA); 4,4'-bis[N-(4-diphenylaminophenyl)-N-phenylamino]biphenyl (abbreviation: DPAB); 4,4'-bis(N-{4-[N'-(3-methylphenyl)-N'-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Note that the carbazole derivative of the present invention which is described in Embodiment Mode 1 can also be used in a similar manner.

Further, a macromolecular compound (an oligomer, a dendrimer, a polymer, or the like) can also be used. For example, macromolecular compounds such as poly(N-vinylcarbazole) (abbreviation: PVK); poly(4-vinyltriphenylamine) (abbreviation: PVTPA), poly[N-(4-{N'[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD) can be given. In addition, a macromolecular compound, to which acid is added, such as poly(3,4-ethylenedioxythiophene)/poly(styrenesulfonic acid) (PEDOT/PSS) or polyaniline/poly(styrenesulfonic acid) (abbreviation: PAni/PSS) can also be used.

Alternatively, for the first layer 111, the composite material in which a substance having an acceptor property is contained in a substance having a high hole-transporting property can be used. Note that by using the substance having a high hole-transporting property containing a substance having an acceptor property, a material used to form an electrode may be selected regardless of its work function. In other words, not only a material with a high work function but also a material with a low work function can be used as the first electrode 102. Such composite materials can be formed by co-evaporation of a substance having a high hole-transporting property and a substance having an acceptor property. Note that in this specification, "composition" means not only a simple mixture of two materials but also a mixture of a plurality of materials in a condition where an electric charge is given and received among the materials.

As an organic compound used for the composite material, various compounds such as an aromatic amine compound, a carbazole derivative, aromatic hydrocarbon, and a macromolecular compound (an oligomer, a dendrimer, a polymer, or the like) can be used. The organic compound used for the composite material is preferably an organic compound having a high hole-transporting property. Specifically, a substance having a hole mobility of $10^{-6}$ cm²/Vs or more is preferably used. However, other than the above substances may be used as long as the substance has a higher hole-transporting property than an electron-transporting property. The organic compound that can be used for the composite material is specifically shown below.

As an organic compound used for the composite material, for example, an aromatic amine compound such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or a-NPD), and N,N'-bis(3-methylphenyl)-N,N'-diphenyl-[1,1'-biphenyl]-4,4'-diamine (abbreviation: TPD); and a carbazole derivative such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene can be given. Note that the carbazole derivative of the present invention which is described in Embodiment Mode 1 can also be used in a similar manner.

In addition, the following aromatic hydrocarbon compounds can be given: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 9,10-bis[2-(1-naphthyl)phenyl]-2-tert-butyl-anthracene; 9,10-bis[2-(1-naphthyl)phenyl]anthracene; 2,3,6,7-tetramethyl-9,10-di(1-naphthyl)anthracene; and the like.

Further, the following aromatic hydrocarbon compound compounds can also be given: 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; pentacene; coronene; 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

As a substance having an acceptor property, organic compounds such as 7,7,8,8-tetracyano-2,3,5,6-tetrafluoroquinodimethane (abbreviation: F₄-TCNQ) and chloranil, and a transition metal oxide can be given. In addition, oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of a high electron-accepting property. Among these, molybdenum oxide is especially preferable because it is stable in the air and its hygroscopic property is low so that it can be easily treated.

Note that a composite material, which is formed using the above macromolecular compound such as PVK, PVTPA, PTPDMA, or Poly-TPD and the above substance having an acceptor property, may be used for the first layer 111. Note that a composite material, which is formed combining the carbazole derivative of the present invention which is described in Embodiment Mode 1 with the above substance having an acceptor property, can also be used for the first layer 111.

The second layer 112 which is a hole-transporting layer is a hole-transporting layer containing a substance having a high hole-transporting property. Note that the carbazole derivative of the present invention which is described in Embodiment Mode 1 is used for the second layer 112 in Embodiment Mode 2.

In addition, the carbazole derivative of the present invention which is described in Embodiment Mode 1 can also be used for both the first layer 111 and the second layer 112. In this case, an element can be manufactured easily and material use efficiency can also be improved. Moreover, since energy diagrams of the first layer 111 and the second layer 112 are the same or similar, carriers can be transported easily between the first layer 111 and the second layer 112.

The third layer 113 is a light-emitting layer containing a substance having a high light-emitting property. For the third layer 113, any of low molecular organic compounds given below can be used.

As a light-emitting substance for blue emission, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like can be given.

As a light-emitting substance for green emission, the following can be given: N-(9,10-diphenyl-2-anthryl)-N,9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine (abbreviation: 2DPAPA); N-[9,10-bis(1,1'-biphenyl-2-yl)-2-anthryl]-N,N',N'-triphenyl-1,4-phenylenediamine (abbreviation: 2DPABPhA); N-[9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); and the like.

As a light-emitting substance for yellow light emission, rubrene, 5,12-bis(1,1'-biphenyl-4-yl)-6,11-diphenyltetracene (abbreviation: BPT), and the like can be given. Further, as a light-emitting substance for red light emission, N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3,10-diamine (abbreviation: p-mPhAFD), and the like can be given.

Further, the third layer 113 may have a structure in which the above substance having a high light-emitting property is dispersed in another substance. Note that in the case of dispersing, the concentration of the substance to be dispersed is preferably set 20% or less of the total in mass ratio. Further, as a substance in which the substance having a light-emitting property is dispersed, a known substance can be used. It is preferable to use a substance having a lowest unoccupied molecular orbital level (LUMO level) deeper (the absolute value is larger) than that of the substance having a light-emitting property and having a highest occupied molecular orbital level (HOMO level) shallower (the absolute value is smaller) than that of the substance having a light-emitting property.

Specifically, any of the following metal complexes can be used: tris(8-quinolinolato)aluminum(III) (abbreviation: Alq); tris(4-methyl-8-quinolinolato)aluminum(III) (abbreviation: Almq$_3$); bis(10-hydroxybenzo[h]quinolinato)beryllium(II) (abbreviation: BeBq$_2$); bis(2-methyl-8-quinolinolato)(4-phenylphenolato)aluminum(III) (abbreviation: BAlq); bis(8-quinolinolato)zinc(II) (abbreviation: Znq); bis[2-(2-benzoxazolyl)phenolato]zinc(II) (abbreviation: ZnPBO); bis[2-(2-benzothiazolyl)phenolato]zinc(II) (abbreviation: ZnBTZ); and the like.

In addition, any of the following heterocyclic compounds can be used: 2-(biphenyl-4-yl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(biphenyl-4-yl)-4-phenyl-5-(4-tert-butylphenyl)-1,2,4-triazole (abbreviation: TAZ); 2,2',2"-(1,3,5-benzenetriyl)tris(1-phenyl-1H-benzimidazole) (abbreviation: TPBI); bathophenanthroline (abbreviation: BPhen); bathocuproine (BCP); and the like.

Besides, any of the following condensed aromatic compounds can also be used: 9-[4-(10-phenyl-9-anthryl)phenyl]-9H-Carbazole (abbreviation: CzPA); 3,6-diphenyl-9-[4-(10-phenyl-9-anthryl)phenyl]-9H-Carbazole (abbreviation: DPCzPA); 9,10-bis(3,5-diphenylphenyl)anthracene (abbreviation: DPPA); 9,10-di(2-naphthyl)anthracene (abbreviation: DNA); 2-tert-butyl-9,10-di(2-naphthyl)anthracene (abbreviation: t-BuDNA); 9,9'-bianthryl (abbreviation: BANT); 9,9'-(stilbene-3,3'-diyl)diphenanthrene (abbreviation: DPNS); 9,9'-(stilbene-4,4'-diyl)diphenanthrene (abbreviation: DPNS2); 3,3',3"-(benzene-1,3,5-triyl)tripyrene (abbreviation: TPB3); and the like.

As the substance in which the substance having a light-emitting property is dispersed, a plurality of kinds of substances can be used. For example, in order to suppress crystallization, a substance for suppressing crystallization of rubrene or the like may be further added. In addition, NPB, Alq, or the like may be further added in order to efficiently transfer energy to the substance having a light-emitting property. Thus, with the structure in which the substance having a high light-emitting property is dispersed in another substance, crystallization of the third layer 113 can be suppressed. Further, concentration quenching which results from the high concentration of the substance having a high light-emitting property can be suppressed.

Further, in particular, among the above substances, a substance having an electron-transporting property is preferably used so that the substance having a light-emitting property is dispersed therein to form the third layer 113. Specifically, it is also possible to use any of the above metal complexes and heterocyclic compounds; CzPA, DNA, and t-BuDNA among the above condensed aromatic compounds; and further macromolecular compounds which will be given later as a substance that can be used for the fourth layer 114.

Alternatively, for the third layer 113, the following macromolecular compound can be used.

As a light-emitting substance for blue light emission, poly(9,9-dioctylfluorene-2,7-diyl) (abbreviation: POF), poly[(9,9-dioctylfluorene-2,7-diyl)-co-(2,5-dimethoxybenzen-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like can be given.

As a light-emitting substance for green light emission, poly(p-phenylenvinylene) (abbreviation: PPV), poly[(9,9-dihexylfluorene-2,7-diyl)-alt-co-(benzo[2,1,3]thiadiazol-4,7-diyl)](abbreviation: PFBT), poly[(9,9-dioctyl-2,7-divinylenfluorenylene)-alt-co-(2-methoxy-5-(2-ethylhexyloxy)-1, 4-phenylene)], and the like can be given.

As light-emitting substances for orange to red light emission, poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like can be given.

The fourth layer 114 is an electron-transporting layer containing a substance having a high electron-transporting property. For the fourth layer 114, for example, as a low molecular organic compound, a metal complex such as Alq, Almq$_3$, BeBq$_2$, BAlq, Znq, ZnPBO, or ZnBTZ, or the like can be used. Alternatively, instead of the metal complex, a heterocyclic compound such as PBD, OXD-7, TAZ, TPBI, BPhen, or BCP can be used. The substances described here are mainly substances having an electron mobility of $10^{-6}$ cm$^2$/Vs or more. Note that other than the above substances may be used for the electron-transporting layer as long as the substance has a higher electron-transporting property than a hole-transporting property. Further, the electron-transporting layer is not limited to a single layer but may also be a stack layer of two or more layers formed of the above substances.

Alternatively, for the fourth layer 114, a macromolecular compound can be used. For example, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy), or the like can be used.

Further, the fifth layer 115 is an electron-injecting layer containing a substance having a high electron-injecting property. For the fifth layer 115, an alkali metal, an alkaline earth metal, or a compound thereof such as lithium fluoride (LiF), cesium fluoride (CsF), or calcium fluoride (CaF$_2$) can be used. Alternatively, a layer formed of a substance having an electron-transporting property which contains an alkali metal, an alkaline earth metal, or a compound thereof, specifically, a layer formed of Alq which contains magnesium (Mg), or the like may be used. Note that in this case, electrons can be more efficiently injected from a second electrode 104.

For the second electrode 104, a metal, an alloy, an electrically conductive compound, a mixture thereof, or the like having a low work function (specifically, a work function of 3.8 eV or less) can be used. As a specific example of such a cathode material, an element belonging to Group 1 or 2 of the periodic table, that is, an alkali metal such as lithium (Li) or cesium (Cs), an alkaline earth metal such as magnesium (Mg), calcium (Ca), or strontium (Sr), an alloy containing any of these metals (such as an MgAg alloy or an AlLi alloy), a rare-earth metal such as europium (Eu) or ytterbium (Yb), an alloy containing such rare-earth metals, and the like can be given.

Note that in the case where the second electrode 104 is formed using an alkali metal, an alkaline-earth metal, or an alloy thereof, a vacuum evaporation method or a sputtering method can be employed. Note that in the case of using a silver paste or the like, a coating method, an ink-jet method, or the like can be used.

Note that by providing the fifth layer 115, the second electrode 104 can be formed using any of a variety of conductive materials such as Al, Ag, ITO, and indium tin oxide containing silicon or silicon oxide regardless of their work functions. These conductive materials can be formed by a sputtering method, an ink-jet method, a spin coating method, or the like.

Further, as a formation method of the EL layer 103 in which the first layer (hole-injecting layer) 111, the second layer (hole-transporting layer) 112, the third layer (light-emitting layer) 113, the fourth layer (electron-transporting layer) 114, and the fifth layer (electron-injecting layer) 115 are sequentially stacked, any of a variety of methods can be employed regardless of whether the method is a dry process or a wet process. For example, a vacuum evaporation method, an ink-jet method, a spin coating method, or the like can be used. Note that a different formation method may be employed for each layer.

The second electrode 104 can also be formed by a wet process such as a sol-gel method using a paste of a metal material in addition to a dry process such as a sputtering method or a vacuum evaporation method.

In the light-emitting element of the present invention described above, current flows due to a potential difference generated between the first electrode 102 and the second electrode 104 and holes and electrons recombine in the EL layer 103, whereby light is emitted. Then, this light emission is extracted outside through one of or both the first electrode 102 and the second electrode 104. Therefore, one of or both the first electrode 102 and the second electrode 104 are an electrode having a light-transmitting property.

Figure 2A:
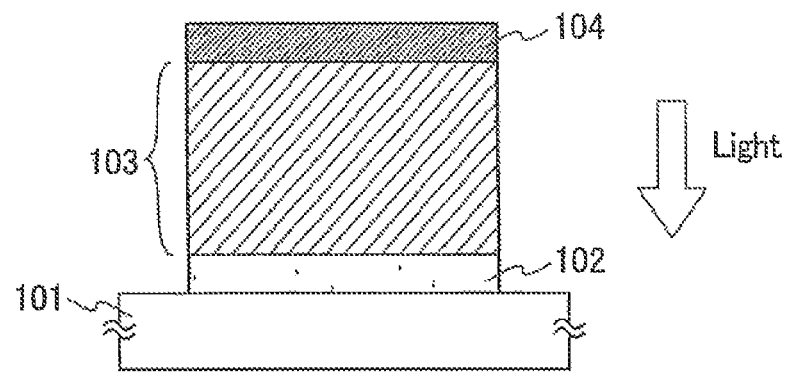
FIGS. 2A to 2C are cross-sectional views each showing a mode of light emission of a light-emitting element in Embodiment Mode 2.
Figure 2B:
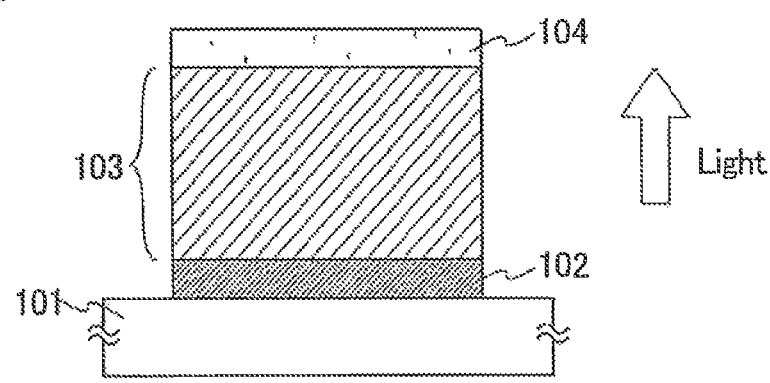
Figure 2C:
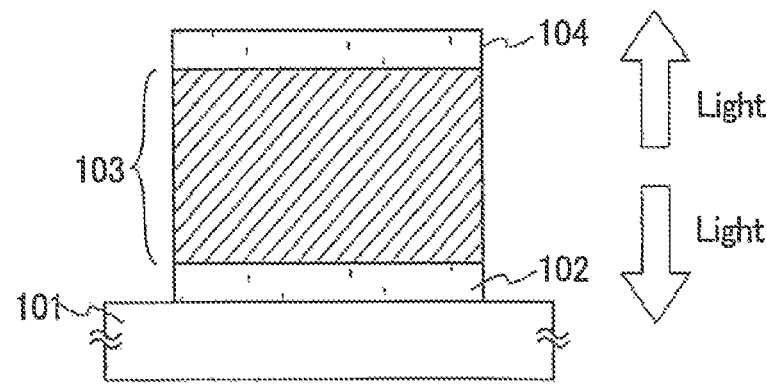

Note that when only the first electrode 102 is an electrode having a light-transmitting property, light emitted from the EL layer 103 is extracted from the substrate 101 side through the first electrode 102, as shown in FIG. 2A. Alternatively, when only the second electrode 104 is an electrode having a light-transmitting property, light emitted from the EL layer 103 is extracted from the opposite side to the substrate 101 side through the second electrode 104, as shown in FIG. 2B. Further alternatively, when the first electrode 102 and the second electrode 104 are both electrodes having a light-transmitting property, light emitted from the EL layer 103 is extracted to both the substrate 101 side and the opposite side to the substrate 101 side, through the first electrode 102 and the second electrode 104, as shown in FIG. 2C.

The structure of the layers provided between the first electrode 102 and the second electrode 104 is not limited to the above. Structures other than the above may be employed as long as at least the second layer 112 which is a hole-transporting layer and the third layer 113 which is a light-emitting layer are included.

Figure 1B:
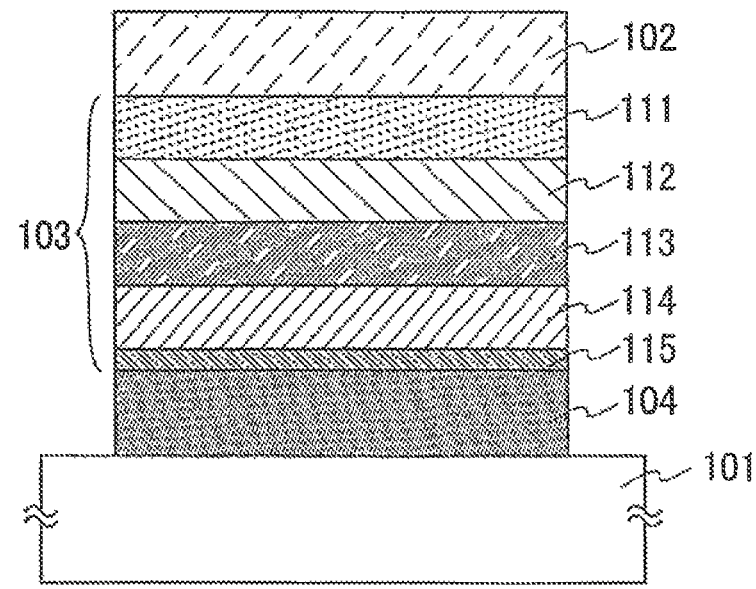

Alternatively, as shown in FIG. 1B, a structure may be employed in which the second electrode 104 which functions as a cathode, the EL layer 103, and the first electrode 102 which functions as an anode are sequentially stacked over the substrate 101. Note that the EL layer 103 in this case has a structure in which the fifth layer 115, the fourth layer 114, the third layer 113, the second layer 112, the first layer 111, and the first electrode 102 are sequentially stacked over the second electrode 104.

Note that by using the light-emitting element of the present invention, a passive matrix light-emitting device or an active matrix light-emitting device in which drive of the light-emitting element is controlled by a thin film transistor (TFT) can be manufactured.

Note that there is no particular limitation on the structure of the TFT in the case of manufacturing an active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is no particular limitation on the crystallinity of a semiconductor film used for the TFT. Either an amorphous semiconductor film or a crystalline semiconductor film may be used for the TFT.

Since the second layer (hole-transporting layer) 112 is formed using the carbazole derivative of the present invention in the light-emitting element which is shown in Embodiment Mode 2, not only improvement in element efficiency but also suppress of increase in drive voltage can be realized.

Note that Embodiment Mode 2 can be combined with any of the structures described in Embodiment Mode 1 as appropriate.

Embodiment Mode 3

Figure 3:
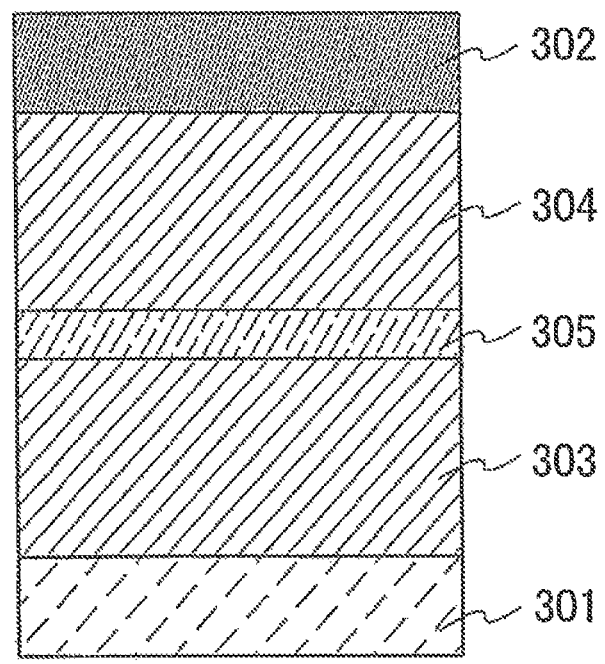
FIG. 3 is a cross-sectional view showing a stacked-layer structure of a light-emitting element in Embodiment Mode 3.

In Embodiment Mode 3, a light-emitting element having a plurality of EL layers any of the light-emitting elements described in Embodiment Mode 2 (hereinafter referred to as a stacked-type light-emitting element) will be described with reference to FIG. 3. This light-emitting element is a stacked-type light-emitting element that has a plurality of EL layers (a first EL layer 303 and a second EL layer 304) between a first electrode 301 and a second electrode 302. Note that although a structure of two EL layers is described in Embodiment Mode 3, a structure of three or more EL layers may also be employed.

In Embodiment Mode 3, the first electrode 301 functions as an anode, and the second electrode 302 functions as a cathode. Note that for the first electrode 301 and the second electrode 302, structures similar to those described in Embodiment Mode 1 can be employed. Further, for the plurality of EL layers (the first EL layer 303 and the second EL layer 304), structures similar to those described in Embodiment Mode 2 can be employed. Note that structures of the first EL layer 303 and the second EL layer 304 may be the same or different from each other and can be similar to those described in Embodiment Mode 2.

Further, a charge generation layer 305 is provided between the plurality of EL layers (the first EL layer 303 and the second EL layer 304). The charge generation layer 305 has a function of injecting electrons into one of the EL layers and injecting holes into the other of the EL layers when voltage is applied to the first electrode 301 and the second electrode 302. In Embodiment Mode 3, when voltage is applied so that the potential of the first electrode 301 is higher than that of the second electrode 302, the charge generation layer 305 injects electrons into the first EL layer 303 and injects holes into the second EL layer 304.

Note that the charge generation layer 305 preferably has a light-transmitting property in terms of light extraction efficiency. Further, the charge generation layer 305 functions even when it has lower conductivity than the first electrode 301 or the second electrode 302.

The charge generation layer 305 may have either a structure in which a substance having an acceptor property is added to a substance having a high hole-transporting property or a structure in which a substance having a donor property is added to a substance having a high electron-transporting property. Alternatively, both of these structures may be stacked.

In the case of employing the structure in which a substance having an acceptor property is added to a substance having a high hole-transporting property, as the substance having a high hole-transporting property, for example, an aromatic amine compound such as 4,4'-bis[N-(1-naphthyl)-N-phenylamino]biphenyl (abbreviation: NPB or a-NPD), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), or 4,4'-bis[N-(spiro-9,9'-bifluoren-2-yl)-N-phenylamino]-1,1'-biphenyl (abbreviation: BSPB) can be used. The substances described here are mainly substances having a hole mobility of greater than or equal to $10^{-6}$ cm$^2$/Vs. Note that substances other than the substances described above may also be used as long as the hole-transporting properties thereof are higher than the electron-transporting properties thereof.

In addition, as the substance having an acceptor property, 7,7,8,8-tetracyano-2,3,5,6-tetrafluoroquinodimethane (abbreviation: F$_4$-TCNQ), chloranil, and the like can be given. In addition, a transition metal oxide can be given. Moreover, oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of a high electron-accepting property. Among these, molybdenum oxide is especially preferable because it is stable in the air and its hygroscopic property is low so that it can be easily treated.

On the other hand, in the case of employing the structure in which a substance having a donor property is added to a substance having a high electron-transporting property, as the substance having a high electron-transporting property, for example, a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), or bis(2-methyl-8-quinolinolato)(4-phenylphenolato)aluminum(III) (abbreviation: BAlq), can be used. Besides, a metal complex having an oxazole-based ligand or a thiazole-based ligand, such as bis[2-(2'-hydroxyphenyl)benzoxazolato]zinc(II) (abbreviation: Zn(BOX)2) or bis[2-(2'-hydroxyphenyl)benzothiazolato]zinc(II) (abbreviation: Zn(BTZ)$_2$), can also be used. Further, other than the metal complexes, any of the following can also be used: 2-(4-biphenylyl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(4-biphenylyl)-4-phenyl-5-(4-tert-butylphenyl)-1,2,4-triazole (abbreviation: TAZ); bathophenanthroline (abbreviation: BPhen); bathocuproine (BCP); or the like. The substances described here are mainly substances having an electron mobility of $10^{-6}$ cm$^2$/Vs or more. Note that other than the above substances may be used as long as the substance has a higher electron-transporting property than a hole-transporting property.

Further, for the substance having a donor property, an alkali metal, an alkaline-earth metal, a rare-earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the substance having a donor property.

Note that by forming the charge generation layer 305 using any of the above materials, increase in drive voltage in the case where the EL layers are stacked can be suppressed.

Although the light-emitting element having two EL layers is described in Embodiment Mode 3, the present invention can be similarly applied to a light-emitting element in which three or more EL layers are stacked. By arranging a plurality of EL layers to be partitioned from each other with a charge generation layer between a pair of electrodes, like the light-emitting element according to Embodiment Mode 3, a long lifetime element in a high luminance region can be realized while current density is kept low. In a case where the light-emitting element is applied to lighting as an application example, voltage drop due to resistance of an electrode material can be reduced. Accordingly, light can be uniformly emitted in a large area. Moreover, a light-emitting device which consumes low power and is driven at low voltage can be achieved.

Further, when the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that "complementary color" means a relation between colors which becomes an achromatic color when they are mixed. That is, white light emission can be obtained by mixture of lights obtained from substances emitting the lights of complementary colors.

Also in a light-emitting element having three EL layers, for example, white light as a whole light-emitting element can be similarly obtained when an emission color of a first EL layer is red, an emission color of a second EL layer is green, and an emission color of a third EL layer is blue.

Note that Embodiment Mode 3 can be combined with any of the structures described in Embodiment Modes 1 and 2 as appropriate.

Embodiment Mode 4

Figure 4A:
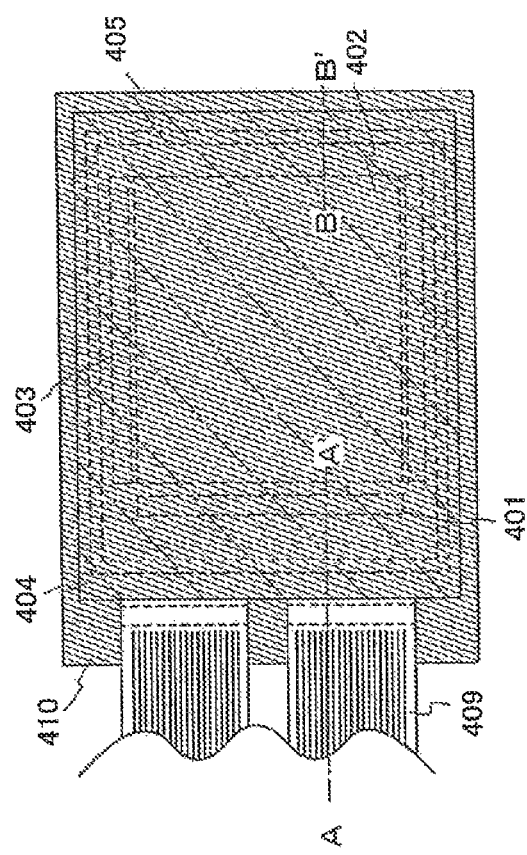
FIGS. 4A and 4B are respectively a top view and a cross-sectional view of an active matrix light-emitting device in Embodiment Mode 4.
Figure 4B:
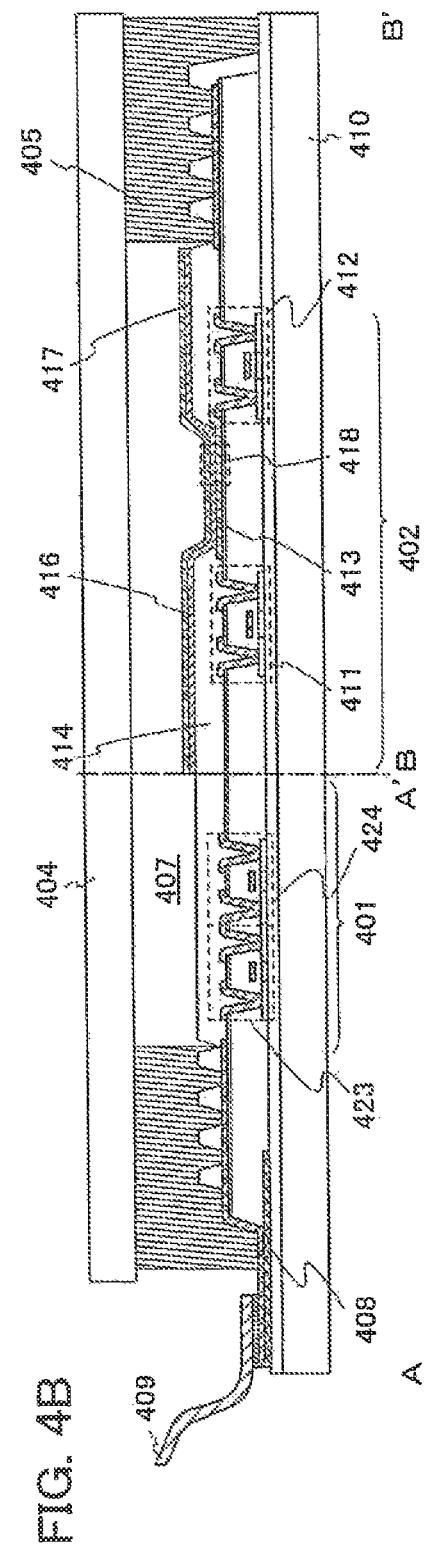

In Embodiment Mode 4, a light-emitting device having the light-emitting element of the present invention in a pixel portion will be described with reference to FIGS. 4A and 4B. FIG. 4A is a top view of the light-emitting device, and FIG. 4B is a cross sectional view taken along A-A' and B-B' in FIG. 4A.

In FIG. 4A, reference numerals 401, 402, and 403 which are shown by a dotted line denote a driver circuit portion (a source driver circuit), a pixel portion, and a driver circuit portion (a gate driver circuit), respectively. Reference numerals 404 and 405 denote a sealing substrate and a sealant, respectively, and an inner side region enclosed by the sealant 405 is a space 407.

A lead wiring 408 is a wiring to transmit a signal to be inputted to the source driver circuit portion 401 and the gate driver circuit 403, and receives a video signal, a clock signal, a start signal, a reset signal, and the like from a flexible printed circuit (FPC) 409 which serves as an external input terminal. Although only the FPC is shown here, this FPC may be provided with a printed wiring board (PWB). Further, the light-emitting device in this specification includes not only a light-emitting device itself but also a light-emitting device attached with an FPC or a PWB.

Next, a cross-sectional structure of the light-emitting device will be described with reference to FIG. 4B. The driver circuit portion and the pixel portion are formed over an element substrate 410. Here, one pixel in the pixel portion 402 and the source driver circuit 401 which is the driver circuit portion are shown. As the source driver circuit 401, a CMOS circuit which is obtained by combining an n-channel TFT 423 and a p-channel TFT 424 is formed. The driver circuit may be formed by various CMOS circuits, PMOS circuits, or NMOS circuits. In Embodiment Mode 4, although a driver-integrated type structure in which a driver circuit is formed over a substrate is described, a driver circuit is not necessarily formed over a substrate but can be formed externally from a substrate.

The pixel portion 402 is formed of a plurality of pixels having a switching TFT 411, a current control TFT 412, and a first electrode 413 electrically connected to a drain of the current control TFT 412. An insulator 414 is formed to cover an end portion of the first electrode 413.

The insulator 414 is preferably formed so as to have a curved surface with curvature at an upper end portion or a lower end portion thereof in order to obtain favorable coverage. For example, by using positive-type photosensitive acrylic as a material of the insulator 414, the insulator 414 can be formed to have a curved surface with a curvature radius (0.2 μm to 3 μm) only at the upper end portion. Further, either a negative-type photosensitive material which becomes insoluble in an etchant by light irradiation or a positive-type photosensitive material which becomes soluble in an etchant by light irradiation can be used as the insulator 414.

An EL layer 416 and a second electrode 417 are formed over the first electrode 413. Here, the first electrode 413 can be formed using any of a variety of materials such as metals, alloys, and electrically conductive compounds, or a mixture thereof. Note that as specific materials, the materials which are shown in Embodiment Mode 2 as a material that can be used for the first electrode can be used.

In addition, the EL layer 416 is formed by any of a variety of methods such as an evaporation method using an evaporation mask, an ink-jet method, or a spin coating method. The EL layer 416 has the structure described in Embodiment Mode 2. As another material included in the EL layer 416, a low molecular compound or a macromolecular compound (including an oligomer or a dendrimer) may be used. As the material for the EL layer, not only an organic compound but also an inorganic compound may also be used.

As a material for the second electrode 417, any of a variety of metals, alloys, and electrically conductive compounds, or a mixture thereof can be used. In the case where the second electrode 417 is used as a cathode, a metal, an alloy, an electrically conductive compound, a mixture thereof, or the like with a low work function (a work function of 3.8 eV or less) is preferably used, among others. For example, an element belonging to Group 1 or 2 of the periodic table, that is, an alkali metal such as lithium (Li) or cesium (Cs), an alkaline-earth metal such as magnesium (Mg), calcium (Ca), or strontium (Sr), or an alloy containing any of these metals (such as a MgAg alloy or an AlLi alloy); and the like can be given.

Note that in the case where light generated in the EL layer 416 is transmitted through the second electrode 417, for the second electrode 417, a stack of a metal thin film with a reduced thickness and a transparent conductive film (indium tin oxide (ITO), indium tin oxide containing silicon or silicon oxide, indium zinc oxide (IZO), or indium oxide containing tungsten oxide and zinc oxide, or the like) can also be used.

By attaching the sealing substrate 404 and the element substrate 410 with the sealant 405, there is a structure where a light-emitting element 418 is provided in the space 407 surrounded by the element substrate 410, the sealing substrate 404, and the sealant 405. Note that the space 407 is filled with a filler such as an inert gas (e.g., nitrogen, argon, or the like) or the sealant 405.

It is preferable to use an epoxy-based resin as the sealant 405. In addition, it is preferable that the material do not transmit moisture and oxygen as much as possible. As a material for the sealing substrate 404, a plastic substrate formed of FRP (Fiberglass-Reinforced Plastics), PVF (polyvinyl fluoride), polyester, acrylic, or the like can be used as well as a glass substrate or a quartz substrate.

As described above, an active matrix light-emitting device having the light-emitting element of the present invention can be obtained.

Figure 5A:
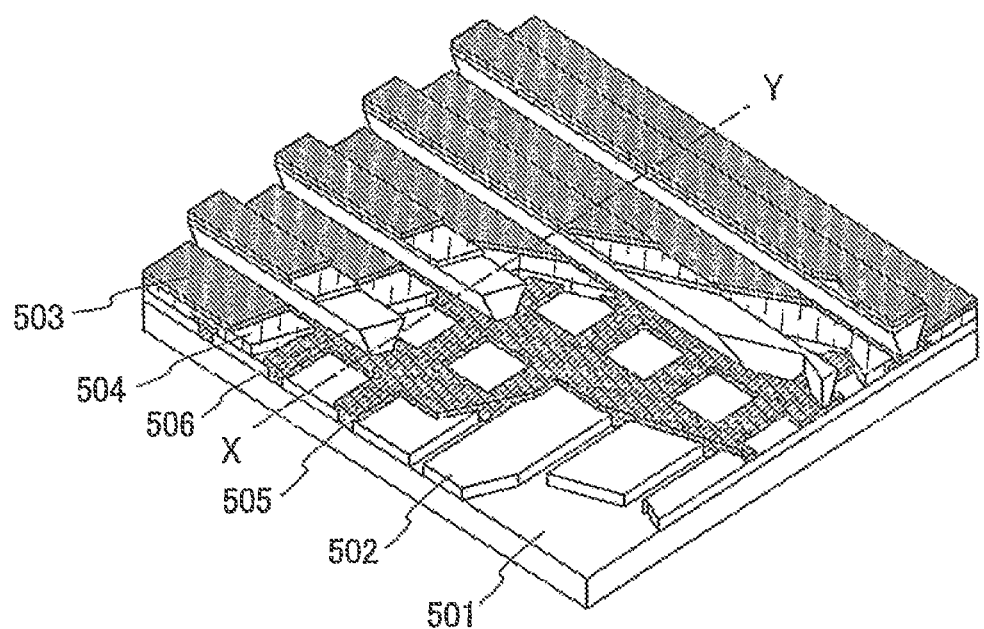
FIGS. 5A and 5B are respectively a perspective view and a cross-sectional view of a passive matrix light-emitting device in Embodiment Mode 4.
Figure 5B:
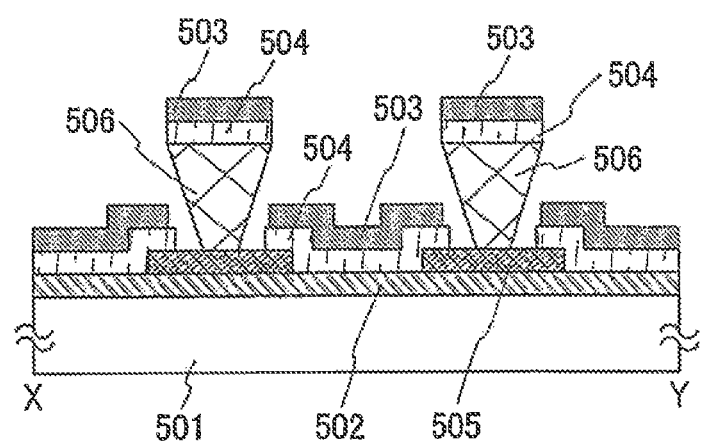

Further, the light-emitting element of the present invention can also be used for a passive matrix light-emitting device in addition to the above active matrix light-emitting device. FIGS. 5A and 5B respectively show a perspective view and a cross-sectional view of a passive matrix light-emitting device using the light-emitting element of the present invention. Note that FIG. 5A is a perspective view of the light-emitting device, and FIG. 5B is a cross-sectional view of FIG. 5A taken along line X-Y.

In FIGS. 5A and 5B, an EL layer 504 is provided between a first electrode 502 and a second electrode 503 over a substrate 501. An edge portion of the first electrode 502 is covered with an insulating layer 505. Then, a partition layer 506 is provided over the insulating layer 505. Sidewalls of the partition layer 506 have a slant such that a distance between one sidewall and the other sidewall becomes narrower as the sidewalls gets closer to a surface of the substrate. In other words, a cross section of the partition layer 506 in the direction of a short side is trapezoidal, and a lower base (a side facing a similar direction as a plane direction of the insulating layer 505 and in contact with the insulating layer 505) is shorter than an upper base (a side facing a similar direction as the plane direction of the insulating layer 505 and not in contact with the insulating layer 505). By providing the partition layer 506 in such a manner, a defect of the light-emitting element due to static electricity or the like can be prevented.

Through the above process, the passive matrix light-emitting device using the light-emitting element of the present invention can be obtained.

Note that any of the light-emitting devices described in Embodiment Mode 4 (the active matrix light-emitting device and the passive matrix light-emitting device) are formed using the light-emitting element of the present invention, which has high luminous efficiency, and accordingly a light-emitting device having reduced power consumption can be obtained.

Note that Embodiment Mode 4 can be combined with any of the structures described in Embodiment Modes 1 to 3 as appropriate.

Embodiment Mode 5

In Embodiment Mode 5, an electronic device including, as part thereof, the light-emitting device of the present invention which is shown in Embodiment Mode 4 will be described. Examples of the electronic device include cameras such as video cameras or digital cameras, goggle type displays, navigation systems, audio reproducing devices (e.g., car audio systems and audio components), computers, game machines, portable information terminals (e.g., mobile computers, cellular phones, portable game machines, and electronic books), image reproducing devices in which a recording medium is provided (specifically, devices that are capable of reproducing recording media such as digital versatile discs (DVDs) and equipped with a display unit that can display images), and the like. Specific examples of these electronic devices are shown in FIGS. 6A to 6D.

Figure 6A:
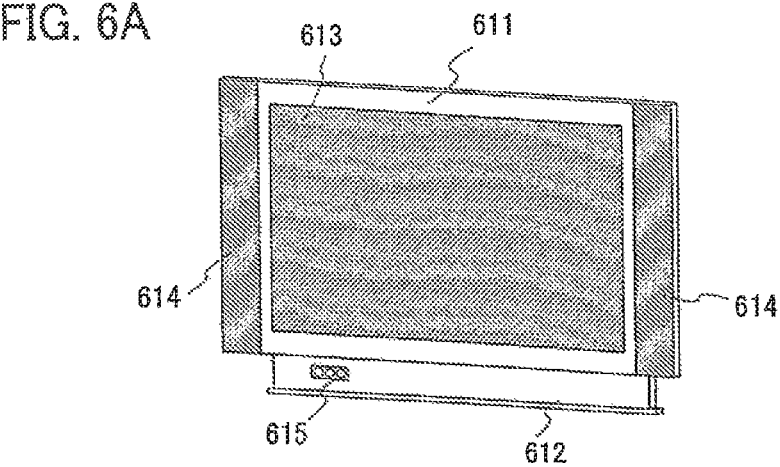
FIGS. 6A to 6D are views each showing an electronic device in Embodiment Mode 5.

FIG. 6A shows a television set according to the present invention, which includes a housing 611, a supporting base 612, a display portion 613, speaker portions 614, video input terminals 615, and the like. In this television set, the light-emitting device of the present invention can be applied to the display portion 613. Since the light-emitting device of the present invention has a feature of high luminous efficiency, a television set having reduced power consumption can be obtained by applying the light-emitting device of the present invention.

Figure 6B:
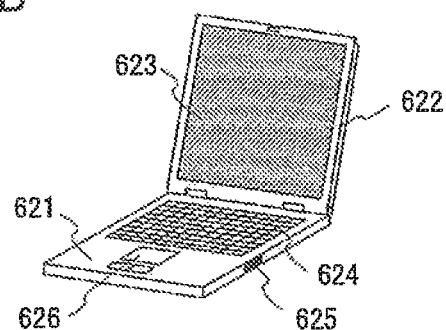

FIG. 6B shows a computer according to the present invention, which includes a main body 621, a housing 622, a display portion 623, a keyboard 624, an external connection port 625, a pointing device 626, and the like. In this computer, the light-emitting device of the present invention can be applied to the display portion 623. Since the light-emitting device of the present invention has a feature of high luminous efficiency, a computer having reduced power consumption can be obtained by applying the light-emitting device of the present invention.

Figure 6C:
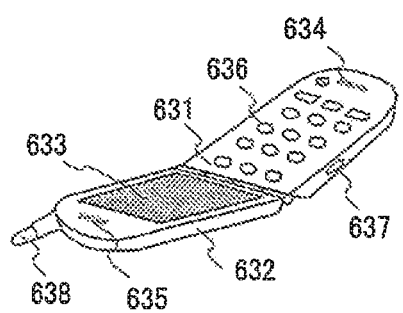

FIG. 6C shows a cellular phone according to the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. Since the light-emitting device of the present invention has a feature of high luminous efficiency, a cellular phone having reduced power consumption can be obtained by applying the light-emitting device of the present invention.

Figure 6D:
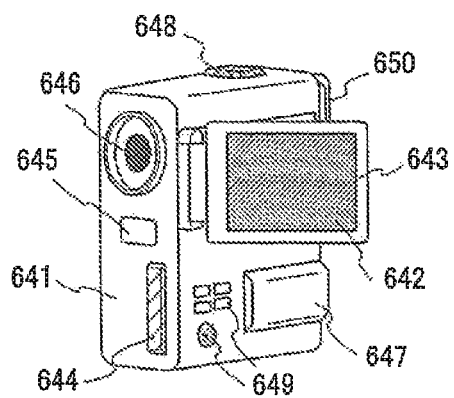

FIG. 6D shows a camera according to the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of the present invention can be applied to the display portion 642. Since the light-emitting device of the present invention has a feature of high luminous efficiency, a camera having reduced power consumption can be obtained by applying the light-emitting device of the present invention.

As described above, the applicable range of the light-emitting device of the present invention is so wide that the light-emitting device can be applied to electronic devices in a variety of fields.

Figure 7:
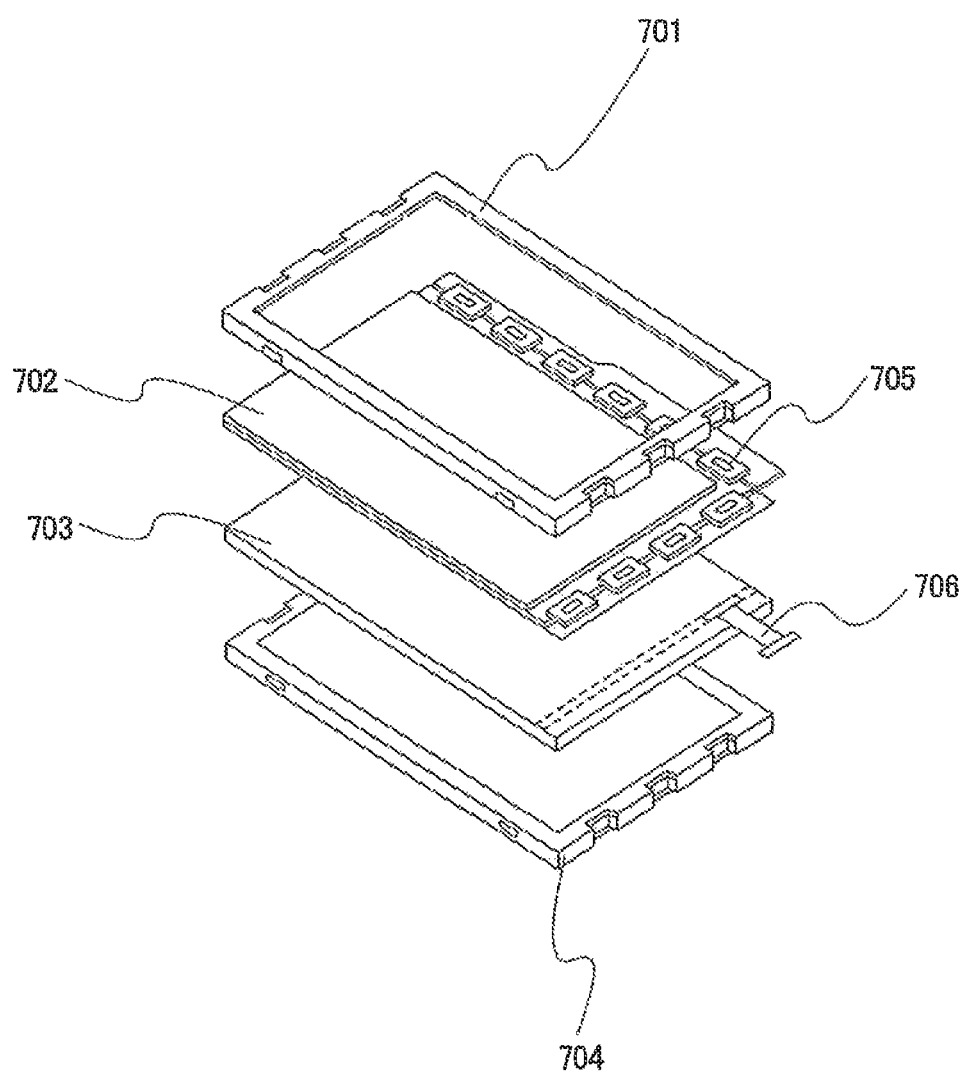
FIG. 7 is a view showing a liquid crystal display device using a light-emitting device of the present invention as a backlight.

The light-emitting device of the present invention can also be used as a lighting device. FIG. 7 is an example of a liquid crystal display device in which the light-emitting device of the present invention is used as a backlight. The liquid crystal display device shown in FIG. 7 includes a housing 701, a liquid crystal layer 702, a backlight 703, and a housing 704. The liquid crystal layer 702 is connected to a driver IC 705. The light-emitting device of the present invention is used for the backlight 703, and current is supplied through a terminal 706.

With the use of the light-emitting device of the present invention as a backlight of a liquid crystal display device as described above, a backlight which consumes low power can be obtained. Further, since the light-emitting device of the present invention is a plane emitting lighting device and the area thereof can be enlarged, the backlight can also have a large area. Therefore, a larger-area liquid crystal display device which consumes low power can be obtained.

Figure 8:
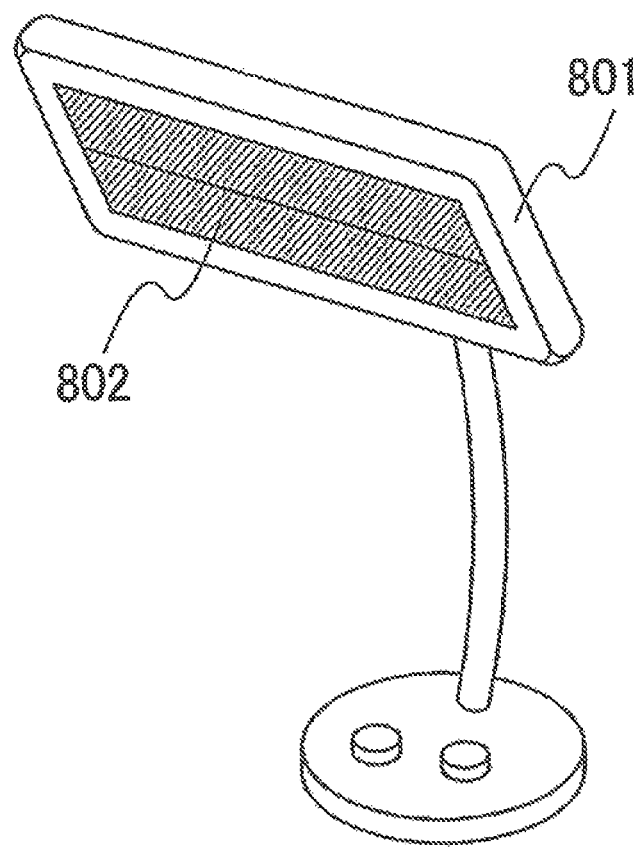
FIG. 8 is a view showing a table lamp using a light-emitting device of the present invention.

FIG. 8 shows an example of using the light-emitting device, to which the present invention is applied, as a table lamp, which is a lighting device. A table lamp shown in FIG. 8 has a housing 801 and a light source 802, and the light-emitting device of the present invention is used as the light source 802. The light-emitting device of the present invention has the light-emitting element having high luminous efficiency and therefore can be used as a desk lamp which consumes low power.

Figure 9:
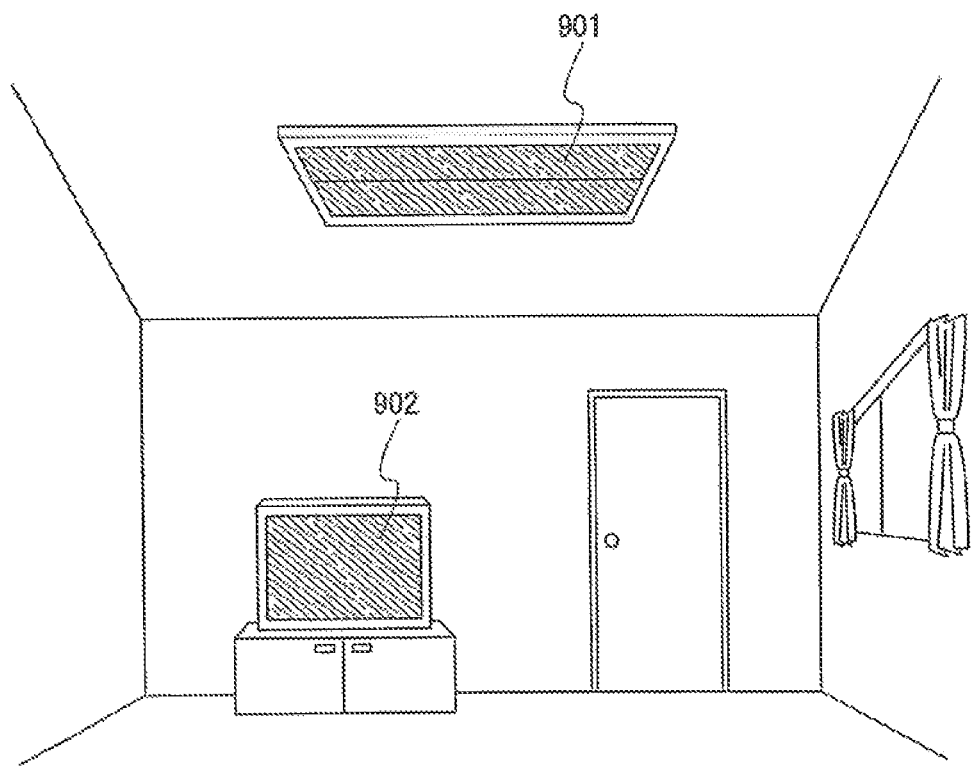
FIG. 9 is a view showing an indoor lighting device using a light-emitting device of the present invention.

FIG. 9 shows an example of using the light-emitting device, to which the present invention is applied, as an indoor lighting device 901. Since the area of the light-emitting device of the present invention can also be enlarged, the light-emitting device of the present invention can be used as a lighting device having a large area. In addition, the light-emitting device of the present invention has the light-emitting element having high luminous efficiency and therefore can be used as a lighting device which consumes low power. When a television set 902 according to the present invention as described in FIG. 6A is placed in a room in which the light-emitting device, to which the present invention is applied, is used as the indoor lighting device 901, public broadcasting and movies can be watched.

Note that Embodiment Mode 5 can be combined with any of the structures described in Embodiment Modes 1 to 4 as appropriate.

Embodiment 1

In Embodiment 1, a synthetic method of a carbazole derivative of the present invention, 4-phenyl-4'-(9-phenyl-9H-carbazol-3-yl)triphenylamine (abbreviation: PCBA1BP) represented by a structural formula (5), will be specifically described.

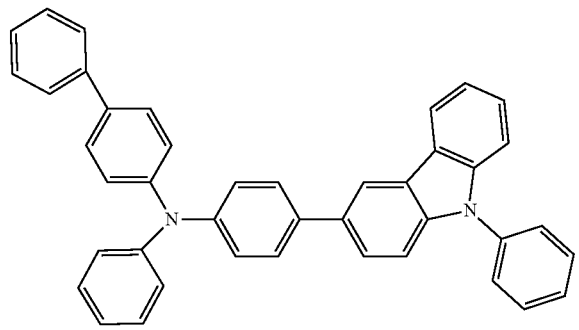

(5)

Step 1: Synthesis of 4-bromo-diphenylamine

A synthetic scheme of 4-bromo-diphenylamine in Step 1 is shown in the following (D-1).

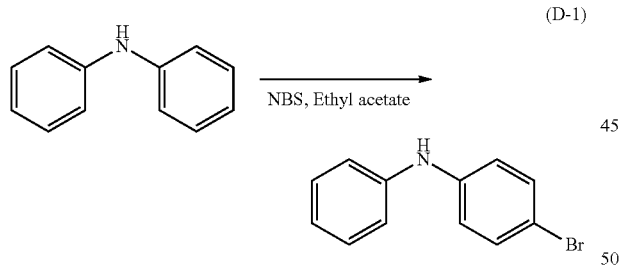

(D-1)

After 51 g (0.3 mol) of diphenylamine was dissolved in 700 mL of ethyl acetate in a 1-L conical flask, 54 g (0.3 mol) of N-bromo succinimide (abbreviation: NBS) was added to this solution. About 300 hours later, this mixture solution was washed with water and then magnesium sulfate was added thereto to remove moisture. This mixture solution was filtrated, and the filtrate was concentrated and collected. Accordingly, 70 g of a dark brown oil-like object was obtained at a yield of 94%.

Step 2-1: Synthesis of 3-bromo-9-phenyl-9H-carbazole

A synthetic scheme of 3-bromo-9-phenyl-9H-carbazole in Step 2-1 is shown in the following (D-2-1).

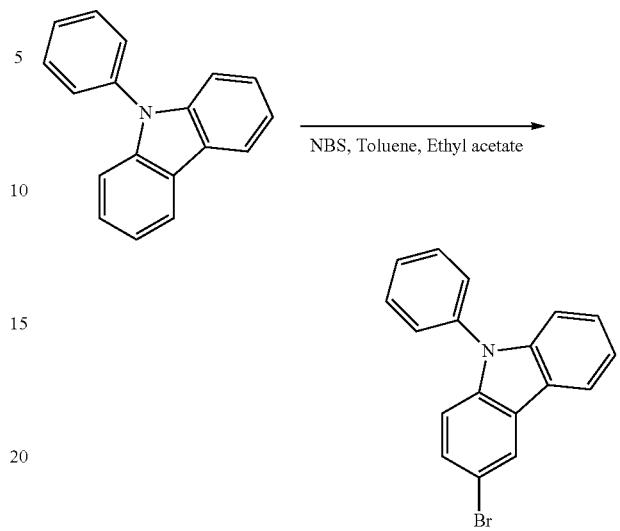

(D-2-1)

In a 1000 mL conical flask, 24 g (100 mmol) of 9-phenyl-9H-carbazole, 18 g (100 mmol) of N-bromo succinimide, 450 mL of toluene, and 200 mL of ethyl acetate were added, and the mixture was stirred at room temperature for 45 hours. This suspension was washed with water and then magnesium sulfate was added thereto to remove moisture. This suspension was filtrated, and the obtained filtrate was concentrated and dried. Accordingly, 32 g of a caramel-like object, 3-bromo-9-phenyl-9H-carbazole, was obtained at a yield of 99%.

Step 2-2: Synthesis of 9-phenyl-9H-carbazol-3-boronic acid

A synthetic scheme of 9-phenyl-9H-carbazol-3-boronic acid in Step 2-2 is shown in the following (D-2-2).

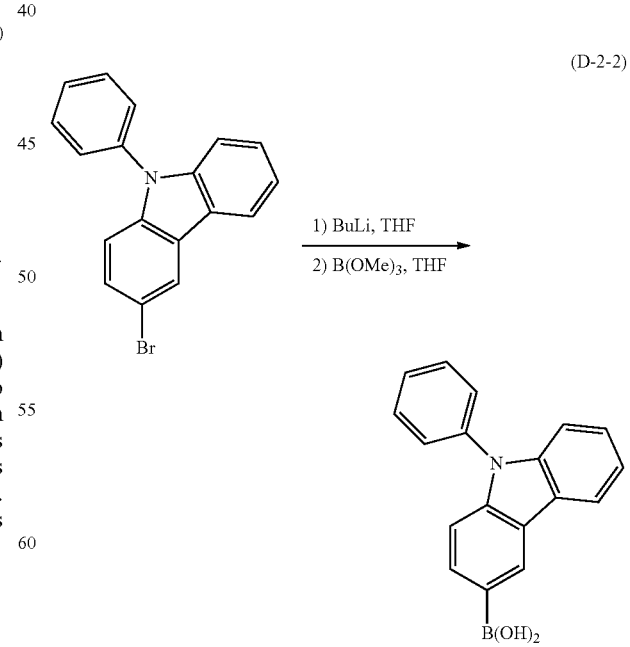

(D-2-2)

In a 500-mL conical flask, 29 g (90 mmol) of 3-bromo-9-phenyl-9H-carbazole and 200 mL of tetrahydrofuran (THF) were stirred at −78° C. to be a solution. After that, 110 mL (69 mmol) of n-butyllithium (a 1.57 mol/L hexane solution) was dropped into this solution and was stirred at the same temperature for 2 hours. Further, 13 mL (140 mmol) of trimethyl borate was added to this solution, and the solution was stirred at room temperature for 24 hours.

After completion of the reaction, 200 mL of hydrochloric acid (1.0 mol/L) was added to the reaction mixture, and then the mixture was stirred at room temperature for 1 hour. This mixture was washed with a sodium hydroxide aqueous solution and water in this order, and magnesium sulfate was added to remove moisture. This suspension was filtrated, the obtained filtrate was concentrated, and chloroform and hexane were added thereto. The mixture was irradiated with supersonic. After that, recrystallization was performed. Accordingly, 21 g of an objective white powder, 9-phenyl-9H-carbazol-3-boronic acid, was obtained at a yield of 80%.

Step 3: Synthesis of 4-(9-phenyl-9H-carbazol-3-yl)diphenylamine (abbreviation: PCBA)

A synthetic scheme of 4-(9-phenyl-9H-carbazol-3-yl)diphenylamine (abbreviation: PCBA) in Step 3 is shown in the following (D-3).

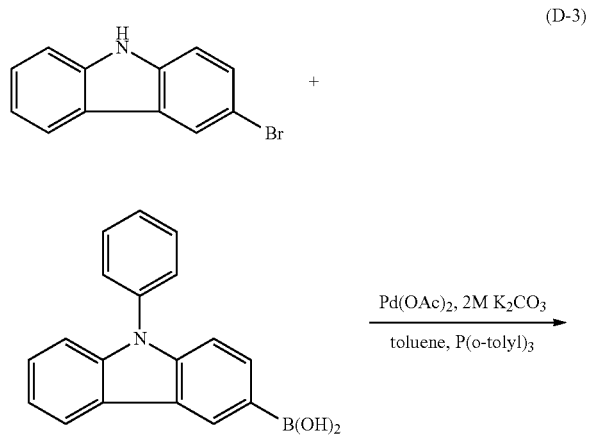

(D-3)

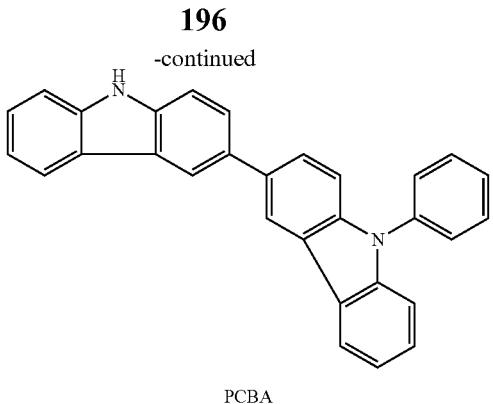

PCBA

In a 500-mL three-neck flask, 6.5 g (26 mmol) of 4-bromodiphenylamine, 7.5 g (26 mmol) of 9-phenyl-9H-carbazol-3-boronic acid, and 400 mg (1.3 mmol) of tri(o-tolyl)phosphine were put, and the atmosphere in the flask was substituted by nitrogen. Then, 100 mL of toluene, 50 mL of ethanol, and 14 mL of potassium carbonate solution (0.2 mol/L) were added to this mixture. This mixture was deaerated while being stirred under low pressure. After the deaeration, 67 mg (30 mmol) of palladium(II) acetate was added thereto.

This mixture was refluxed at 100° C. for 10 hours. After the reflux, the aqueous layer of this mixture was extracted with toluene. Then, the extracted solution was combined with an organic layer, followed by washing with a saturated saline solution. After the moisture of the organic layer was removed by magnesium sulfate, this mixture was naturally filtrated, and the obtained filtrate was concentrated to obtain an oily light-brown substance. This oily substance was purified by silica gel column chromatography (developing solvent, hexane: toluene=4:6). A white solid which was obtained after the purification was recrystallized with dichloromethane/hexane, and 4.9 g of an objective white solid was obtained at a yield of 45%.

Step 4: Synthesis of 4-phenyl-4'-(9-phenyl-9H-carbazol-3-yl)triphenylamine (abbreviation: PCBA1BP)

A synthetic scheme of 4-phenyl-4'-(9-phenyl-9H-carbazol-3-yl)triphenylamine (abbreviation: PCBA1BP) in Step 4 is shown in the following (D-4).

(D-4)

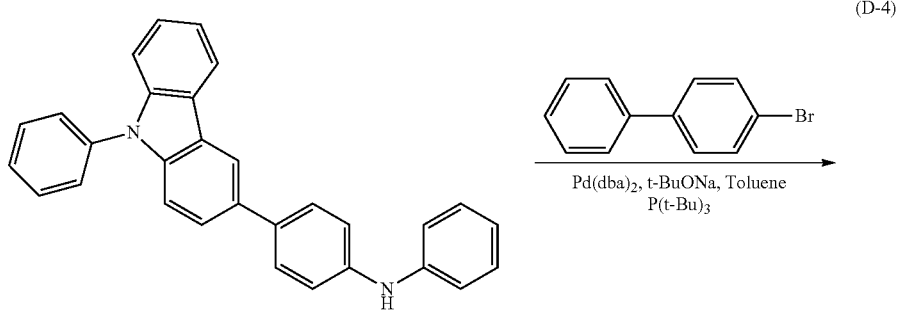

-continued

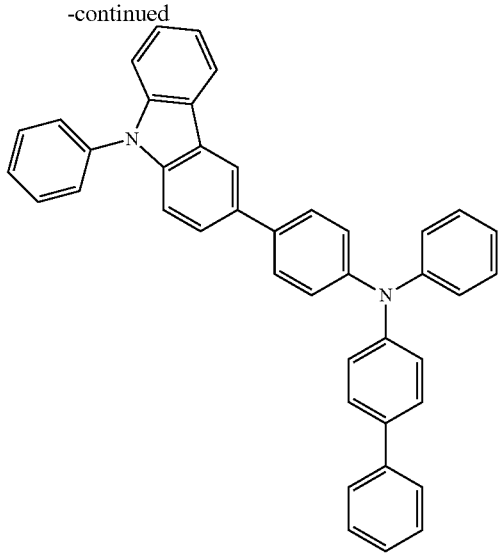

In a 100-mL three-neck flask, 2.0 g (4.9 mmol) of 4-(9-phenyl-9H-carbazol-3-yl)diphenylamine, 1.1 g (4.9 mmol) of 4-bromobiphenyl, and 2.0 g (20 mmol) of sodium tert-butoxide were put, and the atmosphere in the flask was substituted by nitrogen. Then, 50 mL of toluene and 0.30 mL of tri(tert-butyl)phosphine (10 wt % hexane solution) were added to this mixture.

This mixture was deaerated while being stirred under low pressure. After the deaeration, 0.10 g of bis(dibenzylideneacetone)palladium(0) was added thereto. Next, this mixture was stirred at 80° C. for 5 hours to be reacted. After the reaction, toluene was added to the reaction mixture, and suction filtration was performed on this suspension through Celite, alumina, and then Florisil to obtain filtrate. The obtained filtrate was washed with a saturated sodium carbonate solution and a saturated saline solution in this order. Magnesium sulfate was added to the organic layer, and the organic layer was dried. After the drying, suction filtration was performed on this mixture to remove the magnesium sulfate; thus, the filtrate was obtained.

The obtained filtrate was concentrated and purified by silica gel column chromatography. The silica gel column chromatography was performed by, first, using a mixture solvent of toluene: hexane=1:9 as a developing solvent, and then using a mixture solvent of toluene: hexane=3:7 as another developing solvent. A solid which was obtained by concentrating the obtained fraction was recrystallized with a mixture solvent of chloroform and hexane to obtain 2.3 g of a white powder-like solid at a yield of 84%.

Sublimation purification of 1.2 g of the obtained white solid was performed by a train sublimation method. The sublimation purification was performed under a reduced pressure of 7.0 Pa, with a flow rate of argon at 3 mL/min, at 280° C. for 20 hours. Accordingly, 1.1 g of the white solid was obtained at a yield of 89%.

Figure 10A:
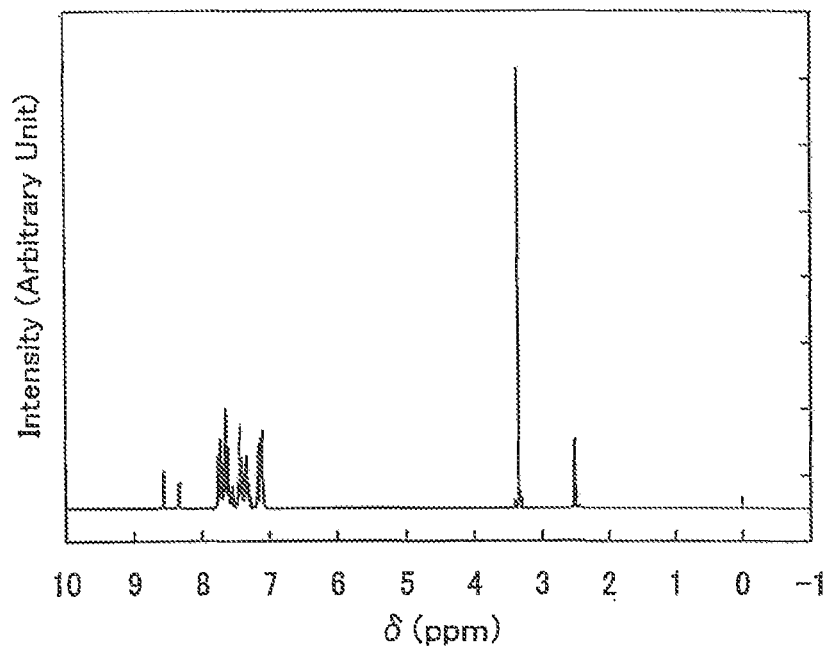
FIGS. 10A and 10B are graphs showing $^1$H NMR charts of PCBA1BP (abbreviation)
Figure 10B:
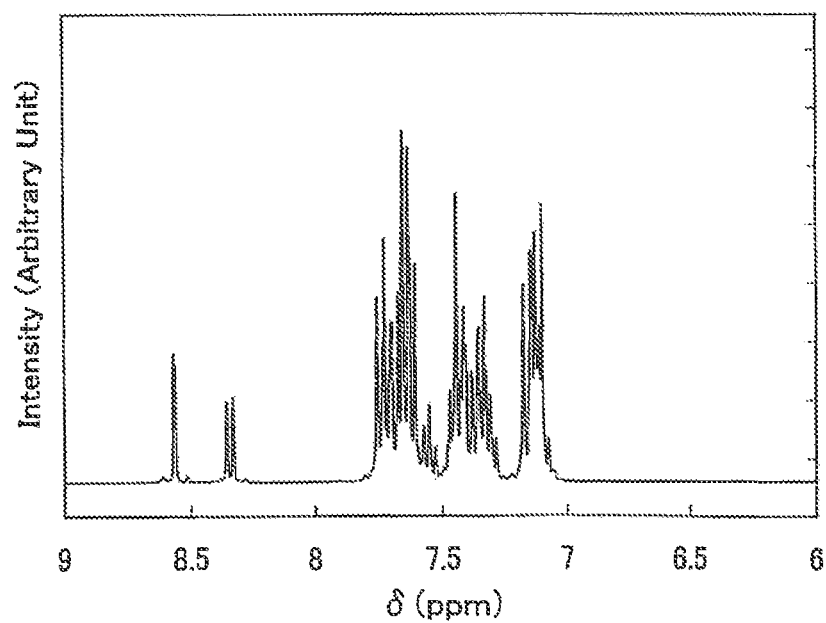

A compound which was obtained through the above Step 4 was measured by a nuclear magnetic resonance method ($^1$H NMR). The measurement result is described below, and the $^1$H NMR chart is shown in FIGS. 10A and 10B. It was found from the measurement result that the carbazole derivative of the present invention, 4-phenyl-4'-(9-phenyl-9H-carbazol-3-yl)triphenylamine (abbreviation: PCBA1BP) represented by the above structural formula (5), was obtained.

$^1$H NMR (DMSO-d, 300 MHz): δ (ppm)=7.05-7.20 (m, 7H), 7.28-7.78 (m, 21H), 8.34 (d, J=7.8 Hz, 1H), 8.57 (s, 1H).

Figure 11A:
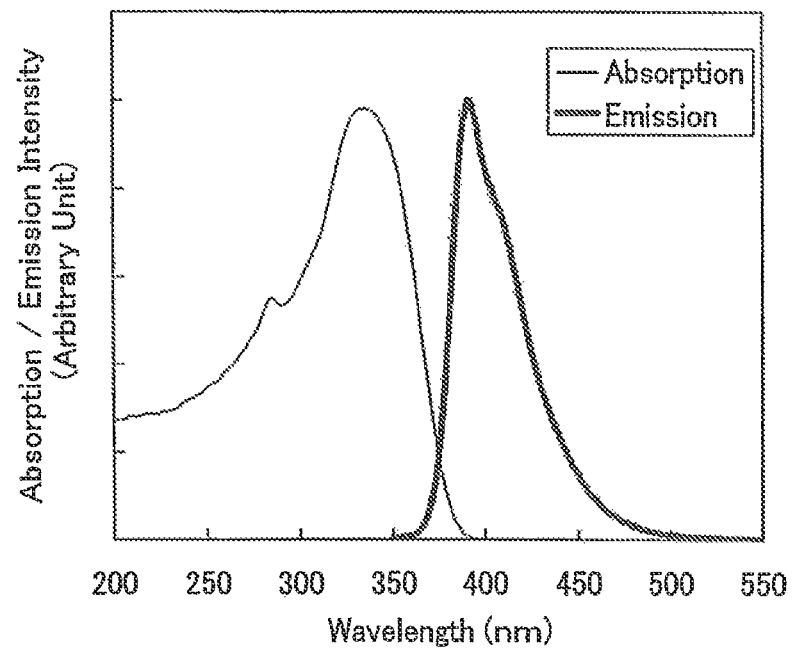
FIGS. 11A and 11B are graphs showing an absorption spectrum and an emission spectrum of PCBA1BP (abbreviation)
Figure 11B:
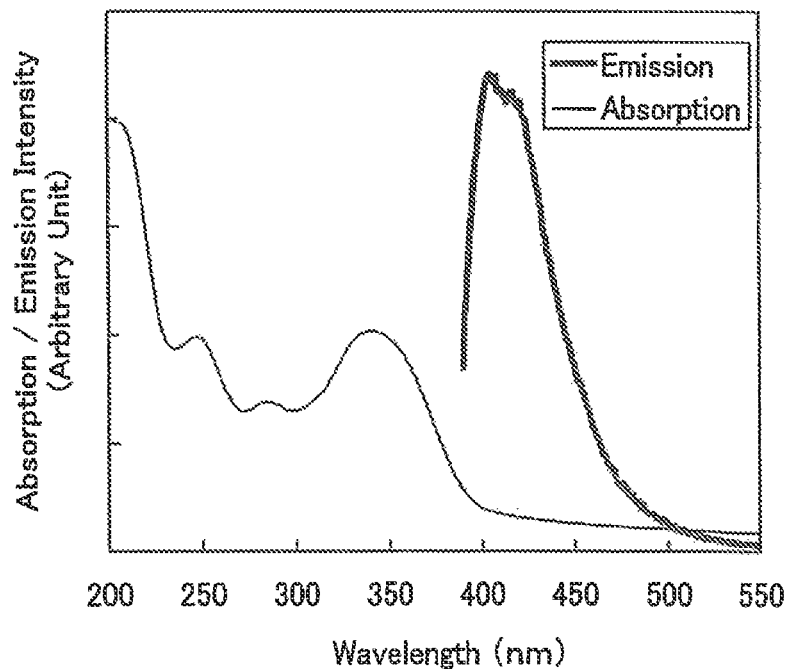

In addition, an absorption spectrum of a toluene solution of PCBA1BP (abbreviation) is shown in FIG. 11A. In addition, an absorption spectrum of a thin film of PCBA1BP (abbreviation) is shown in FIG. 11B. An ultraviolet-visible spectrophotometer (V-550, manufactured by JASCO Corporation) was used for the measurement. The spectrum of the solution was measured in a quartz cell. The sample of the thin film was fabricated by vapor evaporation of PCBA1BP (abbreviation) over a quartz substrate. The absorption spectrum of the solution which was obtained by subtracting the quartz cell from the measured sample is shown in FIG. 11A, and the absorption spectrum of the thin film which was obtained by subtracting the quartz substrate from the measured sample is shown in FIG. 11B.

In FIGS. 11A and 11B, the horizontal axis indicates the wavelength (nm) and the vertical axis indicates the absorption intensity (arbitrary unit). In the case of the toluene solution, an absorption peak was observed at around 335 nm, and in the case of the thin film, an absorption peak was observed at around 341 nm. In addition, an emission spectrum of the toluene solution (excitation wavelength: 346 nm) of PCBA1BP (abbreviation) is shown in FIG. 11A. In addition, an emission spectrum of the thin film (excitation wavelength: 386 nm) of PCBA1BP (abbreviation) is shown in FIG. 11B. In FIGS. 11A and 11B, the horizontal axis indicates the wavelength (nm) and the vertical axis indicates the light emission intensity (arbitrary unit). The maximum emission wavelength was 391 nm (excitation wavelength: 346 nm) in the case of the toluene solution and 416 nm (excitation wavelength: 386 nm) in the case of the thin film.

An oxidation-reduction reaction characteristic of PCBA1BP (abbreviation) was examined by a cyclic voltammetry (CV) measurement. An electrochemical analyzer (ALS model 600A or 600C, manufactured by BAS Inc.) was used for the measurement.

As for a solution used in the CV measurement, dehydrated dimethylformamide (DMF) (manufactured by Aldrich, 99.8%, catalog number: 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (20° C. to 25° C.). In addition, the scan speed at the CV measurement was 0.1 V/sec.

(Calculation of the Potential Energy of the Reference Electrode with Respect to the Vacuum Level)

First, potential energy (eV) of the reference electrode (Ag/Ag$^+$ electrode) used in Embodiment 1 with respect to the vacuum level was calculated. That is, the Fermi level of the Ag/Ag$^+$ electrode was calculated. It is known that the oxidation-reduction potential of ferrocene in methanol is +0.610 V [vs. SHE] with respect to a standard hydrogen electrode (Reference: Christian R. Goldsmith et al., J. Am. Chem. Soc., Vol. 124, No. 1, pp. 83-96, 2002). On the other hand, the oxidation-reduction potential of ferrocene in methanol measured by using the reference electrode used in Embodiment 1 was found to be +0.11 V [vs. Ag/Ag$^+$]. Therefore, it was found that the potential energy of the reference electrode used in Embodiment 1 was less than that of the standard hydrogen electrode by 0.50 [eV].

Here, it is also known that the potential energy of the standard hydrogen electrode with respect to the vacuum level is (−4.44 eV (Reference: Toshihiro Ohnishi and Tamami Koyama, *Macromolecular EL material*, Kyoritsu Shuppan, pp. 64-67). As described above, the potential energy of the reference electrode used in Embodiment 1 with respect to the vacuum level was calculated to be −4.44−0.50=−4.94 [eV].

Figure 41:
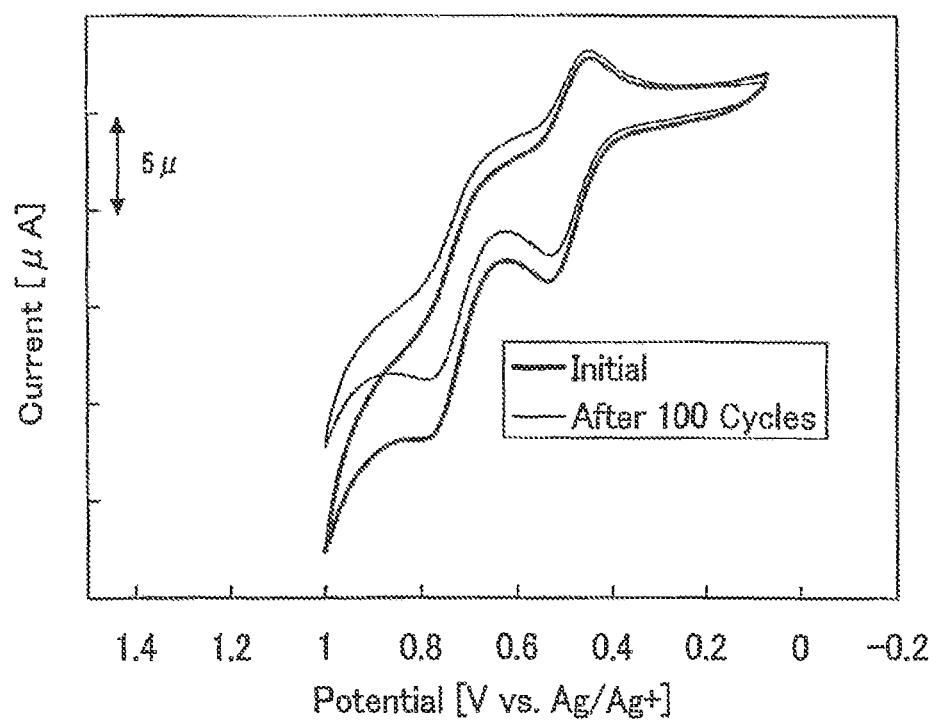
FIG. 41 is a graph showing CV characteristics of PCBA1BP (abbreviation)

FIG. 41 shows the CV measurement result on the oxidation reaction characteristics. Note that the measurement of the oxidation reaction characteristics was performed by the steps of scanning the potential of the working electrode with respect to the reference electrode in ranges of (1) 0.07 V to 1.00 V, and then (2) 1.00 V to 0.07 V.

First, the calculation of the HOMO level of PCBA1BP (abbreviation) by CV measurement is described in detail. As shown in FIG. 41, an oxidization peak potential $E_{pa}$ was 0.536 V. In addition, a reduction peak potential $E_{pc}$ was 0.446 V. Therefore, a half-wave potential (an intermediate potential between $E_{pc}$ and $E_{pa}$) can be calculated to be 0.49 V. This shows that PCBA1BP (abbreviation) can be oxidized by an electrical energy of 0.49 V [vs. Ag/Ag$^+$], and this energy corresponds to the HOMO level. Here, the potential energy of the reference electrode used in Embodiment 1 with respect to the vacuum level is −4.94 [eV] as described above. Therefore, the HOMO level of PCBA1BP (abbreviation) was found to be −4.94−0.49=−5.43 [eV]. In addition, the oxidation peak took a similar value even after the 100 cycles. Accordingly, it was found that repetition of the oxidation reduction between an oxidation state and a neutral state had favorable characteristics.

Embodiment 2

In Embodiment 2, a synthetic method of a carbazole derivative of the present invention, 4,4'-diphenyl-4''-(9-phenyl-9-H-carbazol-3-yl)triphenylamine (abbreviation: PCBBi1BP) represented by a structural formula (6), will be specifically described.

(6)

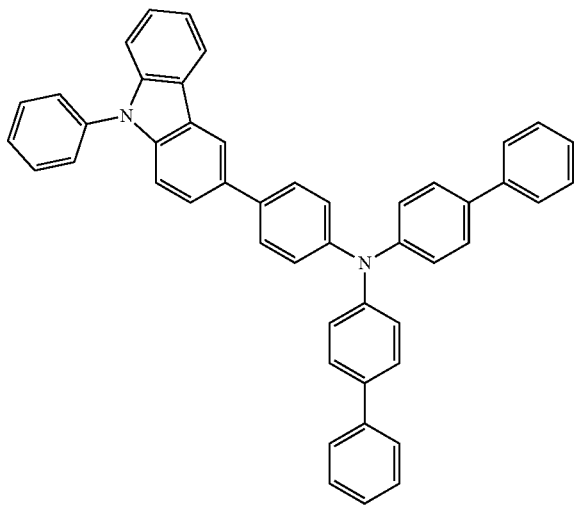

Step 1-1: Synthesis of 4-phenyl-diphenylamine

A synthetic scheme of 4-phenyl-diphenylamine in Step 1-1 is shown in the following (E-1-1).

(E-1-1)

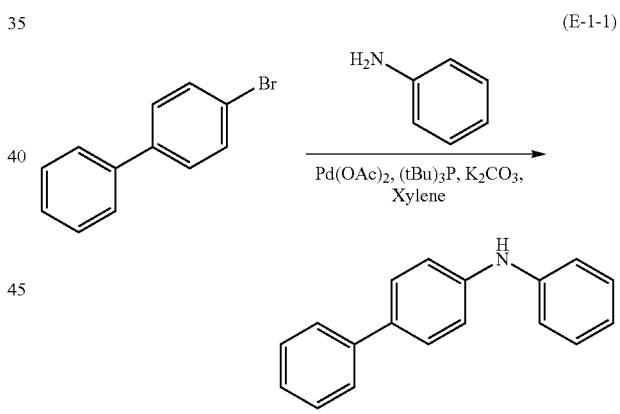

In a three-neck flask, 5.2 g (2.5 mmol) of tri-tert-butylphosphine (10 wt % hexane solution) was added to a dehydrated xylene suspension (150 mL) containing 20.0 g (85.8 mmol) of 4-bromobiphenyl, 16.0 g (172 mmol) of aniline, 0.19 g (0.86 mmol) of palladium(II) acetate, and 23.7 g (172 mmol) of potassium carbonate, and a mixture thereof was refluxed under a nitrogen atmosphere at 120° C. for 10 hours. After completion of the reaction, the reaction mixture was washed with water and separated into an organic layer and an aqueous layer, and the aqueous layer was extracted with toluene.

The above obtained toluene layer was combined with the above organic layer, followed by washing with a saturated saline solution. Then, magnesium sulfate was added thereto to remove moisture in the organic layer. Suction filtration was performed on this mixture to concentrate the obtained filtrate. The obtained residue was purified by silica gel column chromatography (a developing was solvent: toluene). Accordingly, 13.5 g of a white solid of 4-phenyl-diphenylamine, which was obtained by concentrating the obtained solution, was obtained at a yield of 64%.

Step 1-2: Synthesis of 4,4'-diphenyltriphenylamine

A synthetic scheme of 4,4'-diphenyltriphenylamine in Step 1-2 is shown in the following (E-1-2).

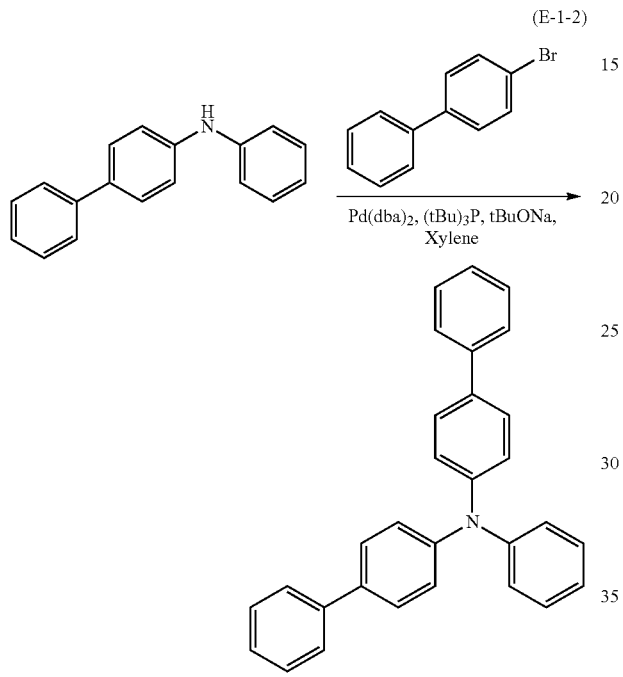

In a 100-mL three-neck flask, 3.7 g (15 mmol) of 4-phenyl-diphenylamine, 3.5 g (15 mmol) of 4-bromobiphenyl, 2.5 g (25 mmol) of sodium tert-butoxide, and 10 mg (0.02 mmol) of bis(dibenzylideneacetone)palladium(0) were put, and the atmosphere in the flask was substituted by nitrogen. Then, 40 mL of dehydrated xylene was added to this mixture. The mixture was deaerated while being stirred under low pressure. After the deaeration, 0.2 mL (60 mmol) of tri(tert-butyl)phosphine (10 wt % hexane solution) was added thereto.

Next, this mixture was stirred at 120° C. for 5 hours, to be reacted. After the reaction, toluene was added to the reaction mixture, and suction filtration was performed on this suspension through Celite, alumina, and then Florisil to obtain filtrate. The obtained filtrate was washed with a saturated sodium carbonate solution and a saturated saline solution in this order. Magnesium sulfate was added to the obtained organic layer to remove moisture. Suction filtration was performed on this mixture through Celite, alumina, and then Florisil to concentrate the obtained filtrate. Acetone and methanol were added to the obtained residue, and the residue was irradiated with supersonic and then recrystallized to obtain 5.4 g of a white powder-like solid at a yield of 92%.

Step 1': Synthesis of 4,4'-diphenyltriphenylamine

In addition to Step 1-1 and Step 1-2 which are described above, 4,4'-diphenyltriphenylamine can also be synthesized using a synthetic method shown in Step 1'. Note that a synthetic scheme of 4,4'-diphenyltriphenylamine in Step 1' is shown in the following (E-1').

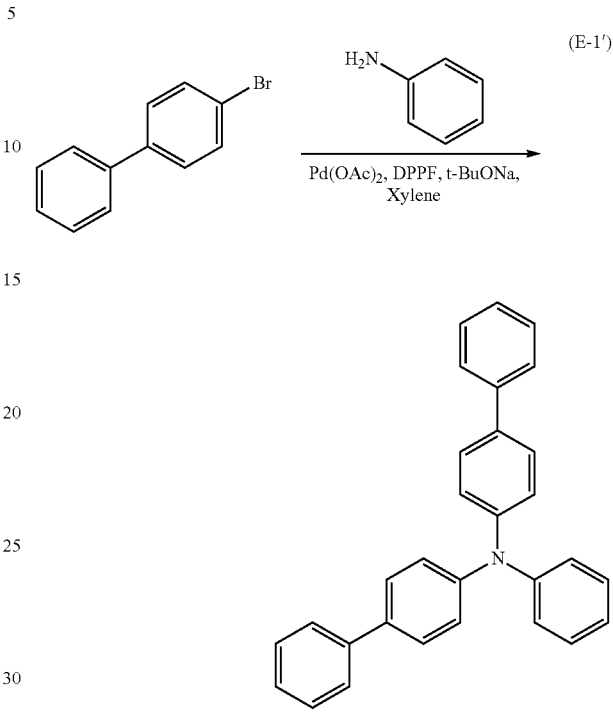

In a 200-mL three-neck flask, 1.9 g (20 mmol) of aniline, 9.3 g (40 mmol) of 4-bromobiphenyl, 4.5 g (45 mmol) of sodium tert-butoxide, 0.4 g (2.0 mmol) of palladium(II) acetate, and 1.1 g (2.0 mmol) of 1,1-bis(diphenylphosphino)ferrocene (abbreviation: DPPF) were put, and the atmosphere in the flask was substituted by nitrogen. Then, 70 mL of dehydrated xylene was added to this mixture. This mixture was deaerated while being stirred under low pressure, and the mixture was stirred at 110° C. for 3 hours to be reacted. After the reaction, toluene was added to the reaction mixture, and suction filtration was performed on this suspension through Celite, alumina, and then Florisil to obtain filtrate. The obtained filtrate was washed with a saturated sodium carbonate solution and a saturated saline solution in this order. Magnesium sulfate was added to the obtained organic layer to remove moisture. Suction filtration was performed on this mixture through Celite, alumina, and then Florisil to concentrate the obtained filtrate. Acetone and hexane were added to the obtained residue, and the residue was irradiated with supersonic and then recrystallized to obtain 5.4 g of a white powder-like solid at a yield of 67%.

Step 2: Synthesis of 4-bromo-4',4''-diphenyltriphenylamine

With the use of Step 1-1 and Step 1-2 which are described above, or 4,4'-diphenyltriphenylamine which was synthesized using a synthetic method shown in Step 1', 4-bromo-4',4''-diphenyltriphenylamine is synthesized. Note that a synthetic scheme of 4-bromo-4',4''-diphenyltriphenylamine in Step 2 is shown in the following (E-2).

(E-2)

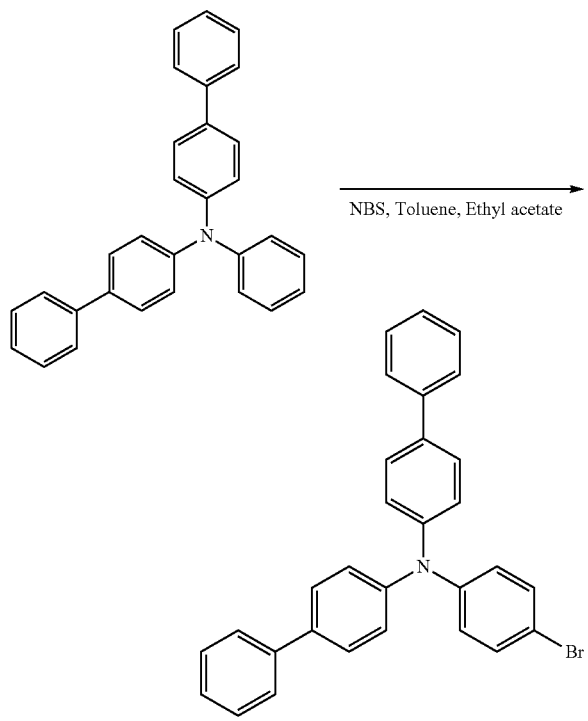

After 4.0 g (10 mmol) of 4,4'-diphenyltriphenylamine was dissolved in a mixture solvent of 50 mL of toluene and 50 mL of ethyl acetate in a conical flask, N-bromo succinimide (abbreviation: NBS) was added to this solution. After that, this mixture was stirred at room temperature for 120 hours. After completion of the reaction, this mixture solution was washed with water, and magnesium sulfate was added thereto to remove moisture. This mixture solution was filtrated and the obtained filtrate was concentrated to perform recrystallization. Accordingly, 4.5 g of an objective white powder was obtained at a yield of 95%.

Step 3: Synthesis of 4,4'-diphenyl-4''-(9-phenyl-9-H-carbazol-3-yl)triphenylamine (abbreviation: PCBBi1BP)

A synthetic scheme of 4,4'-diphenyl-4''-(9-phenyl-9-H-carbazol-3-yl)triphenylamine (abbreviation: PCBBi1BP) in Step 3 is shown in the following (E-3).

(E-3)

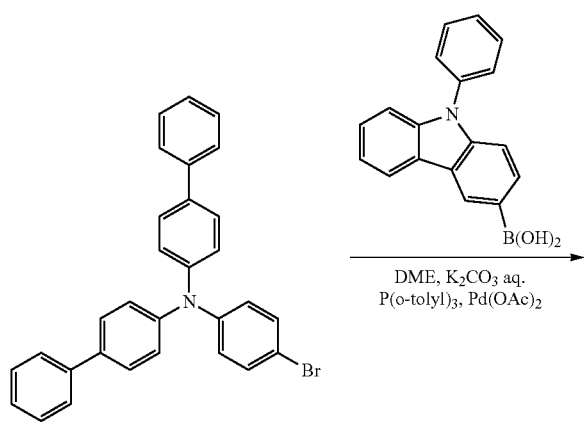

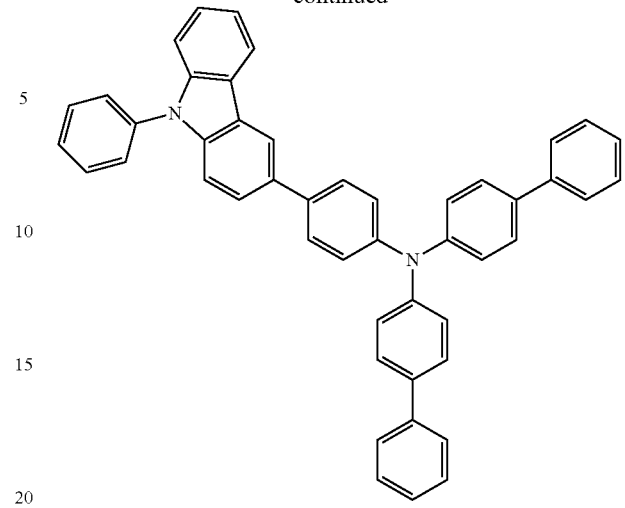

In a 100-mL three-neck flask, 1.5 g (3.1 mmol) of 4-bromo-4',4''-diphenyltriphenylamine, 0.9 g (3.1 mmol) of 9-phenyl-9H-carbazol-3-boronic acid, 50 mg (0.023 mmol) of palladium(II) acetate, and 0.050 g (0.17 mmol) of tri(o-tolyl)phosphine were put, and the atmosphere in the flask was substituted by nitrogen. Note that since a synthetic method of 9-phenyl-9H-carbazol-3-boronic acid is similar to that described in Embodiment 1, the description is to be referred thereto; thus, description here is omitted. 30 mL of ethyleneglycoldimethylether (DME) and 15 mL of potassium carbonate solution (2 mol/L) were added to this mixture. This mixture was deaerated while being stirred under low pressure. After the deaeration, this mixture was stirred at 90° C. for 5 hours to be reacted.

After the reaction, ethyl acetate was added to the reaction mixture, and this suspension was washed with a saturated sodium hydrogen carbonate solution and a saturated saline solution. Magnesium sulfate was added to an organic layer, and the organic layer was dried. After the drying, suction filtration was performed on this mixture to remove the magnesium sulfate; thus, filtrate was obtained. Toluene was added to a solid which was obtained by concentrating the obtained filtrate and the mixture was dissolved. Then, suction filtration was performed on this solution through Celite, alumina and Florisil to obtain filtrate. The obtained filtrate was concentrated and purified by silica gel column chromatography. The silica gel column chromatography was performed by, first, using a mixture solvent of toluene: hexane=1:9 as a developing solvent, and then using a mixture solvent of toluene: hexane=3:7 as another developing solvent.

A solid which was obtained by concentrating the obtained fraction was recrystallized with a mixture solvent of dichloromethane and hexane to obtain 1.3 g of an objective white solid at a yield of 66%. Sublimation purification of 1.1 g of the obtained white solid was performed by a train sublimation method. The sublimation purification was performed under a reduced pressure of 7.0 Pa, with a flow rate of argon at 4 mL/min, at 305° C. for 15 hours. Accordingly, 840 mg of the white solid was obtained at a yield of 76%.

Figure 12A:
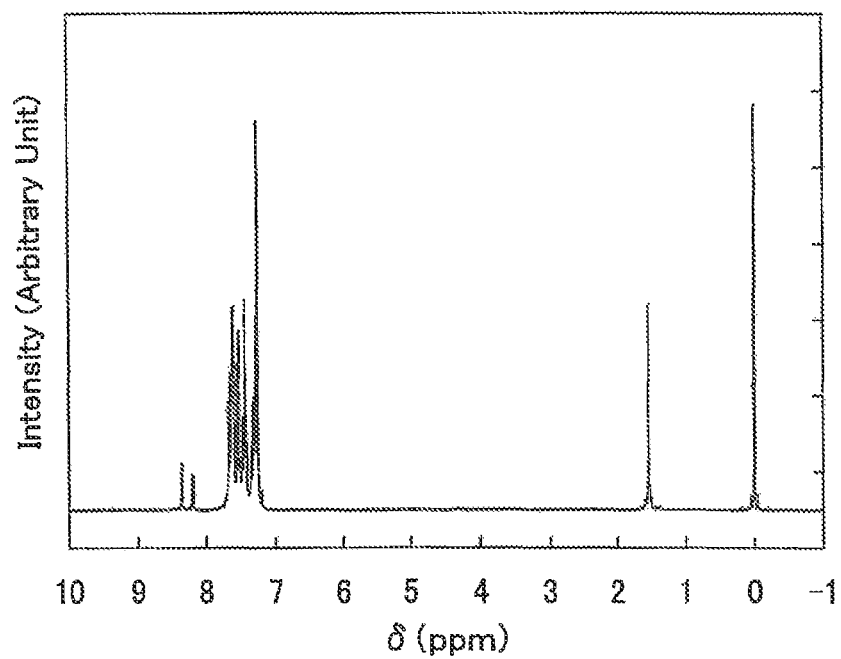
FIGS. 12A and 12B are graphs showing $^1$H NMR charts of PCBBi1BP (abbreviation)
Figure 12B:
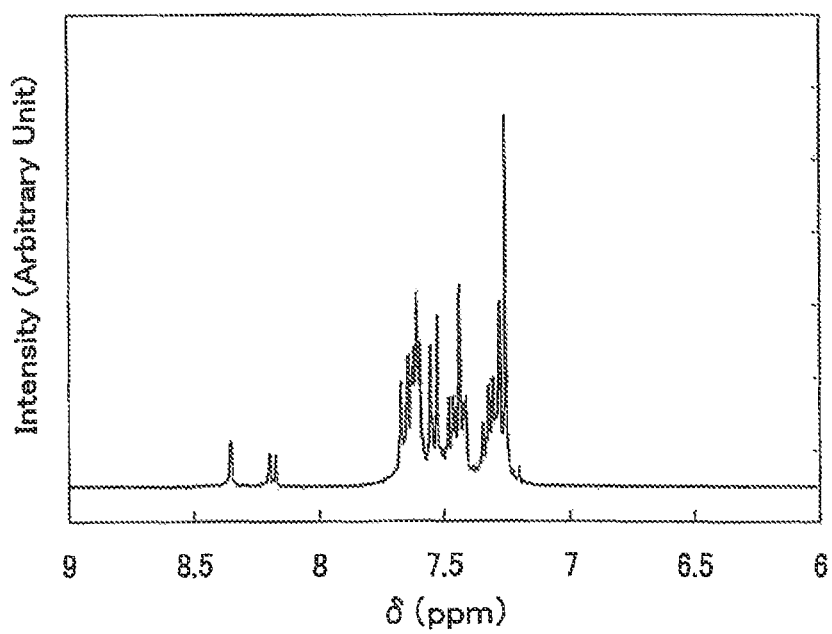

A compound which was obtained through the above Step 4 was measured by a nuclear magnetic resonance method ($^1$H NMR). The measurement result is described below, and the $^1$H NMR chart is shown in FIGS. 12A and 12B. It was found from the measurement result that the carbazole derivative of the present invention, 4,4'-diphenyl-4"-(9-phenyl-9-H-carbazol-3-yl)triphenylamine (abbreviation: PCBBi1BP) represented by the above structural formula (6), was obtained.

$^1$H NMR (CDCl$_3$, 300 MHz): δ (ppm)=7.25-7.69 (m, 32H), 8.19 (d, J=7.3 Hz, 1H), 8.35 (s, 1H).

Figure 13A:
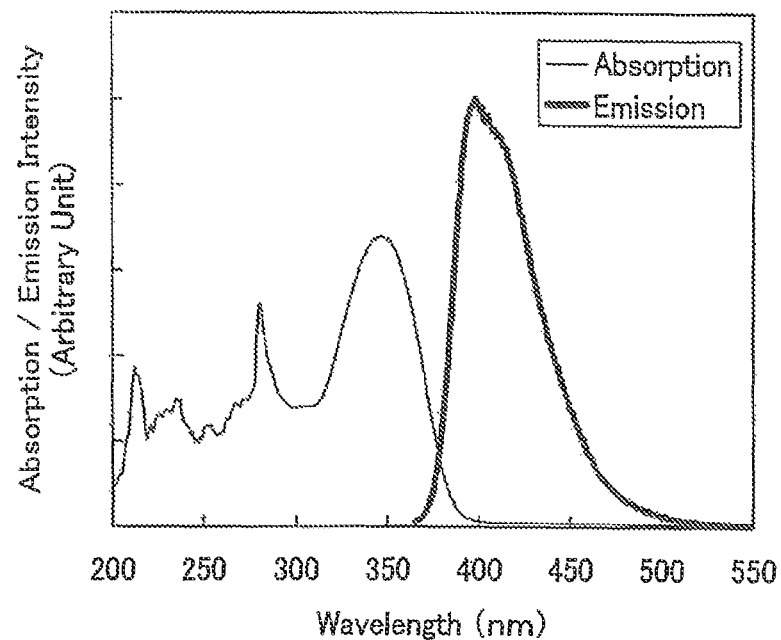
FIGS. 13A and 13B are graphs showing an absorption spectrum and an emission spectrum of PCBBi1BP (abbreviation)
Figure 13B:
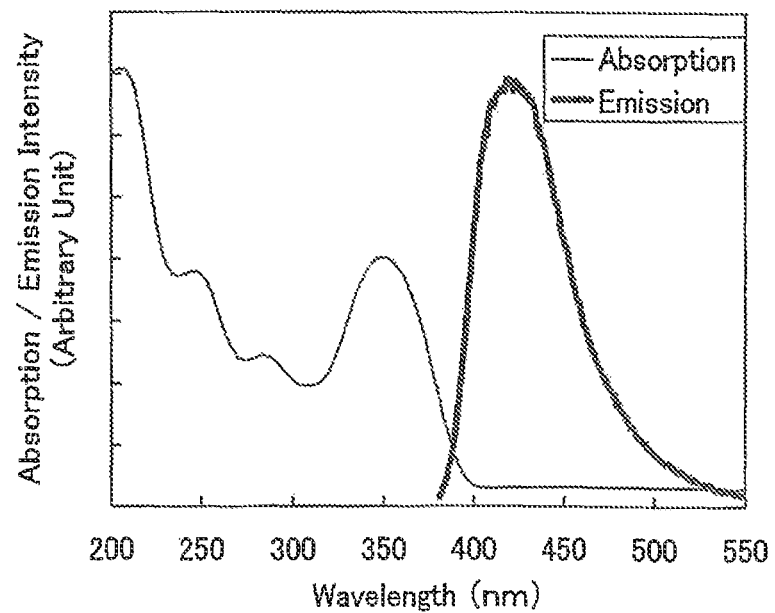

In addition, an absorption spectrum of a toluene solution of PCBBi1BP (abbreviation) is shown in FIG. 13A. In addition, an absorption spectrum of a thin film of PCBBi1BP (abbreviation) is shown in FIG. 13B. An ultraviolet-visible spectrophotometer (V-550, manufactured by JASCO Corporation) was used for the measurement. The spectrum of the solution was measured in a quartz cell. The sample of the thin film was fabricated by vapor evaporation of PCBBi1BP (abbreviation) over a quartz substrate. The absorption spectrum of the solution which was obtained by subtracting the quartz cell from the measured sample is shown in FIG. 13A, and the absorption spectrum of the thin film which was obtained by subtracting the quartz substrate from the measured sample is shown in FIG. 13B. In FIGS. 13A and 13B, the horizontal axis indicates the wavelength (nm) and the vertical axis indicates the absorption intensity (arbitrary unit). In the case of the toluene solution, an absorption peak was observed at around 347 nm, and in the case of the thin film, an absorption peak was observed at around 350 nm. In addition, an emission spectrum of the toluene solution (excitation wavelength: 358 nm) of PCBBi1BP (abbreviation) is shown in FIG. 13A. In addition, an emission spectrum of the thin film (excitation wavelength: 366 nm) of PCBBi1BP (abbreviation) is shown FIG. 13B. In FIGS. 13A and 1313, the horizontal axis indicates the wavelength (nm) and the vertical axis indicates the light emission intensity (arbitrary unit). The maximum emission wavelength was 399 nm (excitation wavelength: 358 nm) in the case of the toluene solution and 417 nm (excitation wavelength: 366 nm) in the case of the thin film.

An oxidation-reduction reaction characteristic of PCBBi1BP (abbreviation) was examined by a cyclic voltammetry (CV) measurement. Since the measurement method is similar to that of Embodiment 1, the description is omitted.

Figure 42:
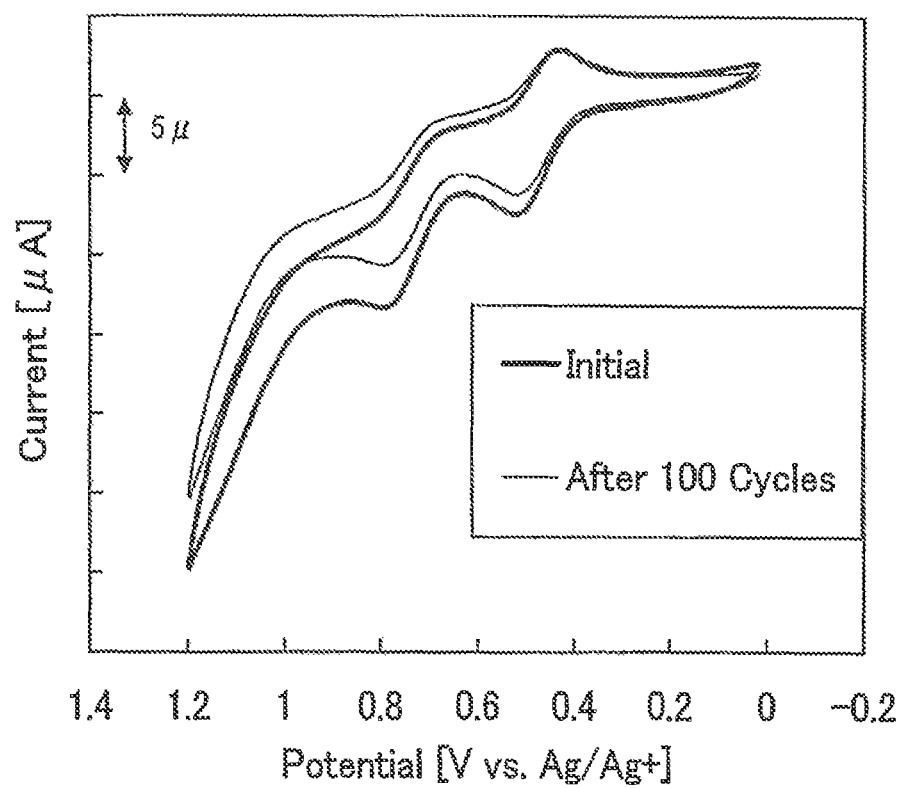
FIG. 42 is a graph showing CV characteristics of PCBBi1BP (abbreviation)

FIG. 42 shows the CV measurement result on the oxidation reaction characteristics. As shown in FIG. 42, an oxidization peak potential $E_{pa}$ can be read as 0.521 V, and a reduction peak potential $E_{pc}$ can be read as +0.431 V. Therefore, a half-wave potential (an intermediate potential between $E_{pc}$ and $E_{pa}$) can be calculated to be +0.48 V. According to the calculation similar to that of Embodiment 1, the HOMO level of PCBBi1BP (abbreviation) was found to be =−5.42 [eV]. In addition, the oxidation peak took a similar value even after the 100 cycles. Accordingly, it was found that repetition of the oxidation reduction between an oxidation state and a neutral state had favorable characteristics.

The result of measuring the thin film using a photoelectron spectrometer (AC-2, manufactured by Riken Keiki Co., Ltd.) under the atmosphere indicated that the HOMO level of PCBBi1BP (abbreviation) was −5.34 eV. The Tauc plot of the absorption spectrum of the thin film revealed that the absorption edge was 3.15 eV. Thus, the energy gap in the solid state was estimated to be 3.15 eV, which means that the LUMO level of PCBBi1BP (abbreviation) is −2.19 eV.

In addition, the glass transition temperature of PCBBi1BP (abbreviation) was examined with a differential scanning calorimetry (Pyris 1 DSC, manufactured by Perkin Elmer Co., Ltd.). According to the measurement results, it was found that the glass transition temperature was 123° C. In this manner, PCBBi1BP (abbreviation) has a high glass transition temperature and favorable heat resistance. In addition, the crystallization peak does not exist; thus, it was found that PCBBi1BP (abbreviation) is a substance which is hard to be crystallized.

Embodiment 3

In Embodiment 3, a synthetic method of a carbazole derivative of the present invention, 9,9-dimethyl-N-phenyl-N-[4-(9-phenyl-9H-carbazol-3-yl)phenyl]-fluorene-2-amine (abbreviation: PCBAF) represented by a structural formula (7), will be specifically described.

(7)

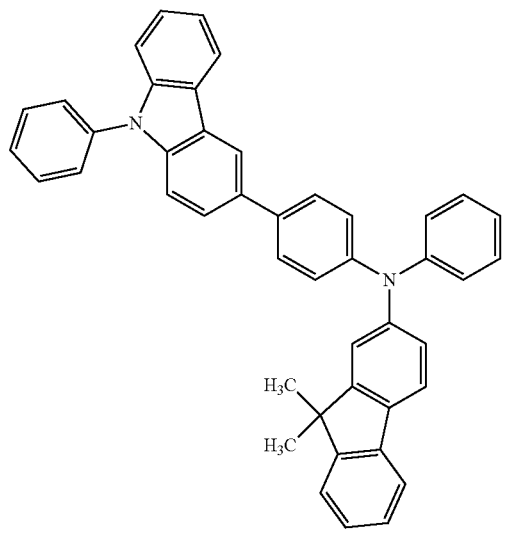

Step 1: Synthesis of 2-bromo-9,9-dimethylfluoren

A synthetic scheme of 2-bromo-9,9-dimethylfluoren in Step 1 is shown in the following (F-1).

(F-1)

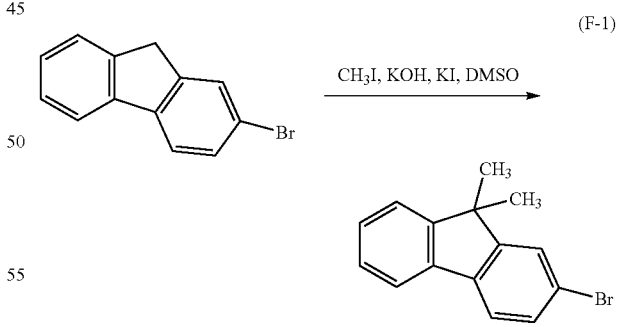

In a 500-mL conical flask, 12.5 g (51 mmol) of 2-bromofluorene, 8.5 g (51 mmol) of potassium iodide, 14.3 g (0.50 mol) of potassium hydroxide, and 250 mL of dimethyl sulfoxide were stirred for 30 minutes. Then, 10 mL of methyl iodide was added to this mixture little by little. This mixture was stirred at room temperature for 48 hours. After the reaction, 400 mL of chloroform was added to the reaction solution and this mixture was stirred. This solution was washed with 1N hydrochloric acid, a saturated sodium carbonate solution, and a saturated saline solution in this order. Magnesium sulfate was added to the obtained organic layer to remove moisture.

This mixture was subjected to suction filtration and concentrated. Then, a residue thereof was purified by silica gel column chromatography. The silica gel column chromatography was performed by, first, using hexane as a developing solvent, and then using a mixture solvent of ethyl acetate: hexane=1:5 as another developing solvent. The corresponding fractions were concentrated and dried to obtain 12 g of a brown oily substance at a yield of 97%.

Step 2: Synthesis of 9,9-dimethyl-N-phenyl-N-[4-(9-phenyl-9H-carbazol-3-yl)phenyl]-fluorene-2-amine (abbreviation: PCBAF)

A synthetic scheme of 9,9-dimethyl-N-phenyl-N-[4-(9-phenyl-9H-carbazol-3-yl)phenyl]-fluorene-2-amine (abbreviation: PCBAF) in Step 2 is shown in the following (F-2).

being stirred under low pressure. After the deaeration, 0.10 g of bis(dibenzylideneacetone)palladium(0) was added thereto. Next, the mixture was stirred at 80° C. for 5 hours to be reacted. After the reaction, toluene was added to the reaction mixture, and suction filtration was performed on this suspension through Celite, alumina, and then Florisil to obtain filtrate.

The obtained filtrate was concentrated and purified by silica gel column chromatography. The silica gel column chromatography was performed by, first, using a mixture solvent of toluene: hexane=1:9 as a developing solvent, and then using a mixture solvent of toluene: hexane=3:7 as another developing solvent. A solid which was obtained by concentrating the obtained fraction was recrystallized with a mixture solvent of chloroform and hexane to obtain 1.3 g of an objective compound at a yield of 44%.

Sublimation purification of 1.3 g of the obtained light yellow solid was performed by a train sublimation method.

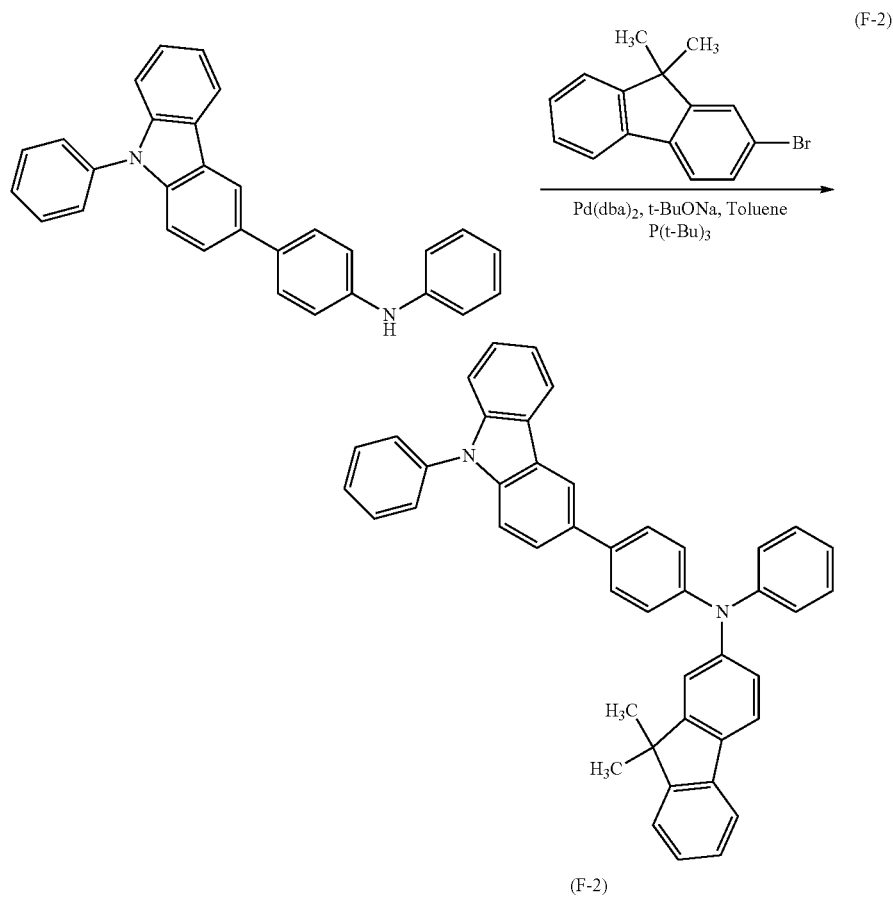

(F-2)

In a 100-mL three-neck flask, 2.0 g (4.9 mmol) of 4-(9-phenyl-9H-carbazol-3-yl)diphenylamine (abbreviation: PCBA), 1.3 g (4.9 mmol) of 2-bromo-9,9-dimethylfluoren, and 2.0 g (20 mmol) of sodium tert-butoxide were put, and the atmosphere in the flask was substituted by nitrogen. Note that since a synthetic method of PCBA (abbreviation) is similar to that described in Embodiment 2, the description is to be referred thereto; thus, description here is omitted. Then, 50 mL of toluene and 0.30 mL of tri(tert-butyl)phosphine (10 wt % hexane solution) were added to this mixture. The mixture was deaerated while The sublimation purification was performed under a reduced pressure of 7.0 Pa, with a flow rate of argon at 3 mL/min, at 270° C. for 20 hours. Accordingly, 1.0 g of the light yellow solid was obtained at a yield of 77%.

Figure 14A:
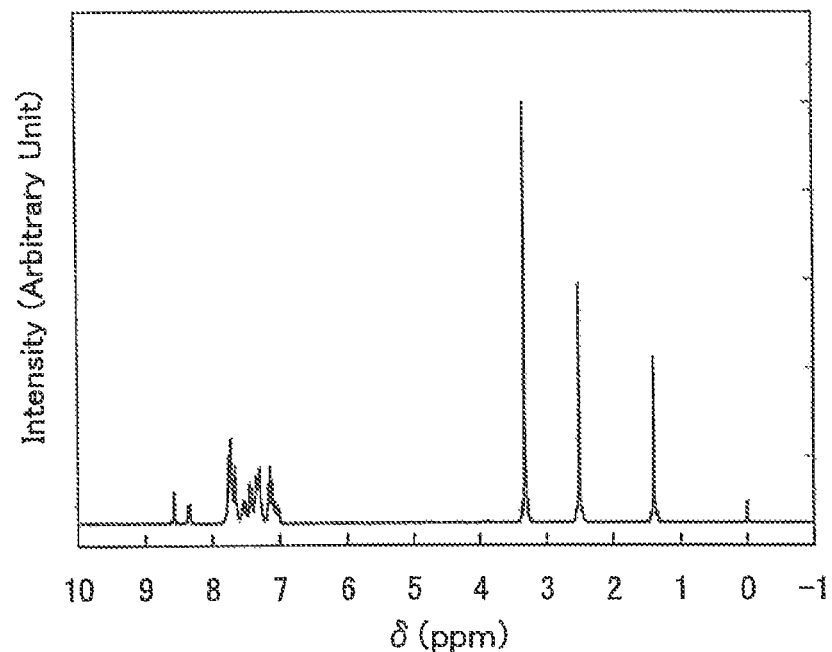
FIGS. 14A and 14B are graphs showing $^1$H NMR charts of PCBAF (abbreviation)
Figure 14B:
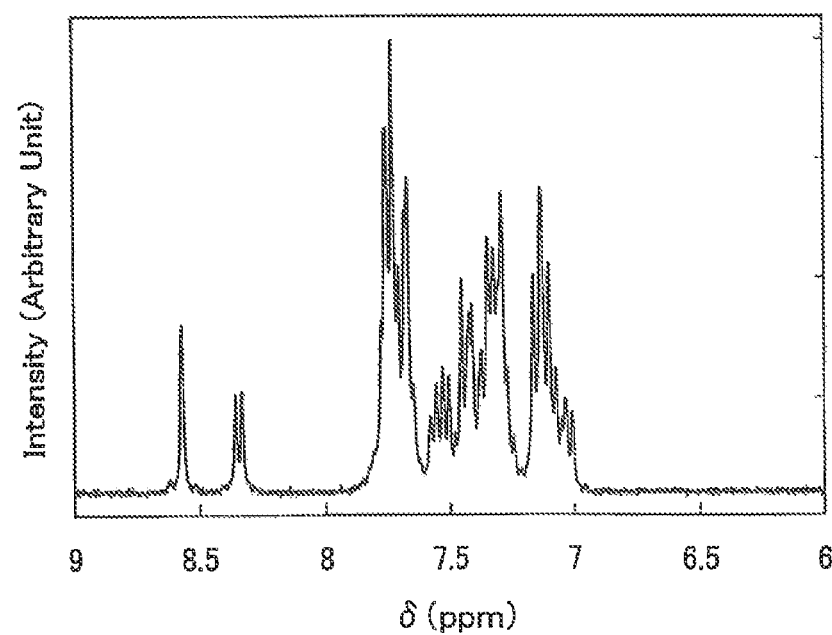

A compound which was obtained through the above Step 2 was measured by a nuclear magnetic resonance method ($^1$H NMR). The measurement result is described below, and the $^1$H NMR chart is shown in FIGS. 14A and 14B. It was found from the measurement result that the carbazole derivative of the present invention, 9,9-dimethyl-N-phenyl- N-[4-(9-phenyl-9H-carbazol-3-yl)phenyl]-fluorene-2-amine (abbreviation: PCBAF) represented by the above structural formula (7), was obtained.

$^1$H NMR (DMSO-d, 300 MHz): δ (ppm)=1.39 (s, 6H) 6.98-7.82 (m, 26H), 8.35 (d, J=6.8 Hz, 1H), 8.57 (s, 1H).

Figure 15A:
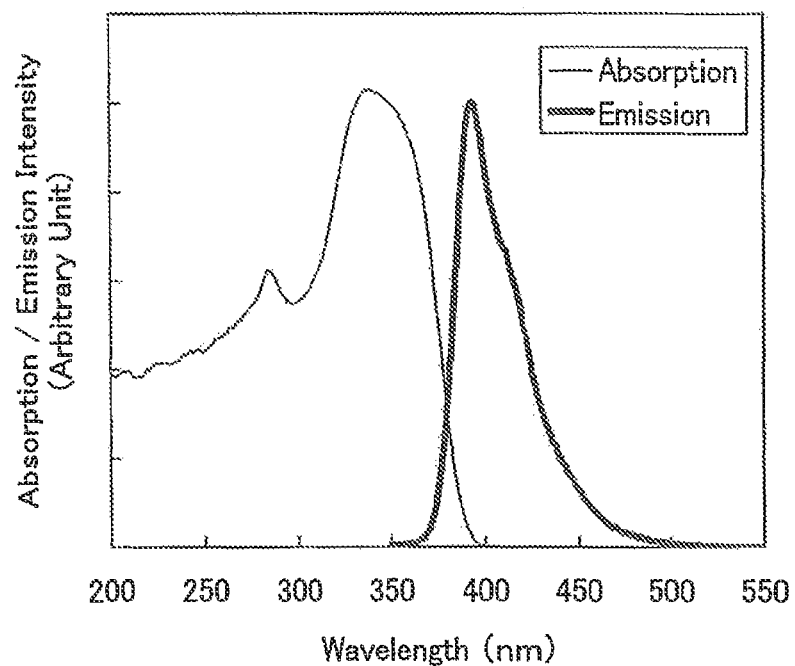
FIGS. 15A and 15B are graphs showing an absorption spectrum and an emission spectrum of PCBAF (abbreviation)
Figure 15B:
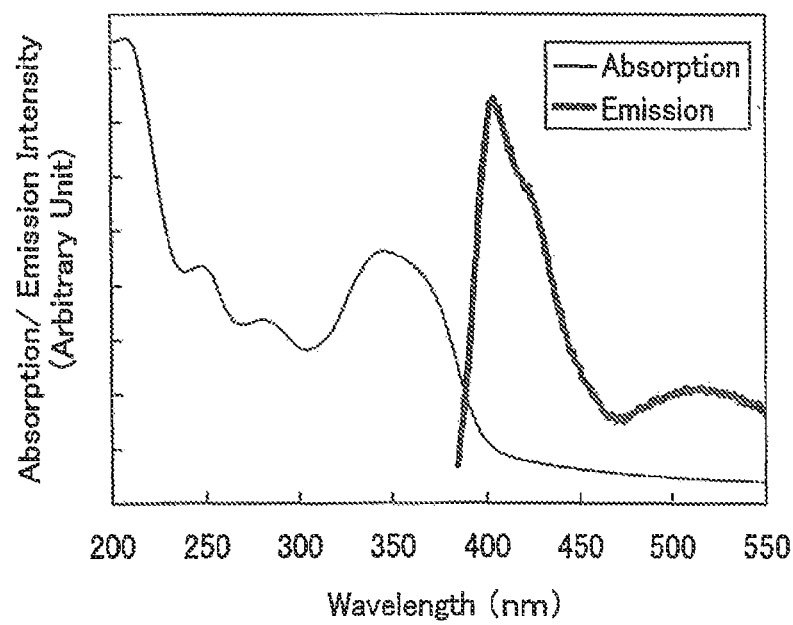

In addition, an absorption spectrum of a toluene solution of PCBAF (abbreviation) is shown in FIG. 15A. In addition, an absorption spectrum of a thin film of PCBAF (abbreviation) is shown in FIG. 15B. An ultraviolet-visible spectrophotometer (V-550, manufactured by JASCO Corporation) was used for the measurement. The spectrum of the solution was measured in a quartz cell. The sample of the thin film was fabricated by vapor evaporation of PCBAF (abbreviation) over a quartz substrate. The absorption spectrum of the solution which was obtained by subtracting the quartz cell from the measured sample is shown in FIG. 15A, and the absorption spectrum of the thin film which was obtained by subtracting the quartz substrate from the measured sample is shown in FIG. 15B. In FIGS. 15A and 15B, the horizontal axis indicates the wavelength (nm) and the vertical axis indicates the absorption intensity (arbitrary unit). In the case of the toluene solution, an absorption peak was observed at around 339 nm, and in the case of the thin film, an absorption peak was observed at around 345 nm. In addition, an emission spectrum of the toluene solution (excitation wavelength: 347 nm) of PCBAF (abbreviation) is shown in FIG. 15A. In addition, an emission spectrum of the thin film (excitation wavelength: 370 nm) of PCBAF (abbreviation) is shown FIG. 15B. In FIGS. 15A and 15B, the horizontal axis indicates the wavelength (nm) and the vertical axis indicates the light emission intensity (arbitrary unit). The maximum emission wavelength was 394 nm (excitation wavelength: 347 nm) in the case of the toluene solution and 404 nm (excitation wavelength: 370 nm) in the case of the thin film.

An oxidation-reduction reaction characteristic of PCBAF (abbreviation) was examined by a cyclic voltammetry (CV) measurement. Since the measurement method is similar to that of Embodiment 1, the description is omitted.

Figure 43:
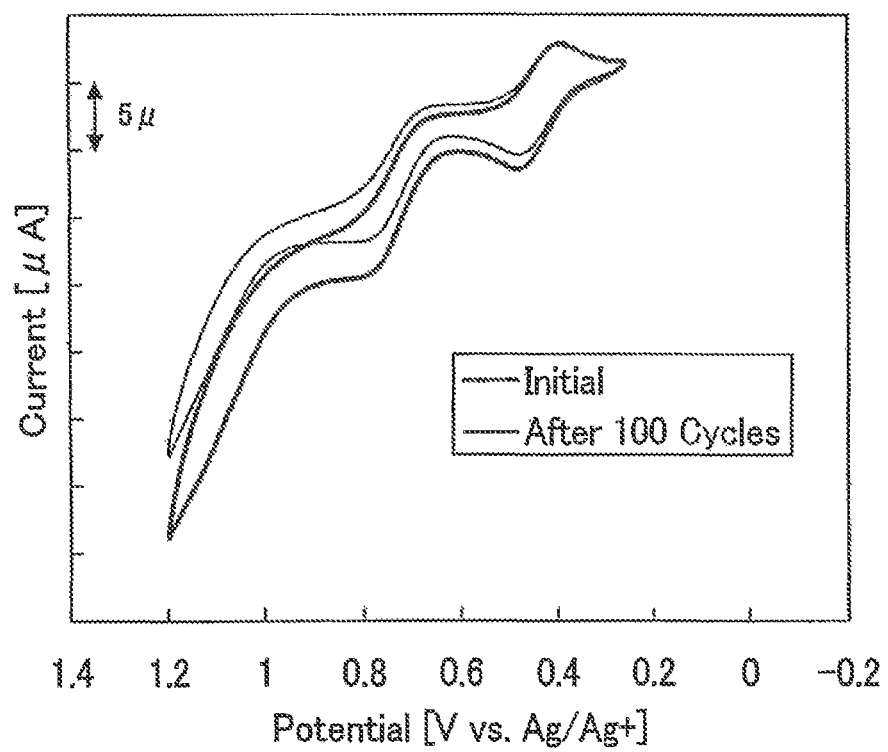
FIG. 43 is a graph showing CV characteristics of PCBAF (abbreviation)

FIG. 43 shows the CV measurement result on the oxidation reaction characteristics. As shown in FIG. 43, an oxidization peak potential $E_{pa}$ can be read as 0.481 V, and a reduction peak potential $E_{pc}$ can be read as +0.393 V. Therefore, a half-wave potential (an intermediate potential between $E_{pc}$ and $E_{pa}$) can be calculated to be +0.44 V. According to the calculation similar to that of Embodiment 1, the HOMO level of PCBAF (abbreviation) was found to be =−5.38 [eV]. In addition, the oxidation peak took a similar value even after the 100 cycles. Accordingly, it was found that repetition of the oxidation reduction between an oxidation state and a neutral state had favorable characteristics.

Embodiment 4

In Embodiment 4, a synthetic method of a carbazole derivative of the present invention, N-phenyl-N-[4-(9-phenyl-9H-carbazol-3-yl)phenyl]-spiro-9,9'-bifluoren-2-amine (abbreviation: PCBASF) represented by a structural formula (8), will be specifically described.

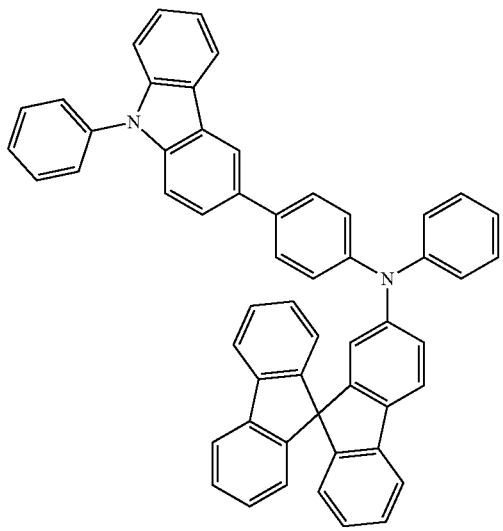

(8)

Step 1-1: Synthesis of 9-(biphenyl-2-yl)-2-bromofluoren-9-ol

A synthetic scheme of 9-(biphenyl-2-yl)-2-bromofluoren-9-ol in Step 1-1 is shown in the following (G-1-1).

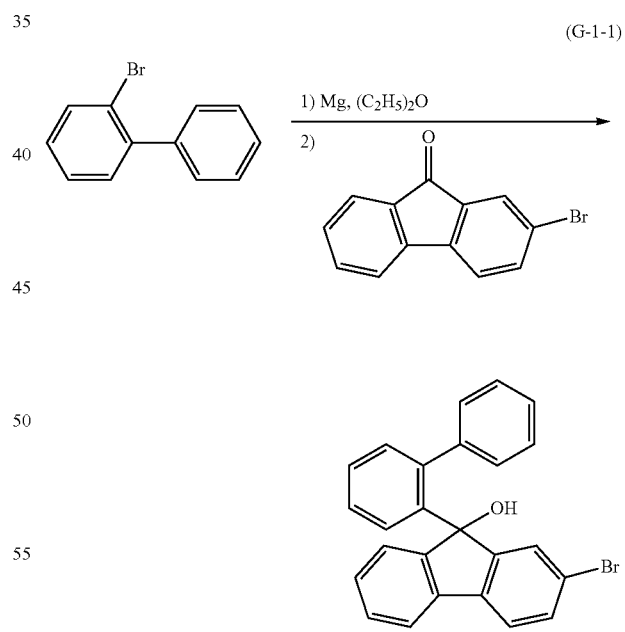

(G-1-1)

In a 100-mL three-neck flask to which a dropping funnel and a Dimroth condenser were connected, 1.26 g (0.052 mol) of magnesium was put, and the flask was evacuated. The magnesium was activated by heating and stirring for 30 minutes. After cooling to room temperature, the flask was placed under a nitrogen gas flow. Then, 5 mL of diethyl ether and several drops of dibromoethane were added thereto, and 11.65 g (0.050 mol) of 2-bromobiphenyl dissolved in 15 mL of diethyl ether was slowly dropped from the dropping funnel into the mixture. After completion of the dropping, the mixture was refluxed for 3 hours and made into a Grignard reagent.

In a 200-mL three-neck flask to which a dropping funnel and a Dimroth condenser were connected, 11.7 g (0.045 mol) of 2-bromo-9-fluorenone and 40 mL of diethyl ether were put. To this reaction solution, the synthesized Grignard reagent was slowly dropped from the dropping funnel. After completion of the dropping, the mixture was refluxed for 2 hours, and then stirred at room temperature overnight. After completion of the reaction, the solution was washed twice with a saturated ammonia chloride solution, and separated into an aqueous layer and an organic layer. The obtained aqueous layer was extracted twice with ethyl acetate, and this ethyl acetate solution and the obtained organic layer were washed with a saturated saline solution. After moisture was removed by magnesium sulfate, suction filtration and concentration were performed to obtain 18.76 g of a solid of 9-(biphenyl-2-yl)-2-bromo-9-fluorenol at a yield of 90%.

Step 1-2: Synthesis of 2-bromo-spiro-9,9'-bifluoren

A synthetic scheme of 2-bromo-spiro-9,9'-bifluoren in Step 1-2 is shown in the following (G-1-2).

In a 200-mL three-neck flask, 18.76 g (0.045 mol) of the synthesized 9-(biphenyl-2-yl)-2-bromo-9-fluorenol and 100 mL of glacial acetic acid were put, several drops of concentrated hydrochloric acid were added thereto, and the mixture was refluxed for 2 hours. After completion of the reaction, a precipitate was collected by suction filtration, and the precipitate was filtered and washed with a saturated sodium hydrogen carbonate solution and water. The obtained brown solid was recrystallized with ethanol to obtain 10.24 g of a light-brown powder-like solid at a yield of 57%.

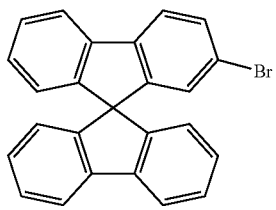

(G-1-2)

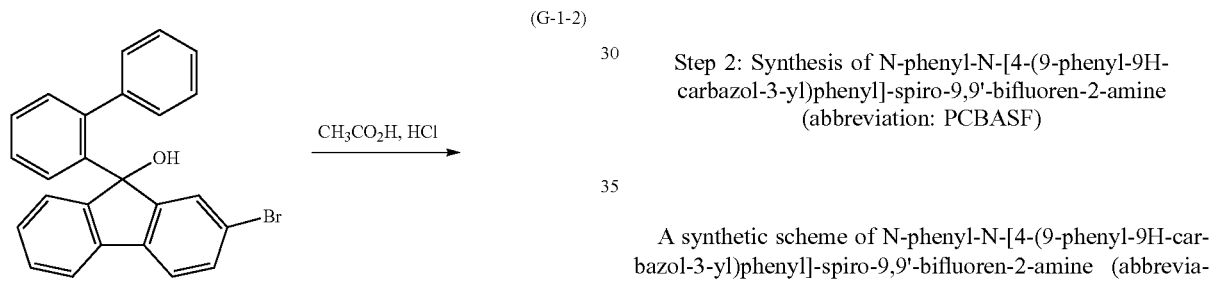

Step 2: Synthesis of N-phenyl-N-[4-(9-phenyl-9H-carbazol-3-yl)phenyl]-spiro-9,9'-bifluoren-2-amine (abbreviation: PCBASF)

A synthetic scheme of N-phenyl-N-[4-(9-phenyl-9H-carbazol-3-yl)phenyl]-spiro-9,9'-bifluoren-2-amine (abbreviation: PCBASF) in Step 2 is shown in the following (G-2).

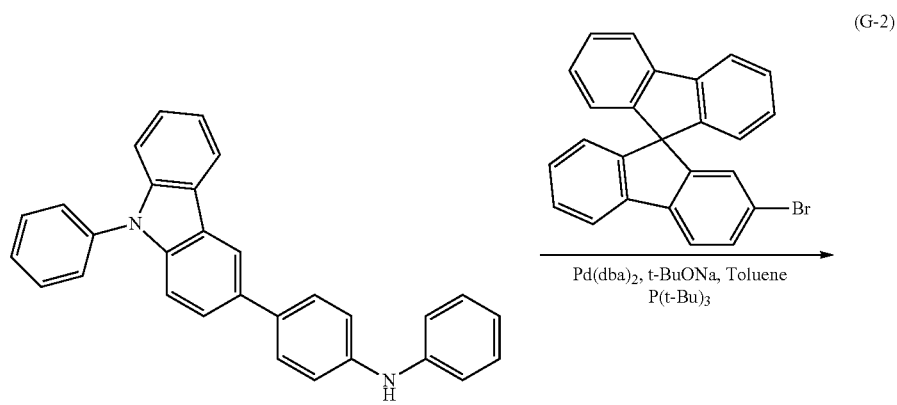

(G-2)

-continued

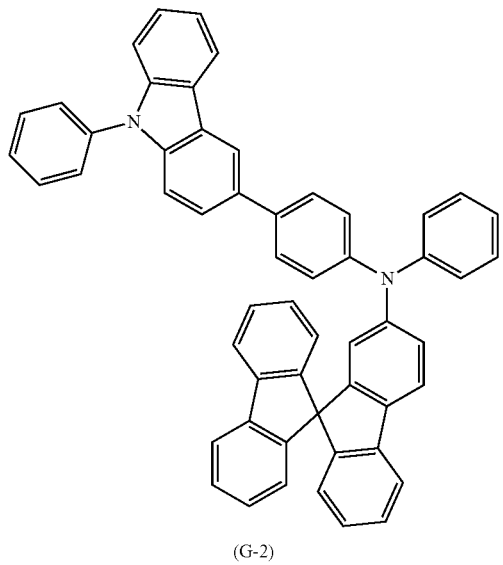

(G-2)

In a 100-mL three-neck flask, 2.0 g (4.9 mmol) of 4-(9-phenyl-9H-carbazol-3-yl)diphenylamine (abbreviation: PCBA), 1.9 g (4.9 mmol) of 2-bromo-spiro-9,9'-bifluoren, and 2.0 g (20 mmol) of sodium tert-butoxide were put, and the atmosphere in the flask was substituted by nitrogen. Then, 50 mL of toluene and 0.30 mL of tri(tert-butyl)phosphine (10 wt % hexane solution) were added to this mixture. This mixture was deaerated while being stirred under low pressure. After the deaeration, 0.10 g of bis(dibenzylideneacetone)palladium(0) was added thereto.

Next, this mixture was stirred at 80° C. for 5 hours to be reacted. After the reaction, toluene was added to the reaction mixture, and suction filtration was performed on this suspension through Celite, alumina, and then Florisil to obtain filtrate. The obtained filtrate was washed with a saturated sodium carbonate solution and a saturated saline solution in this order. After magnesium sulfate was added to an organic layer to remove moisture, suction filtration was performed on this mixture and the magnesium sulfate was removed to obtain filtrate. A solid which was obtained by concentrating the obtained filtrate was recrystallized with a mixture solvent of chloroform and hexane to obtain 3.4 g of a white powder-like solid at a yield of 94%. Sublimation purification of 2.3 g of the obtained white solid was performed by a train sublimation method. The sublimation purification was performed under a reduced pressure of 7.0 Pa, with a flow rate of argon at 3 mL/min, at 310° C. for 20 hours. Accordingly, 1.7 g of the white solid was obtained at a yield of 74%.

Figure 16A:
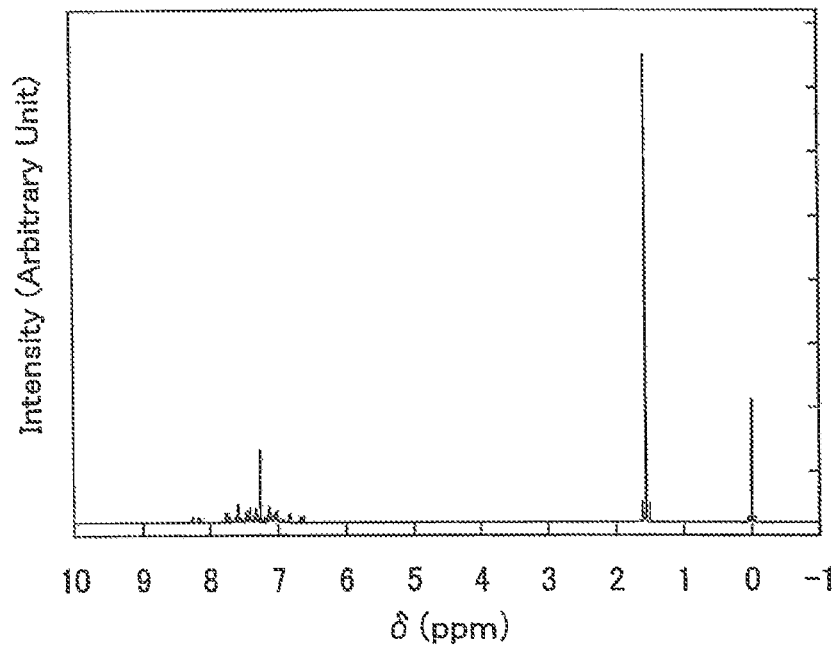
FIGS. 16A and 16B are graphs showing $^1$H NMR charts of PCBASF (abbreviation)
Figure 16B:
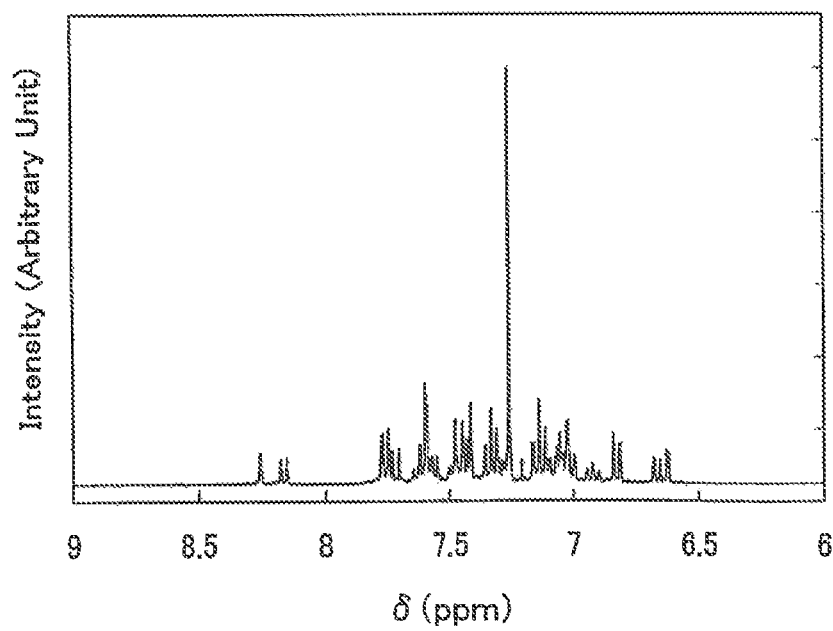

A compound which was obtained through the above Step 2 was measured by a nuclear magnetic resonance method ($^1$H NMR). The measurement result is described below, and the $^1$H NMR chart is shown in FIGS. 16A and 16B. It was found from the measurement result that the carbazole derivative of the present invention, N-phenyl-N-[4-(9-phenyl-9H-carbazol-3-yl)phenyl]-spiro-9,9'-bifluoren-2-amine (abbreviation: PCBASF) represented by the above structural formula (8), was obtained.

$^1$H NMR (CDCl$_3$, 300 MHz): δ (ppm)=6.61-6.70 (m, 2H), 6.83 (d, J=8.3 Hz, 2H), 6.88-7.79 (m, 30H), 8.16 (d, J=8.3 Hz, 1H), 8.26 (s, 1H).

Figure 17A:
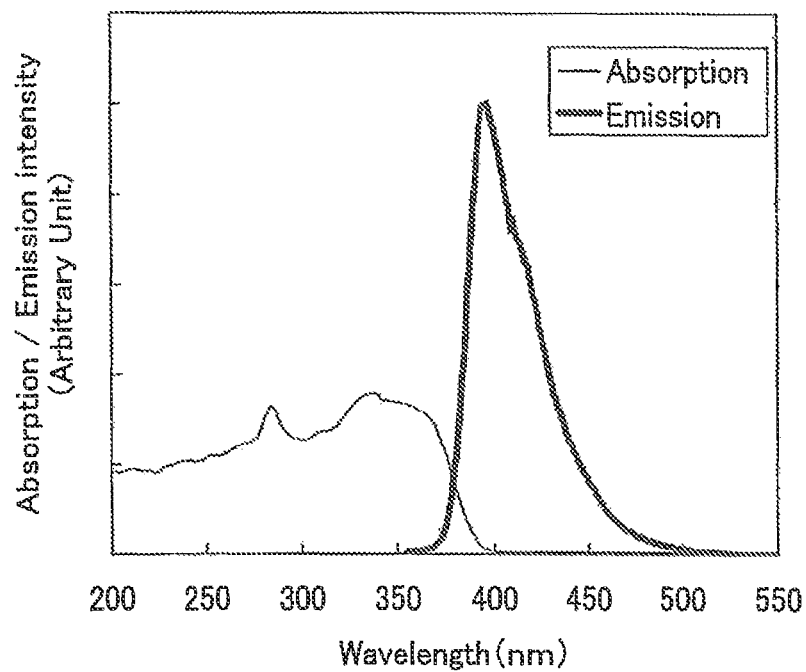
FIGS. 17A and 17B are graphs showing an absorption spectrum and an emission spectrum of PCBASF (abbreviation)
Figure 17B:
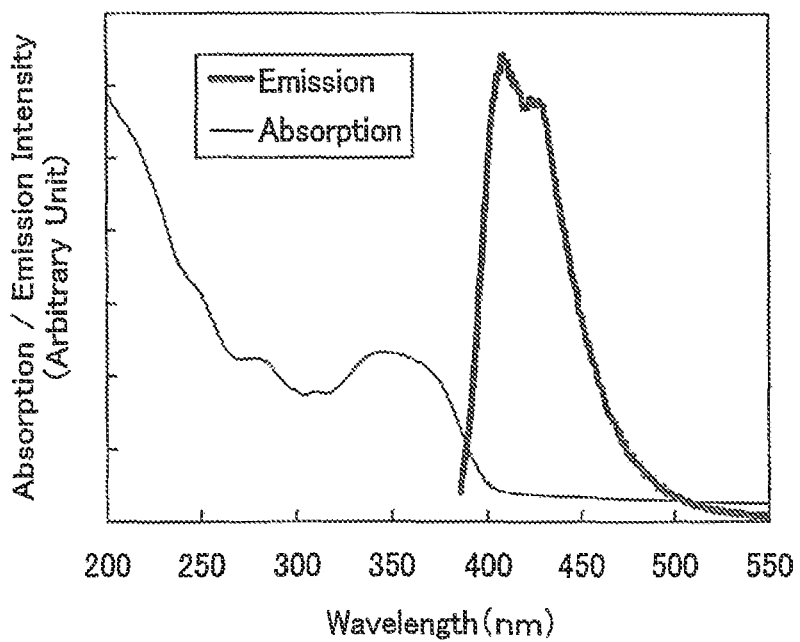

In addition, an absorption spectrum of a toluene solution of PCBASF (abbreviation) is shown in FIG. 17A. In addition, an absorption spectrum of a thin film of PCBASF (abbreviation) is shown in FIG. 17B. An ultraviolet-visible spectrophotometer (V-550, manufactured by JASCO Corporation) was used for the measurement. The spectrum of the solution was measured in a quartz cell. The sample of the thin film was fabricated by vapor evaporation of PCBASF (abbreviation) over a quartz substrate. The absorption spectrum of the solution which was obtained by subtracting the quartz cell from the measured sample is shown in FIG. 17A, and the absorption spectrum of the thin film which was obtained by subtracting the quartz substrate from the measured sample is shown in FIG. 17B. In FIGS. 17A and 17B, the horizontal axis indicates the wavelength (nm) and the vertical axis indicates the absorption intensity (arbitrary unit). In the case of the toluene solution, an absorption peak was observed at around 338 nm, and in the case of the thin film, an absorption peak was observed at around 345 nm. In addition, an emission spectrum of the toluene solution (excitation wavelength: 352 nm) of PCBASF (abbreviation) is shown in FIG. 17A. In addition, an emission spectrum of the thin film (excitation wavelength: 371 nm) of PCBASF (abbreviation) is shown FIG. 17B. In FIGS. 17A and 17B, the horizontal axis indicates the wavelength (nm) and the vertical axis indicates the light emission intensity (arbitrary unit). The maximum emission wavelength was 396 nm (excitation wavelength: 352 nm) in the case of the toluene solution and 427 nm (excitation wavelength: 371 nm) in the case of the thin film.

An oxidation-reduction reaction characteristic of PCBASF (abbreviation) was examined by a cyclic voltammetry (CV) measurement. Since the measurement method is similar to that of Embodiment 1, the description is omitted.

Figure 44:
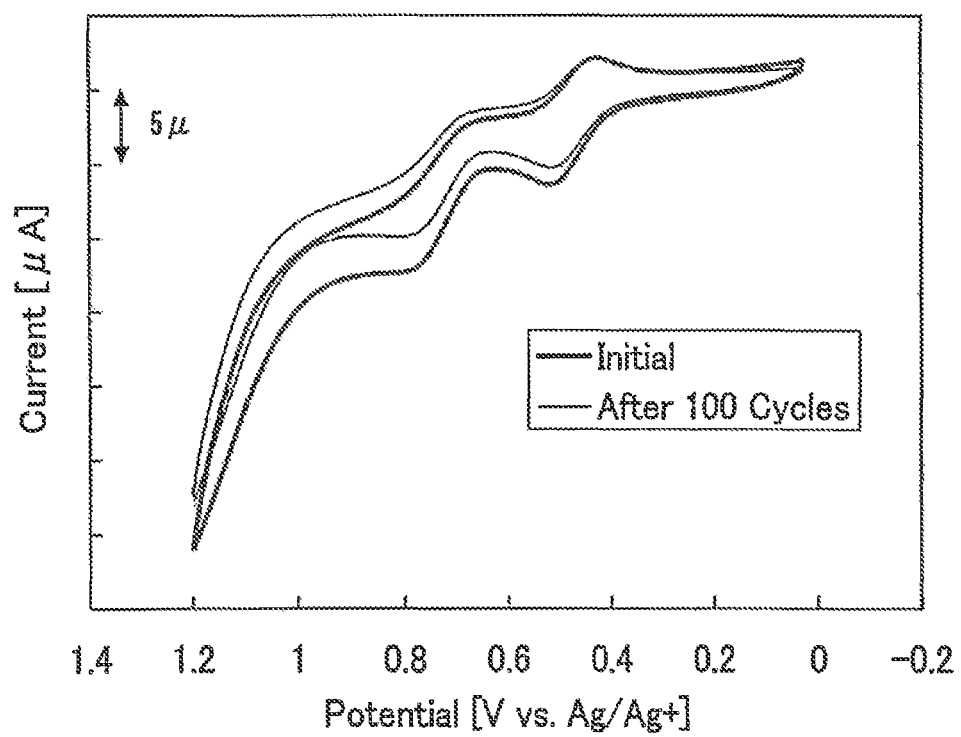
FIG. 44 is a graph showing CV characteristics of PCBASF (abbreviation)

FIG. 44 shows the CV measurement result on the oxidation reaction characteristics. As shown in FIG. 44, an oxidization peak potential $E_{pa}$ can be read as 0.52 V, and a reduction peak potential $E_{pc}$ can be read as +0.428 V. Therefore, a half-wave potential (an intermediate potential between $E_{pc}$ and $E_{p}a$) can be calculated to be +0.47 V.

According to the calculation similar to that of Embodiment 1, the HOMO level of PCBASF (abbreviation) was found to be =−5.41 [eV]. In addition, the oxidation peak took a similar value even after the 100 cycles. Accordingly, it was found that repetition of the oxidation reduction between an oxidation state and a neutral state had favorable characteristics.

Embodiment 5

In Embodiment 5, a method for manufacturing a light-emitting element 2, a light-emitting element 3, a light-emitting element 4, and a light-emitting element 5, which were formed using carbazole derivatives of the present invention that are synthesized in Embodiments 1 to 4 and measurement results of their element characteristics will be described. The light-emitting element 2 was formed using 4-phenyl-4'-(9-phenyl-9H-carbazol-3-yl)triphenylamine (abbreviation: PCBA1BP), the light-emitting element 3 was formed using 4,4'-diphenyl-4"-(9-phenyl-9-H-carbazol-3-yl)triphenylamine (abbreviation: PCBBi1BP), the light-emitting element 4 was formed using 9,9-dimethyl-N-phenyl-N-[4-(9-phenyl-9H-carbazol-3-yl)phenyl]-fluorene-2-amine (abbreviation: PCBAF), and the light-emitting element 5 was formed using N-phenyl-N-[4-(9-phenyl-9H-carbazol-3-yl)phenyl]-spiro-9,9'-bifluoren-2-amine (abbreviation: PCBASF).

Figure 18:
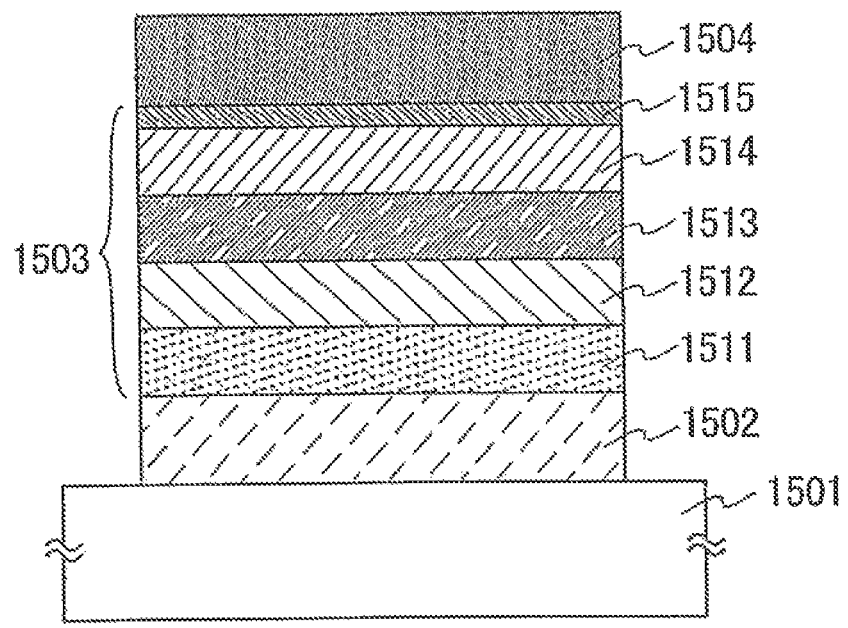
FIG. 18 is a cross-sectional view showing an element structure of a light-emitting element in Embodiment 5.

Note that each element structure of the light-emitting elements in Embodiment 5 is a structure shown in FIG. 18, in which a hole-transporting layer 1512 is formed using the above carbazole derivative of the present invention. In addition, a light-emitting element 1 which is a comparative light-emitting element is formed using 4,4'-bis[N-(1-naphthyl)-N-phenylamino]biphenyl (abbreviation: NPB) for the hole-transporting layer 1512. In order to make comparative conditions of the light-emitting element 1 with each of the light-emitting elements 2 to 5 the same, the light-emitting element 1 was formed over the same substrates as the light-emitting elements 2 to 5, and the light-emitting element 1 was compared to the light-emitting elements 2 to 5. A structural formula of an organic compound used in Embodiment 5 is shown below.

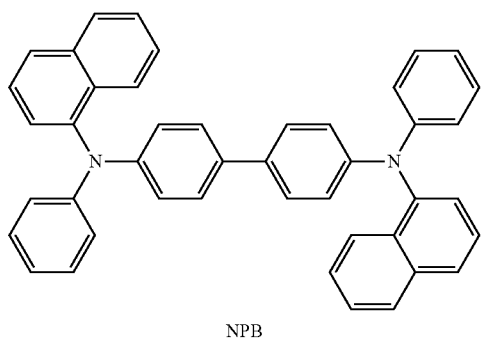

NPB

-continued

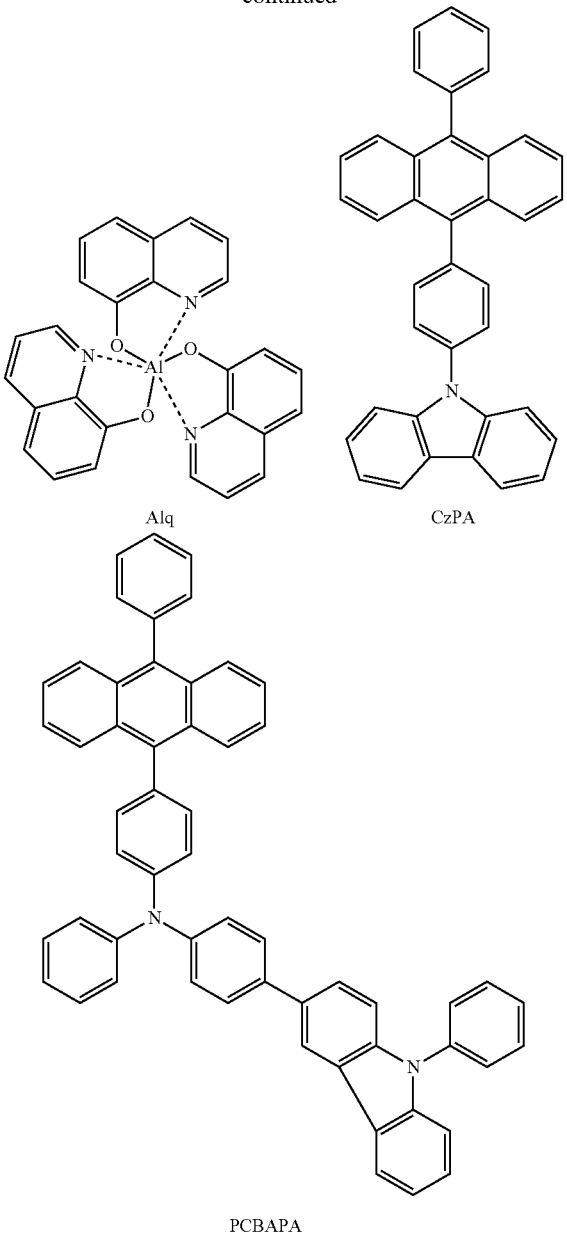

Alq     CzPA

PCBAPA

First, indium tin oxide containing silicon oxide was deposited over a substrate 1501 which is a glass substrate by a sputtering method to form a first electrode 1502. The thickness of the first electrode 1502 was set to be 110 nm, and the area was set to be 2 mm×2 mm.

Next, an EL layer 1503 in which a plurality of layers are stacked over the first electrode 1502 was formed. In Embodiment 5, the EL layer 1503 has a structure in which a first layer 1511 which is a hole-injecting layer, a second layer 1512 which is a hole-transporting layer, a third layer 1513 which is a light-emitting layer, a fourth layer 1514 which is an electron-transporting layer, and a fifth layer 1515 which is an electron-injecting layer are sequentially stacked.

The substrate having the first electrode 1502 was fixed to a substrate holder provided in a vacuum evaporation apparatus in such a way that the surface of the first electrode 1502 faced downward, and then the pressure was reduced to about 104 Pa. Then, 4,4'-bis[N-(1-naphthyl)-N-phenylamino]biphenyl (abbreviation: NPB) and molybdenum(VI) oxide were co-evaporated on the first electrode 1502, whereby the first layer 1511 which is a hole-injecting layer was formed. The evaporation rate was controlled so that the thickness of the first layer which is a hole-injecting layer could be 50 nm and the weight ratio of NPB to molybdenum(VI) oxide could be 4:1 (=NPB: molybdenum oxide). Note that the co-evaporation method is an evaporation method in which evaporation is performed using a plurality of evaporation sources at the same time in one treatment chamber.

Next, a hole-transporting material was deposited over the first layer 1511 to a thickness of 10 nm by an evaporation method using resistive heating, and the second layer 1512 which is a hole-transporting layer was formed. Note that 4,4'-bis[N-(1-naphthyl)-N-phenylamino]biphenyl (abbreviation: NPB) was used in the case of forming the light-emitting element 1, 4-phenyl-4'-(9-phenyl-9H-carbazol-3-yl)triphenylamine (abbreviation: PCBA1BP) was used in the case of forming the light-emitting element 2, 4,4'-diphenyl-4''-(9-phenyl-9-H-carbazol-3-yl)triphenylamine (abbreviation: PCBBi1BP) was used in the case of forming the light-emitting element 3, 9,9-dimethyl-N-phenyl-N-[4-(9-phenyl-9H-carbazol-3-yl)phenyl]-fluorene-2-amine (abbreviation: PCBAF) was used in the case of forming the light-emitting element 4, and N-phenyl-N-[4-(9-phenyl-9H-carbazol-3-yl)phenyl]-spiro-9,9'-bifluoren-2-amine (abbreviation: PCBASF) were used in the case of forming the light-emitting element 5.

Next, the third layer 1513 which is a light-emitting layer was formed over the second layer 1512 by an evaporation method using resistive heating. The third layer 1513 was formed by co-evaporating 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA) to a thickness of 30 nm. Here, the evaporation rate was controlled so that the weight ratio of CzPA to PCBAPA could be 1:0.10 (=CzPA: PCBAPA).

Further, tris(8-quinolinolato)aluminum(III) (abbreviation: Alq) was deposited over the third layer 1513 to be a thickness of 10 nm by an evaporation method using resistive heating. Then, the fourth layer 1514 which is an electron-transporting layer was formed by depositing bathophenanthroline (abbreviation: BPhen) over the third layer 1513 to a thickness of 20 nm.

Then, the fifth layer 1515 which is an electron-injecting layer was formed by depositing lithium fluoride (LiF) to a thickness of 1 nm over the fourth layer 1514.

Finally, a second electrode 1504 was formed by depositing aluminum to a thickness of 200 nm by an evaporation method using resistance heating, and the light-emitting elements 1 to 5 were formed.

The light-emitting elements 1 to 5 obtained through the process described above were put into a glove box with a nitrogen atmosphere so that the light-emitting elements were sealed without being exposed to atmospheric air. After that, the operating characteristics of these light-emitting elements were measured. Note that the measurement was performed at room temperature (an atmosphere kept at 25° C.).

Figure 19:
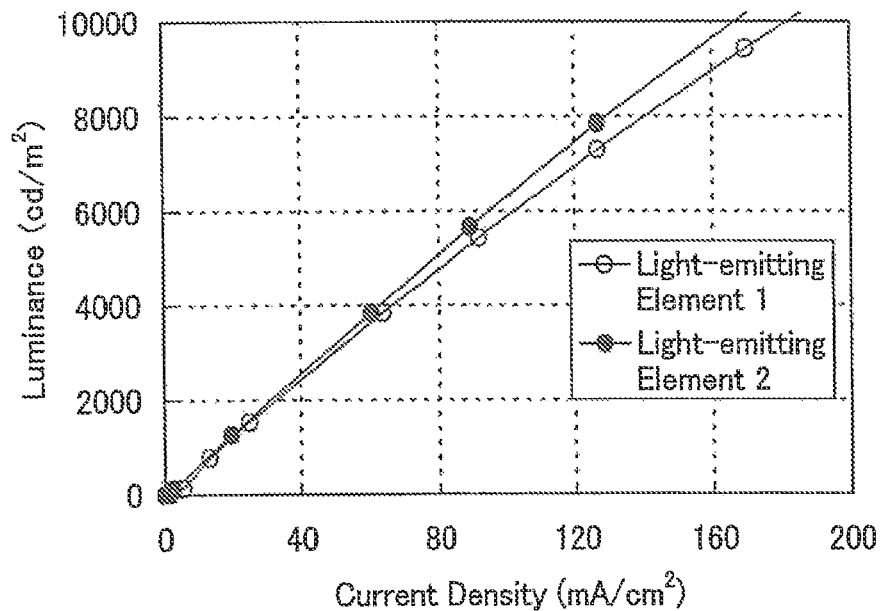
FIG. 19 is a graph showing the current density vs. luminance characteristics of a light-emitting element 1 and a light-emitting element 2.
Figure 20:
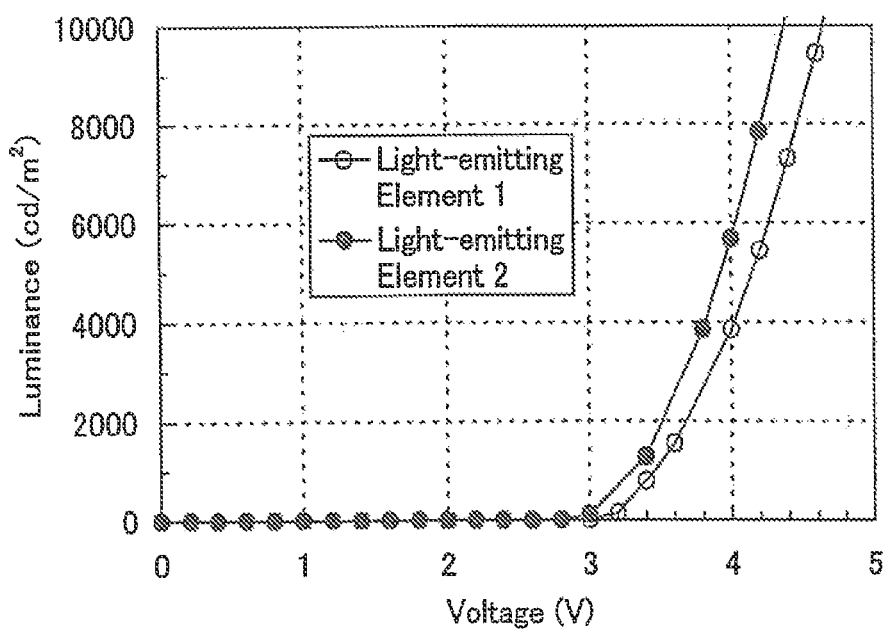
FIG. 20 is a graph showing the voltage vs. luminance characteristics of the light-emitting element 1 and the light-emitting element 2.
Figure 21:
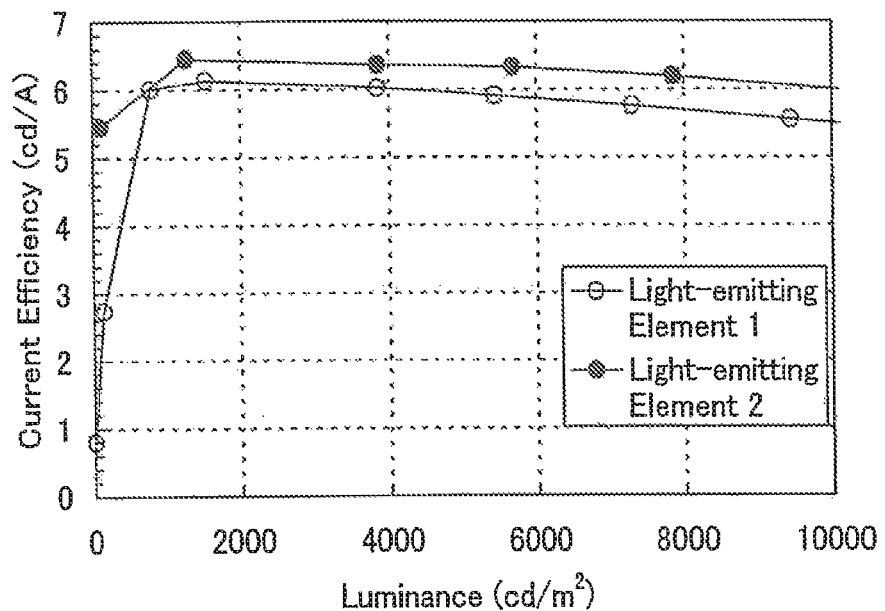
FIG. 21 is a graph showing the luminance vs. current efficiency characteristics of the light-emitting element 1 and the light-emitting element 2.
Figure 22:
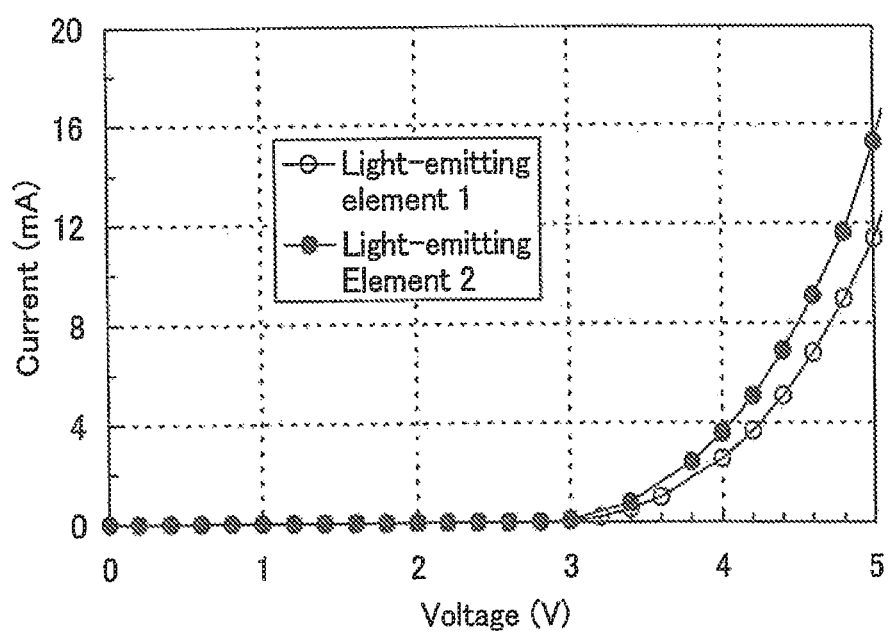
FIG. 22 is a graph showing the voltage vs. current characteristics of the light-emitting element 1 and the light-emitting element 2.

FIG. 19 shows the current density vs. luminance characteristics of the light-emitting elements 1 and 2. FIG. 20 shows the voltage vs. luminance characteristics of the light-emitting elements 1 and 2. FIG. 21 shows the luminance vs. current efficiency characteristics of the light-emitting elements 1 and 2. FIG. 22 shows the voltage vs. current characteristics of the light-emitting elements 1 and 2.

When the drive voltage of the light-emitting element 2 was 3.4 V, the luminance and the current value were 1277 cd/m$^2$ and 0.79 mA, respectively. It was found that the light-emitting element 2 using PCBA1BP (abbreviation) for the second layer 1512 showed higher luminance, even when the light-emitting element 2 was compared to the light-emitting element 1 using NPB for the second layer 1512. Further, it was found that the current efficiency was high with respect to the current density or the luminance.

Figure 23:
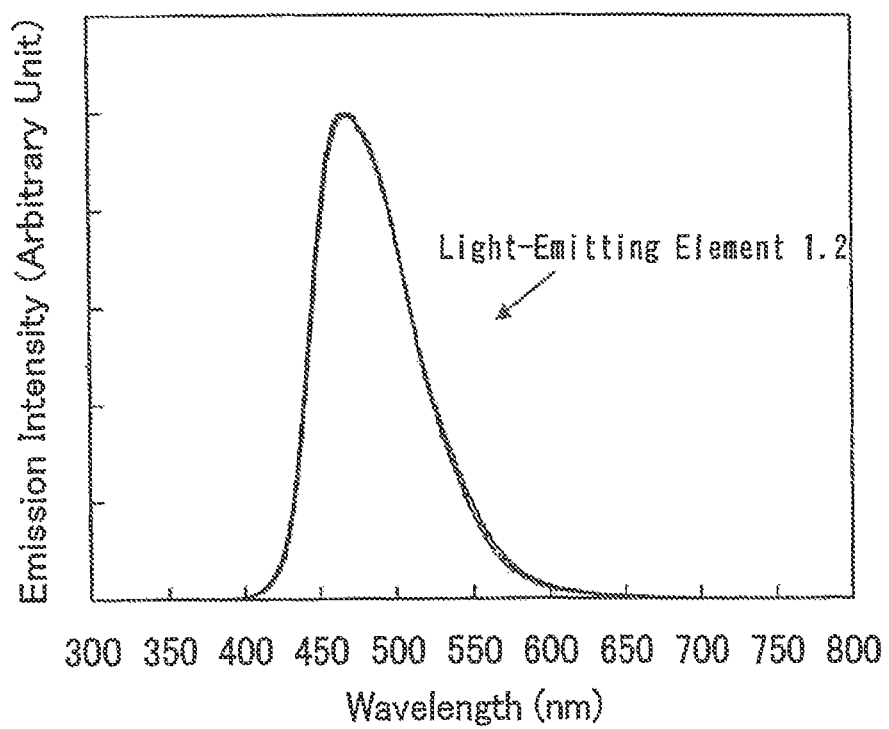
FIG. 23 is a graph showing emission spectra of the light-emitting element 1 and the light-emitting element 2.

In addition, in the light-emitting element 2, an emission wavelength derived from PCBAPA which is a blue light-emitting material was observed but an emission wavelength derived from the hole-transporting material was not observed from emission spectrum shown in FIG. 23. Thus, it was found that favorable carrier balance was realized in the structure of the light-emitting element 2 using PCBA1BP (abbreviation) of the present invention.

Figure 24:
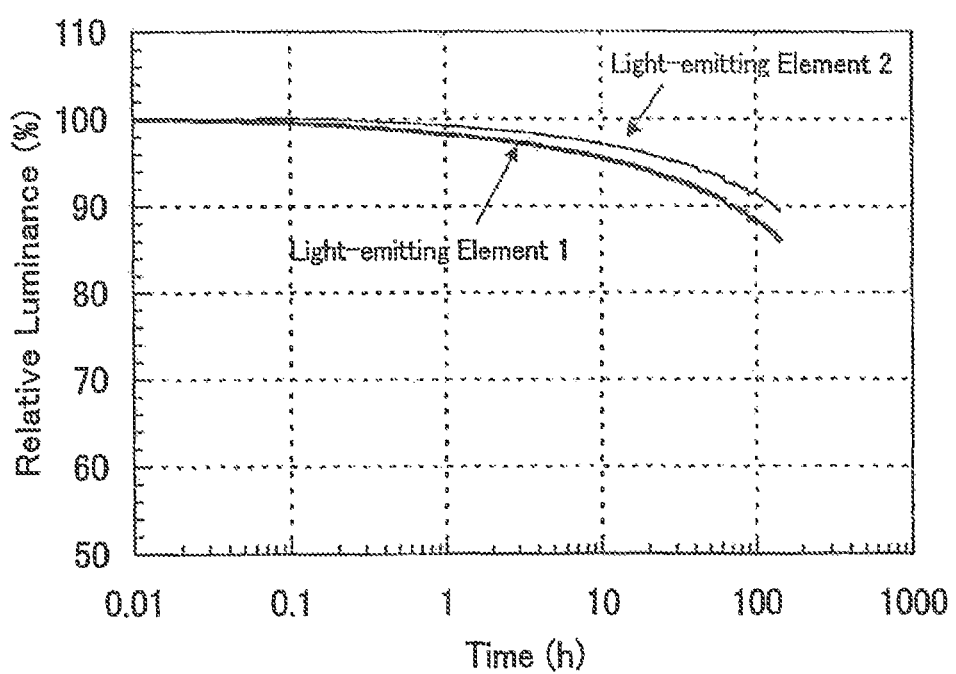
FIG. 24 is a graph showing the result of a continuous lighting test of the light-emitting element 1 and the light-emitting element 2 by constant current driving.

FIG. 24 shows the results of a continuous lighting test in which the light-emitting element 2 was continuously lit by constant current driving with the initial luminance set at 1000 cd/m$^2$ (the vertical axis indicates the relative luminance on the assumption that 1000 cd/m$^2$ is 100%). From the results in FIG. 24, the light-emitting element 2 exhibits 92% of the initial luminance even after 160 hours, and was found to have a longer lifetime, as compared to the light-emitting element 1. Thus, a long lifetime light-emitting element can be obtained by applying PCBA1BP (abbreviation) of the present invention.

Figure 25:
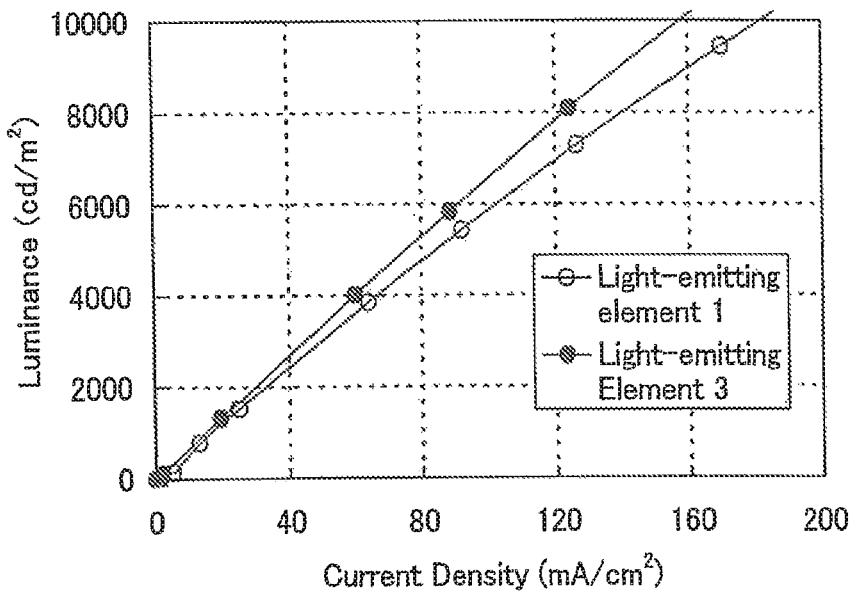
FIG. 25 is a graph showing the current density vs. luminance characteristics of the light-emitting element 1 and a light-emitting element 3.
Figure 26:
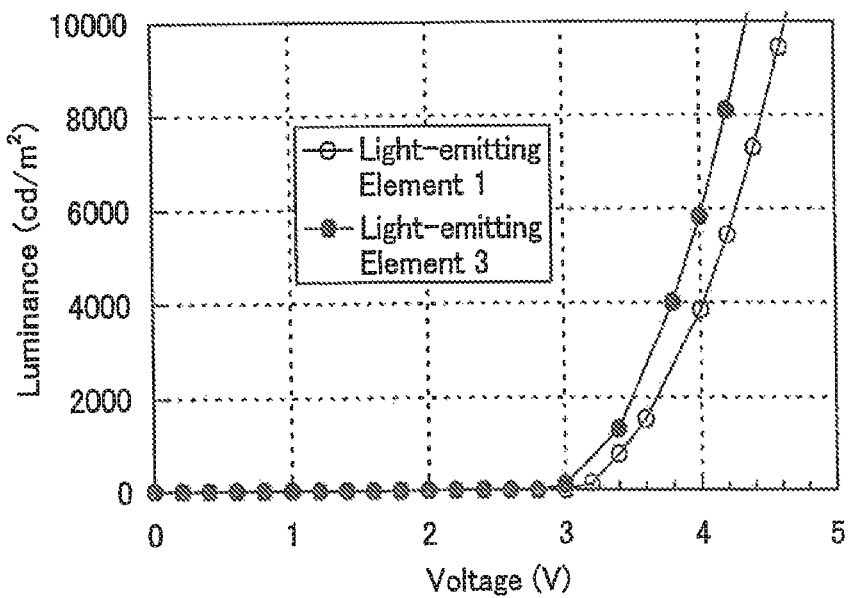
FIG. 26 is a graph showing the voltage vs. luminance characteristics of the light-emitting element 1 and the light-emitting element 3.
Figure 27:
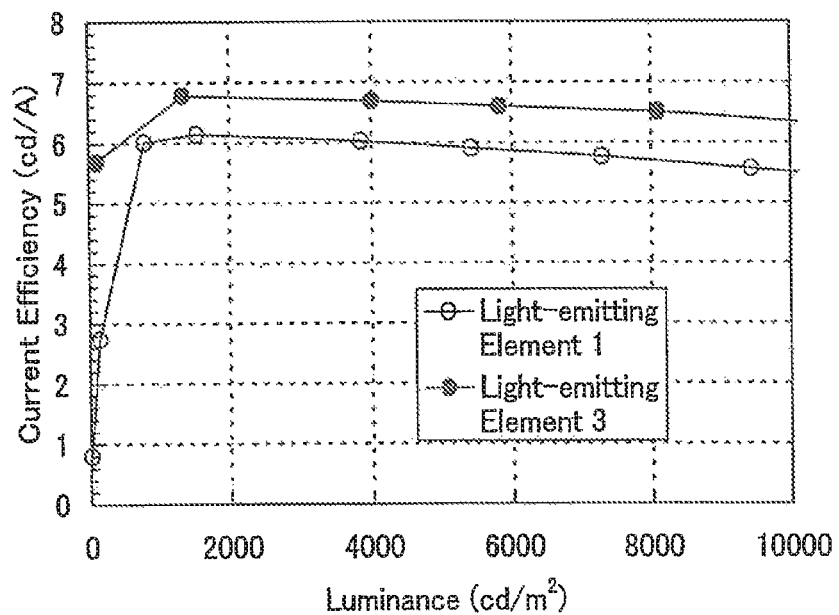
FIG. 27 is a graph showing the luminance vs. current efficiency characteristics of the light-emitting element 1 and the light-emitting element 3.
Figure 28:
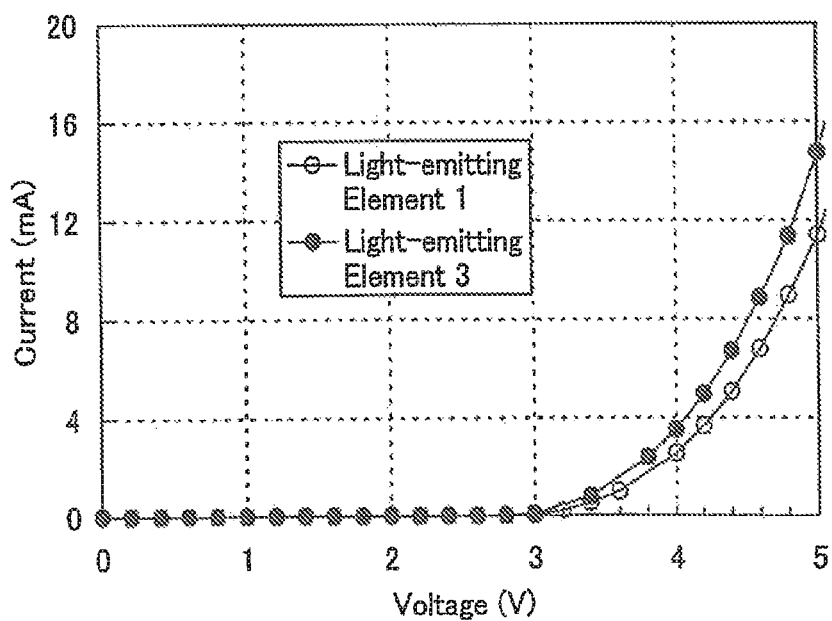
FIG. 28 is a graph showing the voltage vs. current characteristics of the light-emitting element 1 and the light-emitting element 3.

FIG. 25 shows the current density vs. luminance characteristics of the light-emitting elements 1 and 3. FIG. 26 shows the voltage vs. luminance characteristics of the light-emitting elements 1 and 3. FIG. 27 shows the luminance vs. current efficiency characteristics of the light-emitting elements 1 and 3. FIG. 28 shows the voltage vs. current characteristics of the light-emitting elements 1 and 3.

When the drive voltage of the light-emitting element 3 was 3.4 V, the luminance and the current value were 1328 cd/m$^2$ and 0.78 mA, respectively. It was found that the light-emitting element 3 using PCBBi1BP (abbreviation) for the second layer 1512 showed higher luminance, even when the light-emitting element 3 was compared to the light-emitting element 1 using NPB for the second layer 1512. Further, it was found that the current efficiency was high with respect to the current density or the luminance.

Figure 29:
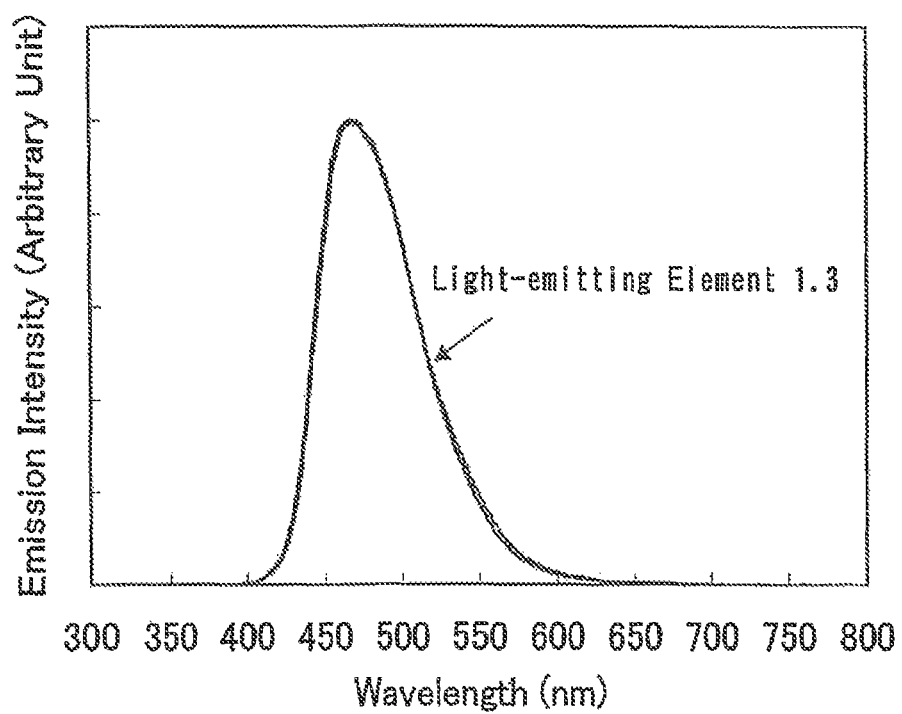
FIG. 29 is a graph showing emission spectra of the light-emitting element 1 and the light-emitting element 3.

In addition, in the light-emitting element 3, an emission wavelength derived from PCBAPA which is a blue light-emitting material was observed but an emission wavelength derived from the hole-transporting material was not observed from emission spectrum shown in FIG. 29. Thus, it was found that favorable carrier balance was realized in the structure of the light-emitting element 3 using PCBBi1BP (abbreviation) of the present invention.

Figure 30:
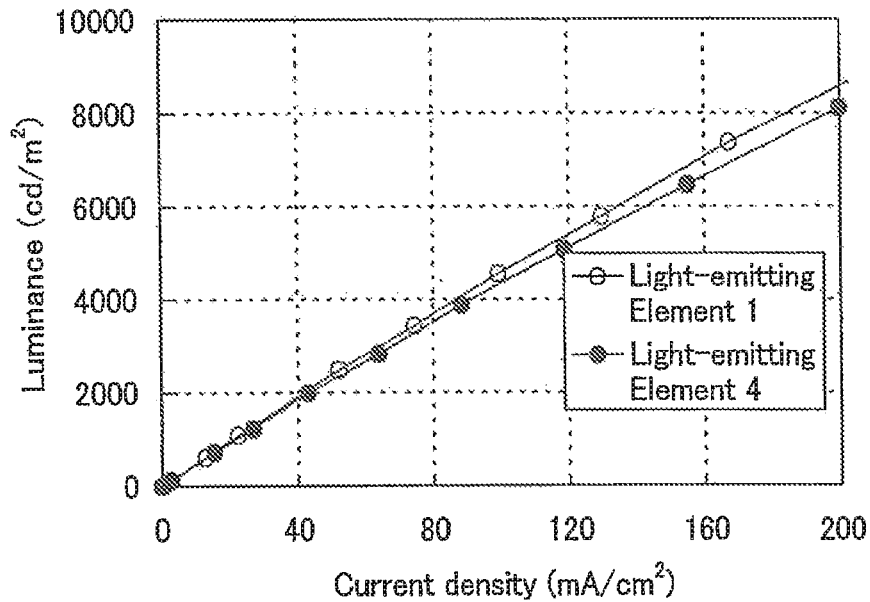
FIG. 30 is a graph showing the current density vs. luminance characteristics of the light-emitting element 1 and a light-emitting element 4.
Figure 31:
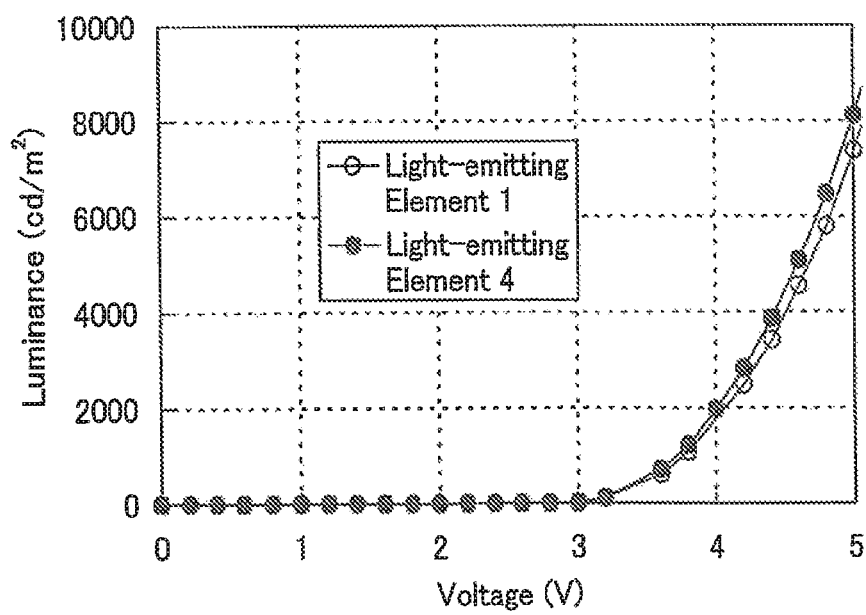
FIG. 31 is a graph showing the voltage vs. luminance characteristics of the light-emitting element 1 and the light-emitting element 4.
Figure 32:
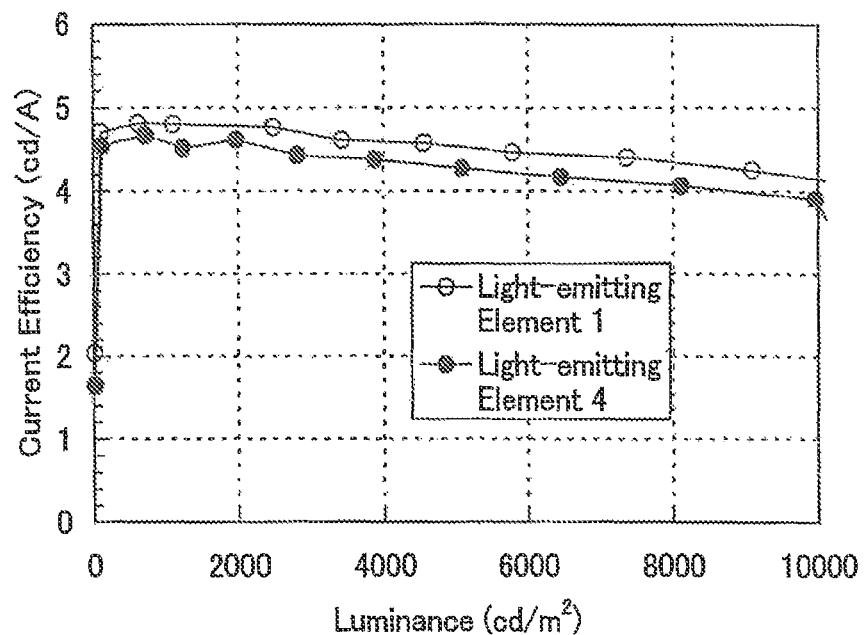
FIG. 32 is a graph showing the luminance vs. current efficiency characteristics of the light-emitting element 1 and the light-emitting element 4.
Figure 33:
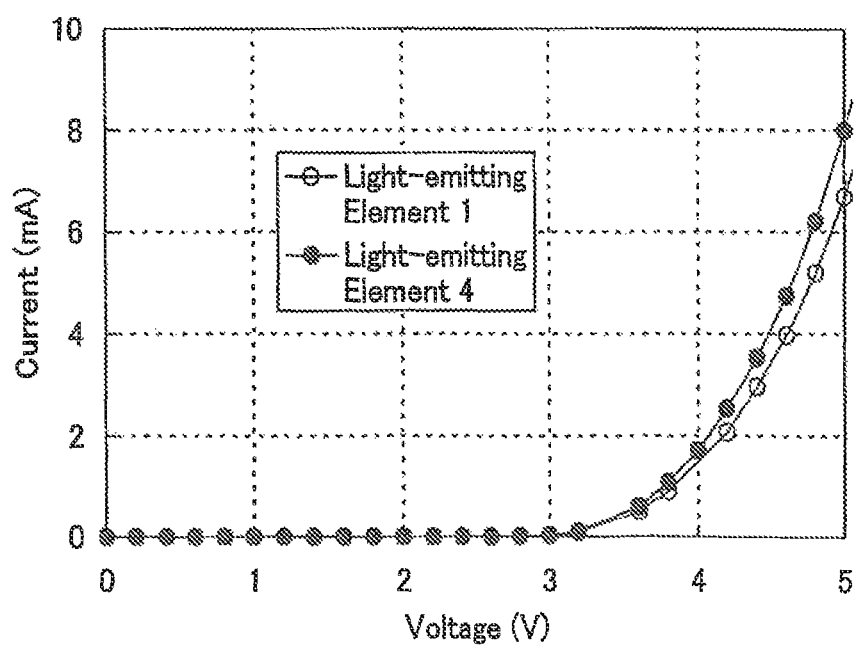
FIG. 33 is a graph showing the voltage vs. current characteristics of the light-emitting element 1 and the light-emitting element 4.

FIG. 30 shows the current density vs. luminance characteristics of the light-emitting elements 1 and 4. FIG. 31 shows the voltage vs. luminance characteristics of the light-emitting elements 1 and 4. FIG. 32 shows the luminance vs. current efficiency characteristics of the light-emitting elements 1 and 4. FIG. 33 shows the voltage vs. current characteristics of the light-emitting elements 1 and 4.

When the drive voltage of the light-emitting element 4 was 3.8 V, the luminance and the current value were 1328 cd/m$^2$ and 1.08 mA, respectively. It was found that the light-emitting element 4 using PCBAF (abbreviation) for the second layer 1512 showed higher luminance, even when the light-emitting element 4 was compared to the light-emitting element 1 using NPB for the second layer 1512.

Figure 34:
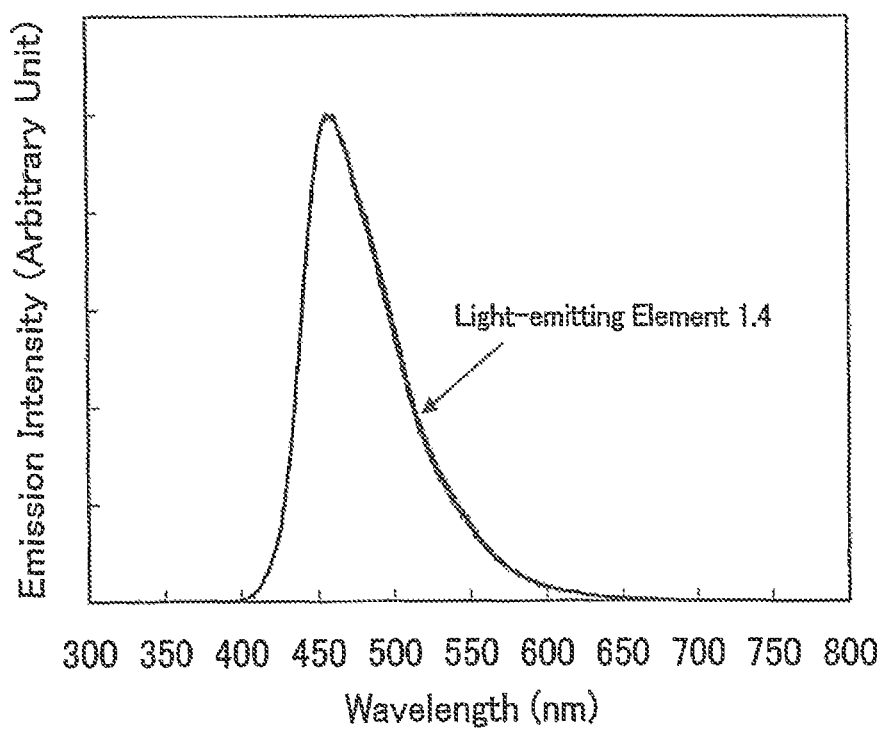
FIG. 34 is a graph showing emission spectra of the light-emitting element 1 and the light-emitting element 4.

In addition, in the light-emitting element 4, an emission wavelength derived from PCBAPA which is a blue light-emitting material was observed but an emission wavelength derived from the hole-transporting material was not observed from emission spectrum shown in FIG. 34. Thus, it was found that favorable carrier balance was realized in the structure of the light-emitting element 4 using PCBAF (abbreviation) of the present invention.

Figure 35:
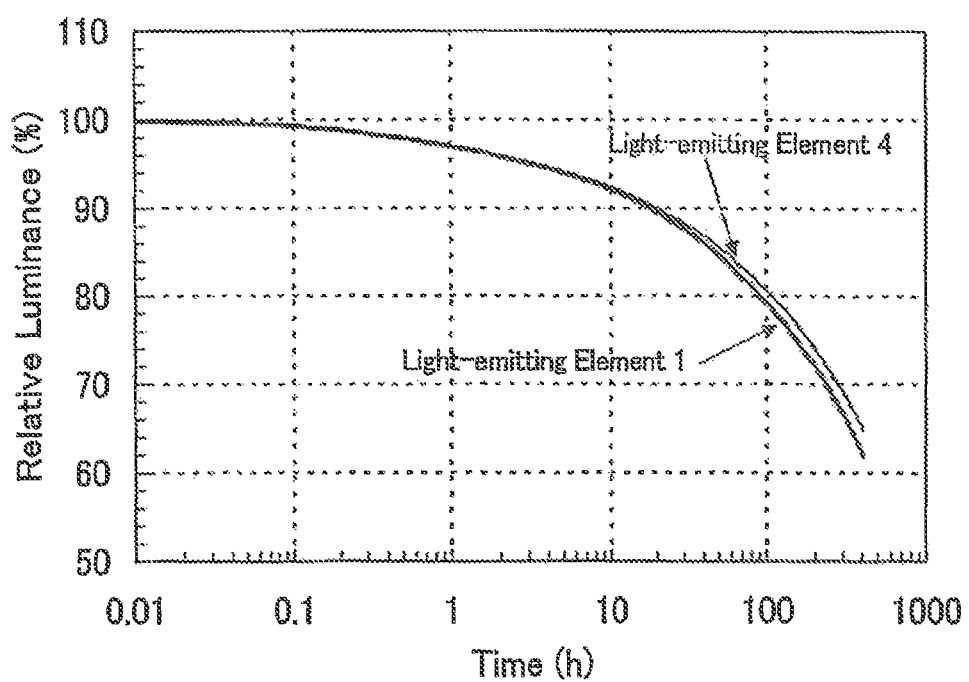
FIG. 35 is a graph showing the result of a continuous lighting test of the light-emitting element 1 and the light-emitting element 4 by constant current driving.

FIG. 35 shows the results of a continuous lighting test in which the light-emitting element 4 was continuously lit by constant current driving with the initial luminance set at 1000 cd/m$^2$ (the vertical axis indicates the relative luminance on the assumption that 1000 cd/m$^2$ is 100%). From the results in FIG. 35, the light-emitting element 4 exhibits 92% of the initial luminance even after 160 hours and was found to have a longer lifetime, as compared to the light-emitting element 1. Thus, a long lifetime light-emitting element can be obtained by applying PCBAF (abbreviation) of the present invention.

Figure 36:
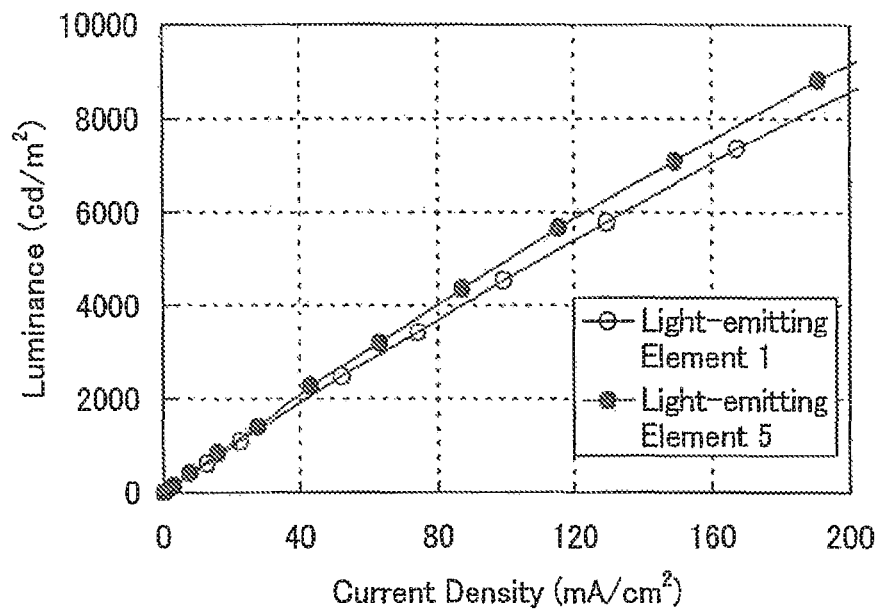
FIG. 36 is a graph showing the current density vs. luminance characteristics of the light-emitting element 1 and a light-emitting element 5.
Figure 37:
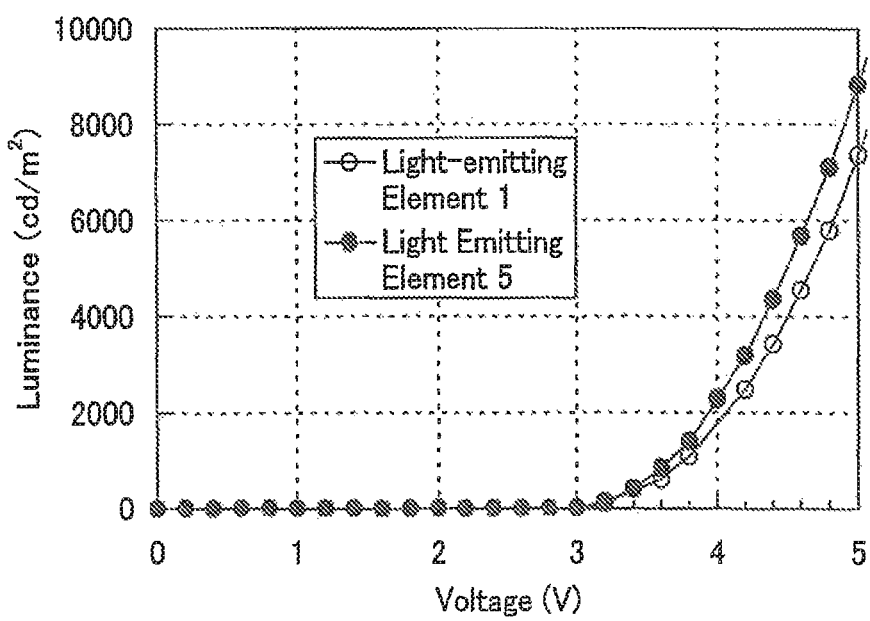
FIG. 37 is a graph showing the voltage vs. luminance characteristics of the light-emitting element 1 and the light-emitting element 5.
Figure 38:
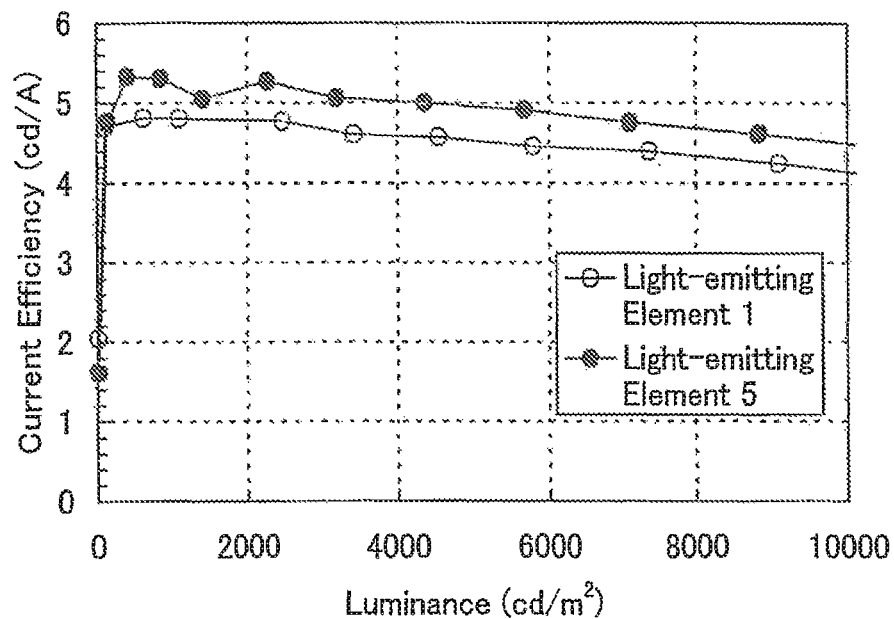
FIG. 38 is a graph showing the luminance vs. current efficiency characteristics of the light-emitting element 1 and the light-emitting element 5.
Figure 39:
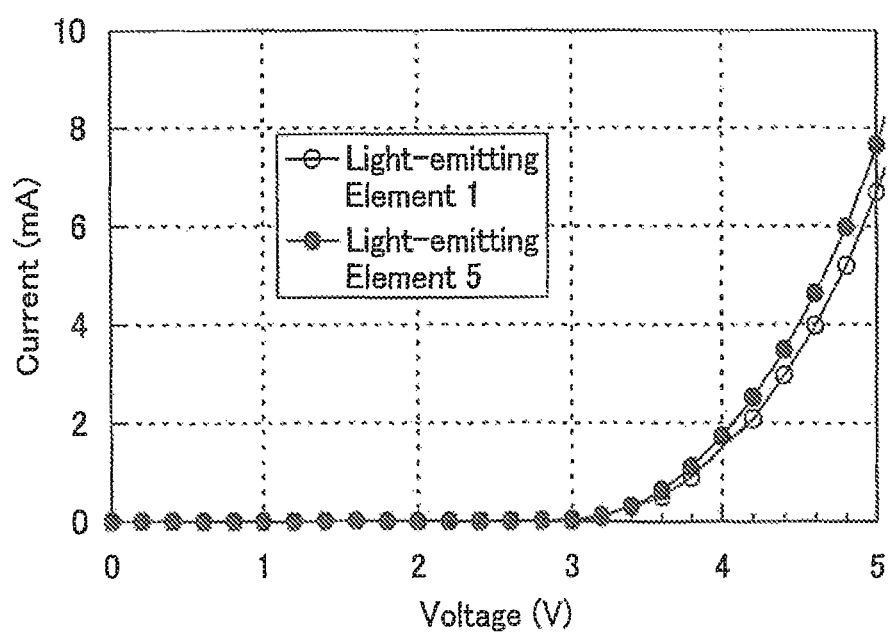
FIG. 39 is a graph showing the voltage vs. current characteristics of the light-emitting element 1 and the light-emitting element 5.

FIG. 36 shows the current density vs. luminance characteristics of the light-emitting elements 1 and 5. FIG. 37 shows the voltage vs. luminance characteristics of the light-emitting elements 1 and 5. FIG. 38 shows the luminance vs. current efficiency characteristics of the light-emitting elements 1 and 5. FIG. 39 shows the voltage vs. current characteristics of the light-emitting elements 1 and 5.

When the drive voltage of the light-emitting element 5 was 3.8 V, the luminance and the current value were 1398 cd/m$^2$ and 1.11 mA, respectively. It was found that the light-emitting element 5 using PCBASF (abbreviation) for the second layer 1512 showed higher luminance, even when the light-emitting element 5 was compared to the light-emitting element 1 using NPB for the second layer 1512. Further, it was found that the current efficiency was high with respect to the current density or the luminance.

Figure 40:
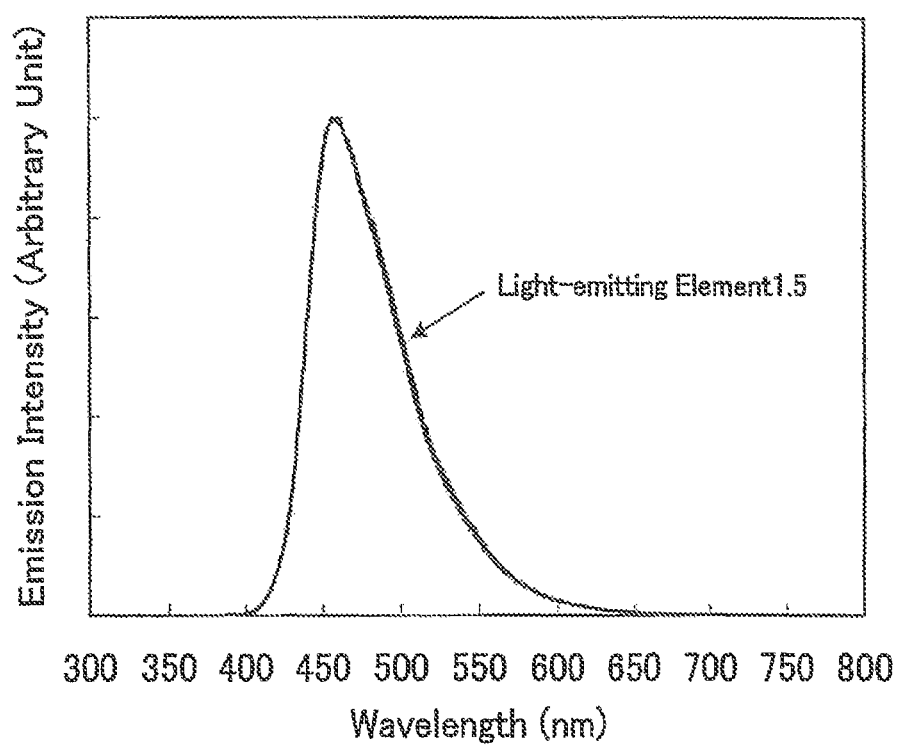
FIG. 40 is a graph showing emission spectra of the light-emitting element 1 and the light-emitting element 5.

In addition, in the light-emitting element 5, an emission wavelength derived from PCBAPA which is a blue light-emitting material was observed but an emission wavelength derived from the hole-transporting material was not observed from emission spectrum shown in FIG. 40. Thus, it was found that favorable carrier balance was realized in the structure of the light-emitting element 5 using PCBASF (abbreviation) of the present invention.

As described above, it was found that the light-emitting elements 2 to 5 which were formed using the carbazole derivatives of the present invention exhibited an equivalent level of efficiency to the light-emitting element 1. Thus, it was found that a light-emitting element having high efficiency can be obtained by applying the present invention.

In addition, as another structure of the light-emitting element 1 shown in Embodiment 5, PCBA1BP (abbreviation) was used instead of NPB (abbreviation), which was used at the time of forming the first layer 1511, and was co-evaporated with molybdenum(VI) oxide to form the first layer 1511. With the efficiency, the drive voltage at a luminance of about 1000 cd/m$^2$, and the reliability of such a light-emitting element 1, favorable values equivalent to those of a light-emitting element 8 were obtained. The light-emitting element 8 will be formed in Embodiment 10 by using a co-evaporation film of NPB and molybdenum (VI) oxide for a hole-injecting layer and using PCBBiNB (abbreviation) for a hole-transporting layer. When the drive voltage of the light-emitting element 1 was 3.8 V, the luminance and the current value were 949 cd/m$^2$ and 0.65 mA, respectively, and the light-emitting element 1 exhibited 64% of the initial luminance when driven for 1500 hours.

As thus described, it was found that PCBA1BP (abbreviation) was a favorable material also as a hole-injecting material. In addition, it was found that favorable characteristics can also be obtained by using the co-evaporation film with molybdenum(VI) oxide for the hole-injecting layer.

In addition, as another structure of the light-emitting element 2 shown in Embodiment 5, PCBA1BP (abbreviation) was used instead of NPB (abbreviation), which was used at the time of forming the first layer 1511, and was co-evaporated with molybdenum(VI) oxide to form the first layer 1511. With the efficiency, the drive voltage at a luminance of about 1000 cd/m$^2$, and the reliability of such a light-emitting element 2, favorable values equivalent to those of a light-emitting element 8 were obtained. The light-emitting element 8 will be formed in Embodiment 10 by using a co-evaporation film of NPB and molybdenum (VI) oxide for a hole-injecting layer and using PCBBiNB (abbreviation) for a hole-transporting layer. When the drive voltage of the light-emitting element 2 was 3.6 V, the luminance and the current value were 843 cd/m$^2$ and 0.53 mA, respectively, and the light-emitting element 2 exhibited 65% of the initial luminance when driven for 1500 hours.

As thus described, it was found that PCBA1BP (abbreviation) was a favorable material which can be used for both the first layer 1511 which is a hole-injecting layer and the second layer 1512 which is a hole-transporting layer at the same time. Accordingly, an element could be manufactured easily and material use efficiency could also be improved.

Embodiment 6

In Embodiment 6, a synthetic method of a carbazole derivative of the present invention, (biphenyl-4-yl)(phenyl) [4'-(9-phenyl-9H-carbazol-3-yl)biphenyl-4-yl]amine (abbreviation: PCTA1BP) represented by a structural formula (15), will be specifically described.

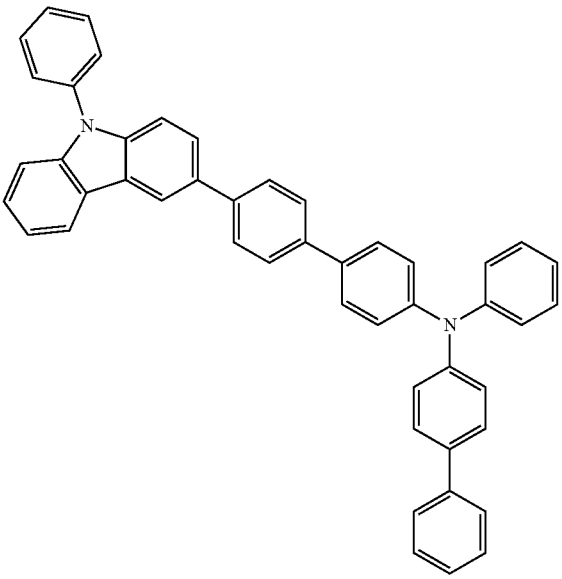

(15)

Step 1: Synthesis of 4-[N-(biphenyl-4-yl)-N-phenyl] aminophenylboronic acid

A synthetic scheme of 4-[N-(biphenyl-4-yl)-N-phenyl] aminophenylboronic acid in Step 1 is shown in the following (H-1).

(H-1)

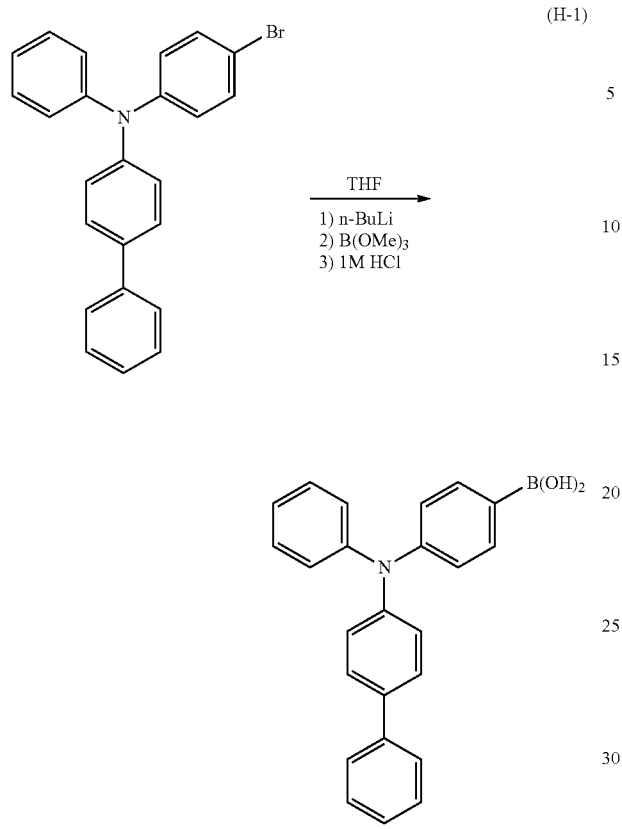

In a 300-mL three-neck flask, 7.0 g (18 mmol) of 4-bromo-4'-phenyltriphenylamine was put, and the atmosphere in the flask was substituted by nitrogen. Then, 80 mL of tetrahydrofuran (abbreviation: THF) was added thereto, and the mixture was stirred at −78° C. for 10 minutes. After that, 13 mL (21 mmol) of an n-butyllithium hexane solution (1.63 mol/L) was dropped onto this solution from a syringe, and the solution was stirred at −78° C. for 1 hour. After the stirring, 3.5 mL (31 mmol) of trimethyl borate was added to the reaction mixture, and the mixture was stirred at −78° C. for 1 hour and at room temperature for 24 hours. After the reaction, 100 mL of 1M dilute hydrochloric acid was added to the reaction solution, and the mixture was stirred at room temperature for 1 hour. After the stirring, this solution was extracted with ethyl acetate, and an organic layer was washed with a saturated saline solution. After the washing, magnesium sulfate was added to the organic layer, and the organic layer was dried. After the drying, magnesium sulfate was removed by suction filtration to obtain filtrate. The obtained filtrate was concentrated and recrystallized with a mixture solvent of chloroform and hexane to obtain 3.6 g of an object at a yield of 56%.

Step 2: Synthesis of (biphenyl-4-yl)(phenyl)[4'-(9-phenyl-9H-carbazol-3-yl)biphenyl-4-yl]amine (abbreviation: PCTA1BP)

A synthetic scheme of (biphenyl-4-yl)(phenyl)[4'-(9-phenyl-9H-carbazol-3-yl)biphenyl-4-yl]amine in Step 2 is shown in the following (H-2).

(H-2)

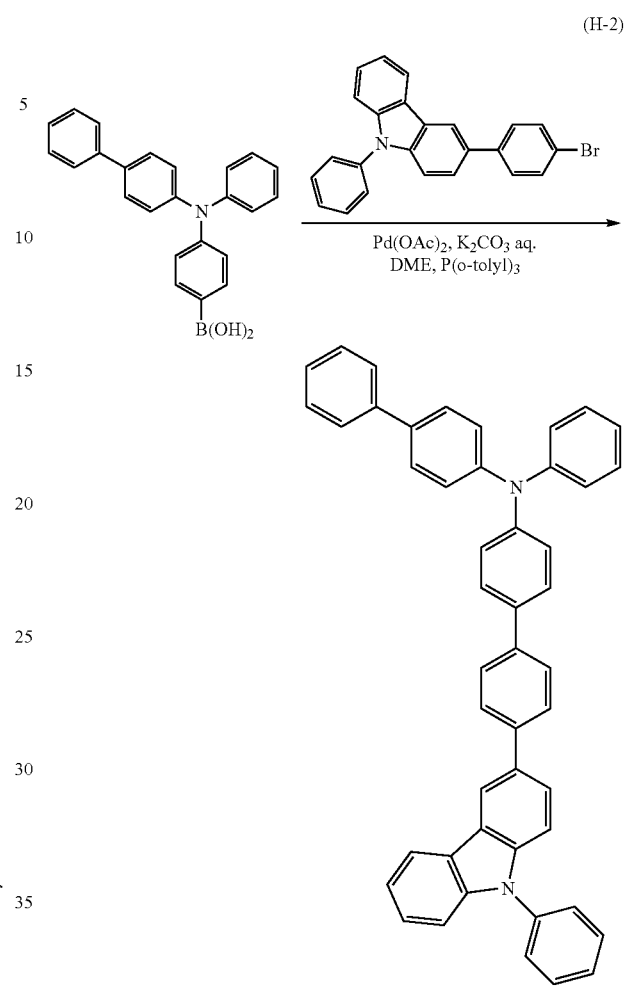

In a 100-mL three-neck flask, 2.2 g (5.5 mmol) of 4-[N-(biphenyl-4-yl)-N-phenyl]aminophenylboronic acid, 2.0 g (5.5 mmol) of 3-(4-bromophenyl)-9-phenyl-9H-carbazole, 10 mg (0.045 mmol) of palladium(II) acetate, and 0.69 g (0.23 mmol) of tri(o-tolyl)phosphine were put, and 10 mL of a potassium carbonate solution (2.0 mol/L) and 20 mL of ethylene glycol dimethyl ether (abbreviation: DME) were added thereto. This mixture was deaerated while being stirred under low pressure, and the atmosphere in the flask was substituted by nitrogen. This mixture was stirred at 90° C. for 5 hours. After the stirring, toluene was added to the reaction mixture, and the mixture was heated at 90° C.

After the heating, this suspension was separated into an organic layer and an aqueous layer. After the separation, the organic layer was washed with a saturated sodium hydrogen carbonate solution and a saturated saline solution. Magnesium sulfate was added to the organic layer, and the organic layer was dried. Suction filtration was performed on this mixture through Celite, alumina, and then Florisil to obtain filtrate. The obtained filtrate was concentrated to obtain a solid. The obtained filtrate was dissolved and purified by silica gel column chromatography. The silica gel column chromatography was performed by, first, using a mixture solvent of toluene: hexane=1:9 as a developing solvent, and then using a mixture solvent of toluene: hexane=2:3 as another developing solvent. A solid which was obtained by concentrating the obtained fraction was dissolved in chloroform and purified by high performance liquid chromatography (HPLC) (developing solvent, chloroform). A solid which was obtained by concentrating the obtained fraction was recrystallized with a mixture solvent of chloroform and hexane to obtain 1.7 g of an objective white solid at a yield of 48%.

Sublimation purification of 1.0 g of the obtained white solid was performed by a train sublimation method. The sublimation purification was performed under a reduced pressure of 7.0 Pa, with a flow rate of argon at 4 mL/min, at 300° C. for 15 hours to obtain 0.62 g of the white solid at a yield of 62%.

Figure 45A:
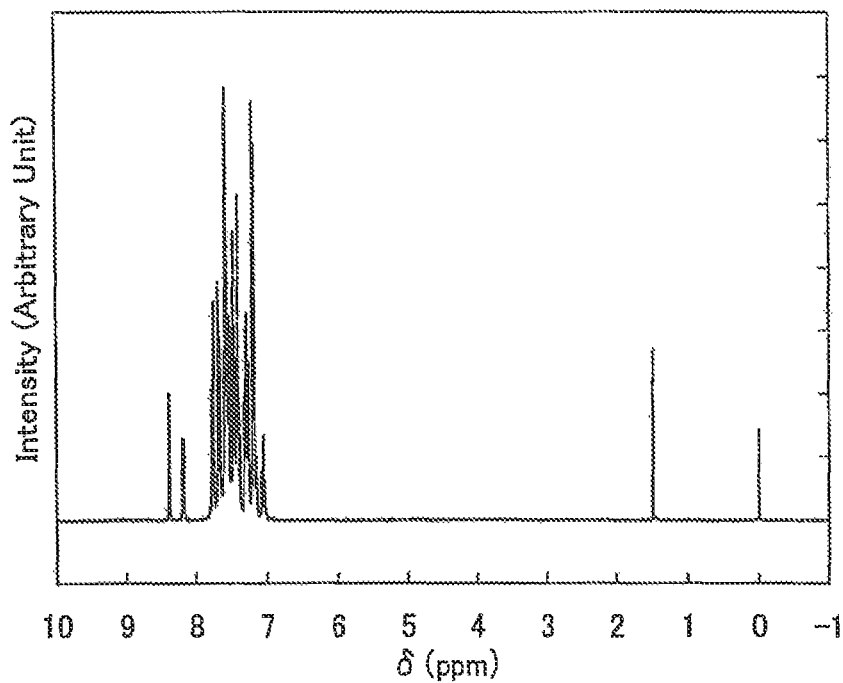
FIGS. 45A and 45B are graphs showing $^1$H NMR charts of PCTA1BP (abbreviation)
Figure 45B:
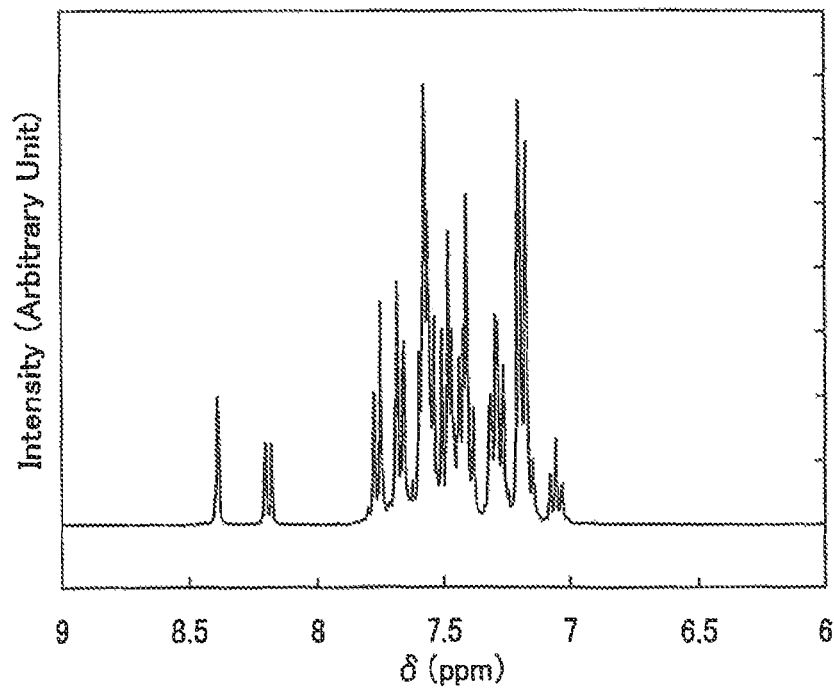

A compound which was obtained through the above Step 2 was measured by a nuclear magnetic resonance method ($^1$H NMR). The measurement result is described below, and the $^1$H NMR chart is shown in FIGS. 45A and 45B. It was found from the measurement result that the carbazole derivative of the present invention, PCTA1BP (abbreviation) represented by the above structural formula (15), was obtained. $^1$H NMR (CDCl$_3$, 300 MHz): δ (ppm)=7.02-7.79 (m, 32H), 8.19 (d, J=7.3 Hz, 1H), 8.39 (s, I H).

In addition, an absorption spectrum of PCTA1BP (abbreviation) (measurement range: 200 nm to 800 nm) was measured. In the case of the toluene solution, an absorption peak on a long wavelength side was observed at around 349 nm, and in the case of the thin film, an absorption peak on a long wavelength side was observed at around 357 nm.

In addition, an emission spectrum of PCTA1BP (abbreviation) (measurement range: 370 nm to 550 nm) was measured. In the case of the toluene solution, a maximum emission wavelength was 405 nm (excitation wavelength: 320 nm), and in the case of the thin film, a maximum emission wavelength was 420 nm (excitation wavelength: 284 nm). Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCTA1BP (abbreviation) was −5.49 eV. The Tauc plot of the absorption spectrum of the thin film revealed that the absorption edge was 3.10 eV. Thus, the energy gap in the solid state was estimated to be 3.10 eV, which means that the LUMO level of PCTA1BP (abbreviation) is −2.39 eV.

An oxidation-reduction reaction characteristic of PCTA1BP (abbreviation) was examined by a cyclic voltammetry (CV) measurement. Since the measurement method is similar to that of Embodiment 1, the description is omitted. According to the calculation similar to that of Embodiment 1, the HOMO level of PCTA1BP (abbreviation) was found to be =−5.48 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCTA1BP (abbreviation) was examined with a differential scanning calorimetry (Pyris 1 DSC, manufactured by Perkin Elmer Co., Ltd.). According to the measurement results, it was found that the glass transition temperature was 118° C. In this manner, PCTA1BP (abbreviation) has a high glass transition temperature and favorable heat resistance. In addition, the crystallization peak does not exist; thus, it was found that PCTA1BP (abbreviation) is a substance which is hard to be crystallized.

Note that with the efficiency, the drive voltage at a luminance of about 1000 cd/m$^2$, and the reliability of a light-emitting element formed using PCTA1BP (abbreviation) which was synthesized in Embodiment 6 in a manner similar to that of Embodiment 5 for a hole-transporting layer, favorable values equivalent to those of a light-emitting element 8 which will be formed using PCBBiNB in Embodiment 10 were obtained. When the drive voltage of the light-emitting element was 3.6 V, the luminance and the current value were 1044 cd/m$^2$ and 0.67 mA, respectively, and the light-emitting element exhibited 52% of the initial luminance when driven for 1100 hours.

Embodiment 7

In Embodiment 7, a synthetic method of a carbazole derivative of the present invention, bis(biphenyl-4-yl)[4'-(9-phenyl-9H-carbazol-3-yl)biphenyl-4-yl]amine (abbreviation: PCTBi1BP) represented by a structural formula (190), will be specifically described.

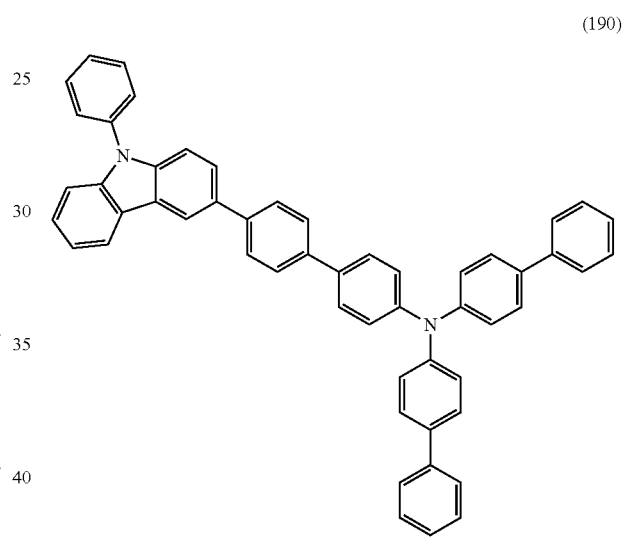

(190)

Step 1: Synthesis of 4-[bis(biphenyl-4-yl)amino]phenylboronic acid

A synthetic scheme of 4-[bis(biphenyl-4-yl)amino]phenylboronic acid in Step 1 is shown in the following (1-1).

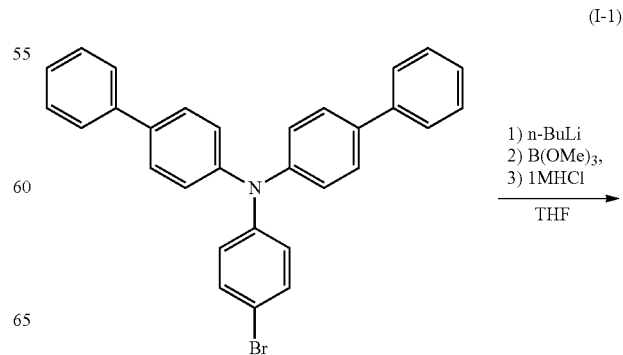

(I-1)

1) n-BuLi
2) B(OMe)$_3$,
3) 1MHCl

THF

-continued

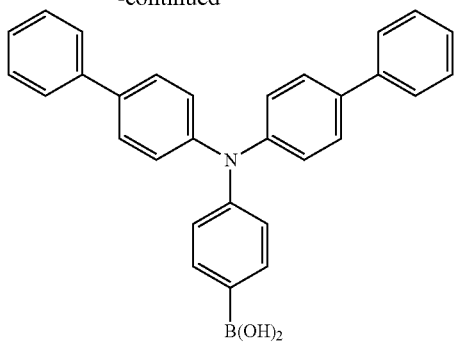

In a 300-mL three-neck flask, 6.0 g (13 mmol) of 4-bromo-4',4''-diphenyltriphenylamine was put, and the atmosphere in the flask was substituted by nitrogen. Then, 80 mL of tetrahydrofuran (abbreviation: THF) was added thereto, and the mixture was stirred at −78° C. for 10 minutes. After that, 10 mL of an n-butyllithium hexane solution (1.63 mol/L) was dropped onto this solution from a syringe, and the solution was stirred at −78° C. for 1 hour. After the stirring, 2.8 mL (25 mmol) of trimethyl borate was added to the reaction mixture, and the mixture was stirred at −78° C. for 1 hour and further at room temperature for 24 hours. After the stirring, about 50 mL of dilute hydrochloric acid was added to the reaction mixture, and the mixture was stirred at room temperature for 30 minutes. After the stirring, ethyl acetate was added to this mixture to perform extraction. After the extraction, an organic layer was washed with a saturated saline solution. Then, magnesium sulfate was added to the organic layer, and the organic layer was dried. After the drying, suction filtration was performed on this mixture to obtain filtrate. The obtained filtrate was concentrated and recrystallized with a mixture solvent of chloroform and hexane to obtain 4.8 g of an objective white powder-like solid at a yield of 86%.

Step 2: Synthesis of bis(biphenyl-4-yl)[4'-(9-phenyl-9H-carbazol-3-yl)biphenyl-4-yl]amine (abbreviation: PCTBi1BP)

A synthetic scheme of bis(biphenyl-4-yl)[4'-(9-phenyl-9H-carbazol-3-yl)biphenyl-4-yl]amine in Step 2 is shown in the following (I-2).

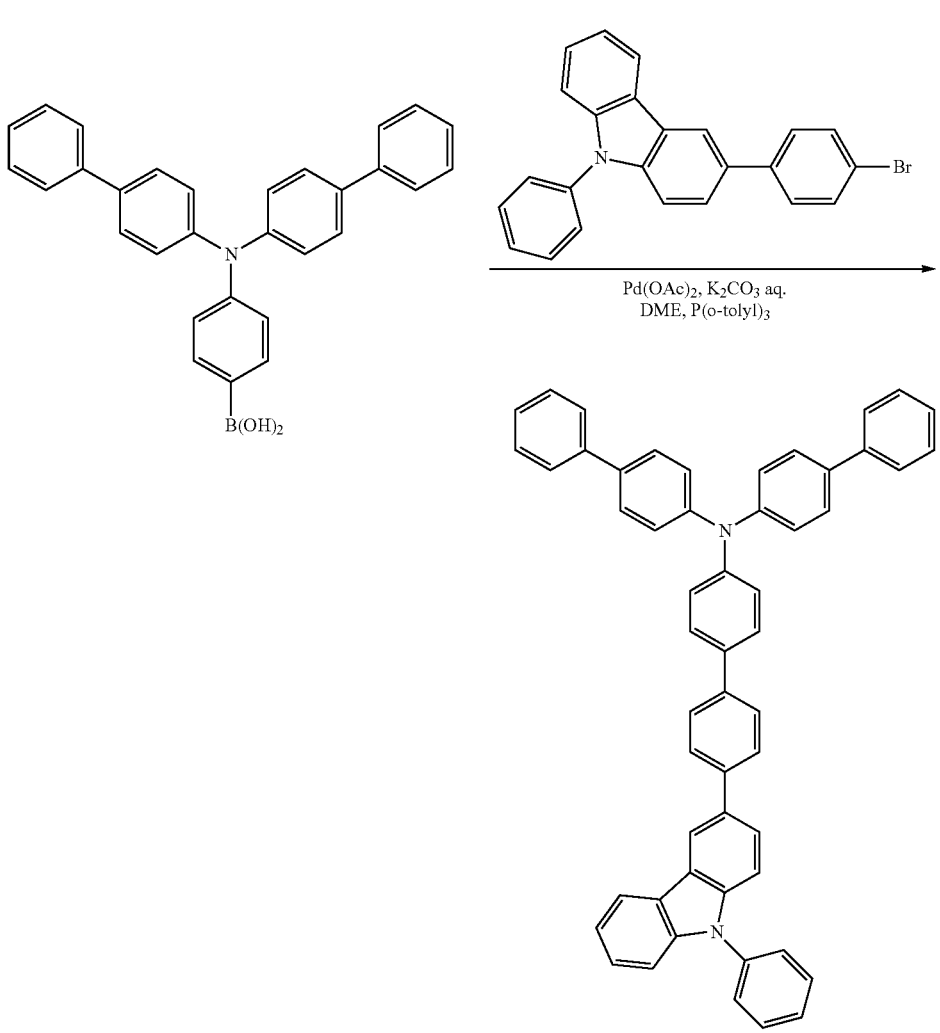

(I-2)

In a 100-mL three-neck flask, 2.0 g (4.5 mmol) of 4-[bis(biphenyl-4-yl)amino]phenylboronic acid, 1.8 g (4.5 mmol) of 3-(4-bromophenyl)-9-phenyl-9H-carbazole, 10 mg (0.045 mmol) of palladium(II) acetate, and 0.69 g (0.23 mmol) of tri(o-tolyl)phosphine were put, and 10 mL of a potassium carbonate solution (2.0 mol/L) and 20 mL of ethylene glycol dimethyl ether (abbreviation: DME) were added thereto. This mixture was deaerated while being stirred under low pressure, and the atmosphere in the flask was substituted by nitrogen. This mixture was stirred at 90° C. for 5 hours. After the stirring, toluene was added to the reaction mixture, and the mixture was heated at 90° C.

After the heating, this suspension was separated into an organic layer and an aqueous layer. After the separation, the organic layer was washed with a saturated sodium hydrogen carbonate solution and a saturated saline solution. Magnesium sulfate was added to the organic layer, and the organic layer was dried. Suction filtration was performed on this mixture through Celite, alumina, and then Florisil to obtain filtrate. The obtained filtrate was concentrated to obtain a solid. The obtained filtrate was dissolved in toluene and purified by silica gel column chromatography. The silica gel column chromatography was performed by using toluene as a developing solvent. A solid which was obtained by concentrating the obtained fraction was recrystallized with a mixture solvent of toluene and hexane to obtain 2.4 g of an objective white solid at a yield of 74%.

Sublimation purification of the obtained white solid was performed by a train sublimation method. The sublimation purification was performed under a reduced pressure of 7.0 Pa, with a flow rate of argon at 3 mL/min, at 340° C. for 20 hours to obtain 0.70 g of the white solid, the theoretical yield of which is 1.5 g, at a yield of 46%.

Figure 46A:
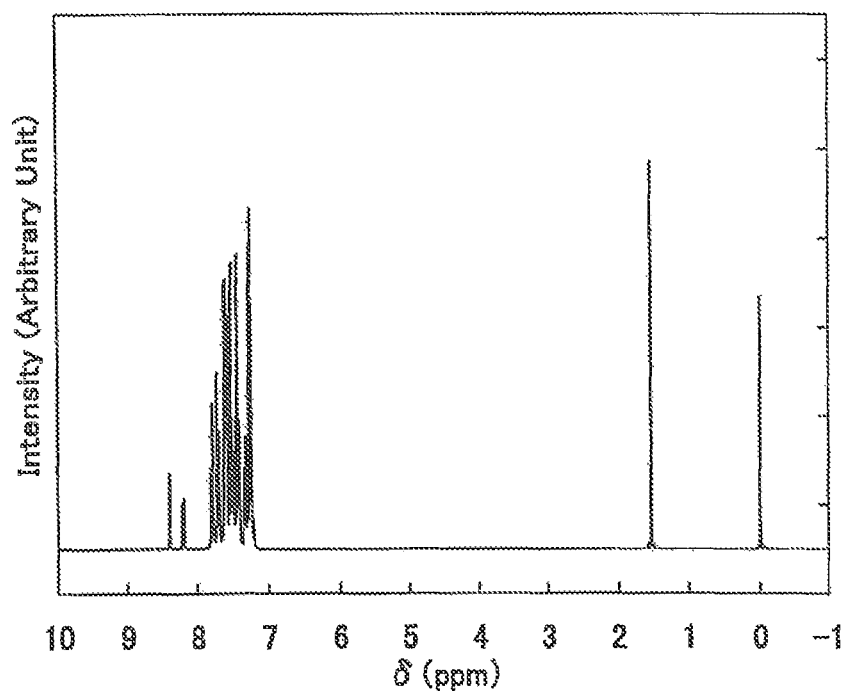
FIGS. 46A and 46B are graphs showing $^1$H NMR charts of PCTBi1BP (abbreviation)
Figure 46B:
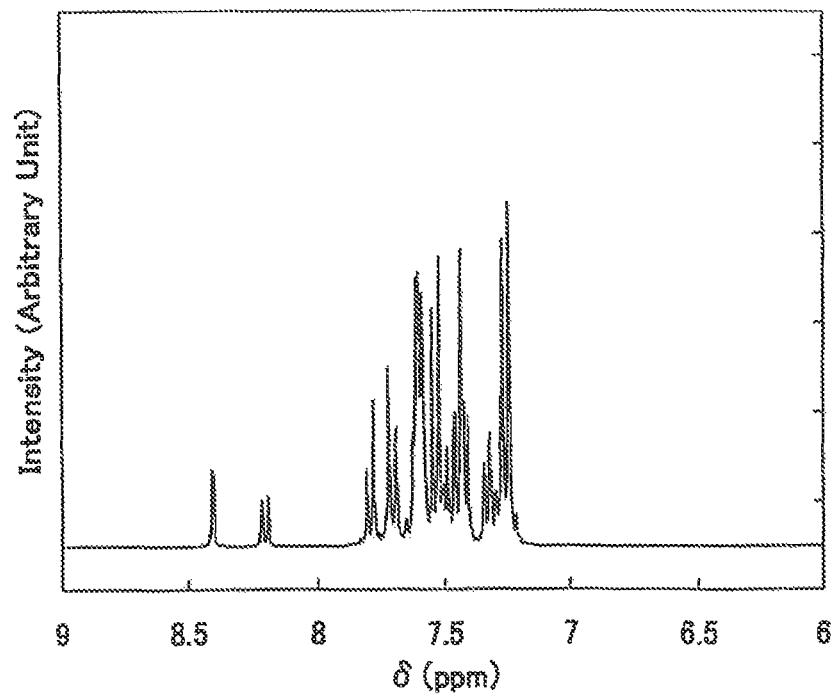

A compound which was obtained through the above Step 2 was measured by a nuclear magnetic resonance method ($^1$H NMR). The measurement result is described below, and the $^1$H NMR chart is shown in FIGS. 46A and 46B. It was found from the measurement result that the carbazole derivative of the present invention, PCTBi1BP (abbreviation) represented by the above structural formula (190), was obtained. $^1$H NMR (CDCl$_3$, 300 MHz): δ (ppm)=7.18-7.83 (m, 36H), 8.21 (d, J=7.3 Hz, 1H), 8.40 (s, 1H).

In addition, an absorption spectrum of PCTBi1BP (abbreviation) (measurement range: 200 nm to 800 nm) was measured. In the case of the toluene solution, an absorption peak on a long wavelength side was observed at around 350 nm, and in the case of the thin film, an absorption peak on a long wavelength side was observed at around 357 nm.

In addition, an emission spectrum of PCTBi1BP (abbreviation) (measurement range: 370 nm to 550 nm) was measured. In the case of the toluene solution, a maximum emission wavelength was 410 nm (excitation wavelength: 320 nm), and in the case of the thin film, a maximum emission wavelength was 447 nm (excitation wavelength: 340 nm). Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCTBi1BP (abbreviation) was −5.50 eV. The Tauc plot of the absorption spectrum of the thin film revealed that the absorption edge was 3.14 eV. Thus, the energy gap in the solid state was estimated to be 3.14 eV, which means that the LUMO level of PCTBi1BP (abbreviation) is −2.36 eV.

An oxidation-reduction reaction characteristic of PCTBi1BP (abbreviation) was examined by a cyclic voltammetry (CV) measurement. Since the measurement method is similar to that of Embodiment 1, the description is omitted.

According to the calculation similar to that of Embodiment 1, the HOMO level of PCTBi1BP (abbreviation) was found to be =−5.46 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCTBi1BP (abbreviation) was examined with a differential scanning calorimetry (Pyris 1 DSC, manufactured by Perkin Elmer Co., Ltd.). According to the measurement results, it was found that the glass transition temperature was 133° C. In this manner, PCTBi1BP (abbreviation) has a high glass transition temperature and favorable heat resistance. In addition, the crystallization peak does not exist; thus, it was found that PCTBi1BP (abbreviation) is a substance which is hard to be crystallized.

Note that with the efficiency, the drive voltage at a luminance of about 1000 cd/m$^2$, and the reliability of a light-emitting element formed using PCTBi1BP (abbreviation) which was synthesized in Embodiment 7 in a manner similar to that of Embodiment 5 for a hole-transporting layer, favorable values equivalent to those of a light-emitting element 8 which will be formed using PCBBiNB in Embodiment 10 were obtained. When the drive voltage of the light-emitting element was 3.6 V, the luminance and the current value were 873 cd/m$^2$ and 0.56 mA, respectively, and the light-emitting element exhibited 80% of the initial luminance when driven for 110 hours.

Embodiment 8

In Embodiment 8, a synthetic method of a carbazole derivative of the present invention, 4-(1-naphthyl)-4'-(9-phenyl-9H-carbazol-3-yl)-triphenylamine (abbreviation: PCBANB) represented by a structural formula (343), will be specifically described.

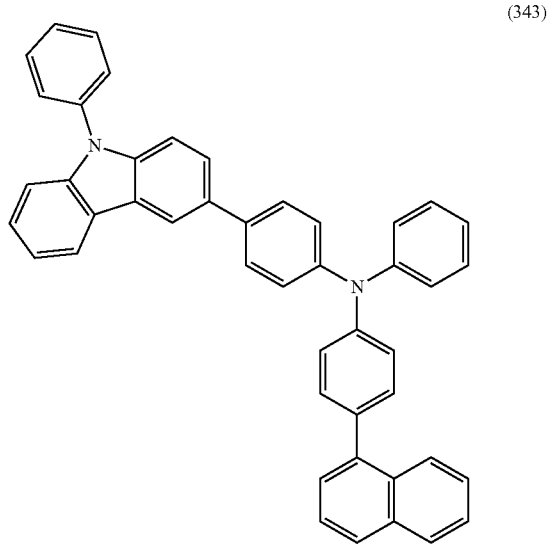 [SMILES: c1ccc(N(c2ccc(-c3ccc4c(c3)c3ccccc3n4-c3ccccc3)cc2)c2ccc(-c3cccc4ccccc34)cc2)cc1]

(343)

Step 1: Synthesis of 3-(4-bromophenyl)-9-phenyl-9H-carbazole

A synthetic scheme of 3-(4-bromophenyl)-9-phenyl-9H-carbazole in Step 1 is shown in the following (J-1).

Step 2: Synthesis of 4-(1-naphthyl)diphenylamine

A synthetic scheme of 4-(1-naphthyl)diphenylamine in Step 2 is shown in the following (J-2).

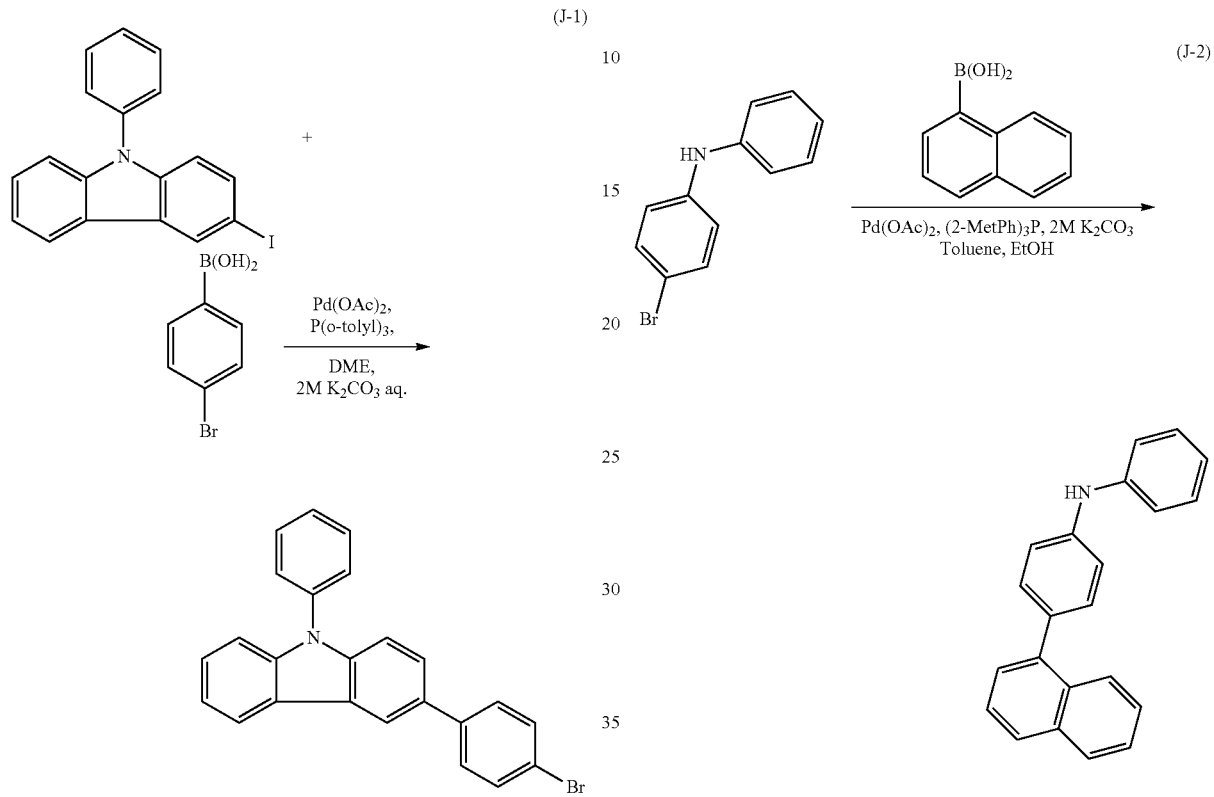

In a 200-mL three-neck flask, 3.7 g (9.9 mmol) of 3-iodo-9-phenyl-9H-carbazole, 2.0 g (9.9 mmol) of 4-bromo phenylboronic acid, and 0.61 g (2.0 mmol) of tri(o-tolyl)phosphine were put, and 50 mL of ethylene glycol dimethyl ether (abbreviation: DME) and 10 mL of a potassium carbonate solution (2 mol/L) were added to this mixture. This mixture was deaerated while being stirred under low pressure, and the atmosphere in the flask was substituted by nitrogen after the deaeration.

Then, 0.11 g (0.50 mmol) of palladium(II) acetate was added to this mixture. This mixture was stirred at 80° C. for 9.5 hours. After the stirring, this mixture was cooled to room temperature and then washed twice with water. The obtained aqueous layer was extracted twice with toluene. Then, the extracted solution was combined with an organic layer, followed by washing with a saturated saline solution. The organic layer was dried with magnesium sulfate, this mixture was naturally filtrated, and then the filtrate was concentrated.

The obtained oily substance was dissolved in about 20 mL of toluene, and suction filtration was performed on this solution through Celite, alumina, and then Florisil. A solid which was obtained by concentrating the obtained filtrate was purified by silica gel column chromatography (developing solvent, toluene: hexane=1:4) to obtain 1.9 g of an objective white powder-like solid at a yield of 49%.

In a 200-mL three-neck flask, 12 g (50 mmol) of 4-bromodiphenylamine, 8.6 g (50 mmol) of 1-naphthaleneboronic acid, 22 mg (0.1 mmol) of palladium(II) acetate, and 60 mg (0.2 mmol) of tri(o-tolyl)phosphine were put, and 50 mL of toluene, 20 mL of ethanol, and 35 mL of a potassium carbonate solution (2 mol/L) were added to this mixture. This mixture was deaerated while being stirred under low pressure. After the deaeration, the mixture was stirred under a nitrogen atmosphere at 90° C. for 2 hours to be reacted.

After the reaction, 100 mL of toluene was added to this reaction mixture, and this suspension was filtrated through Florisil and then Celite. The obtained filtrate was washed with water. Then, magnesium sulfate was added to remove moisture. This suspension was concentrated and purified by silica gel column chromatography (developing solvent, toluene: hexane:ethyl acetate=1:8:1). The obtained fraction was concentrated, and methanol was added thereto. The mixture was irradiated with supersonic and then recrystallized to obtain 3.0 g of an objective white powder at a yield of 20%.

Step 3: Synthesis of 4-(1-naphthyl)-4'-(9-phenyl-9H-carbazol-3-yl)-triphenylamine (abbreviation: PCBANB)

A synthetic scheme of 4-(1-naphthyl)-4'-(9-phenyl-9H-carbazol-3-yl)-triphenylamine in Step 3 is shown in the following (J-3).

(J-3)

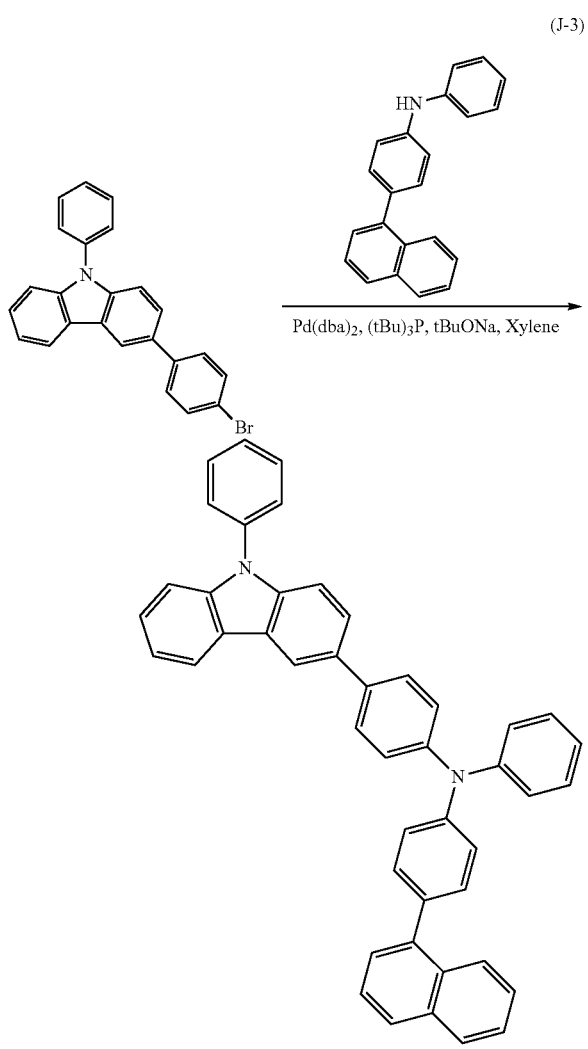

In a 50-mL three-neck flask, 1.2 g (3.0 mmol) of 3-(4-bromophenyl)-9-phenyl-9H-carbazole, 0.9 g (3.0 mmol) of 4-(1-naphthyl)diphenylamine, 0.5 g (5.0 mmol) of sodium tert-butoxide, and 6.0 mg (0.01 mmol) of bis(dibenzylideneacetone)palladium(0) were put, and 15 mL of dehydrated xylene was added to this mixture. This mixture was deaerated while being stirred under low pressure. After the deaeration, 0.06 mL (0.03 mmol) of tri(tert-butyl)phosphine (10 wt % hexane solution) was added thereto. This mixture was stirred under a nitrogen atmosphere at 120° C. for 4.5 hours to be reacted.

After the reaction, 250 mL of toluene was added to this reaction mixture, and this suspension was filtrated through Florisil, silica gel, alumina, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and acetone and methanol were added thereto. The mixture was irradiated with supersonic and then recrystallized to obtain 1.5 g of an objective white powder at a yield of 82%.

An Rf value of the objective substance by a silica gel thin layer chromatography (TLC) (developing solvent, ethyl acetate: hexane=1:10) was 0.34, that of 3-(4-bromophenyl)-9-phenyl-9H-carbazole was 0.46, and that of 4-(1-naphthyl)diphenylamine was 0.25.

Figure 47A:
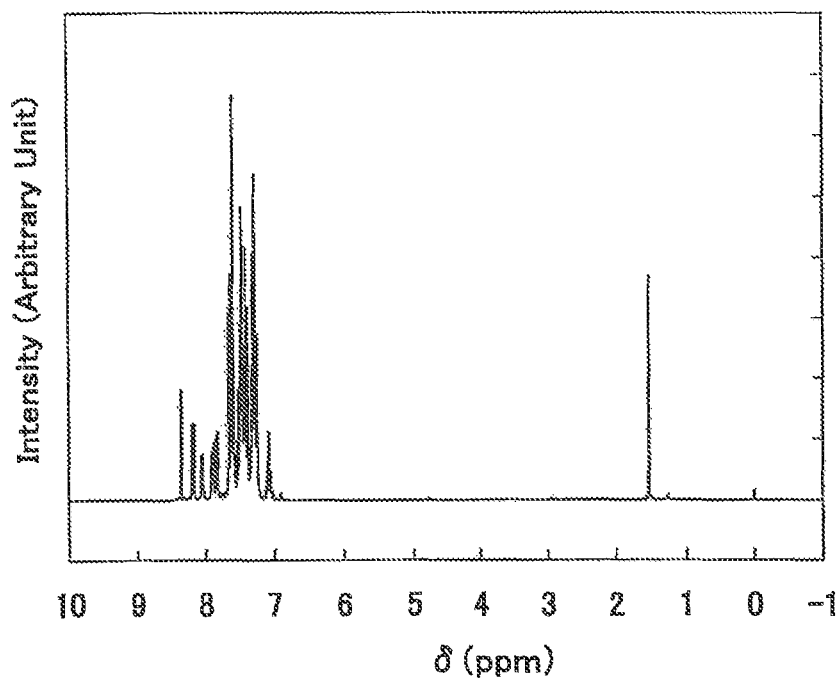
FIGS. 47A and 47B are graphs showing $^1$H NMR charts of PCBANB (abbreviation)
Figure 47B:
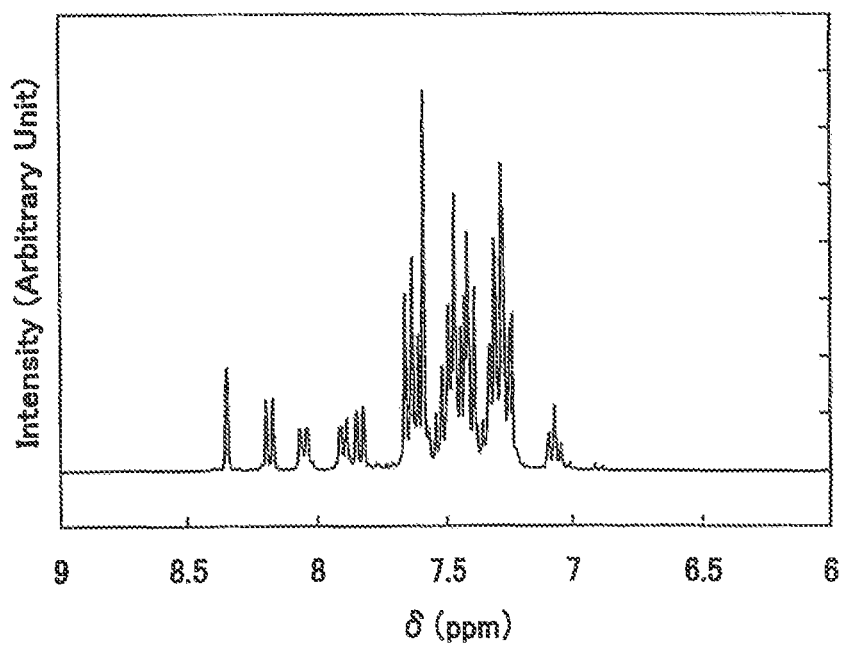

A compound which was obtained through the above Step 3 was measured by a nuclear magnetic resonance method ($^1$H NMR). The measurement result is described below, and the $^1$H NMR chart is shown in FIGS. 47A and 47B. It was found from the measurement result that the carbazole derivative of the present invention, PCBANB (abbreviation) represented by the above structural formula (343), was obtained. $^1$H NMR (CDCl$_3$, 300 MHz): δ (ppm)=7.07 (t, J=6.6 Hz, 1H), 7.25-7.67 (m, 26H), 7.84 (d, J=7.8 Hz, 1H), 7.89-7.92 (m, 1H), 8.03-8.07 (m, 1H), 8.18 (d, J=7.8 Hz, 1H), 8.35 (d, J=0.9 Hz, 1H).

In addition, an absorption spectrum of PCBANB (abbreviation) (measurement range: 200 nm to 800 nm) was measured. In the case of the toluene solution, an absorption peak on a long wavelength side was observed at around 335 nm, and in the case of the thin film, an absorption peak on a long wavelength side was observed at around 341 nm.

In addition, an emission spectrum of PCBANB (abbreviation) (measurement range: 370 nm to 550 nm) was measured. In the case of the toluene solution, a maximum emission wavelength was 410 nm (excitation wavelength: 345 nm), and in the case of the thin film, a maximum emission wavelength was 433 nm (excitation wavelength: 341 nm).

Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCBANB (abbreviation) was −5.44 eV. The Tauc plot of the absorption spectrum of the thin film revealed that the absorption edge was 3.25 eV. Thus, the energy gap in the solid state was estimated to be 3.25 eV, which means that the LUMO level of PCBANB (abbreviation) is −2.19 eV.

An oxidation-reduction reaction characteristic of PCBANB (abbreviation) was examined by a cyclic voltammetry (CV) measurement. Since the measurement method is similar to that of Embodiment 1, the description is omitted.

According to the calculation similar to that of Embodiment 1, the HOMO level of PCBANB (abbreviation) was found to be =−5.44 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBANB (abbreviation) was examined with a differential scanning calorimetry (Pyris 1 DSC, manufactured by Perkin Elmer Co., Ltd.). According to the measurement results, it was found that the glass transition temperature was 115° C. In this manner, PCBANB (abbreviation) has a high glass transition temperature and favorable heat resistance. In addition, the crystallization peak does not exist; thus, it was found that PCBANB (abbreviation) is a substance which is hard to be crystallized.

In addition, FIGS. 56 to 59 show the measurement results in element characteristics of the light-emitting element 6 which was formed using, for a hole-transporting layer, PCBANB (abbreviation) which is the carbazole derivative of the present invention that was synthesized in Embodiment 8 in a manner similar to that of Embodiment 5. It was found that the hole-transporting material of the present invention which was used for the light-emitting element 6 showed higher luminance, even when the hole-transporting material of the present invention which was used for the light-emitting element 6 was compared to NPB of the light-emitting element 1. Note that the light-emitting element 1 which is a comparative light-emitting element was formed using 4,4'-bis[N-(1-naphthyl)-N-phenylamino]biphenyl (abbreviation: NPB) for the hole-transporting layer 151 in a manner similar to that of Embodiment 5.

Figure 59:
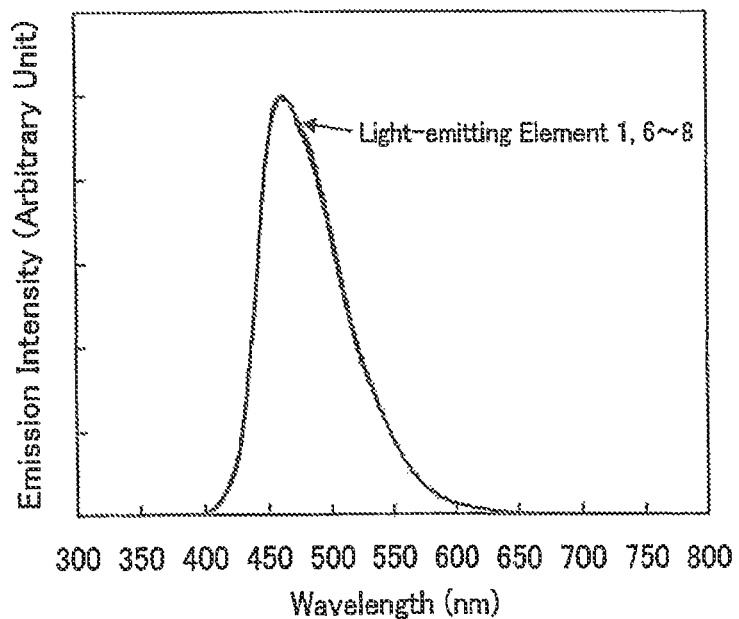
FIG. 59 is a graph showing emission spectra of the light-emitting element 1 and the light-emitting elements 6 to 8.

In addition, in the light-emitting element 6, an emission wavelength derived from PCBAPA which is a blue light-emitting material was observed but an emission wavelength derived from the hole-transporting material was not observed from emission spectrum shown in FIG. 59. Thus, it was found that the hole-transporting material of the present invention realizes favorable carrier balance in the structure of the light-emitting element 6.

Figure 60:
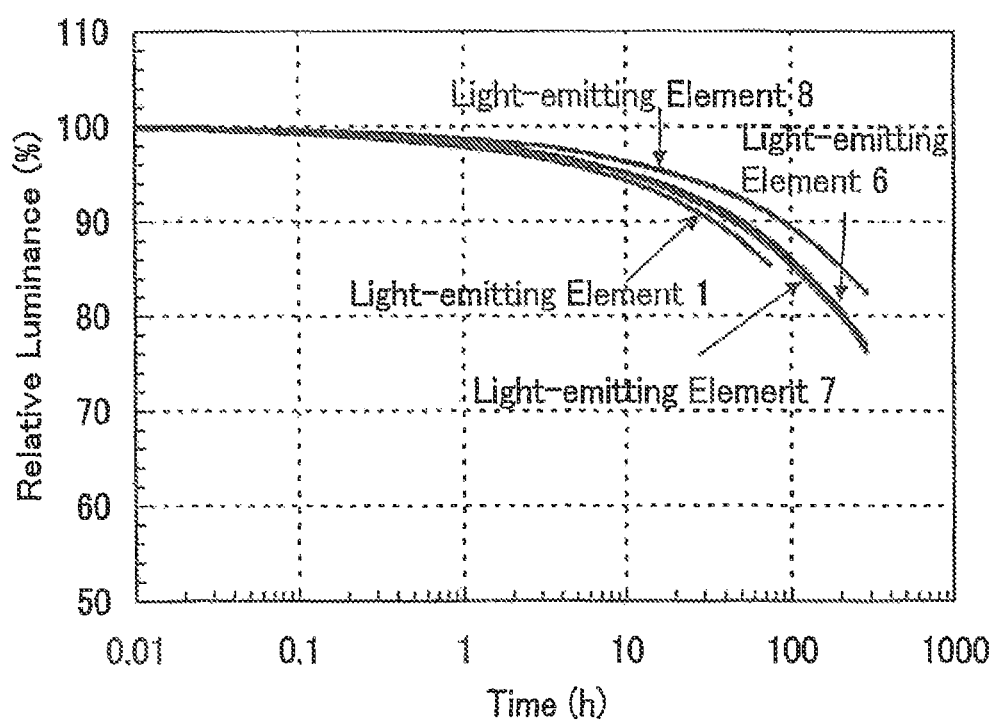
FIG. 60 is a graph showing the result of a continuous lighting test of the light-emitting element 1 and the light-emitting elements 6 to 8 by constant current driving.

FIG. 60 shows the result of a continuous lighting test in which the light-emitting element 6 was continuously lit by constant current driving with the initial luminance set at 1000 cd/m$^2$ (the vertical axis indicates the relative luminance on the assumption that 1000 cd/m$^2$ is 100%). From the results in FIG. 60, the light-emitting element 6 was found to have a longer lifetime, as compared to the light-emitting element 1. Thus, a long lifetime light-emitting element can be obtained by applying the present invention.

Embodiment 9

In Embodiment 9, a synthetic method of a carbazole derivative of the present invention, 4,4'-di(1-naphthyl)-4"-(9-phenyl-9H-carbazol-3-yl)-triphenylamine (abbreviation: PCBNBB) represented by a structural formula (229), will be specifically described.

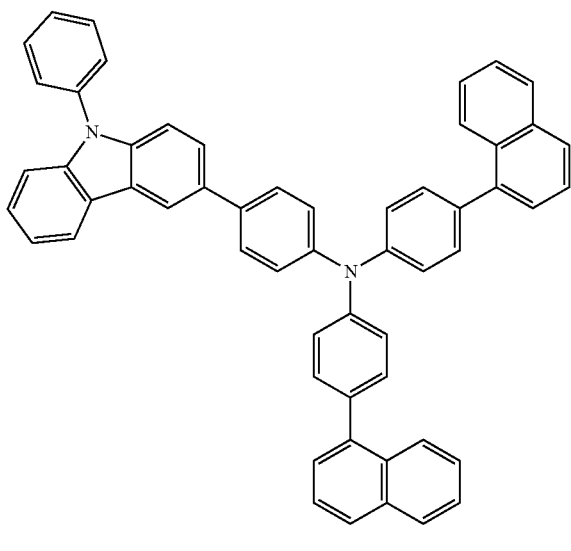

(229)

Step 1: Synthesis of 4,4'-dibromotriphenylamine

A synthetic scheme of 4,4'-dibromotriphenylamine in Step 1 is shown in the following (K-1).

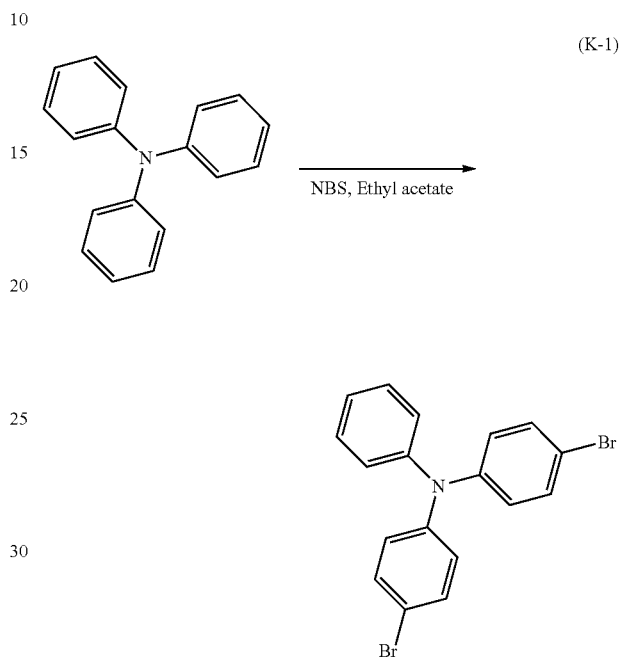

(K-1)

After 12 g (50 mmol) of triphenylamine was dissolved in a mixture solvent of 250 mL of ethyl acetate in a 500-mL conical flask, 18 g (100 mmol) of N-bromo succinimide (abbreviation: NBS) was added to this solution. After that, this mixture was stirred at room temperature for 24 hours. After completion of the reaction, this mixture solution was washed with water, and magnesium sulfate was added thereto to remove moisture. This mixture solution was filtrated and the obtained filtrate was concentrated and dried to obtain 20 g of an objective white solid at a yield of 99%.

Step 2: Synthesis of 4,4'-di(1-naphthyl)triphenylamine

A synthetic scheme of 4,4'-di(1-naphthyl)triphenylamine in Step 2 is shown in the following (K-2).

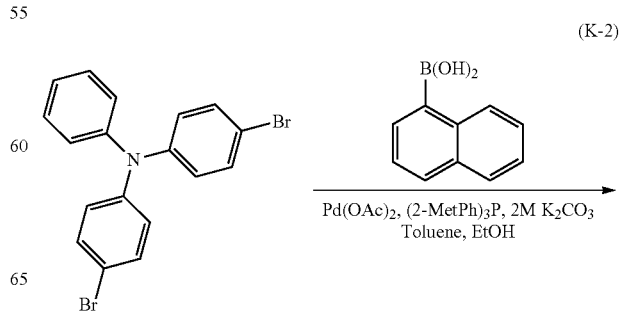

(K-2)

235
-continued

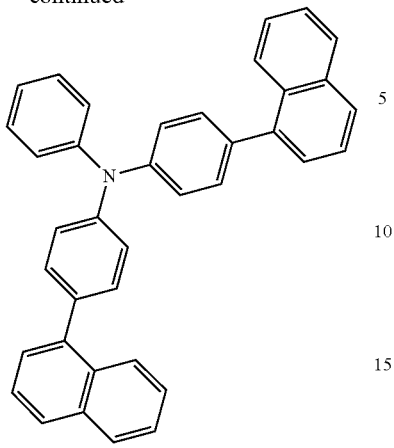

236
-continued

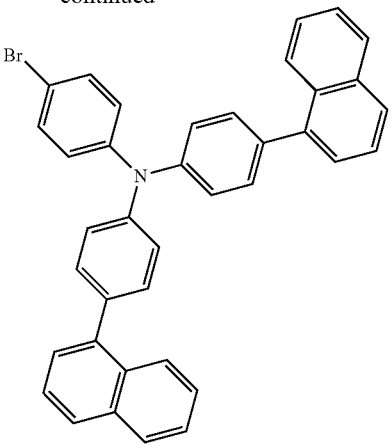

In a 100-mL three-neck flask, 6.0 g (15 mmol) of 4,4'-dibromotriphenylamine, 5.2 g (30 mmol) of 1-naphthaleneboronic acid, 2.0 mg (0.01 mmol) of palladium(II) acetate, and 6.0 mg (0.02 mmol) of tri(o-tolyl)phosphine were put, and 20 mL of toluene, 5 mL of ethanol, and 20 mL of a potassium carbonate solution (2 mol/L) were added to this mixture. This mixture was deaerated while being stirred under low pressure. After the deaeration, the mixture was stirred under a nitrogen atmosphere at 90° C. for 4.5 hours to be reacted.

After the reaction, 150 mL of toluene was added to this reaction mixture, and on this suspension was filtrated through Florisil and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and methanol was added thereto. The mixture was irradiated with supersonic and then recrystallized to obtain 6.4 g of an objective white powder at a yield of 86%.

An Rf value of the objective substance by a silica gel thin layer chromatography (TLC) (developing solvent, ethyl acetate: hexane=1:10) was 0.53 and that of 4,4'-dibromotriphenylamine was 0.69.

Step 3: Synthesis of 4-bromo-4',4''-di(1-naphthyl)triphenylamine

A synthetic scheme of 4-bromo-4',4''-di(1-naphthyl)triphenylamine in Step 3 is shown in the following (K-3).

After 6.4 g (13 mmol) of 4,4'-di(1-naphthyl)triphenylamine was dissolved in 150 mL of ethyl acetate in a 300-mL conical flask, 2.3 g (13 mmol) of N-bromo succinimide (abbreviation: NBS) was added to this solution. After that, this mixture was stirred at room temperature for 24 hours. After completion of the reaction, this mixture solution was washed with water, and magnesium sulfate was added thereto to remove moisture. This mixture solution was filtrated, the obtained filtrate was concentrated, and methanol was added thereto. The mixture was irradiated with supersonic and then recrystallized to be purified by silica gel column chromatography (developing solvent, toluene: hexane=1:5). Accordingly, 1.6 g of an objective white powder was obtained at a yield of 22%.

Step 4: Synthesis of 4,4'-di(1-naphthyl)-4''-(9-phenyl-9H-carbazol-3-yl)-triphenylamine (abbreviation: PCBNBB)

A synthetic scheme of 4,4'-di(1-naphthyl)-4''-(9-phenyl-9H-carbazol-3-yl)-triphenylamine in Step 4 is shown in the following (K-4).

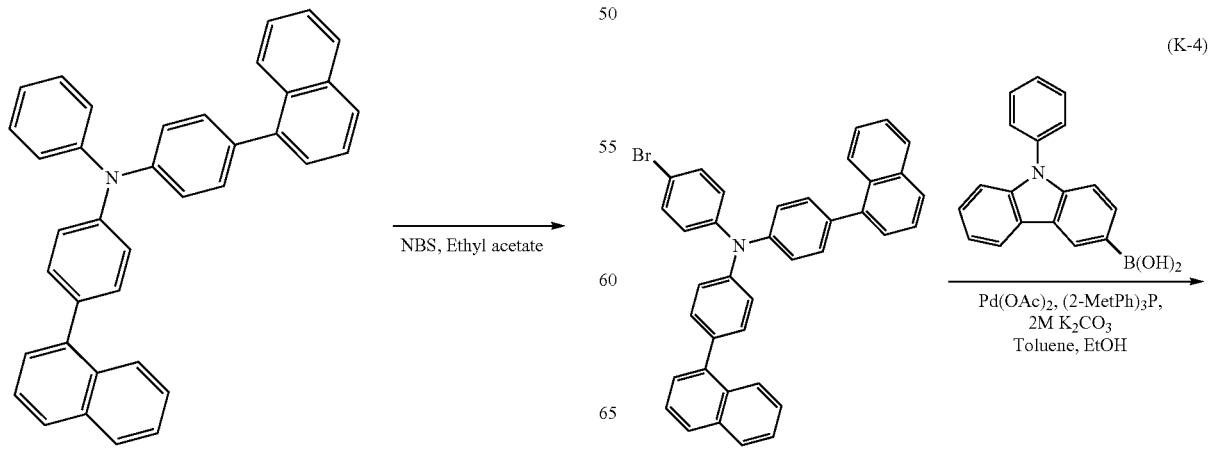

-continued

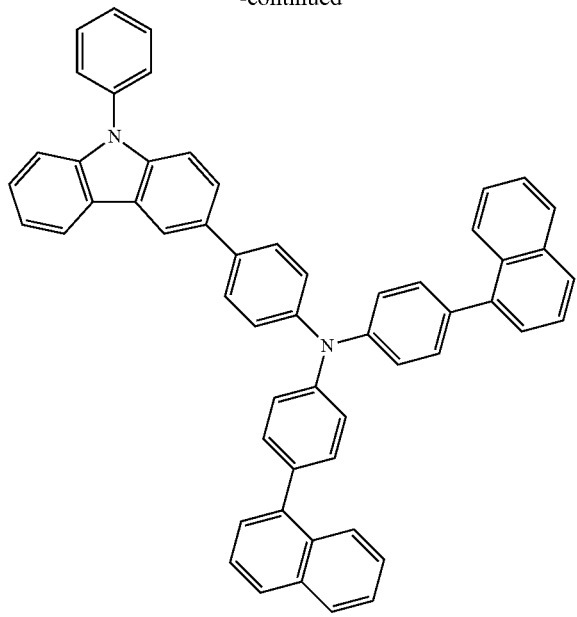

In a 50-mL three-neck flask, 1.4 g (2.5 mmol) of 4-bromo-4',4''-di(1-naphthyl)triphenylamine, 0.7 g (2.5 mmol) of 9-phenyl-9H-carbazol-3-yl-boronic acid, 4.0 mg (0.02 mmol) of palladium(II) acetate, and 6.0 mg (0.02 mmol) of tri(o-tolyl)phosphine were put, and 20 mL of toluene, 5 mL of ethanol, and 2.5 mL of a potassium carbonate solution (2 mol/L) were added to this mixture. This mixture was deaerated while being stirred under low pressure. After the deaeration, the mixture was stirred under a nitrogen atmosphere at 90° C. for 6.5 hours to be reacted.

After the reaction, 150 mL of toluene was added to this reaction mixture, and this suspension was filtrated through Florisil and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene:hexane=1:4). The obtained fraction was concentrated, and methanol was added thereto. The mixture was irradiated with supersonic and then recrystallized to obtain 0.4 g of an objective white powder at a yield of 22%.

Figure 48A:
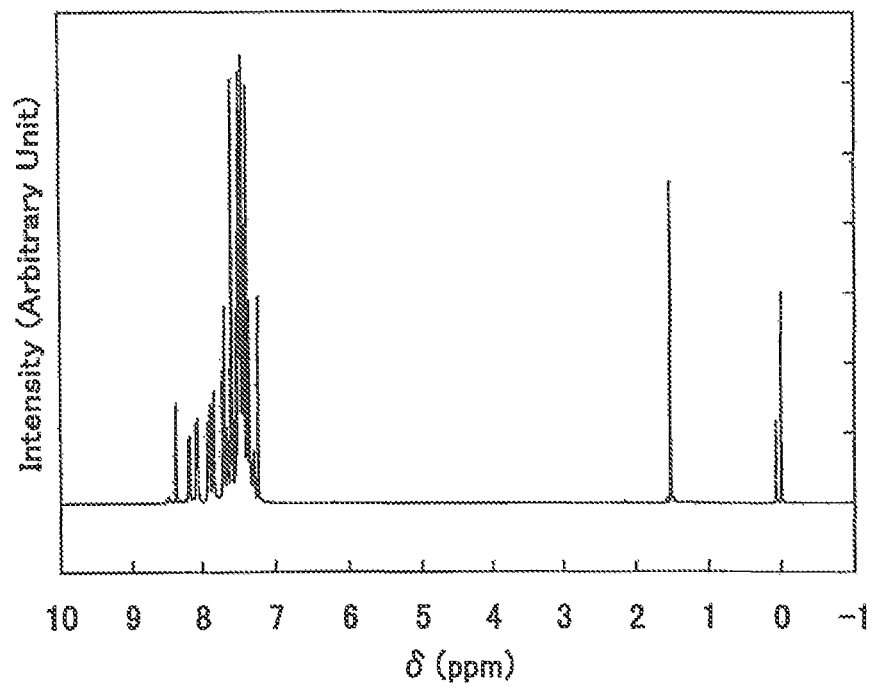
FIGS. 48A and 48B are graphs showing $^1$H NMR charts of PCBNBB (abbreviation)
Figure 48B:
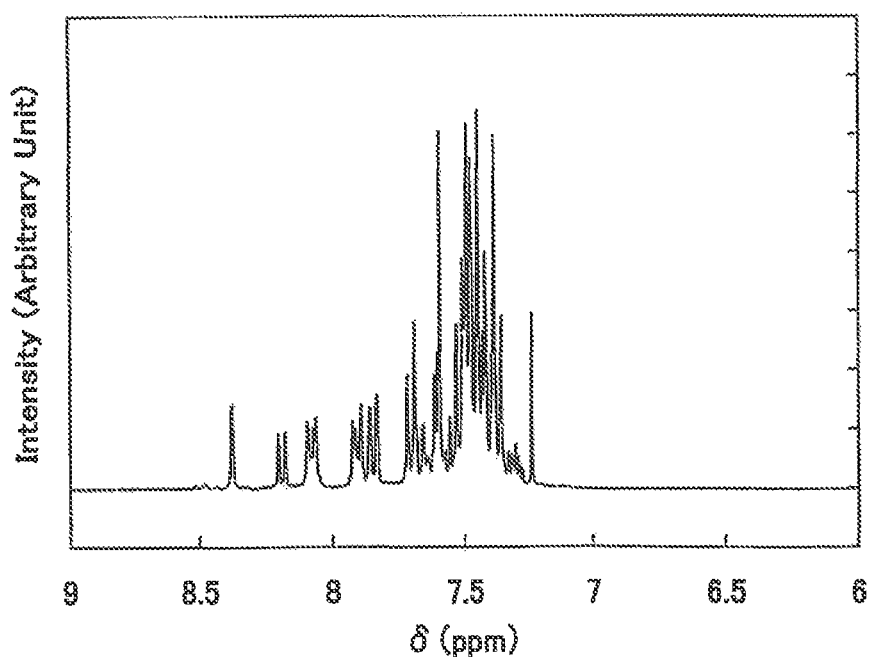

A compound which was obtained through the above Step 4 was measured by a nuclear magnetic resonance method ($^1$H NMR). The measurement result is described below, and the $^1$H NMR chart is shown in FIGS. 48A and 48B. It was found from the measurement result that the carbazole derivative of the present invention, PCBNBB (abbreviation) represented by the above structural formula (229), was obtained. $^1$H NMR (CDCl$_3$, 300 MHz): δ (ppm)=7.28-7.72 (m, 30H), 7.85 (d, J=7.8 Hz, 2H), 7.90-7.93 (m, 2H), 8.06-8.09 (m, 2H), 8.19 (d, J=7.5 Hz, 1H), 8.38 (d, J=1.5 Hz, 1H).

In addition, an absorption spectrum of PCBNBB (abbreviation) (measurement range: 200 nm to 800 nm) was measured. In the case of the toluene solution, an absorption peak on a long wavelength side was observed at around 345 nm, and in the case of the thin film, an absorption peak on a long wavelength side was observed at around 355 nm.

In addition, an emission spectrum of PCBNBB (abbreviation) (measurement range: 370 nm to 550 nm) was measured. In the case of the toluene solution, a maximum emission wavelength was 413 nm (excitation wavelength: 355 nm), and in the case of the thin film, a maximum emission wavelength was 428 nm (excitation wavelength: 370 nm).

Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCBNBB (abbreviation) was −5.46 eV. The Tauc plot of the absorption spectrum of the thin film revealed that the absorption edge was 3.15 eV. Thus, the energy gap in the solid state was estimated to be 3.15 eV, which means that the LUMO level of PCBNBB (abbreviation) is −2.31 eV.

An oxidation-reduction reaction characteristic of PCBNBB (abbreviation) was examined by a cyclic voltammetry (CV) measurement. Since the measurement method is similar to that of Embodiment 1, the description is omitted. According to the calculation similar to that of Embodiment 1, the HOMO level of PCBNBB (abbreviation) was found to be =−5.43 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBNBB (abbreviation) was examined with a differential scanning calorimetry (Pyris 1 DSC, manufactured by Perkin Elmer Co., Ltd.). According to the measurement results, it was found that the glass transition temperature was 136° C. In this manner, PCBNBB (abbreviation) has a high glass transition temperature and favorable heat resistance. In addition, the crystallization peak does not exist; thus, it was found that PCBNBB (abbreviation) is a substance which is hard to be crystallized.

In addition, FIGS. 56 to 59 show the measurement results in element characteristics of the light-emitting element 7 which was formed using, for a hole-transporting layer, PCBNBB (abbreviation) which is the carbazole derivative of the present invention that was synthesized in Embodiment 9 in a manner similar to that of Embodiment 5. It was found that the hole-transporting material of the present invention which was used for the light-emitting element 7 showed higher luminance, even when the hole-transporting material of the present invention which was used for the light-emitting element 7 was compared to NPB of the light-emitting element 1. Note that the light-emitting element 1 which is a comparative light-emitting element was formed using 4,4'-bis[N-(1-naphthyl)-N-phenylamino]biphenyl (abbreviation: NPB) for the hole-transporting layer 151 in a manner similar to that of Embodiment 5.

In addition, in the light-emitting element 7, an emission wavelength derived from PCBAPA which is a blue light-emitting material was observed but an emission wavelength derived from the hole-transporting material was not observed from emission spectrum shown in FIG. 59. Thus, it was found that the hole-transporting material of the present invention realizes favorable carrier balance in the structure of the light-emitting element 7.

FIG. 60 shows the result of a continuous lighting test in which the light-emitting element 7 was continuously lit by constant current driving with the initial luminance set at 1000 cd/m$^2$ (the vertical axis indicates the relative luminance on the assumption that 1000 cd/m$^2$ is 100%). From the results in FIG. 60, the light-emitting element 7 was found to have a longer lifetime, as compared to the light-emitting element 1.

Embodiment 10

In Embodiment 10, a synthetic method of a carbazole derivative of the present invention, 4-(1-naphthyl)-4'-phenyl-4"-(9-phenyl-9H-carbazol-3-yl)triphenylamine (abbreviation: PCBBiNB) represented by a structural formula (220), will be specifically described.

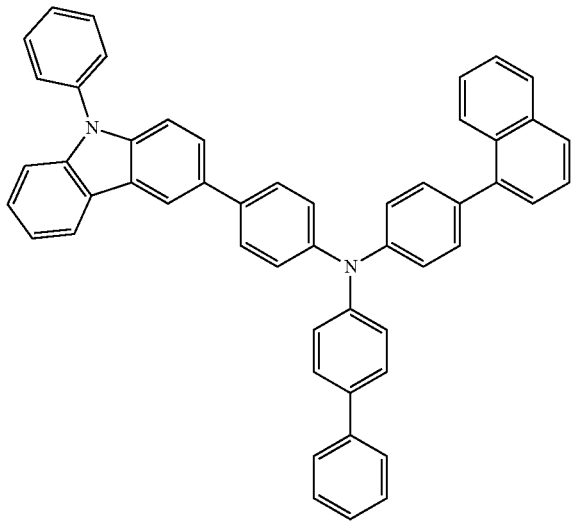

(220)

Step 1: Synthesis of 4-phenyltriphenylamine

A synthetic scheme of 4-phenyltriphenylamine in Step 1 is shown in the following (L-1).

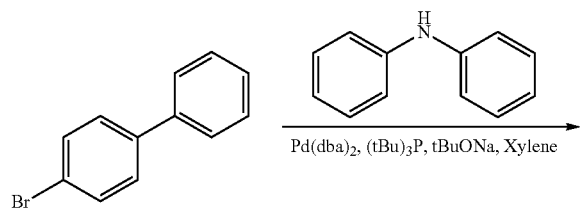

(L-1)

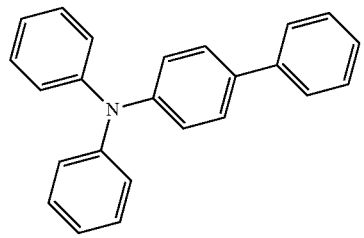

In a 300-mL three-neck flask, 9.3 g (40 mmol) of 4-bromophenyl, 6.8 g (40 mmol) of diphenylamine, 5.0 g (50 mol) of sodium tert-butoxide, and 10 mg of bis(dibenzylideneacetone)palladium(0) were put, and the atmosphere in the flask was substituted by nitrogen. Then, 100 mL of xylene and 0.6 mL of tri(tert-butyl)phosphine (10 wt % hexane solution) were added to this mixture.

This mixture was deaerated while being stirred under low pressure. After the atmosphere was substituted by nitrogen, the mixture was stirred at 130° C. for 3.5 hours. After the stirring, 250 mL of toluene was added to the reaction mixture, and this suspension was filtrated through Celite, alumina, and then Florisil. The obtained filtrate was washed with water and dried, and magnesium sulfate was added thereto. This mixture was filtrated through Celite, alumina, and then Florisil to obtain filtrate. The obtained filtrate was concentrated, and methanol was added thereto. The mixture was irradiated with supersonic and then recrystallized to obtain 11 g of an objective white powder at a yield of 89%.

Step 2: Synthesis of 4-bromo-4'-phenyltriphenylamine

A synthetic scheme of 4-bromo-4'-phenyltriphenylamine in Step 2 is shown in the following (L-2).

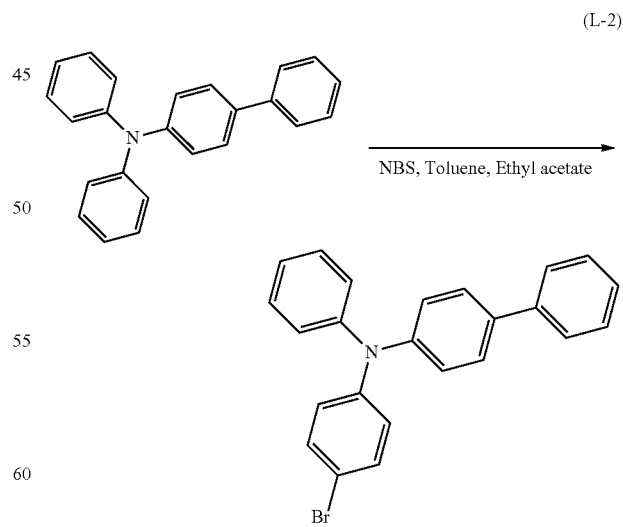

(L-2)

In a 500-mL conical flask, 6.4 g (20 mmol) of 4-phenyltriphenylamine, 250 mL of ethyl acetate, and 150 mL of toluene were added and the mixture was stirred, and then 3.6 g (20 mmol) of N-bromo succinimide (abbreviation: NBS)

Step 3: Synthesis of 4-(1-naphthyl)-4'-phenyltriphenylamine

A synthetic scheme of 4-(1-naphthyl)-4'-phenyltriphenylamine in Step 3 is shown in the following (L-3).

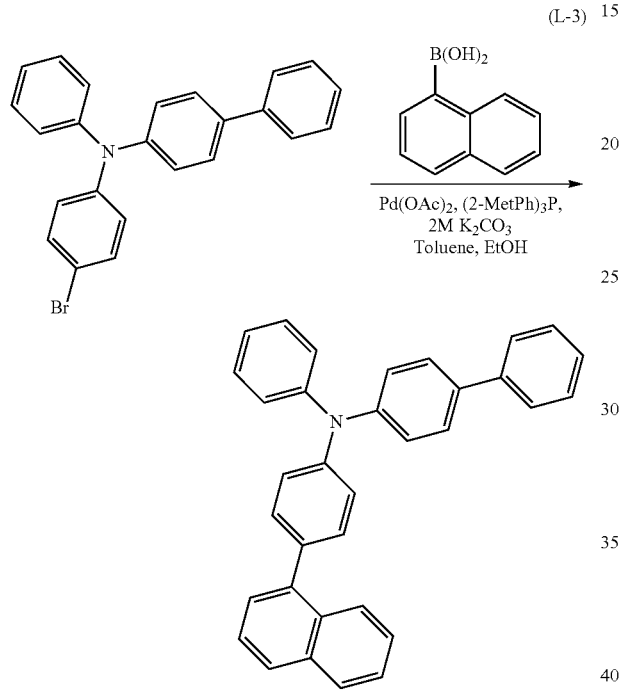

(L-3)

In a 100-mL three-neck flask, 8.0 g (20 mmol) of 4-bromo-4'-phenyltriphenylamine, 3.4 g (20 mmol) of 1-naphthaleneboronic acid, 44 mg (0.2 mmol) of palladium (II) acetate, and 60 mg (0.4 mmol) of tri(o-tolyl)phosphine were put, and 20 mL of toluene, 10 mL of ethanol, and 15 mL of a potassium carbonate solution (2 mol/L) were added to this mixture. This mixture was deaerated while being stirred under low pressure. After the deaeration, the mixture was stirred under a nitrogen atmosphere at 90° C. for 6.5 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and methanol was added thereto. The mixture was irradiated with supersonic and then recrystallized to obtain 8.6 g of an objective white powder at a yield of 97%.

An Rf value of the objective substance by a silica gel thin layer chromatography (TLC) (developing solvent, ethyl acetate: hexane=1:10) was 0.43 and that of 4-bromo-4'-phenyltriphenylamine was 0.50.

Step 4: Synthesis of 4-bromo-4'-(1-naphthyl)-4''-phenyl-triphenylamine

A synthetic scheme of 4-bromo-4'-(1-naphthyl)-4''-phenyl-triphenylamine in Step 4 is shown in the following (L4).

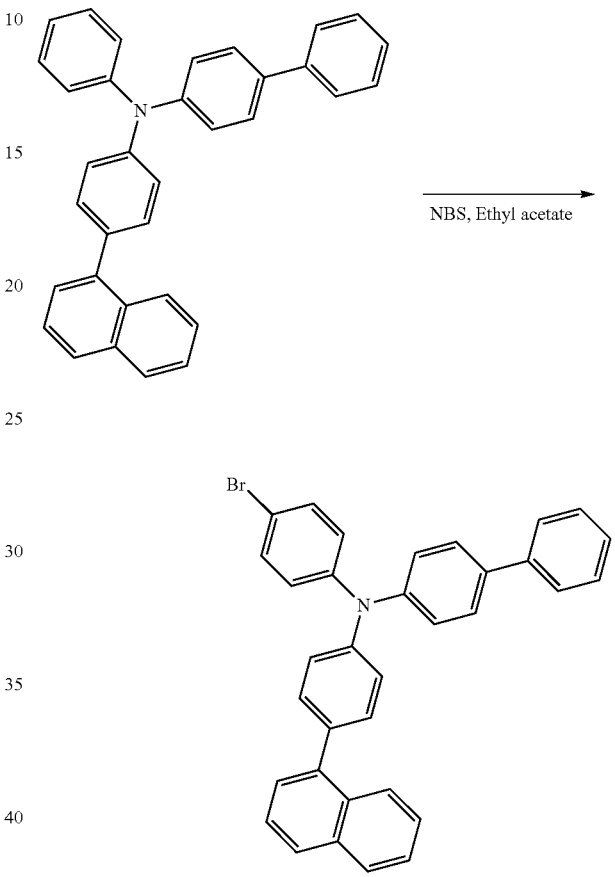

(L-4)

After 8.6 g (19 mmol) of 4-(1-naphthyl)-4'-phenyltriphenylamine was dissolved in 150 mL of ethyl acetate in a 300-mL conical flask, 3.4 g (19 mmol) of N-bromo succinimide (abbreviation: NBS) was added to this solution. After that, this mixture was stirred at room temperature for 24 hours. After completion of the reaction, this mixture solution was washed with water, and magnesium sulfate was added thereto to remove moisture. This mixture solution was filtrated. The obtained filtrate was concentrated and purified by silica gel column chromatography (developing solvent, toluene: hexane=1:4). The obtained fraction was concentrated, and methanol was added thereto. The mixture was irradiated with supersonic and then recrystallized to obtain 8.1 g of an objective white powder at a yield of 80%.

Step 5: Synthesis of 4-(1-naphthyl)-4'-phenyl-4''-(9-phenyl-9H-carbazol-3-yl)triphenylamine (abbreviation: PCBBiNB)

A synthetic scheme of 4-(1-naphthyl)-4'-phenyl-4''-(9-phenyl-9H-carbazol-3-yl)triphenylamine in Step 5 is shown in the following (L-5).

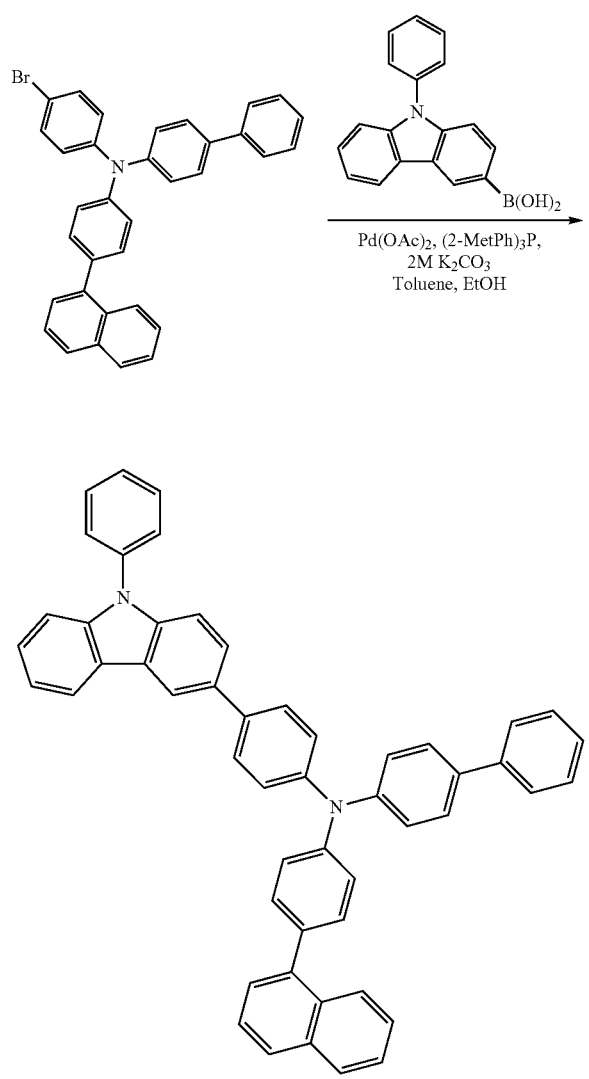

(L-5)

In a 50-mL three-neck flask, 1.6 g (3.0 mmol) of 4-bromo-4'-(1-naphthyl)-4"-phenyl-triphenylamine, 0.9 g (30 mmol) of 9-phenyl-9H-carbazol-3-yl-boronic acid, 12 mg (0.06 mmol) of palladium(II) acetate, and 36 mg (0.12 mmol) of tri(o-tolyl)phosphine were put, and 15 mL of toluene, 15 mL of ethanol, and 3 mL of a potassium carbonate solution (2 mol/L) were added to this mixture. This mixture was deaerated while being stirred under low pressure. After the deaeration, the mixture was stirred under a nitrogen atmosphere at 90° C. for 2 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene: hexane=1:4). The obtained fraction was concentrated, acetone and methanol were added thereto. The mixture was irradiated with supersonic and then recrystallized to obtain 0.9 g of an objective white powder at a yield of 44%.

An Rf value of the objective substance by a silica gel thin layer chromatography (TLC) (developing solvent, ethyl acetate: hexane=1:10) was 0.26 and that of 4-bromo-4'-(1-naphthyl)-4"-phenyl-triphenylamine was 0.45.

Figure 49A:
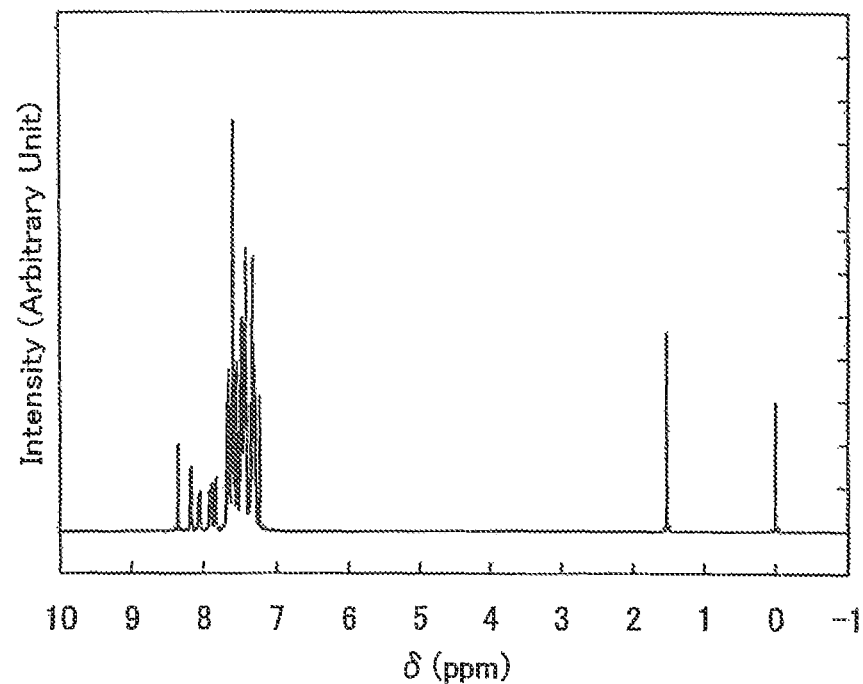
FIGS. 49A and 49B are graphs showing $^1$H NMR charts of PCBB1NB (abbreviation)
Figure 49B:
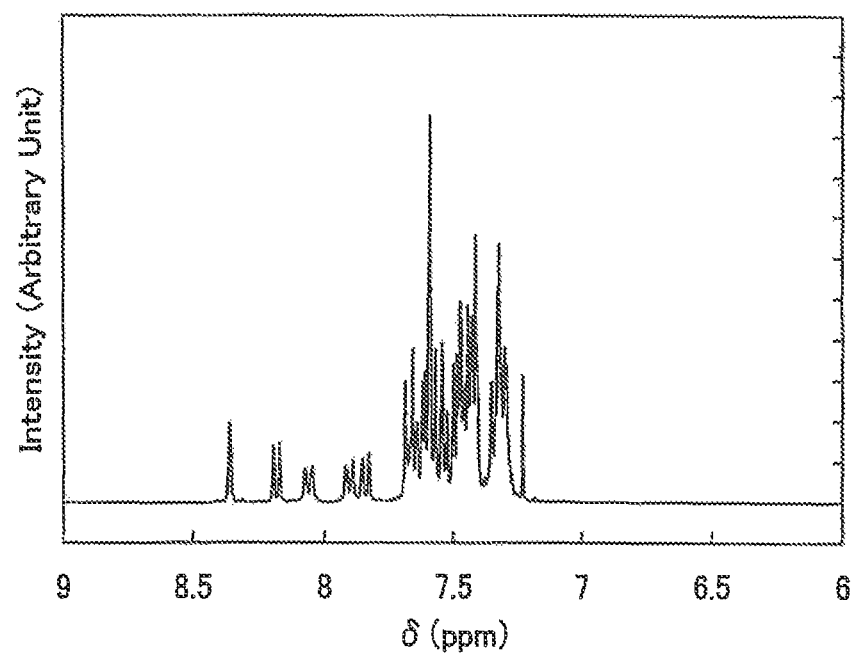

A compound which was obtained through the above Step 5 was measured by a nuclear magnetic resonance method ($^1$H NMR). The measurement result is described below, and the $^1$H NMR chart is shown in FIGS. 49A and 49B. It was found from the measurement result that the carbazole derivative of the present invention, PCBBiNB (abbreviation) represented by the above structural formula (220), was obtained. $^1$H NMR (CDCl$_3$, 300 MHz): δ (ppm)=7.27-7.69 (m, 31H), 7.84 (d, J=7.8 Hz, 1H), 7.89-7.92 (m, 1H), 8.04-8.08 (m, 1H), 8.18 (d, J=7.8 Hz, 1H), 8.36 (d, J=1.5 Hz, 1H).

In addition, an absorption spectrum of PCBBiNB (abbreviation) (measurement range: 200 nm to 800 nm) was measured. In the case of the toluene solution, an absorption peak on a long wavelength side was observed at around 342 nm, and in the case of the thin film, an absorption peak on a long wavelength side was observed at around 351 nm.

In addition, an emission spectrum of PCBBiNB (abbreviation) (measurement range: 370 nm to 550 nm) was measured. In the case of the toluene solution, a maximum emission wavelength was 409 nm (excitation wavelength: 355 nm), and in the case of the thin film, a maximum emission wavelength was 433 nm (excitation wavelength: 336 nm).

Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCBBiNB (abbreviation) was −5.35 eV. The Tauc plot of the absorption spectrum of the thin film revealed that the absorption edge was 3.18 eV. Thus, the energy gap in the solid state was estimated to be 3.18 eV, which means that the LUMO level of PCBBiNB (abbreviation) is −2.17 eV.

An oxidation-reduction reaction characteristic of PCBBiNB (abbreviation) was examined by a cyclic voltammetry (CV) measurement. Since the measurement method is similar to that of Embodiment 1, the description is omitted.

According to the calculation similar to that of Embodiment 1, the HOMO level of PCBBiNB (abbreviation) was found to be =−5.42 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBBiNB (abbreviation) was examined with a differential scanning calorimetry (Pyris 1 DSC, manufactured by Perkin Elmer Co., Ltd.). According to the measurement results, it was found that the glass transition temperature was 143° C. In this manner, PCBBiNB (abbreviation) has a high glass transition temperature and favorable heat resistance. In addition, the crystallization peak does not exist; thus, it was found that PCBBiNB (abbreviation) is a substance which is hard to be crystallized.

In addition, FIGS. 56 to 59 show the measurement results in element characteristics of the light-emitting element 8 which was formed using, for a hole-transporting layer, PCBBiNB (abbreviation) which is the carbazole derivative of the present invention that was synthesized in Embodiment 10 in a manner similar to that of Embodiment 5. It was found that the hole-transporting material of the present invention which was used for the light-emitting element 8 showed higher luminance, even when the hole-transporting material of the present invention which was used for the light-emitting element 8 was compared to NPB of the light-emitting element 1. Note that the light-emitting element 1 which is a comparative light-emitting element was formed using 4,4'-bis[N-(1-naphthyl)-N-phenylamino]biphenyl (abbreviation: NPB) for the hole-transporting layer 151 in a manner similar to that of Embodiment 5.

In addition, in the light-emitting element 8, an emission wavelength derived from PCBAPA which is a blue light-emitting material was observed but an emission wavelength derived from the hole-transporting material was not observed from emission spectrum shown in FIG. 59. Thus, it was found that the hole-transporting material of the present invention realizes favorable carrier balance in the structure of the light-emitting element 8.

FIG. 60 shows the result of a continuous lighting test in which the light-emitting element 8 was continuously lit by constant current driving with the initial luminance set at 1000 cd/m$^2$ (the vertical axis indicates the relative luminance on the assumption that 1000 cd/m$^2$ is 100%). From the results in FIG. 60, the light-emitting element 8 was found to have a longer lifetime, as compared to the light-emitting element 1. Thus, a long lifetime light-emitting element can be obtained by applying the present invention.

In addition, as another structure of the light-emitting element 8 shown in Embodiment 10, PCBBiNB (abbreviation) was used instead of NPB (abbreviation), which was used at the time of forming the first layer 1511, and was co-evaporated with molybdenum(VI) oxide to form the first layer 1511. With the efficiency, the drive voltage at a luminance of about 1000 cd/m$^2$, and the reliability of such a light-emitting element 8, favorable values equivalent to those of the light-emitting element 8 were obtained. The light-emitting element 8 was formed in Embodiment 10 by using a co-evaporation film of NPB and molybdenum(VI) oxide for a hole-injecting layer and using PCBBiNB (abbreviation) for a hole-transporting layer. When the drive voltage of the light-emitting element 8 was 4.2 V, the luminance and the current value were 1062 cd/m$^2$ and 0.75 mA, respectively, and the light-emitting element 8 exhibited 81% of the initial luminance when driven for 350 hours.

As thus described, it was found that PCBBiNB (abbreviation) was a favorable material which can be used for both the first layer 1511 which is a hole-injecting layer and the second layer 1512 which is a hole-transporting layer at the same time. Accordingly, an element could be manufactured easily and material use efficiency could also be improved.

Embodiment 11

In Embodiment 11, a synthetic method of a carbazole derivative of the present invention, [4'-(1-naphthyl)biphenyl-4-yl](phenyl)[4-(9-phenyl-9H-carbazol-3-yl)phenyl]amine (abbreviation: PCBANT) represented by a structural formula (355), will be specifically described.

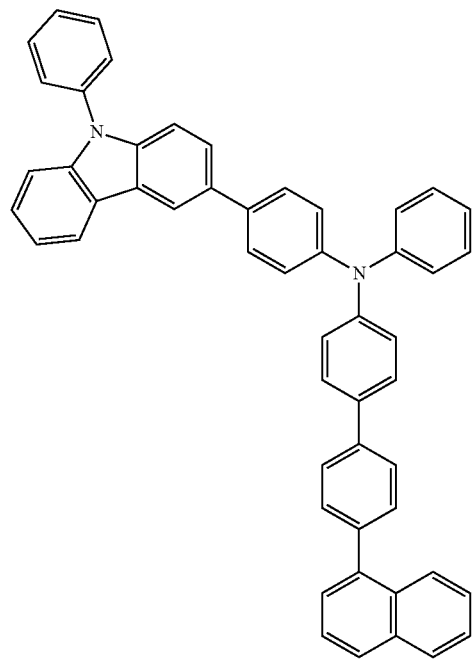

(355)

Step 1: Synthesis of 4-(4-bromophenyl)-4'-phenyl-triphenylamine

A synthetic scheme of 4-(4-bromophenyl)-4'-phenyl-triphenylamine in Step 1 is shown in the following (M-1).

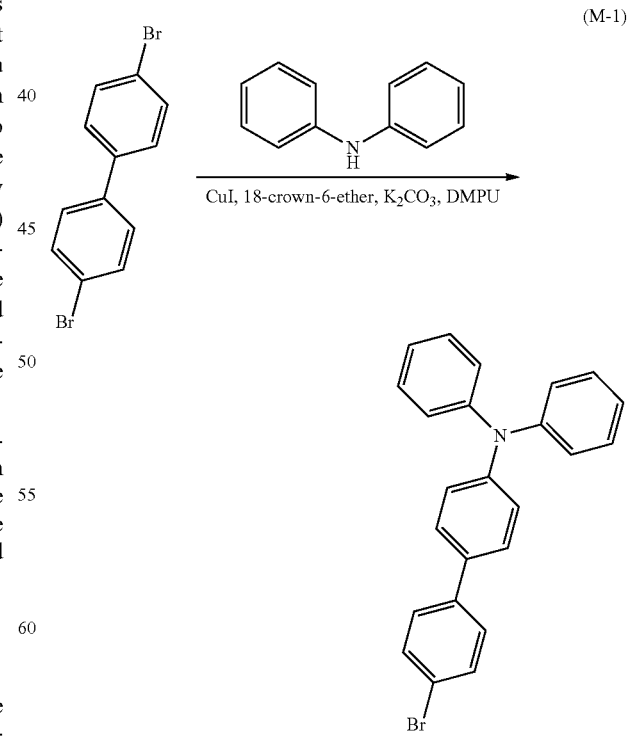

(M-1)

In a 500-mL three-neck flask, 22 g (70 mmol) of 4,4'-dibromobiphenyl, 8.5 g (50 mmol) of diphenylamine, 1.9 g (10 mmol) of copper(I) iodide, 2.6 g (10 mmol) of 18-crown-6-ether, 6.9 g (50 mmol) of potassium carbonate, and 50 mL of 1,3-dimethyl-3,4,5,6-tetrahydro-2(1H)pyrimidinone (abbreviation: DMPU) were put, and the mixture was stirred under a nitrogen atmosphere at 180° C. for 37 hours.

After the reaction, 500 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene: hexane=1:4). The obtained fraction was concentrated, and hexane and methanol were added thereto. The mixture was irradiated with supersonic and then recrystallized to obtain 5.3 g of an objective white powder at a yield of 27%.

An Rf value of the objective substance by a silica gel thin layer chromatography (TLC) (developing solvent, ethyl acetate: hexane=1:10) was 0.5 and that of 4,4'-dibromobiphenyl was 0.59.

Step 2: Synthesis of [4'-(1-naphthyl)biphenyl-4-yl]diphenylamine

A synthetic scheme of [4'-(1-naphthyl)biphenyl-4-yl]diphenylamine in Step 2 is shown in the following (M-2).

In a 100-mL three-neck flask, 4.0 g (10 mmol) of 4-(4-bromophenyl)-4'-phenyl-triphenylamine, 1.7 g (10 mmol) of 1-naphthaleneboronic acid, 11 mg (0.05 mmol) of palladium (II) acetate, and 15 mg (0.05 mmol) of tri(o-tolyl)phosphine were put, and 20 mL of toluene, 5 mL of ethanol, and 10 mL of a potassium carbonate solution (2 mol/L) were added to this mixture. This mixture was deaerated while being stirred under low pressure. After the deaeration, the mixture was stirred under a nitrogen atmosphere at 90° C. for 7 hours to be reacted.

After the reaction, 150 mL of toluene was added to this reaction mixture, and this suspension was filtrated through silica gel, alumina, and then Celite. The obtained filtrate was washed with water. Then, magnesium sulfate was added to remove moisture. This suspension was filtrated through silica gel, alumina, and then Celite to obtain filtrate. The obtained filtrate was concentrated, and methanol was added thereto. The mixture was irradiated with supersonic and then recrystallized to obtain 3.6 g of an objective white powder at a yield of 80%.

An Rf value of the objective substance by a silica gel thin layer chromatography (TLC) (developing solvent, ethyl acetate: hexane=1:10) was 0.58 and that of 4-bromophenyl-4'-phenyl-triphenylamine was 0.65.

Step 3: Synthesis of (4-bromophenyl)[4'-(1-naphthyl)biphenyl-4-yl]phenylamine

A synthetic scheme of (4-bromophenyl)[4'-(1-naphthyl)biphenyl-4-yl]phenylamine in Step 3 is shown in the following (M-3).

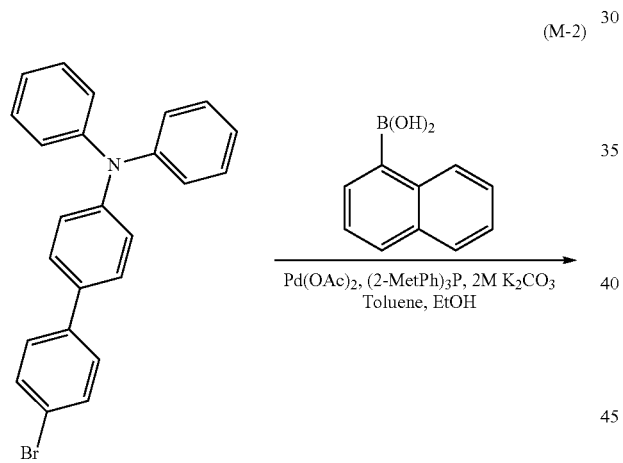

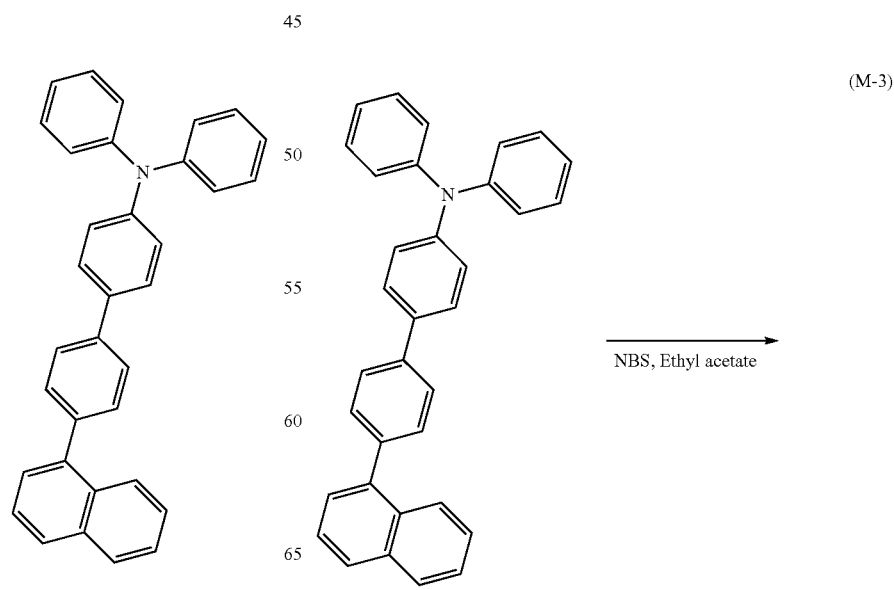

-continued

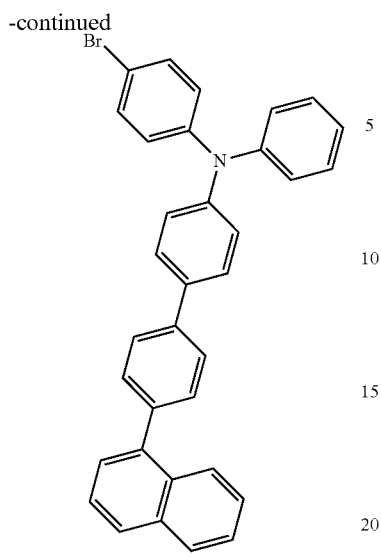

After 3.6 g (8.0 mmol) of [4'-(1-naphthyl)biphenyl-4-yl]diphenylamine was dissolved in 100 mL of ethyl acetate in a 200-mL conical flask, 1.4 g (8.0 mmol) of N-bromo succinimide (abbreviation: NBS) was added to this solution. After that, this mixture was stirred at room temperature for 72 hours. After completion of the reaction, this mixture solution was washed with water, and magnesium sulfate was added thereto to remove moisture. This mixture solution was filtrated, the obtained filtrate was concentrated, and methanol was added thereto. The mixture was irradiated with supersonic and then recrystallized to obtain 3.9 g of an objective white powder at a yield of 93%.

Step 4: Synthesis of [4'-(1-naphthyl)biphenyl-4-yl](phenyl)[4-(9-phenyl-9H-carbazol-3-yl)phenyl]amine (abbreviation: PCBANT)

A synthetic scheme of [4'-(1-naphthyl)biphenyl-4-yl](phenyl)[4-(9-phenyl-9H-carbazol-3-yl)phenyl]amine in Step 4 is shown in the following (M-4).

(M-4)

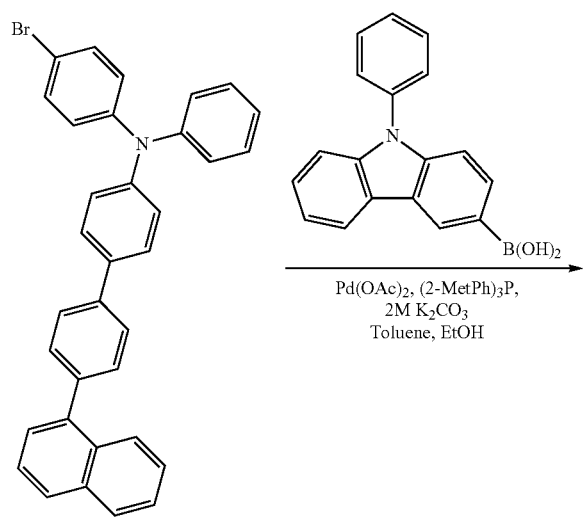

-continued

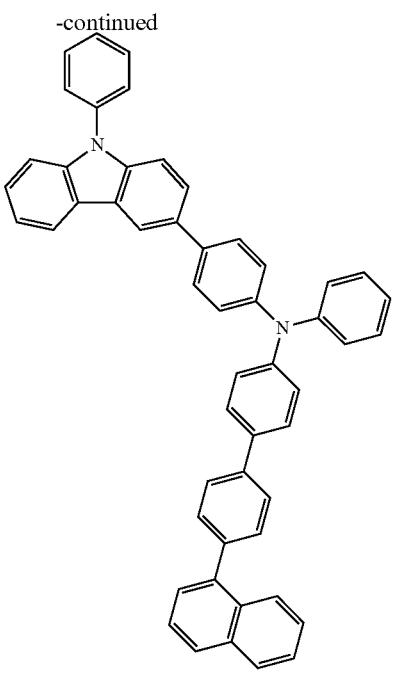

In a 100-mL three-neck flask, 1.6 g (3 mmol) of (4-bromophenyl)[4'-(1-naphthyl)biphenyl-4-yl]phenylamine, 0.8 g (3 mmol) of 9-phenyl-9H-carbazol-3-boronic acid, 6.0 mg (0.03 mmol) of palladium(II) acetate, and 18 mg (0.03 mmol) of tri(o-tolyl)phosphine were put, and 20 mL of toluene, 5 mL of ethanol, and 3 mL of a potassium carbonate solution (2 mol/L) were added to this mixture. This mixture was deaerated while being stirred under low pressure. After the deaeration, the mixture was stirred under a nitrogen atmosphere at 80° C. for 6.5 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, and then Celite to obtain filtrate. The obtained filtrate was concentrated and purified by silica gel column chromatography (developing solvent, toluene:hexane=1:4). The obtained fraction was concentrated, and methanol was added thereto. The mixture was irradiated with supersonic and then recrystallized to obtain 1.2 g of an objective white powder at a yield of 60%.

An Rf value of the objective substance by a silica gel thin layer chromatography (TLC) (developing solvent, ethyl acetate: hexane=1:10) was 0.28 and that of (4-bromophenyl)[4'-(1-naphthyl)biphenyl-4-yl]phenylamine was 0.42.

Figure 50A:
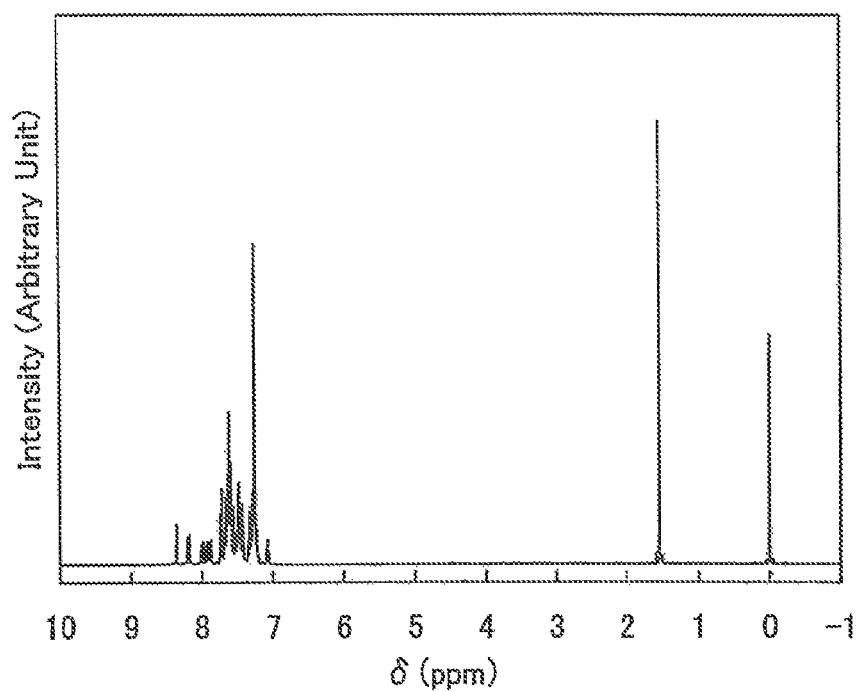
FIGS. 50A and 50B are graphs showing $^1$H NMR charts of PCBANT (abbreviation)
Figure 50B:
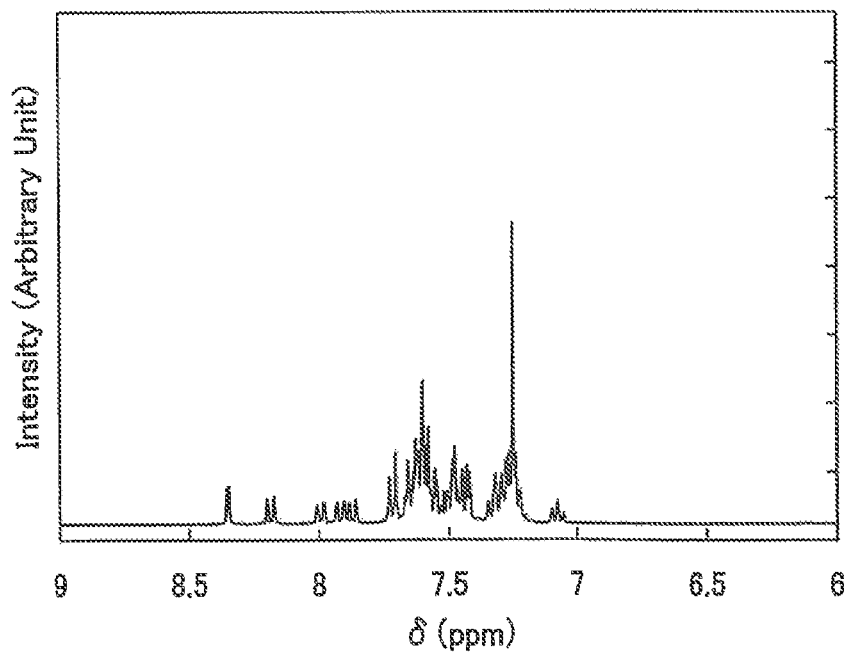

A compound which was obtained through the above Step 4 was measured by a nuclear magnetic resonance method ($^1$H NMR). The measurement result is described below, and the $^1$H NMR chart is shown in FIGS. 50A and 50B. It was found from the measurement result that the carbazole derivative of the present invention, PCBANT (abbreviation) represented by the above structural formula (355), was obtained. $^1$H NMR (CDCl$_3$, 300 MHz): δ (ppm)=7.08 (t, J=7.5 Hz, 1H), 7.20-7.73 (m, 30H), 7.87 (d, J=8.1 Hz, 1H), 7.92 (d, J=7.2 Hz, 1H), 8.00 (d, J=8.4 Hz, 1H), 8.19 (d, J=7.8 Hz, 1H), 8.35 (d, J=1.8 Hz, 1H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 689.30 (mode is ES+) was detected, and it was confirmed that an objective PCBANT (abbreviation) was obtained.

In addition, an absorption spectrum of PCBANT (abbreviation) (measurement range: 200 nm to 800 nm) was measured. In the case of the toluene solution, an absorption peak on a long wavelength side was observed at around 342 nm, and in the case of the thin film, an absorption peak on a long wavelength side was observed at around 351 nm.

In addition, an emission spectrum of PCBANT (abbreviation) (measurement range: 370 nm to 550 nm) was measured. In the case of the toluene solution, a maximum emission wavelength was 414 nm (excitation wavelength: 355 nm), and in the case of the thin film, a maximum emission wavelength was 342 nm (excitation wavelength: 365 nm). Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCBANT (abbreviation) was −5.38 eV. The Tauc plot of the absorption spectrum of the thin film revealed that the absorption edge was 3.11 eV. Thus, the energy gap in the solid state was estimated to be 3.11 eV, which means that the LUMO level of PCBANT (abbreviation) is −2.27 eV.

An oxidation-reduction reaction characteristic of PCBANT (abbreviation) was examined by a cyclic voltammetry (CV) measurement. Since the measurement method is similar to that of Embodiment 1, the description is omitted.

According to the calculation similar to that of Embodiment 1, the HOMO level of PCBANT (abbreviation) was found to be =−5.43 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBANT (abbreviation) was examined with a differential scanning calorimetry (Pyris 1 DSC, manufactured by Perkin Elmer Co., Ltd.). According to the measurement results, it was found that the glass transition temperature was 131° C. In this manner, PCBANT (abbreviation) has a high glass transition temperature and favorable heat resistance. In addition, the crystallization peak does not exist; thus, it was found that PCBANT (abbreviation) is a substance which is hard to be crystallized.

Note that the efficiency, the drive voltage at a luminance of about 1000 cd/m$^2$, and the reliability of a light-emitting element formed using PCBANT (abbreviation) which was synthesized in Embodiment 11 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 1186 cd/m$^2$ and 0.73 mA, respectively, and the light-emitting element exhibited 65% of the initial luminance when driven for 180 hours.

Embodiment 12

In Embodiment 12, a synthetic method of a carbazole derivative of the present invention, 4-[9-(biphenyl-4-yl)-9H-carbazol-3-yl)-4'-phenyl-triphenylamine (abbreviation: BCBA1BP) represented by a structural formula (63), will be specifically described.

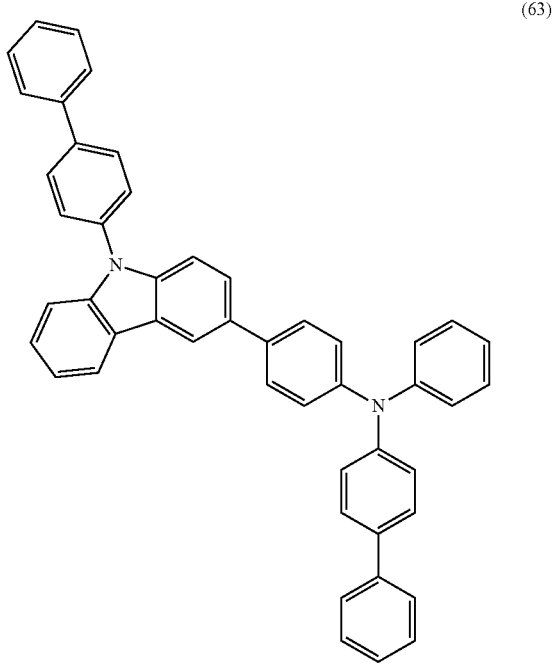 [SMILES: c1ccc(-c2ccc(N(c3ccccc3)c3ccc(-c4ccc5c(c4)c4ccccc4n5-c4ccc(-c5ccccc5)cc4)cc3)cc2)cc1]

(63)

Step 1: Synthesis of 9-(biphenyl-4-yl)-9H-carbazole

A synthetic scheme of 9-(biphenyl-4-yl)-9H-carbazole in Step 1 is shown in the following (N-1).

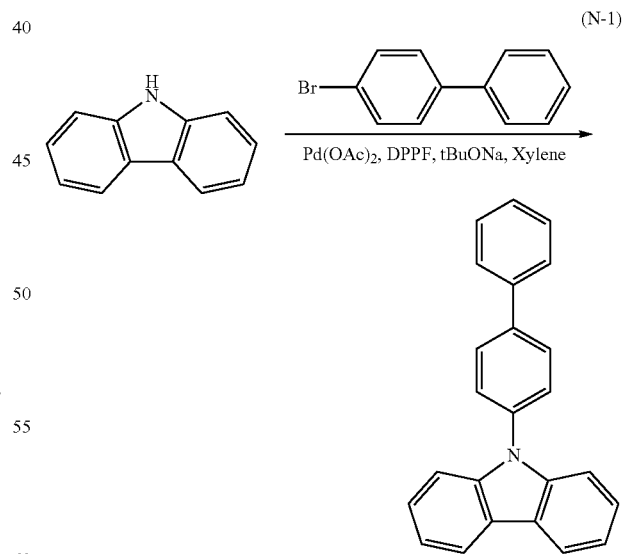

(N-1)

In a 200-mL three-neck flask, 12 g (50 mmol) of 4-bromobiphenyl, 8.4 g (50 mmol) of carbazole, 230 mg (1 mmol) of palladium acetate (abbreviation: Pd(OAc)(II)), 1.8 g (3.0 mmol) of 1,1-bis(diphenylphosphino)ferrocene (abbreviation: DPPF), and 13 g (180 mmol) of sodium tert-butoxide were put, and the atmosphere of the flask was substituted by nitrogen. Then, 80 mL of dehydrated xylene was added to this mixture. This mixture was deaerated while being stirred under low pressure, and the mixture was stirred under a nitrogen atmosphere at 120° C. for 7.5 hours to be reacted.

After completion of the reaction, about 600 mL of heated toluene was added to this suspension, and filtrated twice through Florisil, alumina, and then Celite. The obtained filtrate was concentrated, and hexane was added thereto. The mixture was recrystallized to obtain 14 g of an objective white powder at a yield of 87%.

Step 2: Synthesis of 9-(biphenyl-4-yl)-3-bromo-9H-carbazole

A synthetic scheme of 9-(biphenyl-4-yl)-3-bromo-9H-carbazole in Step 2 is shown in the following (N-2).

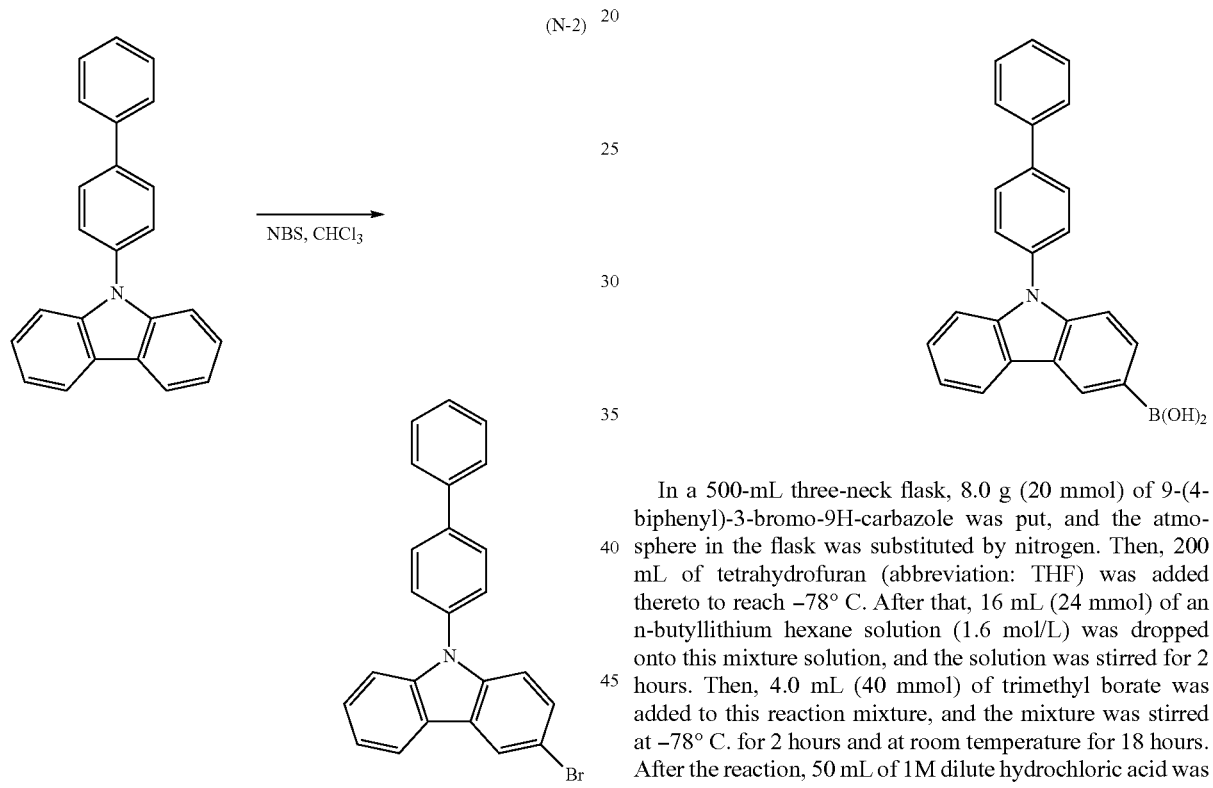

After 3.1 g (10 mmol) of 9-(biphenyl-4-yl)-9H-carbazole was dissolved in 100 mL of chloroform in a 200-mL conical flask, 1.8 g (10 mmol) of N-bromo succinimide (abbreviation: NBS) was added to this solution. After that, this mixture was stirred at room temperature for 24 hours. After completion of the reaction, this mixture solution was washed with water, and magnesium sulfate was added thereto to remove moisture. This mixture solution was filtrated, and the obtained filtrate was concentrated and dried to obtain 3.7 g of an objective white powder at a yield of 95%.

Step 3: Synthesis of [9-(biphenyl-4-yl)-9H-carbazol-3-yl]boronic acid

A synthetic scheme of [9-(biphenyl-4-yl)-9H-carbazol-3-yl]boronic acid in Step 3 is shown in the following (N-3).

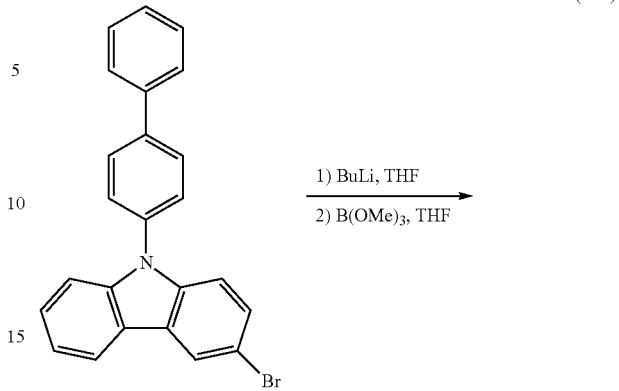

In a 500-mL three-neck flask, 8.0 g (20 mmol) of 9-(4-biphenyl)-3-bromo-9H-carbazole was put, and the atmosphere in the flask was substituted by nitrogen. Then, 200 mL of tetrahydrofuran (abbreviation: THF) was added thereto to reach −78° C. After that, 16 mL (24 mmol) of an n-butyllithium hexane solution (1.6 mol/L) was dropped onto this mixture solution, and the solution was stirred for 2 hours. Then, 4.0 mL (40 mmol) of trimethyl borate was added to this reaction mixture, and the mixture was stirred at −78° C. for 2 hours and at room temperature for 18 hours. After the reaction, 50 mL of 1M dilute hydrochloric acid was added to this reaction solution, and the mixture was stirred for 3 hours. This mixture was extracted with toluene, and the obtained organic layer was washed with a saturated saline solution. After the washing, magnesium sulfate was added to the organic layer to remove moisture. This suspension was filtrated, the obtained filtrate was concentrated, and hexane was added thereto. The mixture was irradiated with supersonic and then recrystallized to obtain 6.6 g of an objective white powder at a yield of 91%.

Step 4: Synthesis of 4-[9-(biphenyl-4-yl)-9H-carbazol-3-yl)-4'-phenyl-triphenylamine (abbreviation: BCBA1BP)

A synthetic scheme of 4-[9-(biphenyl-4-yl)-9H-carbazol-3-yl)-4'-phenyl-triphenylamine in Step 4 is shown in the following (N-4).

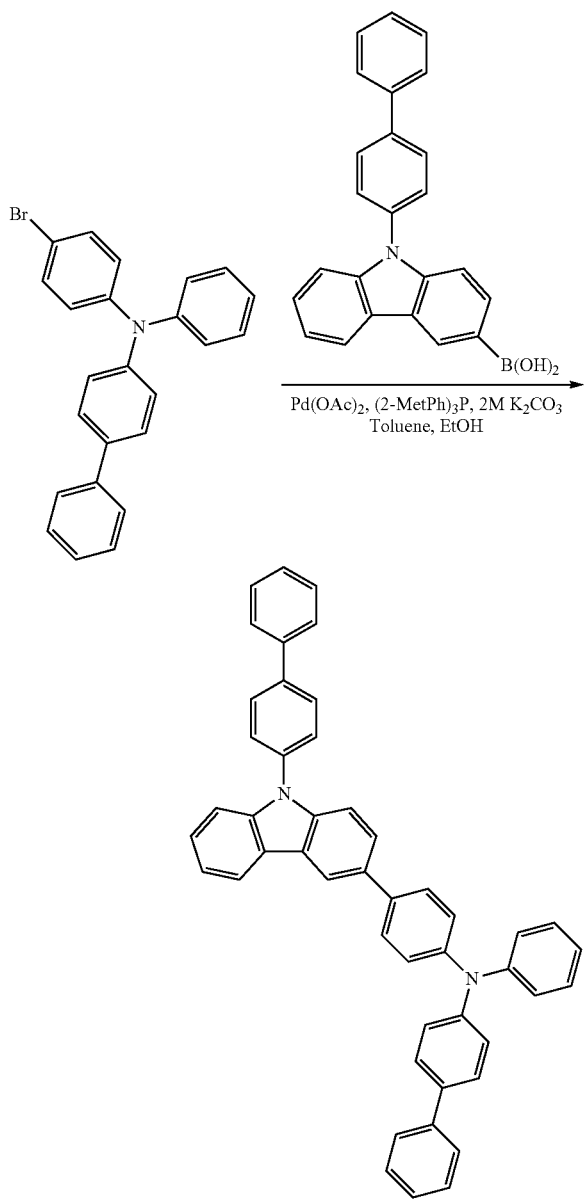

(N-4)

Pd(OAc)₂, (2-MetPh)₃P, 2M K₂CO₃
Toluene, EtOH

In a 50-mL three-neck flask, 1.2 g (3.0 mmol) of 4-bromo-4'-phenyl-triphenylamine, 1.1 g (3.0 mmol) of [9-(biphenyl-4-yl)-9H-carbazol-3-yl]boronic acid, 6.0 mg (0.03 mmol) of palladium(II) acetate, and 18 mg (0.06 mmol) of tri(o-tolyl)phosphine were put, and 20 mL of toluene, 5 mL of ethanol, and 3 mL of a potassium carbonate solution (2 mol/L) were added to this mixture. This mixture was deaerated while being stirred under low pressure. After the deaeration, the mixture was stirred under a nitrogen atmosphere at 90° C. for 6.5 hours to be reacted.

After the reaction, 150 mL of toluene was added to this reaction mixture, and this suspension was filtrated through Florisil and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and acetone and methanol were added thereto. The mixture was irradiated with supersonic and then recrystallized to obtain 1.5 g of an objective white powder at a yield of 79%.

An Rf value of the objective substance by a silica gel thin layer chromatography (TLC) (developing solvent, ethyl acetate: hexane=1:10) was 0.45 and that of 4-bromo-4'-phenyl-triphenylamine was 0.68.

Figure 51A:
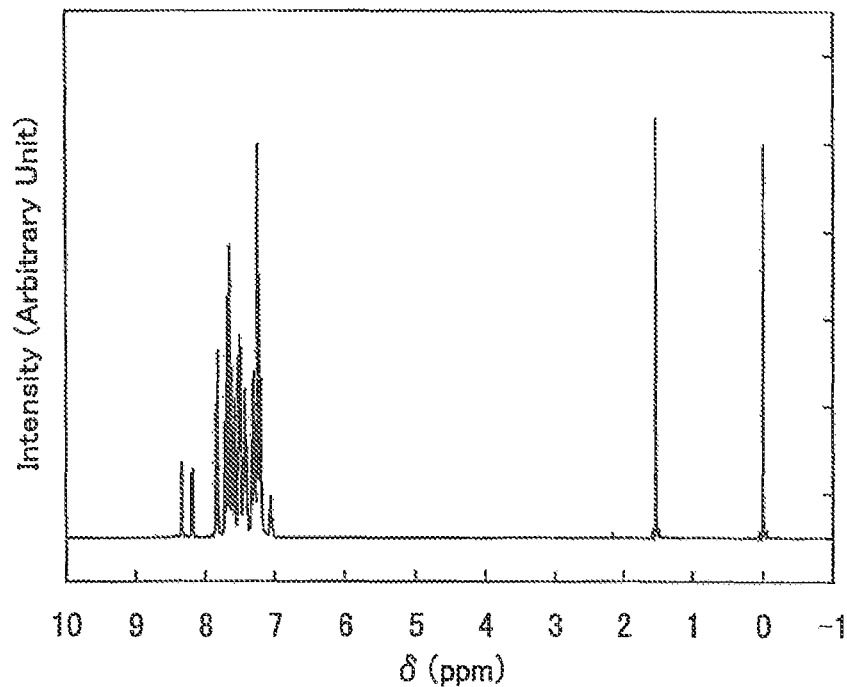
FIGS. 51A and 51B are graphs showing $^1$H NMR charts of BCBA1BP (abbreviation)
Figure 51B:
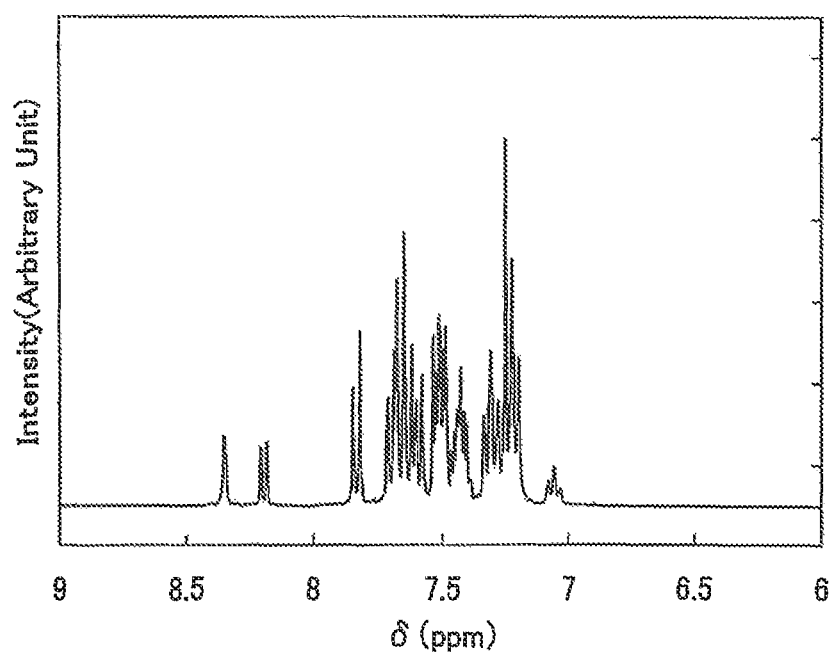

A compound which was obtained through the above Step 4 was measured by a nuclear magnetic resonance method ($^1$H NMR). The measurement result is described below, and the $^1$H NMR chart is shown in FIGS. 51A and 51B. It was found from the measurement result that the carbazole derivative of the present invention, BCBA1BP (abbreviation) represented by the above structural formula (63), was obtained. $^1$H NMR (CDCl$_3$, 300 MHz): δ (ppm)=7.06 (t, J=7.2 Hz, 1H), 7.20-7.72 (m, 29H), 7.83 (d, J=8.4 Hz, 2H), 8.19 (d, J=7.8 Hz, 1H), 8.35 (s, 1H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 638.27 (mode is ES+) was detected, and it was confirmed that an objective BCBA1BP (abbreviation) was obtained.

In addition, an absorption spectrum of PCBA1BP (abbreviation) (measurement range: 200 nm to 800 nm) was measured. In the case of the toluene solution, an absorption peak on a long wavelength side was observed at around 336 nm, and in the case of the thin film, an absorption peak on a long wavelength side was observed at around 342 nm.

In addition, an emission spectrum of PCBA1BP (abbreviation) (measurement range: 370 nm to 550 nm) was measured. In the case of the toluene solution, a maximum emission wavelength was 394 nm (excitation wavelength: 350 nm), and in the case of the thin film, a maximum emission wavelength was 408 nm (excitation wavelength: 301 nm). Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of PCBA1BP (abbreviation) was −5.48 eV. The Tauc plot of the absorption spectrum of the thin film revealed that the absorption edge was 3.19 eV. Thus, the energy gap in the solid state was estimated to be 3.19 eV, which means that the LUMO level of PCBA1BP (abbreviation) is −2.29 eV.

An oxidation-reduction reaction characteristic of PCBA1BP (abbreviation) was examined by a cyclic voltammetry (CV) measurement. Since the measurement method is similar to that of Embodiment 1, the description is omitted.

According to the calculation similar to that of Embodiment 1, the HOMO level of PCBA1BP (abbreviation) was found to be =−5.43 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBA1BP (abbreviation) was examined with a differential scanning calorimetry (Pyris 1 DSC, manufactured by Perkin Elmer Co., Ltd.). According to the measurement results, it was found that the glass transition temperature was 122° C. In this manner, PCBA1BP (abbreviation) has a high glass transition temperature and favorable heat resistance. In addition, the crystallization peak does not exist; thus, it was found that PCBA1BP (abbreviation) is a substance which is hard to be crystallized.

Note that the efficiency, the drive voltage at a luminance of about 1000 cd/m$^2$, and the reliability of a light-emitting element formed using PCBA1BP (abbreviation) which was synthesized in Embodiment 12 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 1031 cd/m$^2$ and 0.72 mA, respectively, and the light-emitting element exhibited 89% of the initial luminance when driven for 180 hours.

Embodiment 13

In Embodiment 13, a synthetic method of a carbazole derivative of the present invention, 4-[9-(biphenyl-4-yl)-9H-carbazol-3-yl]-4'-(1-naphthyl)triphenylamine (abbreviation: BCBANB) represented by a structural formula (364), will be specifically described.

(364)

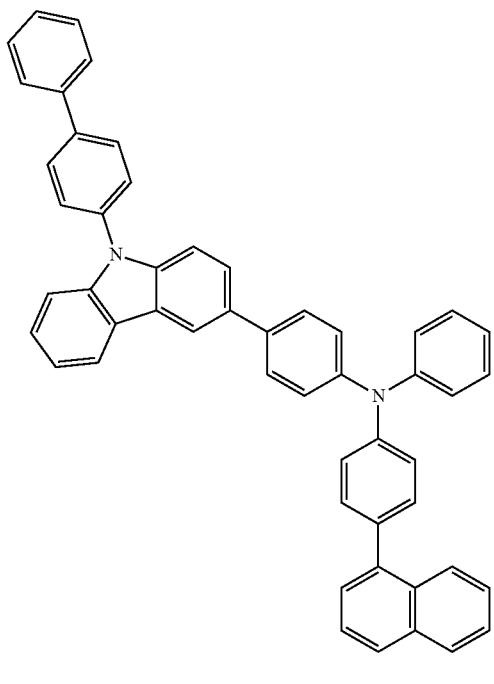

Step 1: Synthesis of 4-bromotriphenylamine

A synthetic scheme of 4-bromotriphenylamine in Step 1 is shown in the following (0-1).

(0-1)

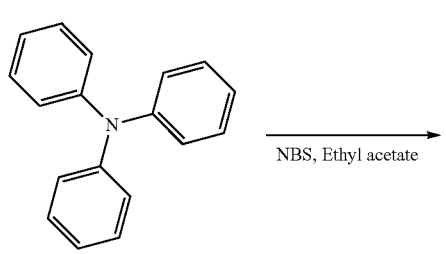

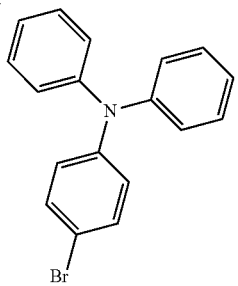

To 1.5 L of an ethyl acetate solution containing 54.0 g (220 mmol) of triphenylamine, 35.6 g (200 mmol) of N-bromo succinimide (abbreviation: NBS) was added. Then, the mixture was stirred for 24 hours. After the obtained suspension was concentrated to 1 L, the concentrated suspension was washed with 1 L of an aqueous solution containing 5% of sodium acetate. After the washing, this solution was further concentrated to about 50 mL. Then, methanol was added to the concentrated solution and the solution was precipitated. The obtained precipitate was filtered and dried to obtain 46.5 g of an objective white powder at a yield of 73%.

Step 2: Synthesis of 4-(1-naphthyl)triphenylamine

A synthetic scheme of 4-(1-naphthyl)triphenylamine in Step 2 is shown in the following (0-2).

(0-2)

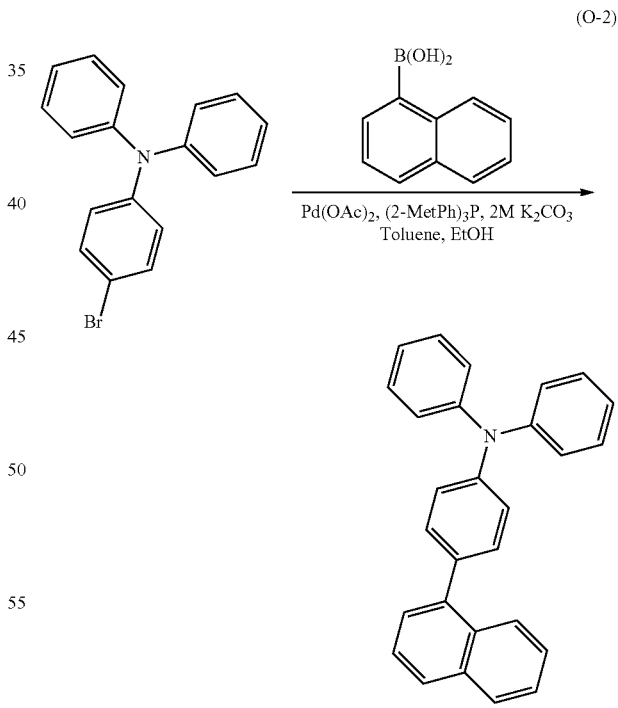

In a 20 mL three-neck flask, 9.7 g (30 mmol) of 4-bromotriphenylamine, 5.7 g (33 mmol) of 1-naphthaleneboronic acid, 67 mg (0.3 mmol) of palladium(II) acetate, and 91 g (0.3 mmol) of tri(o-tolyl)phosphine were put, and 20 mL of toluene, 20 mL of ethanol, and 20 mL of a potassium carbonate solution (2 mol/L) were added to this mixture. This mixture was deaerated while being stirred under low pressure. After the deaeration, the mixture was stirred under a nitrogen atmosphere at 90° C. for 2 hours to be reacted.

After the reaction, 150 mL of toluene was added to this reaction mixture, and this suspension was filtrated through Florisil, silica gel, and then Celite. The obtained filtrate was washed with sodium hydrogen carbonate solution and water in this order, and magnesium sulfate was added thereto to dry the filtrate. After the drying, this suspension was filtrated through Florisil, alumina, silica gel, and then Celite to obtain filtrate. The obtained filtrate was concentrated and dried to obtain 11 g of an objective light-yellow solid at a yield of 99%.

An Rf value of the objective substance by a silica gel thin layer chromatography (TLC) (developing solvent, ethyl acetate: hexane=1:10) was 0.48 and that of 4-bromotriphenylamine was 0.55.

A compound which was obtained through the above Step 2 was measured by a nuclear magnetic resonance method ($^1$H NMR). It was found from the measurement result that the compound of the present invention represented by the above structural formula (364) was obtained. $^1$H NMR (CDCl$_3$, 300 MHz): δ (ppm)=7.07 (t, J=7.5 Hz, 1H), 7.22-7.61 (m, 21H), 7.83 (d, J=7.8 Hz, 1H), 7.88-7.91 (m, 1H), 8.02-8.05 (m, 1H).

Step 3: Synthesis of 4-bromo-4'-(1-naphthyl)triphenylamine

A synthetic scheme of 4-bromo-4'-(1-naphthyl)triphenylamine in Step 3 is shown in the following (0-3).

(0-3)

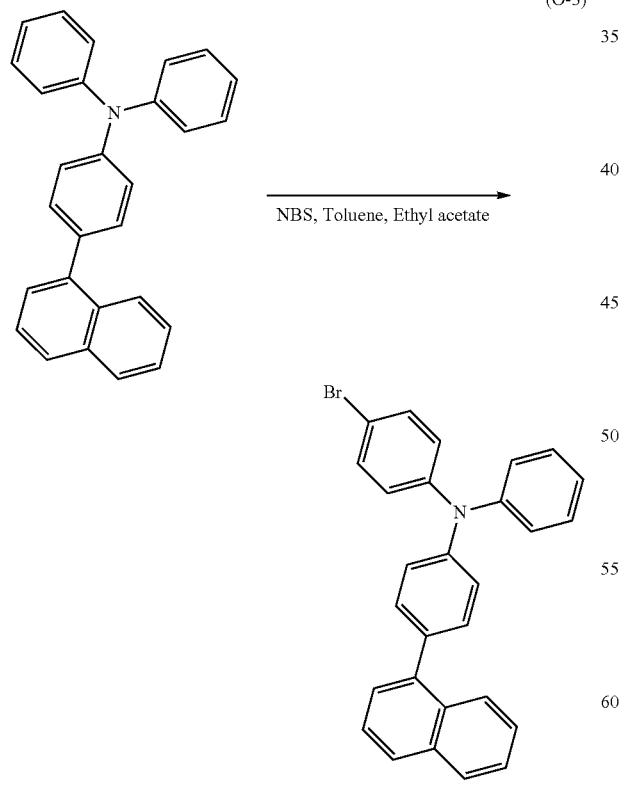

After 11 g (30 mmol) of 4-(1-naphthyl)triphenylamine was dissolved in 300 mL of ethyl acetate in a 500-mL recovery flask, 5.3 g (30 mmol) of N-bromo succinimide (abbreviation: NBS) was added to this solution. After that, this mixture was stirred at room temperature for 168 hours. After completion of the reaction, this mixture solution was washed with water, and magnesium sulfate was added thereto to remove moisture. This mixture solution was filtrated, and the obtained filtrate was concentrated and purified by silica gel column chromatography (developing solvent, toluene: hexane=1:4). The obtained fraction was concentrated, and methanol was added thereto. The mixture was irradiated with supersonic and then recrystallized to obtain 7.8 g of an objective white powder at a yield of 43%.

Step 4: Synthesis of 4-[9-(biphenyl-4-yl)-9H-carabazol-3-yl]-4'-(1-naphthyl)triphenylamine (abbreviation: BCBANB)

A synthetic scheme of 4-[9-(biphenyl-4-yl)-9H-carabazol-3-yl]-4'-(1-naphthyl)triphenylamine in Step 4 is shown in the following (0-4).

(0-4)

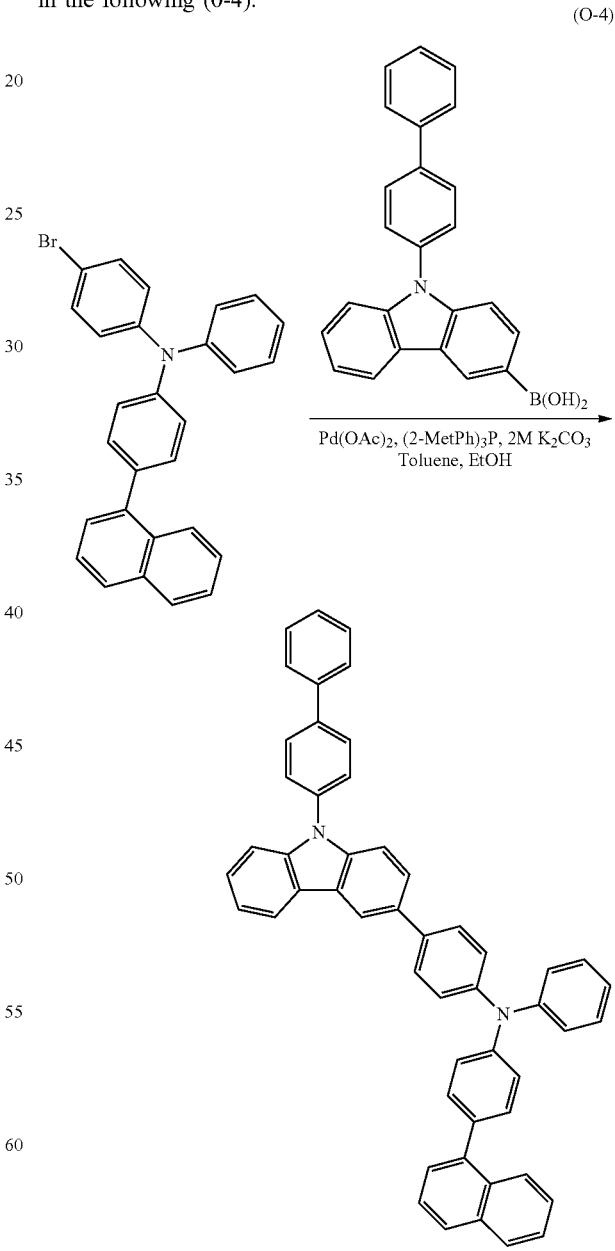

In a 100-mL three-neck flask, 1.35 g (3.0 mmol) of 4-bromo-4'-(1-naphthyl)triphenylamine, 1.1 g (3.0 mmol) of

[9-(biphenyl-4-yl)-9H-carbazol-3-yl]boronic acid, 6.0 mg (0.02 mmol) of palladium(II) acetate, and 9.0 mg (0.06 mmol) of tri(o-tolyl)phosphine were put, and 20 mL of toluene, 5 mL of ethanol, and 3 mL of a potassium carbonate solution (2 mol/L) were added to this mixture. This mixture was deaerated while being stirred under low pressure. After the deaeration, the mixture was stirred under a nitrogen atmosphere at 90° C. for 3 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene:hexane=1:4). The obtained fraction was concentrated, and acetone and methanol were added thereto. The mixture was irradiated with supersonic and then recrystallized to obtain 1.0 g of an objective white powder at a yield of 50%.

An Rf value of the objective substance by a silica gel thin layer chromatography (TLC) (developing solvent, ethyl acetate: hexane=1:10) was 0.45 and that of 4-bromo-4'-(1-naphthyl)triphenylamine was 0.66.

Figure 52A:
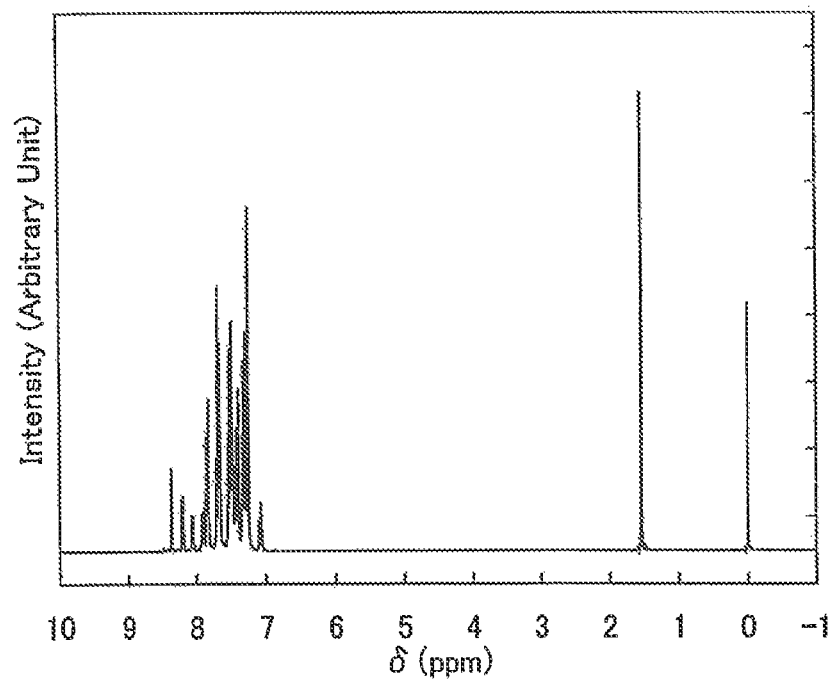
FIGS. 52A and 52B are graphs showing $^1$H NMR charts of BCBANB (abbreviation)
Figure 52B:
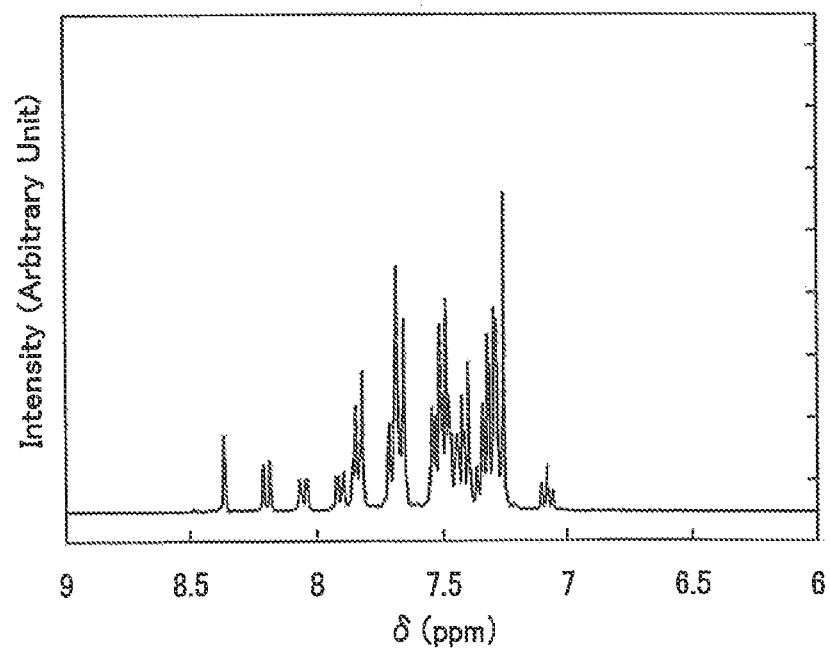

A compound which was obtained through the above Step 4 was measured by a nuclear magnetic resonance method ($^1$H NMR). The measurement result is described below, and the $^1$H NMR chart is shown in FIGS. 52A and 52B. It was found from the measurement result that the carbazole derivative of the present invention, BCBANB (abbreviation) represented by the above structural formula (364), was obtained. $^1$H NMR (CDCl$_3$, 300 MHz): δ (ppm)=7.08 (t, J=6.9 Hz, 1H), 7.28-7.71 (m, 28H), 7.82-7.86 (m, 3H), 7.89-7.92 (m, 1H), 8.04-8.07 (m, 1H), 8.20 (d, J=7.8 Hz, 1H), 8.37 (d, J=1.2 Hz, 1H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the forminc acid solution, 80/20 vol/vol) was used as a solvent. Accordingly, a main peak with a molecular weight of 556.52 (mode is ES+) was detected, and it was confirmed that an objective BCBANB (abbreviation) was obtained.

In addition, an absorption spectrum of BCBANB (abbreviation) (measurement range: 200 nm to 800 nm) was measured. In the case of the toluene solution, an absorption peak on a long wavelength side was observed at around 335 nm, and in the case of the thin film, an absorption peak on a long wavelength side was observed at around 344 nm.

In addition, an emission spectrum of BCBANB (abbreviation) (measurement range: 370 nm to 550 nm) was measured. In the case of the toluene solution, a maximum emission wavelength was 410 nm (excitation wavelength: 345 nm), and in the case of the thin film, a maximum emission wavelength was 422 nm (excitation wavelength: 328 nm).

Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of BCBANB (abbreviation) was −5.42 eV. The Tauc plot of the absorption spectrum of the thin film revealed that the absorption edge was 3.19 eV. Thus, the energy gap in the solid state was estimated to be 3.19 eV, which means that the LUMO level of BCBANB (abbreviation) is −2.23 eV.

An oxidation-reduction reaction characteristic of BCBANB (abbreviation) was examined by a cyclic voltammetry (CV) measurement. Since the measurement method is similar to that of Embodiment 1, the description is omitted.

According to the calculation similar to that of Embodiment 1, the HOMO level of BCBANB (abbreviation) was found to be =−5.45 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of BCBANB (abbreviation) was examined with a differential scanning calorimetry (Pyris 1 DSC, manufactured by Perkin Elmer Co., Ltd.). According to the measurement results, it was found that the glass transition temperature was 130° C. In this manner, BCBANB (abbreviation) has a high glass transition temperature and favorable heat resistance. In addition, the crystallization peak does not exist; thus, it was found that BCBANB (abbreviation) is a substance which is hard to be crystallized.

Note that the efficiency, the drive voltage at a luminance of about 1000 cd/m$^2$, and the reliability of a light-emitting element formed using BCBANB (abbreviation) which was synthesized in Embodiment 13 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 848 cd/m$^2$ and 0.52 mA, respectively.

Embodiment 14

In Embodiment 14, a synthetic method of a carbazole derivative of the present invention, 4-[9-(biphenyl-4-yl)-9H-carbazol-3-yl)-4'-(1-naphthyl)4"-phenyl-triphenylamine (abbreviation: BCBBiNB) represented by a structural formula (366), will be specifically described.

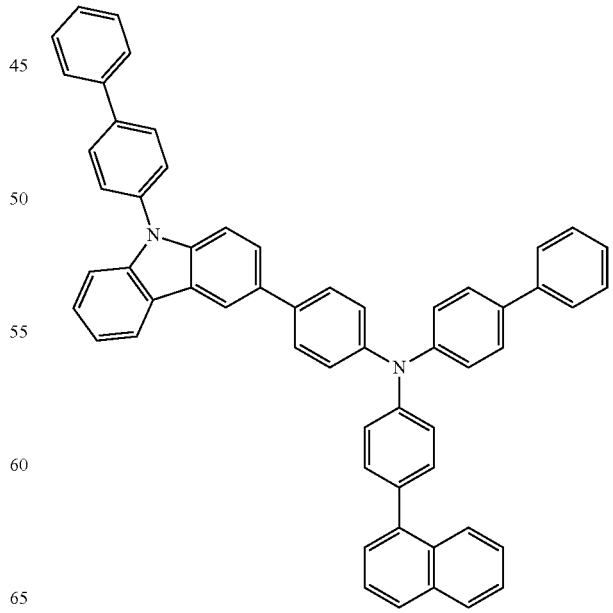

(366)

Step 1: Synthesis of 4-[9-(biphenyl-4-yl)-9H-carbazol-3-yl)-4'-(1-naphthyl)4"-phenyl-triphenylamine (abbreviation: BCBBiNB)

A synthetic scheme of 4-[9-(biphenyl-4-yl)-9H-carbazol-3-yl)-4'-(1-naphthyl)4"-phenyl-triphenylamine in Step 1 is shown in the following (P-1).

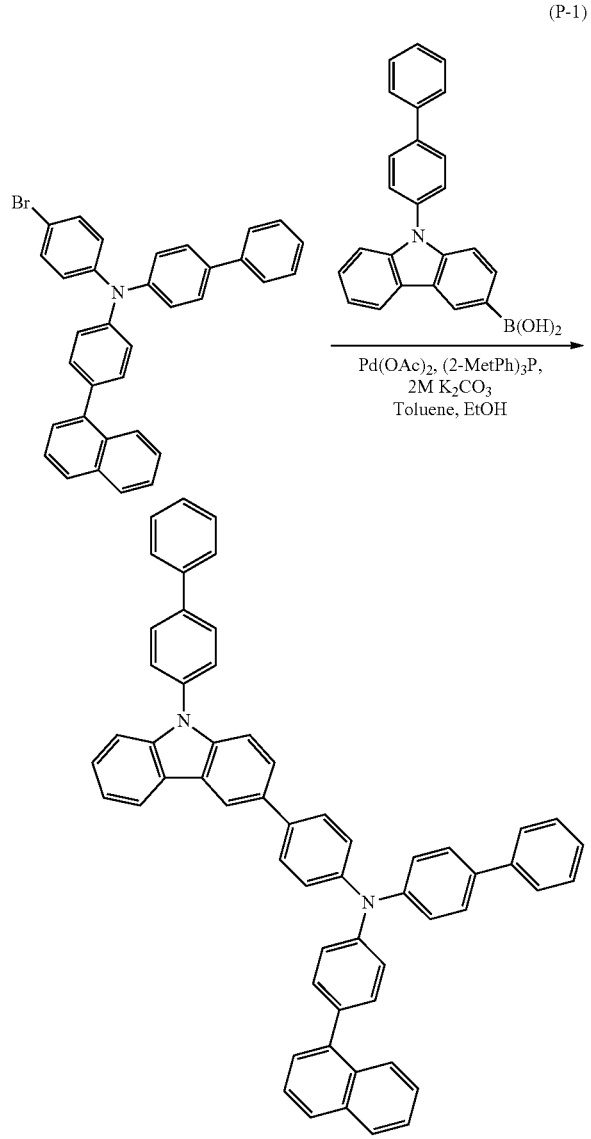

(P-1)

In a 100-mL three-neck flask, 1.6 g (3.0 mmol) of 4-bromo-4'-(1-naphthyl)-4"-phenyl-triphenylamine, 1.1 g (3.0 mmol) of [9-(biphenyl-4-yl)-9H-carbazol-3-yl]boronic acid, 6.0 mg (0.03 mmol) of palladium(II) acetate, and 18 mg (0.03 mmol) of tri(o-tolyl)phosphine were put, and 20 mL of toluene, 5 mL of ethanol, and 3 mL of a potassium carbonate solution (2 mol/L) were added to this mixture. This mixture was deaerated while being stirred under low pressure. After the deaeration, the mixture was stirred under a nitrogen atmosphere at 90° C. for 6.5 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene: hexane=1:4). The obtained fraction was concentrated, and acetone and methanol were added thereto. The mixture was irradiated with supersonic and then recrystallized to obtain 1.4 g of an objective white powder at a yield of 60%.

An Rf value of the objective substance by a silica gel thin layer chromatography (TLC) (developing solvent, ethyl acetate: hexane=1:10) was 0.26 and that of 4-bromo-4'-(1-naphthyl)-4"-phenyl-triphenylamine was 0.46.

Figure 53A:
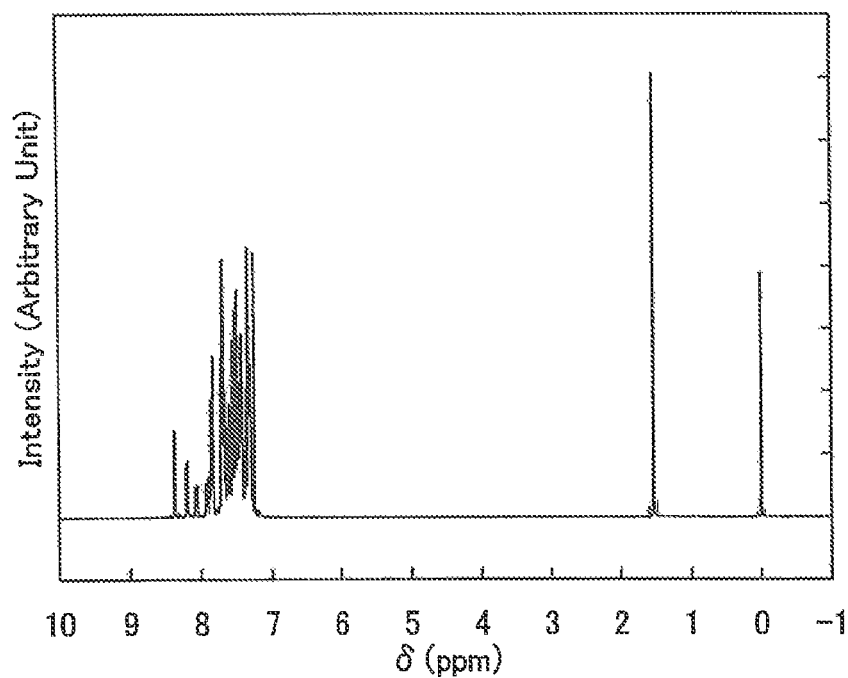
FIGS. 53A and 53B are graphs showing $^1$H NMR charts of BCBBiNB (abbreviation)
Figure 53B:
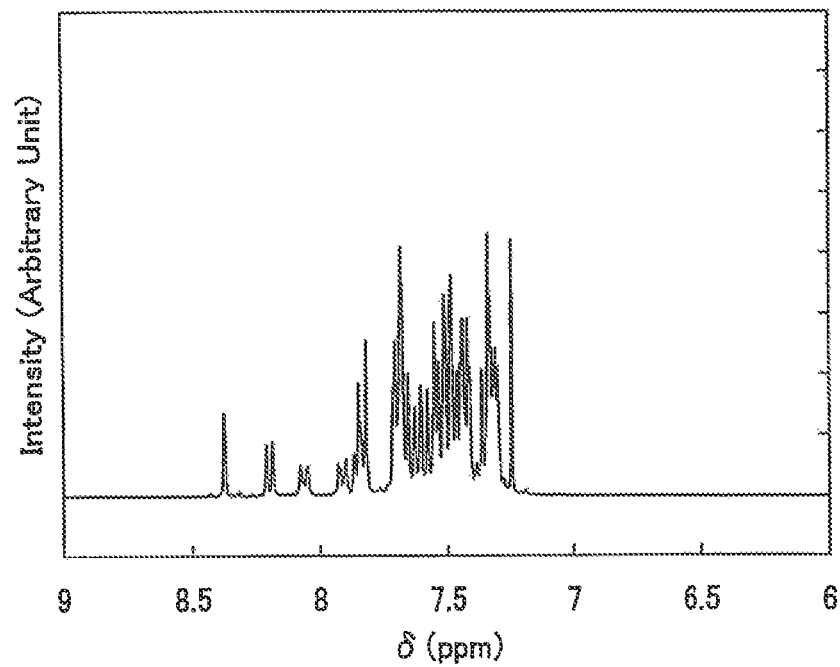

A compound which was obtained through the above Step 1 was measured by a nuclear magnetic resonance method ($^1$H NMR). The measurement result is described below, and the $^1$H NMR chart is shown in FIGS. 53A and 53B. It was found from the measurement result that the carbazole derivative of the present invention, BCBBiNB (abbreviation) represented by the above structural formula (366), was obtained. $^1$H NMR (CDCl$_3$, 300 MHz): δ (ppm)=7.30-7.71 (m, 33H), 7.82-7.86 (m, 3H), 7.90-7.93 (m, 1H), 8.05-8.08 (m, 1H), 8.20 (d, J=7.8 Hz, 1 H), 8.38 (d, J=1.5 Hz, 1H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the formine acid solution, 80/20 vol/vol) was used as a solvent. Accordingly, a main peak with a molecular weight of 765.32 (mode is ES+) was detected, and it was confirmed that an objective BCBBiNB (abbreviation) was obtained.

In addition, an absorption spectrum of BCBBiNB (abbreviation) (measurement range: 200 nm to 800 nm) was measured. In the case of the toluene solution, an absorption peak on a long wavelength side was observed at around 342 nm, and in the case of the thin film, an absorption peak on a long wavelength side was observed at around 351 nm.

In addition, an emission spectrum of BCBBiNB (abbreviation) (measurement range: 370 nm to 550 nm) was measured. In the case of the toluene solution, a maximum emission wavelength was 409 nm (excitation wavelength: 355 nm), and in the case of the thin film, a maximum emission wavelength was 433 nm (excitation wavelength: 336 nm).

Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of BCBBiNB (abbreviation) was −5.35 eV. The Tauc plot of the absorption spectrum of the thin film revealed that the absorption edge was 3.18 eV. Thus, the energy gap in the solid state was estimated to be 3.18 eV, which means that the LUMO level of BCBBiNB (abbreviation) is −2.17 eV.

An oxidation-reduction reaction characteristic of BCBBiNB (abbreviation) was examined by a cyclic voltammetry (CV) measurement. Since the measurement method is similar to that of Embodiment 1, the description is omitted.

According to the calculation similar to that of Embodiment 1, the HOMO level of BCBBiNB (abbreviation) was found to be =−5.42 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of BCBBiNB (abbreviation) was examined with a differential scanning calorimetry (Pyris 1 DSC, manufactured by Perkin Elmer Co., Ltd.). According to the measurement results, it was found that the glass transition temperature was 143° C. In this manner, BCBBiNB (abbreviation) has a high glass transition temperature and favorable heat resistance. In addition, the crystallization peak does not exist; thus, it was found that BCBBiNB (abbreviation) is a substance which is hard to be crystallized.

Note that the efficiency, the drive voltage at a luminance of about 1000 $cd/m^2$, and the reliability of a light-emitting element formed using BCBBiNB (abbreviation) which was synthesized in Embodiment 14 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 996 $cd/m^2$ and 0.59 mA, respectively, and the light-emitting element exhibited 84% of the initial luminance when driven for 180 hours.

Embodiment 15

In Embodiment 15, a synthetic method of a carbazole derivative of the present invention, 4-{9-[4-(1-naphthyl)phenyl]-9H-carbazol-3-yl}-4'-phenyl-triphenylamine (abbreviation: NBCBA1BP) represented by a structural formula (386), will be specifically described.

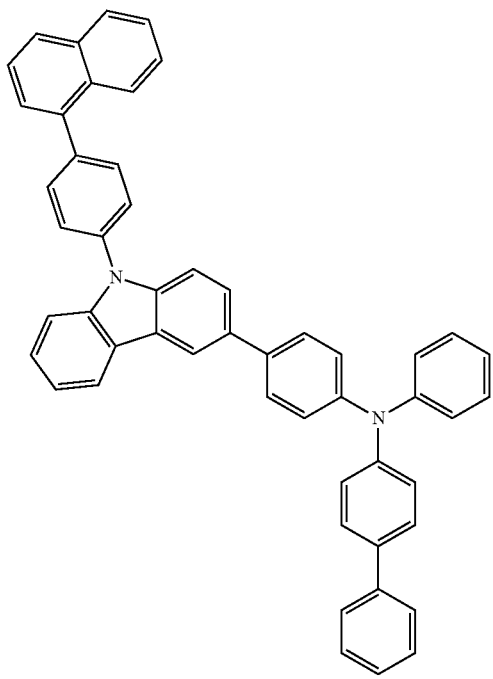

(386)

Step 1: Synthesis of 9-(4-bromophenyl)-9H-carbazole

A synthetic scheme of 9-(4-bromophenyl)-9H-carbazole in Step 1 is shown in the following (Q-1).

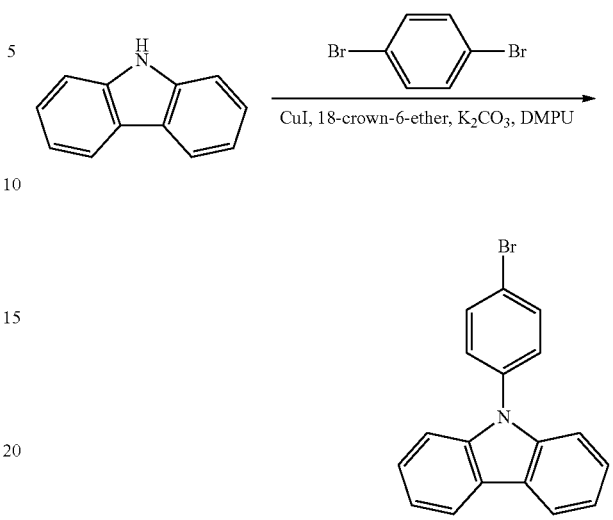

(Q-1)

In a 300-mL three-neck flask, 56 g (240 mmol) of 1,4-dibromobenzene, 31 g (180 mmol) of 9H-carabazole, 4.6 g (24 mmol) of copper(I) iodide, 2.1 g (8.0 mmol) of 18-crown-6-ether, 66 g (480 mmol) of potassium carbonate, and 8 mL of 1,3-dimethyl-3,4,5,6-tetrahydro-2(1H)pyrimidinone (abbreviation: DMPU) were put, and the mixture was stirred under a nitrogen atmosphere at 180° C. for 6 hours.

After the reaction, this suspension was filtrated, and the filtrate was washed with dilute hydrochloric acid, a saturated sodium hydrogen carbonate solution, and a saturated saline solution in this order. Then, moisture was removed by magnesium sulfate. This suspension was filtrated, and the obtained filtrate was concentrated and purified by silica gel column chromatography (developing solvent, toluene: hexane=9:1). The obtained fraction was concentrated, and chloroform and hexane were added thereto. The mixture was irradiated with supersonic and then recrystallized to obtain 21 g of an objective light brown plate-like crystal at a yield of 35%.

Step 2: Synthesis of 9-[4-(1-naphthyl)phenyl]-9H-carbazole

A synthetic scheme of 9-[4-(1-naphthyl)phenyl]-9H-carbazole in Step 2 is shown in the following (Q-2).

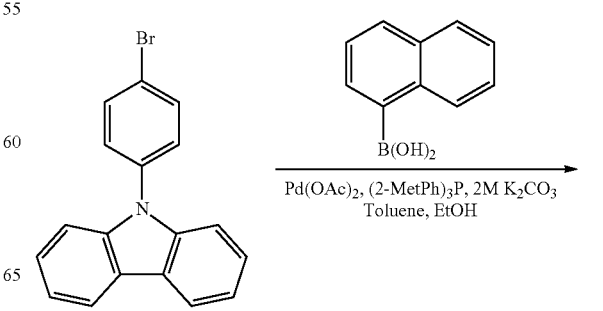

(Q-2)

267
-continued

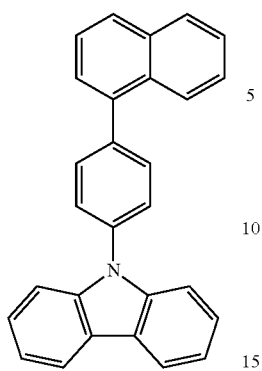

In a 100-mL three-neck flask, 4.8 g (15 mmol) of 9-(4-bromophenyl)-9H-carbazole, 2.6 g (15 mmol) of 1-naphthaleneboronic acid, 2.0 mg (0.01 mmol) of palladium(II) acetate, and 6.0 mg (0.02 mmol) of tri(o-tolyl)phosphine were put, and 20 mL of toluene, 10 mL of ethanol, and 10 mL of a potassium carbonate solution (2 mol/L) were added to this mixture. This mixture was deaerated while being stirred under low pressure. After the deaeration, the mixture was stirred under a nitrogen atmosphere at 90° C. for 9 hours to be reacted.

After the reaction, 150 mL of toluene was added to this reaction mixture, and this suspension was filtrated through Florisil and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and acetone and methanol were added thereto. The mixture was irradiated with supersonic and then recrystallized to obtain 5.0 g of an objective white powder at a yield of 90%.

An Rf value of the objective substance by a silica gel thin layer chromatography (TLC) (developing solvent, ethyl acetate: hexane=1:10) was 0.46 and that of 9-(4-bromophenyl)-9H-carbazole was 0.54.

Step 3: Synthesis of 3-bromo-9-[4-(1-naphthyl)phenyl]-9H-carbazole

A synthetic scheme of 3-bromo-9-[4-(1-naphthyl)phenyl]-9H-carbazole in Step 3 is shown in the following (Q-3).

268
-continued

After 5.0 g (14 mmol) of 9-[4-(1-naphthyl)phenyl]-9H-carbazole was dissolved in a mixture solvent of 50 mL of toluene and 250 mL of ethyl acetate in a 300-mL conical flask, 2.5 g (14 mmol) of N-bromo succinimide (abbreviation: NBS) was added to this solution. After that, this mixture was stirred at room temperature for 168 hours. After completion of the reaction, this mixture solution was filtrated through Florisil and then Celite. Then, the obtained filtrate was washed with water, and magnesium sulfate was added thereto to remove moisture. This mixture solution was filtrated, the obtained filtrate was concentrated, and hexane was added thereto. Then, the mixture was irradiated with supersonic to obtain 6.1 g of an objective white powder at a yield of 99%.

Step 4: Synthesis of 9-[4-(1-naphthyl)phenyl]-9H-carbazol-3-boronic acid

A synthetic scheme of 9-[4-(1-naphthyl)phenyl]-9H-carbazol-3-boronic acid in Step 4 is shown in the following (Q-4).

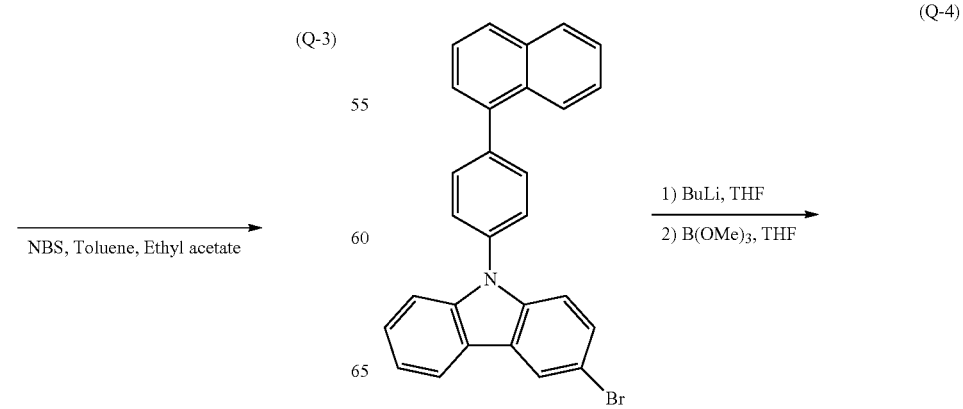

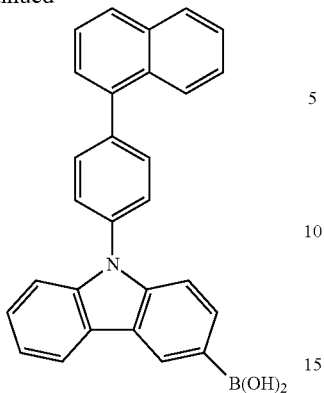

In a 500-mL three-neck flask, 5.0 g (14 mmol) of 3-bromo-9-[4-(1-naphthyl)phenyl]-9H-carbazole was put, and the atmosphere in the flask was substituted by nitrogen. Then, 200 mL of tetrahydrofuran (abbreviation: THF) was added thereto to reach −78° C. 11 mL (17 mmol) of an n-butyllithium hexane solution (1.6 mol/L) was dropped onto this mixture solution, and the solution was stirred for 4 hours. After that, 2.7 mL (27 mmol) of trimethyl borate was added to this reaction mixture, and the mixture was stirred at −78° C. for 2 hours and at room temperature for 16 hours. After the reaction, 50 mL of 1M dilute hydrochloric acid was added to this reaction solution, and the mixture was stirred for 4 hours. This mixture was extracted with toluene, and the obtained organic layer was washed with a saturated saline solution. After the washing, magnesium sulfate was added to the organic layer to remove moisture. This suspension was filtrated, the obtained filtrate was concentrated, and chloroform and hexane were added thereto. The mixture was irradiated with supersonic and then recrystallized to obtain 3.5 g of an objective white powder at a yield of 63%.

Step 5: Synthesis of 4-{9-[4(1-naphthyl)phenyl]-9H-carbazol-3-yl}-4'-phenyl-triphenylamine (abbreviation: NBCBA1BP)

A synthetic scheme of 4-{9-[4(1-naphthyl)phenyl]-9H-carbazol-3-yl}-4'-phenyl-triphenylamine in Step 5 is shown in the following (Q-5).

(Q-5)

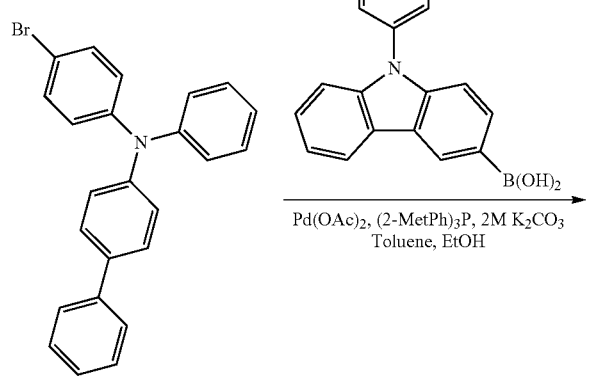

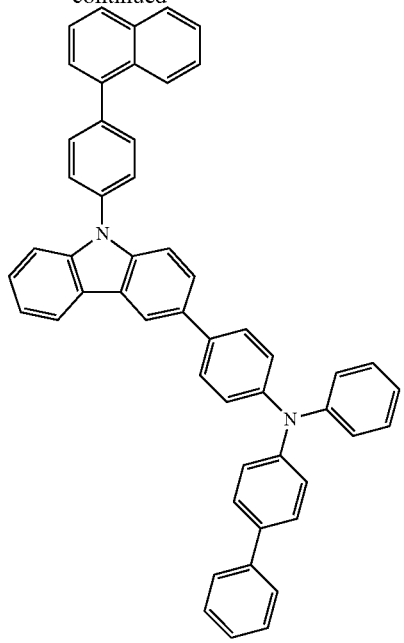

In a 50-mL three-neck flask, 1.0 g (2.5 mmol) of 4-bromo-4'-phenyl-triphenylamine, 1.0 g (2.5 mmol) of 9-[4-(1-naphthyl)phenyl]-9H-carbazol-3-boronic acid, 4.0 mg (0.02 mmol) of palladium(II) acetate, and 6.0 mg (0.02 mmol) of tri(o-tolyl)phosphine were put, and 20 mL of toluene, 5 mL of ethanol, and 2.5 mL of a potassium carbonate solution (2 mol/L) were added to this mixture. This mixture was deaerated while being stirred under low pressure. After the deaeration, the mixture was stirred under a nitrogen atmosphere at 90° C. for 13 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and acetone and methanol were added thereto. The mixture was irradiated with supersonic and then recrystallized to obtain 1.2 g of an objective white powder at a yield of 70%.

An Rf value of the objective substance by a silica gel thin layer chromatography (TLC) (developing solvent, ethyl acetate: hexane=1:10) was 0.41 and that of 4-bromo-4'-phenyl-triphenylamine was 0.62.

Figure 54A:
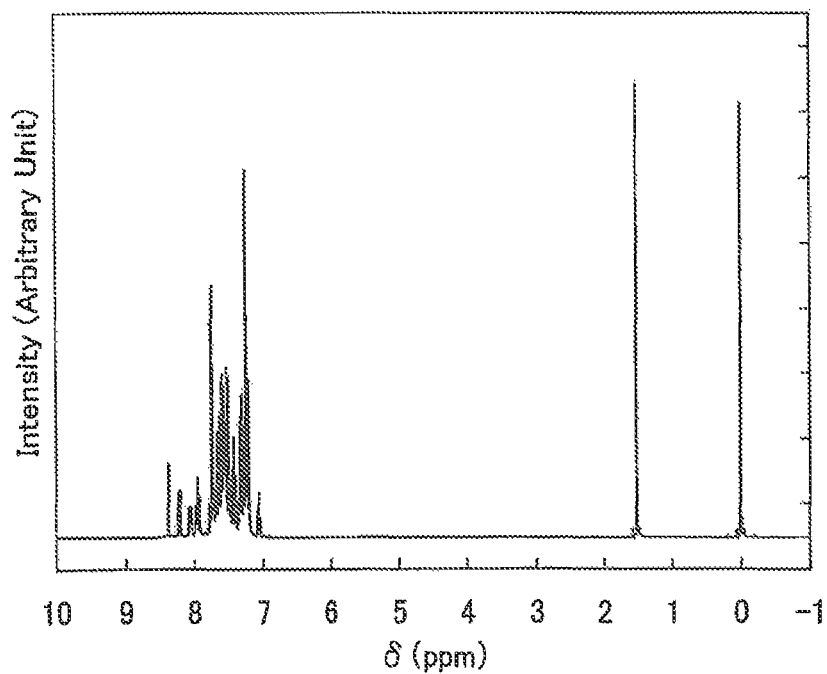
FIGS. 54A and 54B are graphs showing $^1$H NMR charts of NBCBA1BP (abbreviation)
Figure 54B:
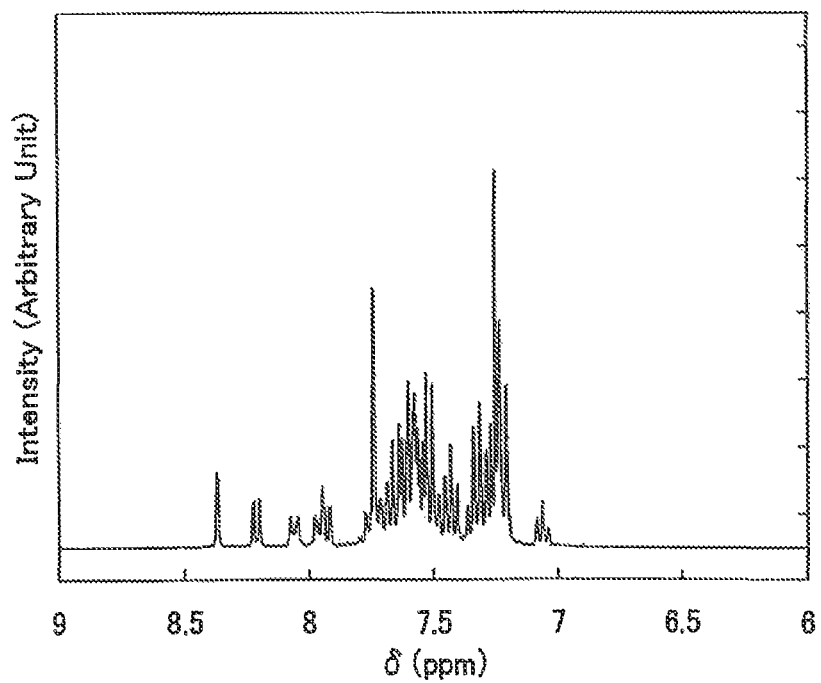

A compound which was obtained through the above Step 5 was measured by a nuclear magnetic resonance method ($^1$H NMR). The measurement result is described below, and the $^1$H NMR chart is shown in FIGS. 54A and 54B. It was found from the measurement result that the carbazole derivative of the present invention, NBCBA1BP (abbreviation) represented by the above structural formula (386), was obtained. $^1$H NMR (CDCl$_3$, 300 MHz): δ (ppm)=7.06 (t, J=6.6 Hz, 1H), 7.21-7.77 (m, 30H), 7.92-7.98 (m, 2H), 8.04-8.08 (m, 1H), 8.22 (d, J=7.8 Hz, 1H), 8.37 (d, J=1.5 Hz, 1H).

In addition, an absorption spectrum of NBCBA1BP (abbreviation) (measurement range: 200 nm to 800 nm) was measured. In the case of the toluene solution, an absorption peak on a long wavelength side was observed at around 333 nm, and in the case of the thin film, an absorption peak on a long wavelength side was observed at around 340 nm.

In addition, an emission spectrum of NBCBA1BP (abbreviation) (measurement range: 370 nm to 550 nm) was measured. In the case of the toluene solution, a maximum emission wavelength was 393 nm (excitation wavelength: 350 nm), and in the case of the thin film, a maximum emission wavelength was 488 nm (excitation wavelength: 302 nm).

Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of NBCBA1BP (abbreviation) was −5.53 eV. The Tauc plot of the absorption spectrum of the thin film revealed that the absorption edge was 3.22 eV. Thus, the energy gap in the solid state was estimated to be 3.22 eV, which means that the LUMO level of NBCBA1BP (abbreviation) is −2.31 eV.

An oxidation-reduction reaction characteristic of NBCBA1BP (abbreviation) was examined by a cyclic voltammetry (CV) measurement. Since the measurement method is similar to that of Embodiment 1, the description is omitted.

According to the calculation similar to that of Embodiment 1, the HOMO level of NBCBA1BP (abbreviation) was found to be =−5.43 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of NBCBA1BP (abbreviation) was examined with a differential scanning calorimetry (Pyris I DSC, manufactured by Perkin Elmer Co., Ltd.). According to the measurement results, it was found that the glass transition temperature was 132° C. In this manner, NBCBA1BP (abbreviation) has a high glass transition temperature and favorable heat resistance. In addition, the crystallization peak does not exist; thus, it was found that NBCBA1BP (abbreviation) is a substance which is hard to be crystallized.

Note that the efficiency, the drive voltage at a luminance of about 1000 cd/m$^2$, and the reliability of a light-emitting element formed using NBCBA1BP (abbreviation) which was synthesized in Embodiment 15 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 3.6 V, the luminance and the current value were 773 cd/m$^2$ and 0.47 mA, respectively.

Embodiment 16

In Embodiment 16, a synthetic method of a carbazole derivative of the present invention, 4-[9-(1-naphthyl)-9H-carbazol-3-yl]-4'-phenyl-triphenylamine (abbreviation: NCBA1BP) represented by a structural formula (395), will be specifically described.

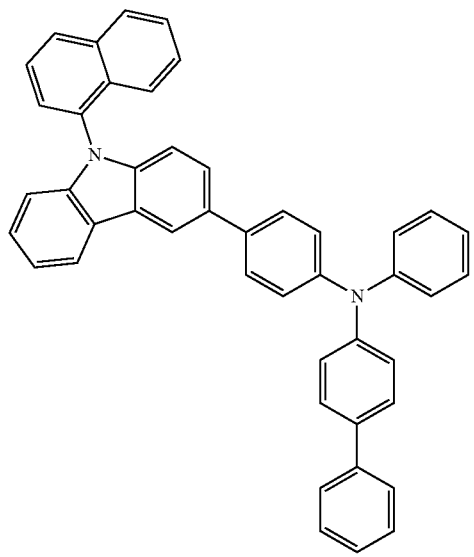

(395)

Step 1: Synthesis of 9-(1-naphthyl)-9H-carbazole

A synthetic scheme of 9-(1-naphthyl)-9H-carbazole in Step 1 is shown in the following (R-1).

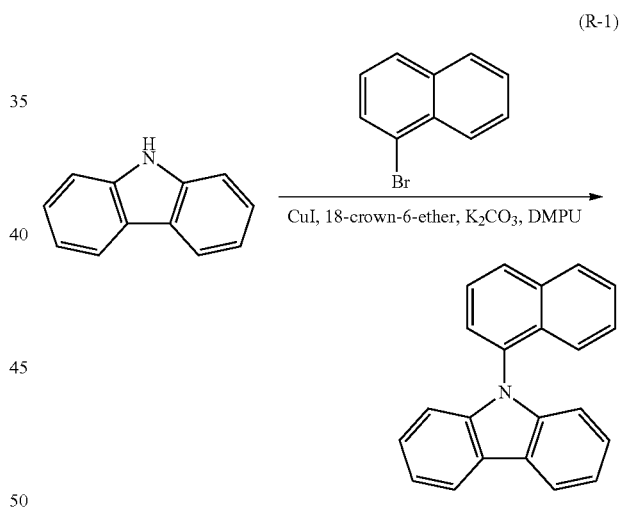

(R-1)

In a 500-mL three-neck flask, 21 g (100 mmol) of 1-bromonaphthalene, 17 g (100 mmol) of carabazole, 0.1 g (5.0 mmol) of copper(I) iodide, 0.7 g (2.5 mmol) of 18-crown-6-ether, 33 g (240 mmol) of potassium carbonate, and 80 mL of 1,3-dimethyl-3,4,5,6-tetrahydro-2(1H)pyrimidinone (abbreviation: DMPU) were put, and the mixture was stirred under a nitrogen atmosphere at 170° C. for 6 hours. Then, 10 g (50 mmol) of 1-bromonaphthalene, 2.0 g (10 mmol) of copper(I) iodide, and 2.6 g (10 mmol) of 18-crown-6-ether were further added to this reaction mixture, and the mixture was further stirred at 170° C. for 7.5 hours. After that, 10 g (50 mmol) of 1-bromonaphthalene was further added to this reaction mixture, and the mixture was further stirred at 180° C. for 6 hours.

After the reaction, about 200 mL of toluene and about 100 mL of hydrochloric acid (1 mol/L) were added to this reaction mixture, and the mixture was filtered through Celite. The obtained filtrate was filtrated through Florisil and Celite. The obtained filtrate was separated into an organic layer and an aqueous layer. After this organic layer was washed with hydrochloric acid (1 mol/L) and water in this order, magnesium sulfate was added to remove moisture. This suspension was filtered through Florisil and Celite. Then, hexane was added to the oily substance obtained by concentrating the obtained filtrate, and the mixture was irradiated with supersonic and then recrystallized to obtain 22 g of an objective white powder at a yield of 75%.

An Rf value of the objective substance by a silica gel thin layer chromatography (TLC) (developing solvent, ethyl acetate: hexane=1:10) was 0.61, that of 1-bromonaphthalene was 0.74, and that of carbazole was 0.24.

Step 2: Synthesis of 3-bromo-9-(1-naphthyl)-9H-carbazole

A synthetic scheme of 3-bromo-9-(1-naphthyl)-9H-carbazole in Step 2 is shown in the following (R-2).

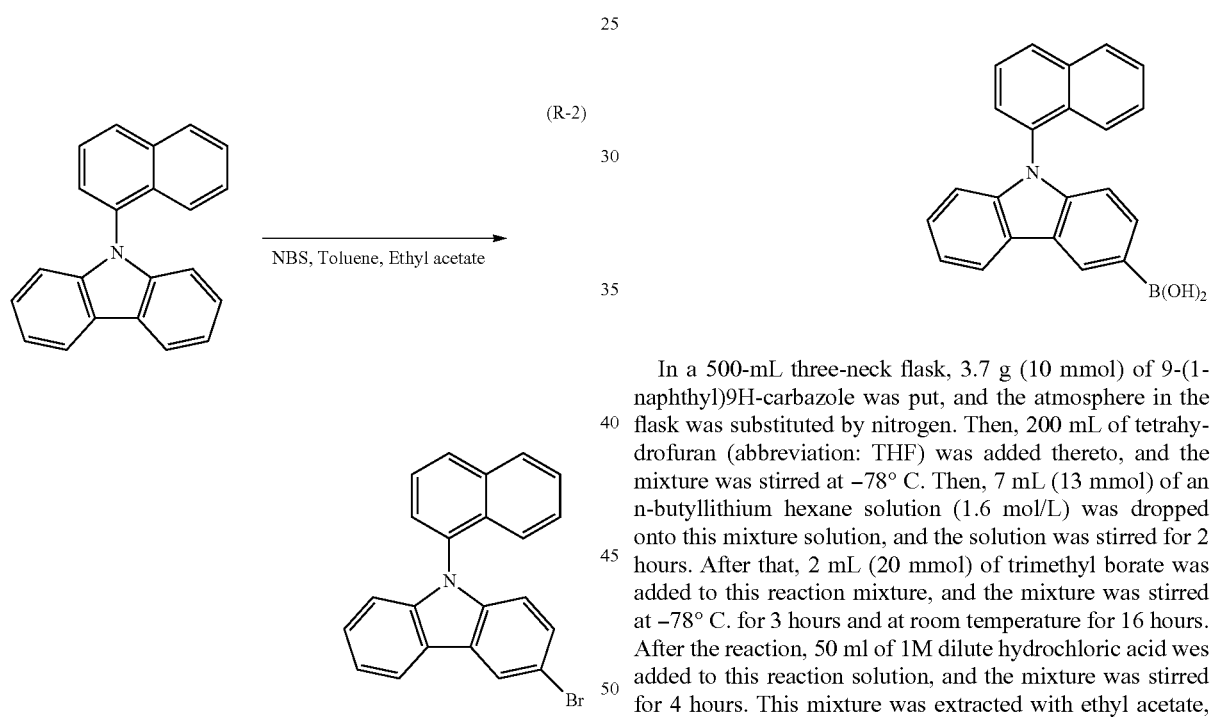

(R-2)

After 5.9 g (20 mmol) of 9-(1-naphthyl)-9H-carbazole was dissolved in a mixture solvent of 50 mL of toluene and 50 mL of ethyl acetate in a 500-mL conical flask, 3.6 g (20 mmol) of N-bromo succinimide (abbreviation: NBS) was added to this solution. After that, this mixture was stirred at room temperature for 170 hours. After completion of the reaction, this mixture solution was washed with water, and magnesium sulfate was added thereto to remove moisture. This mixture solution was filtrated, and the obtained filtrate was concentrated and dried to obtain 7.4 g of an objective white powder at a yield of 99%.

An Rf value of the objective substance by a silica gel thin layer chromatography (TLC) (developing solvent, ethyl acetate: hexane=1:10) was 0.43 and that of 9-(1-naphthyl) 9H-carbazole was 0.35.

Step 3: Synthesis of 9-(1-naphthyl)9H-carbazol-3-boronic acid

A synthetic scheme of 9-(1-naphthyl)9H-carbazol-3-boronic acid in Step 3 is shown in the following (R-3).

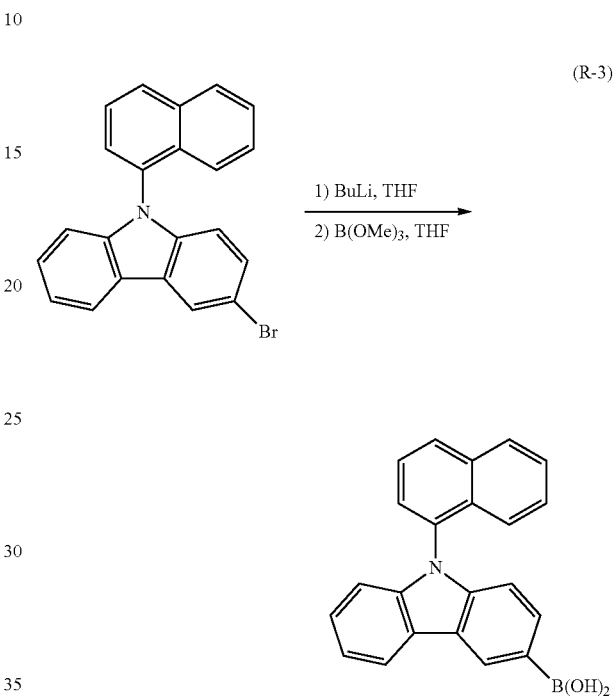

(R-3)

In a 500-mL three-neck flask, 3.7 g (10 mmol) of 9-(1-naphthyl)9H-carbazole was put, and the atmosphere in the flask was substituted by nitrogen. Then, 200 mL of tetrahydrofuran (abbreviation: THF) was added thereto, and the mixture was stirred at −78° C. Then, 7 mL (13 mmol) of an n-butyllithium hexane solution (1.6 mol/L) was dropped onto this mixture solution, and the solution was stirred for 2 hours. After that, 2 mL (20 mmol) of trimethyl borate was added to this reaction mixture, and the mixture was stirred at −78° C. for 3 hours and at room temperature for 16 hours. After the reaction, 50 ml of 1M dilute hydrochloric acid wes added to this reaction solution, and the mixture was stirred for 4 hours. This mixture was extracted with ethyl acetate, and the obtained organic layer was washed with a saturated saline solution. After the washing, magnesium sulfate was added to the organic layer to remove moisture. This suspension was filtrated, the obtained filtrate was concentrated, and chloroform and hexane were added thereto. The mixture was irradiated with supersonic and then recrystallized to obtain 2.6 g of an objective yellow powder at a yield of 78%.

Step 4: Synthesis of 4-[9-(1-naphthyl)-9H-carbazol-3-yl]-4'-phenyl-triphenylamine (abbreviation: NCBA1BP)

A synthetic scheme of 4-[9-(1-naphthyl)-9H-carbazol-3-yl]-4'-phenyl-triphenylamine (abbreviation: NCBA1BP) in Step 4 is shown in the following (R-4).

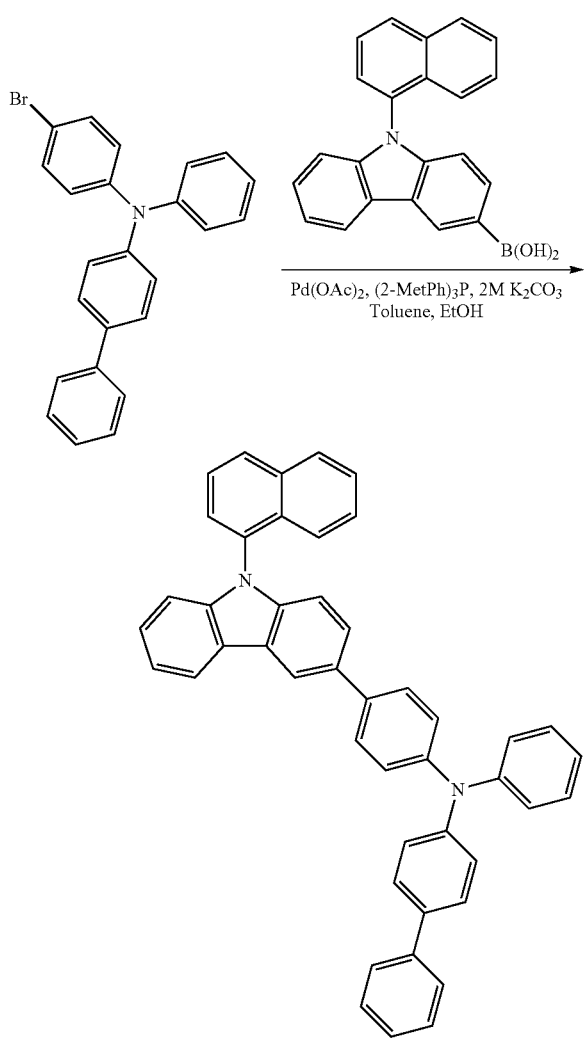

(R-4)

In a 50-mL three-neck flask, 1.2 g (3.0 mmol) of 4-bromo-4'-phenyl-triphenylamine, 1.0 g (3.0 mmol) of 9-(1-naphthyl)9H-carbazol-3-boronic acid, 6.0 mg (0.03 mmol) of palladium(II) acetate, and 0.03 mg (18 mmol) of tri(o-tolyl)phosphine were put, and 15 mL of toluene, 5 mL of ethanol, and 3 mL of a potassium carbonate solution (2 mol/L) were added to this mixture. This mixture was deaerated while being stirred under low pressure. After the deaeration, the mixture was stirred under a nitrogen atmosphere at 90° C. for 6.5 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene:hexane=1:3). The obtained fraction was concentrated, and methanol was added thereto. The mixture was irradiated with supersonic and then recrystallized to obtain 0.5 g of an objective white powder at a yield of 25%.

An Rf value of the objective substance by a silica gel thin layer chromatography (TLC) (developing solvent, ethyl acetate: hexane=1:10) was 0.34 and that of 4-bromo-4'-phenyl-triphenylamine was 0.54.

Figure 55A:
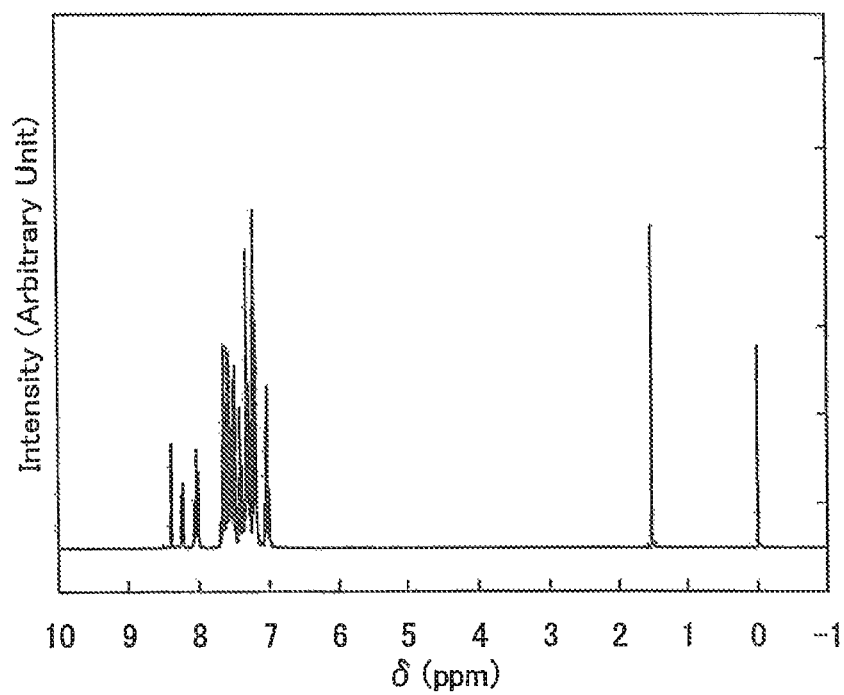
FIGS. 55A and 55B are graphs showing $^1$H NMR charts of NCBA1BP (abbreviation)
Figure 55B:
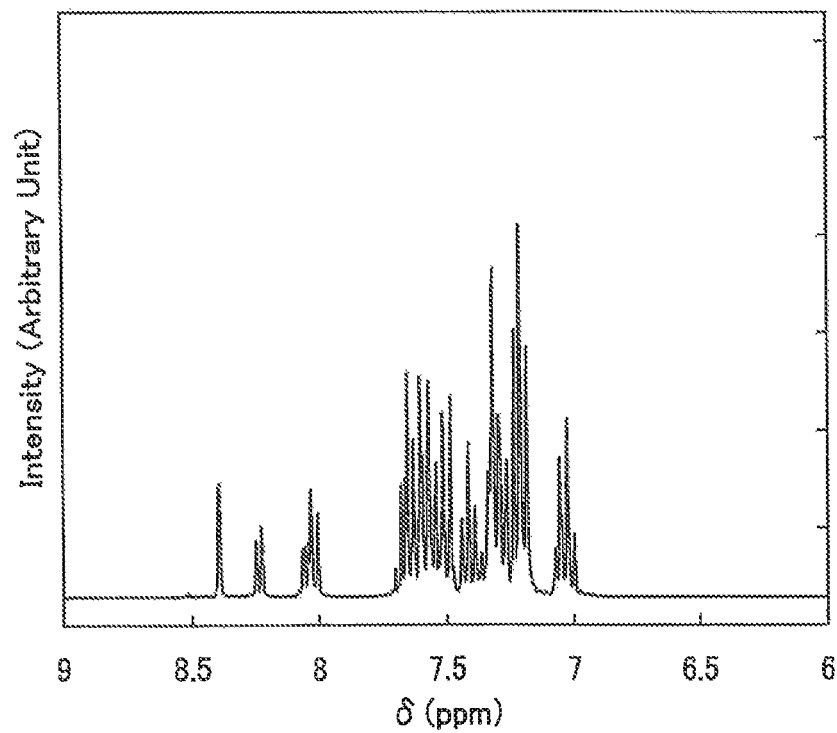
Figure 56:
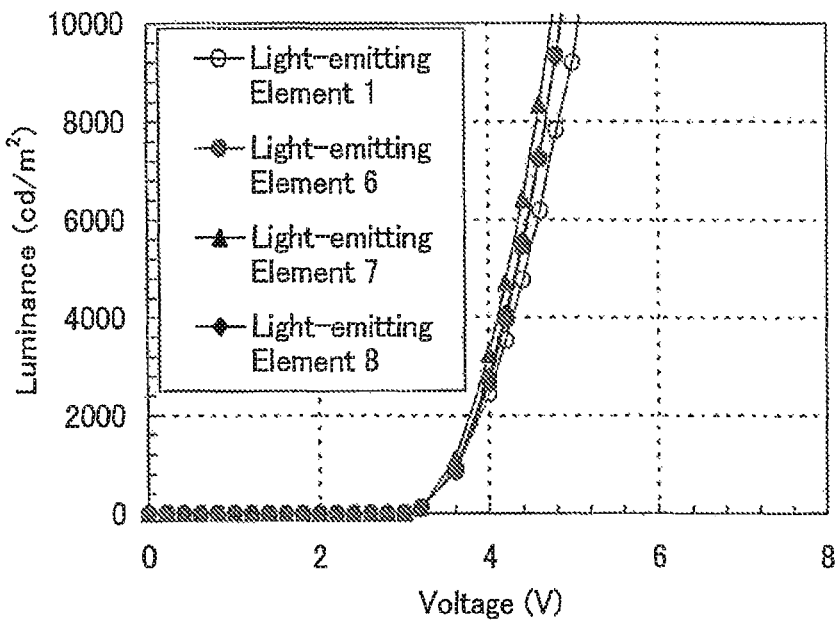
FIG. 56 is a graph showing the voltage vs. luminance characteristics of the light-emitting element 1 and light-emitting elements 6 to 8.
Figure 57:
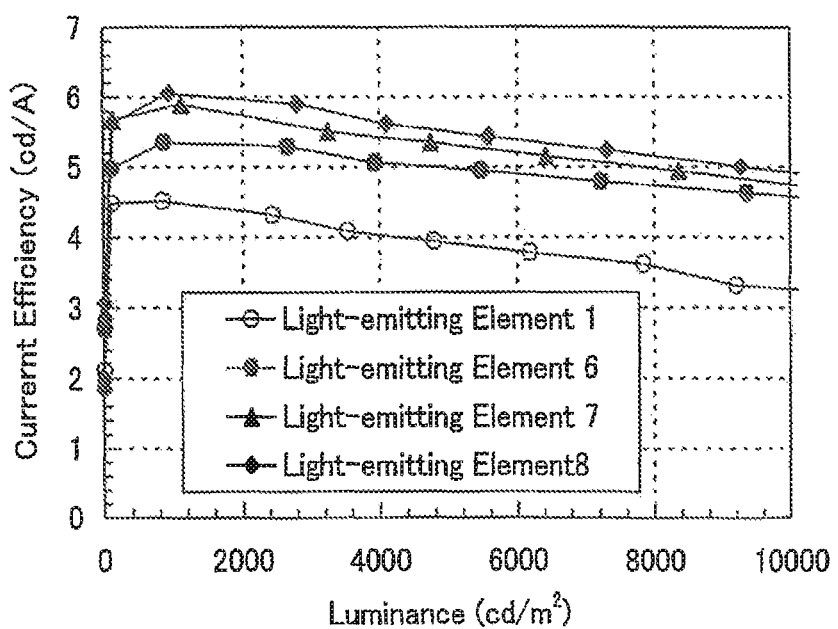
FIG. 57 is a graph showing the luminance vs. current efficiency characteristics of the light-emitting element 1 and the light-emitting elements 6 to 8.
Figure 58:
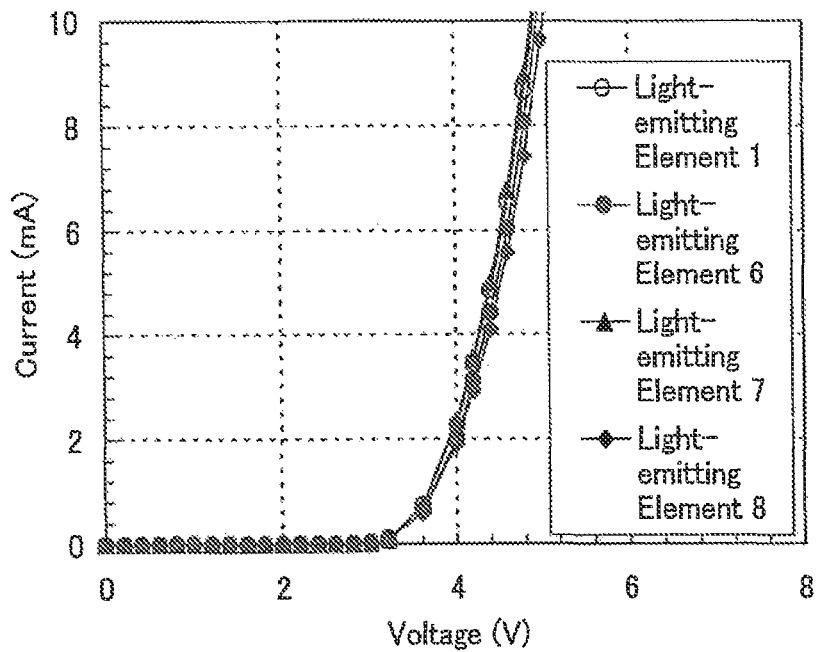
FIG. 58 is a graph showing the voltage vs. current characteristics of the light-emitting element 1 and the light-emitting elements 6 to 8.

A compound which was obtained through the above Step 4 was measured by a nuclear magnetic resonance method ($^1$H NMR). The measurement result is described below, and the $^1$H NMR chart is shown in FIGS. 55A and 55B. It was found from the measurement result that the carbazole derivative of the present invention, NCBA1BP (abbreviation) represented by the above structural formula (395), was obtained. $^1$H NMR (CDCl$_3$, 300 MHz): δ (ppm)=7.00-7.07 (m, 3H), 7.19-8.00 (m, 25H), 8.03-8.07 (m, 2H), 8.22-8.25 (m, 1H), 8.40 (d, J=1.5, 1H).

In addition, an absorption spectrum of NCBA1 BP (abbreviation) (measurement range: 200 nm to 800 nm) was measured. In the case of the toluene solution, an absorption peak on a long wavelength side was observed at around 333 nm, and in the case of the thin film, an absorption peak on a long wavelength side was observed at around 340 nm.

In addition, an emission spectrum of NCBA1BP (abbreviation) (measurement range: 370 nm to 550 nm) was measured. In the case of the toluene solution, a maximum emission wavelength was 392 nm (excitation wavelength: 345 nm), and in the case of the thin film, a maximum emission wavelength was 426 nm (excitation wavelength: 328 nm). Since the measurement method of an absorption spectrum and an emission spectrum is similar to that of Embodiment 1, the description is omitted.

The result of measuring the thin film using a photoelectron spectrometer (AC-2, manufactured by Riken Keiki Co., Ltd.) under the atmosphere indicated that the HOMO level of NCBA1BP (abbreviation) was −5.44 eV. The Tauc plot of the absorption spectrum of the thin film revealed that the absorption edge was 3.19 eV. Thus, the energy gap in the solid state was estimated to be 3.19 eV, which means that the LUMO level of NCBA1BP (abbreviation) is −2.25 eV.

An oxidation-reduction reaction characteristic of NCBA1BP (abbreviation) was examined by a cyclic voltammetry (CV) measurement. Since the measurement method is similar to that of Embodiment 1, the description is omitted. According to the calculation similar to that of Embodiment 1, the HOMO level of NCBA1BP (abbreviation) was found to be =−5.43 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of NCBA1BP (abbreviation) was examined with a differential scanning calorimetry (Pyris 1 DSC, manufactured by Perkin Elmer Co., Ltd.). According to the measurement results, it was found that the glass transition temperature was 128° C. In this manner, NCBA1BP (abbreviation) has a high glass transition temperature and favorable heat resistance. In addition, the crystallization peak does not exist; thus, it was found that NCBA1BP (abbreviation) is a substance which is hard to be crystallized.

Note that the efficiency, the drive voltage at a luminance of about 1000 cd/m$^2$, and the reliability of a light-emitting element formed using NCBA1BP (abbreviation) which was synthesized in Embodiment 16 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 1198 cd/M² and 0.82 mA, respectively.

Embodiment 17

In Embodiment 17, a synthetic method of a carbazole derivative of the present invention, 4,4'-diphenyl-4"-(6,9-diphenyl-9H-carbazol-3-yl)triphenylamine (abbreviation: PCBBi1BPIII) represented by a structural formula (422), will be specifically described.

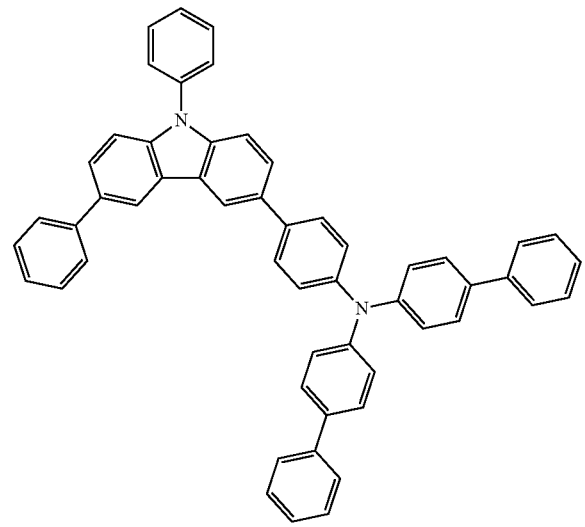

(422)

Step 1: Synthesis of 3-bromo-6,9-diphenyl-9H-carbazole

A synthetic scheme of 3-bromo-6,9-diphenyl-9H-carbazole in Step 1 is shown in the following (S-1).

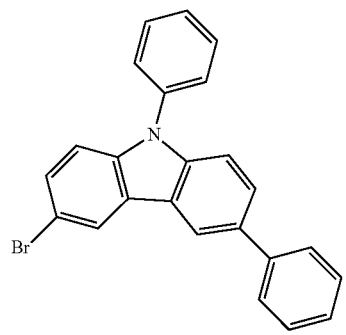

In a 300-mL erlenmayer flask, 4.8 g (15 mmol) of 3,9-diphenyl-9H-carbazole was put, and 250 mL of a mixture solvent (ethyl acetate: toluene=4:1) was added to this solution. After that, this mixture was stirred for 30 minutes. Then, 2.7 g (15 mmol) of N-bromo succinimide (abbreviation: NBS) was added to this solution little by little, and the solution was stirred for 48 hours.

After the stirring, this mixture was washed with a saturated sodium hydrogen carbonate solution and a saturated saline solution in this order. After the washing, moisture of the obtained organic layer was removed by magnesium sulfate. Then, suction filtration was performed on this mixture and the magnesium sulfate was removed to obtain filtrate. A small amount of ethanol was added to an oily substance which was obtained by concentrating the obtained filtrate. Then, the mixture was irradiated with supersonic to precipitate a solid. The precipitated solid was collected by suction filtration to obtain 5.4 g of a white powder-like solid at a yield of 90%.

Step 2: Synthesis of 4,4'-diphenyl-4"-(6,9-diphenyl-9H-carbazol-3-yl)triphenylamine (abbreviation: PCBBi1BPIII)

A synthetic scheme of 4,4'-diphenyl-4"-(6,9-diphenyl-9H-carbazol-3-yl)triphenylamine in Step 2 is shown in the following (S-2).

(S-1)

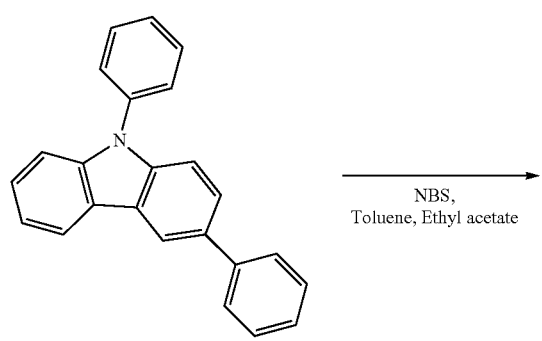

(S-2)

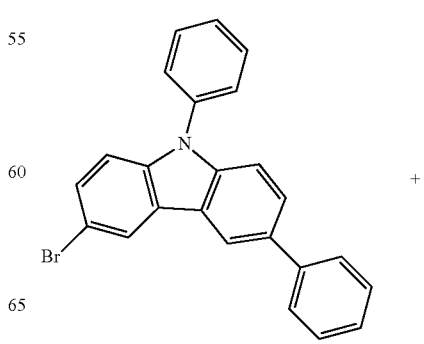

+

-continued

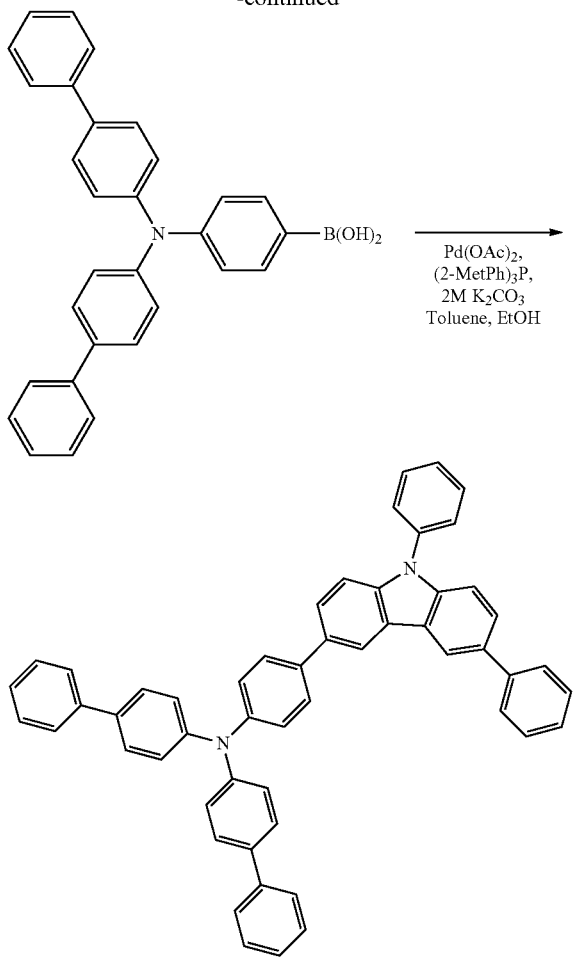

In a 100-mL three-neck flask, 1.7 g (3.8 mmol) of N,N-bis(biphenyl-4-yl)aminophenyl-4-boronic acid, 1.5 g (3.8 mmol) of 3-bromo-6,9-diphenyl-9H-carbazole, 8.4 mg (0.038 mmol) of palladium(II) acetate, and 0.080 mg (0.26 mmol) of tri(o-tolyl)phosphine were put. Then, 10 mL of toluene, 2 mL of ethanol, and 10 mL of a 2M potassium carbonate solution were added to this mixture. After this mixture was deaerated under low pressure, the atmosphere in the flask was substituted by nitrogen. This mixture was stirred at 100° C. for 3 hours.

After the stirring, toluene was added to this reaction mixture, and this mixture was heated at 50° C. and stirred. After this suspension was brought back to room temperature, the suspension was separated into an organic layer and an aqueous layer. The obtained organic layer was washed with a saturated sodium carbonate solution and a saturated saline solution in this order. After the washing, magnesium sulfate was added to the obtained organic layer to remove moisture. Suction filtration was performed on this mixture to obtain filtrate. Suction filtration was performed on the obtained filtrate through Celite (Wako Pure Chemical Industries, Ltd., catalog No.: 531-16855), Florisil (Wako Pure Chemical Industries, Ltd., catalog No.: 540-00135), and alumina to obtain filtrate. The obtained filtrate was concentrated and purified by silica gel column chromatography. The silica gel column chromatography was performed by, first, using a mixture solvent of toluene: hexane=1:4 as a developing solvent, and then using a mixture solvent of toluene: hexane=1:1 as another developing solvent. A solid which was obtained by concentrating the obtained fraction was recrystallized with a mixture solvent of chloroform and hexane to obtain 2.3 g of a white powder-like solid at a yield of 87%.

Sublimation purification of 2.3 g of the obtained white solid was performed by a train sublimation method. The sublimation purification was performed under a reduced pressure of 7.0 Pa, with a flow rate of argon at 4 mL/min, at 320° C. for 18 hours to obtain 1.8 g of the white solid at a yield of 78%.

Figure 61A:
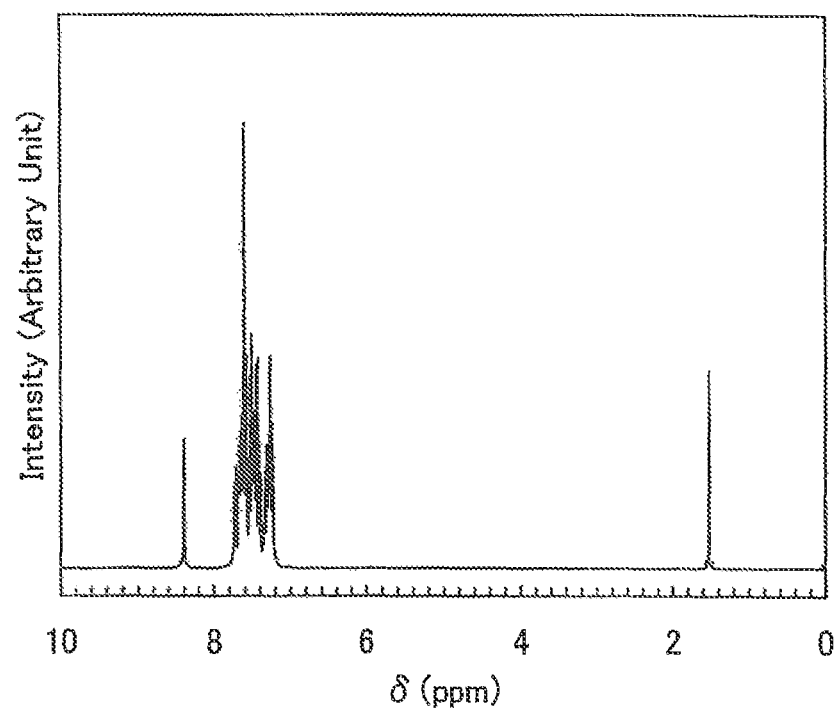
FIGS. 61A and 61B are graphs showing $^1$H NMR charts of PCBBi1BPIII (abbreviation)
Figure 61B:
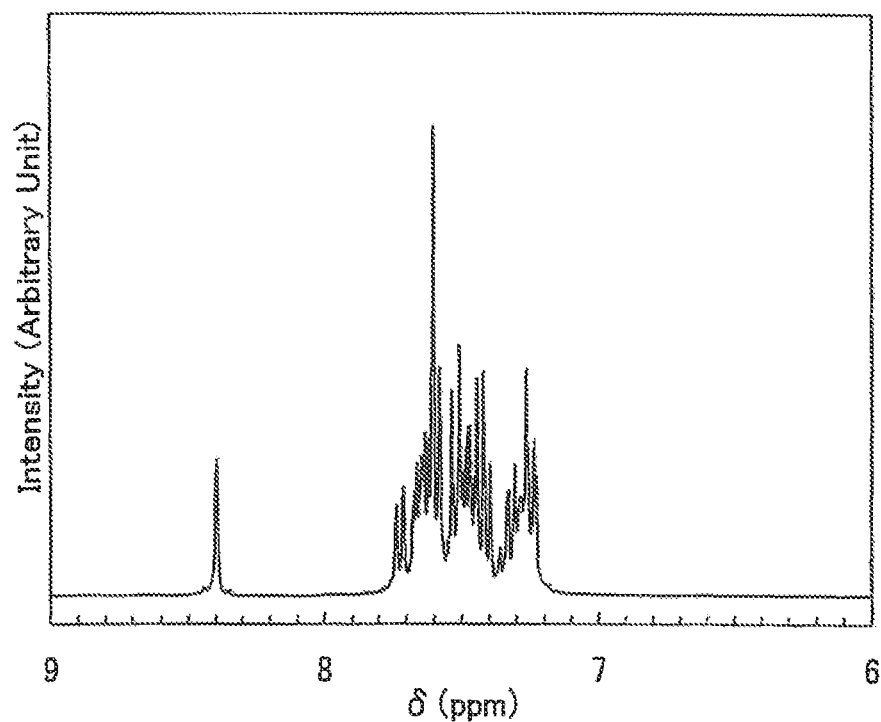

A compound which was obtained through the above Step 2 was measured by a nuclear magnetic resonance method ($^1$H NMR). The measurement result is described below, and the $^1$H NMR chart is shown in FIGS. 61A and 61B. It was found from the measurement result that the carbazole derivative of the present invention, PCBBi1BPIII (abbreviation) represented by the above structural formula (422), was obtained. $^1$H NMR (CDCl$_3$, 300 MHz): δ (ppm)=7.22-7.77 (m, 36H), 8.38-8.42 (m, 2H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the forminc acid solution, 80/20 vol/vol) was used as a solvent. Accordingly, a main peak with a molecular weight of 714.30 (mode is ES+) was detected, and it was confirmed that an objective PCBBi1BPIII (abbreviation) was obtained.

In addition, various physical properties of PCBBi1BPIII (abbreviation) were measured as described below.

In addition, an absorption spectrum of PCBBi1BPIII (abbreviation) (measurement range: 200 nm to 800 nm) was measured. In the case of the toluene solution, an absorption peak on a long wavelength side was observed at around 348 nm, and in the case of the thin film, an absorption peak on a long wavelength side was observed at around 352 nm. In addition, an emission spectrum of PCBBi1BPIII (abbreviation) (measurement range: 390 nm to 550 nm) was measured. In the case of the toluene solution, a maximum emission wavelength was 397 nm (excitation wavelength: 358 nm), and in the case of the thin film, a maximum emission wavelength was 439 nm (excitation wavelength: 369 nm).

The result of measuring the thin film using a photoelectron spectrometer (AC-2, manufactured by Riken Keiki Co., Ltd.) under the atmosphere indicated that the HOMO level of PCBBi1BPIII (abbreviation) was −5.46 eV. The Tauc plot of the absorption spectrum of the thin film revealed that the absorption edge was 3.21 eV. Thus, the energy gap in the solid state was estimated to be 3.21 eV, which means that the LUMO level of PCBBi1BPIII (abbreviation) is −2.25 eV.

An oxidation-reduction reaction characteristic of PCBBi1BPIII (abbreviation) was examined by a cyclic voltammetry (CV) measurement. Since the measurement method is similar to that of Embodiment 1, the description is omitted. According to the calculation similar to that of Embodiment 1, the HOMO level of PCBBi1BPIII (abbreviation) was found to be =−41 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBBi1BPIII (abbreviation) was examined with a differential scanning calorimetry (Pyris I DSC, manufactured by Perkin Elmer Co., Ltd.). According to the measurement results, it was found that the glass transition temperature was 138° C. In this manner, PCBBi1BPIII (abbreviation) has a high glass transition temperature and favorable heat resistance. In addition, the crystallization peak does not exist; thus, it was found that PCBBi1BPIII (abbreviation) is a substance which is hard to be crystallized.

Note that the efficiency, the drive voltage at a luminance of about 1000 cd/m², and the reliability of a light-emitting element formed using PCBBi1BPIII (abbreviation) which was synthesized in Embodiment 17 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.2 V, the luminance and the current value were 1070 cd/m² and 0.75 mA, respectively, and the light-emitting element exhibited 74% of the initial luminance when driven for 360 hours.

Embodiment 18

In Embodiment 18, a synthetic method of a carbazole derivative of the present invention, 3,3'-dimethyl-4"-phenyl-4-(9-phenyl-9H-carbazol-3-yl)-triphenylamine (abbreviation: PCBA1BPIV) represented by a structural formula (423), will be specifically described.

(423)

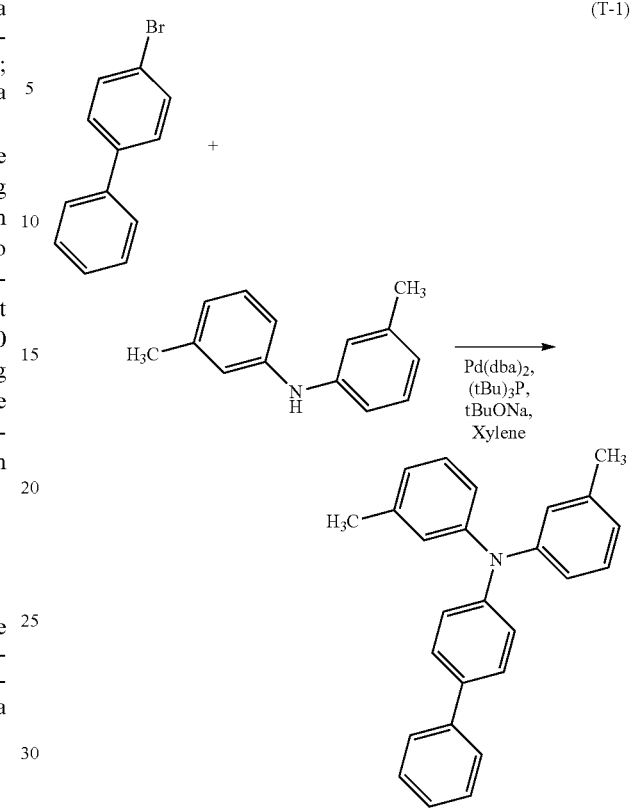

(T-1)

Step 1: Synthesis of 3,3'-dimethyl-4"-phenyl-triphenylamine

A synthetic scheme of 3,3'-dimethyl-4"-phenyl-triphenylamine in Step 1 is shown in the following (T-1).

In a 100-mL three-neck flask, 5.8 g (25 mmol) of 4-bromobiphenyl, 4.9 g (25 mmol) of m,m'-Ditolylamine, 3.0 (30 mmol) of sodium tert-butoxide, and 140 mg (0.25 mmol) of bis(dibenzylideneacetone)palladium(0) were put, and the atmosphere of the flask was substituted by nitrogen. Then, 50 mL of dehydrated xylene was added to this mixture. This mixture was deaerated while being stirred under low pressure. After the deaeration, 1.0 mL (0.5 mmol) of tri(tert-butyl)phosphine (10 wt % hexane solution) was added thereto. This mixture was stirred under a nitrogen atmosphere at 130° C. for 1.5 hours to be reacted.

After the reaction, 80 mL of toluene and 420 mL of hexane were added to this reaction mixture, and this suspension was filtered through Florisil, silica gel, and then Celite. The obtained filtrate was washed with water. Then, magnesium sulfate was added to remove moisture. This suspension was filtered through Florisil and then Celite to obtain filtrate. The obtained filtrate was concentrated, and methanol was added thereto. The mixture was irradiated with supersonic and then recrystallized to obtain 8.5 g of an objective white powder at a yield of 97%.

A compound which was obtained through the above Step 1 was measured by a nuclear magnetic resonance method ($^1$H NMR). $^1$H NMR (CDCl$_3$, 300 MHz): δ (ppm)=2.28 (s, 6H), 6.85 (d, J=6.9, 2H), 6.91-6.95 (m, 4H), 7.09-7.18 (m, 4H), 7.29 (t, J=7.5, 1H), 7.38-7.48 (m, 4H), 7.56-7.59 (m, 2H).

Step 2: Synthesis of 4-bromo-3,3'-dimethyl-4"-phenyl-triphenylamine

A synthetic scheme of 4-bromo-3,3'-dimethyl-4"-phenyl-triphenylamine in Step 2 is shown in the following (T-2).

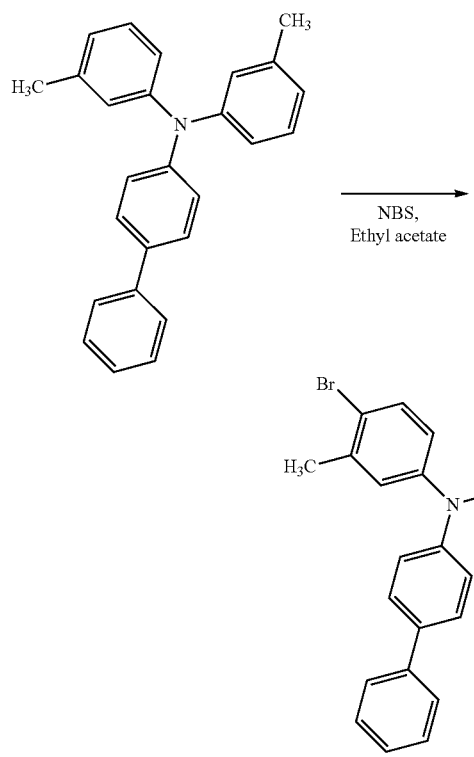

(T-2)

After 2.5 g (24 mmol) of 3,3'-dimethyl-4"-phenyl-triphenylamine was dissolved in 200 mL of ethyl acetate in a 200-mL conical flask, 4.3 g (24 mmol) of N-bromo succinimide (abbreviation: NBS) was added to this solution. After that, this mixture was stirred at room temperature for 48 hours. After completion of the reaction, this mixture solution was washed with water, and magnesium sulfate was added thereto to remove moisture. This mixture solution was filtrated and the obtained filtrate was concentrated and dried to obtain 9.1 g of an objective caramel-like solid at a yield of 88%.

Step 3: Synthesis of 3,3'-dimethyl-4"-phenyl-4-(9-phenyl-9H-carbazol-3-yl)-triphenylamine (abbreviation: PCBA1BPIV)

A synthetic scheme of 3,3'-dimethyl-4"-phenyl-4-(9-phenyl-9H-carbazol-3-yl)-triphenylamine in Step 3 is shown in the following (T-3).

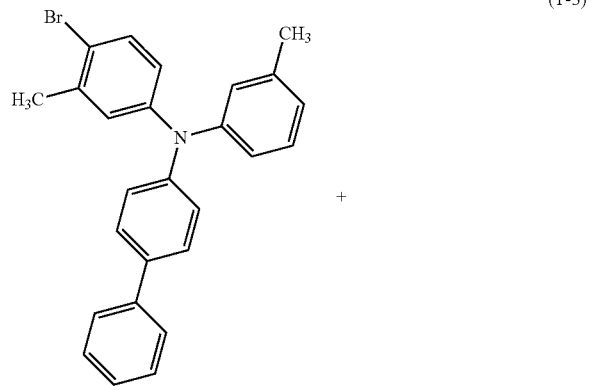

(T-3)

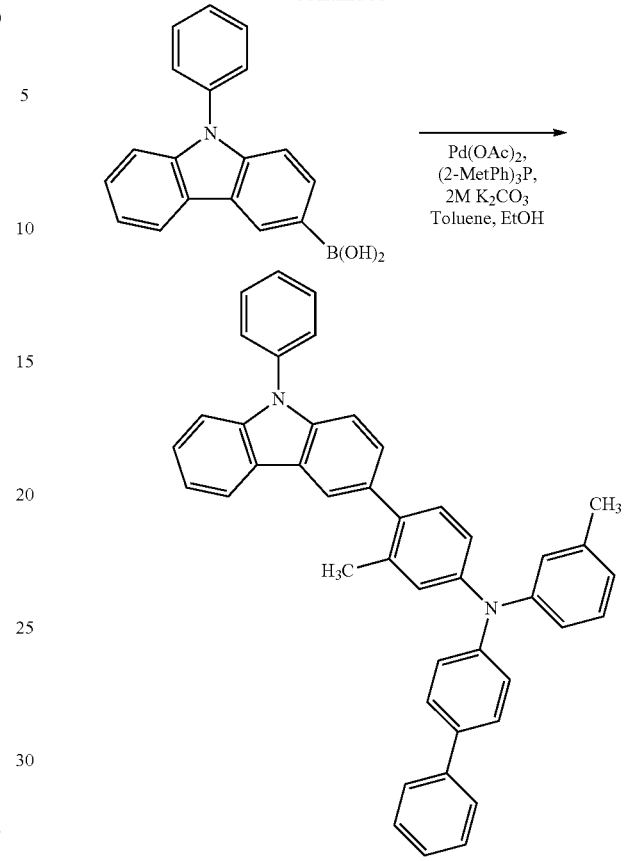

In a 300-mL recovery flask, 1.7 g (4.0 mmol) of 4-bromo-3,3'-dimethyl-4"-phenyl-triphenylamine, 1.4 g (5.0 mmol) of 9-phenyl-9H-carbazol-3-boronic acid, 5.0 mg (0.02 mmol) of palladium(II) acetate, and 6.0 mg (0.02 mmol) of tri(o-tolyl)phosphine were put, and 30 mL of toluene, 5 mL of ethanol, and 3.5 mL of a potassium carbonate solution (2 mol/L) were added to this mixture. This mixture was deaerated while being stirred under low pressure. After the deaeration, the mixture was stirred under a nitrogen atmosphere at 90° C. for 3 hours to be reacted.

After the reaction, 150 mL of toluene was added to this reaction mixture, and this suspension was filtrated through Florisil and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene: hexane=1:4). The obtained fraction was concentrated, and hexane and acetone were added thereto. The mixture was irradiated with supersonic and then recrystallized to obtain 1.0 g of an objective white powder at a yield of 42%.

An Rf value of the objective substance by a silica gel thin layer chromatography (TLC) (developing solvent, ethyl acetate: hexane=1:10) was 0.51 and that of 4-bromo3,3'-dimethyl-4"-phenyl-triphenylamine was 0.62.

Figure 62A:
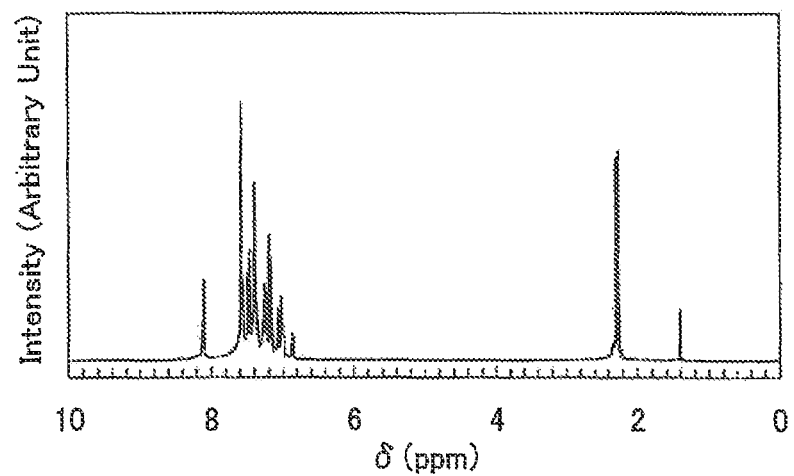
FIGS. 62A to 62C are graphs showing $^1$H NMR charts of PCBA1BPIV (abbreviation)
Figure 62B:
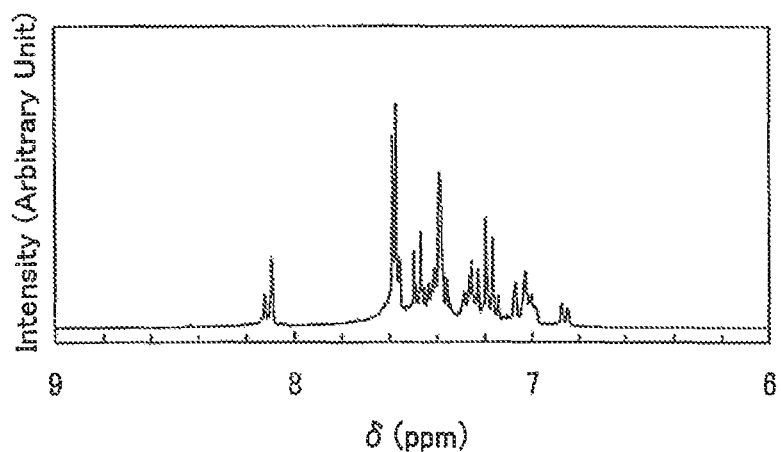
Figure 62C:
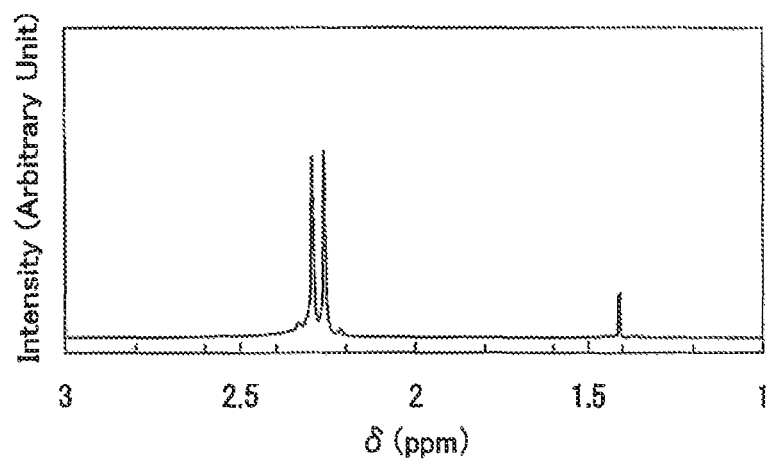

A compound which was obtained through the above Step 3 was measured by a nuclear magnetic resonance method ($^1$H NMR). The measurement result is described below, and the $^1$H NMR chart is shown in FIGS. 62A to 62C. It was found from the measurement result that the carbazole derivative of the present invention, PCBA1BPIV (abbreviation) represented by the above structural formula (423), was obtained. $^1$H NMR (CDCl$_3$, 300 MHz): δ (ppm)=2.26 (s, 3H), 2.30 (s, 3H), 6.86 (d, J=7.8, 1H), 6.99-7.59 (m, 25H), 8.09-8.13 (m, 2H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the forminc acid solution, 80/20 vol/vol) was used as a solvent. Accordingly, a main peak with a molecular weight of 591.28 (mode is ES+) was detected, and it was confirmed that an objective PCBA1BPIV (abbreviation) was obtained.

In addition, various physical properties of PCBA1BPIV (abbreviation) were measured as described below.

In addition, an absorption spectrum of PCBA1BPIV (abbreviation) (measurement range: 200 nm to 800 nm) was measured. In the case of the toluene solution, an absorption peak on a long wavelength side was observed at around 325 nm, and in the case of the thin film, an absorption peak on a long wavelength side was observed at around 329 nm. In addition, an emission spectrum of PCBA1BPIV (abbreviation) (measurement range: 370 nm to 550 nm) was measured. In the case of the toluene solution, a maximum emission wavelength was 393 nm (excitation wavelength: 330 nm), and in the case of the thin film, a maximum emission wavelength was 422 nm (excitation wavelength: 357 nm).

The result of measuring the thin film using a photoelectron spectrometer (AC-2, manufactured by Riken Keiki Co., Ltd.) under the atmosphere indicated that the HOMO level of PCBA1BPIV (abbreviation) was −5.57 eV. The Tauc plot of the absorption spectrum of the thin film revealed that the absorption edge was 3.36 eV. Thus, the energy gap in the solid state was estimated to be 3.36 eV, which means that the LUMO level of PCBA1BPIV (abbreviation) is −2.21 eV.

In addition, the glass transition temperature of PCBA1BPIV (abbreviation) was examined with a differential scanning calorimetry (Pyris 1 DSC, manufactured by Perkin Elmer Co., Ltd.). According to the measurement results, it was found that the glass transition temperature was 105° C. In this manner, PCBA1BPIV (abbreviation) has a high glass transition temperature and favorable heat resistance. In addition, the crystallization peak does not exist; thus, it was found that PCBA1BPIV (abbreviation) is a substance which is hard to be crystallized.

Note that the efficiency, the drive voltage at a luminance of about 1000 cd/M$^2$, and the reliability of a light-emitting element formed using PCBA1BPIV (abbreviation) which was synthesized in Embodiment 18 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 924 cd/m$^2$ and 0.61 mA, respectively.

Embodiment 19

In Embodiment 19, a synthetic method of a carbazole derivative of the present invention, 4,4'-di(2-naphthyl)-4"-(9-phenyl-9H-carbazol-3-yl)-triphenylamine (abbreviation: PCBNBBβ) represented by a structural formula (345), will be specifically described.

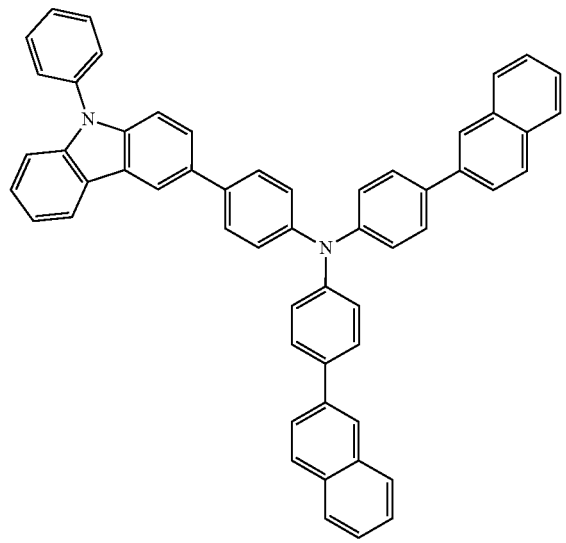

(345)

Step 1: Synthesis of 4,4'-di(2-naphthyl)-triphenylamine

A synthetic scheme of 4,4'-di(2-naphthyl)-triphenylamine in Step 1 is shown in the following (U-1).

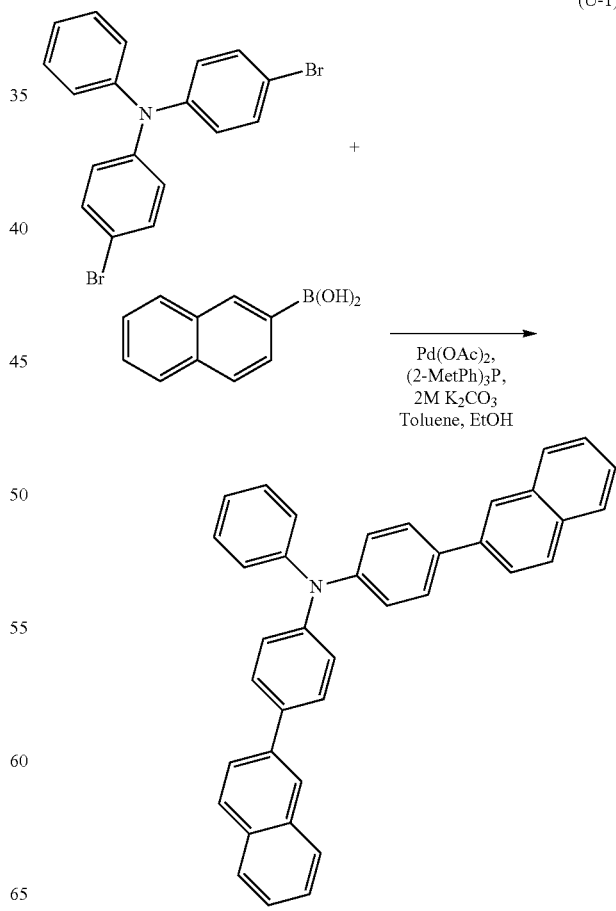

(U-1)

in a 300-mL three-neck flask, 6.0 g (15 mmol) of 4,4'-dibromotriphenylamine, 6.2 g (36 mmol) of 2-naphthaleneboronic acid, 16 mg (0.1 mmol) of palladium(II) acetate, and 21 mg (0.1 mmol) of tri(o-tolyl)phosphine were put, and 50 mL of toluene, 20 mL of ethanol, and 20 mL of a potassium carbonate solution (2 mol/L) were added to this mixture. This mixture was deaerated while being stirred under low pressure. After the deaeration, the mixture was stirred under a nitrogen atmosphere at 90° C. for 4.5 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated, and hexane was added thereto. The mixture was irradiated with supersonic and then recrystallized to obtain 5.6 g of an objective white powder at a yield of 75%.

An Rf value of the objective substance by a silica gel thin layer chromatography (TLC) (developing solvent, ethyl acetate: hexane=1:10) was 0.53 and that of 4,4'-dibromotriphenylamine was 0.78.

Step 2: Synthesis of 4-bromo-4',4''-di(2-naphthyl)-triphenylamine

A synthetic scheme of 4-bromo-4',4''-di(2-naphthyl)-triphenylamine in Step 2 is shown in the following (U-2).

After 4.0 g (8.0 mmol) of 4,4'-di(2-naphthyl)-triphenylamine was dissolved in a mixture solvent of 200 mL of toluene and 250 mL of ethyl acetate in a 500-mL conical flask, 1.4 g (8 mmol) of N-bromo succinimide (abbreviation: NBS) was added to this solution. After that, this mixture was stirred at room temperature for 96 hours. After completion of the reaction, this mixture solution was washed with water, and magnesium sulfate was added thereto to remove moisture. This suspension was filtrated through Florisil and then Celite. The obtained filtrate was concentrated and purified by silica gel column chromatography (developing solvent, toluene: hexane=1:4). The obtained fraction was concentrated, and acetone and hexane were added thereto. The mixture was irradiated with supersonic and then recrystallized to obtain 3.4 g of an objective white powder at a yield of 61%.

A compound which was obtained through the above Step 2 was measured by a nuclear magnetic resonance method ($^1$H NMR). The measurement result is described below. $^1$H NMR (CDCl$_3$, 300 MHz): δ (ppm)=7.09 (d, J=8.4, 2H), 7.24 (d, J=7.8, 4H), 7.40 (d, J=8.4, 2H), 7.47-7.51 (m, 4H), 7.66 (d, J=8.1, 4H), 7.73-7.76 (m, 2H), 7.85-7.93 (m, 6H), 8.03 (s, 2H).

Step 3: Synthesis of 4,4'-di(2-naphthyl)-4''-(9-phenyl-9H-carbazol-3-yl)-triphenylamine (abbreviation: PCBNBBβ)

A synthetic scheme of 4,4'-di(2-naphthyl)-4''-(9-phenyl-9H-carbazol-3-yl)-triphenylamine in Step 3 is shown in the following (U-3).

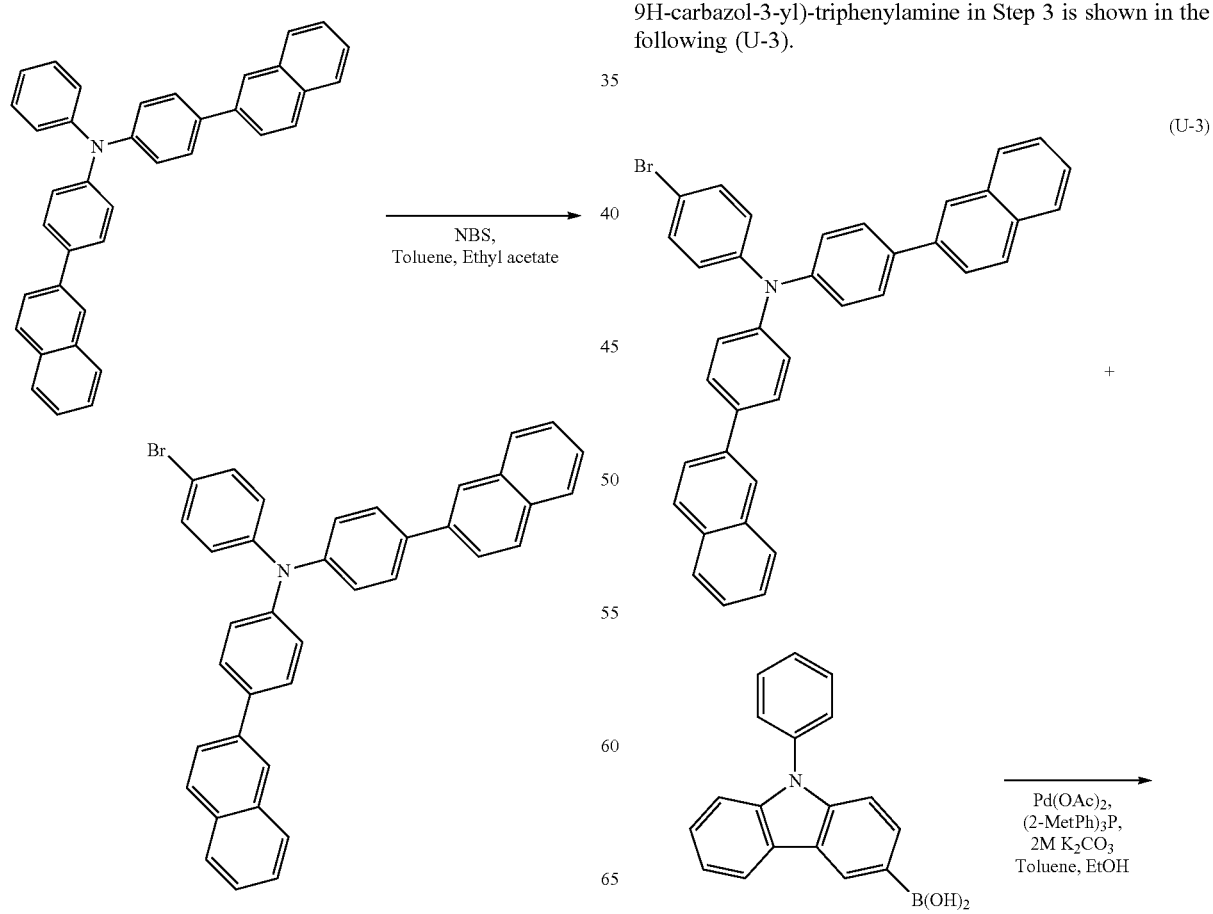

-continued

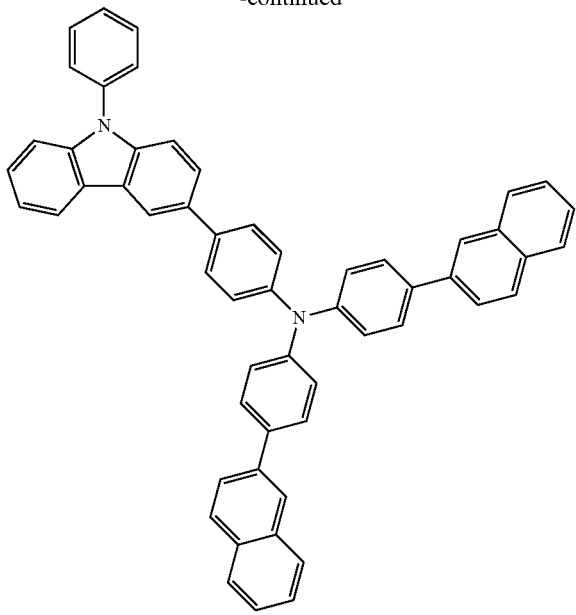

In a 50-mL three-neck flask, 1.0 g (1.7 mmol) of 4-bromo-4',4"-di(2-naphthyl)-triphenylamine, 0.6 g (2.0 mmol) of 9-phenyl-9H-carbazol-3-boronic acid, 2.2 mg (1.0 µmol) of palladium(II) acetate, and 3.0 mg (10 µmol) of tri(o-tolyl) phosphine were put, and 20 mL of toluene, 3 mL of ethanol, and 2.0 mL of a potassium carbonate solution (2 mol/L) were added to this mixture. This mixture was deaerated while being stirred under low pressure. After the deaeration, the mixture was stirred under a nitrogen atmosphere at 90° C. for 14 hours to be reacted.

After the reaction, 150 mL of toluene was added to this reaction mixture, and this suspension was filtrated through Florisil, silica gel, alumina, and then Celite. The obtained filtrate was concentrated and purified by silica gel column chromatography (developing solvent, toluene: hexane=1:4). The obtained fraction was concentrated, and methanol, chloroform, acetone, and hexane were added thereto. The mixture was irradiated with supersonic and then recrystallized to obtain 1.5 g of an objective light-yellow powder at a yield of 95%.

An Rf value of the objective substance by a silica gel thin layer chromatography (TLC) (developing solvent, ethyl acetate: hexane=1:10) was 0.31 and that of 4-bromo-4',4"-di(2-naphthyl)-triphenylamine was 0.56.

Figure 63A:
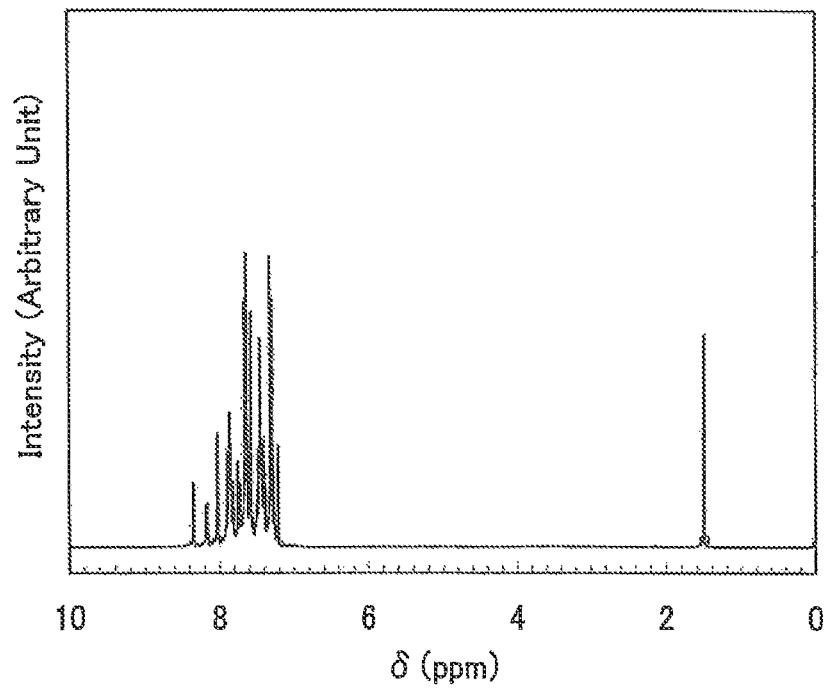
FIGS. 63A and 63B are graphs showing $^1$H NMR charts of PCBNBBβ (abbreviation)
Figure 63B:
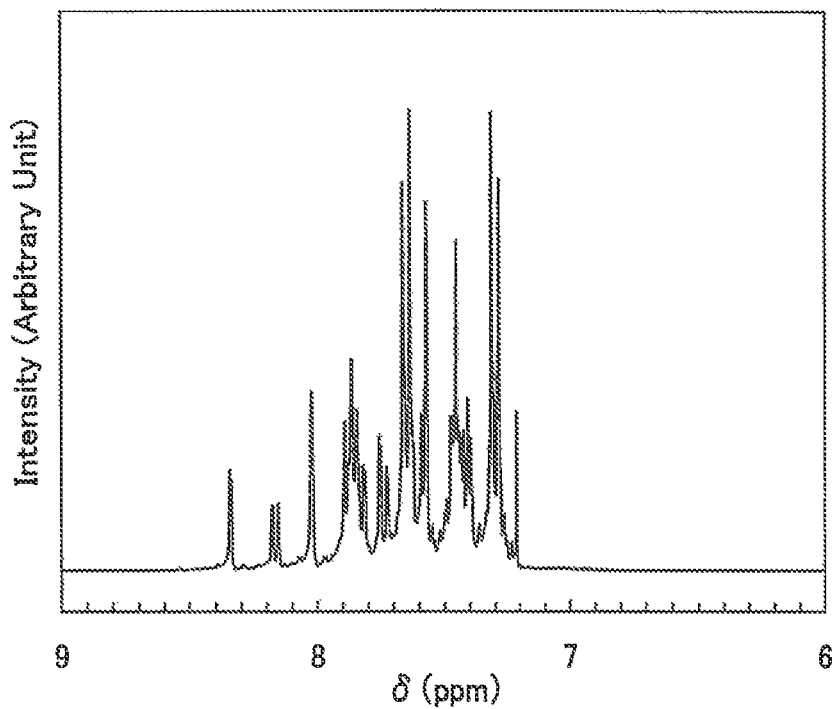

A compound which was obtained through the above Step 3 was measured by a nuclear magnetic resonance method ($^1$H NMR). The measurement result is described below, and the $^1$H NMR chart is shown in FIGS. 63A and 63B. It was found from the measurement result that the carbazole derivative of the present invention, PCBNBBβ (abbreviation) represented by the above structural formula (345), was obtained. $^1$H NMR (CDCl$_3$, 300 MHz): δ (ppm)=7.29-7.90 (m, 34H), 8.03 (s, 2H), 8.16 (d, J=7.2, 1H), 8.34 (d, J=1.5, 1H).

Molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the forminc acid solution, 80/20 vol/vol) was used as a solvent. Accordingly, a main peak with a molecular weight of 739.32 (mode is ES+) was detected, and it was confirmed that an objective PCBNBBβ (abbreviation) was obtained.

In addition, various physical properties of PCBNBBβ (abbreviation) were measured as described below.

In addition, an absorption spectrum of PCBNBBβ (abbreviation) (measurement range: 200 nm to 800 nm) was measured. In the case of the toluene solution, an absorption peak on a long wavelength side was observed at around 357 nm, and in the case of the thin film, an absorption peak on a long wavelength side was observed at around 366 nm. In addition, an emission spectrum of PCBNBBβ (abbreviation) (measurement range: 390 nm to 550 nm) was measured. In the case of the toluene solution, a maximum emission wavelength was 415 nm (excitation wavelength: 360 nm), and in the case of the thin film, a maximum emission wavelength was 449 nm (excitation wavelength: 376 nm).

The result of measuring the thin film using a photoelectron spectrometer (AC-2, manufactured by Riken Keiki Co., Ltd.) under the atmosphere indicated that the HOMO level of PCBNBB3 (abbreviation) was −5.36 eV. The Tauc plot of the absorption spectrum of the thin film revealed that the absorption edge was 3.06 eV. Thus, the energy gap in the solid state was estimated to be 3.06 eV, which means that the LUMO level of PCBNBBβ (abbreviation) is −2.30 eV.

An oxidation-reduction reaction characteristic of PCBNBBβ (abbreviation) was examined by a cyclic voltammetry (CV) measurement. Since the measurement method is similar to that of Embodiment 1, the description is omitted. According to the calculation similar to that of Embodiment 1, the HOMO level of PCBNBBβ (abbreviation) was found to be =−5.41 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBNBBβ (abbreviation) was examined with a differential scanning calorimetry (Pyris 1 DSC, manufactured by Perkin Elmer Co., Ltd.). According to the measurement results, it was found that the glass transition temperature was 129° C. In this manner, PCBNBBβ (abbreviation) has a high glass transition temperature and favorable heat resistance. In addition, the crystallization peak does not exist; thus, it was found that PCBNBBβ (abbreviation) is a substance which is hard to be crystallized.

Note that the efficiency, the drive voltage at a luminance of about 1000 cd/m$^2$, and the reliability of a light-emitting element formed using PCBNBBβ (abbreviation) which was synthesized in Embodiment 19 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.4 V, the luminance and the current value were 1104 cd/m$^2$ and 0.74 mA, respectively, and the light-emitting element exhibited 75% of the initial luminance when driven for 650 hours.

Embodiment 20

In Embodiment 20, a synthetic method of a carbazole derivative of the present invention, 4-pheny-4'-(9-phenyl-9H-carbazol-3-yl)-4"-(9-phenylfluoren-9-yl)-triphenylamine (abbreviation: PCBBiFLP) represented by a structural formula (424), will be specifically described. Note that the above compound is the carbazole derivative represented by the general formula (1) in which R¹ is hydrogen, R² is a phenyl group, l is 0, m is 1, n is 0, α² is a 1,4-phenylene group, α⁴ is a 1,4-phenylene group, Ar¹ is a biphenyl-4-yl group, Ar² is a fuluoren-9-yl group, and the nineth position of the fuluoren-9-yl group is substituted by a phenyl group.

(424)

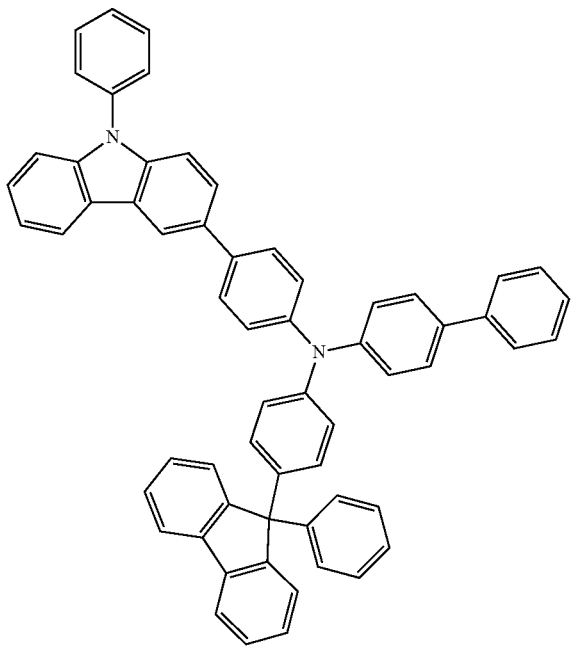

Step 1: Synthesis of
4-bromo-4'-phenyl-diphenylamine

A synthetic scheme of 4-bromo-4'-phenyl-diphenylamine in Step 1 is shown in the following (V-1).

(V-1)

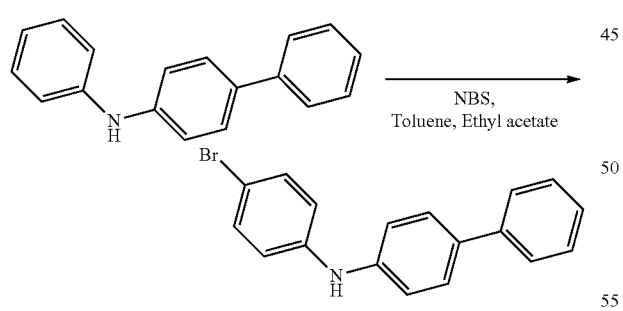

After 37 g (150 mmol) of 4-phenyl-diphenylamine was dissolved in 400 mL of ethyl acetate in a 1000-mL conical flask, 27 g (150 mmol) of N-bromo succinimide (abbreviation: NBS) was added to this solution. After that, this mixture was stirred at room temperature for 24 hours.

After completion of the reaction, this mixture solution was washed with water, and magnesium sulfate was added thereto to remove moisture. This mixture solution was filtrated through Florisil, silica gel, alumina, and then Celite, the obtained filtrate was concentrated, and toluene and hexane were added thereto. The mixture was irradiated with supersonic and then recrystallized to obtain 4.0 g of an objective white powder. In addition, the filtrate which was obtained at the time of this recrystallization was purified by silica gel column chromatography (developing solvent, toluene: hexane=1:4). The obtained fraction was concentrated, and methanol was added thereto. The mixture was irradiated with supersonic and then recrystallized to obtain 4.5 g of an objective white powder. Thus, in total, 8.5 g of an objective white powder was obtained at a yield of 73%.

Step 2: Synthesis of 4-phenyl-4'-(9-phenyl-9H-carbazol-3-yl)-diphenylamine

A synthetic scheme of 4-phenyl-4'-(9-phenyl-9H-carbazol-3-yl)-diphenylamine in Step 2 is shown in the following (V-2).

(V-2)

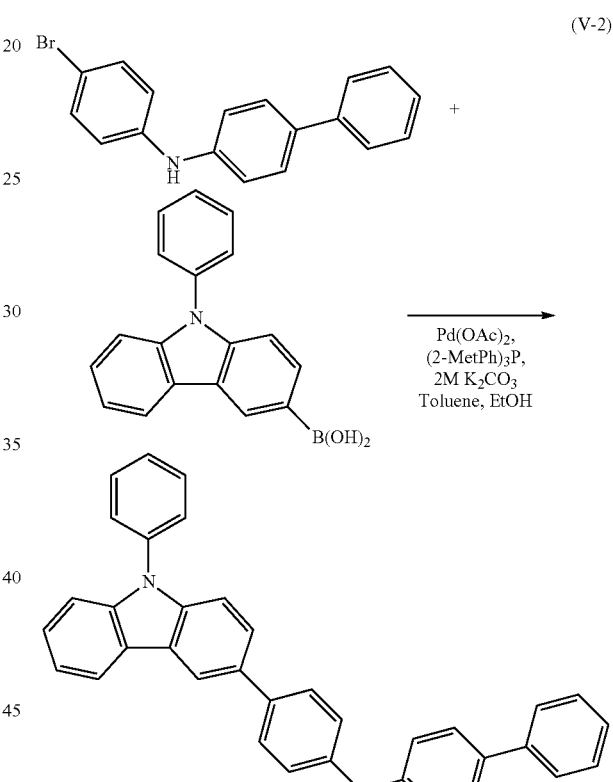

In a 200-mL three-neck flask, 16 g (50 mmol) of 4-bromo-4'-phenyl-diphenylamine, 16 g (55 mmol) of 9-phenyl-9H-carbazol-3-boronic acid, 110 mg (0.4 mmol) of palladium (II) acetate, and 150 mg (0.4 mmol) of tri(o-tolyl)phosphine were put, and 70 mL of toluene, 5 mL of ethanol, and 23 mL of a potassium carbonate solution (2 mol/L) were added to this mixture. This mixture was deaerated while being stirred under low pressure. After the deaeration, the mixture was stirred under a nitrogen atmosphere at 90° C. for 7.5 hours to be reacted.

After the reaction, 150 mL of toluene was added to this reaction mixture, and this suspension was filtrated through Florisil, silica gel, and then Celite. The obtained filtrate was washed with water. Then, magnesium sulfate was added to remove moisture. This suspension was filtrated through Florisil, alumina, silica gel, and then Celite to obtain filtrate. The obtained filtrate was concentrated and purified by silica gel column chromatography (developing solvent, toluene:hexane=1:4). The obtained fraction was concentrated, and chloroform and methanol were added thereto. The mixture was irradiated with supersonic and then recrystallized to obtain 10 g of an objective light-yellow powder at a yield of 41%.

Step 3: Synthesis of 9-(4-bromophenyl)-9-phenylfluorene

A synthetic scheme of 9-(4-bromophenyl)-9-phenylfluorene in Step 3 is shown in the following (V-3).

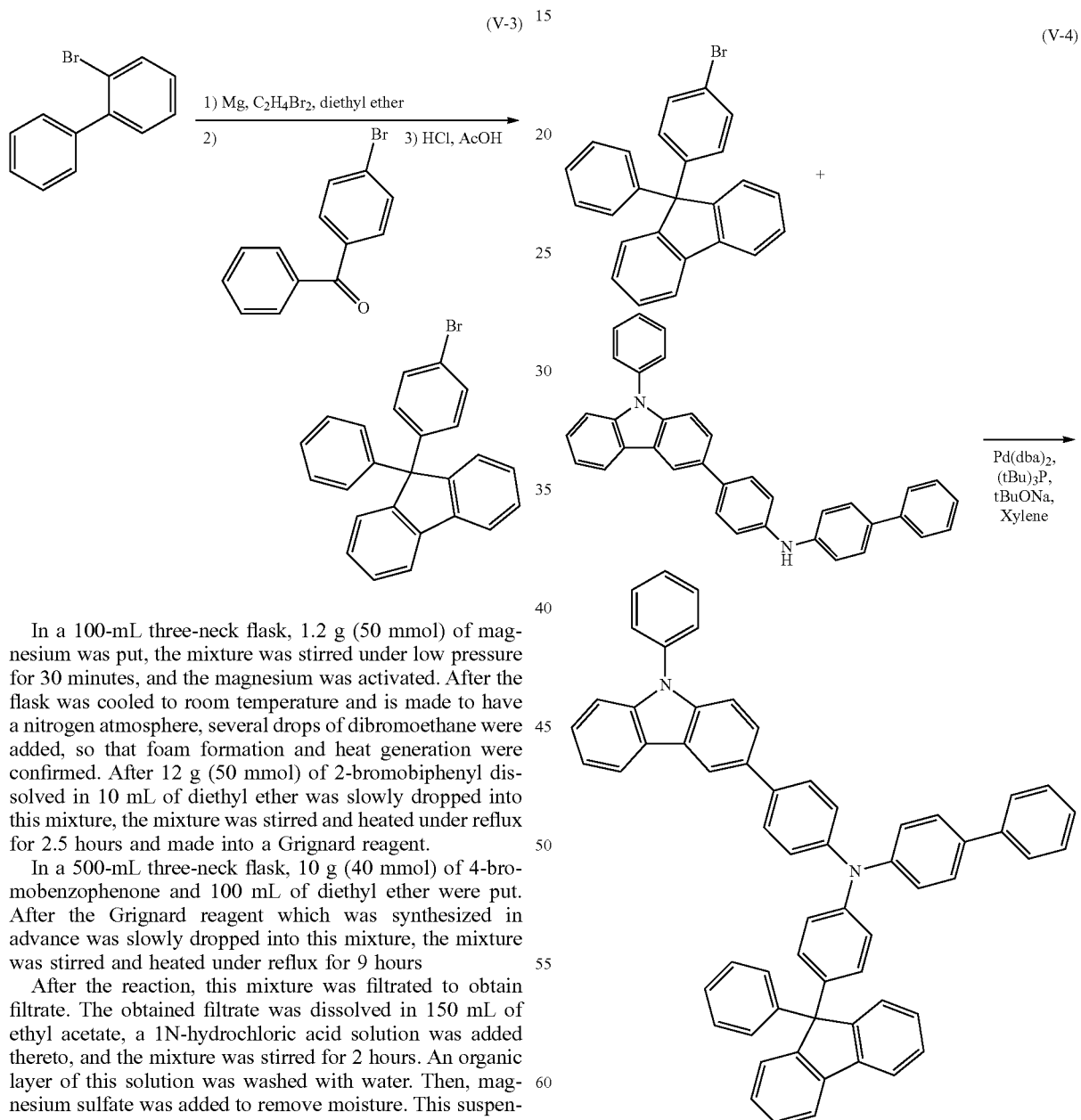

In a 100-mL three-neck flask, 1.2 g (50 mmol) of magnesium was put, the mixture was stirred under low pressure for 30 minutes, and the magnesium was activated. After the flask was cooled to room temperature and is made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dropped into this mixture, the mixture was stirred and heated under reflux for 2.5 hours and made into a Grignard reagent.

In a 500-mL three-neck flask, 10 g (40 mmol) of 4-bromobenzophenone and 100 mL of diethyl ether were put. After the Grignard reagent which was synthesized in advance was slowly dropped into this mixture, the mixture was stirred and heated under reflux for 9 hours After the reaction, this mixture was filtrated to obtain filtrate. The obtained filtrate was dissolved in 150 mL of ethyl acetate, a 1N-hydrochloric acid solution was added thereto, and the mixture was stirred for 2 hours. An organic layer of this solution was washed with water. Then, magnesium sulfate was added to remove moisture. This suspension was filtrated and the obtained filtrate was concentrated to obtain a candy-like substance.

In a 500-mL recovery flask, this candy-like substance, 50 mL of glacial acetic acid, and 1.0 mL of hydrochloric acid were put, and the mixture was stirred under a nitrogen atmosphere at 130° C. for 1.5 hours to be reacted. After the reaction, this reactiom mixture solution was filtrated to obtain filtrate. The obtained filtrate was washed with water, a sodium hydroxide aqueous solution, water, and methanol in this order to obtain 11 g of an objective white power at a yield of 69%.

Step 4: Synthesis of 4-pheny-4'-(9-phenyl-9H-carbazol-3-yl)-4''-(9-phenylfluoren-9-yl)-triphenylamine (abbreviation: PCBBiFLP)

A synthetic scheme of 4-pheny-4'-(9-phenyl-9H-carbazol-3-yl)-4''-(9-phenylfluoren-9-yl)-triphenylamine in Step 4 is shown in the following (V-4).

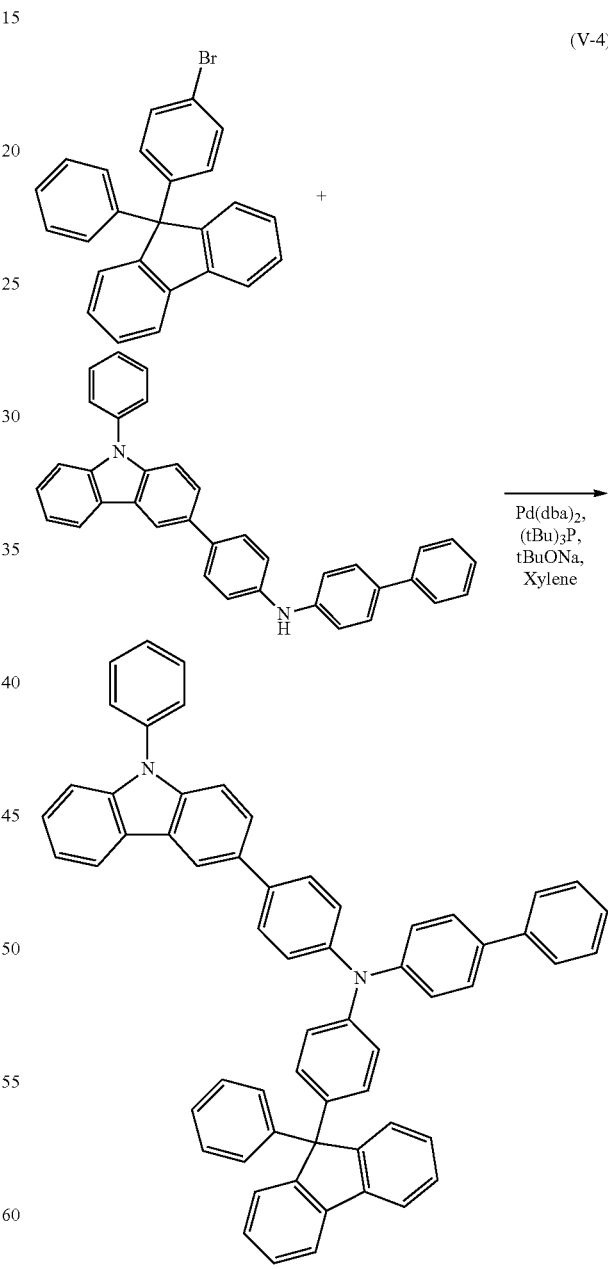

In a 100-mL three-neck flask, 1.2 g (3.0 mmol) of 9-(4-bromophenyl)-9-phenylfluorene, 1.5 g (3.0 mmol) of 4-phenyl-4'-(9-phenyl-9H-carbazol-3-yl)-diphenylamine, 0.4 mg (4.0 mmol) of sodium tert-butoxide, and 17 mg (0.03 mmol) of bis(dibenzylideneacetone)palladium(0) were put, and the atmosphere of the flask was substituted by nitrogen. Then, 20 mL of dehydrated xylene was added to this mixture. This mixture was deaerated while being stirred under low pressure. After the deaeration, 0.2 mL (0.1 mmol) of tri(tert-butyl)phosphine (10 wt % hexane solution) was added thereto. This mixture was stirred under a nitrogen atmosphere at 130° C. for 5.5 hours to be reacted.

After the reaction, 150 mL of toluene was added to this reaction mixture, and this suspension was filtrated through Florisil and then Celite. The obtained filtrate was concentrated and purified by silica gel column chromatography (developing solvent, toluene: hexane=1:4). The obtained fraction was concentrated, and acetone and methanol were added thereto. The mixture was irradiated with supersonic and then recrystallized to obtain 1.8 g of an objective white powder at a yield of 76%.

An Rf value of the objective substance by a silica gel thin layer chromatography (TLC) (developing solvent, ethyl acetate: hexane=1:10) was 0.35, that of 9-(4-bromophenyl)-9-phenylfluorene was 0.65, and that of 4-phenyl-4'-(9-phenyl-9H-carbazol-3-yl)-diphenylamine was 0.19.

Figure 64A:
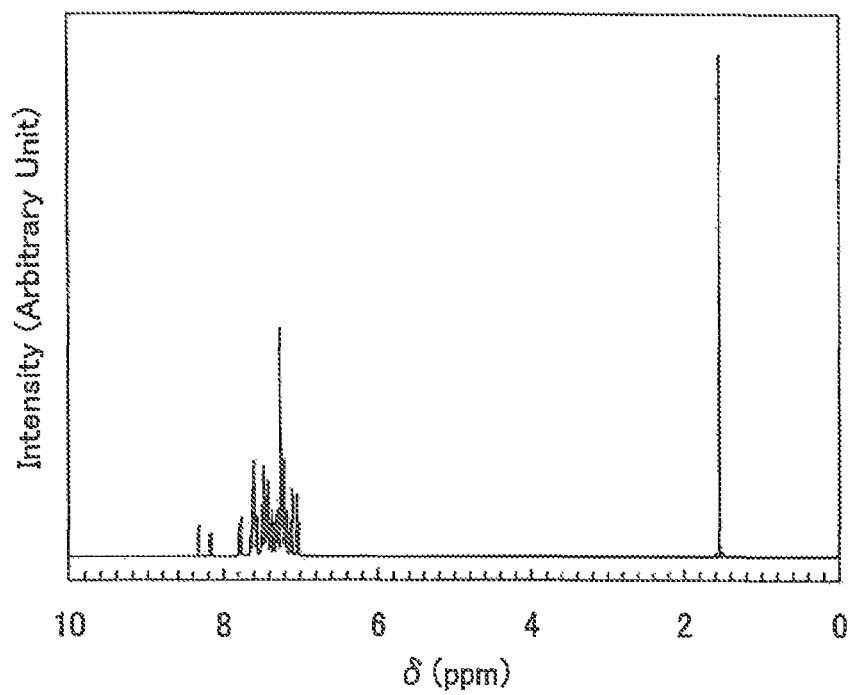
FIGS. 64A and 64B are graphs showing $^1$H NMR charts of PCBBiFLP (abbreviation).
Figure 64B:
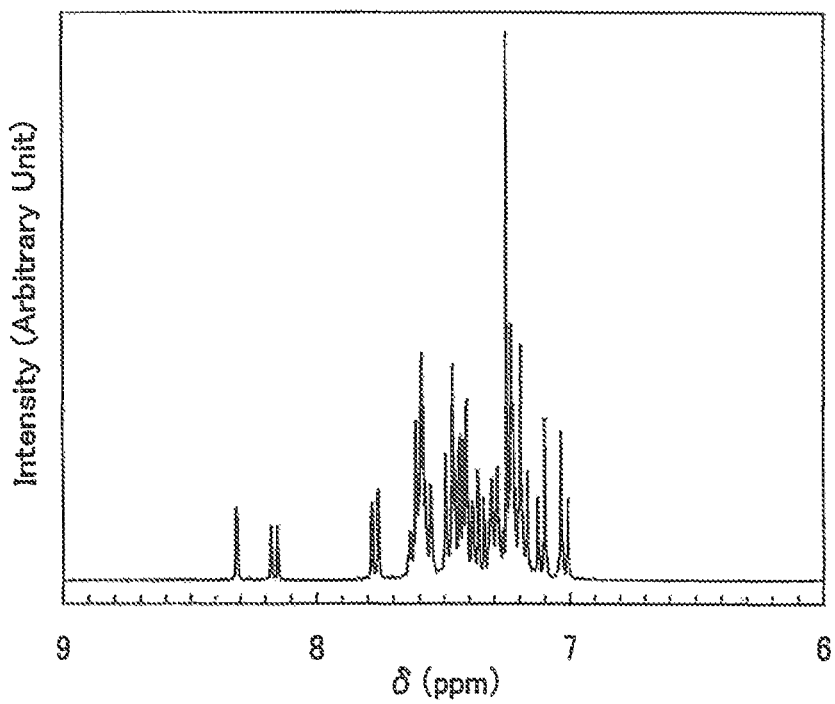

A compound which was obtained through the above Step 4 was measured by a nuclear magnetic resonance method ($^1$H NMR). The measurement result is described below, and the $^1$H NMR chart is shown in FIGS. 64A and 64B. It was found from the measurement result that the carbazole derivative of the present invention, PCBBiFLP (abbreviation) represented by the above structural formula (424), was obtained. $^1$H NMR (CDCl$_3$, 300 MHz): δ (ppm)=7.02 (d, J=8.7, 2H), 7.12 (d, J=8.7, 2H), 7.17-7.64 (m, 36H), 7.77 (d, J=6.9, 2H).

In addition, various physical properties of PCBBiFLP (abbreviation) were measured as described below.

In addition, an absorption spectrum of PCBBiFLP (abbreviation) (measurement range: 200 nm to 800 nm) was measured. In the case of the toluene solution, an absorption peak on a long wavelength side was observed at around 337 nm, and in the case of the thin film, an absorption peak on a long wavelength side was observed at around 339 nm. In addition, an emission spectrum of PCBBiFLP (abbreviation) (measurement range: 390 nm to 550 nm) was measured. In the case of the toluene solution, a maximum emission wavelength was 395 nm (excitation wavelength: 343 nm), and in the case of the thin film, a maximum emission wavelength was 425 nm (excitation wavelength: 361 nm).

The result of measuring the thin film using a photoelectron spectrometer (AC-2, manufactured by Riken Keiki Co., Ltd.) under the atmosphere indicated that the HOMO level of PCBBiFLP (abbreviation) was −5.53 eV. The Tauc plot of the absorption spectrum of the thin film revealed that the absorption edge was 3.28 eV. Thus, the energy gap in the solid state was estimated to be 3.28 eV, which means that the LUMO level of PCBBiFLP (abbreviation) is −2.25 eV.

An oxidation-reduction reaction characteristic of PCBBiFLP (abbreviation) was examined by a cyclic voltammetry (CV) measurement. Since the measurement method is similar to that of Embodiment 1, the description is omitted. According to the calculation similar to that of Embodiment 1, the HOMO level of PCBBiFLP (abbreviation) was found to be =−5.42 [eV]. In addition, the oxidation peak took a similar value even after the 100 cycles. Accordingly, it was found that repetition of the oxidation reduction between an oxidation state and a neutral state had favorable characteristics.

In addition, the glass transition temperature of PCBBiFLP (abbreviation) was examined with a differential scanning calorimetry (Pyris 1 DSC, manufactured by Perkin Elmer Co., Ltd.). According to the measurement results, it was found that the glass transition temperature was 156° C. In this manner, PCBBiFLP (abbreviation) has a high glass transition temperature and favorable heat resistance. In addition, the crystallization peak does not exist; thus, it was found that PCBBiFLP (abbreviation) is a substance which is hard to be crystallized.

Note that the efficiency, the drive voltage at a luminance of about 1000 cd/m$^2$, and the reliability of a light-emitting element formed using PCBBiFLP (abbreviation) which was synthesized in Embodiment 20 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.4 V, the luminance and the current value were 1104 cd/m$^2$ and 0.74 mA, respectively, and the light-emitting element exhibited 75% of the initial luminance when driven for 650 hours.

Note that the efficiency, the drive voltage at a luminance of about 1000 cd/m$^2$, and the reliability of a light-emitting element formed using PCBBiFLP (abbreviation) which was synthesized in Embodiment 20 in a manner similar to that of Embodiment 5 for a hole-transporting layer, favorable values equivalent to those of the light-emitting element 8 which was formed using PCBBiNB in Embodiment 10 were obtained. When the drive voltage of the light-emitting element was 4.0 V, the luminance and the current value were 1171 cd/m$^2$ and 0.65 mA, respectively, and the light-emitting element exhibited 74% of the initial luminance when driven for 360 hours.

Embodiment 21

In Embodiment 21, a synthetic method of a carbazole derivative of the present invention, 4-(I-naphthyl)-4'-(9-phenyl-9H-carbazol-3-yl)-triphenylamine (abbreviation: PCBANB) represented by a structural formula (343), which is different from that in Embodiment 8, will be specifically described.

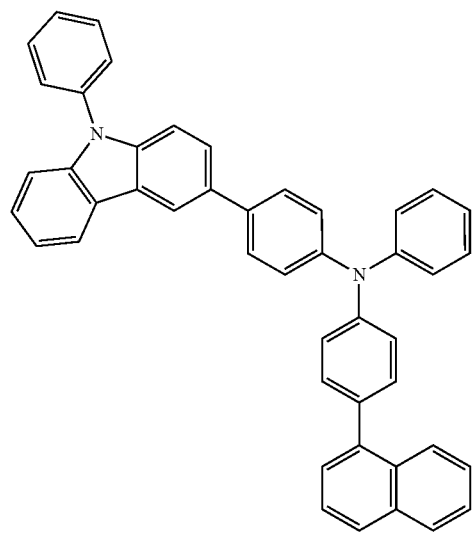

(343)

Step 1: Synthesis of 1-(4-bromophenyl)-naphthalene

A synthetic scheme of 1-(4-bromophenyl)-naphthalene in Step 1 is shown in the following (W-1).

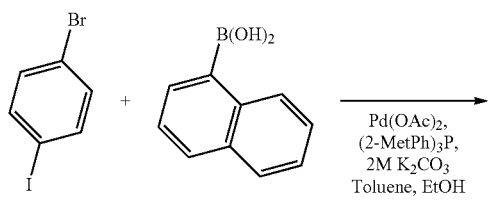

(W-1)

In a 500-mL three-neck flask, 46 g (160 mmol) of 4-bromoiodobenzene, 24 g (140 mmol) of 1-naphthaleneboronic acid, 45 mg (0.2 mmol) of palladium(II) acetate, and 60 mg (0.2 mmol) of tri(o-tolyl)phosphine were put, and 100 mL of toluene, 20 mL of ethanol, and 11 mL of a potassium carbonate solution (2 mol/L) were added to this mixture. This mixture was deaerated while being stirred under low pressure. After the deaeration, the mixture was stirred under a nitrogen atmosphere at 90° C. for 4 hours to be reacted.

After the reaction, 500 mL of toluene was added to this reaction mixture, and this suspension was filtrated through Florisil and then Celite. The obtained filtrate was washed with water. Then, magnesium sulfate was added to remove moisture. This suspension was filtrated through Florisil and then Celite to obtain filtrate. The obtained filtrate was concentrated and purified by silica gel column chromatography (developing solvent, hexane). The obtained fraction was concentrated to obtain 25 g of an objective colorless transparent liquid at a yield of 62%.

An Rf value of the objective substance by a silica gel thin layer chromatography (TLC) (developing solvent, hexane) was 0.38 and that of 4-bromoiodobenzene was 0.57.

Step 2: Synthesis of 4-(1-naphthyl)-4'-(9-phenyl-9H-carbazol-3-yl)-triphenylamine (abbreviation: PCBANB)

A synthetic scheme of 4-(1-naphthyl)-4'-(9-phenyl-9H-carbazol-3-yl)-triphenylamine in Step 2 is shown in the following (W-2).

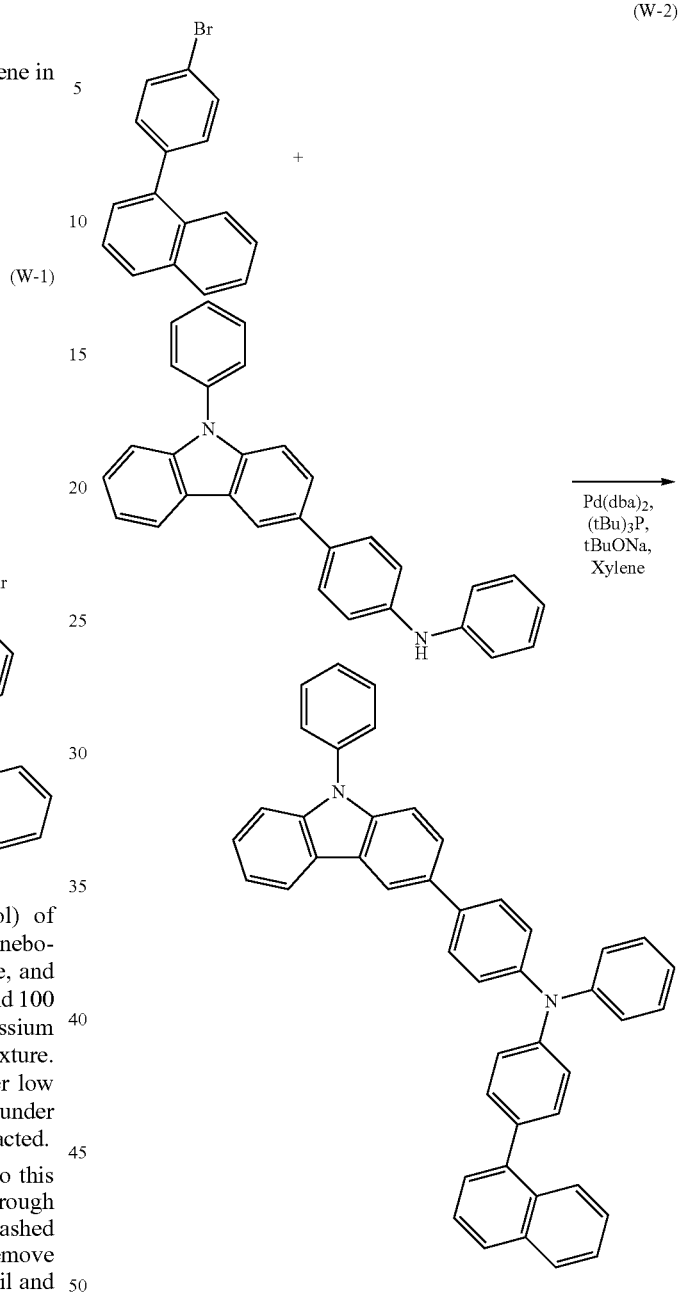

In a 100-mL three-neck flask, 2.8 g (10 mmol) of 1-(4-bromophenyl)-naphthalene, 4.1 g (10 mmol) of 4-(9-phenyl-9H-carbazol-3-yl)-diphenylamine, 1.2 g (12 mmol) of sodium tert-butoxide, and 11 mg (0.02 mmol) of bis(dibenzylideneacetone)palladium(0) were put, and the atmosphere of the flask was substituted by nitrogen. Then, 30 mL of dehydrated xylene was added to this mixture. This mixture was deaerated while being stirred under low pressure. After the deaeration, 0.1 mL (0.06 mmol) of tri(tert-butyl)phosphine (10 wt % hexane solution) was added thereto. This mixture was stirred under a nitrogen atmosphere at 110° C. for 6 hours to be reacted.

After the reaction, 150 mL of toluene was added to this reaction mixture, and this suspension was filtrated through Florisil, silica gel, and then Celite. The obtained filtrate was concentrated and purified by silica gel column chromatography (developing solvent, toluene: hexane=1:4). The obtained fraction was concentrated, and acetone and methanol were added thereto. The mixture was irradiated with supersonic and then recrystallized to obtain 5.2 g of an objective white powder at a yield of 85%.

Note that unless otherwise specified, for the Florisil and the Celite which are described in each sythesitic method of the above embodiments of the present invention, Florisil (Wako Pure Chemical Industries, Ltd., catalog No.: 540-00135) and Celite (Wako Pure Chemical Industries, Ltd., catalog No.: 531-16855) are used, respectively.

The present application is based on Japanese Patent Application serial No. 2007-312509 and Japanese Patent Application serial No. 2008-129917 which are filed with Japan Patent Office on Dec. 3, 2007 and May 16, 2008, respectively, the entire contents of which are hereby incorporated by reference.

The invention claimed is:

1. A compound represented by a formula (1):

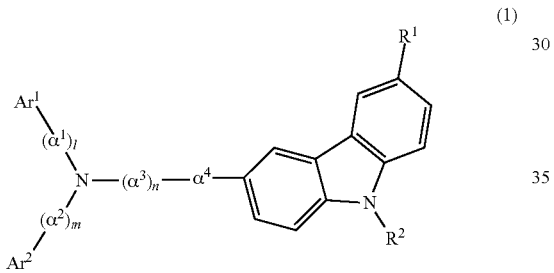

wherein:
$\alpha^1$, $\alpha^2$, $\alpha^3$, and $\alpha^4$ each represent a formula (2-1),
$Ar^1$ represents a formula (3-6),
$Ar^2$ is a phenyl group,
$R^1$ represents a hydrogen atom,
$R^2$ represents any of an alkyl group having 1 to 6 carbon atoms, an unsubstituted phenyl group, and an unsubstituted biphenyl group, and
l is 0, m is 1, and n is 0,

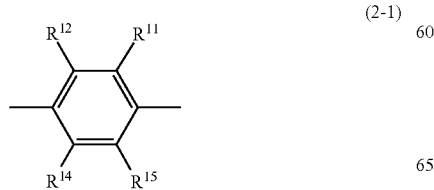

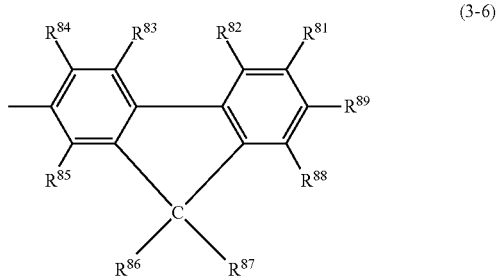

wherein:
$R^{11}$, $R^{12}$, $R^{14}$, and $R^{15}$ each represent any of a hydrogen atom, an alkyl group having 1 to 6 carbon atoms, and an unsubstituted phenyl group;
$R^{81}$ to $R^{85}$, $R^{88}$, and $R^{89}$ each represent any of a hydrogen atom, an alkyl group having 1 to 6 carbon atoms, and an unsubstituted phenyl group; and
$R^{86}$ and $R^{87}$ each are an alkyl group having 1 to 6 carbon atoms.

2. A compound represented by a formula (1):

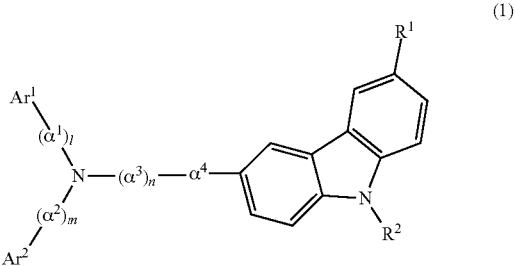

wherein:
$\alpha^1$, $\alpha^2$, $\alpha^3$, and $\alpha^4$ each represent a formula (2-1),
$Ar^1$ represents a formula (3-6),
$Ar^2$ represents an aryl group having 6 to 13 carbon atoms forming a ring,
$R^1$ represents a hydrogen atom,
$R^2$ represents any of an alkyl group having 1 to 6 carbon atoms, an unsubstituted phenyl group, and an unsubstituted biphenyl group, and
l, m, and n each are 0 or 1,

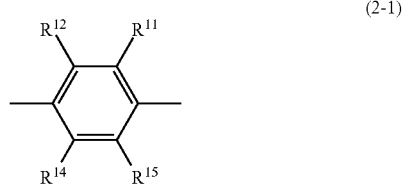

-continued

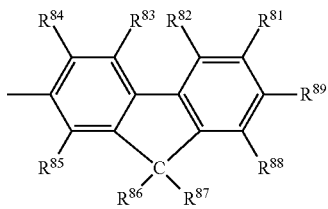

(3-6)

wherein:
$R^{11}$, $R^{12}$, $R^{14}$, and $R^{15}$ each represent any of a hydrogen atom, an alkyl group having 1 to 6 carbon atoms, and an unsubstituted phenyl group;
$R^{81}$ to $R^{85}$, $R^{88}$, and $R^{89}$ each represent any of a hydrogen atom, an alkyl group having 1 to 6 carbon atoms, and an unsubstituted phenyl group; and
$R^{86}$ and $R^{87}$ each are a phenyl group; and
$R^{86}$ and $R^{87}$ are connected to each other to form a ring.

3. A light-emitting element comprising a light-emitting layer, wherein the light-emitting layer comprises the compound according to claim 1.

4. A light-emitting element comprising a light-emitting layer, wherein the light-emitting layer comprises the compound according to claim 2.

5. A light-emitting element comprising a layer between a first electrode and a light-emitting layer,
wherein the layer comprises the compound according to claim 1.

6. A light-emitting element comprising a layer between a first electrode and a light-emitting layer,
wherein the layer comprises the compound according to claim 2.

7. The compound according to claim 2, represented by a formula (8):

(8)

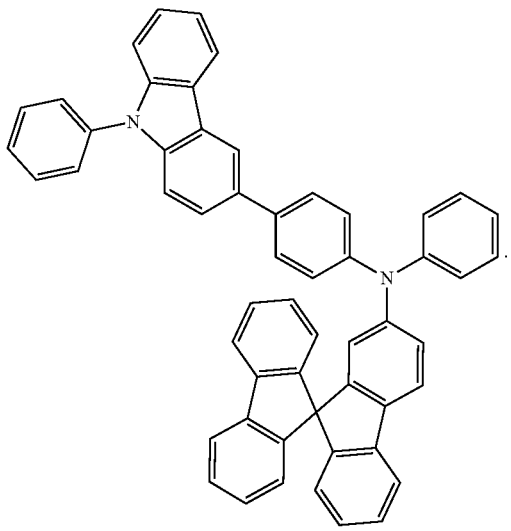

* * * * *